United States Patent
Jones et al.

(10) Patent No.: US 11,596,670 B2
(45) Date of Patent: Mar. 7, 2023

(54) TREATMENT OF A DISEASE OF THE GASTROINTESTINAL TRACT WITH IL-10 OR AN IL-10 AGONIST

(71) Applicant: BIORA THERAPEUTICS, INC., San Diego, CA (US)

(72) Inventors: Mitchell Lawrence Jones, La Jolla, CA (US); Sharat Singh, Rancho Santa Fe, CA (US); Christopher Loren Wahl, San Diego, CA (US); Harry Stylli, La Jolla, CA (US)

(73) Assignee: BIORA THERAPEUTICS, INC., San Diego, CA (US)

( * ) Notice: Subject to any disclaimer, the term of this patent is extended or adjusted under 35 U.S.C. 154(b) by 28 days.

(21) Appl. No.: 16/497,117

(22) PCT Filed: Mar. 30, 2018

(86) PCT No.: PCT/US2018/025523
§ 371 (c)(1),
(2) Date: Sep. 24, 2019

(87) PCT Pub. No.: WO2018/183931
PCT Pub. Date: Oct. 4, 2018

(65) Prior Publication Data
US 2021/0121533 A1    Apr. 29, 2021

Related U.S. Application Data

(60) Provisional application No. 62/507,008, filed on May 16, 2017, provisional application No. 62/478,744, filed on Mar. 30, 2017, provisional application No. 62/545,232, filed on Aug. 14, 2017, provisional application No. 62/583,806, filed on Nov. 9, 2017, provisional application No. 62/598,957, filed on Dec. 14, 2017.

(51) Int. Cl.
| | |
|---|---|
| *A61K 38/20* | (2006.01) |
| *A61P 1/04* | (2006.01) |
| *A61M 31/00* | (2006.01) |
| *C07K 14/54* | (2006.01) |

(52) U.S. Cl.
CPC ........ *A61K 38/2066* (2013.01); *A61M 31/002* (2013.01); *A61P 1/04* (2018.01); *C07K 14/5428* (2013.01)

(58) Field of Classification Search
CPC ............ A61M 31/002; C07K 14/5428; A61K 38/2066
See application file for complete search history.

(56) References Cited

U.S. PATENT DOCUMENTS

| | | |
|---|---|---|
| 3,773,919 A | 11/1973 | Boswell et al. |
| 4,120,649 A | 10/1978 | Schechter |
| 4,190,328 A | 2/1980 | Levine et al. |
| 4,223,680 A | 9/1980 | Jobsis |
| 4,292,961 A | 10/1981 | Kawashima |
| 4,522,811 A | 6/1985 | Eppstein et al. |
| 4,665,077 A | 5/1987 | Stringfellow et al. |
| 4,676,980 A | 6/1987 | Segal et al. |
| 4,816,567 A | 3/1989 | Cabilly et al. |
| 5,114,721 A | 5/1992 | Cohen et al. |
| 5,314,805 A | 5/1994 | Haugland et al. |
| 5,516,636 A | 5/1996 | McCapra |
| 5,705,622 A | 1/1998 | McCapra |
| 5,759,808 A | 6/1998 | Casterman et al. |
| 5,763,602 A | 6/1998 | Li et al. |
| 6,171,586 B1 | 1/2001 | Lam et al. |
| 6,251,581 B1 | 6/2001 | Ullman et al. |
| 6,267,958 B1 | 7/2001 | Andya et al. |
| 6,331,530 B1 | 12/2001 | Breslow et al. |
| 6,693,113 B2 | 2/2004 | Lindstrom et al. |
| 6,936,586 B1 | 8/2005 | Larsen et al. |
| 7,217,531 B2 | 5/2007 | Singh et al. |
| 7,709,273 B2 | 5/2010 | Singh et al. |
| 8,247,180 B2 | 8/2012 | Pidaparthi et al. |
| 8,394,034 B2 | 3/2013 | Iddan et al. |
| 8,615,284 B2 | 12/2013 | Arneson et al. |
| 8,691,205 B2 | 4/2014 | Blaisdell et al. |
| 8,865,652 B2 | 10/2014 | Oft et al. |
| 8,907,081 B2 | 12/2014 | Vail et al. |
| 9,259,478 B2 | 2/2016 | Blaisdell et al. |
| 9,324,145 B1 | 4/2016 | Cherevatsky et al. |
| 9,364,517 B2 | 6/2016 | Oft et al. |
| 9,593,313 B2 | 3/2017 | Capron et al. |
| 10,172,598 B2 | 1/2019 | Amoako-Tuffour et al. |
| 2003/0117491 A1 | 6/2003 | Avni et al. |

(Continued)

FOREIGN PATENT DOCUMENTS

| | | |
|---|---|---|
| CN | 104473611 | 4/2015 |
| EP | 0340109 | 11/1989 |

(Continued)

OTHER PUBLICATIONS

Aslam et al (Journal of Drug Delivery & Therapeutics; 2012, 2(3): 1-3) (Year: 2012).*
Xitian et al. International Journal of Pharmaceutics, 2009, vol. 382, pp. 160-164) (Year: 2009).*
Menssa et al. Plant Biotechnology Journal (2007) 5, pp. 50-59) (Year: 2007).*
Guido et al. Virtual Screening and Its Integration with Modern Drug Design Technologies. Curr Med Chem. 2008; 15(1):37-46 (Year: 2008).*

(Continued)

*Primary Examiner* — Vanessa L. Ford
*Assistant Examiner* — Sandra Dillahunt
(74) *Attorney, Agent, or Firm* — Procopio, Cory, Hargreaves & Savitch LLP

(57) ABSTRACT

This disclosure features methods and compositions for treating diseases of the gastrointestinal tract with IL-10 or an IL-10 agonist.

27 Claims, 70 Drawing Sheets

Specification includes a Sequence Listing.

(56) References Cited

U.S. PATENT DOCUMENTS

| | | | |
|---|---|---|---|
| 2003/0191430 A1 | 10/2003 | D'Andrea et al. | |
| 2005/0049462 A1 | 3/2005 | Kanazawa | |
| 2005/0065441 A1 | 3/2005 | Glukhovsky | |
| 2005/0260186 A1 | 11/2005 | Bookbinder et al. | |
| 2005/0266074 A1* | 12/2005 | Zilberstein | A61B 6/425 424/464 |
| 2006/0069317 A1 | 3/2006 | Horn et al. | |
| 2006/0104968 A1 | 5/2006 | Bookbinder et al. | |
| 2006/0269485 A1 | 11/2006 | Friedman et al. | |
| 2007/0027362 A1 | 2/2007 | Handa et al. | |
| 2007/0059316 A1 | 3/2007 | Pallenberg et al. | |
| 2008/0051633 A1 | 2/2008 | Blijevsky | |
| 2008/0081031 A1 | 4/2008 | Oft et al. | |
| 2008/0208077 A1 | 8/2008 | Iddan et al. | |
| 2009/0214471 A1 | 8/2009 | Oft et al. | |
| 2010/0045786 A1 | 2/2010 | Kitamura | |
| 2011/0091419 A1 | 4/2011 | Oft et al. | |
| 2011/0125031 A1 | 5/2011 | Blit et al. | |
| 2011/0250163 A1 | 10/2011 | Blaisdell et al. | |
| 2012/0136209 A1* | 5/2012 | Kostenich | G01J 3/0272 600/109 |
| 2013/0013031 A1 | 1/2013 | Ben-Yehuda et al. | |
| 2013/0158344 A1 | 6/2013 | Taniguchi | |
| 2013/0171247 A1* | 7/2013 | Imran | A61M 25/10 604/174 |
| 2013/0289368 A1 | 10/2013 | Covington et al. | |
| 2014/0227223 A1 | 8/2014 | Lee et al. | |
| 2014/0296666 A1 | 10/2014 | Rabinovitz et al. | |
| 2015/0079031 A1 | 3/2015 | Oft et al. | |
| 2015/0086505 A1 | 3/2015 | Blaisdell et al. | |
| 2015/0118264 A1 | 4/2015 | Baumhof et al. | |
| 2016/0166647 A1 | 6/2016 | Lee et al. | |
| 2016/0193352 A1 | 7/2016 | Blaisdell et al. | |
| 2016/0249793 A1 | 9/2016 | Wang | |
| 2016/0375101 A1 | 12/2016 | Oft | |
| 2017/0006202 A1 | 1/2017 | Otani et al. | |
| 2017/0284956 A1 | 10/2017 | Kalantar-Zadeh et al. | |
| 2017/0296092 A1 | 10/2017 | Jones et al. | |
| 2018/0049725 A1 | 2/2018 | Jones et al. | |
| 2018/0070857 A1 | 3/2018 | Jones et al. | |
| 2018/0070928 A1 | 3/2018 | Jones et al. | |
| 2018/0164221 A1 | 6/2018 | Singh et al. | |
| 2018/0168488 A1 | 6/2018 | Jones et al. | |
| 2018/0193003 A1 | 7/2018 | Jones et al. | |
| 2018/0206726 A1 | 7/2018 | Singh et al. | |
| 2018/0279908 A1 | 10/2018 | Jones et al. | |
| 2019/0307434 A1 | 10/2019 | Jones et al. | |
| 2019/0367689 A1 | 12/2019 | Hirai et al. | |

FOREIGN PATENT DOCUMENTS

| | | |
|---|---|---|
| JP | 2005-073888 | 3/2005 |
| JP | 2008-500126 | 1/2008 |
| JP | 2015-509744 | 4/2015 |
| JP | 2017-516962 | 6/2017 |
| KR | 100931946 | 12/2009 |
| WO | WO 1990008187 | 7/1990 |
| WO | WO 1990011294 | 10/1990 |
| WO | WO 1991000349 | 1/1991 |
| WO | WO 1991001133 | 2/1991 |
| WO | WO 1996001318 | 1/1996 |
| WO | WO 1996027011 | 9/1996 |
| WO | WO 1999042838 | 8/1999 |
| WO | WO 2000073457 | 12/2000 |
| WO | WO 2004066903 | 8/2004 |
| WO | WO 2006044908 | 4/2006 |
| WO | 2006131013 A3 | 12/2006 |
| WO | WO 2007024715 | 3/2007 |
| WO | WO 2008024188 | 2/2008 |
| WO | WO 2008104968 | 9/2008 |
| WO | WO 2008122965 | 10/2008 |
| WO | WO 2008122967 | 10/2008 |
| WO | 2009046168 A1 | 4/2009 |
| WO | 2009104110 A1 | 8/2009 |
| WO | WO 2011016002 | 2/2011 |
| WO | 2013080050 A2 | 6/2013 |
| WO | WO 2013088444 | 6/2013 |
| WO | WO 2013120184 | 8/2013 |
| WO | WO 2013130913 | 9/2013 |
| WO | WO 2014188377 | 11/2014 |
| WO | WO 2015099749 | 7/2015 |
| WO | WO 2015103072 | 7/2015 |
| WO | WO 2015112575 | 7/2015 |
| WO | WO 2016049602 | 3/2016 |
| WO | WO 2016197181 | 12/2016 |

OTHER PUBLICATIONS

Clark et al. Discovery and Development of Janus Kinase (JAK) Inhibitors for Inflammatory Diseases. J. Med. Chem., 2014, 57 (12), pp. 5023-5038 (Year: 2014).*

Bowie et al. Deciphering the Message in Protein Sequences: Tolerance to Amino Acid Substitutions. Science, 1990, 247:1306-1310 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

Bork. Powers and Pitfalls in Sequence Analysis: The 70% Hurdle. Genome Research, 2000, 10:398-400 (Year: 2000).*

Aagaard et al. RNAi therapeutics: Principles, prospects and challenges. Advanced Drug Delivery Reviews 59 (2007) 75-86 (Year: 2007).*

Warzocha et al. Antisense Strategy: Biological Utility and Prospects in the Treatment of Hematological Malignancies. Leukemia and Lymphoma, 1997; 24(3-4): 267-281 (Year: 1997).*

Vajdos et al. Comprehensive Functional Maps of the Antigenbinding Site of an Anti-ErbB2 Antibody Obtained with Shotgun Scanning Mutagenesis. J Mol Biol. Jul. 5, 2002;320(2):415-28 (Year: 2002).*

Brown et al. Tolerance to Single, but Not Multiple, Amino Acid Replacements in Antibody V, CDR2. J Immunol. May 1996; 156(9): 3285-91 (Year: 1996).*

Menassa et al. Therapeutic effectiveness of orally administered transgenic low-alkaloid tobacco expressing human interleukin-10 in a mouse model of colitis. Plant Biotechnology Journal (2007) 5: 50-59 (Year: 2007).*

Al-Lazikani et al., "Standard conformations for the canonical structures of immunoglobulins," J. Molec. Biol., 1997, 273:927-948.

Aslam and Majeed, "Ingestible electronically controlled drug-capsule in the gut," J. Drug Delivery & Therapeutics, 2012, 2(3):1-3.

Barbeau et al., "Application Note: Screening for inhibitors of TNFa/sTNFRI Binding using AlphaScreen Technology," Perkin Elmer Technical Note ASC-016, 2002, 5 pages.

Basar et al., "Ingestible Wireless Capsule Technology: A Review of Development and Future Indication," International Journal of Antennas and Propagation, 2012, Article ID 807165, 14 pages.

Berleman and Auer, "The role of bacterial outer membrane vesicles for intra- and interspecies delivery," Environmental Microbiology, 2012, 15(2):347-354.

Bernkop-Schnurch, "Thiomers: a new generation of mucoadhesive polymer," Adv. Drug Deliv. Rev., 2005, 57(11):1569-1582.

Best et al., "Rederived values of the eight coefficients of the Crohn's Disease Activity Index (CDAI)," Gastroenterology, 1979, 77:843-846.

Braat et al., "A Phase I Trial With Transgenic Bacteria Expressing interleukin-10 in Crohn's Disease," Clin. Gastroenterol. Heptol., 4:754-759, 2006.

Brennan et al., "Preparation of bispecific antibodies by chemical recombination of monoclonal immunoglobulin G1 fragments," Science, 1985, 229:81-83.

Brunius, "Technical aspects of the use of 3',6'-Diacetylfluorescein for vital fluorescent staining of bacteria," Current Microbiol., 1980, 4:321-323.

Capron et al., "Mol696. Treatment With P28GST, a Recombinant Enzyme From Schistosome Helminth Parasite Prevents Hapten-Induced Colitis by Inducing a Regulatory Th2 Response," Gastroenterology, 2014, 146(5):S-638.

(56) References Cited

OTHER PUBLICATIONS

Cavalcante et al., "Expression of the interleukin-10 Signaling Pathway Genes in Individuals With Down Syndrome and Periodontitis," J. Periodontol., 83(7):926-935, 2012.
Chamekh et al., "Delivery of Biologically Active Anti-Inflammatory Cytokines IL-10 and IL-Ira In Vivo by the Shigella Type III Secretion Apparatus," J Immunol., 180(6):4292-4298, 2008.
Chan et al., "PEGylated IL-10 Activates Kupffer Cells to Control Hypercholesterolemia," PLoS One, 11(6):e0156229, 2016.
Chang and Lichtenstein, "Drug Insight: antagonists of tumor-necrosis factor-α in the treatment of inflammatory bowel disease," Nat. Clin. Pract. Gastroenterol. Hepatology, 2006, 3:220-228.
Chatellard et al., "The IE2 Promoter/Enhancer Region From Mouse CMV Provides High Levels of Therapeutic Protein Expression in Mammalian Cells," Biotechnol. Bioeng., 96:106-117, 2007.
Cheal et al., "Preclinical evaluation of multistep targeting of diasialoganglioside GD2 using an IgG-scFv bispecific antibody with high affinity for GD2 and DOTA metal complex," Mol. Cancer Ther., 2014, 13(7):1803-1812.
Chelius et al., "Structural and functional characterization of the trifunctional antibody catumaxomab," Mabs, 2010, 2(3):309-319.
Choung et al., "Serologic microbial associated markers can predict Crohn's disease behaviour years before disease diagnosis," Aliment. Pharmacol. Ther., 2016, 43(12):1300-1310.
Ciuti et al., "Frontiers of robotic endoscopic capsules: a review," Journal of Micro-Bio Robotics, 11:1-18, 2016.
Collins and Franzblau, "Microplate alamar blue assay versus BACTEC 460 system for high-throughput screening of compounds against *Mycobacterium tuberculosis* and *Mycobacterium avium*," Antimicrob. Agents Chemother., 1997, 41(5):1004-1009.
Cuesta et al., "Multivalent antibodies: when design surpasses evolution," Trends in Biotechnol., 2010, 28(7):355-362.
Daperno et al., "Development and validation of a new, simplified endoscopic activity score for Crohn's disease: the SES-CD," Gastrointest. Endosc., 2004, 60(4):505-512.
Davies, "A comparison of fluorochromes for direct viable counts by image analysis," Lett. Appl. Microbiol., 1991, 13:58.
Detkova et al., "Different patterns of serum interleukin 10 response to treatment with anti-tumor necrosis factor alpha antibody (infliximab) in Crohn's disease," Physiol. Res., 2003, 52:95-100.
DeWitt, "Making antibodies more human," Nature Biotech., 17:214, 1999.
Driss et al., "The schistosome glutathione S-transferase P28GST, a unique helminth protein, prevents intestinal inflammation in experimental colitis through a Th2-type response with mucosal eosinophils," Mucosal Immunology, 2016, 9:322-335.
Dumoulin et al., "A camelid antibody fragment inhibits the formation of amyloid fibrils by human lysozyme," Nature, 2003, 424:783-788.
Durie et al., "Prevention of collagen-induced arthritis with an antibody to gp39, the ligand for CD40," Science, 1993, 261:1328-1330.
Elluri et al., "Outer Membrane Vesicles Mediate Transport of Biologically Active Vibrio cholerae Cytolysin (VCC) from V. cholerae Strains," PLoS One, 2014, 9:e106731, 13 pages.
Elrefaei et al., "HIV-specific IL-10-positive CD8+ T cells suppress cytolysis and IL-2 production by CD8+ T cells," J. Immunol., 178:3265-3271, 2007.
Faure et al., "Serotonin signaling is altered in irritable bowel syndrome with diarrhea but not in functional dyspepsia in pediatric age patients," Gastroenterology, 2010, 139(1):249-258.
Fillatreau et al., "B Cells Regulate Autoimmunity by Provision of IL-10," Nat. Immunol., 3:944-950, 2002.
Fillatreau et al., "Not Always the Bad Guys: B Cells as Regulators of Autoimmune Pathology," Nat. Rev. Immunol., 8:391-397, 2008.
Finck et al., "Treatment of murine lupus with CTLA4Ig," Science, 1994, 265:1225-1227.
Fioranelli, "Journal of Integrative Cardiology," J. Integr. Cardiol., 1:1, 2014.
Fiorentino et al., "Two Types of Mouse T Helper Cell. IV. Th2 Clones Secrete a Factor That Inhibits Cytokine Production by Th1 Clones," J Exp. Med., 170:2081-2095, 1989.
Fleming et al., "Surface interleukin-10 inhibits listericidal activity by primary macrophages," J. Leukocyte Biol., 66:961-967, 1999.
Franz et al., "Targeted Delivery of interleukin-10 to Chronic Cardiac Allograft Rejection Using a Human Antibody Specific to the Extra Domain A of Fibronectin," Int. J. Cardiol., 195:311-322, 2015.
Fukuda et al., "A novel dual regulator of tumor necrosis factor-alpha and interleukin-10 protects mice from endotoxin-induced shock," Eur. J. Pharmacol., 2000, 391(3):317-320.
Galeazzi et al., "A Phase IB Clinical Trial With Dekavil (F8-IL10), an Immunoregulatory 'Armed Antibody' for the Treatment of Rheumatoid Arthritis, Used in Combination with Methotrexate," Isr. Med Assoc. J., 16(10):666, 2014.
Gant et al., "The application of flow cytometry to the study of bacterial responses to antibiotics," J. Med. Microbiol., 1993, 39:147-154.
Gasink et al., "Abstract 1679: Evaluation of an Interim Crohn's Disease Outcome Measure (PRO-2) Based on 2 Patient-Reported Components (Stool Frequency, Abdominal Pain) of the Crohn's Disease Activity Index (CDAI) in the Ustekinumab CERTIFI Study," ACG Annual Meeting, 2014, S497.
Gazzinelli et al., "In the Absence of Endogenous IL-10, Mice Acutely Infected With Toxoplasma Gondii Succumb to a Lethal Immune Response Dependent on CD4+ T Cells and Accompanied by Overproduction of IL-12, IFN-gamma and TNF-alpha," J. Immunol., 157:798-805, 1996.
Ghosal, "Importance of secreted bacterial RNA in bacterial-host interactions in the gut," Microbial Pathogenesis, 2017, 104:161-163.
Goodgame, "Viral infections of the gastrointestinal tract," Curr. Gastroenterol. Rep., 1(4):292-300, 1999.
Gruber et al., "Efficient tumor cell lysis mediated by a bispecific single chain antibody expressed in *Escherichia coli*," J. Immunol., 1994, 152:5368-5374.
Guo et al., "Extracellular domain of 4-1BBL enhanced the antitumoral efficacy of peripheral blood lymphocytes mediated by anti-CD3 × anti-Pgp bispecific diabody against human multidrug-resistant leukemia," Cell. Immunol. 251(2):102-108, 2008.
Gupte et al., "In-vitro generation of interleukin-10 secreting B-regulatory cells from donor adipose tissue derived mesenchymal stem cells and recipient peripheral blood mononuclear cells for potential cell therapy," Biomed J., 40(1):49-54, 2017.
Hanauer et al., "Maintenance infliximab for Crohn's disease: the ACCENT I randomised trial," Lancet., 2002, 359:1541-1549.
Hanson et al., "Oral delivery of IL-27 recombinant bacteria attenuates immune colitis in mice," Gastroenterology, 2014, 146(1):210-221.
Harding et al., "Biopolymer Mucoadhesives," Biotechnol. Genet. Eng. News, 1999, 16(1):41-86.
Hasler et al., "VNAR single-domain antibodies specific for BAFF inhibit B cell development by molecular mimicry," Mol. Immunol., 2016, 75:28-37.
Hayashi et al., "A Single Strain of Clostridium Butyricum Induces Intestinal IL-10-producing Macrophages to Suppress Acute Experimental Colitis in Mice," Cell Host Microbe, 13:711-722, 2013.
Hirsch et al., "Easily reversible desthiobiotin binding to streptavidin, avidin, and other biotin-binding proteins: uses for protein labeling, detection, and isolation," Anal. Biochem., 2002, 308(2):343-357.
Hoentjen and van Bodegraven, "Safety of anti-tumor necrosis factor therapy in inflammatory bowel disease," World J. Gastroenterol., 2009, 15(17):2067-2073.
Holliger et al., ""Diabodies": small bivalent and bispecific antibody fragments.," Proc. Natl. Acad. Sci. USA, 1993, 90:6444-6448.
Holscher et al., "Tumor Necrosis Factor Alpha-Mediated Toxic Shock in Trypanosoma cruzi-Infected Interleukin 10-Deficient Mice," Infect. Immun., 68:4075-4083, 2000.
Holt et al., "Domain antibodies: proteins for therapy," Trends Biotechnol., 2003, 21(11):484-490.

(56) References Cited

OTHER PUBLICATIONS

Hu et al., "Crosstalk among Jak-STAT, Toll-like receptor, and ITAM-dependent pathways in macrophage activation," J. Leukoc. Biol., 82(2):237-243, 2007.
Hudson and Kortt, "High avidity scFv multimers: diabodies and triabodies," J. Immunol. Methods, 1999, 23(1-2):177-189.
Hunter et al., "IL-10 Is Required to Prevent Immune Hyperactivity During Infection With Trypanosoma Cruzi," J. Immunol., 158:3311-3316, 1997.
Huston et al., "Engineered antibodies take center stage," Human Antibodies, 2001, 10(3-4):127-142.
Infante et al., "A first-in-human dose escalation study of PEGylated recombinant human IL-10 (AM0010) in advanced solid tumors," J. Clin. Oncol., 33(15 suppl):3017, 2015.
International Preliminary Report on Patentability in PCT Appln. No. PCT/US2018/025523, dated Oct. 1, 2019, 18 pages.
International Search Report and Written Opinion in PCT Appln. No. PCT/US2018/025523, dated Jul. 6, 2018, 30 pages.
Janeway, "Immunotherapy by peptides?" Nature, 1989, 341:482-483.
Jankovic et al., "Conventional T-bet(+)Foxp3(−) Th1 Cells Are the Major Source of Host-Protective Regulatory IL-10 During Intracellular Protozoan Infection," J. Exp. Med., 204:273-283, 2007.
Jenkins et al., "A Novel Viral Transcript with Homology to Human Interleukin-10 Is Expressed during Latent Human Cytomegalovirus Infection," J. Virol., 78(3):1440-1447, 2004.
Ji et al., "HIV-1 Induces IL-10 Production in Human Monocytes via a CD4-independent Pathway," Int. Immunol., 17:729-736, 2005.
Jones and Senft, "An improved method to determine cell viability by simultaneous staining—with fluorescein diacetate—propidium iodide," J. Histochem. Cytochem., 1985, 33:77-79.
Jones et al., "Crystal structure of human cytomegalovirus IL-10 bound to soluble human IL-10R1," Proc. Natl. Acad. Sci. USA, 99(14):9404-9409, 2002.
Kanofsky, "Singlet oxygen production by chloroperoxidase-hydrogen peroxide-halide systemes," J. Biol. Chem., 1984, 259:5596-5600.
Kaprelyants and Kell, "Rapid assessment of bacterial viability and vitality by rhodamine 123 and flow cytometry," J. Appl. Bacteriol., 1992, 72:410-422.
Khanna et al., "A retrospective analysis: the development of patient reported outcome measures for the assessment of Crohn's disease activity," Aliment. Pharmacol. Ther., 2015, 41:77-86.
Khanna et al., "A systematic review of measurement of endoscopic disease activity and mucosal healing in Crohn's disease: recommendations for clinical trial design," Inflamm. Bowel Dis., 2014, 20:1850-1861.
Kharenko et al., "Mucoadhesive drug delivery systems (review)," Pharmaceutical Chemistry Journal, 2009, 43(4):200-208.
Kim et al., "Can Crohn's disease activity index differentiate clinical remission induced by placebo versus biologics treatment?—Analyses of sic clinical trials for Crohn's disease," Gastroenterology, 2014, 146:(5 Suppl. 1): S-368.
Kim et al., "Effective Therapeutic Approach for Head and Neck Cancer by an Engineered Minibody Targeting the EGFR Receptor," PLoS One, 2014, 10(1):e113442, 16 pages.
Kimura et al., "Accumulation of advanced glycation end products of the Maillard reaction with age in human hippocampal neurons," Neurosci. Lett., 1996, 208:53-56.
Kohler and Milstein, "Continuous cultures of fused cells secreting antibody of predefined specificity," Nature, 1975, 256:495-497.
Konstantinov et al., "S Layer Protein A of Lactobacillus Acidophilus NCFM Regulates Immature Dendritic Cell and T Cell Functions," Proc. Natl. Acad. Sci. USA, 105(49):19474-19479, 2008.
Kontermann and Brinkmann, "Bispecific antibodies," Drug Discovery Today, 2015, 20(7):838-847.
Korzenik et al., "Sargramostim for active Crohn's disease" N. Engl. J. Med., 2005, 352:2193-2201.
Kostelny et al., "Formation of a bispecific antibody by the use of leucine zippers," J. Immunol., 1992, 148(5):1547-1553.
Kotenko et al., "Human cytomegalovirus harbors its own unique IL-10 homolog (cmvIL-10)," Proc. Natl. Acad. Sci. USA, 97(4):1695-1700, 2000.
Kuhn et al., "Interleukin-10-deficient Mice Develop Chronic Enterocolitis," Cell, 75:263-274, 1993.
Kullberg et al., "Bacteria-triggered CD4+ T Regulatory Cells Suppress Helicobacter hepaticus-induced Colitis," J. Exp. Med., 196:505-515, 2002.
Kulp and Kuehn, "Biological functions and biogenesis of secreted bacterial outer membrane vesicles," Annual Review of Microbiology, 2010, 64:163-184.
Lennard-Jones, "Classification of inflammatory bowel disease," Scand. J. Gastroenterol. Suppl., 1989, 170:2-6.
Leon et al., "Role of IL-10 in Inflammation. Studies Using Cytokine Knockout Mice," Ann. NY Acad. Sci., 856:69-75, 1998.
Li and He, "IL-10 and its related cytokines for treatment of inflammatory bowel disease," World J. Gastroenterol., 2004, 10(5):620-625.
Li et al., "Selection of similar single domain antibodies from two immune VHH libraries obtained from two alpacas by using different selection methods," Immunol. Lett., 2017, 188:89-95.
Lichtenstein et al., "Management of Crohn's disease in adults," Am. J. Gastroenterol., 2009, 104:465-483.
Lin et al., "Identification of Novel Viral Interleukin-10 Isoforms of Human Cytomegalovirus AD169," Virus Res., 131(2):213-223, 2008.
Lindmark et al., "Outer membrane vesicle-mediated release of cytolethal distending toxin (CDT) from Campylobacter jejuni," BMC Microbiology, 2009, 9:220, 10 pages.
Lindsay and Hodgson, "The immunoregulatory cytokine interleukin-10: a therapy for Crohn's disease?" Aliment. Pharmacol. Ther., 2001, 15(11):1709-1716.
Liu et al., "The EBV IL-10 Homologue Is a Selective Agonist With Impaired Binding to the IL-10 Receptor," J. Immunol., 158(2):604-613, 1997.
Lopez et al., "A synthetic peptide homologous to IL-10 functional domain you induce monocyte TGF-β differentiation to tolerogenic dendritic cells," Immunobiology, 216(10):1117-1126, 2011.
Lv et al., "Concise review: the surface markers and identity of human mesenchymal stem cells," Stem Cells, 2014, 32:1408-1419.
Mackay and Mackay, "The role of BAFF in B-cell maturation, T-cell activation and autoimmunity," Trends Immunol., 2002, 23:113-115.
Maini et al., "1161: rHUIL-10 in subjects with active rheumatoid arthritis (RA): a phase I and cytokine response study," Arthritis Rheum., 40(Suppl):S224, 1997.
Maloy and Powrie, "Regulatory T Cells in the Control of Immune Pathology," Nat. Immunol., 2(9):816-822, 2001.
Mary and Modigliani, "Development and validation of an endoscopic index of the severity for Crohn's disease: a prospective multicentre study. Groupe d'Etudes Thérapeutiques des Affections Inflammatoires du Tube Digestif (GETAID)," Gut, 1989, 39:983-989.
Maynard et al., "Diversity in the Contribution of interleukin-10 to T-cell-mediated Immune Regulation," Immunol. Rev., 226:219-233, 2008.
McCafferty et al., "Phage antibodies: filamentous phage displaying antibody variable domains," Nature, 1990, 348:552-554.
McFeters et al., "Acridine orange staining reaction as an index of physiological activity in *Escherichia coli*," J. Microbiol. Methods, 1991, 13:87-97.
McHutchison et al., "A Pilot Study of Daily Subcutaneous interleukin-10 in Patients With Chronic Hepatitis C Infection," J. Interferon. Cytokine Res., 19(11):1265-1270, 1999.
Menassa et al., "Therapeutic effectiveness of orally administered transgenic low-alkaloid tobacco expressing human interleukin-10 in a mouse model of colitis," Plant Biotech. J., 2007, 5(1):50-59.
Milstein and Cuello, "Hybrid hybridomas and their use in immunohistochemistry," Nature, 1983, 305:537-539.
Mohamadzadeh et al., "Regulation of induced colonic inflammation by Lactobacillus acidophilus deficient in lipoteichoic acid," Proc. Natl. Acad. Sci. USA, 108(suppl 1):4623-4630, 2011.

(56) References Cited

OTHER PUBLICATIONS

Mohamed et al., "Intestinal stem cells and stem cell-based therapy for intestinal diseases," Cytotechnology, 2015, 67(2):177-189.
Mohan et al., "Interaction between CD40 and its ligand gp39 in the development of murine lupus nephritis," J. Immunol., 1995, 154:1470-1480.
Montagnoli et al., "B7/CD28-Dependent CD4+CD25+ Regulatory T Cells Are Essential Components of the Memory-Protective Immunity to Candida albicans," J. Immunol., 169:6298-6308, 2002.
Moore et al., "Interleukin-10 and the interleukin-10 Receptor," Annu. Rev. Immunol., 19:683-765, 2001.
Morrison et al., "Chimeric human antibody molecules: mouse antigen-binding domains with human constant region domains," Proc. Natl. Acad. Sci. USA, 1984, 81:6851-6855.
Mosmann, "Properties and Functions of interleukin-10," Adv. Immunol., 56:1-16, 1994.
Mosser and Zhang, "Interleukin-10: New Perspectives on an Old Cytokine," Immunol. Rev., 226:205-218, 2009.
Muller et al., "The serotonin system in autism spectrum disorder: From biomarker to animal models," Neuroscience, 2016, 321:24-41.
Mumm et al., "IL-10 Elicits IFNγ-dependent Tumor Immune Surveillance," Cancer Cell, 20(6):781-796, 2011.
Murray, "The primary mechanism of the IL-10-regulated antiinflammatory response is to selectively inhibit transcription," Proc. Natl. Acad. Sci. USA, 102(24):8686-8691, 2005.
Narula et al., "Novel therapies in inflammatory bowel disease: an evaluation of the evidence," Am. J. Gastroenterol. Suppl., 2016, 3:38-44.
Natsume et al., "Fucose removal from complex-type oligosaccharide enhances the antibody-dependent cellular cytotoxicity of single-gene-encoded bispecific antibody comprising of two single-chain antibodies linked to the antibody constant region," J. Biochem., 2006, 140(3):359-368.
Netea et al., "Toll-Like Receptor 2 Suppresses Immunity against Candida albicans through Induction of IL-10 and Regulatory T Cells," J Immunol., 172:3712-3718, 2004.
Nociari et al., "A novel one-step, highly sensitive fluorometric assay to evaluate cell-mediated cytotoxicity," J. Immunol. Methods, 1998, 213(2):157-167.
Offner et al., "T cell receptor peptide therapy triggers autoregulation of experimental encephalomyelitis," Science, 1991, 251:430-432.
Osman et al., "IT 9302, a synthetic interleukin-10 agonist, diminishes acute lung injury in rabbits with acute necrotizing pancreatitis," Surgery, 124(3):584-92, 1998.
Pajkrt et al., "Attenuation of proinflammatory response by recombinant human IL-10 in human endotoxemia: effect of timing of recombinant human IL-10 administration.," J. Immunol., 158:3971-3977, 1997.
Peppas et al., "Hydrogels as mucoadhesive and bioadhesive materials: a review," Biomaterials, 1996, 17(16):1553-1561.
Pleschberger et al., "Generation of a Functional Monomolecular Protein Lattice Consisting of an S-Layer Fusion Protein Comprising the Variable Domain of a Camel Heavy Chain Antibody," Bioconjugate Chem., 2003, 14(2):440-448.
Poljak, "Production and structure of diabodies," Structure, 1994, 2(12):1121-1123.
Poole et al., "Latency-Associated Viral Interleukin-10 (IL-10) Encoded by Human Cytomegalovirus Modulates Cellular IL-10 and CCL8 Secretion during Latent Infection through Changes in the Cellular MicroRNA hsa-miR-92a," J. Virol., 88(24):13947-13955, 2014.
Redpath et al., "Murine Cytomegalovirus Infection Down-Regulates MHC Class II Expression on Macrophages by Induction of IL-10," J. Immunol., 162:6701-6707, 1999.
Reed et al., "IL-10 mediates susceptibility to Trypanosoma cruzi infection," J. Immunol., 153:3135-3140, 1994.
Regula et al., "Targeting key angiogenic pathways with a bispecific CrossMAb optimized for neovascular eye diseases," EMBO Mol. Med., 2017, 9(7):985.

Reineke et al., "A synthetic mimic of a discontinuous binding site on interleukin-10," Nature BIotech., 17:271-275, 1999.
Reinheimer and Demkow, "Comparison of rapid tests for assessing UHT milk sterility," J. Dairy Res., 1990, 57:239-243.
Reusch et al., "A novel tetravalent bispecific TandAb (CD30/CD16A) efficiently recruits NK cells for the lysis of CD30+ tumor cells," Mabs, 2014, 6(3):728-739.
Roers et al., "T Cell-Specific Inactivation of the Interleukin 10 Gene in Mice Results in Enhanced T Cell Responses but Normal Innate Responses to Lipopolysaccharide or Skin Irritation," J. Exp. Med., 200:1289-1297, 2004.
Roncarolo et al., "Interleukin-10-secreting Type 1 Regulatory T Cells in Rodents and Humans," Immunol. Rev., 212:28-50, 2006.
Rosenblum et al., "Preclinical Safety Evaluation of Recombinant Human Interleukin-10," Regul. Toxicol. Pharmacol., 35:56-71, 2002.
Ross et al., "Estimation of cell survival by flow cytometric quantification of fluorescein diacetate/propidium iodide viable cell number," Cancer Research, 1989, 49:3776-3782.
Roszak and Colwell, "Survival strategies of bacteria in the natural environment," Microbiol. Rev., 1987, 51:365-379.
Ryan et al., "Mast Cell Homeostasis: A Fundamental Aspect of Allergic Disease," Crit. Rev. Immunol., 27:15-32, 2007.
Salamat-Miller et al., "The use of mucoadhesive polymers in buccal drug delivery," Adv. Drug Deliv. Reviews, 2005, 57(11):1666-1691.
Sandborn et al., "Adalimumab induction therapy for Crohn disease previously treated with infliximab: a randomized trial," Ann. Intern. Med., 2007, 146:829-838.
Sandborn et al., "Natalizumab induction and maintenance therapy for Crohn's disease," N. Engl. J. Med., 2005, 353:1912-1925.
Sandler et al., "Development of a Crohn's index for survey research," J. Clin. Epidemiol., 1988, 41:451-458.
Sanz et al., "Antibodies and gene therapy: teaching old 'magic bullets' new tricks," Trends in Immunol., 2004, 25(2):85-91.
Schnitzler et al., "Long-term outcome of treatment with infliximab in 614 patients with Crohn's disease: results from a single-centre cohort," Gut, 2009, 58:492-500.
Schoonooghe et al., "Efficient production of human bivalent and trivalent anti-MUC1 Fab-scFv antibodies in Pichia pastoris," BMC Biotechnol, 2009, 9:70, 14 pages.
Schreiber et al., "Safety and efficacy of recombinant human interleukin 10 in chronic active Crohn's disease," Gastroenterology, 119(6):1461-1472, 2000.
Schwager et al., "Preclinical Characterization of DEKAVIL (F8-IL10), a Novel Clinical-Stage Immunocytokine Which Inhibits the Progression of Collagen-Induced Arthritis," Arthritis Res. Ther., 11(5):R142, 2009.
Sellon et al., "Resident Enteric Bacteria Are Necessary for Development of Spontaneous Colitis and Immune System Activation in interleukin-10-deficient Mice," Infect. Immun., 66:5224-5231, 1998.
Shalaby et al., "Development of humanized bispecific antibodies reactive with cytotoxic lymphocytes and tumor cells overexpressing the HER2 protooncogene," J. Exp. Med., 1992, 175:217-225.
Shand and Forbes, "Potential therapeutic role for cytokine or adhesion molecule manipulation in Crohn's disease: in the shadow of infliximab?" Int. J. Colorectal Disease, 2003, 18(1):1-11.
Shen et al., "Outer membrane vesicles of a human commensal mediate immune regulation and disease protection," Cell Host Microbe., 2012, 12(4):509-520.
Shimizu, "Smart pills for oral drug delivery," Intl. Pharm. Industry, 2014, 6(3):72-74.
Shimokawa et al., "Advanced glycosylation end products in adrenal lipofuscin," J. Gerontol., 1998, 53A:B49-B51.
Simon et al., "Determining target engagement in living systems," Nature Chemical Biology, 9(4):200-205, 2013.
Sjostrom et al., "Membrane vesicle-mediated release of bacterial RNA," Scientific Reports, 2015, 5:15329, 10 pages.
Sokol et al., "Faecalibacterium Prausnitzii Is an Anti-Inflammatory Commensal Bacterium Identified by Gut Microbiota Analysis of Crohn Disease Patients," Proc. Natl. Acad. Sci. USA, 105(43):16731-16736, 2008.
Sokolowska-Wedzina et al., "High-affinity internalizing human scFv-Fc antibody for targeting FGFR1-overexpressing lung cancer," Mol. Cancer Res., 2017, 15(8):1040-1050.

(56) References Cited

OTHER PUBLICATIONS

Steidler et al., "Treatment of Murine Colitis by Lactococcus Lactis Secreting interleukin-10," Science, 289:1352-1355, 2000.
Stijlemans et al., "Efficient Targeting of Conserved Cryptic Epitopes of Infectious Agents by Single Domain Antibodies," J. Biol. Chem., 2004, 279:1256-1261.
Stocks, "Intrabodies: production and promise," Drug Discov. Today, 2004, 9(22):960-966.
Stumhofer et al., "Interleukins 27 and 6 Induce STAT3-mediated T Cell Production of Interleukin 10," Nat. Immunol., 8:1363-1371, 2007.
Suresh et al., "Bispecific monoclonal antibodies from hybrid hybridomas," Methods in Enzymology, 1986, 121:210-288.
Teng and Maya, "Absolute bioavailability and regional absorption of ticagrelor in healthy volunteers," Journal of Drug Assessment, 2014, 3(1):43-50.
Teng et al., "Stable IL-10: a new therapeutic that promotes tumor immunity," Cancer Cell, 20(6):691-693, 2011.
Than et al., "A review of localization systems for robotic endoscopic capsules," IEEE Trans. Biomed. Eng., 2012, 59(9):2387-2399.
Thia et al., "Short CDAI: development and validation of a shortened and simplified Crohn's disease activity index," Inflamm. Bowel Dis., 2011, 17:105-111.
Tiede et al., "Affimer proteins are versatile and renewable affinity reagents," eLife, 2017, 6:e24903, 35 pages.
Tominaga et al., "A water-soluble tetrazolium salt useful for colorimetric cell viability assay," Anal. Commun., 1999, 36:47-50.
Trachsel et al., "Antibody-mediated Delivery of IL-10 Inhibits the Progression of Established Collagen-Induced Arthritis," Arthritis Res. Ther., 9(1):R9, 2007.
Truelove et al., "Cortisone in ulcerative colitis," L.J. Br. Med. J., 1955, 2:1041-1048.
Tsai et al., "CD19×CD3 DART protein mediates human B-cell depletion in vivo in humanized BLT mice," Mol. Ther. Oncolytics, 2016, 3:15024, 9 pages.
Tutt et al., "Trispecific F(ab')3 derivatives that use cooperative signaling via the TCR/CD3 complex and CD2 to activate and redirect resting cytotoxic T cells," J. Immunol., 1991, 147:60-69.
Van Assche et al., "The second European evidence-based Consensus on the diagnosis and management of Crohn's disease: Special situations," J. Crohns Colitis., 2010, 4:63-101.
Van der Schaar et al., "A novel ingestible electronic drug delivery and monitoring device," Gastrointestinal Endoscopy, 2013, 78(3):520-528.
Velayudhan et al., "Demonstration of Functional Similarity of Proposed Biosimilar ABP 501 to Adalimumab," BioDrugs, 2016, 30:339-351.
Visser, "Oxygen requirements of yeasts," Appl. Environ. Microbiol., 1990, 56(12):3785-3792.
Wai et al., "The release of outer membrane vesicles from the strains of enterotoxigenic *Escherichia coli*," Microbiology and Immunology, 1995, 39:451-456.
Walmsley et al., "Interleukin-10 Inhibition of the Progression of Established Collagen-Induced Arthritis," Arthritis Rheum., 39:495-503, 1996.
Walmsley et al., "A simple clinical colitis activity index," Gut, 1998, 43:29-32.
Wheeler et al., "Intrabody and intrakine strategies for molecular therapy," Mol. Ther., 2006, 8(3):355-366.
White et al., "Assessment of neuronal viability with Alamar blue in cortical and granule cell cultures," J. Neurosci., Methods, 1996, 70:195-200.
Wilson et al., "A Critical Role for IL-10 in Limiting Inflammation During Toxoplasmic Encephalitis," J. Neuroimmunol., 165:63-74, 2005.
Wu et al., "Simultaneous Targeting of Multiple Disease Mediators by a Dual-Variable-Domain Immunoglobulin," Nat. Biotechnol., 25(11):1290-1297, 2007.
Yoshida et al., "Immunohistochemical study of human advanced glycation end-products (AGE) and growth factors in cardiac tissues of patients on maintenance dialysis and with kidney transplantation," Clin. Nephrol., 1998, 49:273-280.
Zapata et al., "Engineering linear F(ab')2 fragments for efficient production in *Escherichia coli* and enhanced antiproliferative activity," Protein Eng., 1995, 8(10):1057-1062.
Zhi-Jun et al., "A dye-based lymphocyte proliferation assay that permits multiple immunological analyses: mRNA, cytogenetic, apoptosis, and immunophenotyping studies," J. Immunol. Methods, 1997, 210:25-39.
Chen et al., "Developing assessment system for wireless capsule endoscopy videos based on event detection," Proc. SPIE, Mar. 2009, 7260(72601G):11 pages.
Lee et al., "Automatic classification of digestive organs in wireless capsule endoscopy videos," Proceedings of the 2007 ACM symposium on Applied computing, Mar. 2007, 1041-1045.
Muheem, Abdul, et al. "A review on the strategies for oral delivery of proteins and peptides and their clinical perspectives." Saudi Pharmaceutical Journal 24.4 (2016): 413-428.
Keohane, Kieran, et al. "Enhanced colonic delivery of ciclosporin A self-emulsifying drug delivery system encapsulated in coated minispheres." Drug Development and Industrial Pharmacy 42.2 (2016): 245-253.
Atreya, Raja, et al. "In vivo imaging using fluorescent antibodies to tumor necrosis factor predicts therapeutic response in Crohn's disease." Nature medicine 20.3 (2014): 313-318.
Maroni, Alessandra, et al. "Enteric coatings for colonic drug delivery: state of the art." Expert opinion on drug delivery 14.9 (2017): 1027-1029.
Zhang, Sufeng, Robert Langer, and Giovanni Traverse. "Nanoparticulate drug delivery systems targeting inflammation for treatment of inflammatory bowel disease." Nano Today 16 (2017): 82-96.
Munoz, Fredy, Gursel Alici, and Weihua Li. "A review of drug delivery systems for capsule endoscopy." Advanced drug delivery reviews 71 (2014): 77-85.
Steiger, Christoph, et al. "Ingestible electronics for diagnostics and therapy." Nature Reviews Materials 4.2 (2019): 83-98.
Crowe, S., et al. "Gastrointestinal Stability and Tissue Penetration of V565: a Novel Orally Administered Anti-TNF-alpha VorabodyTM." PEGS Europe Protein and Antibody Engineering Summit (Nov. 13-17, 2017)(Poster I) (2017).
Mattheakis, Larry, et al. "P-126 PTG-100, An Oral Peptide Antagonist of Integrin [alpha] 4 [beta] 7 that Alters Trafficking of Gut Homing T Cells in Preclinical Animal Models." Inflammatory Bowel Diseases 22 (2016): S48.

\* cited by examiner

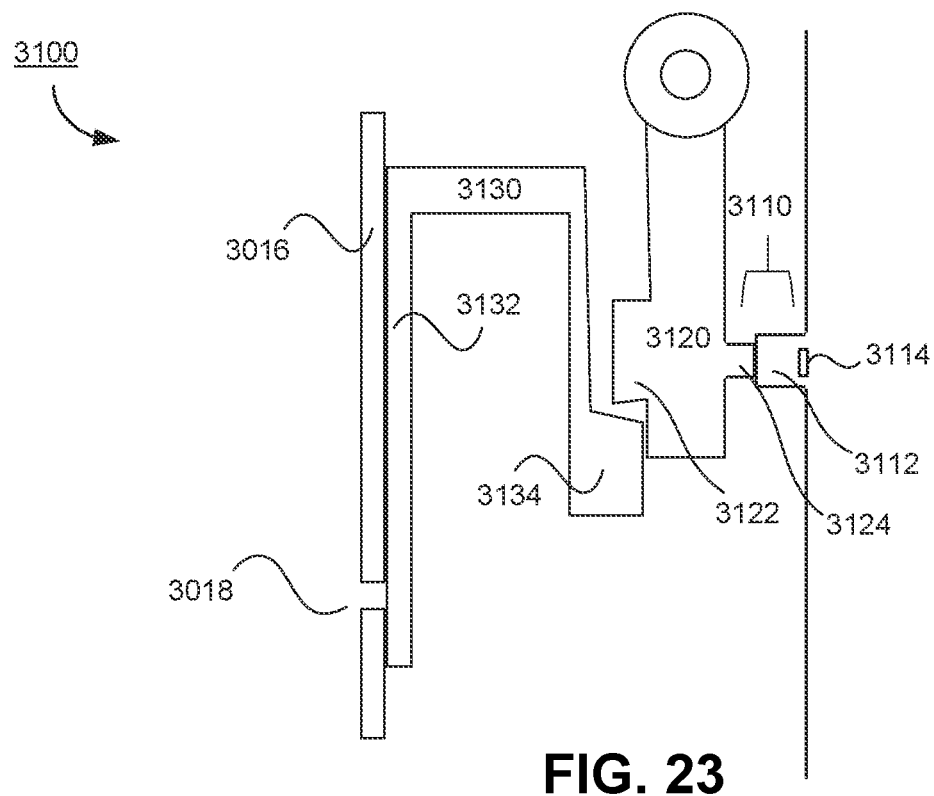
FIG. 23
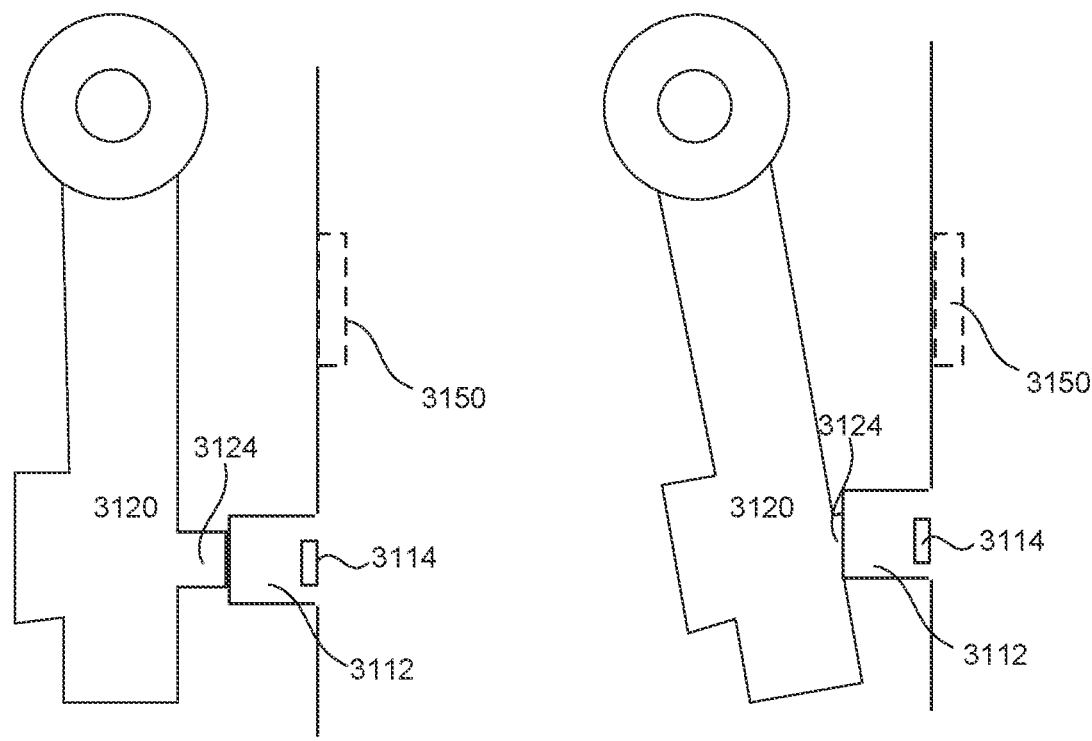
FIG. 24A  FIG. 24B

| Time | SQ Adalimumab Plasma concentration µgs/ml | Topical Adalimumab Plasma concentration µgs/ml |
|---|---|---|
| 6hrs | 16 +/-8 | 0.01 |
| 12hrs | 13 +/-4 | 0.01 |
| 24hrs | 13 +/-3 | 0.01 |
| 48hrs | 16 +/-5 | 0.01 |

FIG. 52

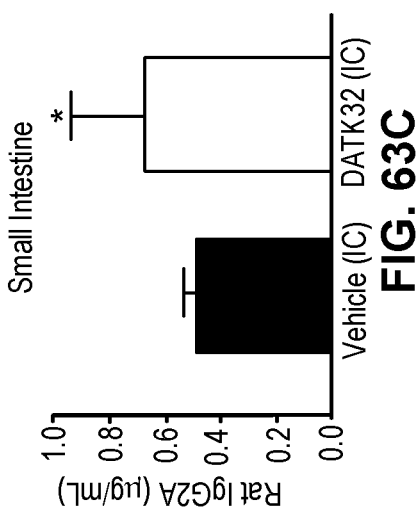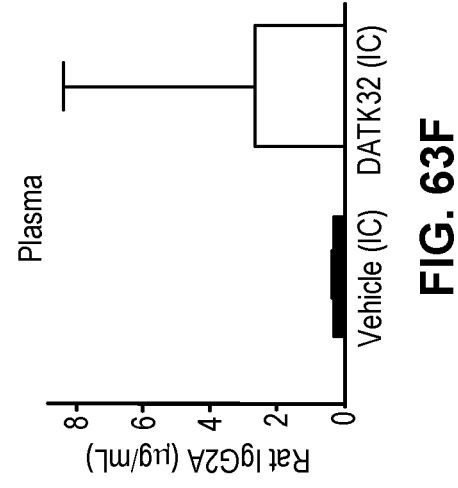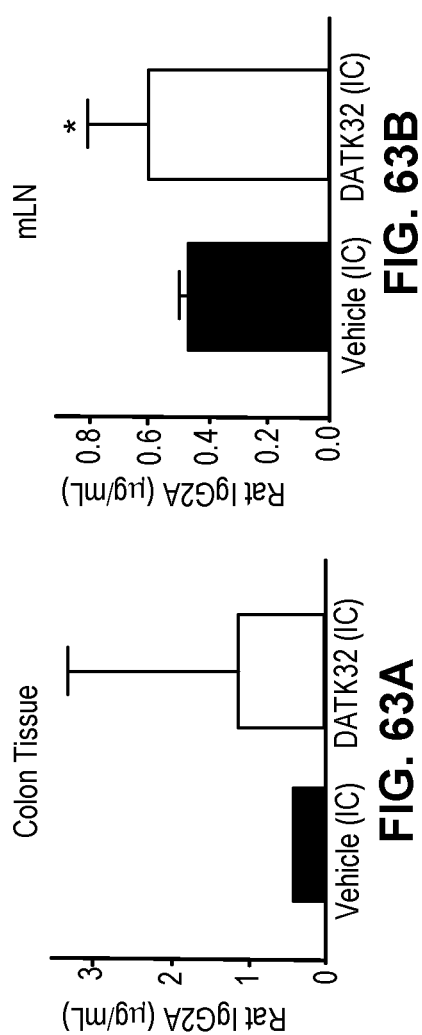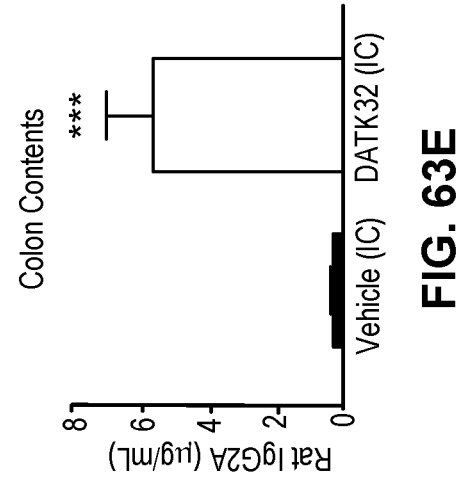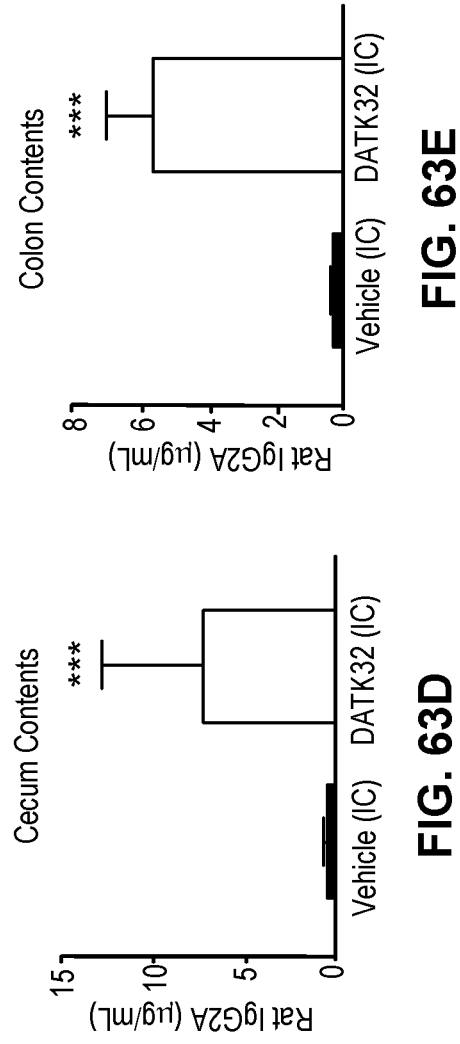

| Route | PO | IC | IC | IC |
|---|---|---|---|---|
| Dose (mg.kg) | 0.09 | 0.02 | 0.04 | 0.09 |
| Tmax | 1 | 1 | 1 | 1 |
| Cmax | 3.531 ± 3.84 | 2.39 ± 0.565 | 9.197 ± 3.30 | 21.8 ± 4.73 |
| Trough (12hr) | 0.568 ± 0.291 | 0.746 ± 0.038 | 1.96 ± 0.491 | 4.35 ± 0.516 |
| AUC 0-12hr (ng*h/ml) | 16.83 ± 3.641 | 15.29 ± 2.356 | 51.35 ± 4.04 | 129.6 ± 7.827 |

Quantitative histological grading of colitis.

| Feature graded | Grade | Description |
|---|---|---|
| Inflammation | 0 | None |
| | 1 | Slight |
| | 2 | Moderate |
| | 3 | Severe |
| Extent | 0 | None |
| | 1 | Mucosa |
| | 2 | Mucosa and submucosa |
| | 3 | Transmural |
| Regeneration | 0 | Complete regeneration or normal tissue |
| | 1 | Almost complete regeneration |
| | 2 | Regeneration with crypt depletion |
| | 3 | Surface epithelium not intact |
| | 4 | No tissue repair |
| Crypt damage | 0 | None |
| | 1 | Basal 1/3 damaged |
| | 2 | Basal 2/3 damaged |
| | 3 | Only surface epithelium intact |
| | 4 | Entire crypt and epithelium lost |
| Percent involvement | 1 | 1-25% |
| | 2 | 26-50% |
| | 3 | 51-75% |
| | 4 | 76-100% |

FIG. 93

SEQUENCE LISTING

<160> NUMBER OF SEQ ID NOS: 16

<210> SEQ ID NO 1
<211> LENGTH: 178
<212> TYPE: PRT
<213> ORGANISM: Homo sapiens

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 2
<211> LENGTH: 160
<212> TYPE: PRT
<213> ORGANISM: Homo sapiens

<400> SEQUENCE: 2

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

```
Ile Phe Ile Asn Tyr Ile Glu Ala Tyr Met Thr Met Lys Ile Arg Asn
145                 150                 155                 160
```

<210> SEQ ID NO 3
<211> LENGTH: 1629
<212> TYPE: DNA
<213> ORGANISM: Homo sapiens

<400> SEQUENCE: 3

```
acacatcagg ggcttgctct tgcaaaacca aaccacaaga cagacttgca aaagaaggca    60
tgcacagctc agcactgctc tgttgcctgg tcctcctgac tggggtgagg ccagcccag   120
gccagggcac ccagtctgag aacagctgca cccacttccc aggcaacctg cctaacatgc   180
ttcgagatct ccgagatgcc ttcagcagag tgaagacttt ctttcaaatg aaggatcagc   240
tggacaactt gttgttaaag gagtccttgc tggaggactt aagggttac ctgggttgcc    300
aagccttgtc tgagatgatc cagtttacc tggaggaggt gatgcccaa gctgagaacc     360
aagacccaga catcaaggcg catgtgaact ccctggggga gaacctgaag accctcaggc   420
tgaggctacg gcgctgtcat cgatttcttc cctgtgaaaa caagagcaag gccgtggagc   480
aggtgaagaa tgcctttaat aagctccaag agaaaggcat ctacaaagcc atgagtgagt   540
ttgacatctt catcaactac atagaagcct acatgacaat gaagatacga actgagaca    600
tcagggtggc gactctatag actctaggac ataaattaga ggtctccaaa atcggatctg   660
gggctctggg atagctgacc cagccccttg agaaacctta ttgtacctct cttatagaat   720
atttattacc tctgatacct caacccccat ttctatttat ttactgagct tctctgtgaa   780
cgatttagaa agaagcccaa tattataatt tttttcaata tttattattt tcacctgttt   840
ttaagctgtt tccatagggt gacacactat ggtatttgag tgttttaaga taaattataa   900
gttacataag ggaggaaaaa aaatgttctt tggggagcca acagaagctt ccattccaag   960
cctgaccacg ctttctagct gttgagctgt tttccctgac ctccctctaa tttatcttgt  1020
ctctgggctt ggggcttcct aactgctaca aatactctta ggaagagaaa ccagggagcc  1080
cctttgatga ttaattcacc ttccagtgtc tcggagggat tccctaacc tcattcccca    1140
accacttcat tcttgaaagc tgtggccagc ttgttattta taacaaccta aatttggttc   1200
taggccgggc gcggtggctc acgcctgtaa tcccagcact tgggaggct gaggcgggtg    1260
gatcacttga ggtcaggagt tcctaaccag cctggtcaac atggtgaaac ccgtctcta   1320
ctaaaaatac aaaaattagc cgggcatggt ggcgcgcacc tgtaatccca gctacttggg  1380
aggctgaggc aagagaattg cttgaaccca ggagatggaa gttgcagtga gctgatatca  1440
tgccctgta ctccagcctg ggtgacagag caagactctg tctcaaaaaa taaaaataaa    1500
aataaattg gttctaatag aactcagttt taactagaat ttattcaatt cctctgggaa    1560
tgttacattg tttgtctgtc ttcatagcag attttaattt tgaataaata aatgtatctt   1620
attcacatc                                                          1629
```

<210> SEQ ID NO 4
<211> LENGTH: 178
<212> TYPE: PRT
<213> ORGANISM: Mus musculus

<400> SEQUENCE: 4

```
Met Pro Gly Ser Ala Leu Leu Cys Cys Leu Leu Leu Leu Thr Gly Met
1               5                   10                  15
```

Arg Ile Ser Arg Gly Gln Tyr Ser Arg Glu Asp Asn Asn Cys Thr His
        20                  25                  30

Phe Pro Val Gly Gln Ser His Met Leu Leu Glu Leu Arg Thr Ala Phe
    35                  40                  45

Ser Gln Val Lys Thr Phe Phe Gln Thr Lys Asp Gln Leu Asp Asn Ile
50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser

<210> SEQ ID NO 5
<211> LENGTH: 1306
<212> TYPE: DNA
<213> ORGANISM: Mus musculus

<400> SEQUENCE: 5

```
acatttagag acttgctctt gcactaccaa agccacaagg cagccttgca gaaaagagag    60
ctccatcatg cctggctcag cactgctatg ctgcctgctc ttactgactg catgaggat    120
cagcaggggc cagtacagcc gggaagacaa taactgcacc cacttcccag tcggccagag    180
ccacatgctc ctagagctgc ggactgcctt cagccaggtg aagactttct ttcaaacaaa    240
ggaccagctg gacaacatac tgctaaccga ctccttaatg caggacttta agggttactt    300
gggttgccaa gccttatcgg aaatgatcca gttttacctg gtagaagtga tgccccaggc    360
agagaagcat ggcccagaaa tcaaggagca tttgaattcc ctgggtgaga agctgaagac    420
cctcaggatg cggctgaggc gctgtcatcg atttctcccc tgtgaaaata gagcaaggc    480
agtggagcag gtgaagagtg attttaataa gctccaagac caaggtgtct acaaggccat    540
gaatgaattt gacatcttca tcaactgcat agaagcatac atgatgatca aatgaaaag    600
ctaaaacacc tgcagtgtgt attgagtctg ctggactcca ggacctagac agagctctct    660
aaatctgatc cagggatctt agctaacgga aacaactcct tggaaaacct cgtttgtacc    720
tctctccgaa atatttatta cctctgtac ctcagttccc attctatta ttcactgagc    780
ttctctgtga actatttaga aagaagccca atattataat tttacagtat ttattatttt    840
taacctgtgt ttaagctgtt tccattgggg acactttata gtatttaaag ggagattata    900
ttatatgatg ggagggttc ttccttggga agcaattgaa gcttctattc taaggctggc    960
cacacttgag agctgcaggg cccttttgcta tggtgtcctt tcaattgctc tcatccctga   1020
gttcagagct cctaagagag ttgtgaagaa actcatgggt cttgggaaga gaaaccaggg   1080
agatcctttg atgatcattc ctgcagcagc tcagagggtt cccctactgt catccccag    1140
ccgcttcatc cctgaaaact gtggccagtt tgttatttat aaccacctaa aattagttct   1200
```

```
aatagaactc attttttaact agaagtaatg caattcctct gggaatggtg tattgtttgt    1260
ctgcctttgt agcagactct aattttgaat aaatggatct tattcg                    1306

<210> SEQ ID NO 6
<211> LENGTH: 178
<212> TYPE: PRT
<213> ORGANISM: Rattus norvegicus

<400> SEQUENCE: 6

Met Pro Gly Ser Ala Leu Leu Cys Cys Leu Leu Leu Leu Ala Gly Val
1               5                   10                  15

Lys Thr Ser Lys Gly His Ser Ile Arg Gly Asp Asn Asn Cys Thr His
            20                  25                  30

Phe Pro Val Ser Gln Thr His Met Leu Arg Glu Leu Arg Ala Ala Phe
        35                  40                  45

Ser Gln Val Lys Thr Phe Phe Gln Lys Asp Gln Leu Asp Asn Ile
    50                  55                  60

Leu Leu Thr Asp Ser Leu Leu Gln Asp Phe Lys Gly Tyr Leu Gly Cys
65              70                  75                  80

Gln Ala Leu Ser Glu Met Ile Lys Phe Tyr Leu Val Glu Val Met Pro
                85                  90                  95

Gln Ala Glu Asn His Gly Pro Glu Ile Lys Glu His Leu Asn Ser Leu
            100                 105                 110

Gly Glu Lys Leu Lys Thr Leu Trp Ile Gln Leu Arg Arg Cys His Arg
        115                 120                 125

Phe Leu Pro Cys Glu Asn Lys Ser Lys Ala Val Glu Gln Val Lys Asn
    130                 135                 140

Asp Phe Asn Lys Leu Gln Asp Lys Gly Val Tyr Lys Ala Met Asn Glu
145                 150                 155                 160

Phe Asp Ile Phe Ile Asn Cys Ile Glu Ala Tyr Val Thr Leu Lys Met
                165                 170                 175

Lys Asn

<210> SEQ ID NO 7
<211> LENGTH: 682
<212> TYPE: DNA
<213> ORGANISM: Rattus norvegicus

<400> SEQUENCE: 7
catgcctggc tcagcactgc tatgttgcct gctcttactg gctggagtga agaccagcaa     60
aggccattcc atccggggtg acaataactg cacccacttc ccagtcagcc agacccacat    120
gctccgagag ctgagggctg ccttcagtca agtgaagact tcctttcaaa agaaggacca    180
gctggacaac atactgctga cagattcctt actgcaggac tttaagggtt acttgggttg    240
ccaagccttg tcagaaatga tcaagtttta cctggtagaa gtgatgcccc aggcagagaa    300
ccatggccca gaaatcaagg agcatttgaa ttccctggga gagaagctga gaccctctg    360 gatacagctg cgacgctgtc atcgatttct cccctgtgag aataaaagca aggcagtgga    420
gcaggtgaag aatgatttta ataagctcca agacaaaggt gtctacaagg ccatgaatga    480
gtttgacatc ttcatcaact gcatagaagc ctacgtgaca ctcaaaatga aaaattgaac    540
cacccggcat ctactggact gcaggacata aatagagctt ctaaatctga tccagagatc    600
ttagctaacg ggagcaactc cttggaaaac ctcgtttgta cctctctcca aaatatttat    660
tacctctgat acctcagttc cc                                              682
```

<210> SEQ ID NO 8
<211> LENGTH: 178
<212> TYPE: PRT
<213> ORGANISM: Oryctolagus cuniculus

<400> SEQUENCE: 8

```
Met Leu Ser Ser Ala Leu Leu Cys Cys Leu Val Phe Leu Gly Gly Thr
1               5                   10                  15
Gly Ala Ser Arg Gly Gln Asp Thr Pro Ala Glu Asn Ser Cys Ile His
            20                  25                  30
Phe Pro Gly Gly Leu Pro His Met Leu Arg Glu Leu Arg Ala Ala Phe
        35                  40                  45
Gly Arg Val Lys Thr Phe Phe Gln Ser Lys Asp Gln Leu Asn Ser Met
    50                  55                  60
Leu Leu Thr Glu Ser Leu Leu Glu Asp Leu Lys Gly Tyr Leu Gly Cys
65                  70                  75                  80
Gln Ala Leu Ser Glu Met Ile Gln Phe Tyr Leu Lys Asp Val Met Pro
                85                  90                  95
Gln Ala Glu Asn His Ser Pro Ala Ile Arg Glu His Val Asn Ser Leu
            100                 105                 110
Gly Glu Asn Leu Lys Thr Leu Arg Leu Arg Leu Arg Gln Cys His Arg
        115                 120                 125
Phe Leu Pro Cys Glu Asn Lys Ser Lys Ala Val Glu Gln Val Lys Ser
    130                 135                 140
Ala Phe Ser Lys Leu Gln Glu Glu Gly Val Tyr Lys Ala Met Ser Glu
145                 150                 155                 160
Phe Asp Ile Phe Ile Asn Tyr Ile Glu Thr Tyr Met Thr Met Lys Ile
                165                 170                 175
Lys Ser
```

<210> SEQ ID NO 9
<211> LENGTH: 1089
<212> TYPE: DNA
<213> ORGANISM: Oryctolagus cuniculus

<400> SEQUENCE: 9

| | | | | | |
|---|---|---|---|---|---|
| aaagcaaacc | acaaggcgga | ctcgtagaag | caggcagagt | tccaccatgc | tcagctcagc | 60 |
| tctgctatgt | tgcctggtct | tcctgggtgg | gacaggggcc | agccgaggcc | aggacacccc | 120 |
| tgctgagaac | agctgcattc | actttccagg | cggcctgccc | cacatgctcc | gcgagctccg | 180 |
| tgctgccttt | ggcagggtga | agactttctt | tcaatcgaag | gatcagctga | acagcatgtt | 240 |
| gttaaccgag | tccctgctgg | aggaccttaa | gggttacctg | ggatgccaag | ccttgtcgga | 300 |
| gatgatccag | ttttacctga | aggacgtgat | gccgcaagct | gagaaccaca | gtccagccat | 360 |
| cagggagcac | gtgaactccc | tgggggaaaa | cctgaagacc | ctcaggctga | ggctgcgaca | 420 |
| atgtcaccga | tttctcccct | gtgaaaacaa | gagcaaggca | gtggagcagg | tgaagagcgc | 480 |
| cttcagcaag | ctgcaagagg | aaggcgtcta | caaagccatg | agtgagtttg | acatcttcat | 540 |
| caactacata | gaaacctaca | tgacaatgaa | gataaaaagc | taaaagcccc | aggatggcaa | 600 |
| ctcggctaga | gtctaggaca | tcagttaggg | acctgcacac | cctgggtcag | ctgacccagc | 660 |
| accttggaaa | gctgttgtac | ctctcaatat | ttattacctc | tgatacctca | gctcccgatc | 720 |
| ctatttattt | accgagcttc | tctgtgaact | ctttagaaag | aagcccacta | ttataatttt | 780 |
| ttcagtattt | attattttca | cctgcattta | agctgtaccc | atggggtgat | gccctgtggg | 840 |

```
atttgagtgt cttaggagaa attataattt atgtgaaagg gaaaatgtgc cttggggagc    900
cgactgaggc ttccattcct tctgtgcctg accacacttt ctaactccta agccgagctc    960
cctcttaccc tctggagccc ggacctgggt ctcgagtgtt ccagagactc ctagcctctt   1020
aggaagagag accggaagcc cttgggtggt gaccttccgg cagctcagag ggaggctcct   1080
gacctcgat                                                           1089
```

<210> SEQ ID NO 10
<211> LENGTH: 178
<212> TYPE: PRT
<213> ORGANISM: Macaca mulatta

<400> SEQUENCE: 10

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr Arg
            20                  25                  30

Phe Pro Gly Asn Leu Pro His Met Leu Arg Asp Leu Arg Asp Ala Phe
        35                  40                  45

Ser Arg Val Lys Thr Phe Phe Gln Met Lys Asp Gln Leu Asp Asn Ile
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn His Asp Pro Asp Ile Lys Glu His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Ser Lys Leu Gln Glu Lys Gly Val Tyr Lys Ala Met Ser Glu
145                 150                 155                 160

Phe Asp Ile Phe Ile Asn Tyr Ile Glu Ala Tyr Met Thr Met Lys Ile
                165                 170                 175

Gln Asn
```

<210> SEQ ID NO 11
<211> LENGTH: 643
<212> TYPE: DNA
<213> ORGANISM: Macaca mulatta

<400> SEQUENCE: 11

```
agaaggcatg cacagctcag cactgctctg ttgcctagtc ctcctgactg gggtgagggc     60
cagcccaggc cagggcaccc agtctgagaa cagctgcacc cgcttcccag caacctgcc    120
tcacatgctt cgagacctcc gagatgcctt cagcagagtg aagactttct ttcaaatgaa   180
ggatcagctg gacaacatat tgttaaagga gtccttgctg gaggacttta agggttacct   240
gggttgccaa gccttgtctg agatgatcca gttttacctg gaggaggtga tgccccaagc   300
tgagaaccac gacccagaca tcaaggagca tgtgaactcc ctgggggaga atctgaagac   360
cctcaggctg aggctgcggc gctgtcatcg atttcttccc tgtgaaaaca gagcaaggc   420
cgtggagcag gtgaagaatg cctttagtaa gctccaagag aaaggcgtct acaaagccat   480
gagtgagttt gacatcttca tcaactacat agaagcctac atgacaatga agatacaaaa   540
```

```
ctgagacatc agggtggcga ctctatagac tctaggacat aaattagagg tctccaaaat    600
cagatccagg gttctgggat agctgaccca gccccttgag aaa                     643
```

<210> SEQ ID NO 12
<211> LENGTH: 578
<212> TYPE: PRT
<213> ORGANISM: Homo sapiens

<400> SEQUENCE: 12

```
Met Leu Pro Cys Leu Val Val Leu Ala Leu Leu Ser Leu Arg
1               5                   10                  15

Leu Gly Ser Asp Ala His Gly Thr Glu Leu Pro Ser Pro Ser Val
                20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
        50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Ser Val Leu Leu Phe
            260                 265                 270

Lys Lys Pro Ser Pro Phe Ile Phe Ile Ser Gln Arg Pro Ser Pro Glu
        275                 280                 285

Thr Gln Asp Thr Ile His Pro Leu Asp Glu Glu Ala Phe Leu Lys Val
    290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Arg Glu
            340                 345                 350
```

Pro Pro Val Leu Gly Asp Ser Cys Ser Ser Gly Ser Ser Asn Ser Thr
            355                 360                 365

Asp Ser Gly Ile Cys Leu Gln Glu Pro Ser Leu Ser Pro Ser Thr Gly
370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Glu Pro Glu Val
            420                 425                 430

Pro Gly Glu Glu Asp Pro Ala Ala Val Ala Phe Gln Gly Tyr Leu Arg
            435                 440                 445

Gln Thr Arg Cys Ala Glu Glu Lys Ala Thr Lys Thr Gly Cys Leu Glu
            450                 455                 460

Glu Glu Ser Pro Leu Thr Asp Gly Leu Gly Pro Lys Phe Gly Arg Cys
465                 470                 475                 480

Leu Val Asp Glu Ala Gly Leu His Pro Pro Ala Leu Ala Lys Gly Tyr
                485                 490                 495

Leu Lys Gln Asp Pro Leu Glu Met Thr Leu Ala Ser Ser Gly Ala Pro
            500                 505                 510

Thr Gly Gln Trp Asn Gln Pro Thr Glu Glu Trp Ser Leu Leu Ala Leu
            515                 520                 525

Ser Ser Cys Ser Asp Leu Gly Ile Ser Asp Trp Ser Phe Ala His Asp
            530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 13
<211> LENGTH: 3672
<212> TYPE: DNA
<213> ORGANISM: Homo sapiens

<400> SEQUENCE: 13

```
gtcagtccca gcccaagggt agctggaggc gcgcaggccg gctccgctcc ggccccggac     60
gatgcggcgc gcccaggatg ctgccgtgcc tcgtagtgct gctggcggcg ctcctcagcc    120
tccgtcttgg ctcagacgct catgggacag agctgcccag ccctccgtct gtgtggtttg    180
aagcagaatt tttccaccac atcctccact ggacacccat cccaaatcag tctgaaagta    240
cctgctatga agtggcgctc tgaggtatg aatagagtc ctggaactcc atctccaact    300
gtagccagac cctgtcctat gaccttaccg cagtgacctt ggacctgtac cacagcaatg    360
gctaccgggc cagagtgcgg gctgtggacg gcagccggca ctccaactgg accgtcacca    420
acaccgcctt ctctgtggat gaagtgactc tgacagttgg cagtgtgaac ctagagatcc    480
acaatggctt catcctcggg aagattcagc tacccaggcc caagatggcc cccgcaaatg    540
acacatatga agcatcttc agtcacttcc gagagtatga gattgccatt cgcaaggtgc    600
cgggaaactt cacgttcaca cacaagaaag taaacatga aacttcagc ctcctaacct    660
ctggagaagt gggagagttc tgtgtccagg tgaaaccatc tgtcgcttcc cgaagtaaca    720
aggggatgtg gtctaaagag gagtgcatct ccctcaccag gcagtatttc accgtgacca    780
acgtcatcat cttctttgcc tttgtcctgc tgctctccgg agccctcgcc tactgcctgg    840
```

```
ccctccagct gtatgtgcgg cgccgaaaga agctacccag tgtcctgctc ttcaagaagc      900
ccagccccct catcttcatc agccagcgtc cctccccaga gacccaagac accatccacc      960
cgcttgatga ggaggccttt ttgaaggtgt ccccagagct gaagaacttg gacctgcacg     1020
gcagcacaga cagtggcttt ggcagcacca agccatccct gcagactgaa gagcccagt     1080
tcctcctccc tgaccctcac ccccaggctg acagaacgct gggaaacagg gagcccctg     1140
tgctggggga cagctgcagt agtggcagca gcaatagcac agacagcggg atctgcctgc     1200
aggagcccag cctgagcccc agcacagggc ccacctggga gcaacaggtg gggagcaaca     1260
gcaggggcca ggatgacagt ggcattgact tagttcaaaa ctctgagggc cgggctgggg     1320
acacacaggg tggctcggcc ttgggccacc acagtccccc ggagcctgag gtgcctgggg     1380
aagaagaccc agctgctgtg gcattccagg gttacctgag gcagaccaga tgtgctgaag     1440
agaaggcaac caagacaggc tgcctggagg aagaatcgcc cttgacagat ggccttggcc     1500
ccaaattcgg gagatgcctg gttgatgagg caggcttgca tccaccagcc ctggccaagg     1560
gctatttgaa acaggatcct ctagaaatga ctctggcttc ctcaggggcc caacgggac      1620
agtggaacca gcccactgag gaatggtcac tcctggcctt gagcagctgc agtgacctgg     1680
gaatatctga ctggagcttt gcccatgacc ttgcccctct aggctgtgtg gcagcccag      1740
gtggtctcct gggcagcttt aactcagacc tggtcaccct gccccctcatc tctagcctgc    1800
agtcaagtga gtgactcggg ctgagaggct gcttttgatt ttagccatgc ctgctcctct     1860
gcctggacca ggaggagggc ccctggggca gaagttaggc acgaggcagt ctgggcactt     1920
ttctgcaagt ccactggggc tggccccagc caggccctgc agggctggtc agggtgtctg     1980
gggcaggagg aggccaactc actgaactag tgcagggtat gtgggtggca ctgacctgtt     2040
ctgttgactg gggccctgca gactctggca gagctgagaa gggcagggac cttctcccct     2100
ctaggaactc tttcctgtat cataaaggat tatttgctca ggggaaccat ggggctttct     2160
ggagttgtgg tgaggccacc aggctgaagt cagctcagac ccagacctcc ctgcttaggc     2220
cactcgagca tcagagcttc cagcaggagg aagggctgta ggaatggaag cttcagggcc     2280
ttgctgctgg ggtcattttt aggggaaaaa ggaggatatg atggtcacat ggggaacctc     2340
ccctcatcgg gcctctgggg caggaagctt gtcactggaa gatcttaagg tatatatttt     2400
ctggacactc aaacacatca taatggattc actgagggga gacaaaggga gccgagaccc     2460
tggatggggc ttccagctca gaacccatcc ctctggtggg tacctctggc acccatctgc     2520
aaatatctcc ctctctccaa caaatggagt agcatccccc tggggcactt gctgaggcca     2580
agccactcac atcctcactt tgctgcccca ccatcttgct gacaacttcc agagaagcca     2640
tggttttttg tattggtcat aactcagccc tttgggcggc ctctgggctt gggcaccagc     2700
tcatgccagc cccagagggt cagggttgga ggcctgtgct tgtgtttgct gctaatgtcc     2760
agctacagac ccagaggata agccactggg cactgggctg gggtccctgc cttgttggtg     2820
ttcagctgtg tgattttgga ctagccactt gtcagagggc ctcaatctcc catctgtgaa     2880
ataaggactc cacctttagg ggaccctcca tgtttgctgg gtattagcca agctggtcct     2940
gggagaatgc agatactgtc cgtggactac caagctggct tgtttcttat gccagaggct     3000
aacagatcca atgggagtcc atggtgtcat gccaagacag tatcagacac agccccagaa     3060
gggggcatta tgggccctgc ctccccatag gccatttgga ctctgccttc aaacaaaggc     3120
agttcagtcc acaggcatgg aagctgtgag gggacaggcc tgtgcgtgcc atccagagtc     3180
```

```
atctcagccc tgcctttctc tggagcattc tgaaaacaga tattctggcc cagggaatcc      3240
agccatgacc cccaccccctc tgccaaagta ctcttaggtg ccagtctggt aactgaactc     3300
cctctggagg caggcttgag ggaggattcc tcagggttcc cttgaaagct ttatttattt      3360
attttgttca tttatttatt ggagaggcag cattgcacag tgaaagaatt ctggatatct     3420
caggagcccc gaaattctag ctctgacttt gctgtttcca gtggtatgac cttggagaag     3480
tcacttatcc tcttggagcc tcagtttcct catctgcaga ataatgactg acttgtctaa     3540
ttcgtaggga tgtgaggttc tgctgaggaa atgggtatga atgtgccttg aacacaaagc    3600
tctgtcaata agtgatacat gttttttatt ccaataaatt gtcaagacca caggaaaaaa     3660
aaaaaaaaaa aa                                                          3672

<210> SEQ ID NO 14
<211> LENGTH: 3802
<212> TYPE: DNA
<213> ORGANISM: Homo sapiens

<400> SEQUENCE: 14
gtcagtccca gcccaagggt agctggaggc gcgcaggccg gctccgctcc ggccccggac       60
gatgcggcgc gcccaggatg ctgccgtgcc tcgtagtgct gctggcggcg ctcctcagcc      120
tccgtcttgg ctcagacgct catggctcac ctgttgtgga agtggaagag gctgaaattg      180
acaggaactg acggattggg aaggatagag aagtatgcgc aaggccaaac ccccaacccg      240
caaacctcat catccaccca cttctagatg agccggacag agctgcccag ccctccgtct      300
gtgtggtttg aagcagaatt ttccaccac atcctccact ggacaccat cccaaatcag      360 tctgaaagta cctgctatga agtggcgctc ctgaggtatg aatagagtc ctggaactcc      420 atctccaact gtagccagac cctgtcctat gaccttaccg cagtgacctt ggacctgtac     480
cacagcaatg ctaccgggc cagagtgcgg gctgtggacg cagccggca ctccaactgg      540 accgtcacca cacccgctt ctctgtggat gaagtgactc tgacagttgg cagtgtgaac    600
ctagagatcc acaatggctt catcctcggg aagattcagc tacccaggcc caagatggcc    660
cccgcaaatg acacatatga aagcatcttc agtcacttcc gagagtatga gattgccatt    720
cgcaaggtgc cgggaaactt cacgttcaca cacaagaaag taaaacatga aaacttcagc    780 ctcctaaccct ctggagaagt gggagagttc tgtgtccagg tgaaaccatc tgtcgcttcc    840
cgaagtaaca aggggatgtg gtctaaagag gagtgcatct ccctcaccag gcagtatttc     900
accgtgacca acgtcatcat cttcttttgcc tttgtcctgc tgctctccgg agccctcgcc   960
tactgcctgg ccctccagct gtatgtgcgg cgccgaaaga agctacccag tgtcctgctc   1020
ttcaagaagc ccagcccctt catcttcatc agccagcgtc cctccccaga gacccaagac   1080
accatccacc gcttgatga ggaggccttt ttgaaggtgt cccagagct gaagaacttg    1140 gacctgcacg gcagcacaga cagtggcttt ggcagcacca gccatccct gcagactgaa   1200 gagccccagt tcctcctccc tgaccctcac ccccaggctg acagaacgct gggaaacagg   1260
gagccccctg tgctggggga cagctgcagt agtggcagca gcaatagcac agacagcggg   1320
atctgcctgc aggagcccag cctgagcccc agcacagggc ccaccctggga gcaacaggtg   1380 gggagcaaca gcaggggcca ggatgacagt ggcattgact tagttcaaaa ctctgagggc    1440
cgggctgggg acacacaggg tggctcggcc ttgggccacc acagtccccc ggagcctgag   1500
gtgcctgggg aagaagaccc agctgctgtg gcattccagg gttacctgag gcagaccaga    1560
tgtgctgaag agaaggcaac caagacaggc tgcctggagg aagaatcgcc cttgacagat   1620
```

| | |
|---|---:|
| ggccttggcc ccaaattcgg gagatgcctg gttgatgagg caggcttgca tccaccagcc | 1680 |
| ctggccaagg gctatttgaa acaggatcct ctagaaatga ctctggcttc ctcaggggcc | 1740 |
| ccaacgggac agtggaacca gcccactgag gaatggtcac tcctggcctt gagcagctgc | 1800 |
| agtgacctgg gaatatctga ctggagcttt gcccatgacc ttgcccctct aggctgtgtg | 1860 |
| gcagccccag gtggtctcct gggcagcttt aactcagacc tggtcaccct gcccctcatc | 1920 |
| tctagcctgc agtcaagtga gtgactcggg ctgagaggct gcttttgatt ttagccatgc | 1980 |
| ctgctcctct gcctggacca ggaggagggc ccctgggca gaagttaggc acgaggcagt | 2040 |
| ctgggcactt ttctgcaagt ccactgggc tggccccagc caggccctgc agggctggtc | 2100 |
| agggtgtctg gggcaggagg aggccaactc actgaactag tgcagggtat gtgggtggca | 2160 |
| ctgacctgtt ctgttgactg ggccctgca gactctggca gagctgagaa gggcagggac | 2220 |
| cttctccctc ctaggaactc tttcctgtat cataaaggat tatttgctca ggggaaccat | 2280 |
| ggggctttct ggagttgtgg tgaggccacc aggctgaagt cagctcagac ccagacctcc | 2340 |
| ctgcttaggc cactcgagca tcagagcttc cagcaggagg aagggctgta ggaatggaag | 2400 |
| cttcagggcc ttgctgctgg ggtcattttt aggggaaaaa ggaggatatg atggtcacat | 2460 |
| ggggaacctc ccctcatcgg gcctctgggg caggaagctt gtcactggaa gatcttaagg | 2520 |
| tatatatttt ctggacactc aaacacatca taatggattc actgagggga gacaaaggga | 2580 |
| gccgagaccc tggatggggc ttccagctca gaacccatcc ctctggtggg tacctctggc | 2640 |
| acccatctgc aaatatctcc ctctctccaa caaatggagt agcatccccc tggggcactt | 2700 |
| gctgaggcca agccactcac atcctcactt tgctgcccca ccatcttgct gacaacttcc | 2760 |
| agagaagcca tggtttttg tattggtcat aactcagccc tttgggcggc ctctgggctt | 2820 |
| gggcaccagc tcatgccagc cccagagggt cagggttgga ggcctgtgct tgtgttgct | 2880 |
| gctaatgtcc agctacagac ccagaggata agccactggg cactgggctg gggtccctgc | 2940 |
| cttgttggtg ttcagctgtg tgattttgga ctagccactt gtcagagggc ctcaatctcc | 3000 |
| catctgtgaa ataaggactc caccttagg ggaccctcca tgtttgctgg gtattagcca | 3060 |
| agctggtcct gggagaatgc agatactgtc cgtggactac caagctggct tgtttcttat | 3120 |
| gccagaggct aacagatcca atgggagtcc atggtgtcat gccaagacag tatcagacac | 3180 |
| agccccagaa gggggcatta tgggccctgc ctccccatag gccatttgga ctctgccttc | 3240 |
| aaacaaaggc agttcagtcc acaggcatgg aagctgtgag gggacaggcc tgtgcgtgcc | 3300 |
| atccagagtc atctcagccc tgcctttctc tggagcattc tgaaaacaga tattctggcc | 3360 |
| cagggaatcc agccatgacc cccacccctc tgccaaagta ctcttaggtg ccagtctggt | 3420 |
| aactgaactc cctctggagg caggcttgag ggaggattcc tcagggttcc cttgaaagct | 3480 |
| ttatttattt attttgttca tttatttatt ggagaggcag cattgcacag tgaaagaatt | 3540 |
| ctggatatct caggagcccc gaaattctag ctctgacttt gctgtttcca gtggtatgac | 3600 |
| cttggagaag tcacttatcc tcttggagcc tcagtttcct catctgcaga ataatgactg | 3660 |
| acttgtctaa ttcgtaggga tgtgaggttc tgctgaggaa atgggtatga atgtgccttg | 3720 |
| aacacaaagc tctgtcaata agtgatacat gttttttatt ccaataaatt gtcaagacca | 3780 |
| caggaaaaaa aaaaaaaaaa aa | 3802 |

```
<210> SEQ ID NO 15
<211> LENGTH: 325
<212> TYPE: PRT
```

<213> ORGANISM: Homo sapiens

<400> SEQUENCE: 15

Met Ala Trp Ser Leu Gly Ser Trp Leu Gly Cys Leu Leu Val Ser
1               5                   10                  15

Ala Leu Gly Met Val Pro Pro Glu Asn Val Arg Met Asn Ser Val
                20                  25                  30

Asn Phe Lys Asn Ile Leu Gln Trp Glu Ser Pro Ala Phe Ala Lys Gly
            35                  40                  45

Asn Leu Thr Phe Thr Ala Gln Tyr Leu Ser Tyr Arg Ile Phe Gln Asp
        50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
290                 295                 300

Gly Lys Gln Asn Pro Gly Asp Ser Cys Ser Leu Gly Thr Pro Pro Gly
305                 310                 315                 320

Gln Gly Pro Gln Ser
                325

<210> SEQ ID NO 16
<211> LENGTH: 1966
<212> TYPE: DNA
<213> ORGANISM: Homo sapiens

<400> SEQUENCE: 16
cccgcccatc tccgctggtt cccggaagcc gccgcggaca agctctcccg ggcgcgggcg      60
ggggtcgtgt gcttggagga agccgcggaa cccccagcgt ccgtccatgg cgtggagcct     120

```
tgggagctgg ctgggtggct gcctgctggt gtcagcattg ggaatggtac caccctcccga    180 aaatgtcaga atgaattctg ttaatttcaa gaacattcta cagtgggagt cacctgcttt    240
tgccaaaggg aacctgactt tcacagctca gtacctaagt tataggatat tccaagataa    300
atgcatgaat actaccttga cggaatgtga tttctcaagt cttccaagt atggtgacca    360 caccttgaga gtcagggctg aatttgcaga tgagcattca gactgggtaa acatcacctt    420
ctgtcctgtg gatgacacca ttattggacc ccctggaatg caagtagaag tacttgctga    480
ttctttacat atgcgtttct tagcccctaa aattgagaat gaatacgaaa cttggactat    540
gaagaatgtg tataactcat ggacttataa tgtgcaatac tggaaaaacg gtactgatga    600
aaagtttcaa attactcccc agtatgactt tgaggtcctc agaaacctgg agccatggac    660
aacttattgt gttcaagttc gagggtttct tcctgatcgg aacaaagctg gggaatggag    720
tgagcctgtc tgtgagcaaa caacccatga cgaaacggtc ccctcctgga tggtggccgt    780
catcctcatg gcctcggtct tcatggtctg cctggcactc ctcggctgct tcgccttgct    840
gtggtgcgtt tacaagaaga caaagtacgc cttctcccct aggaattctc ttccacagca    900
cctgaaagag ttttgggcc atcctcatca taacacactt ctgttttct cctttccatt    960 gtcggatgag aatgatgttt ttgacaagct aagtgtcatt gcagaagact ctgagagcgg   1020
caagcagaat cctggtgaca gctgcagcct cgggacccg cctgggcagg ggccccaaag   1080
ctaggctctg agaaggaaac acactcggct gggcacagtg acgtactcca tctcacatct   1140
gcctcagtga gggatcaggg cagcaaacaa gggccaagac catctgagcc agccccacat   1200
ctagaactcc cagaccctgg acttagccac cagagagcta cattttaaag gctgtcttgg   1260
caaaaatact ccatttggga actcactgcc ttataaaggc tttcatgatg ttttcagaag   1320
ttggccactg agagtgtaat tttcagcctt ttatatcact aaaataagat catgttttaa   1380
ttgtgagaaa cagggccgag cacagtggct cacgcctgta ataccagcac cttagaggtc   1440
gaggcaggcg gatcacttga ggtcaggagt tcaagaccag cctggccaat atggtgaaac   1500
ccagtctcta ctaaaaatac aaaaattagc taggcatgat ggcgcatgcc tataatccca   1560
gctactcgag tgcctgaggc aggagaattg catgaaccccg ggaggaggag gaggaggttg   1620
cagtgagccg agatagcggc actgcactcc agcctgggtg acaaagtgag actccatctc   1680
aaaaaaaaaa aaaaaaaaaa ttgtgagaaa cagaaatact taaaatgagg aataagaatg   1740
gagatgttac atctggtaga tgtaacattc taccagatta tggatggact gatctgaaaa   1800
tcgacctcaa ctcaagggtg gtcagctcaa tgctacacag agcacggact tttggattct   1860
ttgcagtact ttgaatttat ttttctacct atatatgttt tatatgctgc tggtgctcca   1920
ttaaagtttt actctgtgtt gcactatatg tgttcatgat aaaaaa                  1966
```

TREATMENT OF A DISEASE OF THE GASTROINTESTINAL TRACT WITH IL-10 OR AN IL-10 AGONIST

CROSS-REFERENCE TO RELATED APPLICATIONS

This application is a National Stage application under 35 U.S.C. § 371 of International Application No. PCT/US2018/025523, filed Mar. 30, 2018, which claims priority to U.S. Provisional Patent Application Ser. No. 62/507,008, filed May 16, 2017; U.S. Provisional Patent Application Ser. No. 62/545,232, filed Aug. 14, 2017; U.S. Provisional Patent Application Ser. No. 62/583,806, filed Nov. 9, 2017; U.S. Patent Application Provisional Application Ser. No. 62/598,957, filed Dec. 14, 2017; and U.S. Provisional Patent Application Ser. No. 62/478,744, filed Mar. 30, 2017; the entire contents of each of which are hereby incorporated by reference.

TECHNICAL FIELD

This disclosure features methods and compositions for treating diseases of the gastrointestinal tract with IL-10 or an IL-10 agonist.

BACKGROUND

Interleukin 10 (IL-10) is a key immunoregulator of various types of infection, including but not limited to: *Toxoplasma gondii* infection (see, e.g., Gazzinelli et al., *J. Immunol.* 157:798-805, 1996; Wilson et al., *J. Neuroimmunol.* 165:63-74, 2005; Jankovic et al., *J. Exp. Med.* 204:273-283, 2007; Roers et al., *J. Exp. Med.* 200:1289-1297, 2004), *Trypansoma cruzi* infection (see, e.g., Hunter et al., *J. Immunol.* 158:3311-3316, 1997; Reed et al., *J. Immunol.* 153:3135-3140, 1994; Holscher et al., *Infect. Immun.* 68:4075-4083, 2000), *Streptococcus pyogenes* infection (see, e.g., Stumhofer et al., *Nat. Immunol.* 8:1363-1371, 2007), *Helicobacter* infection (see, e.g., Kullberg et al., *J. Exp. Med.* 196: 505-515, 2002), *Listeria monocytogenes* infection (see, e.g., Fleming et al., *J. Leukocyte Biol.* 66:961-967, 1999), human immunodeficiency virus infection (see, e.g., Ji et al., *Int. Immunol.* 17:729-736, 2005; Elrefaei et al., *J. Immunol.* 178:3265-3271, 2007), MCMV infection (see, e.g., Redpath et al., *J. Immunol.* 162:6701-6707, 1999), and *Candida albicans* infection (see, e.g., Netea et al., *J. Immunol.* 172:3712-3718, 2004; and Montagnoli et al., *J. Immunol.* 169:6298-6308, 2002).

IL-10 was first discovered as a T helper 2 specific cytokine (Fiorentino et al., *J. Exp. Med.* 170:2081-2095, 1989). However, numerous innate and adaptive immune cells are able to produce and secrete IL-10, such as mast cells, natural killer cells, eosinophils, neutrophils macrophages, regulatory T cells, dendritic cells, B cells (see, e.g., Fillatreau et al., *Nat. Immunol.* 3:944-950, 2002; Maloy and Powrie, *Nat. Immunol.* 2:816-822, 2001; Maynard et al., *Immunol.* Rev. 226:219-233, 2008; Moore et al., *Annu. Rev. Immunol.* 19:683-765, 2001; and Roncarolo et al., *Immunol. Rev.* 212: 28-50, 2006).

IL-10 deficient mice develop colitis and colorectal cancer indicating the crucial role of IL-10 in intestinal homeostasis; and has suggested a role of IL-10 in control of gut flora (Kuhn et al., *Cell* 75:263-274, 1993; Leon et al., *Ann. N.Y. Acad. Sci.* 856:69-75, 1998; Sellon et al., *Infect. Immun.* 66:5224-5231, 1998).

IL-10 is an anti-inflammatory cytokine and inhibits the production of an array of inflammatory mediators by STAT3 activation (Murray, *Proc. Natl. Acad. Sci. U.S.A.* 102(24): 8686-8691, 2005; Moore et al., *Annu. Rev. Immunol.* 19:683-765, 2001; Mosmann, *Ad. Immunol.* 56:1-16, 1994). Treatment with an IL-10 receptor agonist may therefore provide relief for patients suffering from diseases with extensive and excessive inflammation (Fioranelli, *J. Integr. Cardiol.* 1:1, 2014).

The gastrointestinal (GI) tract generally provides a therapeutic medium for an individual's body. At times, therapeutic drugs may need to be dispensed to specified locations within the small intestine or large intestine, which is more effective than oral administration of the therapeutic drugs to cure or alleviate the symptoms of some medical conditions. For example, therapeutic drugs dispensed directly within the small intestine would not be contaminated, digested or otherwise compromised in the stomach, and thus allow a higher dose to be delivered at a specific location within the small intestine. However, dispensing therapeutic drugs directly within the small intestine inside a human body (e.g., the cecum, the ascending colon) can be difficult, because a device or mechanism (e.g., special formulation) would be needed to transport a therapeutically effective dose of drug to a desired location within the small intestine and then automatically deliver the therapeutic drug at the desired location. Dispensing therapeutic drugs directly within other locations in the GI tract of the human body can be similarly difficult. Such a device or mechanism also would also need to be operated in a safe manner in that the device or mechanism needs to physically enter the human body.

In sum, there remains a significant unmet medical need for improved treatment regimens for gastrointestinal diseases, such as inflammatory bowel disease (IBD), including a need for regimens which can dispense therapeutics to specific locations within the GI tract, thereby reducing or avoiding the drawbacks of oral or other forms of systemic administration.

SUMMARY

The present disclosure provides novel treatment paradigms for inflammatory conditions of the gastrointestinal tract. The methods and compositions described herein allow for the regio-specific release of therapeutic drugs at or near the site of disease in the gastrointestinal tract. By releasing a therapeutic drug locally instead of systemically, the bioavailability of the drug can be increased at the site of injury and/or decreased in the systemic circulation, thereby resulting in improved overall safety and/or efficacy and fewer adverse side effects. Advantages may include one or more of increased drug engagement at the target, leading to new and more efficacious treatment regimens, and/or lower systemic drug levels, which can translate to reduced toxicity and reduced immunogenicity, e.g., in the case of biologics. In some instances, releasing a therapeutic drug locally also provides for new modes of action that may be unique to local delivery in the GI tract as opposed to systemic administration. For patients, clinicians and payors, this can mean an easier or simpler route of administration, fewer co-medicaments (e.g., immunomodulators), fewer side effects, and/or better outcomes.

For example, a patient may present to a physician with one or more symptoms of a disorder of the GI tract (e.g., inflamatory bowel disease), and the physician can determine the specific discrete location(s) of diseased tissue (e.g., inflamed tissue or a lesion) in the patient's GI tract, and then use any of the devices described herein to administer a therapeutically effective amount of IL-10 or an IL-10 agonist proximate to, proximal to, or directly onto the specific discrete location(s) of diseased tissue in the patient.

In other examples, a patient may present to a physician with one or more symptoms of a disorder of the GI tract (e.g., inflamatory bowel disease) and the physician can use any of the devices provided herein to identify the specific discrete location(s) of diseased tissue (e.g., inflamed tissue or a lesion) in the patient's GI tract, and then use the same device or a different device (e.g., any of the devices described herein) to administer a therapeutically effective amount of IL-10 or an IL-10 agonist proximate to, proximal to, or directly onto the specific discrete locations of diseased tissue in the patient.

As can be appreciated by those in the art, these methods may be performed periodically on a patient at periodic intervals, e.g., approximately twice a month, approximately once a month, approximately every two months, approximately every three months, approximately four months, approximately five months, or approximately every six months. In some examples, these methods can provide for increased efficacy of treatment (e.g., reduced negative side effects and/or increased reduction in the severity, frequency, or number of symptoms) as compared to a patient which is administered an oral dosage form of the same PDE4 inhibitor. In some embodiments, the dosage of the PDE4 inhibitor administered using any of the devices described herein can differ between the different clinical visits based on an observation or measurement of the severity of disease at the specific discrete location(s) of diseased tissue (e.g., inflamed tissue or a lesion) in the patient's GI tract at the time of each clinical visit, or based on one or more observations or measurements of systemic disease markers (e.g., inflammatory markers in the blood) or markers in stool (e.g., calprotectin and lactoferrin). In some examples, over time, new specific discrete location(s) of diseased tissue may be detected or observed in the patient, and any of the devices described herein can be used to administer a therapeutically effective amount of IL-10 or an IL-10 agonist onto or proximal to the new specific discrete location(s) of diseased tissue in the patient's GI tract.

In some examples, the identification of the specific discrete location(s) of diseased tissue (e.g., inflamed tissue or a lesion) in the patient's GI tract and the administration of a therapeutically effective amount of IL-10 or an IL-10 agonist using any of the devices described herein can be performed in a single clinical visit.

In some examples, the diagnosis of a disorder of the GI tract (e.g., irritable bowel syndrome), the identification of the specific discrete location(s) of diseased tissue (e.g., inflamed tissue or a lesion) in the patient's GI tract, and the administration of a therapeutically effective amount of IL-10 or an IL-10 agonist proximate to, proximal, to or directly onto the specific discrete locations of diseased tissue in the patient using any of the devices described herein, can be performed in a single clinical visit.

Accordingly, described herein are methods for treating disorders of the gastrointestinal (GI) tract. The methods can include one or more of:
  diagnosing a GI disease in a subject; and/or
  mapping, sampling, and/or assessing the site, severity, pathology, and extent of a GI disease in the GI tract of a subject and/or mapping, sampling, and/or assessing a patient response to a therapeutic agent, e.g., in the patient's GI tract; and/or
  identifying, quantifying, and/or monitoring one or more markers of a GI disease in the GI tract of the subject and/or one or more markers of patient response to a therapeutic agent, e.g., in the patient's GI tract; and/or
  releasing a therapeutic agent, e.g., proximate to the site of a GI disease.

The present disclosure accordingly provides patients and physicians more personalized treatment options for GI disorders by facilitating regimens which can release a therapeutic agent according to desired (e.g., customized or optimized) dosage, timing, and/or location parameters. In some cases, the treatment methods can employ one or more ingestible devices to achieve the benefits disclosed herein.

In some embodiments, provided herein is a method of treating a disease of the gastrointestinal tract in a subject, comprising:
  administering to the subject a pharmaceutical formulation that comprises IL-10 or an IL-10 agonist,
  wherein the pharmaceutical formulation is released at a location in the gastrointestinal tract of the subject that is proximate to one or more sites of disease.

In some embodiments, provided herein the pharmaceutical formulation is administered in an ingestible device. In some embodiments, the pharmaceutical formulation is released from an ingestible device. In some embodiments, the ingestible device comprises a housing, a reservoir containing the pharmaceutical formulation, and a release mechanism for releasing the pharmaceutical formulation from the device,
  wherein the reservoir is releasably or permanently attached to the exterior of the housing or internal to the housing.

In some embodiments, provided herein is a method of treating a disease of the gastrointestinal tract in a subject, comprising:
  administering to the subject an ingestible device comprising a housing, a reservoir containing a pharmaceutical formulation, and a release mechanism for releasing the pharmaceutical formulation from the device,
  wherein the reservoir is releasably or permanently attached to the exterior of the housing or internal to the housing;
  wherein the pharmaceutical formulation comprises IL-10 or an IL-10 agonist, and
  the ingestible device releases the pharmaceutical formulation at a location in the gastrointestinal tract of the subject that is proximate to one or more sites of disease.

In some embodiments, the housing is non-biodegradable in the GI tract. In some embodiments, the release of the formulation is triggered autonomously. In some embodiments, the device is programmed to release the formulation with one or more release profiles that may be the same or different at one or more locations. In some embodiments, the device is programmed to release the formulation at a location proximate to one or more sites of disease. In some embodiments, the location of one or more sites of disease is predetermined.

In some embodiments, the reservoir is made of a material that allows the formulation to leave the reservoir, such as a biodegradable material.

In some embodiments, the release of the formulation is triggered by a pre-programmed algorithm. In some embodiments, the release of the formulation is triggered by data from a sensor or detector to identify the location of the device. In some more particular embodiments, the data is not based solely on a physiological parameter (such as pH, temperature, and/or transit time).

In some embodiments, the device comprises a detector configured to detect light reflectance from an environment external to the housing. In some more particular embodiments, the release is triggered autonomously or based on the detected reflectance.

In some embodiments, the device releases the formulation at substantially the same time as one or more sites of disease are detected. In some embodiments, the one or more sites of disease are detected by the device (e.g., by imaging the GI tract).

In some embodiments, the release mechanism is an actuation system. In some embodiments, the release mechanism is a chemical actuation system. In some embodiments, the release mechanism is a mechanical actuation system. In some embodiments, the release mechanism is an electrical actuation system. In some embodiments, the actuation system comprises a pump and releasing the formulation comprises pumping the formulation out of the reservoir. In some embodiments, the actuation system comprises a gas generating cell. In some embodiments, the device further comprises an anchoring mechanism. In some embodiments, the formulation comprises a therapeutically effective amount of the IL-10 or IL-10 agonist. In some embodiments, the formulation comprises a human equivalent dose (HED) of the IL-10 or IL-10 agonist.

In some embodiments, the device is a device capable of releasing a solid IL-10 or an IL-10 agonist or a solid formulation comprising the IL-10 or IL-10 agonist. In some embodiments, the device is a device capable of releasing a liquid IL-10 or an IL-10 agonist or a liquid formulation comprising the IL-10 or IL-10 agonist. Accordingly, in some embodiments of the methods herein, the pharmaceutical formulation release from the device is a solid formulation. Accordingly, in some embodiments of the methods herein, the pharmaceutical formulation release from the device is a liquid formulation.

The devices disclosed herein are capable of releasing a IL-10 or an IL-10 agonist or a formulation comprising the IL-10 or IL-10 agonist irrespective of the particular type of IL-10 or an IL-10 agonist. For example, the IL-10 or IL-10 agonist may be a small molecule, a biological, a nucleic acid, an antibody, a fusion protein, and so on.

In some embodiments, provided herein is a method of releasing IL-10 or an IL-10 agonist into the gastrointestinal tract of a subject for treating one or more sites of disease within the gastrointestinal tract, the method comprising:

administering to the subject a therapeutically effective amount of the IL-10 or IL-10 agonist housed in an ingestible device, wherein the ingestible device comprises a detector configured to detect the presence of the one or more sites of disease, and a controller or processor configured to trigger the release of the IL-10 or IL-10 agonist proximate to the one or more sites of disease in response to the detector detecting the presence of the one or more sites of disease.

In some embodiments, provided herein is a method of releasing IL-10 or an IL-10 agonist into the gastrointestinal tract of a subject for treating one or more pre-determined sites of disease within the gastrointestinal tract, the method comprising:

administering to the subject a therapeutically effective amount of the IL-10 or IL-10 agonist contained in an ingestible device, wherein the ingestible device comprises a detector configured to detect the location of the device within the gastrointestinal tract, and a controller or processor configured to trigger the release of the IL-10 or IL-10 agonist proximate to the one or more predetermined sites of disease in response to the detector detecting a location of the device that corresponds to the location of the one or more pre-determined sites of disease.

In some embodiments, provided herein is a method of releasing IL-10 or an IL-10 agonist into the gastrointestinal tract of a subject for treating one or more sites of disease within the gastrointestinal tract, the method comprising:

administering to the subject a therapeutically effective amount of the IL-10 or IL-10 agonist contained in an ingestible device;

receiving at an external receiver from the device a signal transmitting environmental data;

assessing the environmental data to confirm the presence of the one or more sites of disease; and when the presence of the one or more sites of disease is confirmed, sending from an external transmitter to the device a signal triggering the release of the IL-10 or IL-10 agonist proximate to the one or more sites of disease.

In some embodiments, provided herein is a method of releasing IL-10 or an IL-10 agonist into the gastrointestinal tract of a subject for treating one or more sites of disease within the gastrointestinal tract, the method comprising:

administering to the subject a therapeutically effective amount of the IL-10 or IL-10 agonist contained in an ingestible device;

receiving at an external receiver from the device a signal transmitting environmental or optical data;

assessing the environmental or optical data to confirm the location of the device within the gastrointestinal tract; and when the location of the device is confirmed, sending from an external transmitter to the device a signal triggering the release of the IL-10 or IL-10 agonist proximate to the one or more sites of disease.

Provided herein in one embodiment is a method of treating a disease of the gastrointestinal tract in a subject, comprising:

delivering IL-10 or an IL-10 agonist at a location in the gastrointestinal tract of the subject, wherein the method comprises administering to the subject a pharmaceutical composition comprising a therapeutically effective amount of the IL-10 or IL-10 agonist.

Provided herein in one embodiment is a method of treating a disease of the large intestine in a subject, comprising:

delivering IL-10 or an IL-10 agonist at a location in the proximal portion of the large intestine of the subject, wherein the method comprises administering endoscopically to the subject a therapeutically effective amount of the IL-10 or IL-10 agonist.

Provided herein in one embodiment is a method of treating a disease of the gastrointestinal tract in a subject, comprising:

releasing IL-10 or an IL-10 agonist at a location in the gastrointestinal tract of the subject that is proximate to one or more sites of disease, wherein the method comprises administering to the subject a pharmaceutical composition comprising a therapeutically effective amount of the IL-10 or IL-10 agonist.

Provided herein in one embodiment is a method of treating a disease of the gastrointestinal tract in a subject, comprising:

releasing IL-10 or an IL-10 agonist at a location in the gastrointestinal tract of the subject that is proximate to one or more sites of disease, wherein the method comprises administering to the subject a pharmaceutical composition comprising a therapeutically effective amount of the IL-10 or IL-10 agonist, wherein the pharmaceutical composition is an ingestible device and the method comprises administering orally to the subject the pharmaceutical composition.

Provided herein in one embodiment is a method of treating a disease of the gastrointestinal tract in a subject, comprising:

releasing IL-10 or an IL-10 agonist at a location in the gastrointestinal tract of the subject that is proximate to one or more sites of disease, wherein the method comprises administering to the subject a pharmaceutical composition comprising a therapeutically effective amount of the IL-10 or IL-10 agonist, wherein the method provides a concentration of the IL-10 or IL-10 agonist in the plasma of the subject that is less than 3 μg/ml.

Provided herein in one embodiment is a method of treating a disease of the large intestine in a subject, comprising:

releasing IL-10 or an IL-10 agonist at a location in the proximal portion of the large intestine of the subject that is proximate to one or more sites of disease, wherein the method comprises administering endoscopically to the subject a therapeutically effective amount of the IL-10 or IL-10 agonist.

In another aspect of the present invention, there is provided IL-10 or an IL-10 agonist for use in a method of treating a disease of the gastrointestinal tract in a subject, wherein the method comprises orally administering to the subject an ingestible device loaded with the IL-10 or IL-10 agonist, wherein the IL-10 or IL-10 agonist is released by the device at a location in the gastrointestinal tract of the subject that is proximate to one or more sites of disease.

In another aspect, the present invention provides a composition comprising or consisting of an ingestible device loaded with a therapeutically effective amount of IL-10 or an IL-10 agonist, for use in a method of treatment, wherein the method comprises orally administering the composition to the subject, wherein the IL-10 or IL-10 agonist is released by the device at a location in the gastrointestinal tract of the subject that is proximate to one or more sites of disease.

In another aspect, the present invention provides an ingestible device loaded with a therapeutically effective amount of IL-10 or an IL-10 agonist, wherein the device is controllable to release the IL-10 or IL-10 agonist at a location in the gastrointestinal tract of the subject that is proximate to one or more sites of disease. The device may be for use in a method of treatment of the human or animal body, for example, any method as described herein.

In still another aspect, the present invention provides an ingestible device for use in a method of treating a disease of the gastrointestinal tract in a subject, wherein the method comprises orally administering to the subject the ingestible device loaded with a therapeutically effective amount of IL-10 or an IL-10 agonist, wherein the IL-10 or IL-10 agonist is released by the device at a location in the gastrointestinal tract of the subject that is proximate to one or more sites of disease.

An ingestible device as used in the present invention may comprise one or more mechanical and/or electrical mechanisms which actively control release of the IL-10 or IL-10 agonist. For example, in any of the above aspects and embodiments, the ingestible device as used in the present invention may comprise a release mechanism for release of the IL-10 or IL-10 agonist (e.g., from a reservoir comprising the IL-10 or IL-10 agonist) and an actuator controlling the release mechanism.

In one embodiment, the ingestible device comprises:

an ingestible housing comprising a reservoir having a therapeutically effective amount of the IL-10 or IL-10 agonist stored therein;

a release mechanism having a closed state which retains the IL-10 or IL-10 agonist in the reservoir and an open state which releases the IL-10 or IL-10 agonist from the reservoir to the exterior of the device; and an actuator which changes the state of the release mechanism from the closed to the open state.

In one embodiment, the ingestible device comprises a housing defined by a first end, a second end substantially opposite from the first end;

a reservoir located within the housing and containing the IL-10 or IL-10 agonist wherein a first end of the reservoir is attached to the first end of the housing;

a mechanism for releasing the IL-10 or IL-10 agonist from the reservoir;

and an exit valve configured to allow the IL-10 or IL-10 agonist to be released out of the housing from the reservoir.

Here, the exit valve can be considered as the release mechanism having a closed state which retains the IL-10 or IL-10 agonist in the reservoir and an open state which releases the IL-10 or IL-10 agonist from the reservoir to the exterior of the device, and the mechanism for releasing the IL-10 or IL-10 agonist from the reservoir can be considered as the actuator.

In some embodiments of methods of treatment as described herein, the one or more disease sites may have been pre-determined (e.g., determined in a step preceding the administration of the composition of the present invention). The disease site(s) may have been determined by imaging the gastrointestinal tract. For example, the disease site(s) may have been pre-determined by endoscopy (e.g., a step of colonoscopy, enteroscopy, or using a capsule endoscope). Determination that the device is proximate to the disease site may therefore comprise a determining that the device is in a location corresponding to this previously-determined disease site.

In some embodiments, the location of the device in the gut may be detected by tracking the device. For example, the device may comprise a localization mechanism which may be a communication system for transmitting localization data, e.g., by radiofrequency transmission. The device may additionally or alternatively comprise a communication system for receiving a signal remotely triggering the actuator and thus causing release of the IL-10 or IL-10 agonist. The signal may be sent when it is determined that the device is in the correct location in the gut.

Thus, the ingestible device may comprise:

an ingestible housing comprising a reservoir having a therapeutically effective amount of the IL-10 or IL-10 agonist stored therein;

a release mechanism having a closed state which retains the IL-10 or IL-10 agonist in the reservoir and an open state which releases the IL-10 or IL-10 agonist from the reservoir to the exterior of the device;

a communication system for transmitting localization data to an external receiver and for receiving a signal from an external transmitter; and an actuator which changes the state of the release mechanism from the closed to the open state and which can be triggered by the signal.

In other embodiments, the ingestible device as used in the present invention may comprise an environmental sensor for detecting the location of the device in the gut and/or for detecting the presence of disease in the GI tract. For example, the environment sensor may be an image sensor for obtaining images in vivo.

Detecting the presence of disease may comprise, for example, detecting the presence of inflamed tissue, and/or lesions such as ulceration e.g., aphthoid ulcerations, "punched-out ulcers" and/or superficial ulcers of the mucosa, cobblestoning, stenosis, granulomas, crypt abscesses, fissures, e.g., extensive linear fissures, villous atrophy, fibrosis, and/or bleeding.

Detecting the presence of disease may also comprise molecular sensing, such as detecting the amount of an inflammatory cytokine or other marker of inflammation. Such a marker can be measured locally from a biopsy or systemically in the serum.

Where the ingestible device comprises an environmental sensor, actuation of the release mechanism may be triggered by a processor or controller communicably coupled to the environmental sensor. Thus, in some embodiments, the device may not require any external signal or control in order to release the drug.

In one embodiment, the ingestible device may comprise:
an ingestible housing comprising a reservoir having a therapeutically effective amount of the IL-10 or IL-10 agonist stored therein;
a release mechanism having a closed state which retains the IL-10 or IL-10 agonist in the reservoir and an open state which releases the IL-10 or IL-10 agonist from the reservoir to the exterior of the device;
an actuator which controls the transition of the release mechanism from the closed to the open state;
a detector for detecting the location of the device in the gut and/or the presence of diseased tissue; and
a processor or controller which is coupled to the detector and to the actuator and which triggers the actuator to cause the release mechanism to transition from its closed state to its open state when it is determined that the device is in the presence of diseased tissue and/or in a location in the gut that has been predetermined to be proximal to diseased tissue.

In another embodiment, there is provided:
an ingestible housing comprising a reservoir having a therapeutically effective amount of the IL-10 or IL-10 agonist stored therein;
a detector coupled to the ingestible housing, the detector configured to detect when the ingestible housing is proximate to a respective disease site of the one of the one or more sites of disease;
a valve system in fluid communication with the reservoir system; and
a controller communicably coupled to the valve system and the detector, the controller configured to cause the valve system to open in response to the detector detecting that the ingestible housing is proximate to the respective disease site so as to release the therapeutically effective amount of the IL-10 or IL-10 agonist at the respective disease site.

As above, detection that the ingestible housing is proximate to the respective disease site may be based on environmental data indicating the location of the device in the GI tract (and reference to a pre-determined disease site) or on environmental data directly indicating the presence of diseased tissue.

Additionally, or alternatively, the device may further comprise a communication system adapted to transmit the environment data to an external receiver (e.g., outside of the body). This data may be used, for example, for diagnostic purposes. The external receiver may comprise means for displaying the data.

In some embodiments, this data may be analyzed externally to the device and used to determine when the drug should be released: an external signal may then be sent to the device to trigger release of the drug. Thus, the communication system may further be adapted to receive a signal remotely triggering the actuator and thus causing release of the IL-10 or IL-10 agonist. The signal may be sent from an external transmitter in response to receipt/analysis and/or assessment of the environmental data, e.g., data indicating that the device has reached the desired location of the gut (where the location of the diseased tissue has been pre-determined) and/or data indicating the presence of diseased tissue. "External" may be "outside of the body".

Thus, in another embodiment, the ingestible device may comprise:
an ingestible housing comprising a reservoir having a therapeutically effective amount of the IL-10 or IL-10 agonist stored therein;
a release mechanism having a closed state which retains the IL-10 or IL-10 agonist in the reservoir and an open state which releases the IL-10 or IL-10 agonist from the reservoir to the exterior of the device;
an environmental detector for detecting environmental data indicating the location of the device in the gut and/or the presence of diseased tissue;
a communication system for transmitting the environmental data to an external receiver and for receiving a signal from an external transmitter; and an actuator which controls the transition of the release mechanism from the closed to the open state in response to the signal.

It will be understood from the above that when the device comprises one or more environmental detectors, e.g., comprises an image detector, the compositions may be used both for disease detection and for disease treatment.

Accordingly, in a further embodiment, there is provided IL-10 or an IL-10 agonist for use in a method of detecting and treating a disease of the gastrointestinal tract in a subject, wherein the method comprises orally administering to the subject an ingestible device loaded with the IL-10 or IL-10 agonist, wherein the ingestible device comprises an environmental sensor for determining the presence of diseased tissue in the GI tract, and wherein the IL-10 or IL-10 agonist is released by the device at a location in the gastrointestinal tract of the subject that is proximate to one or more sites of disease, as detected by the environmental sensor. The device may be according to any of the embodiments described herein.

In another embodiment, there is provided a composition for use in a method of detecting and treating a disease of the gastrointestinal tract in a subject, wherein the composition comprises or consists of an ingestible device loaded with a therapeutically effective amount of IL-10 or an IL-10 agonist, wherein the ingestible device comprises an environmental sensor for determining the presence of diseased tissue in the GI tract, and wherein the IL-10 or IL-10 agonist is released by the device at a location in the gastrointestinal tract of the subject that is proximate to one or more sites of disease, as detected by the environmental sensor. Again, the device may be according to any of the embodiments described herein.

In some embodiments, where the ingestible device as used in the present invention comprises an environmental sensor for detecting the presence of disease in the GI tract and a communication system as described above, the method of treatment may comprise:

i) receiving at an external receiver from the ingestible device a signal transmitting the environmental data;

ii) assessing the environmental data to confirm the presence of the disease; and iii) when the presence of the disease is confirmed, sending from an external transmitter to the ingestible device a signal triggering release of the IL-10 or IL-10 agonist.

For example, the presence of disease may be confirmed based on the presence of inflamed tissue and/or lesions associated with any of the disease states referred to herein. For example, the presence of disease may be confirmed based on the presence of inflammation, ulceration e.g., aphthoid ulcerations, "punched-out ulcers" and/or superficial ulcers of the mucosa, cobblestoning, stenosis, granulomas, crypt abscesses, fissures, e.g., extensive linear fissures, villous atrophy, fibrosis, and/or bleeding.

In some embodiments, the present invention may relate to a system comprising:

an ingestible device loaded with a therapeutically effective amount of IL-10 or an IL-10 agonist, a release mechanism for release of the IL-10 or IL-10 agonist (e.g., from a reservoir comprising the IL-10 or IL-10 agonist), an actuator controlling the release mechanism, an environmental sensor for determining the location of the device in the gut and/or for detecting the presence of diseased tissue and a communication system adapted to transmit the environment data and receive a signal triggering the actuator;

a receiver and display module for receiving and displaying outside of the body the environment data from the ingestible device;

a transmitter for sending to the ingestible device a signal triggering the actuator.

In any of the above embodiments, the ingestible device may further comprise an anchoring system for anchoring the device or a portion thereof in a location and an actuator for the anchoring system. This may be triggered in response to a determination that the device is at a location in the gastrointestinal tract of the subject proximate to one or more sites of disease. For instance, this may be detected by the environmental sensor. The triggering may be controlled by a processor in the device, that is, autonomously. A device where the triggering is controlled by a processor in the device is said to be an autonomous device. Alternatively, it may be controlled by a signal sent from outside of the body, as described above.

In any of the above aspects and embodiments, disease of the GI tract may be an inflammatory bowel disease.

In some embodiments, the disease of the GI tract is ulcerative colitis.

In some embodiments, the disease of the GI tract is Crohn's disease.

In general, apparatuses, compositions, and methods disclosed herein are useful in the treatment of diseases of the gastrointestinal tract. Exemplary gastrointestinal tract diseases that can be treated include, without limitation, inflammatory bowel disease (IBD), Crohn's disease (e.g., active Crohn's disease, refractory Crohn's disease, or fistulizing Crohn's disease), ulcerative colitis, indeterminate colitis, microscopic colitis, infectious colitis, drug or chemical-induced colitis, diverticulitis, and ischemic colitis, gastritis, peptic ulcers, stress ulcers, bleeding ulcers, gastric hyperacidity, dyspepsia, gastroparesis, Zollinger-Ellison syndrome, gastroesophageal reflux disease, short-bowel (anastomosis) syndrome, a hypersecretory state associated with systemic mastocytosis or basophilic leukemia or hyperhistaminemia, Celiac disease (e.g., nontropical Sprue), enteropathy associated with seronegative arthropathies, microscopic colitis, collagenous colitis, eosinophilic gastroenteritis, colitis associated with radiotherapy or chemotherapy, colitis associated with disorders of innate immunity as in leukocyte adhesion deficiency-1, chronic granulomatous disease, food allergies, gastritis, infectious gastritis or enterocolitis (e.g., *Helicobacter pylori*-infected chronic active gastritis), other forms of gastrointestinal inflammation caused by an infectious agent, pseudomembranous colitis, hemorrhagic colitis, hemolytic-uremic syndrome colitis, diversion colitis, irritable bowel syndrome, irritable colon syndrome, and pouchitis.

In some embodiments, apparatuses, compositions, and methods disclosed herein are used to treat one gastrointestinal disease. In some embodiments, apparatuses, compositions, and methods disclosed herein are used to treat more than one gastrointestinal disease. In some embodiments, apparatuses, compositions, and methods disclosed herein are used to treat multiple gastrointestinal diseases that occur in the same area of the gastrointestinal tract (e.g., each disease can occur in the small intestine, large intestine, colon, or any sub-region thereof). In some embodiments, apparatuses, compositions, and methods disclosed herein are used to treat multiple gastrointestinal diseases that occur in different areas of the gastrointestinal tract. In some embodiments, administration (e.g., local administration to the gastrointestinal tract) of IL-10 or an IL-10 agonist is useful in the treatment of gastrointestinal diseases including, but not limited to, inflammatory bowel disease (IBD), ulcerative colitis, Crohn's disease, or any of the other gastrointestinal diseases described herein.

Aspects and embodiments as described herein are intended to be freely combinable. For example, any details or embodiments described herein for methods of treatment apply equally to IL-10 or an IL-10 agonist, composition or ingestible device for use in said treatment. Any details or embodiments described for a device apply equally to methods of treatment using the device, or to IL-10 or an IL-10 agonist or composition for use in a method of treatment involving the device.

BRIEF DESCRIPTION OF THE DRAWINGS

FIG. 23 illustrates a valve system;

FIGS. 24A and 24B illustrate a portion of a two-stage valve system in its first and second stages, respectively;

FIGS. 25A and 25B illustrate a portion of a two-stage valve system in its first and second stages, respectively;

FIG. 52 is a representative table of the plasma adalimumab concentrations (μg/mL) as shown in FIG. 4.6.

FIGS. 63A-F are graphs showing rat IgG2A concentration as measured in (A) colon homogenate, (B) mLN homogenate, (C) small intestine homogenate, (D) cecum contents, (E) colon contents, and (F) plasma by ELISA. Standards were prepared with plasma matrix. Samples were diluted 1:50 before analysis. Sample 20 was removed from cecum contents analysis graph (outlier). *p<0.05; p<0.01; **p<0.001 were determined using the unpaired t test.

swine as described in Example 13.

Figure 83:
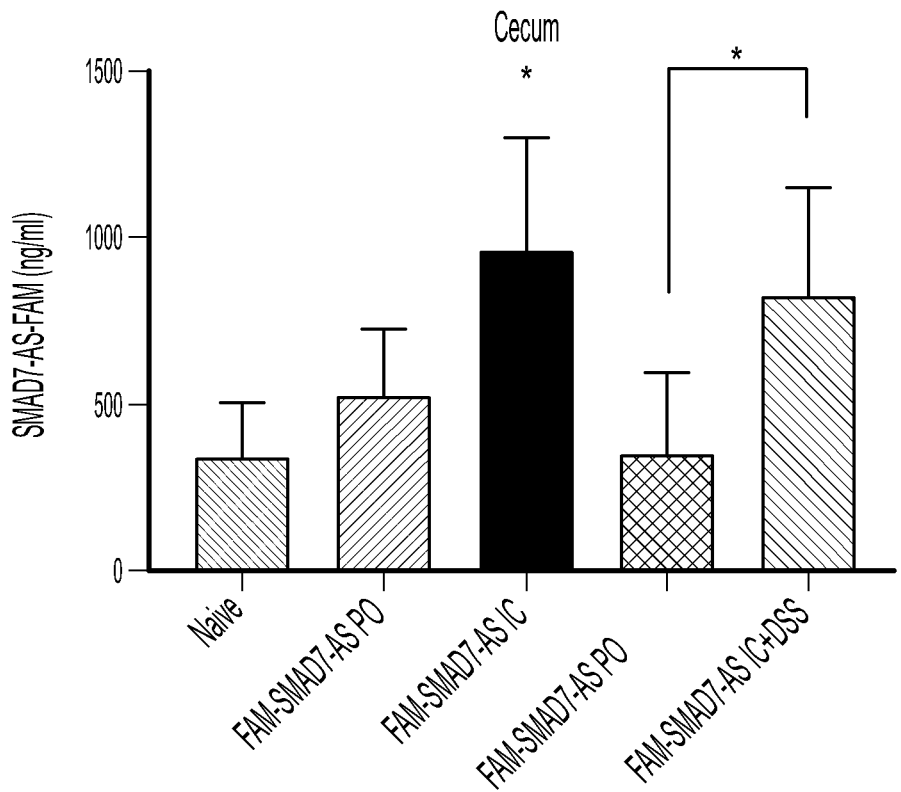

FIG. 83 is a graph showing the mean concentration of a SMAD7 antisense molecule (SMAD7-AS-FAM) in the cecum tissue in untreated swine or in swine after intra-cecal (IC) or oral administration (PO) of SMAD7-AS-FAM as described in Example 9.

Figure 84:
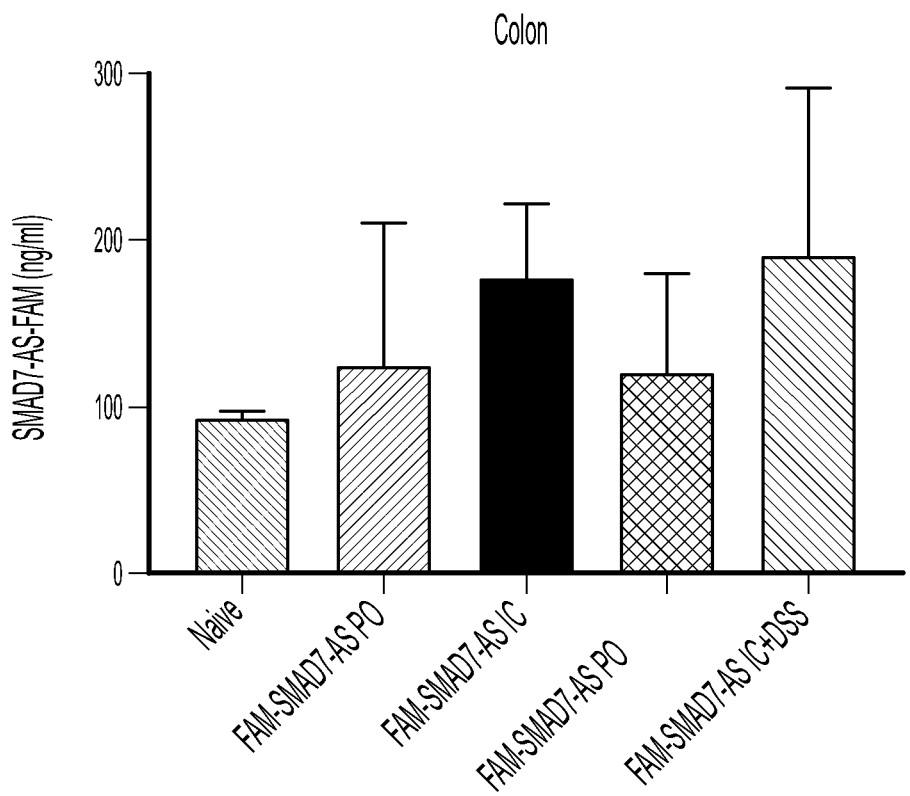

FIG. 84 is a graph showing the mean concentration of SMAD7-AS-FAM in the colon tissue in untreated swine or in swine after intra-cecal (IC) or oral administration (PO) of SMAD7-AS-FAM as described in Example 9.

Figure 85:
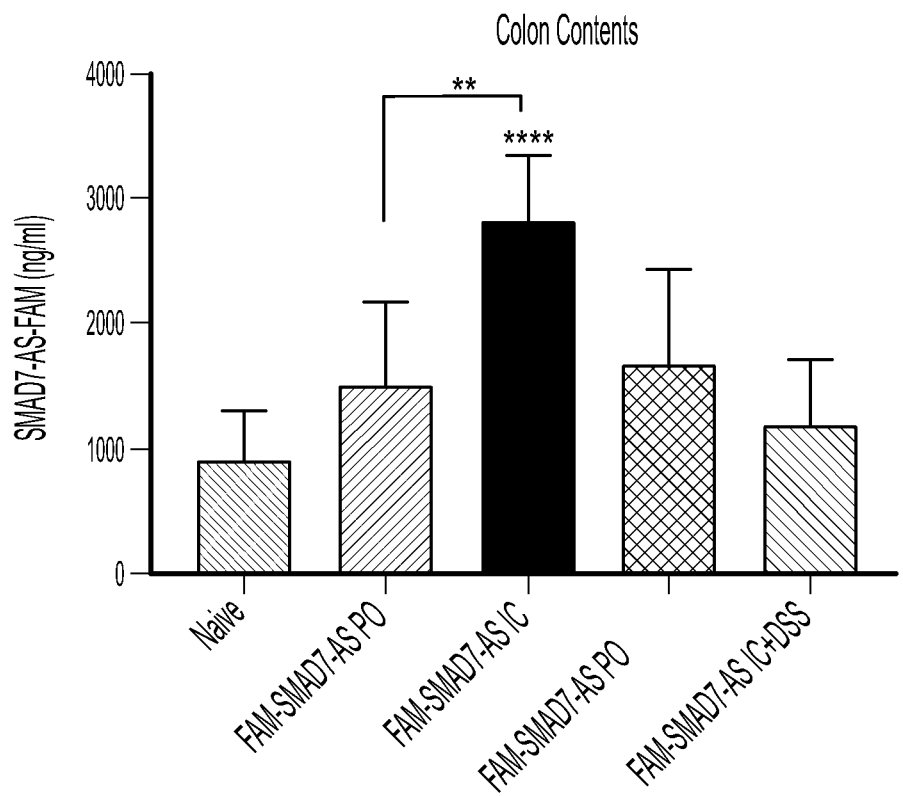

FIG. 85 is a graph showing the mean concentration of SMAD7-AS-FAM in the colon contents in untreated swine or in swine after intra-cecal (IC) or oral administration (PO) of SMAD7-AS-FAM as described in Example 9.

Figure 86:
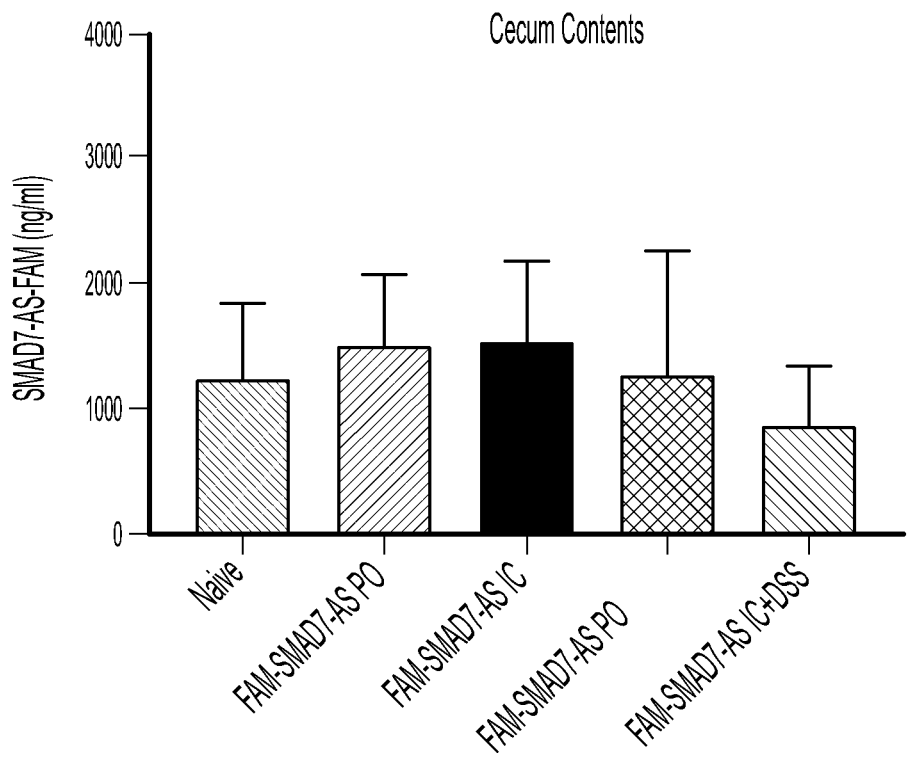

FIG. 86 is a graph showing the mean concentration of SMAD7-AS-FAM in the cecum contents in untreated swine or in swine after intra-cecal (IC) or oral administration (PO) of SMAD7-AS-FAM as described in Example 9.

Figure 87:
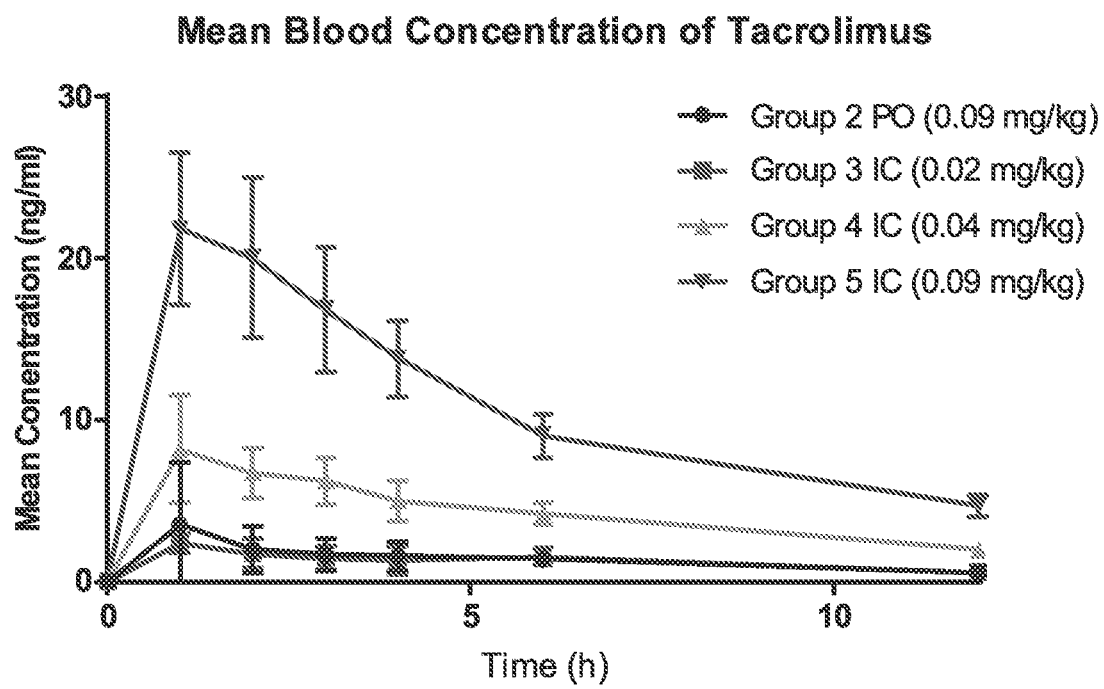

FIG. 87 is a graph showing the mean concentration of tacrolimus in the blood of swine 1 hour, 2 hours, 3 hours, 4 hours, 6 hours, and 12 hours after intra-cecal (IC) or oral administration (PO) of tacrolimus as described in Example 10.

Figure 88:
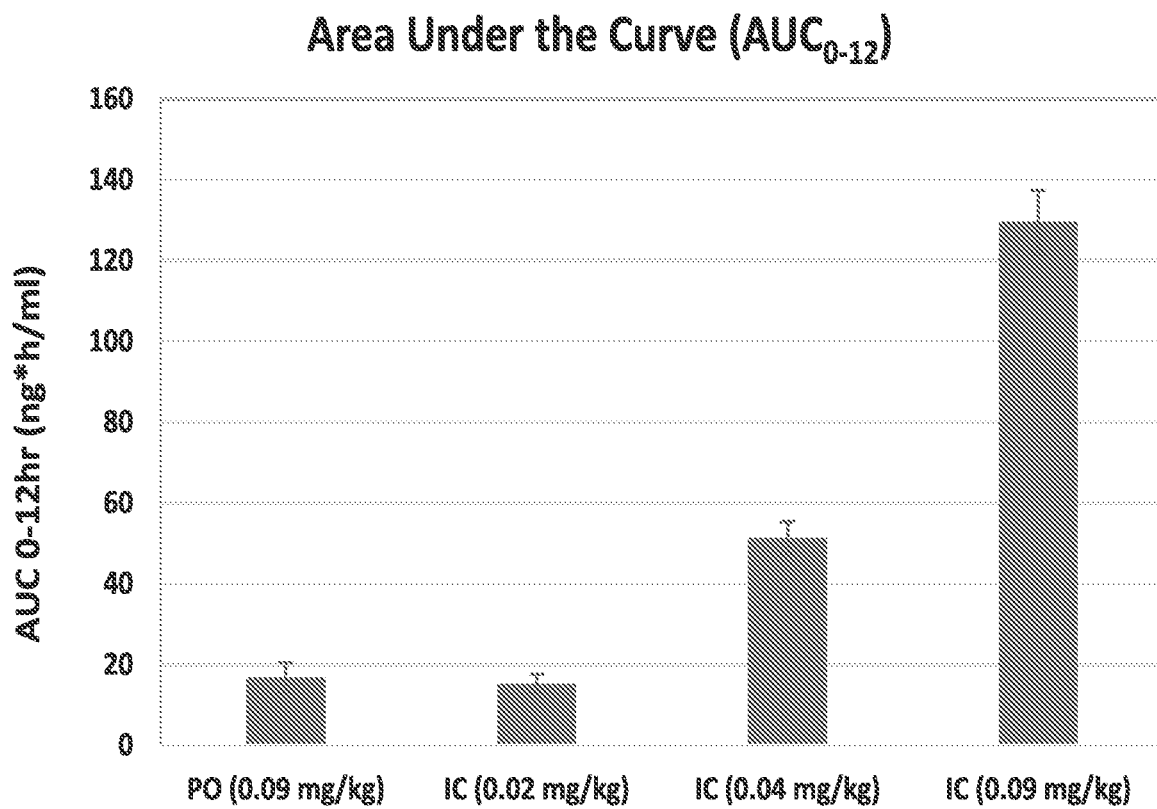

FIG. 88 is a graph showing the $AUC_{0-12}$ hours of tacrolimus in the blood of swine after intra-cecal (IC) or oral administration (PO) of tacrolimus as described in Example 10.

Figures 89, 90:
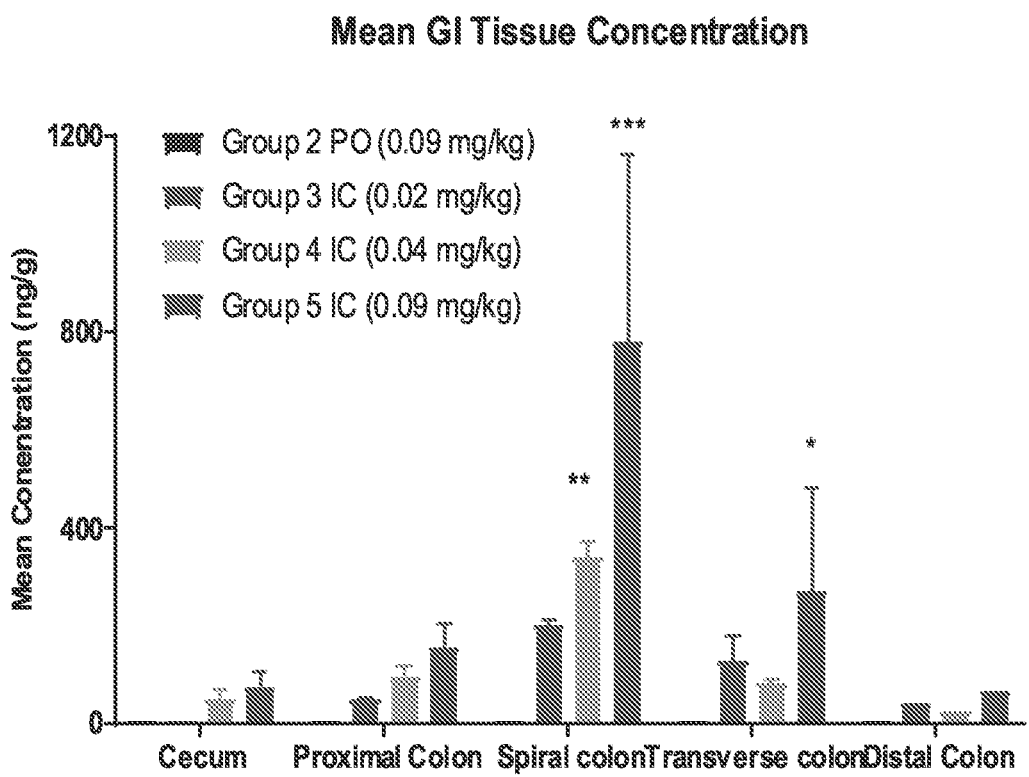

FIG. 89 is a representative table showing the Tmax, Cmax, trough (at 12 hours post-administration), and $AUC_{0-12}$ hours of tacrolimus in swine after intra-cecal (IC) or oral administration (PO) as described in Example 10.

FIG. 90 is a graph showing the mean concentration of tacrolimus in the cecum, the proximal colon, the spiral colon, the transverse colon, and the distal colon of swine after intra-cecal (IC) or oral administration (PO) of tacrolimus as described in Example 10.

Figure 91:
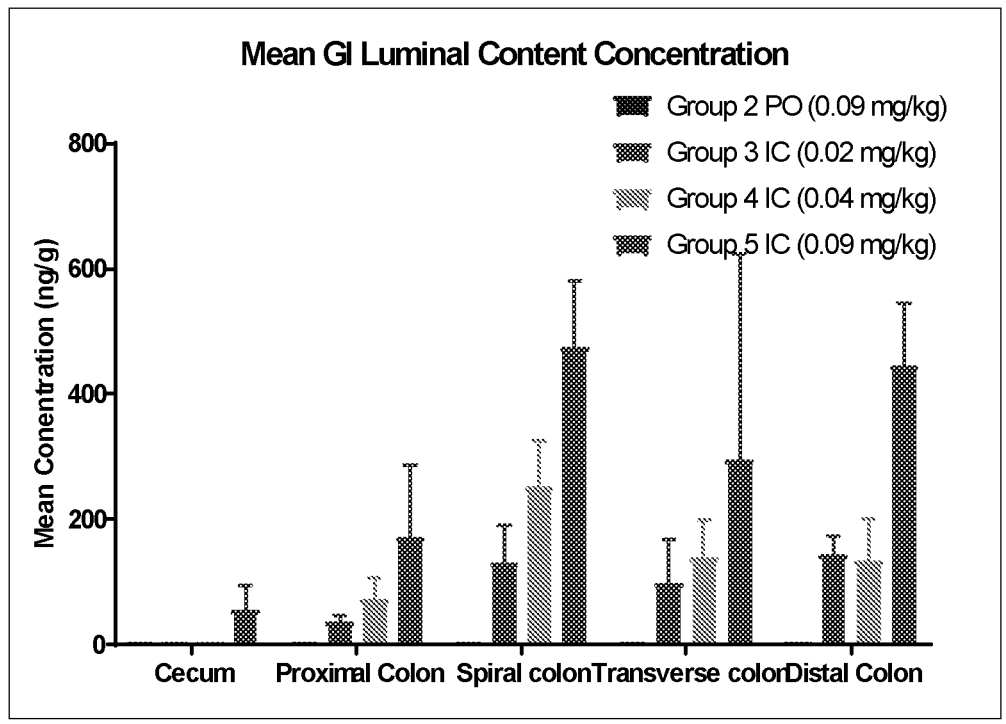

FIG. 91 is a graph showing the mean concentration of tacrolimus in the cecum lumen, the proximal colon lumen, the spiral colon lumen, the transverse colon lumen, and the distal colon lumen of swine after intra-cecal (IC) or oral administration (PO) of tacrolimus as described in Example 10.

Figure 92:
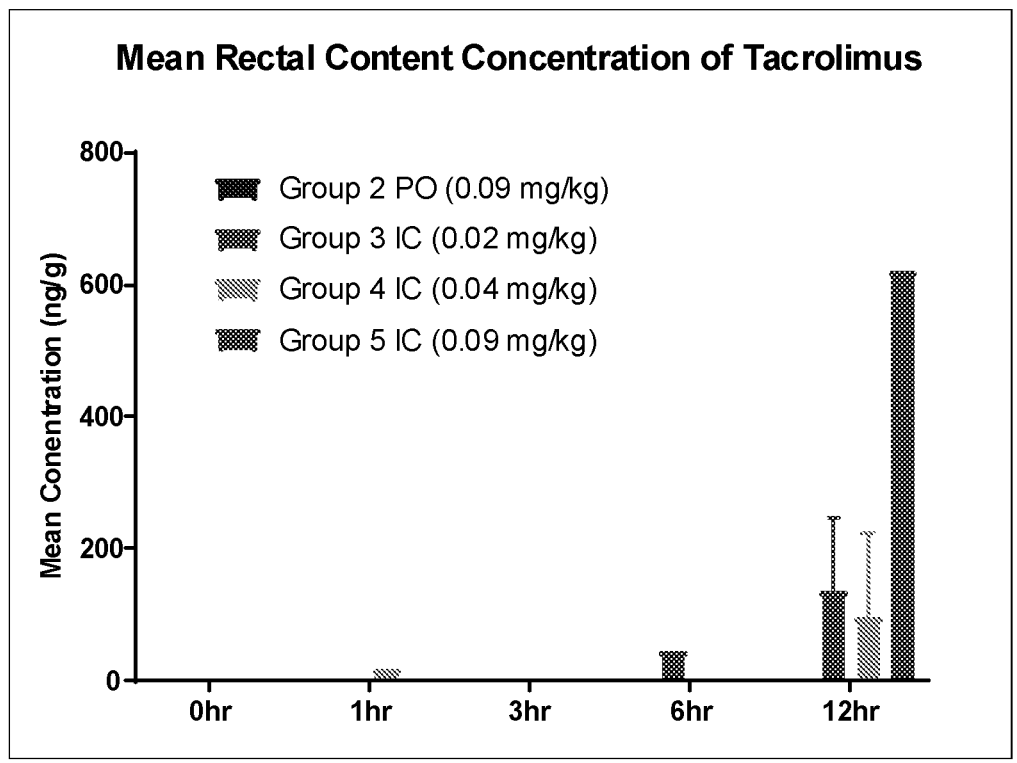

FIG. 92 is a graph showing the mean concentration of tacrolimus in the rectal content of swine at 1 hour, 3 hours, 6 hours, and 12 hours after intra-cecal (IC) or oral administration (PO) of tacrolimus as described in Example 10.

FIG. 93 is a representative table showing the quantitative histological grading of colitis as described in Example 11.

Figure 94:
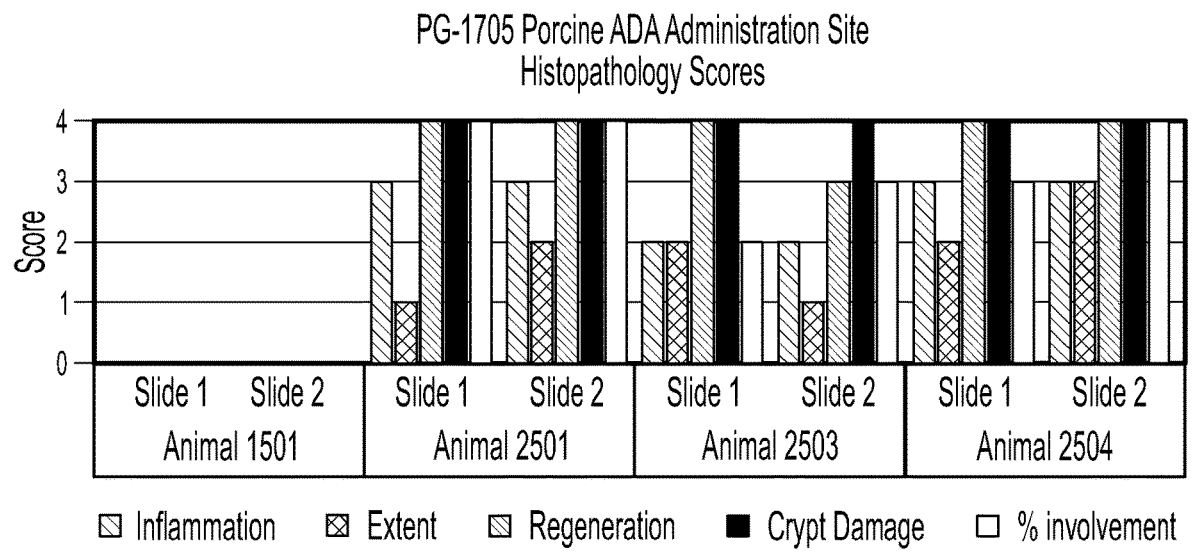

FIG. 94 is a graph showing the histopathological scores of two slides for animal 1502 (healthy control swine treated with placebo), animal 2501 (swine with 8.5% DSS-induced colitis treated with 1.86 mg/kg adalimumab), animal 2503 (swine with 8.5% DSS-induced colitis treated with 1.86 mg/kg adalimumab), and animal 2504 (swine with 8.5% DSS-induced colitis treated with 1.86 mg/kg adalimumab) at the placebo or adalimumab administration site prior to administration of placebo or adalimumab, respectively. Absence of a bar for a particular parameter indicates that the value for this parameter was 0.

Figure 95:
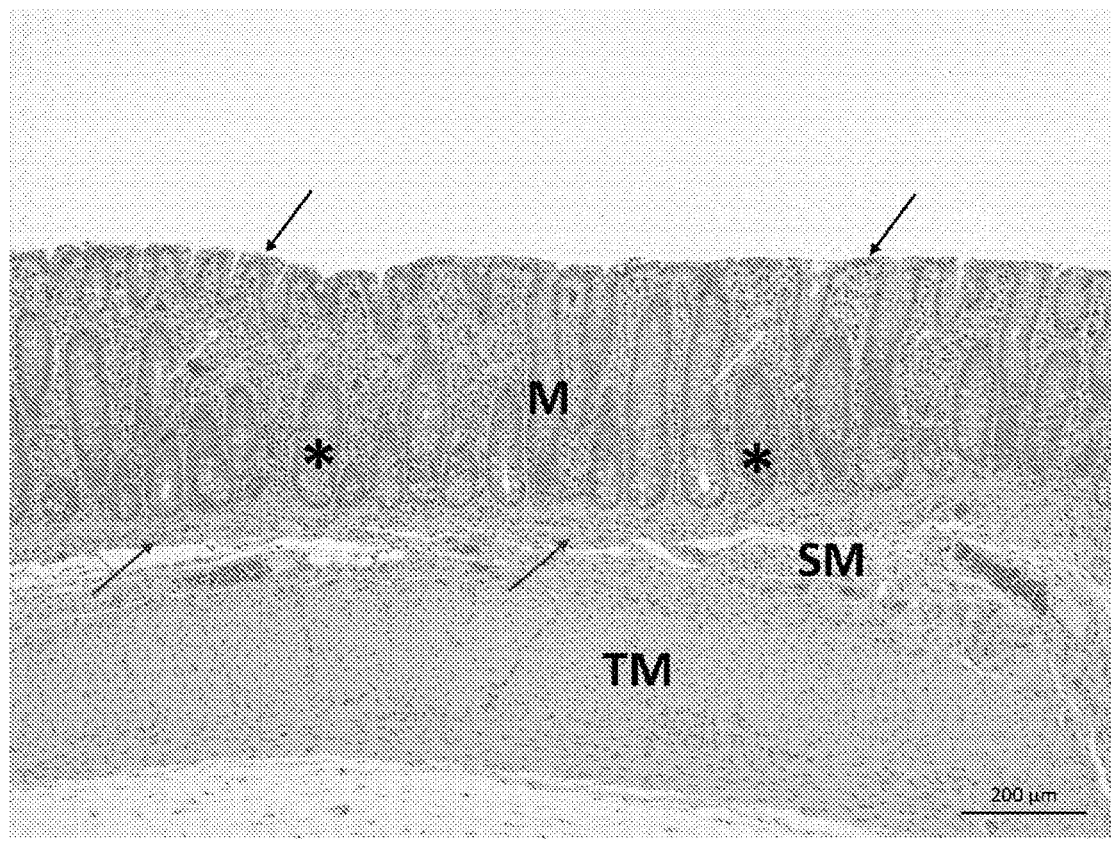

FIG. 95 is a representative hematoxylin- and eosin-stained image of the transverse colon of animal 1501 (healthy control swine). M, mucosa; SM, submucosa; TM, tunica muscularis. Numerous intestinal crypts (asterisks) are present and the surface epithelium (top two arrows) is intact. Mononuclear inflammatory cells are prominent in the lamina propria (light arrows) of the mucosa and extend a short distance into the submucosa (bottom two arrows). This amount of inflammatory cell infiltrate was expected background change and considered unrelated to the experimental protocol.

Figure 96:
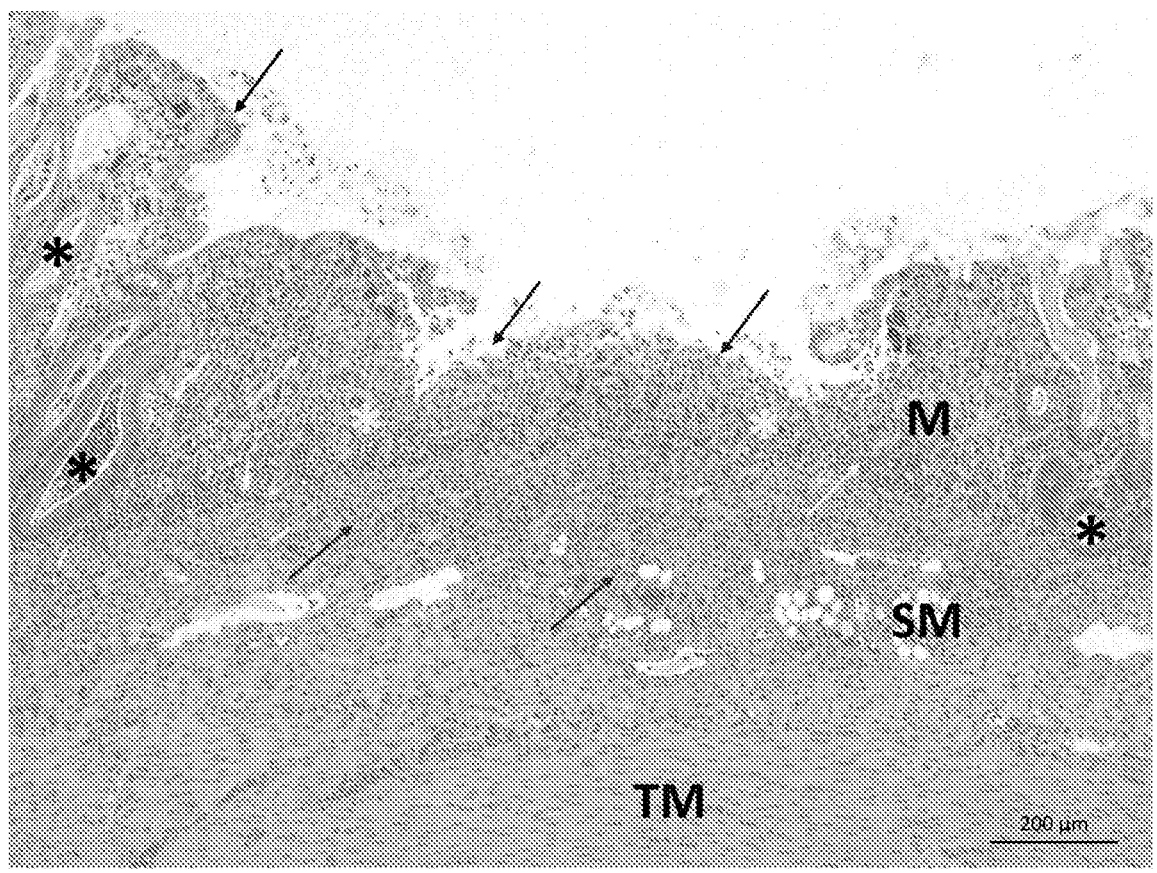

FIG. 96 is a representative hematoxylin- and eosin-stained image of the transverse colon of animal 2504 (8.5% DSS-induced colitis swine administered 1.86 mg/kg adalimumab) prior to administration of adalimumab. M, mucosa; SM, submucosa; TM, tunica muscularis. Extensive loss (light asterisks) of intestinal crypts is present in the mucosa. Scattered crypts remain (dark asterisks) and are often dilated and filled with inflammatory cell debris and mucus. The luminal epithelium persists in some areas (upper left arrow), but is absent in others (erosion; top middle and top right arrows). Inflammatory cells in the mucosa (light arrow) are abundant and extend into the submucosa (bottom left and bottom middle arrows).

Figure 97:
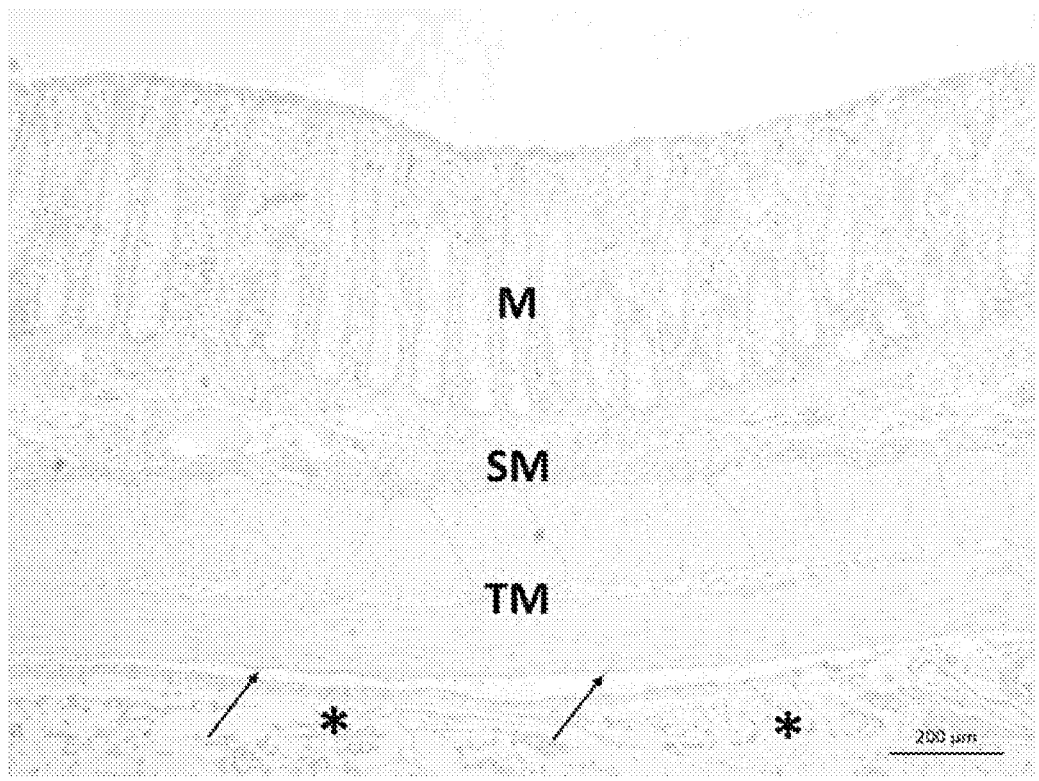

FIG. 97 is a representative immunohistochemistry micrograph of the transverse colon of animal 1501 (healthy control swine) stained for human IgG. M, mucosa; SM, submucosa; TM, tunica muscularis. Serosal surface (arrows) and loose connective mesentery tissue (asterisks) are indicated. Faint 3,3-diaminobenzidine (DAB) staining in this tissue was considered a background effect and not indicative of human IgG.

Figure 98:
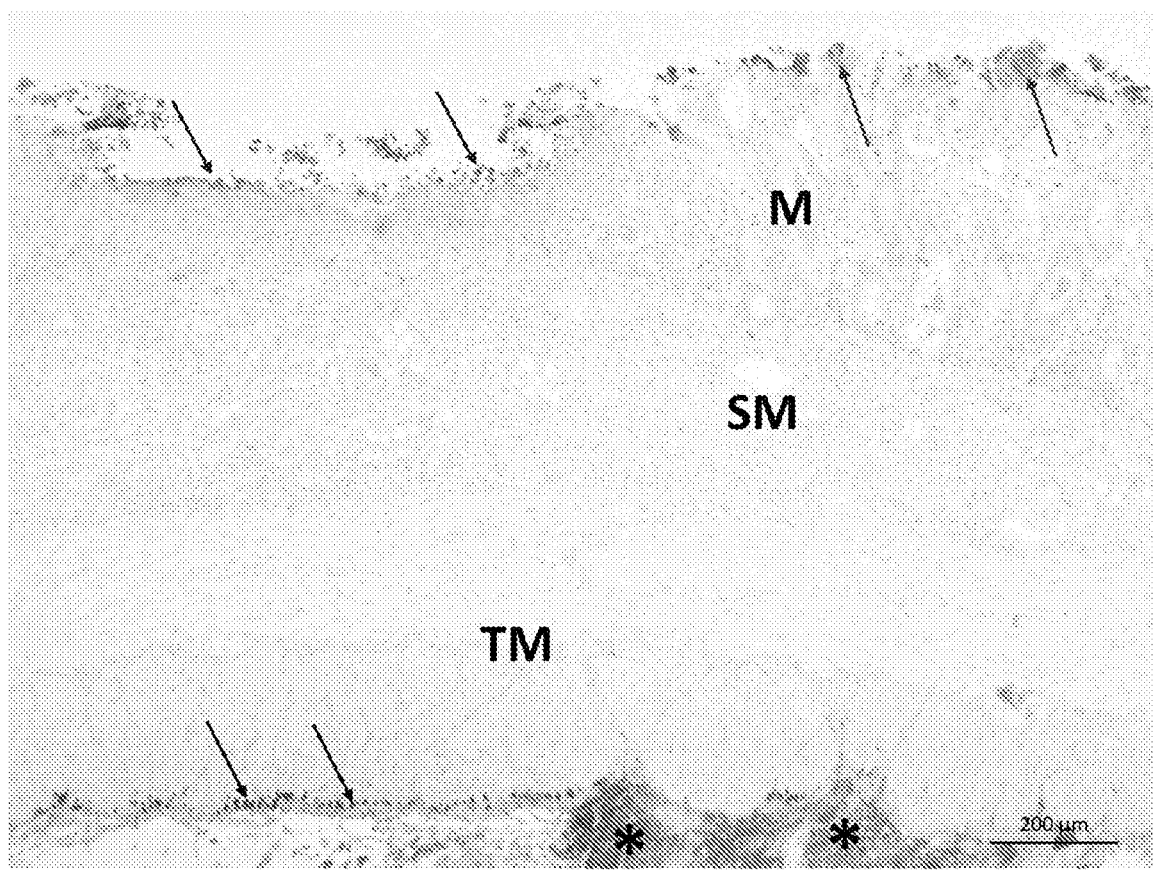

FIG. 98 is a representative immunohistochemistry micrograph of the transverse colon of animal 2504 (8.5% DSS-induced colitis swine treated with 1.86 mg/kg dose of adsalimumab) stained for human IgG. M, mucosa; SM, submucosa; TM, tunica muscularis. DAB staining demonstrates the presence of human IgG at the surface of luminal epithelium (two top right arrows) and at the luminal surface of an area of inflammation and erosion (top two left arrows). Intense staining is also present in the loose connective mesentery tissue (asterisks) and extends a short distance into the outer edge of the tunica muscularis (bottom left two arrows). This type of staining was considered strong (grade 4) or very strong (grade 5).

Figure 99:
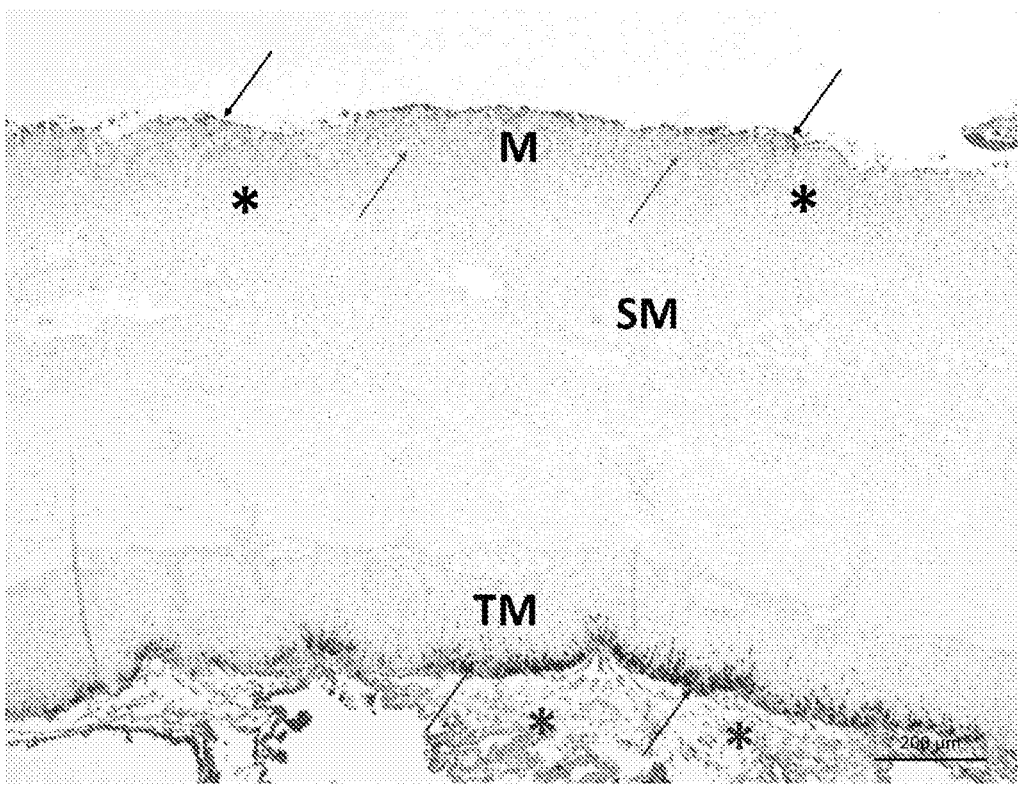

FIG. 99 is a representative immunohistochemistry micrograph of the large intestine of animal 2504 (8.5% DSS-induced colitis swine treated with 1.86 mg/kg adalimumab) stained for human IgG. M, mucosa; SM, submucosa; TM, tunica muscularis. Lesions of DSS-induced colitis are present in this section. The luminal epithelium is absent (erosion) and diffuse loss of crypts (glands) is seen (top two asterisks). Very strong (grade 5) DAB (brown) staining demonstrates the presence of human IgG in the loose mesentery connective tissue (bottom two asterisks) and extending a short distance into the outer edge of the tunica muscularis (bottom two arrows). Strong (grade 4) staining for human IgG is seen at the eroded luminal surface (top two arrows pointing down) and within the inflammatory exudate. Weak (grade 2) staining for human IgG extends into the lamina propria (top two arrows pointing up) near the luminal surface.

Figure 100:
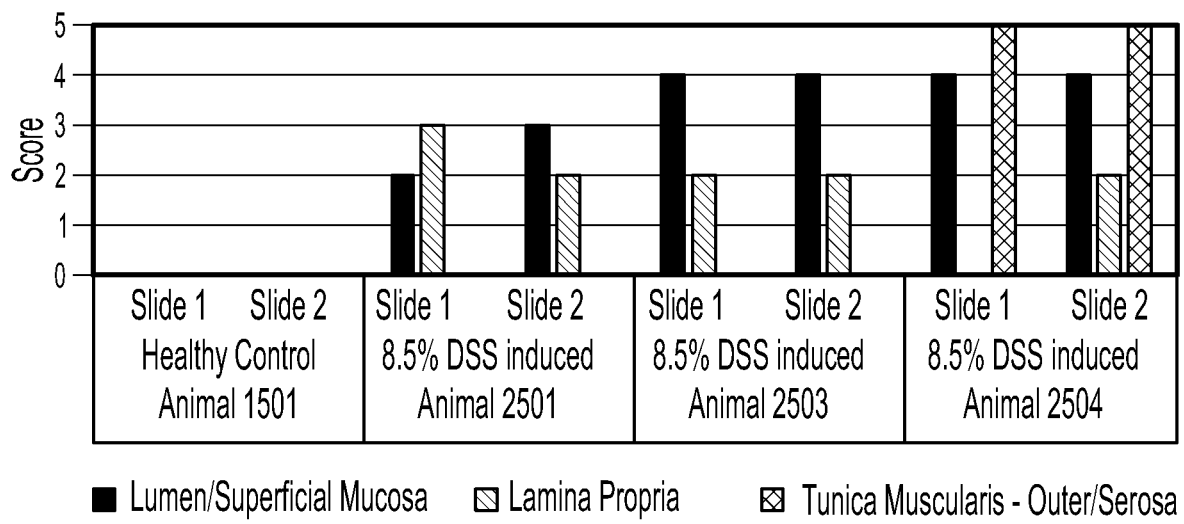

FIG. 100 is a graph showing the presence of human IgG (adalimumab) at the specified locations (lumen/superficial mucosa, lamina propria, and tunica muscularis-outer/serosa) (scored level) in two slides from each of animal 1502 (placebo-treated healthy control swine), animal 2501 (swine with 8.5% DSS-induced colitis treated with 1.86 mg/kg adalimumab), animal 2503 (swine with 8.5% DSS-induced colitis treated with 1.86 mg/kg adalimumab) and animal 2504 (swine with 8.5% DSS-induced colitis treated with 1.86 mg/kg adalimumab) at the placebo or adalimumab administration site. Absence of a bar for a particular location indicates that the value for this location was 0. Scoring: 0=not present; 1=minimal; 2=weak; 3=moderate; 4=strong; and 5=very strong immunolabel.

DETAILED DESCRIPTION

The present disclosure is directed to various methods and formulations for treating diseases of the gastrointestinal tract with IL-10 or an IL-10 agonist. For example, in an embodiment, a method of treating a disease of the gastrointestinal tract in a subject comprises administering to the subject a pharmaceutical formulation comprising IL-10 or an IL-10 agonist wherein the pharmaceutical formulation is released in the subject's gastrointestinal tract proximate to one or more sites of disease. For example, in an embodiment, the pharmaceutical formulation comprises a therapeutically effective amount of IL-10 or an IL-10 agonist.

In some embodiments, the formulation is contained in an ingestible device, and the device releases the formulation at a location proximate to the site of disease. The location of the site of disease may be predetermined. For example, an ingestible device, the location of which within the GI tract can be accurately determined as disclosed herein, may be used to sample one or more locations in the GI tract and to detect one or more analytes, including markers of the disease, in the GI tract of the subject. A pharmaceutical formulation may be then administered via an ingestible device and released at a location proximate to the predetermined site of disease. The release of the formulation may be triggered autonomously, as further described herein.

The following disclosure illustrates aspects of the formulations and methods embodied in the claims.

Formulations, Including Pharmaceutical Formulations

As used herein, a "formulation" of IL-10 or an IL-10 agonist may refer to either the IL-10 or IL-10 agonist in pure form, such as, for example, a lyophilized IL-10 or an IL-10 agonist, or a mixture of the IL-10 or IL-10 agonist with one or more physiologically acceptable carriers, excipients or stabilizers. Thus, therapeutic formulations or medicaments can be prepared by mixing the IL-10 or IL-10 agonist having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) antibody; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX<®>, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

A formulation of IL-10 or an IL-10 agonist as disclosed herein, e.g., sustained-release formulations, can further include a mucoadhesive agent, e.g., one or more of polyvinyl pyrolidine, methyl cellulose, sodium carboxyl methyl cellulose, hydroxyl propyl cellulose, carbopol, a polyacrylate, chitosan, a eudragit analogue, a polymer, and a thiomer. Additional examples of mucoadhesive agents that can be included in a formulation with IL-10 or an IL-10 agonist are described in, e.g., Peppas et al., *Biomaterials* 17(16):1553-1561, 1996; Kharenko et al., *Pharmaceutical Chemistry J.* 43(4):200-208, 2009; Salamat-Miller et al., *Adv. Drug Deliv. Reviews* 57(11):1666-1691, 2005; Bernkop-Schnurch, *Adv. Drug Deliv. Rev.* 57(11):1569-1582, 2005; and Harding et al., *Biotechnol. Genet. Eng. News* 16(1):41-86, 1999.

In some embodiments, components of a formulation may include any one of the following components, or any combination thereof:

Acacia, Alginate, Alginic Acid, Aluminum Acetate, an antiseptic, Benzyl Alcohol, Butyl Paraben, Butylated Hydroxy Toluene, an antioxidant. Citric acid, Calcium carbonate, Candelilla wax, a binder, Croscarmellose sodium, Confectioner sugar, Colloidal silicone dioxide, Cellulose, Carnuba wax, Corn starch, Carboxymethylcellulose calcium, Calcium stearate, Calcium disodium EDTA, Chelation agents, Copolyvidone, Castor oil hydrogenated, Calcium hydrogen phosphate dehydrate, Cetylpyridine chloride, Cysteine HCl, Crosspovidone, Dibasic Calcium Phosphate, Disodium hydrogen phosphate, Dimethicone, Erythrosine Sodium, Ethyl Cellulose, Gelatin, Glyceryl monooleate, Glycerin, Glycine, Glyceryl monostearate, Glyceryl behenate, Hydroxy propyl cellulose, Hydroxyl propyl methyl cellulose, Hypromellose, HPMC Pthalate, Iron oxides or ferric oxide, Iron oxide yellow, Iron oxide red or ferric oxide, Lactose (hydrous or anhydrous or monohydrate or spray dried), Magnesium stearate, Microcrystalline cellulose, Mannitol, Methyl cellulose, Magnesium carbonate, Mineral oil, Methacrylic acid copolymer, Magnesium oxide, Methyl paraben, PEG, Polysorbate 80, Propylene glycol, Polyethylene oxide, Propylene paraben, Polaxamer 407 or 188 or plain, Potassium bicarbonate, Potassium sorbate, Potato starch, Phosphoric acid, Polyoxy140 stearate, Sodium starch glycolate, Starch pregelatinized, Sodium crossmellose, Sodium lauryl sulfate, Starch, Silicon dioxide, Sodium benzoate, Stearic acid, Sucrose base for medicated confectionery, a granulating agent, Sorbic acid, Sodium carbonate, Saccharin sodium, Sodium alginate, Silica gel, Sorbiton monooleate, Sodium stearyl fumarate, Sodium chloride, Sodium metabisulfite, Sodium citrate dehydrate, Sodium starch, Sodium carboxy methyl cellulose, Succinic acid, Sodium propionate, Titanium dioxide, Talc, Triacetin, Triethyl citrate.

Accordingly, in some embodiments of the method of treating a disease as disclosed herein, the method comprises administering to the subject a pharmaceutical composition that is a formulation as disclosed herein. In some embodiments the formulation is a dosage form, which may be, as an example, a solid form such as, for example, a capsule, a tablet, a sachet, or a lozenge; or which may be, as an example, a liquid form such as, for example, a solution, a suspension, an emulsion, or a syrup.

In some embodiments, the formulation is not comprised in an ingestible device. In some embodiments wherein the formulation is not comprised in an ingestible device, the formulation may be suitable for oral administration. The formulation may be, for example, a solid dosage form or a liquid dosage form as disclosed herein. In some embodiments wherein the formulation is not comprised in an ingestible device, the formulation may be suitable for rectal administration. The formulation may be, for example, a dosage form such as a suppository or an enema. In embodiments where the formulation is not comprised in an ingestible device, the formulation releases the IL-10 or IL-10 agonist at a location in the gastrointestinal tract of the subject that is proximate to one or more sites of disease. Such localized release may be achieved, for example, with a formulation comprising an enteric coating. Such localized release may be achieved, an another example, with a formulation comprising a core comprising one or more polymers suitable for controlled release of an active substance. A non-limiting list of such polymers includes: poly(2-(diethylamino)ethyl methacrylate, 2-(dimethylamino)ethyl methacrylate, poly(ethylene glycol), poly(-aminoethyl methacrylate), (2-hydroxypropyl)methacrylamide, poly(β-benzyl-1-aspartate), poly(N-isopropylacrylamide), and cellulose derivatives.

In some embodiments, the formulation is comprised in an ingestible device as disclosed herein. In some embodiments wherein the formulation is comprised in an ingestible device, the formulation may be suitable for oral administration. The formulation may be, for example, a solid dosage form or a liquid dosage form as disclosed herein. In some embodiments the formulation is suitable for introduction and optionally for storage in the device. In some embodiments the formulation is suitable for introduction and optionally for storage in a reservoir comprised in the device. In some embodiments the formulation is suitable for introduction and optionally for storage in a reservoir comprised in the device. Thus, in some embodiments, provided herein is a reservoir comprising a therapeutically effective amount of IL-10 or an IL-10 agonist, wherein the reservoir is configured to fit into an ingestible device. In some embodiments, the reservoir comprising a therapeutically effective amount of IL-10 or an IL-10 agonist is attachable to an ingestible device. In some embodiments, the reservoir comprising a therapeutically effective amount of IL-10 or an IL-10 agonist is capable of anchoring itself to the subject's tissue. As an example, the reservoir capable of anchoring itself to the subject's tissue comprises silicone. As an example, the reservoir capable of anchoring itself to the subject's tissue comprises polyvinyl chloride.

In some embodiments the formulation is suitable for introduction in a spray catheter, as disclosed herein.

The formulation herein may also contain more than one active compound as necessary for the particular indication being treated, for example, those with complementary activities that do not adversely affect each other. For instance, the formulation may further comprise another IL-10 or an IL-10 agonist or a chemotherapeutic agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the IL-10 or IL-10 agonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated IL-10 or an IL-10 agonists remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical formulations may contain one or more IL-10 or an IL-10 agonists. The pharmaceutical formulations may be formulated in any manner known in the art. In some embodiments the formulations include one or more of the following components: a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811, incorporated by reference herein in its entirety). The formulations can be formulated and enclosed in ampules, disposable syringes, or multiple dose vials. Where required, proper fluidity can be maintained by, for example, the use of a coating, such as lecithin, or a surfactant. Controlled release of the IL-10 or IL-10 agonist can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

In some embodiments, the IL-10 or IL-10 agonist is present in a pharmaceutical formulation within the device.

In some embodiments, the IL-10 or IL-10 agonist is present in solution within the device.

In some embodiments, the IL-10 or IL-10 agonist is present in a suspension in a liquid medium within the device.

In some embodiments, the IL-10 or IL-10 agonist is present as a pure, powder (e.g., lyophilized) form of the IL-10 or IL-10 agonist.

Definitions

By "ingestible", it is meant that the device can be swallowed whole.

"Gastrointestinal inflammatory disorders" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

"Inflammatory Bowel Disease" or "IBD" is a chronic inflammatory autoimmune condition of the gastrointestinal (GI) tract. The GI tract can be divided into four main different sections, the oesophagus, stomach, small intestine and large intestine or colon. The small intestine possesses three main subcompartments: the duodenum, jejunum and ileum. Similarly, the large intestine consists of six sections: the cecum, ascending colon, transverse colon, ascending colon, sigmoid colon, and the rectum. The small intestine is about 6 m long, its diameter is 2.5 to 3 cm and the transit time through it is typically 3 hours. The duodenum has a C-shape, and is 30 cm long. Due to its direct connection with the stomach, it is physically more stable than the jejunum and ileum, which are sections that can freely move. The jejunum is 2.4 m in length and the ileum is 3.6 m in length and their surface areas are 180 $m^2$ and 280 $m^2$ respectively. The large intestine is 1.5 m long, its diameter is between 6.3 and 6.5 cm, the transit time though this section is 20 hours and has a reduced surface area of approximately 150 $m^2$. The higher surface area of the small intestine enhances its capacity for systemic drug absorption.

The etiology of IBD is complex, and many aspects of the pathogenesis remain unclear. The treatment of moderate to severe IBD poses significant challenges to treating physicians, because conventional therapy with corticosteroids and immunomodulator therapy (e.g., azathioprine, 6 mercaptopurine, and methotrexate administered via traditional routes such as tablet form, oral suspension, or intravenously) is associated with side effects and intolerance and has not shown proven benefit in maintenance therapy (steroids). Monoclonal antibodies targeting tumor necrosis factor alpha (TNF-α), such as infliximab (a chimeric antibody) and adalimumab (a fully human antibody), are currently used in the management of CD. Infliximab has also shown efficacy and has been approved for use in UC. However, approximately 10%-20% of patients with CD are primary nonresponders to anti TNF therapy, and another ~20%-30% of CD patients lose response over time (Schnitzler et al., Gut 58:492-500 (2009)). Other adverse events (AEs) associated with anti TNFs include elevated rates of bacterial infection, including tuberculosis, and, more rarely, lymphoma and demyelination (Chang et al., Nat Clin Pract Gastroenterol Hepatology 3:220 (2006); Hoentjen et al., World J. Gastroenterol. 15(17):2067 (2009)). No currently available therapy achieves sustained remission in more than 20%-30% of IBD patients with chronic disease (Hanauer et al, Lancet 359: 1541-49 (2002); Sandborn et al, N Engl J Med 353: 1912-25 (2005)). In addition, most patients do not achieve sustained steroid-free remission and mucosal healing, clinical outcomes that correlate with true disease modification.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

A chronic inflammatory autoimmune condition of the gastrointestinal (GI) tract presents clinically as either ulcerative colitis (UC) or Crohn's disease (CD). Both IBD conditions are associated with an increased risk for malignancy of the GI tract.

"Crohn's disease" ("CD") is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living.

CD is frequently complicated by the development of malabsorption, strictures, and fistulae and may require repeated surgery. UC, less frequently, may be complicated by severe bloody diarrhea and toxic megacolon, also requiring surgery. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual. Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

To date, the primary outcome measure in Crohn's Disease clinical trials is the Crohn's Disease Activity Index (CDAI), which has served as the basis for approval of multiple drug treatments, including for example, vedolizumab and natalizumab. The CDAI was developed by regressing clinician global assessment of disease activity on eighteen potential items representing patient reported outcomes (PROs) (i.e. abdominal pain, pain awakening patient from sleep, appetite), physical signs (i.e. average daily temperature, abdominal mass), medication use (i.e. loperamide or opiate use for diarrhea) and a laboratory test (i.e. hematocrit). Backward stepwise regression analysis identified eight independent predictors which are the number of liquid or soft stools, severity of abdominal pain, general well-being, occurrence of extra-intestinal symptoms, need for anti diarrheal drugs, presence of an abdominal mass, hematocrit, and body weight. The final score is a composite of these eight items, adjusted using regression coefficients and standardization to construct an overall CDAI score, ranging from 0 to 600 with higher score indicating greater disease activity. Widely used benchmarks are: CDAI <150 is defined as clinical remission, 150 to 219 is defined as mildly active disease, 220 to 450 is defined as moderately active disease, and above 450 is defined as very severe disease (Best W R, et al., Gastroenterology 77:843-6, 1979). Vedolizumab and natalizumab have been approved on the basis of demonstrated clinical remission, i.e. CDAI <150.

Although the CDAI has been in use for over 40 years, and has served as the basis for drug approval, it has several limitations as an outcome measure for clinical trials. For example, most of the overall score comes from the patient diary card items (pain, number of liquid bowel movements, and general well-being), which are vaguely defined and not standardized terms (Sandler et al., J. Clin. Epidemiol 41:451-8, 1988; Thia et al., Inflamm Bowel Dis 17: 105-11, 2011). In addition, measurement of pain is based on a four-point scale rather than an updated seven-point scale. The remaining 5 index items contribute very little to identifying an efficacy signal and may be a source of measurement noise. Furthermore, concerns have been raised about poor criterion validity for the CDAI, a reported lack of correlation between the CDAI and endoscopic measures of inflammation (which may render the CDAI as a poor discriminator of active CD and irritable bowel syndrome) and high reported placebo rates (Korzenik et al., N Engl J Med. 352:2193-201, 2005; Sandborn W J, et al., N Engl J Med 353: 1912-25, 2005; Sandborn W J, et al., Ann Intern 19; 146:829-38, 2007, Epub 2007 Apr. 30; Kim et al., Gastroenterology 146: (5 supplement 1) S-368, 2014).

It is, thus, generally recognized that additional or alternative measures of CD symptoms are needed, such as new PRO tools or adaptations of the CDAI to derive a new PRO. The PRO2 and PRO3 tools are such adaptations of the CDAI and have been recently described in Khanna et al., Aliment Pharmacol. Ther. 41:77-86, 2015. The PRO2 evaluates the frequency of loose/liquid stools and abdominal pain {Id). These items are derived and weighted accordingly from the CDAI and are the CDAI diary card items, along with general well-being, that contribute most to the observed clinical benefit measured by CDAI (Sandler et al., J. Clin. Epidemiol 41: 451-8, 1988; Thia et al., Inflamm Bowel Dis 17: 105-11, 2011; Kim et al., Gastroenterology 146: (5 supplement 1) S-368, 014). The remission score of <11 is the CDAI-weighted sum of the average stool frequency and pain scores in a 7-day period, which yielded optimum sensitivity and specificity for identification of CDAI remission (score of <150) in a retrospective data analysis of ustekinumab induction treatment for moderate to severe CD in a Phase II clinical study (Gasink C, et al., abstract, ACG Annual Meeting 2014). The PRO2 was shown to be sensitive and responsive when used as a continuous outcome measure in a retrospective data analysis of MTX treatment in active CD (Khanna R, et al., Inflamm Bowel Dis 20: 1850-61, 2014) measured by CDAI. Additional outcome measures include the Mayo Clinic Score, the Crohn disease endoscopic index of severity (CDEIS), and the Ulcerative colitis endoscopic index of severity (UCEIS). Additional outcome measures include Clinical remission, Mucosal healing, Histological healing (transmural), MM or ultrasound for measurement or evaluation of bowel wall thickness, abscesses, fistula and histology.

An additional means of assessing the extent and severity of Crohn's Disease is endoscopy. Endoscopic lesions typical of Crohn's disease have been described in numerous studies and include, e.g., aphthoid ulcerations, "punched-out ulcers," cobblestoning and stenosis. Endoscopic evaluation of such lesions was used to develop the first validated endoscopic score, the Crohn's Disease Endoscopic Index of Severity (CDEIS) (Mary et al., Gut 39:983-9, 1989). More recently, because the CDEIS is time-consuming, complicated and impractical for routine use, a Simplified Endoscopic Activity Score for Crohn's Disease (SES-CD) was developed and validated (Daperno et al., Gastrointest. Endosc. 60(4):505-12, 2004). The SES-CD consists of four endoscopic variables (size of ulcers, proportion of surface covered by ulcers, proportion of surface with any other lesions (e.g., inflammation), and presence of narrowings [stenosis]) that are scored in five ileocolonic segments, with each variable, or assessment, rated from 0 to 3.

To date, there is no cure for CD. Accordingly, the current treatment goals for CD are to induce and maintain symptom improvement, induce mucosal healing, avoid surgery, and improve quality of life (Lichtenstein G R, et al., Am J Gastroenterol 104:465-83, 2009; Van Assche G, et al., J Crohns Colitis. 4:63-101, 2010). The current therapy of IBD usually involves the administration of antiinflammatory or immunosuppressive agents, such as sulfasalazine, corticosteroids, 6-mercaptopurine/azathioprine, or cyclosporine, all of which are not typically delivered by localized release of a drug at the site or location of disease. More recently, biologics like TNF-alpha inhibitors and IL-12/IL-23 blockers, are used to treat IBD. If anti-inflammatory/immunosuppressive/biologic therapies fail, colectomies are the last line of defense. The typical operation for CD not involving the rectum is resection (removal of a diseased segment of bowel) and anastomosis (reconnection) without an ostomy. Sections of the small or large intestine may be removed. About 30% of CD patients will need surgery within the first year after diagnosis. In the subsequent years, the rate is about 5% per year. Unfortunately, CD is characterized by a high rate of recurrence; about 5% of patients need a second surgery each year after initial surgery.

Refining a diagnosis of inflammatory bowel disease involves evaluating the progression status of the diseases using standard classification criteria. The classification systems used in IBD include the Truelove and Witts Index (Truelove S. C. and Witts, L. J. Br Med J. 1955; 2: 1041-1048), which classifies colitis as mild, moderate, or severe, as well as Lennard-Jones. (Lennard-Jones J E. Scand J Gastroenterol Suppl 1989; 170:2-6) and the simple clinical colitis activity index (SCCAI). (Walmsley et. al. Gut. 1998; 43:29-32) These systems track such variables as daily bowel movements, rectal bleeding, temperature, heart rate, hemoglobin levels, erythrocyte sedimentation rate, weight, hematocrit score, and the level of serum albumin.

There is sufficient overlap in the diagnostic criteria for UC and CD that it is sometimes impossible to say which a given patient has; however, the type of lesion typically seen is different, as is the localization. UC mostly appears in the colon, proximal to the rectum, and the characteristic lesion is a superficial ulcer of the mucosa; CD can appear anywhere in the bowel, with occasional involvement of stomach, esophagus and duodenum, and the lesions are usually described as extensive linear fissures.

In approximately 10-15% of cases, a definitive diagnosis of ulcerative colitis or Crohn's disease cannot be made and such cases are often referred to as "indeterminate colitis." Two antibody detection tests are available that can help the diagnosis, each of which assays for antibodies in the blood. The antibodies are "perinuclear anti-neutrophil antibody" (pANCA) and "anti-*Saccharomyces* cervisiae antibody" (ASCA). Most patients with ulcerative colitis have the pANCA antibody but not the ASCA antibody, while most patients with Crohn's disease have the ASCA antibody but not the pANCA antibody. However, these two tests have shortcomings as some patients have neither antibody and some Crohn's disease patients may have only the pANCA antibody. A third test, which measures the presence and accumulation of circulating anti-microbial antibodies—particularly flagellin antibodies, has proven to be useful for detecting susceptibility to Crohn's Disease before disease development. See Choung, R. S., et al. "Serologic microbial associated markers can predict Crohn's disease behaviour years before disease diagnosis." Alimentary pharmacology & therapeutics 43.12 (2016): 1300-1310.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

The terms "antibody" and "immunoglobulin" are used interchangeably in the broadest sense and include monoclonal antibodies (for example, full length or intact monoclonal antibodies), polyclonal antibodies, multivalent antibodies, multispecific antibodies (e.g., bispecific, trispecific etc. antibodies so long as they exhibit the desired biological activity) and may also include certain antibody fragments (as described in greater detail herein). An antibody can be human, humanized and/or affinity matured.

"Antibody fragments" comprise only a portion of an intact antibody, where in certain embodiments, the portion retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, Proc. Natl. Acad. Sci. USA 81:6851-6855 (1984)).

"Treatment regimen" refers to a combination of dosage, frequency of administration, or duration of treatment, with or without addition of a second medication.

"Effective treatment regimen" refers to a treatment regimen that will offer beneficial response to a patient receiving the treatment.

"Effective amount" refers to an amount of drug that offers beneficial response to a patient receiving the treatment. For example, an effective amount may be a Human Equivalent Dose (HED).

"Dispensable", with reference to any substance, refers to any substance that may be released from an ingestible device as disclosed herein, or from a component of the device such as a reservoir. For example, a dispensable substance may be IL-10 or an IL-10 agonist, and/or a formulation comprising IL-10 or an IL-10 agonist.

"Patient response" or "patient responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment. The term "responsiveness" refers to a measurable response, including complete response (CR) and partial response (PR).

As used herein, "complete response" or "CR" means the disappearance of all signs of inflammation or remission in response to treatment. This does not necessarily mean the disease has been cured.

"Partial response" or "PR" refers to a decrease of at least 50% in the severity of inflammation, in response to treatment.

A "beneficial response" of a patient to treatment with a therapeutic agent and similar wording refers to the clinical or therapeutic benefit imparted to a patient at risk for or suffering from a gastrointestinal inflammatory disorder from or as a result of the treatment with the agent. Such benefit includes cellular or biological responses, a complete response, a partial response, a stable disease (without progression or relapse), or a response with a later relapse of the patient from or as a result of the treatment with the agent.

As used herein, "non-response" or "lack of response" or similar wording means an absence of a complete response, a partial response, or a beneficial response to treatment with a therapeutic agent.

"A patient maintains responsiveness to a treatment" when the patient's responsiveness does not decrease with time during the course of a treatment.

A "symptom" of a disease or disorder (e.g., inflammatory bowel disease, e.g., ulcerative colitis or Crohn's disease) is any morbid phenomenon or departure from the normal in structure, function, or sensation, experienced by a subject and indicative of disease.

IL-10 Receptor Agonists

The term "IL-10 receptor agonist", used interchangeably with "IL-10 agonist" herein, is any molecule that binds to and activates a receptor for IL-10 expressed on a mammalian cell or a nucleic acid that encodes any such molecule. A receptor for IL-10 can include, e.g., a complex of two IL-10 receptor-1 (IL-10R1) proteins and two IL-10 receptor 2 (IL-10R2) proteins. In some examples, an IL-10 receptor agonist is an antibody or an antigen-binding antibody fragment that specifically binds to and activates a receptor for IL-10 (e.g., a human receptor for IL-10). In some examples, an IL-10 receptor agonist is a recombinant IL-10 (e.g., human recombinant IL-10). In some examples, an IL-10 receptor agonist is a pegylated recombinant IL-10 (e.g., pegylated recombinant human IL-10). In some examples, an IL-10 receptor agonist is a fusion protein. In some examples, an IL-10 receptor agonist is an IL-10 peptide mimetic.

An IL-10 agonist is an agent which increases IL-10 activity in vitro or in a mammalian cell, e.g., as compared to the level of IL-10 activity in the absence of the agent.

In some embodiments, an IL-10 agonist can increase (e.g., by about 1% to about 99%, by about 1% to about 95%, by about 1% to about 90%, by about 1% to about 85%, by about 1% to about 80%, by about 1% to about 75%, by about 1% to about 70%, by about 1% to about 65%, by about 1% to about 60%, by about 1% to about 55%, by about 1% to about 50%, by about 1% to about 45%, by about 1% to about 40%, by about 1% to about 35%, by about 1% to about 30%, by about 1% to about 25%, by about 1% to about 20%, by about 1% to about 20%, by about 1% to about 15%, by about 1% to about 10%, by about 1% to about 5%, by about 5% to about 99%, by about 5% to about 90%, by about 5% to about 85%, by about 5% to about 80%, by about 5% to about 75%, by about 5% to about 70%, by about 5% to about 65%, by about 5% to about 60%, by about 5% to about 55%, by about 5% to about 50%, by about 5% to about 45%, by about 5% to about 40%, by about 5% to about 35%, by about 5% to about 30%, by about 5% to about 25%, by about 5% to about 20%, by about 5% to about 15%, by about 5% to about 10%, by about 10% to about 99%, about 10% to about 95%, about 10% to about 90%, about 10% to about 85%, by about 10% to about 80%, by about 10% to about 75%, by about 10% to about 70%, by about 10% to about 65%, by about 10% to about 60%, by about 10% to about 55%, by about 10% to about 50%, by about 10% to about 45%, by about 10% to about 40%, by about 10% to about 35%, by about 10% to about 30%, by about 10% to about 25%, by about 10% to about 20%, by about 10% to about 15%, by about 15% to about 99%, by about 15% to about 95%, by about 15% to about 90%, by about 15% to about 85%, by about 15% to about 80%, by about 15% to about 75%, by about 15% to about 70%, by about 15% to about 65%, by about 15% to about 60%, by about 15% to about 55%, by about 15% to about 50%, by about 15% to about 45%, by about 15% to about 40%, by about 15% to about 35%, by about 15% to about 30%, by about 15% to about 25%, by about 15% to about 20%, by about 20% to about 99%, by about 20% to about 95%, by about 20% to about 90%, by about 20% to about 85%, by about 20% to about 80%, by about 20% to about 75%, by about 20% to about 70%, by about 20% to about 65%, by about 20% to about 60%, by about 20% to about 55%, by about 20% to about 50%, by about 20% to about 45%, by about 20% to about 40%, by about 20% to about 35%, by about 20% to about 30%, by about 20% to about 25%, by about 25% to about 99%, about 25% to about 95%, by about 25% to about 90%, by about 25% to about 85%, by about 25% to about 80%, by about 25% to about 75%, by about 25% to about 70%, by about 25% to about 65%, by about 25% to about 60%, by about 25% to about 55%, by about 25% to about 50%, by about 25% to about 45%, by about 25% to about 40%, by about 25% to about 35%, by about 25% to about 30%, by about 30% to about 99%, by about 30% to about 95%, by about 30% to about 90%, by about 30% to about 85%, by about 30% to about 80%, by about 30% to about 75%, by about 30% to about 70%, by about 30% to about 65%, by about 30% to about 60%, by about 30% to about 55%, by about 30% to about 50%, by about 30% to about 45%, by about 30% to about 40%, by about 30% to about 35%, by about 35% to about 99%, by about 35% to about 95%, by about 35% to about 90%, by about 35% to about 85%, by about 35% to about 80%, by about 35% to about 75%, by about 35% to about 70%, by about 35% to about 65%, by about 35% to about 60%, by about 35% to about 55%, by about 35% to about 50%, by about 35% to about 45%, by about 35% to about 40%, by about 40% to about 99%, by about 40% to about 95%, by about 40% to about 90%, by about 40% to about 85%, by about 40% to about 80%, by about 40% to about 75%, by about 40% to about 70%, by about 40% to about 65%, by about 40% to about 60%, by about 40% to about 55%, by about 40% to about 50%, by about 45% to about 99%, by about 45% to about 95%, by about 45% to about 90%, by about 45% to about 85%, by about 45% to about 80%, by about 45% to about 75%, by about 45% to about 70%, by about 45% to about 65%, by about 45% to about 60%, by about 45% to about 55%, by about 45% to about 50%, by about 50% to about 99%, by about 50% to about 95%, by about 50% to about 90%, by about 50% to about 85%, by about 50% to about 80%, by about 50% to about 75%, by about 50% to about 70%, by about 50% to about 65%, by about 50% to about 60%, by about 50% to about 55%, by about 55% to about 99%, by about 55% to about 95%, by about 55% to about 90%, by about 55% to about 85%, by about 55% to about 80%, by about 55% to about 75%, by about 55% to about 70%, by about 55% to about 65%, by about 55% to about 60%, by about 60% to about 99%, by about 60% to about 95%, by about 60% to about 90%, by about 60% to about 85%, by about 60% to about 80%, by about 60% to about 75%, by about 60% to about 70%, by about 65% to about 99%, by about 65% to about 95%, by about 65% to about 90%, by about 65% to about 85%, by about 65% to about 80%, by about 65% to about 75%, by about 65% to about 70%, by about 70% to about 99%, by about 70% to about 95%, by about 70% to about 90%, by about 70% to about 85%, by about 70% to about 80%, by about 70% to about 75%, by about 75% to about 99%, by about 75% to about 95%, by about 75% to about 90%, by about 75% to about 85%, by about 75% to about 80%, by about 80% to about 99%, by about 80% to about 95%, by about 80% to about 90%, by about 80% to about 85%, by about 85% to about 99%, by about 85% to about 95%, by about 85% to about 90%, by about 90% to about 99%, by about 90% to about 95%, or by about 95% to about 99%) the activity of IL-10 protein in a mammalian cell contacted with the agent, e.g., as compared to the level of IL-10 in the same mammalian cell not contacted with the agent.

In some embodiments, an IL-10 agonist can agonize IL-10 activity with an $EC_{50}$ of about 1 pM to about 100 µM, about 1 pM to about 95 µM, about 1 pM to about 90 µM, about 1 pM to about 85 µM, about 1 pM to about 80 µM, about 1 pM to about 75 µM, about 1 pM to about 70 µM, about 1 pM to about 65 µM, about 1 pM to about 60 µM, about 1 pM to about 55 µM, about 1 pM to about 50 µM, about 1 pM to about 45 µM, about 1 pM to about 40 µM, about 1 pM to about 35 µM, about 1 pM to about 30 µM, about 1 pM to about 25 µM, about 1 pM to about 20 µM, about 1 pM to about 15 µM, about 1 pM to about 10 µM, about 1 pM to about 5 µM, about 1 pM to about 1 µM, about 1 pM to about 900 nM, about 1 pM to about 800 nM, about 1 pM to about 700 nM, about 1 pM to about 600 nM, about 1 pM to about 500 nM, about 1 pM to about 400 nM, about 1 pM to about 300 nM, about 1 pM to about 200 nM, about 1 pM to about 100 nM, about 1 pM to about 50 nM, about 1 pM to about 1 nM, about 1 pM to about 800 pM, about 1 pM to about 600 pM, about 1 pM to about 400 pM, about 1 pM to about 200 pM, about 200 pM to about 100 µM, about 200 pM to about 95 µM, about 200 pM to about 90 µM, about 200 pM to about 85 µM, about 200 pM to about 80 µM, about 200 pM to about 75 µM, about 200 pM to about 70 µM, about 200 pM to about 65 µM, about 200 pM to about 60 µM, about 200 pM to about 55 µM, about 200 pM to about 50 µM, about 200 pM to about 45 µM, about 200 pM to about 40 µM, about 200 pM to about 35 µM, about 200 pM to about 30 µM, about 200 pM to about 25 µM, about 200 pM to about 20 µM, about 200 pM to about 15 µM, about 200 pM to about 10 µM, about 200 pM to about 5 µM, about 200 pM to about 1 µM, about 200 pM to about 900 nM, about 200 pM to about 800 nM, about 200 pM to about 700 nM, about 200 pM to about 600 nM, about 200 pM to about 500 nM, about 200 pM to about 400 nM, about 200 pM to about 300 nM, about 200 pM to about 200 nM, about 200 pM to about 100 nM, about 200 pM to about 50 nM, about 200 pM to about 1 nM, about 200 pM to about 800 pM, about 200 pM to about 600 pM, about 200 pM to about 400 pM, about 400 pM to about 100 µM, about 400 pM to about 95 µM, about 400 pM to about 90 µM, about 400 pM to about 85 µM, about 400 pM to about 80 µM, about 400 pM to about 75 µM, about 400 pM to about 70 µM, about 400 pM to about 65 µM, about 400 pM to about 60 µM, about 400 pM to about 55 µM, about 400 pM to about 50 µM, about 400 pM to about 45 µM, about 400 pM to about 40 µM, about 400 pM to about 35 µM, about 400 pM to about 30 µM, about 400 pM to about 25 µM, about 400 pM to about 20 µM, about 400 pM to about 15 µM, about 400 pM to about 10 µM, about 400 pM to about 5 µM, about 400 pM to about 1 µM, about 400 pM to about 900 nM, about 400 pM to about 800 nM, about 400 pM to about 700 nM, about 400 pM to about 600 nM, about 400 pM to about 500 nM, about 400 pM to about 400 nM, about 400 pM to about 300 nM, about 400 pM to about 200 nM, about 400 pM to about 100 nM, about 400 pM to about 50 nM, about 400 pM to about 1 nM, about 400 pM to about 800 pM, 400 pM to about 600 pM, about 600 pM to about 100 µM, about 600 pM to about 95 µM, about 600 pM to about 90 µM, about 600 pM to about 85 µM, about 600 pM to about 80 µM, about 600 pM to about 75 µM, about 600 pM to about 70 µM, about 600 pM to about 65 µM, about 600 pM to about 60 µM, about 600 pM to about 55 µM, about 600 pM to about 50 µM, about 600 pM to about 45 µM, about 600 pM to about 40 µM, about 600 pM to about 35 µM, about 600 pM to about 30 µM, about 600 pM to about 25 µM, about 600 pM to about 20 µM, about 600 pM to about 15 µM, about 600 pM to about 10 µM, about 600 pM to about 5 µM, about 600 pM to about 1 µM, about 600 pM to about 900 nM, about 600 pM to about 800 nM, about 600 pM to about 700 nM, about 600 pM to about 600 nM, about 600 pM to about 500 nM, about 600 pM to about 400 nM, about 600 pM to about 300 nM, about 600 pM to about 200 nM, about 600 pM to about 100 nM, about 600 pM to about 50 nM, about 600 pM to about 1 nM, about 600 pM to about 800 pM, about 800 pM to about 100 µM, about 800 pM to about 95 µM, about 800 pM to about 90 µM, about 800 pM to about 85 µM, about 800 pM to about 80 µM, about 800 pM to about 75 µM, about 800 pM to about 70 µM, about 800 pM to about 65 µM, about 800 pM to about 60 µM, about 800 pM to about 55 µM, about 800 pM to about 50 µM, about 800 pM to about 45 µM, about 800 pM to about 40 µM, about 800 pM to about 35 µM, about 800 pM to about 30 µM, about 800 pM to about 25 µM, about 800 pM to about 20 µM, about 800 pM to about 15 µM, about 800 pM to about 10 µM, about 800 pM to about 5 µM, about 800 pM to about 1 µM, about 800 pM to about 900 nM, about 800 pM to about 800 nM, about 800 pM to about 700 nM, about 800 pM to about 600 nM, about 800 pM to about 500 nM, about 800 pM to about 400 nM, about 800 pM to about 300 nM, about 800 pM to about 200 nM, about 800 pM to about 100 nM, about 800 pM to about 50 nM, about 800 pM to about 1 nM, about 1 nM to about 100 µM, about 1 nM to about 95 µM, about 1 nM to about 90 µM, about 1 nM to about 85 µM, about 1 nM to about 80 µM, about 1 nM to about 75 µM, about 1 nM to about 70 µM, about 1 nM to about 65 µM, about 1 nM to about 60 µM, about 1 nM to about 55 µM, about 1 nM to about 50 µM, about 1 nM to about 45 µM, about 1 nM to about 40 µM, about 1 nM to about 35 µM, about 1 nM to about 30 µM, about 1 nM to about 25 µM, about 1 nM to about 20 µM, about 1 nM to about 15 µM, about 1 nM to about 10 µM, about 1 nM to about 5 µM, about 1 nM to about 1 µM, about 1 nM to about 900 nM, about 1 nM to about 800 nM, about 1 nM to about 700 nM, about 1 nM to about 600 nM, about 1 nM to about 500 nM, about 1 nM to about 400 nM, about 1 nM to about 300 nM, about 1 nM to about 200 nM, about 1 nM to about 100 nM, about 1 nM to about 50 nM, about 50 nM to about 100 µM, about 50 nM to about 95 µM, about 50 nM to about 90 µM, about 50 nM to about 85 µM, about 50 nM to about 80 µM, about 50 nM to about 75 µM, about 50 nM to about 70 µM, about 50 nM to about 65 µM, about 50 nM to about 60 µM, about 50 nM to about 55 µM, about 50 nM to about 50 µM, about 50 nM to about 45 µM, about 50 nM to about 40 µM, about 50 nM to about 35 µM, about 50 nM to about 30 µM, about 50 nM to about 25 µM, about 50 nM to about 20 µM, about 50 nM to about 15 µM, about 50 nM to about 10 µM, about 50 nM to about 5 µM, about 50 nM to about 1 µM, about 50 nM to about 900 nM, about 50 nM to about 800 nM, about 50 nM to about 700 nM, about 50 nM to about 600 nM, about 50 nM to about 500 nM, about 50 nM to about 400 nM, about 50 nM to about 300 nM, about 50 nM to about 200 nM, about 50 nM to about 100 nM, about 100 nM to about 100 µM, about 100 nM to about 95 µM, about 100 nM to about 90 µM, about 100 nM to about 85 µM, about 100 nM to about 80 µM, about 100 nM to about 75 µM, about 100 nM to about 70 µM, about 100 nM to about 65 µM, about 100 nM to about 60 µM, about 100 nM to about 55 µM, about 100 nM to about 50 µM, about 100 nM to about 45 µM, about 100 nM to about 40 µM, about 100 nM to about 35 µM, about 100 nM to about 30 µM, about 100 nM to about 25 µM, about 100 nM to about 20 µM, about 100 nM to about 15 µM, about 100 nM to about 10 µM, about 100 nM to about 5 µM, about 100 nM to about 1 µM, about 100 nM to about 900 nM, about 100 nM to about 800 nM, about 100 nM to about 700 nM, about 100 nM to about 600 nM, about 100 nM to about 500 nM, about 100 nM to about 400 nM, about 100 nM to about 300 nM, about 100 nM to about 200 nM, about 200 nM to about 100 µM, about 200 nM to about 95 µM, about 200 nM to about 90 µM, about 200 nM to about 85 µM, about 200 nM to about 80 µM, about 200 nM to about 75 µM, about 200 nM to about 70 µM, about 200 nM to about 65 µM, about 200 nM to about 60 µM, about 200 nM to about 55 µM, about 200 nM to about 50 µM, about 200 nM to about 45 µM, about 200 nM to about 40 µM, about 200 nM to about 35 µM, about 200 nM to about 30 µM, about 200 nM to about 25 µM, about 200 nM to about 20 µM, about 200 nM to about 15 µM, about 200 nM to about 10 µM, about 200 nM to about 5 µM, about 200 nM to about 1 µM, about 200 nM to about 900 nM, about 200 nM to about 800 nM, about 200 nM to about 700 nM, about 200 nM to about 600 nM, about 200 nM to about 500 nM, about 200 nM to about 400 nM, about 200 nM to about 300 nM, about 300 nM to about 100 µM, about 300 nM to about 95 µM, about 300 nM to about 90 µM, about 300 nM to about 85 µM, about 300 nM to about 80 µM, about 300 nM to about 75 µM, about 300 nM to about 70 µM, about 300 nM to about 65 µM, about 300 nM to about 60 µM, about 300 nM to about 55 µM, about 300 nM to about 50 µM, about 300 nM to about 45 µM, about 300 nM to about 40 µM, about 300 nM to about 35 µM, about 300 nM to about 30 µM, about 300 nM to about 25 µM, about 300 nM to about 20 µM, about 300 nM to about 15 µM, about 300 nM to about 10 µM, about 300 nM to about 5 µM, about 300 nM to about 1 µM, about 300 nM to about 900 nM, about 300 nM to about 800 nM, about 300 nM to about 700 nM, about 300 nM to about 600 nM, about 300 nM to about 500 nM, about 300 nM to about 400 nM, about 400 nM to about 100 µM, about 400 nM to about 95 µM, about 400 nM to about 90 µM, about 400 nM to about 85 µM, about 400 nM to about 80 µM, about 400 nM to about 75 µM, about 400 nM to about 70 µM, about 400 nM to about 65 µM, about 400 nM to about 60 µM, about 400 nM to about 55 µM, about 400 nM to about 50 µM, about 400 nM to about 45 µM, about 400 nM to about 40 µM, about 400 nM to about 35 µM, about 400 nM to about 30 µM, about 400 nM to about 25 µM, about 400 nM to about 20 µM, about 400 nM to about 15 µM, about 400 nM to about 10 µM, about 400 nM to about 5 µM, about 400 nM to about 1 µM, about 400 nM to about 900 nM, about 400 nM to about 800 nM, about 400 nM to about 700 nM, about 400 nM to about 600 nM, about 400 nM to about 500 nM, about 500 nM to about 100 µM, about 500 nM to about 95 µM, about 500 nM to about 90 µM, about 500 nM to about 85 µM, about 500 nM to about 80 µM, about 500 nM to about 75 µM, about 500 nM to about 70 µM, about 500 nM to about 65 µM, about 500 nM to about 60 µM, about 500 nM to about 55 µM, about 500 nM to about 50 µM, about 500 nM to about 45 µM, about 500 nM to about 40 µM, about 500 nM to about 35 µM, about 500 nM to about 30 µM, about 500 nM to about 25 µM, about 500 nM to about 20 µM, about 500 nM to about 15 µM, about 500 nM to about 10 µM, about 500 nM to about 5 µM, about 500 nM to about 1 µM, about 500 nM to about 900 nM, about 500 nM to about 800 nM, about 500 nM to about 700 nM, about 500 nM to about 600 nM, about 600 nM to about 100 µM, about 600 nM to about 95 µM, about 600 nM to about 90 µM, about 600 nM to about 85 µM, about 600 nM to about 80 µM, about 600 nM to about 75 µM, about 600 nM to about 70 µM, about 600 nM to about 65 µM, about 600 nM to about 60 µM, about 600 nM to about 55 µM, about 600 nM to about 50 µM, about 600 nM to about 45 µM, about 600 nM to about 40 µM, about 600 nM to about 35 µM, about 600 nM to about 30 µM, about 600 nM to about 25 µM, about 600 nM to about 20 µM, about 600 nM to about 15 µM, about 600 nM to about 10 µM, about 600 nM to about 5 µM, about 600 nM to about 1 µM, about 600 nM to about 900 nM, about 600 nM to about 800 nM, about 600 nM to about 700 nM, about 700 nM to about 100 µM, about 700 nM to about 95 µM, about 700 nM to about 90 µM, about 700 nM to about 85 µM, about 700 nM to about 80 µM, about 700 nM to about 75 µM, about 700 nM to about 70 µM, about 700 nM to about 65 µM, about 700 nM to about 60 µM, about 700 nM to about 55 µM, about 700 nM to about 50 µM, about 700 nM to about 45 µM, about 700 nM to about 40 µM, about 700 nM to about 35 µM, about 700 nM to about 30 µM, about 700 nM to about 25 µM, about 700 nM to about 20 µM, about 700 nM to about 15 µM, about 700 nM to about 10 µM, about 700 nM to about 5 µM, about 700 nM to about 1 µM, about 700 nM to about 900 nM, about 700 nM to about 800 nM, about 800 nM to about 100 µM, about 800 nM to about 95 µM, about 800 nM to about 90 µM, about 800 nM to about 85 µM, about 800 nM to about 80 µM, about 800 nM to about 75 µM, about 800 nM to about 70 µM, about 800 nM to about 65 µM, about 800 nM to about 60 µM, about 800 nM to about 55 µM, about 800 nM to about 50 µM, about 800 nM to about 45 µM, about 800 nM to about 40 µM, about 800 nM to about 35 µM, about 800 nM to about 30 µM, about 800 nM to about 25 µM, about 800 nM to about 20 µM, about 800 nM to about 15 µM, about 800 nM to about 10 µM, about 800 nM to about 5 µM, about 800 nM to about 1 µM, about 800 nM to about 900 nM, about 900 nM to about 100 µM, about 900 nM to about 95 µM, about 900 nM to about 90 µM, about 900 nM to about 85 µM, about 900 nM to about 80 µM, about 900 nM to about 75 µM, about 900 nM to about 70 µM, about 900 nM to about 65 µM, about 900 nM to about 60 µM, about 900 nM to about 55 µM, about 900 nM to about 50 µM, about 900 nM to about 45 µM, about 900 nM to about 40 µM, about 900 nM to about 35 µM, about 900 nM to about 30 µM, about 900 nM to about 25 µM, about 900 nM to about 20 µM, about 900 nM to about 15 µM, about 900 nM to about 10 µM, about 900 nM to about 5 µM, about 900 nM to about 1 µM, about 1 µM to about 100 µM, about 1 µM to about 95 µM, about 1 µM to about 90 µM, about 1 µM to about 85 µM, about 1 µM to about 80 µM, about 1 µM to about 75 µM, about 1 µM to about 70 µM, about 1 µM to about 65 µM, about 1 µM to about 60 µM, about 1 µM to about 55 µM, about 1 µM to about 50 µM, about 1 µM to about 45 µM, about 1 µM to about 40 µM, about 1 µM to about 35 µM, about 1 µM to about 30 µM, about 1 µM to about 25 µM, about 1 µM to about 20 µM, about 1 µM to about 15 µM, about 1 µM to about 10 µM, about 1 µM to about 5 µM, about 5 µM to about 100 µM, about 5 µM to about 95 µM, about 5 µM to about 90 µM, about 5 µM to about 85 µM, about 5 µM to about 80 µM, about 5 µM to about 75 µM, about 5 µM to about 70 µM, about 5 µM to about 65 µM, about 5 µM to about 60 µM, about 5 µM to about 55 µM, about 5 µM to about 50 µM, about 5 µM to about 45 µM, about 5 µM to about 40 µM, about 5 µM to about 35 µM, about 5 µM to about 30 µM, about 5 µM to about 25 µM, about 5 µM to about 20 µM, about 5 µM to about 15 µM, about 5 µM to about 10 µM, about 10 µM to about 100 µM, about 10 µM to about 95 µM, about 10 µM to about 90 µM, about 10 µM to about 85 µM, about 10 µM to about 80 µM, about 10 µM to about 75 µM, about 10 µM to about 70 µM, about 10 µM to about 65 µM, about 10 µM to about 60 µM, about 10 µM to about 55 µM, about 10 µM to about 50 µM, about 10 µM to about 45 μM, about 10 μM to about 40 μM, about 10 μM to about 35 μM, about 10 μM to about 30 μM, about 10 μM to about 25 μM, about 10 μM to about 20 μM, about 10 μM to about 15 μM, about 15 μM to about 100 μM, about 15 μM to about 95 μM, about 15 μM to about 90 μM, about 15 μM to about 85 μM, about 15 μM to about 80 μM, about 15 μM to about 75 μM, about 15 μM to about 70 μM, about 15 μM to about 65 μM, about 15 μM to about 60 μM, about 15 μM to about 55 μM, about 15 μM to about 50 μM, about 15 μM to about 45 μM, about 15 μM to about 40 μM, about 15 μM to about 35 μM, about 15 μM to about 30 μM, about 15 μM to about 25 μM, about 15 μM to about 20 μM, about 20 μM to about 100 μM, about 20 μM to about 95 μM, about 20 μM to about 90 μM, about 20 μM to about 85 μM, about 20 μM to about 80 μM, about 20 μM to about 75 μM, about 20 μM to about 70 μM, about 20 μM to about 65 μM, about 20 μM to about 60 μM, about 20 μM to about 55 μM, about 20 μM to about 50 μM, about 20 μM to about 45 μM, about 20 μM to about 40 μM, about 20 μM to about 35 μM, about 20 μM to about 30 μM, about 20 μM to about 25 μM, about 25 μM to about 100 μM, about 25 μM to about 95 μM, about 25 μM to about 90 μM, about 25 μM to about 85 μM, about 25 μM to about 80 μM, about 25 μM to about 75 μM, about 25 μM to about 70 μM, about 25 μM to about 65 μM, about 25 μM to about 60 μM, about 25 μM to about 55 μM, about 25 μM to about 50 μM, about 25 μM to about 45 μM, about 25 μM to about 40 μM, about 25 μM to about 35 μM, about 25 μM to about 30 μM, about 30 μM to about 100 μM, about 30 μM to about 95 μM, about 30 μM to about 90 μM, about 30 μM to about 85 μM, about 30 μM to about 80 μM, about 30 μM to about 75 μM, about 30 μM to about 70 μM, about 30 μM to about 65 μM, about 30 μM to about 60 μM, about 30 μM to about 55 μM, about 30 μM to about 50 μM, about 30 μM to about 45 μM, about 30 μM to about 40 μM, about 30 μM to about 35 μM, about 35 μM to about 100 μM, about 35 μM to about 95 μM, about 35 μM to about 90 μM, about 35 μM to about 85 μM, about 35 μM to about 80 μM, about 35 μM to about 75 μM, about 35 μM to about 70 μM, about 35 μM to about 65 μM, about 35 μM to about 60 μM, about 35 μM to about 55 μM, about 35 μM to about 50 μM, about 35 μM to about 45 μM, about 35 μM to about 40 μM, about 40 μM to about 100 μM, about 40 μM to about 95 μM, about 40 μM to about 90 μM, about 40 μM to about 85 μM, about 40 μM to about 80 μM, about 40 μM to about 75 μM, about 40 μM to about 70 μM, about 40 μM to about 65 μM, about 40 μM to about 60 μM, about 40 μM to about 55 μM, about 40 μM to about 50 μM, about 40 μM to about 45 μM, about 45 μM to about 100 μM, about 45 μM to about 95 μM, about 45 μM to about 90 μM, about 45 μM to about 85 μM, about 45 μM to about 80 μM, about 45 μM to about 75 μM, about 45 μM to about 70 μM, about 45 μM to about 65 μM, about 45 μM to about 60 μM, about 45 μM to about 55 μM, about 45 μM to about 50 μM, about 50 μM to about 100 μM, about 50 μM to about 95 μM, about 50 μM to about 90 μM, about 50 μM to about 85 μM, about 50 μM to about 80 μM, about 50 μM to about 75 μM, about 50 μM to about 70 μM, about 50 μM to about 65 μM, about 50 μM to about 60 μM, about 50 μM to about 55 μM, about 55 μM to about 100 μM, about 55 μM to about 95 μM, about 55 μM to about 90 μM, about 55 μM to about 85 μM, about 55 μM to about 80 μM, about 55 μM to about 75 μM, about 55 μM to about 70 μM, about 55 μM to about 65 μM, about 55 μM to about 60 μM, about 60 μM to about 95 μM, about 60 μM to about 90 μM, about 60 μM to about 85 μM, about 60 μM to about 80 μM, about 60 μM to about 75 μM, about 60 μM to about 70 μM, about 60 μM to about 65 μM, about 65 μM to about 100 μM, about 65 μM to about 95 μM, about 65 μM to about 90 μM, about 65 μM to about 85 μM, about 65 μM to about 80 μM, about 65 μM to about 75 μM, about 65 μM to about 70 μM, about 70 μM to about 100 μM, about 70 μM to about 95 μM, about 70 μM to about 90 μM, about 70 μM to about 85 μM, about 70 μM to about 80 μM, about 70 μM to about 75 μM, about 75 μM to about 100 μM, about 75 μM to about 95 μM, about 75 μM to about 90 μM, about 75 μM to about 80 μM, about 80 μM to about 100 μM, about 80 μM to about 95 μM, about 80 μM to about 90 μM, about 80 μM to about 85 μM, about 85 μM to about 100 μM, about 85 μM to about 95 μM, about 85 μM to about 90 μM, about 90 μM to about 100 μM, about 90 μM to about 95 μM, or about 95 μM to about 100 μM.

In some embodiments, an IL-10 agonist can be a small molecule (e.g., an organic, an inorganic, or bioinorganic molecule) having a molecule weight of less than 900 Daltons (e.g., less than 500 Daltons). In some embodiments, an IL-10 agonist can be an inhibitory nucleic acid.

In some embodiments, any of the devices or compositions described herein can contain a recombinant mammalian cell (e.g., a recombinant human cell) that secretes an IL-10 receptor agonist (e.g., a recombinant IL-10, e.g., a recombinant human IL-10). In some embodiments, any of the devices or compositions described herein can contain a mammalian cell (e.g., a human cell) that secretes IL-10 (e.g., human IL-10).

Activation of an IL-10 receptor in a mammalian cell can be determined by detecting an increase in the activation of downstream signaling proteins in a mammalian cell contacted with an IL-10 receptor agonist. For example, activation of an IL-10 receptor in a mammalian cell can be detected by an increase in the phosphorylation and activity of JAK1 and TYK2, phosphorylation and subsequent nuclear translocation of STAT3, and/or increased transcription of BCLXL, Cyclin-D1, Cyclin-D2, Cyclin-D3, Cyclin-A, Pim1, c-Myc, or p19 (INK4D) (see, e.g., Hu et al., *J. Leukoc. Biol.* 82(2):237-243, 2007; and Cavalcante et al., *J. Periodontol.* 83(7):926-935, 2012). Reagents for detecting these downstream events that indicate activation of an IL-10 receptor are available from, e.g., ThermoFisher Scientific.

IL-10 and IL-10 Receptor

Exemplary sequences of human IL-10 proteins and cDNA sequences are shown below.

```
Precursor Human IL-10 Protein (with signal sequence in bold)
                                                       (SEQ ID NO: 1)
  1 mhssallccl vlltgvrasp gqgtqsensc thfpgnlpnm lrdlrdafsr vktffqmkdq 61 ldnlllkesl ledfkgylgc qalsemiqfy leevmpqaen qdpdikahvn slgenlktlr 121 lrlrrchrfl pcenkskave qvknafnklq ekgiykamse fdifinyiea ymtmkirn Mature Human IL-10 Protein
                                                       (SEQ ID NO: 2)
    spgqgtqsensc thfpgnlpnm lrdlrdafsr vktffqmkdq ldnlllkesl
```

```
     ledfkgylgc qalsemiqfy leevmpqaen qdpdikahvn slgenlktlr lrlrrchrfl pcenkskave qvknafnklq ekgiykamse fdifinyiea ymtmkirn Human IL-10 cDNA
                                                              (SEQ ID NO: 3)
   1 acacatcagg ggcttgctct tgcaaaacca aaccacaaga cagacttgca aaagaaggca 61 tgcacagctc agcactgctc tgttgcctgg tcctcctgac tggggtgagg gccagcccag 121 gccagggcac ccagtctgag aacagctgca cccacttccc aggcaacctg cctaacatgc 181 ttcgagatct ccgagatgcc ttcagcagag tgaagacttt ctttcaaatg aaggatcagc 241 tggacaactt gttgttaaag gagtccttgc tggaggactt aagggttac ctgggttgcc 301 aagccttgtc tgagatgatc cagttttacc tggaggaggt gatgcccaa gctgagaacc 361 aagacccaga catcaaggcg catgtgaact ccctggggga gaacctgaag accctcaggc 421 tgaggctacg cgctgtcat cgatttcttc cctgtgaaaa caagagcaag gccgtggagc 481 aggtgaagaa tgcctttaat aagctccaag agaaaggcat ctacaaagcc atgagtgagt 541 ttgacatctt catcaactac atagaagcct acatgacaat gaagatacga aactgagaca 601 tcagggtggc gactctatag actctaggac ataaattaga ggtctccaaa atcggatctg 661 gggctctggg atagctgacc cagccccttg agaaaccta ttgtacctct cttatagaat 721 atttattacc tctgatacct caaccccat ttctatttat ttactgagct tctctgtgaa 781 cgatttagaa agaagcccaa tattataatt tttttcaata tttattattt tcacctgttt 841 ttaagctgtt tccatagggt gacacactat ggtatttgag tgttttaaga taaattataa 901 gttacataag ggaggaaaaa aaatgttctt tggggagcca acagaagctt ccattccaag 961 cctgaccacg ctttctagct gttgagctgt tttccctgac ctccctctaa tttatcttgt 1021 ctctgggctt ggggcttcct aactgctaca aatactctta ggaagagaaa ccagggagcc 1081 cctttgatga ttaattcacc ttccagtgtc tcggagggat tcccctaacc tcattcccca 1141 accacttcat tcttgaaagc tgtggccagc ttgttattta taacaaccta aatttggttc 1201 taggccgggc gcggtggctc acgcctgtaa tcccagcact ttgggaggct gaggcgggtg 1261 gatcacttga ggtcaggagt tcctaaccag cctggtcaac atggtgaaac cccgtctcta 1321 ctaaaaatac aaaaattagc cgggcatggt ggcgcgcacc tgtaatccca gctacttggg 1381 aggctgaggc aagagaattg cttgaaccca ggagatggaa gttgcagtga gctgatatca 1441 tgccctgta ctccagcctg ggtgacagag caagactctg tctcaaaaaa taaaataaa 1501 aataaatttg gttctaatag aactcagttt taactagaat ttattcaatt cctctgggaa 1561 tgttacattg tttgtctgtc ttcatagcag attttaattt tgaataaata aatgtatctt 1621 attcacatc
```

The protein and cDNA sequences of exemplary non-human homologues of IL-10 are shown below.

```
Precursor Mouse IL-10 Protein (with signal sequence in bold)
                                                              (SEQ ID NO: 4)
   1 mpgsallccl llltgmrisr gqysrednnc thfpvgqshm llelrtafsq vktffqtkdq 61 ldnilltdsl mqdfkgylgc qalsemiqfy lvevmpqaek hgpeikehln slgeklktlr 121 mrlrrchrfl pcenkskave qvksdfnklq dqgvykamne fdifinciea ymmikmks Mouse IL-10 cDNA
                                                              (SEQ ID NO: 5)
   1 acatttagag acttgctctt gcactaccaa agccacaagg cagccttgca gaaaagagag
```

-continued

```
 61 ctccatcatg cctggctcag cactgctatg ctgcctgctc ttactgactg gcatgaggat
121 cagcaggggc cagtacagcc gggaagacaa taactgcacc cacttcccag tcggccagag
181 ccacatgctc ctagagctgc ggactgcctt cagccaggtg aagactttct ttcaaacaaa
241 ggaccagctg acaacatac tgctaaccga ctccttaatg caggacttta agggttactt
301 gggttgccaa gccttatcgg aaatgatcca gttttacctg gtagaagtga tgccccaggc
361 agagaagcat ggcccagaaa tcaaggagca tttgaattcc ctgggtgaga agctgaagac
421 cctcaggatg cggctgaggc gctgtcatcg atttctcccc tgtgaaaata gagcaaggc
481 agtggagcag gtgaagagtg attttaataa gctccaagac caaggtgtct acaaggccat
541 gaatgaattt gacatcttca tcaactgcat agaagcatac atgatgatca aaatgaaaag
601 ctaaaacacc tgcagtgtgt attgagtctg ctggactcca ggacctagac agagctctct
661 aaatctgatc cagggatctt agctaacgga acaactcct tggaaaacct cgtttgtacc
721 tctctccgaa atatttatta cctctgatac ctcagttccc attctattta ttcactgagc
781 ttctctgtga actatttaga aagaagccca atattataat tttacagtat ttattatttt
841 taacctgtgt ttaagctgtt tccattgggg cactttata gtatttaaag ggagattata
901 ttatatgatg ggaggggttc ttccttggga agcaattgaa gcttctattc taaggctggc
961 cacacttgag agctgcaggg ccctttgcta tggtgtcctt tcaattgctc tcatccctga
1021 gttcagagct cctaagagag ttgtgaagaa actcatgggt cttgggaaga gaaaccaggg
1081 agatcctttg atgatcattc ctgcagcagc tcagagggtt ccctactgt catcccccag
1141 ccgcttcatc cctgaaaact gtggccagtt tgttatttat aaccacctaa aattagttct
1201 aatagaactc attttaact agaagtaatg caattcctct gggaatggtg tattgtttgt
1261 ctgcctttgt agcagactct aattttgaat aaatggatct tattcg
```

Precursor Rat IL-10 Protein (with signal sequence in bold)

(SEQ ID NO: 6)
```
  1 mpgsallccl lllagvktsk ghsirgdnnc thfpvsqthm lrelraafsq vktffqkkdq
 61 ldnilltdsl lqdfkgylgc qalsemikfy lvevmpqaen hgpeikehln slgeklktlw
121 iqlrrchrfl pcenkskave qvkndfnklq dkgvykamne fdifinciea yvtlkmkn
```

Rat IL-10 cDNA (SEQ ID NO: 7)
```
  1 catgcctggc tcagcactgc tatgttgcct gctcttactg gctggagtga agaccagcaa
 61 aggccattcc atccggggtg acaataactg cacccacttc ccagtcagcc agacccacat
121 gctccgagag ctgagggctg ccttcagtca agtgaagact ttctttcaaa agaaggacca
181 gctggacaac atactgctga cagattcctt actgcaggac tttaagggtt acttgggttg
241 ccaagccttg tcagaaatga tcaagtttta cctggtagaa gtgatgcccc aggcagagaa
301 ccatggccca gaaatcaagg agcatttgaa ttccctggga gaagctgaga ccctctgt
361 gatacagctg cgacgctgtc atcgatttct ccctgtgag aataaaagca aggcagtgga
421 gcaggtgaag aatgatttta ataagctcca agacaaaggt gtctacaagg ccatgaatga
481 gtttgacatc ttcatcaact gcatagaagc ctacgtgaca ctcaaaatga aaattgaac
541 cacccggcat ctactggact gcaggacata aatagagctt ctaaatctga tccagagatc
601 ttagctaacg ggagcaactc cttggaaaac ctcgtttgta cctctctcca aaatatttat
661 tacctctgat acctcagttc cc
```

Precursor Rabbit IL-10 Protein
(SEQ ID NO: 8)

```
  1 mlssallccl vflggtgasr gqdtpaensc ihfpgglphm lrelraafgr vktffqskdq
 61 lnsmlltesl ledlkgylgc qalsemiqfy lkdvmpqaen hspairehvn slgenlktlr
121 lrlrqchrfl pcenkskave qvksafsklq eegvykamse fdifinyiet ymtmkiks
```

Rabbit IL-10 cDNA
(SEQ ID NO: 9)

```
   1 aaagcaaacc acaaggcgga ctcgtagaag caggcagagt tccaccatgc tcagctcagc
  61 tctgctatgt tgcctggtct tcctgggtgg acaggggcc agccgaggcc aggacacccc
 121 tgctgagaac agctgcattc actttccagg cggcctgccc cacatgctcc gcgagctccg
 181 tgctgccttt ggcagggtga agacttttct tcaatcgaag gatcagctga acagcatgtt
 241 gttaaccgag tccctgctgg aggaccttaa gggttacctg ggatgccaag ccttgtcgga
 301 gatgatccag ttttacctga aggacgtgat gccgcaagct gagaaccaca gtccagccat
 361 cagggagcac gtgaactccc tggggaaaa cctgaagacc ctcaggctga ggctgcgaca
 421 atgtcaccga tttctcccct gtgaaaacaa gagcaaggca gtggagcagg tgaagagcgc
 481 cttcagcaag ctgcaagagg aaggcgtcta caaagccatg agtgagtttg acatcttcat
 541 caactacata gaaacctaca tgacaatgaa gataaaaagc taaaagcccc aggatggcaa
 601 ctcggctaga gtctaggaca tcagttaggg acctgcacac cctgggtcag ctgacccagc
 661 accttggaaa gctgttgtac ctctcaatat ttattacctc tgatacctca gctcccgatc
 721 ctatttattt accgagcttc tctgtgaact ctttagaaag aagcccacta ttataatttt
 781 ttcagtattt attattttca cctgcattta agctgtaccc atggggtgat gccctgtggg
 841 atttgagtgt cttaggagaa attataattt atgtgaaagg gaaaatgtgc cttggggagc
 901 cgactgaggc ttccattcct tctgtgcctg accacacttt ctaactccta agccgagctc
 961 cctcttaccc tctggagccc ggacctgggt ctcgagtgtt ccagagactc ctagcctctt
1021 aggaagagag accggaagcc cttgggtggt gaccttccgg cagctcagag ggaggctcct
1081 gacctcgat
```

Precursor Monkey IL-10 Protein (with signal sequence in bold)
(SEQ ID NO: 10)

```
  1 mhssallccl vlltgvrasp gqgtqsensc trfpgnlphm lrdlrdafsr vktffqmkdq
 61 ldnillkesl ledfkgylgc qalsemiqfy leevmpqaen hdpdikehvn slgenlktlr
121 lrlrrchrfl pcenkskave qvknafsklq ekgvykamse fdifinyiea ymtmkiqn
```

Monkey IL-10 cDNA
(SEQ ID NO: 11)

```
  1 agaaggcatg cacagctcag cactgctctg ttgcctagtc ctcctgactg ggtgagggc
 61 cagcccaggc cagggcaccc agtctgagaa cagctgcacc cgcttcccag gcaacctgcc
121 tcacatgctt cgagacctcc gagatgcctt cagcagagtg aagactttct tcaaatgaa
181 ggatcagctg acaacatat tgttaaagga gtccttgctg gaggacttta agggttacct
241 gggttgccaa gccttgtctg agatgatcca gttttacctg gaggaggtga tgccccaagc
301 tgagaaccac gacccagaca tcaaggagca tgtgaactcc ctgggggaga atctgaagac
361 cctcaggctg aggctgcggc gctgtcatcg atttcttccc tgtgaaaaca gagcaaggc
421 cgtggagcag gtgaagaatg cctttagtaa gctccaagag aaaggcgtct acaaagccat
481 gagtgagttt gacatcttca tcaactacat agaagcctac atgacaatga agatacaaaa
541 ctgagacatc agggtggcga ctctatagac tctaggacat aaattagagg tctccaaaat
601 cagatccagg gttctgggat agctgaccca gccccttgag aaa
```

Exemplary protein and cDNA sequences for human IL-10R-1 and human IL-10R-2 are shown below.

```
Precursor Human IL-10R-1 Protein (with signal sequence in bold)
                                                         (SEQ ID NO: 12)
   1 mlpclvvlla allslrlgsd ahgtelpspp svwfeaeffh hilhwtpipn qsestcyeva 61 llrygieswn sisncsqtls ydltavtldl yhsngyrarv ravdgsrhsn wtvtntrfsv 121 devtltvgsv nleihngfil gkiqlprpkm apandtyesi fshfreyeia irkvpgnftf 181 thkkvkhenf slltsgevge fcvqvkpsva srsnkgmwsk eecisltrqy ftvtnviiff 241 afvlllsgal ayclalqlyv rrrkklpsvl lfkkpspfif isqrpspetq dtihpldeea 301 flkvspelkn ldlhgstdsg fgstkpslqt eepqfllpdp hpqadrtlgn reppvlgdsc 361 ssgssnstds giclqepsls pstgptweqq vgsnsrgqdd sgidlvqnse gragdtqggs 421 alghhsppep evpgeedpaa vafqgylrqt rcaeekatkt gcleeesplt dglgpkfgrc 481 lvdeaglhpp alakgylkqd plemtlassg aptgqwnqpt eewsllalss csdlgisdws 541 fandlaplgc vaapgqllgs fnsdlvtlpl isslqsse
Human IL-10R-1 cDNA, transcript variant 1
                                                         (SEQ ID NO: 13)
   1 gtcagtccca gcccaagggt agctggaggc gcgcaggccg gctccgctcc ggccccggac 61 gatgcggcgc gcccaggatg ctgccgtgcc tcgtagtgct gctggcggcg ctcctcagcc 121 tccgtcttgg ctcagacgct catgggacag agctgcccag ccctccgtct gtgtggtttg 181 aagcagaatt tttccaccac atcctccact ggacacccat cccaaatcag tctgaaagta 241 cctgctatga agtggcgctc ctgaggtatg gaatagagtc tggaactcc atctccaact 301 gtagccagac cctgtcctat gaccttaccg cagtgacctt ggacctgtac cacagcaatg 361 gctaccgggc cagagtgcgg gctgtggacg gcagccggca ctccaactgg accgtcacca 421 acacccgctt ctctgtggat gaagtgactc tgacagttgg cagtgtgaac ctagagatcc 481 acaatggctt catcctcggg aagattcagc tacccaggcc caagatggcc ccgcaaatg 541 acacatatga aagcatcttc agtcacttcc gagagtatga gattgccatt cgcaaggtgc 601 cgggaaactt cacgttcaca cacaagaaag taaaacatga aacttcagc ctcctaacct 661 ctggagaagt gggagagttc tgtgtccagg tgaaaccatc tgtcgcttcc cgaagtaaca 721 aggggatgtg gtctaaagag gagtgcatct ccctcaccag gcagtatttc accgtgacca 781 acgtcatcat cttctttgcc tttgtcctgc tgctctccgg agccctcgcc tactgcctgg 841 ccctccagct gtatgtgcgg cgccgaaaga agctacccag tgtcctgctc ttcaagaagc 901 ccagcccctt catcttcatc agccagcgtc cctccccaga gacccaagac accatccacc 961 cgcttgatga ggaggccttt ttgaaggtgt ccccagagct gaagaacttg gacctgcacg 1021 gcagcacaga cagtggcttt ggcagcacca agccatccct gcagactgaa gagccccagt 1081 tcctcctccc tgaccctcac ccccaggctg cagaacgct gggaaacagg agcccccctg 1141 tgctggggga cagctgcagt agtggcagca gcaatagcac agacagcggg atctgcctgc 1201 aggagcccag cctgagcccc agcacagggc ccacctggga gcaacaggtg gggagcaaca 1261 gcaggggcca ggatgacagt ggcattgact tagttcaaaa ctctgagggc cgggctgggg 1321 acacacaggg tggctcggcc ttgggccacc acagtccccc ggagcctgag gtgcctgggg 1381 aagaagaccc agctgctgtg gcattccagg gttacctgag gcagaccaga tgtgctgaag 1441 agaaggcaac caagacaggc tgcctggagg aagaatcgcc cttgacagat ggccttggcc 1501 ccaaattcgg gagatgcctg gttgatgagg caggcttgca tccaccagcc ctggccaagg 1561 gctatttgaa acaggatcct ctagaaatga ctctggcttc ctcaggggcc caacgggac
```

```
-continued
1621 agtggaacca gcccactgag gaatggtcac tcctggcctt gagcagctgc agtgacctgg 1681 gaatatctga ctggagcttt gcccatgacc ttgcccctct aggctgtgtg gcagcccag 1741 gtggtctcct gggcagcttt aactcagacc tggtcaccct gcccctcatc tctagcctgc 1801 agtcaagtga gtgactcggg ctgagaggct gcttttgatt ttagccatgc ctgctcctct 1861 gcctggacca ggaggagggc ccctggggca gaagttaggc acgaggcagt ctgggcactt 1921 ttctgcaagt ccactggggc tggccccagc caggccctgc agggctggtc agggtgtctg 1981 gggcaggagg aggccaactc actgaactag tgcagggtat gtgggtggca ctgacctgtt 2041 ctgttgactg gggccctgca gactctggca gagctgagaa gggcagggac cttctccctc 2101 ctaggaactc tttcctgtat cataaaggat tatttgctca ggggaaccat ggggctttct 2161 ggagttgtgg tgaggccacc aggctgaagt cagctcagac ccagacctcc ctgcttaggc 2221 cactcgagca tcagagcttc cagcaggagg aagggctgta ggaatggaag cttcagggcc 2281 ttgctgctgg ggtcattttt aggggaaaaa ggaggatatg atggtcacat ggggaacctc 2341 ccctcatcgg gcctctgggg caggaagctt gtcactggaa gatcttaagg tatatatttt 2401 ctggacactc aaacacatca taatggattc actgagggga gacaaaggga gccgagaccc 2461 tggatggggc ttccagctca gaacccatcc ctctggtggg tacctctggc acccatctgc 2521 aaatatctcc ctctctccaa caaatggagt agcatccccc tggggcactt gctgaggcca 2581 agccactcac atcctcactt tgctgcccca ccatcttgct gacaacttcc agagaagcca 2641 tggttttttg tattggtcat aactcagccc tttgggcggc ctctgggctt gggcaccagc 2701 tcatgccagc cccagagggt cagggttgga ggcctgtgct tgtgtttgct gctaatgtcc 2761 agctacagac ccagaggata agccactggg cactgggctg gggtccctgc cttgttggtg 2821 ttcagctgtg tgattttgga ctagccactt gtcagagggc ctcaatctcc catctgtgaa 2881 ataaggactc cacctttagg ggaccctcca tgtttgctgg gtattagcca agctggtcct 2941 gggagaatgc agatactgtc cgtggactac caagctggct tgtttcttat gccagaggct 3001 aacagatcca atgggagtcc atggtgtcat gccaagacag tatcagacac agccccagaa 3061 gggggcatta tgggccctgc ctccccatag gccatttgga ctctgccttc aaacaaaggc 3121 agttcagtcc acaggcatgg aagctgtgag gggacaggcc tgtgcgtgcc atccagagtc 3181 atctcagccc tgcctttctc tggagcattc tgaaaacaga tattctggcc cagggaatcc 3241 agccatgacc cccacccctc tgccaaagta ctcttaggtg ccagtctggt aactgaactc 3301 cctctggagg caggcttgag ggaggattcc tcagggttcc cttgaaagct ttatttattt 3361 attttgttca tttatttatt ggagaggcag cattgcacag tgaaagaatt ctggatatct 3421 caggagcccc gaaattctag ctctgacttt gctgtttcca gtggtatgac cttggagaag 3481 tcacttatcc tcttggagcc tcagtttcct catctgcaga ataatgactg acttgtctaa 3541 ttcgtaggga tgtgaggttc tgctgaggaa atgggtatga atgtgccttg aacacaaagc 3601 tctgtcaata agtgatacat gttttttatt ccaataaatt gtcaagacca caggaaaaaa 3661 aaaaaaaaaa aa
Human IL-10R-1 cDNA, transcript variant 2
                                                        (SEQ ID NO: 14)
   1 gtcagtccca gcccaagggt agctggaggc gcgcaggccg gctccgctcc ggccccggac 61 gatgcggcgc gcccaggatg ctgccgtgcc tcgtagtgct gctggcggcg ctcctcagcc 121 tccgtcttgg ctcagacgct catggctcac tgttgtggaa gtggaagag gctgaaattg 181 acaggaactg acggattggg aaggatagaa aagtatgcgc aaggccaaac ccccaacccg 241 caaacctcat catccaccca cttctagatg agccggacag agctgcccag ccctccgtct
```

-continued

```
 301 gtgtggtttg aagcagaatt tttccaccac atcctccact ggacacccat cccaaatcag
 361 tctgaaagta cctgctatga agtggcgctc ctgaggtatg aatagagtc ctggaactcc
 421 atctccaact gtagccagac cctgtcctat gaccttaccg cagtgacctt ggacctgtac
 481 cacagcaatg gctaccgggc cagagtgcgg gctgtggacg gcagccggca ctccaactgg
 541 accgtcacca cacccgctt ctctgtggat gaagtgactc tgacagttgg cagtgtgaac
 601 ctagagatcc acaatggctt catcctcggg aagattcagc tacccaggcc caagatggcc
 661 cccgcaaatg acacatatga aagcatcttc agtcacttcc gagagtatga gattgccatt
 721 cgcaaggtgc cgggaaactt cacgttcaca cacaagaaag taaaacatga aacttcagc
 781 ctcctaacct ctggagaagt gggagagttc tgtgtccagg tgaaaccatc tgtcgcttcc
 841 cgaagtaaca aggggatgtg gtctaaagag gagtgcatct ccctcaccag gcagtatttc
 901 accgtgacca acgtcatcat cttctttgcc tttgtcctgc tgctctccgg agccctcgcc
 961 tactgcctgg ccctccagct gtatgtgcgg cgccgaaaga agctacccag tgtcctgctc
1021 ttcaagaagc ccagcccctt catcttcatc agccagcgtc cctccccaga cccaagac
1081 accatccacc cgcttgatga ggaggccttt ttgaaggtgt ccccagagct gaagaacttg
1141 gacctgcacg gcagcacaga cagtggcttt ggcagcacca agccatccct gcagactgaa
1201 gagccccagt tcctcctccc tgaccctcac ccccaggctg acagaacgct gggaaacagg
1261 gagcccccctg tgctggggga cagctgcagt agtggcagca gcaatagcac agacagcggg
1321 atctgcctgc aggagcccag cctgagcccc agcacagggc ccacctggga gcaacaggtg
1381 gggagcaaca gcaggggcca ggatgacagt ggcattgact tagttcaaaa ctctgagggc
1441 cgggctgggg acacacaggg tggctcggcc ttgggccacc acagtccccc ggagcctgag
1501 gtgcctgggg aagaagaccc agctgctgtg gcattccagg gttacctgag cagaccaga
1561 tgtgctgaag agaaggcaac caagacaggc tgcctggagg aagaatcgcc cttgacagat
1621 ggccttggcc ccaaattcgg gagatgcctg gttgatgagg caggcttgca tccaccagcc
1681 ctggccaagg ctatttgaa acaggatcct ctagaaatga ctctggcttc ctcaggggcc
1741 ccaacgggac agtggaacca gcccactgag gaatggtcac tcctggcctt gagcagctgc
1801 agtgacctgg gaatatctga ctggagcttt gcccatgacc ttgcccctct aggctgtgtg
1861 gcagccccag tggtctcct ggcagcttaa actcagacc tggtcaccct gcccctcatc
1921 tctagcctgc agtcaagtga gtgactcggg ctgagaggct gcttttgatt ttagccatgc
1981 ctgctcctct gcctggacca ggaggagggc ccctgggca gaagttaggc acgaggcagt
2041 ctgggcactt ttctgcaagt ccactggggc tggccccagc caggccctgc agggctggtc
2101 agggtgtctg gggcaggagg aggccaactc actgaactag tgcagggtat gtgggtggca
2161 ctgacctgtt ctgttgactg gggccctgca gactctggca gagctgagaa gggcagggac
2221 cttctccctc ctaggaactc tttcctgtat cataaaggat tatttgctca ggggaaccat
2281 gggctttct ggagttgtgg tgaggccacc aggctgaagt cagctcagac ccagacctcc
2341 ctgcttaggc cactcgagca tcagagcttc cagcaggagg aagggctgta ggaatggaag
2401 cttcagggcc ttgctgctgg ggtcattttt aggggaaaaa ggaggatatg atggtcacat
2461 ggggaacctc ccctcatcgg gcctctgggg caggaagctt gtcactggaa gatcttaagg
2521 tatatatttt ctggacactc aaacacatca taatggattc actgagggga gacaaaggga
2581 gccgagaccc tggatggggc ttccagctca gaacccatcc ctctggtggg tacctctggc
2641 acccatctgc aaatatctcc ctctctccaa caaatggagt agcatccccc tggggcactt
```

-continued

```
2701 gctgaggcca agccactcac atcctcactt tgctgcccca ccatcttgct gacaacttcc
2761 agagaagcca tggttttttg tattggtcat aactcagccc tttgggcggc tctgggctt
2821 gggcaccagc tcatgccagc cccagagggt cagggttgga ggcctgtgct tgtgtttgct
2881 gctaatgtcc agctacagac ccagaggata agccactggg cactgggctg gggtccctgc
2941 cttgttggtg ttcagctgtg tgattttgga ctagccactt gtcagagggc ctcaatctcc
3001 catctgtgaa ataaggactc cacctttagg ggaccctcca tgtttgctgg gtattagcca
3061 agctggtcct gggagaatgc agatactgtc cgtggactac caagctggct tgtttcttat
3121 gccagaggct aacagatcca atgggagtcc atggtgtcat gccaagacag tatcagacac
3181 agccccagaa gggggcatta tgggccctgc ctccccatag gccatttgga ctctgccttc
3241 aaacaaaggc agttcagtcc acaggcatgg aagctgtgag gggacaggcc tgtgcgtgcc
3301 atccagagtc atctcagccc tgcctttctc tggagcattc tgaaaacaga tattctggcc
3361 cagggaatcc agccatgacc cccacccctc tgccaaagta ctcttaggtg ccagtctggt
3421 aactgaactc cctctggagg caggcttgag ggaggattcc tcagggttcc cttgaaagct
3481 ttatttattt attttgttca tttatttatt ggagaggcag cattgcacag tgaaagaatt
3541 ctggatatct caggagcccc gaaattctag ctctgacttt gctgtttcca gtggtatgac
3601 cttggagaag tcacttatcc tcttggagcc tcagtttcct catctgcaga ataatgactg
3661 acttgtctaa ttcgtaggga tgtgaggttc tgctgaggaa atgggtatga atgtgccttg
3721 aacacaaagc tctgtcaata agtgatacat gttttttatt ccaataaatt gtcaagacca
3781 caggaaaaaa aaaaaaaaaa aa
```

Precursor Human IL-10R-2 Protein (with signal sequence in bold)
(SEQ ID NO: 15)

```
  1 mawslgswlg gcllvsalgm vpppenvrmn svnfknilqw espafakgnl tftaqylsyr
 61 ifqdkcmntt ltecdfssls kygdhtlrvr aefadehsdw vnitfcpvdd tiigppgmqv
121 evladslhmr flapkieney etwtmknvyn swtynvqywk ngtdekfqit pqydfevlrn
181 lepwttycvq vrgflpdrnk agewsepvce qtthdetvps wmavailmas vfmvclallg
241 cfallwcvyk ktkyafsprn slpqhlkefl ghphhntllf fsfplsdend vfdklsviae
301 dsesgkqnpg dscslgtppg qgpqs
```

Human IL-10R-2 cDNA
(SEQ ID NO: 16)

```
  1 cccgcccatc tccgctggtt cccggaagcc gccgcggaca agctctcccg ggcgcgggcg
 61 ggggtcgtgt gcttggagga agccgcggaa cccccagcgt ccgtccatgg cgtggagcct
121 tgggagctgg ctgggtggct gcctgctggt gtcagcattg ggaatggtac cacctcccga
181 aaatgtcaga atgaattctg ttaatttcaa gaacattcta cagtgggagt cacctgcttt
241 tgccaaaggg aacctgactt tcacagctca gtacctaagt tataggatat ccaagataa
301 atgcatgaat actaccttga cggaatgtga tttctcaagt ctttccaagt atggtgacca
361 cacccttgaga gtcagggctg aatttgcaga tgagcattca gactgggtaa acatcacctt
421 ctgtcctgtg gatgacacca ttattggacc ccctggaatg caagtagaag tacttgctga
481 ttctttacat atgcgtttct tagccccttaa aattgagaat gaatacgaaa cttggactat
541 gaagaatgtg tataactcat ggacttataa tgtgcaatac tggaaaaacg gtactgatga
601 aaagtttcaa attactcccc agtatgactt tgaggtcctc agaaacctgg agccatggac
661 aacttattgt gttcaagttc gagggtttct tcctgatcgg aacaaagctg gggaatggag
721 tgagcctgtc tgtgagcaaa caacccatga cgaaacggtc cctcctggaa tggtggccgt
781 catcctcatg gcctcggtct tcatggtctg cctggcactc tcggctgct tcgccttgct
```

-continued

```
 841 gtggtgcgtt tacaagaaga caaagtacgc cttctcccct aggaattctc ttccacagca 901 cctgaaagag tttttgggcc atcctcatca taacacactt ctgtttttct cctttccatt 961 gtcggatgag aatgatgttt ttgacaagct aagtgtcatt gcagaagact ctgagagcgg 1021 caagcagaat cctggtgaca gctgcagcct cgggacccog cctgggcagg ggcccaaag 1081 ctaggctctg agaaggaaac acactcggct gggcacagtg acgtactcca tctcacatct 1141 gcctcagtga gggatcaggg cagcaaacaa gggccaagac catctgagcc agccccacat 1201 ctagaactcc cagaccctgg acttagccac cagagagcta cattttaaag gctgtcttgg 1261 caaaaatact ccatttggga actcactgcc ttataaaggc tttcatgatg ttttcagaag 1321 ttggccactg agagtgtaat tttcagcctt ttatatcact aaaataagat catgttttaa 1381 ttgtgagaaa cagggccgag cacagtggct cacgcctgta ataccagcac cttagaggtc 1441 gaggcaggcg gatcacttga ggtcaggagt tcaagaccag cctggccaat atggtgaaac 1501 ccagtctcta ctaaaaatac aaaaattagc taggcatgat ggcgcatgcc tataatccca 1561 gctactcgag tgcctgaggc aggagaattg catgaacccg ggaggaggag gaggaggttg 1621 cagtgagccg agatagcggc actgcactcc agcctgggtg acaaagtgag actccatctc 1681 aaaaaaaaaa aaaaaaaaaa ttgtgagaaa cagaaatact taaaatgagg aataagaatg 1741 gagatgttac atctggtaga tgtaacattc taccagatta tggatggact gatctgaaaa 1801 tcgacctcaa ctcaagggtg gtcagctcaa tgctacacag agcacggact tttggattct 1861 ttgcagtact ttgaatttat ttttctacct atatatgttt tatatgctgc tggtgctcca 1921 ttaaagtttt actctgtgtt gcactatatg tgttcatgat aaaaaa
```

Recombinant IL-10

In some examples, an IL-10 receptor agonist is a recombinant IL-10 protein. In some examples, a recombinant IL-10 protein has an amino acid sequence that is identical to a human IL-10 protein (e.g., SEQ ID NO: 2). Non-limiting commercial sources of recombinant human IL-10 protein are available from Peprotech (Rocky Hill, N.J.), Novus Biologicals (Littleton, Colo.), Stemcell™ Technologies (Cambridge, Mass.), Millipore Sigma (Billerica, Mass.), and R&D Systems (Minneapolis, Minn.). In some examples, a recombinant human IL-10 protein can be Tenovil™ (Schering Corporation).

In some examples, a recombinant IL-10 protein is a functional fragment of human IL-10 protein (e.g., SEQ ID NO: 2). In some examples, a functional fragment of human IL-10 is a fragment of a human IL-10 protein (e.g., SEQ ID NO: 2) that is able to specifically bind to and activate a human receptor of IL-10. For example, a functional fragment of human IL-10 protein can have one, two, three, four, five, six, seven, eight, nine, ten, eleven, twelve, thirteen, fourteen, fifteen, sixteen, seventeen, eighteen, nineteen, or twenty amino acids from the N- and/or C-terminus of SEQ ID NO: 2.

In some examples, a recombinant human IL-10 includes a sequence at least 80% identical (e.g., at least 82% identical, at least 84% identical, at least 86% identical, at least 88% identical, at least 90% identical, at least 92% identical, at least 94% identical, at least 95% identical, at least 96% identical, at least 98% identical, or at least 99% identical) to SEQ ID NO: 2, and is able to specifically bind to and activate a human receptor of IL-10. Mutation of amino acids that are not conserved between different mammalian species less likely to have a negative effect on the activity of a recombinant IL-10 protein.

In some embodiments, the IL-10 receptor agonist is rhuIL-10 (Tenovil) or a variant thereof. See, e.g., McHutchison et al., *J. Interferon Cytokine Res.* 1:1265-1270, 1999; Rosenblum et al., *Regul. Toxicol. Pharmacol.* 35:56-71, 2002; Schreiber et al., *Gastroenterology* 119(6):1461-1472, 2000; Maini et al., *Arthritis Rheum.* 40(Suppl):224, 1997.

Exemplary methods of making a recombinant human IL-10 are described in Pajkrt et al., *J. Immunol.* 158: 3971-3977, 1997). Additional exemplary methods of making recombinant IL-10 are described herein and are known in the art.

In some embodiments, a recombinant IL-10 is a pegylated recombinant IL-10 (e.g., pegylated recombinant human IL-10) (e.g., a 5 kDa N-terminally PEGylated form of IL-10; AM0010) (Infante et al., *ASCO Meeting Abstracts* 33(15_suppl):3017, 2015; Chan et al., *PLoS One* 11(6): e0156229, 2016; Mumm et al., *Cancer Cell* 20(6):781-796, 2011; Teng et al., *Cancer Cell* 20(6):691-693, 2011; U.S. Pat. Nos. 8,691,205; 8,865,652; 9,259,478; and 9,364,517; and U.S. Patent Application Publication Nos. 2008/0081031; 2009/0214471; 2011/0250163; 2011/0091419; 2014/0227223; 2015/0079031; 2015/0086505; 2016/0193352; 2016/0367689; 2016/0375101; and 2016/0166647).

In some embodiments, a recombinant IL-10 is a stabilized isoform of a recombinant IL-10. In some embodiments, the stabilized isoform of a recombinant IL-10 is a viral IL-10 protein (e.g., a human cytomegalovirus IL10 (e.g., cmv-IL10, LA-cmv-IL-10 (e.g., Lin et al., *Virus Res.* 131(2):213-223, 2008; Jenkins et al., *J. Virol.* 78(3):1440-1447, 2004; Kotenko et al., *Proc. Natl. Acad. Sci. U.S.A.* 97(4):1695-1700, 2000; Jones et al., *Proc. Natl. Acad. Sci. U.S.A.* 99(14):9404-9409, 2002) or a latency-associated viral IL-10 protein (e.g., Poole et al., *J. Virol.* 88(24):13947-13955, 2014).

In some embodiments, the recombinant IL-10 is a mammalian IL-10 homolog (see, e.g., WO 00/073457). In some embodiments, a mammalian IL-10 homolog is BCRF1, an EBV homolog of human IL-10, also known as viral IL-10, or a variant thereof (Liu et al., *J. Immunol.* 158(2):604-613, 1997).

Fusion Proteins

In some embodiments, the IL-10 receptor agonist is a fusion protein. In some embodiments, the fusion protein comprises the amino acid sequence of an IL-10 protein (or a functional fragment thereof) and a fusion partner (e.g., an Fc region (e.g., human IgG Fc) or human serum albumin). In some embodiments the fusion partner can be an antibody or an antigen-binding antibody fragment (e.g., an scFv) that targets IL-10 receptor agonist to an inflamed tissue. In some embodiments, the antibody or antigen-binding fragment that is a fusion partner can bind specifically, or preferentially, to inflamed gastrointestinal cells by, e.g., CD69. In some embodiments, an IL-10 receptor agonist that is a fusion protein can be, e.g., F8-IL-10, such as Dekavil (Philogen).

In some embodiments, the fusion protein is a L19-IL-10 fusion protein, a HyHEL10-IL-10 fusion protein, or a variant thereof. See, e.g., Trachsel et al., *Arthritis Res. Ther.* 9(1):R9, 2007, and Walmsley et al., *Arthritis Rheum.* 39: 495-503, 1996.

IL-10 Peptide Mimetic

In some embodiments, the IL-10 receptor agonist is an IL-10 peptide mimetic. A non-limiting example of an IL-10 peptide mimetic is IT 9302 or a variant thereof (Osman et al., *Surgery* 124(3):584-92, 1998; Lopez et al., *Immunobiology* 216(10):1117-1126, 2011). Additional examples of IL-10 peptide mimetics are described in DeWitt, *Nature Biotech.* 17:214, 1999, and Reineke et al., *Nature Biotech.* 17:271-275, 1999.

Antibodies and Antigen-Binding Fragments

In some embodiments, the IL-10 receptor agonist is an antibody or an antigen-binding antibody fragment that binds to and activates an IL-10 receptor (e.g., a human IL-10 receptor). In some embodiments, the antibody or antigen-binding antibody fragment that specifically binds to an epitope on IL-10R-1 protein (e.g., human IL-10R-1 protein). In some embodiments, the antibody or antigen-binding antibody fragment that specifically binds to an epitope on IL-10R-2 protein (e.g., a human IL-10R-2 protein). In some embodiments, the antibody or the antigen-binding antibody fragment that specifically binds to an epitope on IL-10R-1 and IL-10R-2 proteins (e.g., human IL-10R-1 and human IL-10R-2 proteins).

In some embodiments, the antibody can be a humanized antibody, a chimeric antibody, a multivalent antibody, or a fragment thereof. In some embodiments, an antibody can be a scFv-Fc, a VHH domain, a VNAR domain, a (scFv)$_2$, a minibody, or a BiTE. In some embodiments, an antibody can be a DVD-Ig, and a dual-affinity re-targeting antibody (DART), a triomab, kih IgG with a common LC, a crossmab, an ortho-Fab IgG, a 2-in-1-IgG, IgG-ScFv, scFv2-Fc, a bi-nanobody, tanden antibody, a DART-Fc, a scFv-HAS-scFv, DNL-Fab3, DAF (two-in-one or four-in-one), Duta-Mab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H)IgG, IgG(L)-scFv, scFv-(L)-IgG, IgG (L,H)-Fc, IgG(H)-V, V(H)—IgG, IgG (L)-V, V(L)-IgG, KIH IgG-scFab, 2scFv-IgG, IgG-2scFv, scFv4-Ig, Zybody, DVI-IgG, nanobody, nanobody-HSA, a diabody, a TandAb, scDiabody, scDiabody-CH3, Diabody-CH3, Triple Body, miniantibody, minibody, TriBi minibody, scFv-CH3 KIH, Fab-scFv, scFv-CH-CL-scFv, F(ab')$_2$-scFV2, scFv-KIH, Fab-scFv-Fc, tetravalent HCAb, scDiabody-Fc, diabody-Fc, tandem scFv-Fc, intrabody, dock and lock bispecific antibody, ImmTAC, HSAbody, scDiabody-HAS, tandem scFv, IgG-IgG, Cov-X-Body, and scFv1-PEG-scFv$_2$.

Non-limiting examples of an antigen-binding fragment of an antibody include an Fv fragment, a Fab fragment, a F(ab')$_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

In some embodiments, the IL-10 receptor agonist is an antibody (e.g., F8-IL10 (also known as DEKAVIL) or a variant thereof (see, e.g., Schwager et al., *Arthritis Res. Ther.* 11(5):R142, 2009; Franz et al., *Int. J. Cardiol.* 195:311-322, 2015; Galeazzi et al., *Isr. Med. Assoc. J.* 16(10):666, 2014).

In some embodiments, the IL-10 or IL-10 agonist is RG-7880 (Genentech), a monoclonal antibody.

In some embodiments, any of the antibodies or antigen-binding fragments described herein has a dissociation constant ($K_D$) of less than $1\times10^{-5}$ M (e.g., less than $0.5\times10^{-5}$ M, less than $1\times10^{-6}$ M, less than $0.5\times10^{-6}$ M, less than $1\times10^{-7}$ M, less than $0.5\times10^{-7}$ M, less than $1\times10^{-8}$ M, less than $0.5\times10^{-8}$ M, less than $1\times10^{-9}$ M, less than $0.5\times10^{-9}$ M, less than $1\times10^{-10}$ M, less than $0.5\times10^{-10}$ M, less than $1\times10^{-11}$ M, less than $0.5\times10^{-11}$ M, or less than $1\times10^{-12}$ M), e.g., as measured in phosphate buffered saline using surface plasmon resonance (SPR).

In some embodiments, any of the antibodies or antigen-binding fragments described herein has a $K_D$ of about $1\times10^{-12}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, about $0.5\times10^{-10}$ M, about $1\times10^{-11}$ M, or about $0.5\times10^{-11}$ M (inclusive); about $0.5\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, about $0.5\times10^{-10}$ M, or about $1\times10^{-11}$ M (inclusive); about $1\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, or about $0.5\times10^{-10}$ M (inclusive); about $0.5\times10^{-10}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, or about $1\times10^{-10}$ M (inclusive); about $1\times10^{-10}$ M to about $1\times10^{-5}$ M, about $0.5\times10^{-5}$ M, about $1\times10^{-5}$ M, about $0.5\times10^{-5}$ M, about $1\times10^{-7}$ M, about $0.5\times10^{-7}$ M, about $1\times10^{-8}$ M, about $0.5\times10^{-8}$ M, about $1\times10^{-9}$ M, or about $0.5\times10^{-9}$ M (inclusive); about $0.5\times10^{-9}$ M to about $1\times10^{-5}$ M, about $0.5\times10^{-5}$ M, about $1\times10^{-5}$ M, about $0.5\times10^{-5}$ M, about $1\times10^{-7}$ M, about $0.5\times10^{-7}$ M, about $1\times10^{-8}$ M, about $0.5\times10^{-8}$ M, or about $1\times10^{-9}$ M (inclusive); about $1\times10^{-9}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, or about $0.5\times10^{-8}$ M (inclusive); about $0.5\times10^{-8}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, or about $1\times10^{-8}$ M (inclusive); about $1\times10^{-8}$ M to about $1\times10^{-5}$ M, about $0.5\times10^{-5}$ M, about $1\times10^{-6}$ M, about $0.5\times10^{-6}$ M, about $1\times10^{-7}$ M, or about $0.5\times10^{-7}$ M (inclusive); about $0.5\times10^{-7}$ M to about $1\times10^{-5}$ M, about $0.5\times10^{-5}$ M, about $1\times10^{-6}$ M, about $0.5\times10^{-6}$ M, or about $1\times10^{-7}$ M (inclusive); about $1\times10^{-7}$ M to about $1\times10^{-5}$ M, about $0.5\times10^{-5}$ M, about $1\times10^{-6}$ M, or about $0.5\times10^{-6}$ M (inclusive); about $0.5\times10^{-7}$ M to about $1\times10^{-5}$ M, about $0.5\times10^{-5}$ M, or about $1\times10^{-6}$ M (inclusive); about $1\times10^{-6}$ M to about $1\times10^{-5}$ M or about $0.5\times10^{-5}$ M (inclusive); or about $0.5\times10^{-5}$ M to about $1\times10^{-5}$ M (inclusive), e.g., as measured in phosphate buffered saline using surface plasmon resonance (SPR).

In some embodiments, any of the antibodies or antigen-binding fragments described herein has a $K_{off}$ of about $1\times10^{-6}$ s$^{-1}$ to about $1\times10^{-3}$ s$^{-1}$, about $0.5\times10^{-3}$ s$^{-1}$, about $1\times10^{-4}$ s$^{-1}$, about $0.5\times10^{4}$ s$^{-1}$, about $1\times10^{-5}$ s$^{-1}$, or about $0.5\times10^{-5}$ s$^{-1}$ (inclusive); about $0.5\times10^{-5}$ s$^{-1}$ to about $1\times10^{-3}$ s$^{-1}$, about $0.5\times10^{-3}$ s$^{-1}$, about $1\times10^{-4}$ s$^{-1}$, about $0.5\times10^{-4}$ s$^{-1}$, or about $1\times10^{-5}$ s$^{-1}$ (inclusive); about $1\times10^{-5}$ s$^{-1}$ to about $1\times10^{-3}$ s$^{-1}$, about $0.5\times10^{-3}$ s$^{-1}$, about $1\times10^{-4}$ s$^{-1}$, or about $0.5\times10^{-4}$ s$^{-1}$ (inclusive); about $0.5\times10^{-4}$ s$^{-1}$ to about $1\times10^{-3}$ s$^{-1}$, about $0.5\times10^{-3}$ s$^{-1}$, or about $1\times10^{-4}$ s$^{-1}$ (inclusive); about $1\times10^{-4}$ s$^{-1}$ to about $1\times10^{-3}$ s$^{-1}$, or about $0.5\times10^{-3}$ s$^{-1}$ (inclusive); or about $0.5\times10^{-5}$ s$^{-1}$ to about $1\times10^{-3}$ s$^{-1}$ (inclusive), e.g., as measured in phosphate buffered saline using surface plasmon resonance (SPR).

In some embodiments, any of the antibodies or antigen-binding fragments described herein has a $K_{on}$ of about $1\times10^{2}$ M$^{-1}$s$^{-1}$ to about $1\times10^{6}$ M$^{-1}$s$^{-1}$, about $0.5\times10^{6}$ M$^{-1}$s$^{-1}$, about $1\times10^{5}$ M$^{-1}$s$^{-1}$, about $0.5\times10^{5}$ M$^{-1}$s$^{-1}$, about $1\times10^{4}$ M$^{-1}$s$^{-1}$, about $0.5\times10^{4}$ M$^{-1}$s$^{-1}$, about $1\times10^{3}$ M$^{-1}$s$^{-1}$, or about $0.5\times10^{3}$ M$^{-1}$s$^{-1}$ (inclusive); about $0.5\times10^{3}$ M$^{-1}$s$^{-1}$ to about $1\times10^{6}$ M$^{-1}$s$^{-1}$, about $0.5\times10^{6}$ M$^{-1}$s$^{-1}$, about $1\times10^{5}$ M$^{-1}$s$^{-1}$, about $0.5\times10^{5}$ M$^{-1}$s$^{-1}$, about $1\times10^{4}$ M$^{-1}$s$^{-1}$, about $0.5\times10^{4}$ M$^{-1}$s$^{-1}$, or about $1\times10^{3}$ M$^{-1}$s$^{-1}$ (inclusive); about $1\times10^{3}$ M$^{-1}$s$^{-1}$ to about $1\times10^{6}$ M$^{-1}$s$^{-1}$, about $0.5\times10^{6}$ M$^{-1}$s$^{-1}$, about $1\times10^{5}$ M$^{-1}$s$^{-1}$, about $0.5\times10^{5}$ M$^{-1}$s$^{-1}$, about $1\times10^{4}$ M$^{-1}$s$^{-1}$, or about $0.5\times10^{4}$ M$^{-1}$s$^{-1}$ (inclusive); about $0.5\times10^{4}$ M$^{-1}$s$^{-1}$ to about $1\times10^{6}$ M$^{-1}$s$^{-1}$, about $0.5\times10^{6}$ M$^{-1}$s$^{-1}$, about $1\times10^{5}$ M$^{-1}$s$^{-1}$, about $0.5\times10^{5}$ M$^{-1}$s$^{-1}$, or about $1\times10^{4}$ M$^{-1}$s$^{-1}$ (inclusive); about $1\times10^{4}$ M$^{-1}$s$^{-1}$ to about $1\times10^{6}$ M$^{-1}$s$^{-1}$, about $0.5\times10^{6}$ M$^{-1}$s$^{-1}$, about $1\times10^{5}$ M$^{-1}$s$^{-1}$, or about $0.5\times10^{5}$ M$^{-1}$s$^{-1}$ (inclusive); about $0.5\times10^{5}$ M$^{-1}$s$^{-1}$ to about $1\times10^{6}$ M$^{-1}$s$^{-1}$, about $0.5\times10^{6}$ M$^{-1}$s$^{-1}$, or about $1\times10^{5}$ M$^{-1}$s$^{-1}$ (inclusive); about $1\times10^{5}$ M$^{-1}$s$^{-1}$ to about $1\times10^{6}$ M$^{-1}$s$^{-1}$, or about $0.5\times10^{6}$ M$^{-1}$s$^{-1}$ (inclusive); or about $0.5\times10^{6}$ M$^{-1}$s$^{-1}$ to about $1\times10^{6}$ M$^{-1}$s$^{-1}$ (inclusive), e.g., as measured in phosphate buffered saline using surface plasmon resonance (SPR).

Cells Producing a Recombinant IL-10

In some embodiments, any of the devices or compositions described herein can include a recombinant cell (e.g., a recombinant mammalian cell) that secretes a recombinant IL-10 (e.g., any of the recombinant IL-10 proteins described herein). In some embodiments, any of the devices or compositions described herein can include a cell (e.g., a mammalian cell) that secretes IL-10 (e.g., human IL-10). In some embodiments, the mammalian cell can be a mammalian cell obtained from the subject, and after introduction of a nucleic acid encoding the recombinant IL-10 (e.g., any of the recombinant IL-10 proteins described herein) into the cell obtained from the subject, the cell is incorporated into any of the compositions or devices described herein.

A recombinant cell can be generated by introducing a vector including a nucleic acid sequence encoding a recombinant IL-10 protein (e.g., any of the recombinant IL-10 proteins described herein). In some embodiments, the vector or the nucleic acid sequence encoding a recombinant IL-10 protein is integrated into a chromosome of the recombinant mammalian cell. In some embodiments, the vector or the nucleic acid sequence encoding a recombinant IL-10 protein is not integrated into a chromosome of the recombinant mammalian cell.

A vector can be a viral vector. Non-limiting examples of viral vectors include adenovirus vectors, herpes virus vectors, baculovirus vectors, and retroviral vectors. An expression vector can also be a plasmid or a cosmid. Additional examples of vectors are known in the art.

A vector can include a promoter sequence operably linked to the nucleic acid sequence encoding a recombinant IL-10 protein (e.g., any of the recombinant IL-10 proteins described herein). Non-limiting examples of promoter sequences that can be operably linked to the sequence (e.g., cDNA) encoding a recombinant IL-10 protein (e.g., any of the recombinant IL-10 proteins described herein) include: Simian Virus 40 (SV40) early promoter, ribosomal protein 21 (rpS21) promoter, hamster β-actin promoter, cytomegalovirus (CMV) promoter (e.g., CMV immediate early promoter (see, e.g., Teschendorf et al., *Anticancer Res.* 22:3325-3330, 2002), ubiquitin C (UBC) promoter, elongation factor 1-α (EF1A) promoter, phosphoenolpyruvate carboxykinase (PCK) promoter, IE2 promoter/enhancer region from mouse CMV (see, e.g., Chatellard et al., *Biotechnol. Bioeng.* 96:106-117, 2007), and chicken β-actin promoter. Additional non-limiting examples of human gene promoters that can be used in any of the vectors described herein are described in the Mammalian Promoter Database (Wistar Institute website at mrpombdb.wister.upenn.edu). Additional examples of mammalian promoter sequences that can be used in the expression vectors are known in the art.

Non-limiting examples of methods that can be used to introduce a vector or a nucleic acid into a cell (e.g., a mammalian cell) include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. These and other methods of introducing a vector or a nucleic acid into a cell are well known in the art.

In some examples, the recombinant mammalian cell can be a Chinese Hamster Ovary (CHO) cell, a B cell, a CD8$^+$ T cell, a dendritic cell, a keratinocyte or an epithelial cell. See, e.g., Mosser et al., *Immunol. Rev.* 226:205-218, 2009; Fillatreau et al., *Nat. Rev. Immunol.* 8:391-397, 2008; Ryan et al., *Crit. Rev. Immunol.* 27:15-32, 2007; Moore et al., *Annu. Rev. Immunol.* 19:683-765, 2001. In some embodiments, the recombinant mammalian cell can be a mesenchymal stem cell (e.g., Gupte et al., *Biomed. J.* 40(1):49-54, 2017).

Nucleic Acids and Vectors the Encode an IL-10 Receptor Agonist

In some examples, an IL-10 receptor agonist can be a nucleic acid (e.g., a vector) that includes a sequence encoding an IL-10 receptor agonist (e.g., any of the IL-10 proteins described herein). In some embodiments, the nucleic acid includes a sequence encoding IL-10 (e.g., human IL-10). In some embodiments, the nucleic acid includes a sequence encoding a recombinant IL-10 (e.g., a recombinant human IL-10). In some examples, the sequence encoding an IL-10 receptor agonist can be SEQ ID NO: 3. In some embodiments, the sequence encoding an IL-10 receptor agonist can include a sequence that is at least 80% (e.g., at least 82%, at least 84%, at least 86%, at least 88%, at least 90%, at least 92%, at least 94%, at least 95%, at least 96%, at least 98%, or at least 99%) identical to SEQ ID NO: 3.

The nucleic acid can be, e.g., a vector. In some embodiments, a vector can be a viral vector (e.g., an adenovirus vector, a herpes virus vector, a baculovirus vector, or a retrovirus vector). A vector can also be, e.g., a plasmid or a cosmid. Additional examples of vectors are known in the art.

A vector can include a promoter sequence operably linked to the sequence encoding an IL-10 receptor agonist (e.g., any of the recombinant IL-10 proteins described herein). Non-limiting examples of promoter sequences that can be operably linked to the sequence encoding an IL-10 receptor agonist (e.g., any of the recombinant IL-10 proteins described herein) include: Simian Virus 40 (SV40) early promoter, ribosomal protein 21 (rpS21) promoter, hamster β-actin promoter, cytomegalovirus (CMV) promoter (e.g., CMV immediate early promoter (see, e.g., Teschendorf et al., Anticancer Res. 22:3325-3330, 2002), ubiquitin C (UBC) promoter, elongation factor 1-α (EF1A) promoter, phosphoenolpyruvate carboxykinase (PCK) promoter, IE2 promoter/enhancer region from mouse CMV (see, e.g., Chatellard et al., Biotechnol. Bioeng. 96:106-117, 2007), and chicken β-actin promoter. Additional non-limiting examples of human gene promoters that can be used in any of the vectors described herein are described in the Mammalian Promoter Database (Wistar Institute website at mrpombdb.wister.upenn.edu). A promoter can be a constitutive promoter or an inducible promoter. Examples of constitutive promoters and inducible promoters are known in the art. Additional examples and features of mammalian promoter sequences that can be used in the expression vectors are known in the art.

A non-limiting example of a composition including a nucleic acid that encodes an IL-10 receptor agonist is XT-150 (Xalud Therapeutics).

Additional Examples of IL-10 Receptor Agonists

In some embodiments, the recombinant cell is a recombinant Gram-positive bacterial cell (e.g., a genetically modified *Lactococcus lactis* (LL-Thy12) (see, e.g., Steidler et al., Science 289:1352-1355, 2000; Braat et al., Clin. Gastroenterol. Heptal. 4:754-759, 2006). In some embodiments, the recombinant cell is a recombinant Gram-negative bacterial cell (e.g., a *Shigella flexneri* cell) that secretes an IL-10 receptor agonist (e.g., a recombinant IL-10 protein) (Chamekh et al., J. Immunol. 180(6): 4292-4298, 2008).

In some embodiments, the IL-10 receptor agonist is a cell (e.g., a *Clostridium butyricum* cell) that induces IL-10 production and secretion by a different cell (e.g., a macrophage) (e.g., Hayashi et al., Cell Host Microbe 13:711-722, 2013). In some embodiments, the IL-10 receptor agonist is a recombinant bacterial cell (e.g., a *Lactobacillus acidophilus* cell) that is deficient in lipoteichoic acid and induces IL-10 production and secretion by a different cell (e.g., a dendritic cell) (e.g., Mohamadzadeh et al., Proc. Natl. Acad. Sci. U.S.A. 108(suppl 1):4623-4630, 2011; Konstantinov et al., Proc. Natl. Acad. Sci. U.S.A. 105(49):19474-9, 2008). In some embodiments, the IL-10 receptor agonist is a bacterial cell or a fragment of a bacterial cell that is maintained in the supernatant that induces IL-10 secretion in a different cell (e.g., an immune cell) (e.g., a *Faecalibacterium prausnitzii* cell or a *Faecalibacterium prausnitzii* supernatant) (see, e.g., Sokol et al., Proc. Natl. Acad. Sci. U.S.A. 105(43):16731-16736, 2008).

Additional examples of other IL-10 receptor agonists are described in, e.g., U.S. Pat. No. 6,936,586; WO 96/01318; WO 91/00349; WO 13/130913; each incorporated in its entirety herein.

Endoscopes, Ingestible Devices, and Reservoirs

As discussed herein, in some embodiments, a method of treating a disease of the gastrointestinal tract comprises administering to the subject a pharmaceutical formulation wherein the pharmaceutical formulation is delivered proximate to one or more sites of disease by one of various methods. For example, the pharmaceutical formulation may be delivered via a medical device such as an endoscope, ingestible device, or reservoir; the pharmaceutical formulation may be a solid dosage form, a liquid dosage form, a suppository or an enema for rectal administration with different types of release such as sustained or delayed release.

In one embodiment, the pharmaceutical formulation is delivered proximate to one or more sites of disease by an endoscope, ingestible device, or reservoir containing the pharmaceutical formulation.

The GI tract can be imaged using endoscopes, or more recently, by ingestible devices that are swallowed. Direct visualization of the GI mucosa is useful to detect subtle mucosal alterations, as in inflammatory bowel diseases, as well as any flat or sessile lesions.

The technology behind standard colonoscopy consists of a long, semi-rigid insertion tube with a steerable tip (stiff if compared to the colon), which is pushed by the physician from the outside. However, invasiveness, patient discomfort, fear of pain, and—more often than not—the need for conscious sedation limit the take-up of screening colonoscopy. Diagnosis and treatment in the GI tract are dominated by the use of flexible endoscopes. A few large companies, namely Olympus Medical Systems Co. (Tokyo, Japan), Pentax Medical Co. (Montvale, N.J., USA), Fujinon, Inc. (Wayne, N.J., USA) and Karl Storz GmbH & Co. KG (Tuttlingen, Germany), cover the majority of the market in flexible GI endoscopy.

Endoscopes may comprise a catheter. As an example, the catheter may be a spray catheter. As an example, a spray catheter may be used to deliver dyes for diagnostic purposes. As an example, a spray catheter may be used to deliver a therapeutic agent at the site of disease in the GI tract. For example, the Olypmus PW-205V is a ready-to-use spray catheter that enables efficient spraying for maximal differentiation of tissue structures during endoscopy, but may also be used to deliver drugs diseased tissue.

In a review of robotic endoscopic capsules, Journal of Micro-Bio Robotics 11.1-4 (2016): 1-18, Ciuti et al. state that progress in micro-electromechanical systems (MEMS) technologies have led to the development of new endoscopic capsules with enhanced diagnostic capabilities, in addition to traditional visualization of mucosa (embedding, e.g. pressure, pH, blood detection and temperature sensors).

Endoscopic capsules, however, do not have the capability of accurately locating a site autonomously. They require doctor oversight over a period of hours in order to manually determine the location. Autonomous ingestible devices are advantageous in that regard.

Ingestible devices are also advantageous over spray catheters in that they are less invasive, thereby allowing for regular dosing more frequently than spray catheters. Another advantage of ingestible devices is the greater ease with which they can access, relative to a catheter, certain sections of the GI tract such as the ascending colon, the cecum, and all portions of the small intestine.

Methods and Mechanisms for Localization

In addition to, or as an alternative, to directly visualizing the GI tract, one or more different mechanisms can be used to determine the location of an ingestible device within the GI tract. Various implementations may be used for localization of ingestible devices within the GI tract.

Localization

In addition to, or as an alternative, to directly visualizing the GI tract, one or more different mechanisms to determine the location of an ingestible device within the GI tract. For example, various implementations may be used for localization of ingestible devices within the GI tract. For example, certain implementations can include one or more electromagnetic sensor coils, magnetic fields, electromagnetic waves, electric potential values, ultrasound positioning systems, gamma scintigraphy techniques or other radio-tracker technology have been described by others. Alternatively, imaging can be used to localize, for example, using anatomical landmarks or more complex algorithms for 3D reconstruction based on multiple images. Other technologies rely on radio frequency, which relies on sensors placed externally on the body to receive the strength of signals emitted by the capsule. Ingestible devices may also be localized based on reflected light in the medium surrounding the device; pH; temperature; time following ingestion; and/or acoustic signals.

The disclosure provides an ingestible device, as well as related systems and methods that provide for determining the position of the ingestible device within the GI tract of a subject with very high accuracy. In some embodiments, the ingestible device can autonomously determine its position within the GI tract of the subject.

Typically, the ingestible device includes one or more processing devices, and one more machine readable hardware storage devices. In some embodiments, the one or more machine readable hardware storage devices store instructions that are executable by the one or more processing devices to determine the location of the ingestible device in a portion of a GI tract of the subject. In certain embodiments, the one or more machine readable hardware storage devices store instructions that are executable by the one or more processing devices to transmit data to an external device (e.g., a base station external to the subject, such as a base station carried on an article worn by the subject) capable of implementing the data to determine the location of the device within the GI tract of the subject.

In some embodiments, the location of the ingestible device within the GI tract of the subject can be determined to an accuracy of at least 85%, e.g., at least 90%, at least 95%, at least 97%, at least 98%, at least 99%, 100%. In some embodiments, the location of the ingestible device within the GI tract of the subject can be determined to an accuracy of at least 85%, e.g., at least 90%, at least 95%, at least 97%, at least 98%, at least 99%, 100%. In such embodiments, the portion of the GI tract of the subject can include, for example, the esophagus, the stomach, duodenum, the jejunum, and/or the terminal ileum, cecum and colon. An exemplary and non-limiting embodiment is provided below in Example 14.

In certain embodiments, the location of the ingestible device within the esophagus of the subject can be determined to an accuracy of at least 85%, e.g., at least 90%, at least 95%, at least 97%, at least 98%, at least 99%, 100%. An exemplary and non-limiting embodiment is provided below in Example 14.

In some embodiments, the location of the ingestible device within the stomach of the subject can be determined to an accuracy of at least 85%, e.g., at least 90%, at least 95%, at least 97%, at least 98%, at least 99%, 100%. An exemplary and non-limiting embodiment is provided below in Example 14.

In certain embodiments, the location of the ingestible device within the duodenum of the subject can be determined to an accuracy of at least 85%, e.g., at least 90%, at least 95%, at least 97%, at least 98%, at least 99%, 100%. An exemplary and non-limiting embodiment is provided below in Example 14.

In some embodiments, the location of the ingestible device within the jejunum of the subject can be determined to an accuracy of at least 85%, e.g., at least 90%, at least 95%, at least 97%, at least 98%, at least 99%, 100%. An exemplary and non-limiting embodiment is provided below in Example 14.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%. An exemplary and non-limiting embodiment is provided below in Example 14. In such embodiments, the portion of the portion of the GI tract of the subject can include, for example, the esophagus, the stomach, duodenum, the jejunum, and/or the terminal ileum, cecum and colon.

In certain embodiments, the location of the ingestible device within the esophagus of the subject can be determined to an accuracy of at least 85%, e.g., at least 90%, at least 95%, at least 97%, at least 98%, at least 99%, 100%.

In some embodiments, the location of the ingestible device within the stomach of the subject can be determined to an accuracy of at least 85%, e.g., at least 90%, at least 95%, at least 97%, at least 98%, at least 99%, 100%.

In certain embodiments, the location of the ingestible device within the duodenum of the subject can be determined to an accuracy of at least 85%, e.g., at least 90%, at least 95%, at least 97%, at least 98%, at least 99%, 100%.

In some embodiments, the location of the ingestible device within the jejunum of the subject can be determined to an accuracy of at least 85%, e.g., at least 90%, at least 95%, at least 97%, at least 98%, at least 99%, 100%.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Figure 1:
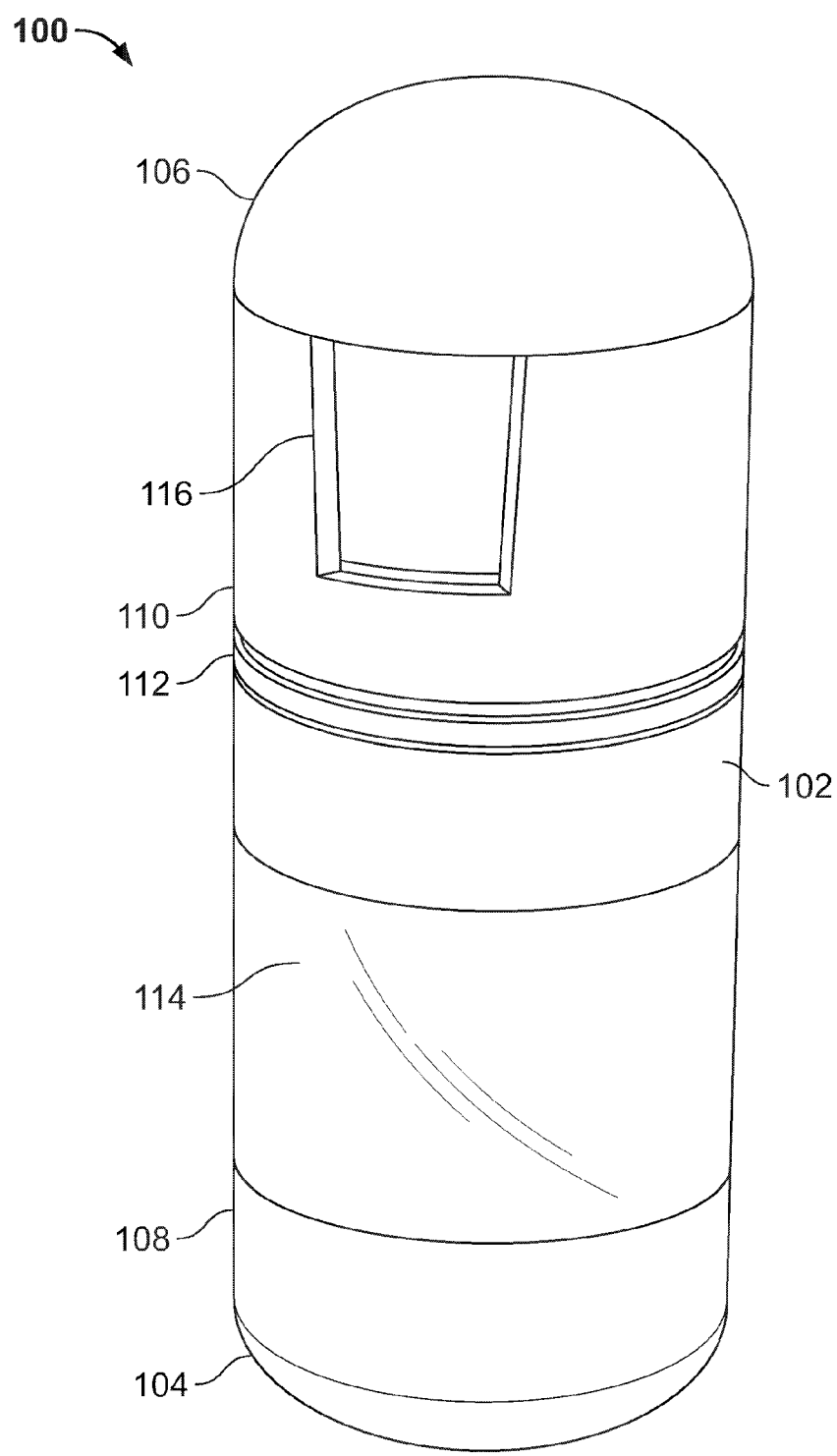
FIG. 1 is a view of an example embodiment of an ingestible device, in accordance with some embodiments of the disclosure.

Referring now to FIG. 1, shown therein is a view of an example embodiment of an ingestible device 100, which may be used to identify a location within a gastrointestinal (GI) tract. In some embodiments, ingestible device 100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 100 may be configured to autonomously determine whether it is located within certain portions of the small intestine or large intestine, such as the duodenum, the jejunum, the cecum, or the colon.

Ingestible device 100 may have a housing 102 shaped similar to a pill or capsule. The housing 102 of ingestible device 100 may have a first end portion 104, and a second end portion 106. The first end portion 104 may include a first wall portion 108, and second end portion 106 may include a second wall portion 110. In some embodiments, first end portion 104 and second end portion 106 of ingestible device 100 may be manufactured separately, and may be affixed together by a connecting portion 112.

In some embodiments, ingestible device 100 may include an optically transparent window 114. Optically transparent window 114 may be transparent to various types of illumination in the visible spectrum, infrared spectrum, or ultraviolet light spectrum, and ingestible device 100 may have various sensors and illuminators located within the housing 102, and behind the transparent window 114. This may allow ingestible device 100 to be configured to transmit illumination at different wavelengths through transparent window 114 to an environment external to housing 102 of ingestible device 100, and to detect a reflectance from a portion of the illumination that is reflected back through transparent window 114 from the environment external to housing 102. Ingestible device 100 may then use the detected level of reflectance in order to determine a location of ingestible device 100 within a GI tract. In some embodiments, optically transparent window 114 may be of any shape and size, and may wrap around the circumference of ingestible device 100. In this case, ingestible device 100 may have multiple sets of sensors and illuminators positioned at different locations azimuthally behind window 114.

In some embodiments, ingestible device 100 may optionally include an opening 116 in the second wall portion 110. In some embodiments, the second wall portion 110 may be configured to rotate around the longitudinal axis of ingestible device 100 (e.g., by means of a suitable motor or other actuator housed within ingestible device 100). This may allow ingestible device 100 to obtain a fluid sample from the GI tract, or release a substance into the GI tract, through opening 116.

Figure 2:
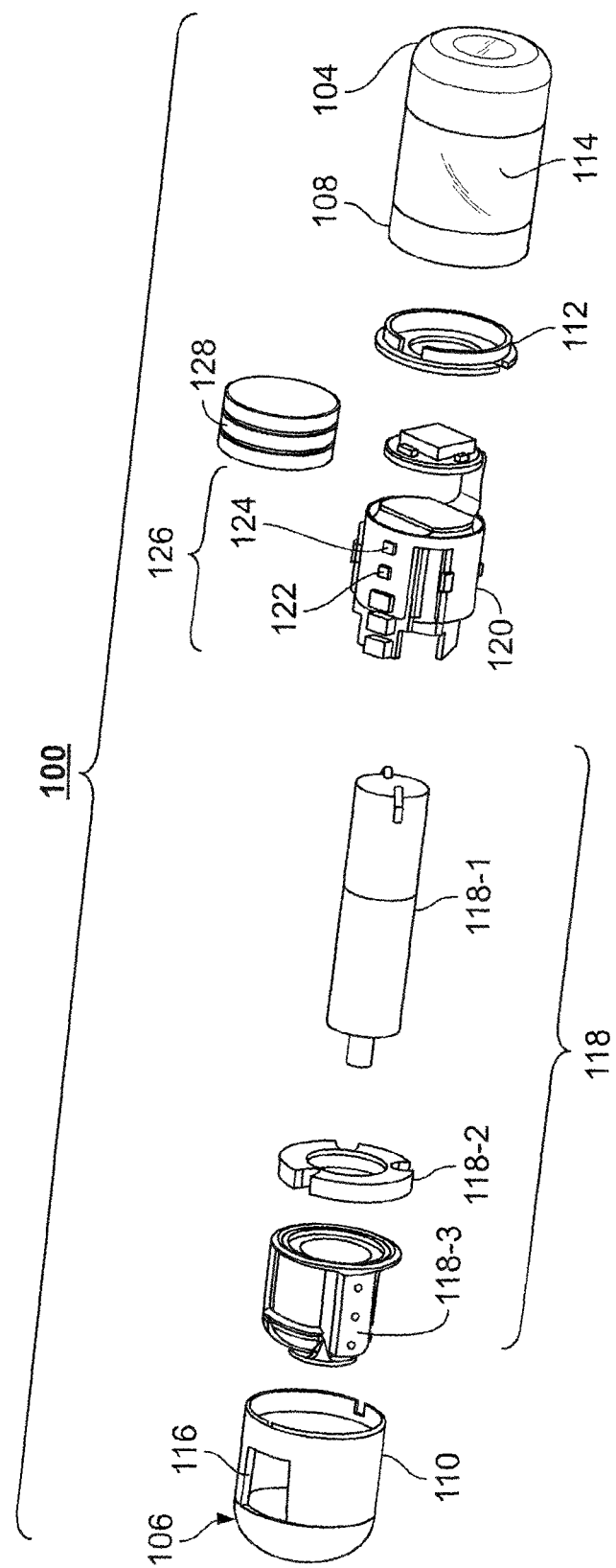
FIG. 2 is an exploded view of the ingestible device of FIG. 1, in accordance with some embodiments of the disclosure.

FIG. 2 shows an exploded view of ingestible device 100. In some embodiments, ingestible device 100 may optionally include a rotation assembly 118. Optional rotation assembly 118 may include a motor 118-1 driven by a microcontroller (e.g., a microcontroller coupled to printed circuit board 120), a rotation position sensing ring 118-2, and a storage sub-unit 118-3 configured to fit snugly within the second end portion 104. In some embodiments, rotation assembly 118 may cause second end portion 104, and opening 116, to rotate relative to the storage sub-unit 118-3. In some embodiments, there may be cavities on the side of storage sub-unit 118-3 that function as storage chambers. When the opening 116 is aligned with a cavity on the side of the storage sub-unit 118-3, the cavity on the side of the storage sub-unit 118-3 may be exposed to the environment external to the housing 102 of ingestible device 100. In some embodiments, the storage sub-unit 118-3 may be loaded with a medicament or other substance prior to the ingestible device 100 being administered to a subject. In this case, the medicament or other substance may be released from the ingestible device 100 by aligning opening 116 with the cavity within storage sub-unit 118-3. In some embodiments, the storage sub-unit 118-3 may be configured to hold a fluid sample obtained from the GI tract. For example, ingestible device 100 may be configured to align opening 116 with the cavity within storage sub-unit 118-3, thus allowing a fluid sample from the GI tract to enter the cavity within storage sub-unit 118-3. Afterwards, ingestible device 100 may be configured to seal the fluid sample within storage sub-unit 118-3 by further rotating the second end portion 106 relative to storage sub-unit 118-3. In some embodiments, storage sub-unit 118-3 may also contain a hydrophilic sponge, which may enable ingestible device 100 to better draw certain types of fluid samples into ingestible device 100. In some embodiments, ingestible device 100 may be configured to either obtain a sample from within the GI tract, or to release a substance into the GI tract, in response to determining that ingestible device 100 has reached a predetermined location within the GI tract. For example, ingestible device 100 may be configured to obtain a fluid sample from the GI tract in response to determining that the ingestible device has entered the jejunum portion of the small intestine (e.g., as determined by process 900 discussed in relation to FIG. 9). Other ingestible devices capable of obtaining samples or releasing substances are discussed in commonly-assigned PCT Application No. PCT/CA2013/000133 filed Feb. 15, 2013, commonly-assigned U.S. Provisional Application No. 62/385,553, and commonly-assigned U.S. Provisional Application No. 62/376,688, which each are hereby incorporated by reference herein in their entirety. It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 100 may include a printed circuit board (PCB) 120, and a battery 128 configured to power PCB 120. PCB 120 may include a programmable microcontroller, and control and memory circuitry for holding and executing firmware or software for coordinating the operation of ingestible device 100, and the various components of ingestible device 100. For example, PCB 120 may include memory circuitry for storing data, such as data sets of measurements collected by sensing sub-unit 126, or instructions to be executed by control circuitry to implement a localization process, such as, for example, one or more of the processes, discussed herein, including those discussed below in connection with one or more of the associated flow charts. PCB 120 may include a detector 122 and an illuminator 124, which together form sensing sub-unit 126. In some embodiments, control circuitry within PCB 120 may include processing units, communication circuitry, or any other suitable type of circuitry for operating ingestible device 100. For illustrative purposes, only a single detector 122 and a single illuminator 124 forming a single sensing sub-unit 126 are shown. However, it is understood that in some embodiments there may be multiple sensing sub-units, each with a separate illuminator and detector, within ingestible device 100. For example, there may be several sensing sub-units spaced azimuthally around the circumference of the PCB 120, which may enable ingestible device 100 to transmit illumination and detect reflectances or ambient light in all directions around the circumference of the device. In some embodiments, sensing sub-unit 126 may be configured to generate an illumination using illuminator 124, which is directed through the window 114 in a radial direction away from ingestible device 100. This illumination may reflect off of the environment external to ingestible device 100, and the reflected light coming back into ingestible device 100 through window 114 may be detected as a reflectance by detector 122.

In some embodiments, window 114 may be of any suitable shape and size. For example, window 114 may extend around a full circumference of ingestible device 100. In some embodiments there may be a plurality of sensing sub-units (e.g., similar to sensing sub-unit 126) located at different positions behind the window. For example, three sensing sub-units may be positioned behind the window at the same longitudinal location, but spaced 120 degrees apart azimuthally. This may enable ingestible device 100 to transmit illuminations in all directions radially around ingestible device 100, and to measure each of the corresponding reflectances.

In some embodiments, illuminator 124 may be capable of producing illumination at a variety of different wavelengths in the ultraviolet, infrared, or visible spectrum. For example, illuminator 124 may be implemented by using Red-Green-Blue Light-Emitting diode packages (RGB-LED). These types of RGB-LED packages are able to transmit red, blue, or green illumination, or combinations of red, blue, or green illumination. Similarly, detector 122 may be configured to sense reflected light of the same wavelengths as the illumination produced by illuminator 124. For example, if illuminator 124 is configured to produce red, blue, or green illumination, detector 122 may be configured to detect different reflectances produced by red, blue, or green illumination (e.g., through the use of an appropriately configured photodiode). These detected reflectances may be stored by ingestible device 100 (e.g., within memory circuitry of PCB 120), and may then be used by ingestible device 100 in determining a location of ingestible device 100 within the GI tract (e.g., through the use of process 500 (FIG. 5), process 600 (FIG. 6), or process 900 (FIG. 9)).

It is understood that ingestible device 100 is intended to be illustrative, and not limiting. It will be understood that modifications to the general shape and structure of the various devices and mechanisms described in relation to FIG. 1 and FIG. 2 may be made without significantly changing the functions and operations of the devices and mechanisms. For example, ingestible device 100 may have a housing formed from a single piece of molded plastic, rather than being divided into a first end portion 104 and a second end portion 106. As an alternate example, the location of window 114 within ingestible device 100 may be moved to some other location, such as the center of ingestible device 100, or to one of the ends of ingestible device 100. Moreover, the systems and methods discussed in relation to FIGS. 1-10 may be implemented on any suitable type of ingestible device, provided that the ingestible device is capable of detecting reflectances or levels of illumination in some capacity. For example, in some embodiments ingestible device 100 may be modified to replace detector 122 with an image sensor, and the ingestible device may be configured to measure relative levels of red, blue, or green light by decomposing a recorded image into its individual spectral components. Other examples of ingestible devices with localization capabilities, which may be utilized in order to implement the systems and methods discussed in relation to FIG. 1-11, are discussed in co-owned PCT Application No. PCT/US2015/052500 filed on Sep. 25, 2015, which is hereby incorporated by reference herein in its entirety. Furthermore, it should be noted that the features and limitations described in any one embodiment may be applied to any other embodiment herein, and the descriptions and examples relating to one embodiment may be combined with any other embodiment in a suitable manner.

Figure 3:
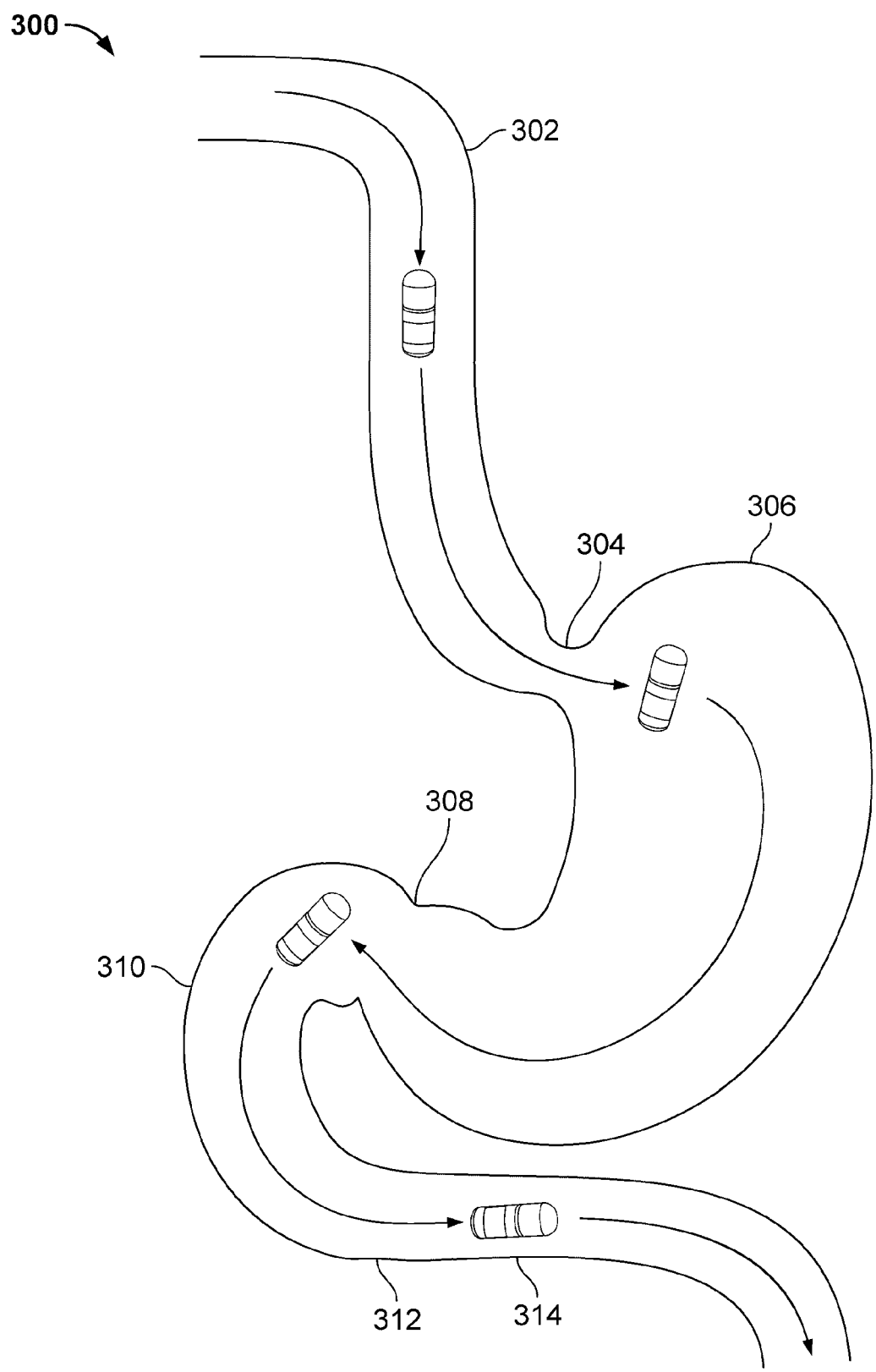
FIG. 3 is a diagram of an ingestible device during an example transit through a GI tract, in accordance with some embodiments of the disclosure.

FIG. 3 is a diagram of an ingestible device during an example transit through a gastrointestinal (GI) tract, in accordance with some embodiments of the disclosure. Ingestible device 300 may include any portion of any other ingestible device discussed in this disclosure (e.g., ingestible device 100 (FIG. 1)), and may be any suitable type of ingestible device with localization capabilities. For example, ingestible device 300 may be one embodiment of ingestible device 100 without the optional opening 116 (FIG. 1) or optional rotation assembly 118 (FIG. 2)). In some embodiments, ingestible device 300 may be ingested by a subject, and as ingestible device 300 traverses the GI tract, ingestible device 300 may be configured to determine its location within the GI tract. For example, the movement of ingestible device 300 and the amount of light detected by ingestible device 300 (e.g., via detector 122 (FIG. 2)) may vary substantially depending on the location of ingestible device 300 within the GI tract, and ingestible device 300 may be configured to use this information to determine a location of ingestible device 300 within the GI tract. For instance, ingestible device 300 may detect ambient light from the surrounding environment, or reflectances based on illumination generated by ingestible device 300 (e.g., generated by illuminator 124 (FIG. 1)), and use this information to determine a location of ingestible device 300 through processes, such as described herein. The current location of ingestible device 300, and the time that ingestible device 300 detected each transition between the various portions of the GI tract, may then be stored by ingestible device 300 (e.g., in memory circuitry of PCB 120 (FIG. 2)), and may be used for any suitable purpose.

Shortly after ingestible device 300 is ingested, ingestible device will traverse the esophagus 302, which may connect the subject's mouth to a stomach 306. In some embodiments, ingestible device 300 may be configured to determine that it has entered the esophagus portion GI tract by measuring the amount and type of light (e.g., via detector 122 (FIG. 2)) in the environment surrounding the ingestible device 300. For instance, ingestible device 300 may detect higher levels of light in the visible spectrum (e.g., via detector 122 (FIG. 2)) while outside the subject's body, as compared to the levels of light detected while within the GI tract. In some embodiments, ingestible device 300 may have previously stored data (e.g., on memory circuitry of PCB 120 (FIG. 2)) indicating a typical level of light detected when outside of the body, and the ingestible device 300 may be configured to determine that entry to the body has occurred when a detected level of light (e.g., detected via detector 122 (FIG. 2)) has been reduced beyond a threshold level (e.g., at least a 20-30% reduction) for a sufficient period of time (e.g., 5.0 seconds).

In some embodiments, ingestible device 300 may be configured to detect a transition from esophagus 302 to stomach 306 by passing through sphincter 304. In some embodiments, ingestible device 300 may be configured to determine whether it has entered stomach 306 based at least in part on a plurality of parameters, such as but not limited to the use of light or temperature measurements (e.g., via detector 122 (FIG. 2) or via a thermometer within ingestible device 300), pH measurements (e.g., via a pH meter within ingestible device 300), time measurements (e.g., as detected through the use of clock circuitry included within PCB 120 (FIG. 2)), or any other suitable information. For instance, ingestible device 300 may be configured to determine that ingestible device 300 has entered stomach 306 after detecting that a measured temperature of ingestible device 300 exceeds 31 degrees Celsius. Additionally or alternately, ingestible device 300 may be configured to automatically determine it has entered stomach 306 after one minute (or another pre-set time duration parameter, 80 seconds, 90 seconds, etc.) has elapsed from the time that ingestible device 300 was ingested, or one minute (or another pre-set time duration parameter, 80 seconds, 90 seconds, etc.) from the time that ingestible device 300 detected that it has entered the GI tract.

Stomach 306 is a relatively large, open, and cavernous organ, and therefore ingestible device 300 may have a relatively large range of motion. By comparison, the motion of ingestible device 300 is relatively restricted within the tube-like structure of the duodenum 310, the jejunum 314, and the ileum (not shown), all of which collectively form the small intestine. Additionally, the interior of stomach 306 has distinct optical properties from duodenum 310 and jejunum 314, which may enable ingestible device 300 to detect a transition from stomach 306 to duodenum 310 through the appropriate use of measured reflectances (e.g., through the use of reflectances measured by detector 122 (FIG. 2)), as used in conjunction with process 600 (FIG. 6)).

In some embodiments, ingestible device 300 may be configured to detect a pyloric transition from stomach 306 to duodenum 310 through the pylorus 308. For instance, in some embodiments, ingestible device 300 may be configured to periodically generate illumination in the green and blue wavelengths (e.g., via illuminator 124 (FIG. 2)), and measure the resulting reflectances (e.g., via detector 122 (FIG. 2)). Ingestible device 300 may be configured to then use a ratio of the detected green reflectance to the detected blue reflectance to determine whether ingestible device 300 is located within the stomach 306, or duodenum 310 (e.g., via process 600 (FIG. 6)). In turn, this may enable ingestible device 300 to detect a pyloric transition from stomach 306 to duodenum 310, an example of which is discussed in relation to FIG. 6.

Similarly, in some embodiments, ingestible device 300 may be configured to detect a reverse pyloric transition from duodenum 310 to stomach 306. Ingestible device 300 will typically transition naturally from stomach 306 to duodenum 310, and onward to jejunum 314 and the remainder of the GI tract. However, similar to other ingested substances, ingestible device 300 may occasionally transition from duodenum 310 back to stomach 306 as a result of motion of the subject, or due to the natural behavior of the organs with the GI tract. To accommodate this possibility, ingestible device 300 may be configured to continue to periodically generate illumination in the green and blue wavelengths (e.g., via illuminator 124 (FIG. 2)), and measure the resulting reflectances (e.g., via detector 122 (FIG. 2)) to detect whether or not ingestible device 300 has returned to stomach 306. An exemplary detection process is described in additional detail in relation to FIG. 6.

After entering duodenum 310, ingestible device 300 may be configured to detect a transition to the jejunum 314 through the duodenojejunal flexure 312. For example, ingestible device 300 may be configured to use reflectances to detect peristaltic waves within the jejunum 314, caused by the contraction of the smooth muscle tissue lining the walls of the jejunum 314. In particular, ingestible device 300 may be configured to begin periodically transmitting illumination (and measuring the resulting reflectances (e.g., via detector 122 and illuminator 124 of sensing sub-unit 126 (FIG. 2)) at a sufficiently high frequency in order to detect muscle contractions within the jejunum 314. Ingestible device 300 may then determine that it has entered the jejunum 314 in response to having detected either a first muscle contraction, or a predetermined number of muscle contractions (e.g., after having detected three muscle contractions in sequence). The interaction of ingestible device 300 with the walls of jejunum 314 is also discussed in relation to FIG. 4, and an example of this detection process is described in additional detail in relation to FIG. 9.

Figure 4:
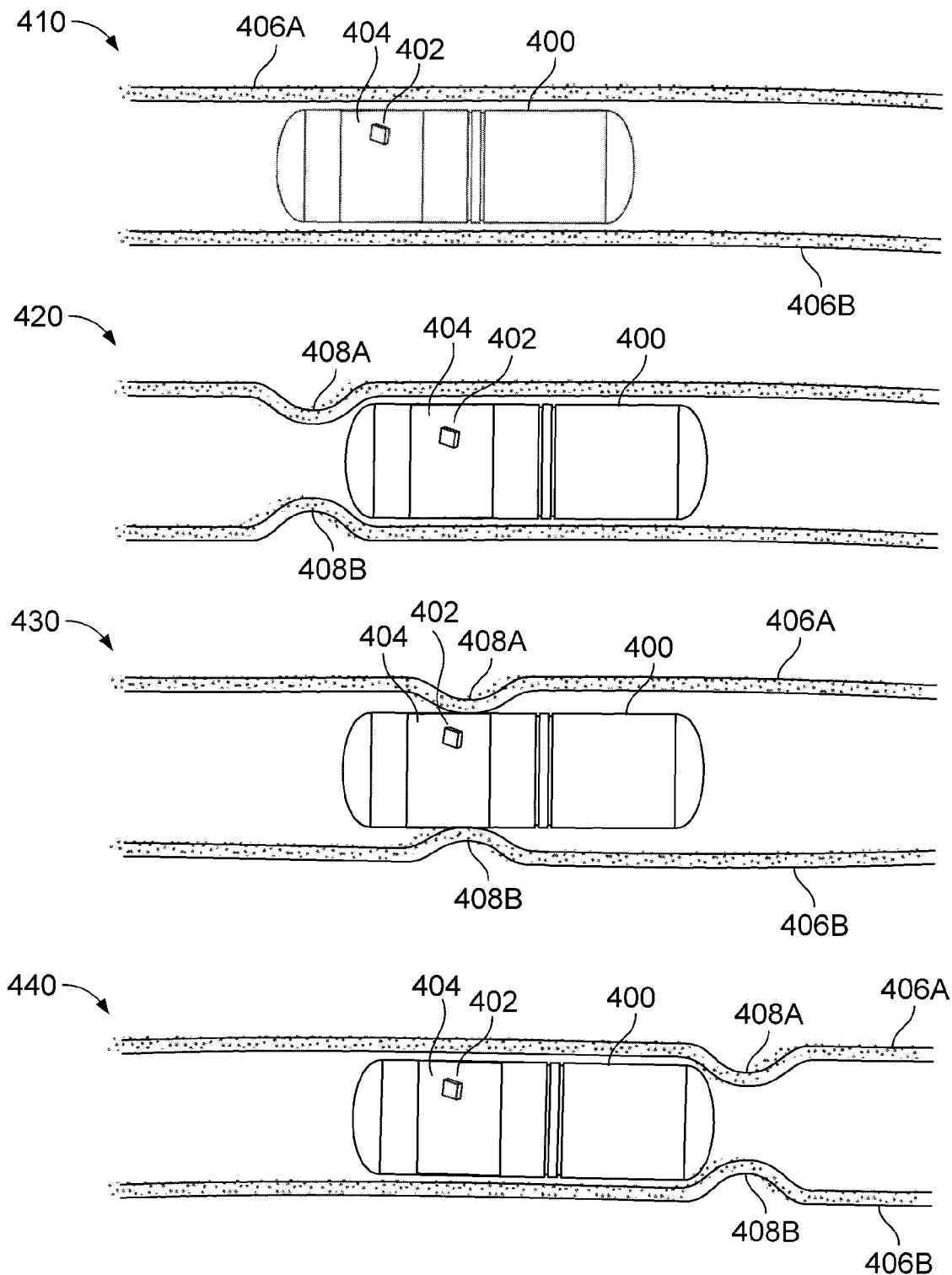
FIG. 4 is a diagram of an ingestible device during an example transit through a jejunum, in accordance with some embodiments of the disclosure.

FIG. 4 is a diagram of an ingestible device during an example transit through a jejunum, in accordance with some embodiments of the disclosure. Diagrams 410, 420, 430, and 440 depict ingestible device 400 as it traverses through a jejunum (e.g., jejunum 314), and how ingestible device 400 interacts with peristaltic waves formed by walls 406A and 406B (collectively, walls 406) of the jejunum. In some implementations, ingestible device 400 may include any portion of any other ingestible device discussed in this disclosure (e.g., ingestible device 100 (FIG. 1) or ingestible device 300 (FIG. 3)), and may be any suitable type of ingestible device with localization capabilities. For example, ingestible device 400 may be substantially similar to the ingestible device 300 (FIG. 3) or ingestible device 100 (FIG. 1), with window 404 being the same as window 114 (FIG. 1), and sensing sub-unit 402 being the same as sensing sub-unit 126 (FIG. 2).

Diagram 410 depicts ingestible device 400 within the jejunum, when the walls 406 of the jejunum are relaxed. In some embodiments, the confined tube-like structure of the jejunum naturally causes ingestible device 400 to be oriented longitudinally along the length of the jejunum, with window 404 facing walls 406. In this orientation, ingestible device 400 may use sensing sub-unit 402 to generate illumination (e.g., via illuminator 124 (FIG. 2)) oriented towards walls 406, and to detect the resulting reflectances (e.g., via detector 122 (FIG. 2)) from the portion of the illumination reflected off of walls 406 and back through window 404. In some embodiments, ingestible device 400 may be configured to use sensing sub-unit 402 to generate illumination and measure the resulting reflectance with sufficient frequency to detect peristaltic waves within the jejunum. For instance, in a healthy human subject, peristaltic waves may occur at a rate of approximately 0.1 Hz to 0.2 Hz.

Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds, which may improve the overall reliability of the detection process due to more data points being available. It is understood that the ingestible device 400 need not gather measurements at precise intervals, and in some embodiments the ingestible device 400 may be adapted to analyze data gathered at more irregular intervals, provided that there are still a sufficient number of appropriately spaced data points to detect 0.1 Hz to 0.2 Hz signals.

Diagram 420 depicts ingestible device 400 within the jejunum, when the walls 406 of the jejunum begin to contract and form a peristaltic wave. Diagram 420 depicts contracting portion 408A of wall 406A and contracting portion 408B of wall 406B (collectively, contracting portion 408 of wall 406) that form a peristaltic wave within the jejunum. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410).

Diagram 430 depicts ingestible device 400 within the jejunum, when the walls 406 of the jejunum continue to contract, squeezing around ingestible device 400. As the peristaltic wave proceeds along the length of the jejunum, contracting portions 408 of wall 406 may squeeze tightly around ingestible device 400, bringing the inner surface of wall 406 into contact with window 404. While in this position, ingestible device 400 may detect a change in a reflectance detected as a result of illumination produced by sensing sub-unit 402. The absolute value of the change in the measured reflectance may depend on several factors, such as the optical properties of the window 404, the spectral components of the illumination, and the optical properties of the walls 406. However, ingestible device 400 may be configured to store a data set with the reflectance values over time, and search for periodic changes in the data set consistent with the frequency of the peristaltic waves (e.g., by analyzing the data set in the frequency domain, and searching for peaks between 0.1 Hz to 0.2 Hz). This may enable ingestible device 400 to detect muscle contractions due to peristaltic waves without foreknowledge of the exact changes in reflectance signal amplitude that may occur as a result of detecting the muscle contractions of the peristaltic wave. An example procedure for detecting muscle contractions is discussed further in relation to FIG. 9, and an example of a reflectance data set gathered while ingestible device 400 is located within the jejunum is discussed in relation to FIG. 10.

Diagram 440 depicts ingestible device 400 within the jejunum, when the peristaltic wave has moved past ingestible device 400. Diagram 440 depicts contracting portions 408 that form the peristaltic wave within the jejunum having moved past the end of ingestible device 400. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410, or diagram 420).

Depending on the species of the subject, peristaltic waves may occur with relatively predictable regularity. After the peristaltic wave has passed over ingestible device 400 (e.g., as depicted in diagram 440), the walls 406 of the jejunum may relax again (e.g., as depicted in diagram 410), until the next peristaltic wave begins to form. In some embodiments, ingestible device 400 may be configured to continue to gather reflectance value data while it is within the GI tract, and may store a data set with the reflectance values over time. This may allow ingestible device 400 to detect each of the muscle contractions as the peristaltic wave passes over ingestible device 400 (e.g., as depicted in diagram 430), and may enable ingestible device 400 to both count the number of muscle contractions that occur, and to determine that a current location of the ingestible device 400 is within the jejunum. For example, ingestible device 400 may be configured to monitor for possible muscle contractions while is inside either the stomach or the duodenum, and may determine that ingestible device 400 has moved to the jejunum in response to detecting a muscle contraction consistent with a peristaltic wave.

Figure 5:
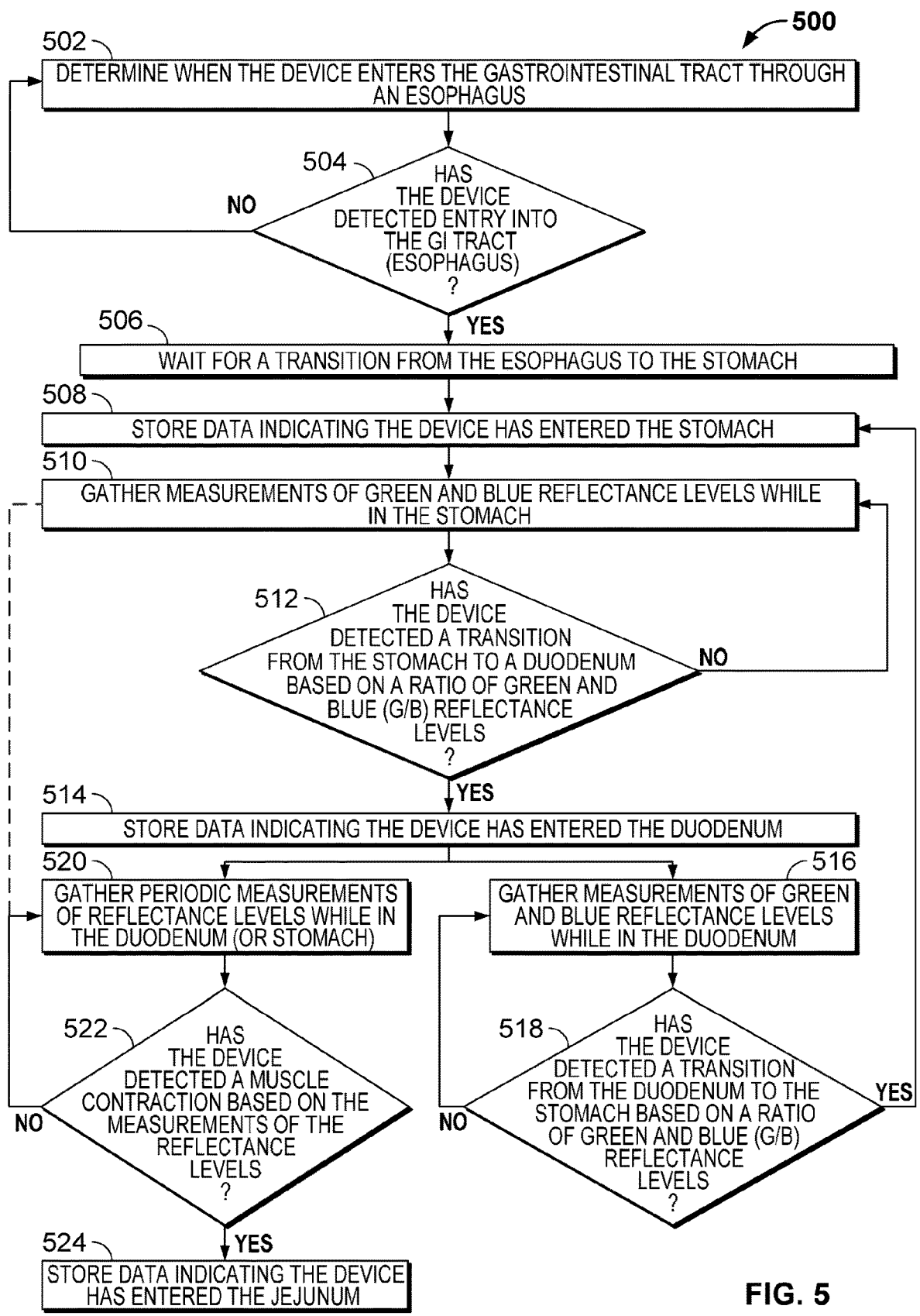
FIG. 5 is a flowchart of illustrative steps for determining a location of an ingestible device as it transits through a GI tract, in accordance with some embodiments of the disclosure.

FIG. 5 is a flowchart illustrating some aspects of a localization process used by the ingestible device. Although FIG. 5 may be described in connection with the ingestible device 100 for illustrative purposes, this is not intended to be limiting, and either portions or the entirety of the localization procedure 500 described in FIG. 5 may be applied to any device discussed in this application (e.g., the ingestible devices 100, 300, and 400), and any of the ingestible devices may be used to perform one or more parts of the process described in FIG. 5. Furthermore, the features of FIG. 5 may be combined with any other systems, methods or processes described in this application. For example, portions of the process in FIG. 5 may be integrated into or combined with the pyloric transition detection procedure described by FIG. 6, or the jejunum detection process described by FIG. 9.

At 502, the ingestible device (e.g., ingestible device 100, 300, or 400) gathers measurements (e.g., through detector 122 (FIG. 2)) of ambient light. For example, ingestible device 100 may be configured to periodically measure (e.g., through detector 122 (FIG. 2)) the level of ambient light in the environment surrounding ingestible device 100. In some embodiments, the type of ambient light being measured may depend on the configuration of detector 122 within ingestible device 100. For example, if detector 122 is configured to measure red, green, and blue wavelengths of light, ingestible device 100 may be configured to measure the ambient amount of red, green, and blue light from the surrounding environment. In some embodiments, the amount of ambient light measured by ingestible device 100 will be larger in the area external to the body (e.g., a well-lit room where ingestible device 100 is being administered to a subject) and in the oral cavity of the subject, as compared to the ambient level of light measured by ingestible device 100 when inside of an esophagus, stomach, or other portion of the GI tract (e.g., esophagus 302, stomach 306, duodenum 310, or jejunum 314 (FIG. 3)).

At 504, the ingestible device (e.g., ingestible device 100, 300, or 400) determines (e.g., via control circuitry within PCB 120 (FIG. 2)) whether the ingestible device has detected entry into the GI tract. For example, ingestible device 100 may be configured to determine when the most recent measurement of ambient light (e.g., the measurement gathered at 502) indicates that the ingestible device has entered the GI tract. For instance, the first time that ingestible device 100 gatherers a measurement of ambient light at 502, ingestible device 100 may store that measurement (e.g., via storage circuitry within PCB 120 (FIG. 2)) as a typical level of ambient light external to the body. Ingestible device 100 may be configured to then compare the most recent measurement of ambient light to the typical level of ambient light external to the body (e.g., via control circuitry within PCB 120 (FIG. 2)), and determine that ingestible device 100 has entered the GI tract when the most recent measurement of ambient light is substantially smaller than the typical level of ambient light external to the body. For example, ingestible device 100 may be configured to detect that it has entered the GI tract in response to determining that the most recent measurement of ambient light is less than or equal to 20% of the typical level of ambient light external to the body. If ingestible device 100 determines that it has detected entry into the GI tract (e.g., that ingestible device 100 has entered at least the esophagus 302 (FIG. 3)), process 500 proceeds to 506. Alternately, if ingestible device 100 determines that it has not detected entry into the GI tract (e.g., as a result of the most recent measurement being similar to the typical level of ambient light external to the body), process 500 proceeds back to 502 where the ingestible device 100 gathers further measurements. For instance, ingestible device 100 may be configured to wait a predetermined amount of time (e.g., five seconds, ten seconds, etc.), and then gather another measurement of the level of ambient light from the environment surrounding ingestible device 100.

At 506, the ingestible device (e.g., ingestible device 100, 300, or 400) waits for a transition from the esophagus to the stomach (e.g., from esophagus 302 to stomach 306 (FIG. 3)). For example, ingestible device 100 may be configured to determine that it has entered the stomach (e.g., stomach 306 (FIG. 3)) after waiting a predetermined period of time after having entered the GI tract. For instance, a typical esophageal transit time in a human patient may be on the order of 15-30 seconds. In this case, after having detected that ingestible device 100 has entered the GI tract at 504 (i.e., after detecting that ingestible device 100 has reached at least esophagus 302 (FIG. 3)), ingestible device 100 may be configured to wait one minute, or a similar amount of time longer than the typical esophageal transit time (e.g., ninety-seconds), before automatically determining that ingestible device 100 has entered at least the stomach (e.g., stomach 306 (FIG. 3)).

In some embodiments, the ingestible device (e.g., ingestible device 100, 300, or 400) may also determine it has entered the stomach based on measurements of pH or temperature. For example, ingestible device 100 may be configured to determine that it has entered the stomach if a temperature of ingestible device has increased to at least 31 degrees Celsius (i.e., consistent with the temperature inside the stomach), or if a measured pH of the environment surrounding ingestible device 100 is sufficiently acidic (i.e., consistent with the acidic nature of gastric juices that may be found inside the stomach).

At 508, the ingestible device (e.g., ingestible device 100, 300, or 400) stores data indicating the ingestible device has entered the stomach (e.g., stomach 306 (FIG. 3)). For example, after having waited a sufficient amount of time at 506, ingestible device 100 may store data (e.g., within storage circuitry of PCB 120 (FIG. 2)) indicative of ingestible device 100 having entered at least the stomach. Once ingestible device 100 reaches at least the stomach, process 500 proceeds to 510 where ingestible device 100 may be configured to gather data to detect entry into the duodenum (e.g., duodenum 310 (FIG. 3)).

In some embodiments, process 500 may also simultaneously proceed from 508 to 520, where ingestible device 100 may be configured to gather data in order to detect muscle contractions and detect entry into the jejunum (e.g., jejunum 314 (FIG. 3)). In some embodiments, ingestible device 100 may be configured to simultaneously monitor for entry into the duodenum at 516-518, as well as detect for entry into the jejunum at 520-524. This may allow ingestible device 100 to determine when it has entered the jejunum (e.g., as a result of detecting muscle contractions), even when it fails to first detect entry into the duodenum (e.g., as a result of very quick transit times of the ingestible device through the duodenum).

At 510, the ingestible device (e.g., ingestible device 100, 300, or 400) gathers measurements of green and blue reflectance levels (e.g., through the use of illuminator 124 and detector 122 of sensing sub-unit 126 (FIG. 2)) while in the stomach (e.g., stomach 306 (FIG. 3)). For example, ingestible device 100 may be configured to periodically gather measurements of green and blue reflectance levels while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within a stomach (e.g., stomach 306 (FIG. 3)), or a duodenum (e.g., duodenum 310 (FIG. 3)).

In some embodiments, the ingestible device (e.g., ingestible device 100, 300, or 400) may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable ingestible device 100 to sufficiently distinguish between the two wavelengths when detecting the reflectances (e.g., via detector 122 (FIG. 2)). It is understood that the separation of 50 nm is intended to be illustrative, and not limiting, and depending on the accuracy of the detectors within ingestible device 100, smaller separations may be possible to be used.

At 512, the ingestible device (e.g., ingestible device 100, 300, or 400) determines (e.g., using control circuitry within PCB 120 (FIG. 2)) whether the ingestible device has detected a transition from the stomach (e.g., stomach 306 (FIG. 3)) to a duodenum (e.g., duodenum 310 (FIG. 3)) based on a ratio of green and blue (GB) reflectance levels. For example, ingestible device 100 may obtain (e.g., from memory circuitry of PCB 120 (FIG. 2)) a data set containing historical data for the respective ratio of the green reflectance to the blue reflectance as measured at a respective time. Generally speaking, a duodenum (e.g., duodenum 310 (FIG. 3)) of a human subject reflects a higher ratio of green light to blue light, as compared to the ratio of green light to blue light that is reflected by a stomach (e.g., stomach 306 (FIG. 3)). Based on this, ingestible device 100 may be configured to take a first set of ratios from the data set, representing the result of recent measurements, and compare them to a second set of ratios from the data set, representing the results of past measurements. When the ingestible device 100 determines that the mean value of the first set of ratios is substantially larger than the mean value of the second set of ratios (i.e., that the ratio of reflected green light to reflected blue light has increased), the ingestible device 100 may determine that it has entered the duodenum (e.g., duodenum 310 (FIG. 3)) from the stomach (e.g., stomach 306 (FIG. 3)). If the ingestible device 100 detects a transition from the stomach (e.g., stomach 306 (FIG. 3)) to a duodenum (e.g., duodenum 310 (FIG. 3)), process 500 proceeds to 514, where ingestible device 100 stores data indicating that the ingestible device 100 has entered the duodenum (e.g., duodenum 310 (FIG. 3)). Alternatively, if the ingestible device determines that the ingestible device has not transitioned from the stomach (e.g., stomach 306 (FIG. 3)) to the duodenum (e.g., duodenum 310 (FIG. 3)), process 500 proceeds back to 510 to gather more measurements of green and blue reflectance levels while still in the stomach (e.g., stomach 306 (FIG. 3)). An example procedure for using measurements of green and blue reflectances to monitor for transitions between the stomach and the duodenum is discussed in greater detail in relation to FIG. 6.

In some embodiments, the first time that ingestible device 100 detects a transition from the stomach (e.g., stomach 306 (FIG. 3)) to the duodenum (e.g., duodenum 310 (FIG. 3)), ingestible device 100 may be configured to take a mean of the second set of data, (e.g., the set of data previously recorded while in stomach 306 (FIG. 3)) and store this as a typical ratio of green light to blue light detected within the stomach (e.g., stomach 306 (FIG. 3)) (e.g., within memory circuitry of PCB 120 (FIG. 2)). This stored information may later be used by ingestible device 100 to determine when ingestible device 100 re-enters the stomach (e.g., stomach 306 (FIG. 3)) from the duodenum (e.g., duodenum 310 (FIG. 3)) as a result of a reverse pyloric transition.

At 514, the ingestible device (e.g., ingestible device 100, 300, or 400) stores data indicating that the ingestible device has entered the duodenum (e.g., duodenum 310 (FIG. 3)). For example, ingestible device 100 may store a flag within local memory (e.g., memory circuitry of PCB 120) indicating that the ingestible device 100 is currently in the duodenum. In some embodiments, the ingestible device 100 may also store a timestamp indicating the time when ingestible device 100 entered the duodenum. Once ingestible device 100 reaches the duodenum, process 500 proceeds to 520 where ingestible device 100 may be configured to gather data in order to detect muscle contractions and detect entry into the jejunum (e.g., jejunum 314 (FIG. 3)). Process 500 also proceeds from 514 to 516, where ingestible device 100 may be configured to gather data additional data in order to detect re-entry into the stomach (e.g., stomach 306 (FIG. 3)) from the duodenum (e.g., duodenum 310 (FIG. 3)).

At 516, the ingestible device (e.g., ingestible device 100, 300, or 400) gathers measurements (e.g., via sensing sub-unit 126 (FIG. 2)) of green and blue reflectance levels while in the duodenum (e.g., duodenum 310 (FIG. 3)). For example, ingestible device 100 may be configured to periodically gather measurements (e.g., via sensing sub-unit 126 (FIG. 2)) of green and blue reflectance levels while in the duodenum, similar to the measurements made at 510 while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within the duodenum (e.g., duodenum 310 (FIG. 3)), or if the ingestible device 100 has transitioned back into the stomach (e.g., stomach 306 (FIG. 3)).

At 518, the ingestible device (e.g., ingestible device 100, 300, or 400) determines a transition from the duodenum (e.g., duodenum 310 (FIG. 3)) to the stomach (e.g., stomach 306 (FIG. 3)) based on a ratio of the measured green reflectance levels to the measured blue reflectance levels. In some embodiments, ingestible device 100 may compare the ratio of the measured green reflectance levels to the measured blue reflectance levels recently gathered by ingestible device 100 (e.g., measurements gathered at 516), and determine whether or not the ratio of the measured green reflectance levels to the measured blue reflectance levels is similar to the average ratio of the measured green reflectance levels to the measured blue reflectance levels seen in the stomach (e.g., stomach 306 (FIG. 3)). For instance, ingestible device 100 may retrieve data (e.g., from memory circuitry of PCB 120 (FIG. 2)) indicative of the average ratio of the measured green reflectance levels to the measured blue reflectance levels seen in the stomach, and determine that ingestible device 100 has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum (e.g., duodenum 310 (FIG. 3)) to the stomach (e.g., stomach 306 (FIG. 3)), process 500 proceeds to 508 to store data indicating the ingestible device has entered the stomach (e.g., stomach 306 (FIG. 3)), and continues to monitor for further transitions. Alternatively, if the ingestible device does not detect a transition from the duodenum (e.g., duodenum 310 (FIG. 3)) to the stomach (e.g., stomach 306 (FIG. 3)), process 500 proceeds to 516 to gather additional measurements of green and blue reflectance levels while in the duodenum (e.g., duodenum 310 (FIG. 3)), which may be used to continuously monitor for possible transitions back into the stomach. An example procedure for using measurements of green and blue reflectances to monitor for transitions between the stomach and the duodenum is discussed in greater detail in relation to FIG. 6.

At 520, the ingestible device (e.g., ingestible device 100, 300, or 400) gathers periodic measurements of the reflectance levels (e.g., via sensing sub-unit 126 (FIG. 2)) while in the duodenum (e.g., duodenum 310 (FIG. 3)). In some embodiments, the ingestible device (e.g., ingestible device 100, 300, or 400) may gather similar periodic measurements while in the stomach as well. In some embodiments, these periodic measurements may enable ingestible device 100 to detect muscle contractions (e.g., muscle contractions due to a peristaltic wave as discussed in relation to FIG. 4), which may be indicative of entry into a jejunum (e.g., jejunum 314 (FIG. 3)). Ingestible device 100 may be configured to gather periodic measurements using any suitable wavelength of illumination (e.g., by generating illumination using illuminator 124, and detecting the resulting reflectance using detector 122 (FIG. 2)), or combinations of wavelengths of illumination. For example, in some embodiments, ingestible device 100 may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by ingestible device 100 at 520 may be sufficiently fast as to detect peristaltic waves in a subject. For instance, in a healthy human subject, peristaltic waves may occur at a rate of approximately 0.1 Hz to 0.2 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds or faster, and store values indicative of the resulting reflectances in a data set (e.g., within memory circuitry of PCB 120 (FIG. 2)). After gathering additional data (e.g., after gathering one new data point, or a predetermined number of new data points), process 500 proceeds to 522, where ingestible device 100 determines whether or not a muscle contraction has been detected.

At 522, the ingestible device (e.g., ingestible device 100, 300, or 400) determines (e.g., via control circuitry within PCB 120 (FIG. 2)) whether the ingestible device detects a muscle contraction based on the measurements of reflectance levels (e.g., as gathered by sensing sub-unit 126 (FIG. 2)). For example, ingestible device 100 may obtain a fixed amount of data stored as a result of measurements made at 520 (e.g., retrieve the past minute of data from memory circuitry within PCB 120 (FIG. 2)). Ingestible device 100 may then convert the obtained data into the frequency domain, and search for peaks in a frequency range that would be consistent with peristaltic waves. For example, in a healthy human subject, peristaltic waves may occur at a rate of approximately 0.1 Hz to 0.2 Hz, and an ingestible device 100 may be configured to search for peaks in the frequency domain representation of the data between 0.1 Hz and 0.2 Hz above a threshold value. If the ingestible device 100 detects a contraction based on the reflectance levels (e.g., based on detecting peaks in the frequency domain representation of the data between 0.1 Hz and 0.2 Hz), process 500 proceeds to 524 to store data indicating that the device has entered the jejunum. Alternatively, if the ingestible device 100 does not detect a muscle contraction, process 500 proceeds to 520 to gather periodic measurements of the reflectance levels while in the duodenum (e.g., duodenum 310 (FIG. 3)). In some embodiments, the ingestible device (e.g., ingestible device 100, 300, or 400) may store data (e.g., within memory circuitry of PCB 120 (FIG. 2)) indicating that a muscle contraction was detected, and process 500 will not proceed from 522 to 524 until a sufficient number of muscle contractions have been detected.

At 524, the ingestible device (e.g., ingestible device 100, 300, or 400) stores data (e.g., within memory circuitry of PCB 120 (FIG. 2)) indicating that the device has entered the jejunum (e.g., jejunum 314 (FIG. 3)). For example, in response to detecting that muscle contraction has occurred at 522, ingestible device 100 may determine that it has entered the jejunum 314, and is no longer inside of the duodenum (e.g., duodenum 310 (FIG. 3)) or the stomach (e.g., stomach 306 (FIG. 3)). In some embodiments, the ingestible device 100 may continue to measure muscle contractions while in the jejunum, and may store data indicative of the frequency, number, or strength of the muscle contractions over time (e.g., within memory circuitry of PCB 120 (FIG. 2)). In some embodiments, the ingestible device 100 may also be configured to monitor for one or more transitions. Such transitions can include a transition from the jejunum to the ileum, an ileoceacal transition from the ileum to the cecum, a transition from the cecum to the colon, or detect exit from the body (e.g., by measuring reflectances, temperature, or levels of ambient light).

In some embodiments, the ingestible device (e.g., ingestible device 100, 300, or 400) may also determine that it has entered the jejunum (e.g., jejunum 314 (FIG. 3)) after a pre-determined amount of time has passed after having detected entry into the duodenum (e.g., duodenum 310 (FIG. 3)). For example, barring a reverse pyloric transition from the duodenum (e.g., duodenum 310 (FIG. 3)) back to the stomach (e.g., stomach 306 (FIG. 3)), the typical transit time for an ingestible device to reach the jejunum from the duodenum in a healthy human subject is less than three minutes. In some embodiments, the ingestible device (e.g., ingestible device 100, 300, or 400) may therefore be configured to automatically determine that it has entered the jejunum after spending at least three minutes within the duodenum. This determination may be made separately from the determination made based on measured muscle contractions (e.g., the determination made at 522), and in some embodiments, ingestible device 100 may determine that it has entered the jejunum in response to either detecting muscle contractions, or after three minutes has elapsed from having entered the duodenum (e.g., as determined by storing data at 514 indicative of the time that ingestible device entered the duodenum).

For illustrative purposes, 512-518 of process 500 describe the ingestible device (e.g., ingestible device 100, 300, or 400) measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 5, are merely illustrative. Any of the steps and descriptions of the flowcharts, including FIG. 5, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. As another example, ingestible device 100 may gather data periodic measurements and detect possible muscle contractions (e.g., at 520-522) while simultaneously gathering green and blue reflectance levels to determine transitions to and from the stomach and duodenum (e.g., at 510-518). Furthermore, it should be noted that the steps and descriptions of FIG. 5 may be combined with any other system, device, or method described in this application, including processes 600 (FIG. 6) and 900 (FIG. 9), and any of the ingestible devices or systems discussed in this application (e.g., ingestible devices 100, 300, or 400) could be used to perform one or more of the steps in FIG. 5.

Figure 6:
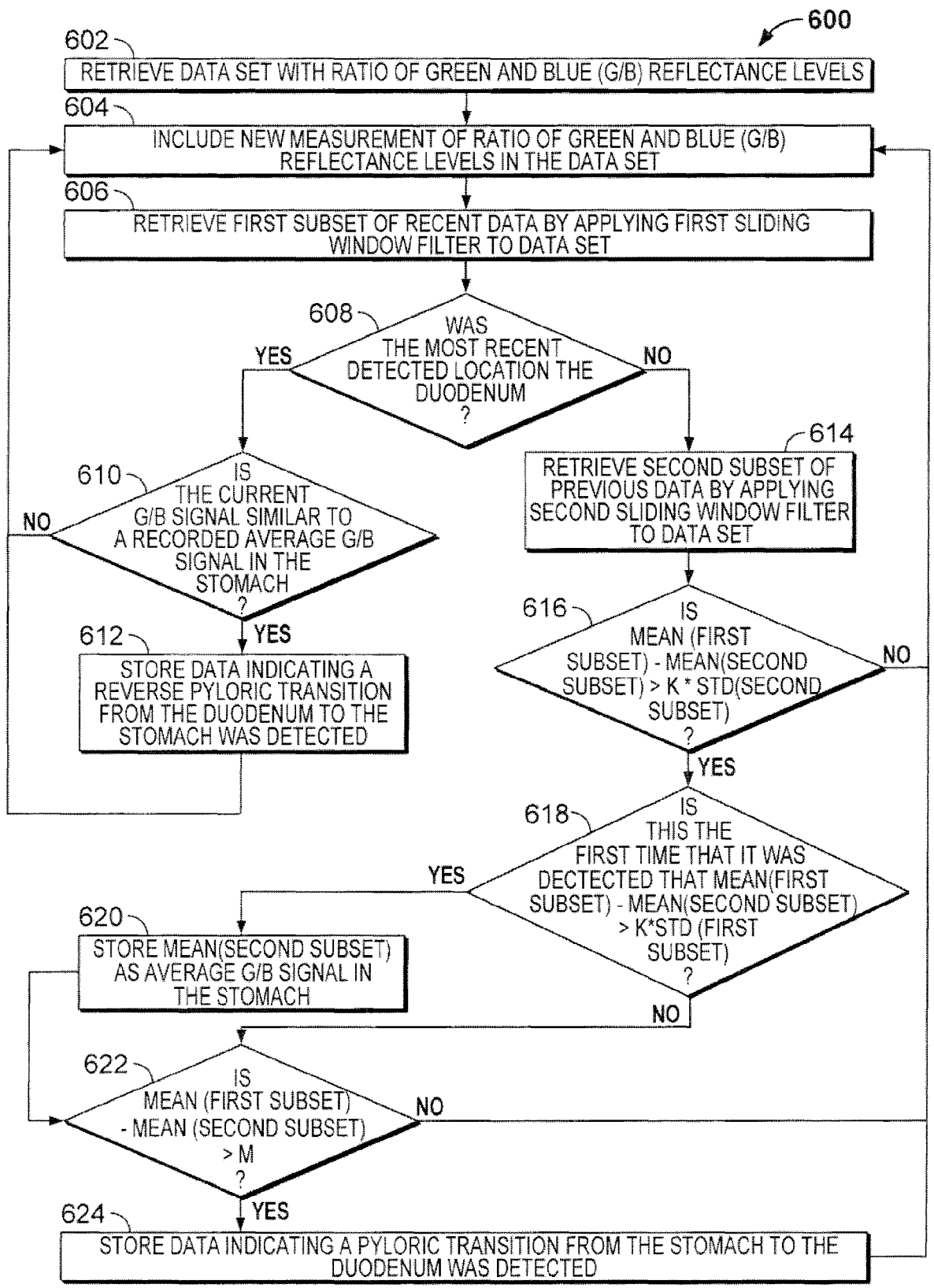
FIG. 6 is a flowchart of illustrative steps for detecting transitions from a stomach to a duodenum and from a duodenum back to a stomach, which may be used when determining a location of an ingestible device as it transits through a GI tract, in accordance with some embodiments of the disclosure.

FIG. 6 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 600 may begin when an ingestible device first detects that it has entered the stomach, and will continue as long as the ingestible device determines that it is within the stomach or the duodenum. In some embodiments, process 600 may only be terminated when an ingestible device determines that it has entered the jejunum, or otherwise progressed past the duodenum and the stomach. Although FIG. 6 may be described in connection with the ingestible device 100 for illustrative purposes, this is not intended to be limiting, and either portions or the entirety of the duodenum detection process 600 described in FIG. 6 may be applied to any device discussed in this application (e.g., the ingestible devices 100, 300, or 400), and any of the ingestible devices may be used to perform one or more parts of the process described in FIG. 6. Furthermore, the features of FIG. 6 may be combined with any other systems, methods or processes described in this application. For example, portions of the process described by the process in FIG. 6 may be integrated into process 500 discussed in relation to FIG. 5.

At 602, the ingestible device (e.g., ingestible device 100, 300, or 400) retrieves a data set (e.g., from memory circuitry within PCB 120 (FIG. 2)) with ratios of the measured green reflectance levels to the measured blue reflectance levels over time. For example, ingestible device 100 may retrieve a data set from PCB 120 containing recently recorded ratios of the measured green reflectance levels to the measured blue reflectance levels (e.g., as recorded at 510 or 516 of process 500 (FIG. 5)). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 7 and FIG. 8.

At 604, the ingestible device (e.g., ingestible device 100, 300, or 400) includes a new measurement (e.g., as made with sensing sub-unit 126 (FIG. 2)) of a ratio of the measured green reflectance level to the measured blue reflectance level in the data set. For example, ingestible device 100 may be configured to occasionally record new data by transmitting green and blue illumination (e.g., via illuminator 124 (FIG. 2)), detecting the amount of reflectance received due to the green and blue illumination (e.g., via detector 122 (FIG. 2)), and storing data indicative of the amount of the received reflectance (e.g., in memory circuitry of PCB 120 (FIG. 2)). The ingestible device 100 may be configured to record new data every five to fifteen seconds, or at any other convenient interval of time. For illustrative purposes, ingestible device 100 is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be "1.0" at that given time); however, it is understood that the green reflectance data and the blue reflectance data may be stored separately within the memory of ingestible device 100 (e.g., stored as two separate data sets within memory circuitry of PCB 120 (FIG. 2)).

At 606, the ingestible device (e.g., ingestible device 100, 300, or 400) retrieves a first subset of recent data by applying a first sliding window filter to the data set. For example, ingestible device 100 may use a sliding window filter to obtain a predetermined amount of the most recent data within the data set, which may include any new values of the ratio of the measured green reflectance level to the measured blue reflectance level obtained at 604. For instance, the ingestible device may be configured to select between ten and forty data points from the data set, or ingestible device 100 may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 614).

In some embodiments, the ingestible device (e.g., ingestible device 100, 300, or 400) may also be configured to remove outliers from the data set, or to smooth out unwanted noise in the data set. For example, ingestible device 100 may select the first subset of data, or any other subset of data, by first obtaining a raw set of values by applying a window filter to the data set (e.g., selecting a particular range of data to be included). Ingestible device 100 may then be configured to identify outliers in the raw set of values; for instance, by identifying data points that are over three standard deviations away from the mean value of the raw set of values, or any other suitable threshold. Ingestible device 100 may then determine the subset of data by removing outliers from the raw set of values. This may enable ingestible device 100 to avoid spurious information when determining whether or not it is located within the stomach or the duodenum.

At 608, the ingestible device (e.g., ingestible device 100, 300, or 400) determines whether the most recently detected location was the duodenum (e.g., duodenum 310 (FIG. 3)). In some embodiments, ingestible device 100 may store a data flag (e.g., within memory circuitry of PCB 120 (FIG. 2)) indicating the most recent portion of the GI tract that the ingestible device 100 detected itself to be within. For instance, every time ingestible device 100 detects entry to the stomach (e.g., detects entry into stomach 306 (FIG. 3) as a result of the decision made at 610), a flag is stored in memory indicating the ingestible device 100 is in the stomach (e.g., as part of storing data at 612). If ingestible device 100 subsequently detects entry into the duodenum (e.g., detects entry into duodenum 310 (FIG. 3) as a result of a decision made at 624), another different flag is stored in memory indicating that the ingestible device 100 is in the duodenum (e.g., as part of storing data at 624). In this case, ingestible device 100 may retrieve the most recently stored flag at 608, and determine whether or not the flag indicates that the ingestible device 100 was most recently within the duodenum. If ingestible device 100 detects that it was most recently in the duodenum, process 600 proceeds to 610 where the ingestible device compares the recent measurements of the ratios of the measured green reflectance levels to the measured blue reflectance levels (e.g., measurements that include the recent measurement made at 606) to the typical ratios measured within the stomach, and uses this information to determine whether a reverse pyloric transition from the duodenum back to the stomach has occurred. Alternately, if ingestible device 100 detects that it was not most recently in the duodenum (e.g., because it was in the stomach instead), process 600 proceeds to 614 where the ingestible device compares the recent measurements of the ratios of the measured green reflectance levels to the measured blue reflectance levels (e.g., measurements that include the recent measurement made at 606) to past measurements, and uses this information to determine whether a pyloric transition from the stomach to the duodenum has occurred.

Process 600 proceeds from 608 to 610 when the ingestible device determined that it was most recently in the duodenum. At 610, the ingestible device (e.g., ingestible device 100, 300, or 400) determines (e.g., via control circuitry within PCB 120 (FIG. 2)) whether the current G/B signal is similar to a recorded average G/B signal in the stomach. For example, ingestible device 100 may be configured to have previously stored data (e.g., within memory circuitry of PCB 120 (FIG. 2)) indicative of the average ratio of the measured green reflectance levels to the measured blue reflectance levels measured in the stomach. Ingestible device 100 may then retrieve this stored data indicative of the average ratio of the measured green reflectance levels to the measured blue reflectance levels in the stomach, and compare this against the recent measurements in order to determine whether or not ingestible device 100 has returned back to the stomach from the duodenum. For instance, ingestible device 100 may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was "1," with a standard deviation of "0.2," ingestible device 100 may determine whether or not the mean value of the first subset of data is less than "1.0+k*0.2," where "k" is a number between zero and five. It is understood that, in some embodiments, the ingestible device 100 may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 600 proceeds to 612 where ingestible device 100 stores data indicating that it has re-entered the stomach from the duodenum. Alternately, in response to determining that the recent ratio of measured green and blue reflectance levels is sufficiently different from the average ratio of measured green and blue reflectance levels seen in the stomach, ingestible device 100 proceeds directly to 604, and continues to obtain new data on an ongoing basis.

At 612, the ingestible device (e.g., ingestible device 100, 300, or 400) stores data indicating a reverse pyloric transition from the duodenum to the stomach was detected. For example ingestible device 100 may store a data flag (e.g., within memory circuitry of PCB 120 (FIG. 2)) indicating that the ingestible device 100 most recently detected itself to be within the stomach portion of the GI tract (e.g., stomach 306 (FIG. 3)). In some embodiments, ingestible device 100 may also store data (e.g., within memory circuitry of PCB 120 (FIG. 2)) indicating a time that ingestible device 100 detected the reverse pyloric transition from the duodenum to the stomach. This information may be used by ingestible device 100 at 608, and as a result process 600 may proceed from 608 to 614, rather than proceeding from 618 to 610.

After ingestible device 100 stores the data indicating a reverse pyloric transition from the duodenum to the stomach was detected, process 600 proceeds to 604 where ingestible device 100 continues to gather additional measurements, and continues to monitor for further transitions between the stomach and the duodenum.

Process 600 proceeds from 608 to 614 when the ingestible device determined that it was not most recently in the duodenum (e.g., as a result of having most recently been in the stomach instead). At 614, the ingestible device (e.g., ingestible device 100, 300, or 400) retrieves a second subset of previous data by applying a second sliding window filter to the data set. For example, ingestible device 100 may use a sliding window filter to obtain a predetermined amount of older data from a past time range, which may be separated from recent time range used to select the first subset of data gathered at 606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, ingestible device 100 may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, ingestible device 100 may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if ingestible device 100 recently transitioned to the stomach from the duodenum (e.g., as determined by checking for recent data stored within ingestible device 100 at 612), ingestible device 100 may select the second subset of data at 614 from a time frame when ingestible device 100 is known to be within the stomach. In some embodiments, ingestible device 100 may alternately select a previously recorded average and standard deviation for ratios of green reflectances and blue reflectances within the stomach (e.g., an average and standard deviation typical of data recorded within the stomach, as previously recorded within memory circuitry of PCB 120 at 620) in place of the second subset of data. In this case, ingestible device 100 may simply use the previously recorded average and previously recorded standard deviation when making a determination at 616, rather than expending resources to calculate the mean and standard deviation of the second subset.

At 616, the ingestible device (e.g., ingestible device 100, 300, or 400) determines whether the difference between the mean of the second subset and the mean of the first subset is greater than a predetermined multiple of the standard deviation of the first subset. For example, ingestible device 100 may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 600 proceeds to 618. Otherwise, process 600 proceeds back to 604, where the ingestible device 604 continues to gather new data to be used in monitoring for transitions between the stomach (e.g., stomach 306 (FIG. 3)) and the duodenum (e.g., duodenum 310 (FIG. 3)).

At 618, the ingestible device (e.g., ingestible device 100, 300, or 400) determines (e.g., via control circuitry within PCB 120 (FIG. 2)) whether the determination made at 616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 600 proceeds to 620 to store the mean of the second subset of past data as an average GB signal in the stomach. Alternatively, if the ingestible device determines that the immediately preceding determination made at 616 is not the first time that the difference between the mean of the first subset of recent data and the mean of the second subset of past data is calculated to be greater than the standard deviation of the second subset, process 600 proceeds directly to 622.

At 620, the ingestible device (e.g., ingestible device 100, 300, or 400) stores the mean of the second subset as an average G/B signal in the stomach. For example, ingestible device 100 may be configured to store the mean of the second subset of past data (e.g., store within memory circuitry of PCB 120 (FIG. 2)) as the average ratio of the measured green reflectance levels to the measured blue reflectance levels measured in the stomach. In some embodiments, ingestible device 100 may also store the standard deviation of the second subset of past data as a typical standard deviation of the ratios of the measured green reflectance levels to the measured blue reflectance levels detected within the stomach. This stored information may be used by the ingestible device later on (e.g., at 610) to compare against future data, which may enable the ingestible device to detect reverse pyloric transitions from the duodenum (e.g., duodenum 310 (FIG. 3)) back to the stomach (e.g., stomach 306 (FIG. 3)), and may generally be used in place of other experimental data gathered from the stomach (e.g., in place of the second subset of data at 616). After storing the mean of the second subset as an average G/B signal in the stomach, process 600 proceeds to 622.

At 622, the ingestible device (e.g., ingestible device 100, 300, or 400) determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 0.1 to 0.5. If ingestible device 100 determines that the difference of the mean of the first subset of recent data to the second subset of past data is greater than a predetermined threshold, process 600 proceeds to 624 to store data indicating that a pyloric transition from the stomach to the duodenum (e.g., from stomach 306 to duodenum 310 (FIG. 3)) was detected. Alternatively, if the ingestible device determines that the ratio of the mean of the first subset to the second subset is less than or equal to the predetermined threshold, "M" (i.e., determines that a transition to the duodenum has not occurred), process 600 proceeds directly to 604 where ingestible device 100 continues to make new measurements and monitor for possible transitions between the stomach and the duodenum.

In some embodiments, instead of using a difference of the mean of the first subset of recent data to the mean of the second subset of past data, the ingestible device (e.g., ingestible device 100, 300, or 400) determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 624, the ingestible device (e.g., ingestible device 100, 300, or 400) stores data indicating a pyloric transition from the stomach to the duodenum was detected. For example ingestible device 100 may store a data flag (e.g., within memory circuitry of PCB 120 (FIG. 2)) indicating that the ingestible device 100 most recently detected itself to be within the duodenum portion of the GI tract (e.g., duodenum 310 (FIG. 3)). In some embodiments, ingestible device 100 may also store data (e.g., within memory circuitry of PCB 120 (FIG. 2)) indicating a time that ingestible device 100 detected the pyloric transition from the stomach to the duodenum. This information may be used by ingestible device 100 at 608, and as a result process 600 may proceed from 608 to 610, rather than proceeding from 618 to 614. After ingestible device 100 stores the data indicating a pyloric transition from the stomach to the duodenum was detected, process 600 proceeds to 604 where ingestible device 100 continues to gather additional measurements, and continues to monitor for further transitions between the stomach and the duodenum.

It will be understood that the steps and descriptions of the flowcharts of this disclosure, including FIG. 6, are merely illustrative. Any of the steps and descriptions of the flowcharts, including FIG. 6, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. Furthermore, it should be noted that the steps and descriptions of FIG. 6 may be combined with any other system, device, or method described in this application, and any of the ingestible devices or systems discussed in this application could be used to perform one or more of the steps in FIG. 6. For example, portions of process 600 may be incorporated into 508-516 of process 500 (FIG. 5), and may be part of a more general process for determining a location of the ingestible device. As another example, the ratio of detected blue and green light (e.g., as measured and added to the data set at 604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 7 and FIG. 8 below.

Figure 7:
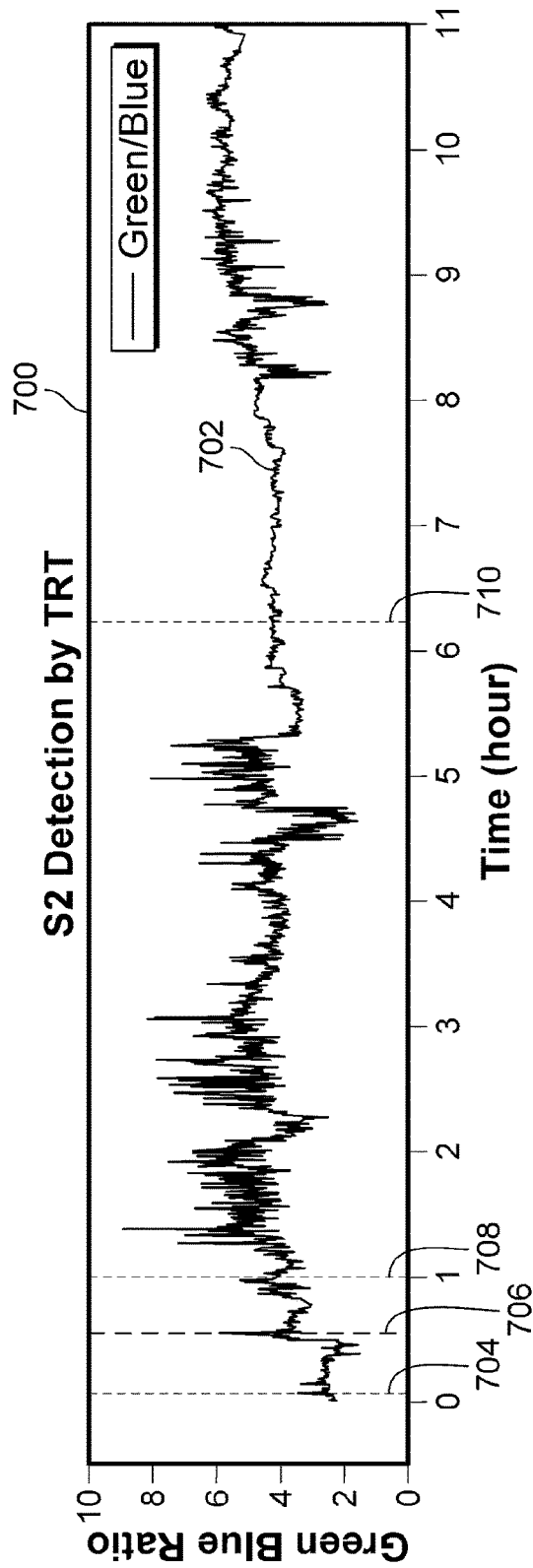
FIG. 7 is a plot illustrating data collected during an example operation of an ingestible device, which may be used when determining a location of an ingestible device as it transits through a GI tract, in accordance with some embodiments of the disclosure.

FIG. 7 is a plot illustrating data collected during an example operation of an ingestible device (e.g., ingestible device 100, 300, or 400), which may be used when determining a location of an ingestible device as it transits through a gastrointestinal (GI) tract, in accordance with some embodiments of the disclosure.

Although FIG. 7 may be described in connection with ingestible device 100 for illustrative purposes, this is not intended to be limiting, and plot 700 and data set 702 may be typical of data gathered by any device discussed in this application. Plot 700 depicts the ratios of the measured green reflectance levels to the measured blue reflectance levels over time. For example, ingestible device 100 may have computed the value for each point in the data set 702 by transmitting green and blue illumination at a given time (e.g., via illuminator 124 (FIG. 2)), measuring the resulting green and blue reflectances (e.g., via detector 122 (FIG. 2)), calculating the ratio of the resulting reflectances, and storing the ratio in the data set along with a timestamp indicating the time that the reflectances were gathered.

At 704, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels, and at 706 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 702 around 706 jump up precipitously, which is indicative of the higher ratios of measured green reflectance levels to measured blue reflectance levels typical of the duodenum.

The remainder of the data set 702 depicts the ratios of the measured green reflectance levels to the measured blue reflectance levels throughout the remainder of the GI tract. At 708, ingestible device 100 has reached the jejunum (e.g., as determined through measurements of muscle contractions, as discussed in relation to FIG. 9), and by 710, ingestible device 100 has reached the cecum. It is understood that, in some embodiments, the overall character and appearance of data set 702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum ingestible device 100 may measure a relatively stable ratio of the measured green reflectance levels to the measured blue reflectance levels. In some embodiments, ingestible device 100 may be configured to determine transitions from the small intestine to the cecum based on these differences. For example, ingestible device 100 may compare recent windows of data to past windows of data, and detect a transition to the cecum in response to determining that the standard deviation of the ratios in the recent window of data is substantially less than the standard deviation of the ratios in the past window of data.

Figure 8:
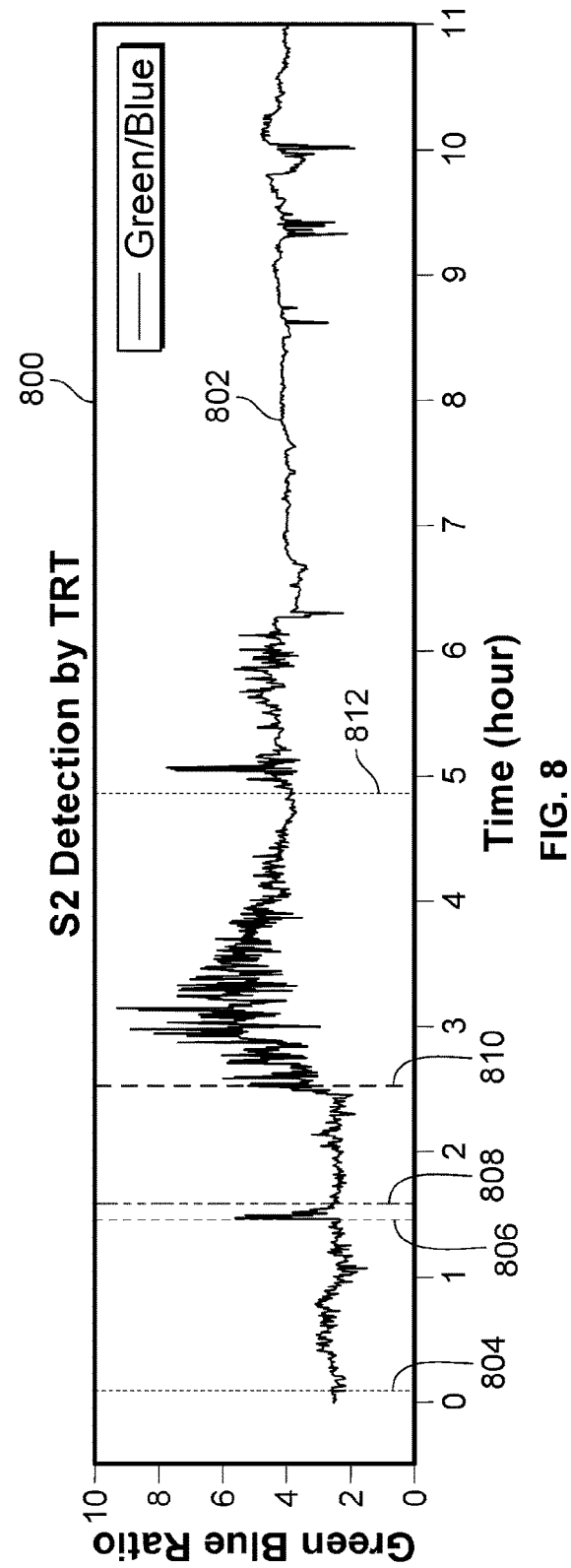
FIG. 8 is another plot illustrating data collected during an example operation of an ingestible device, which may be used when determining a location of an ingestible device as it transits through a GI tract, in accordance with some embodiments of the disclosure.

FIG. 8 is another plot illustrating data collected during an example operation of an ingestible device, which may be used when determining a location of an ingestible device as it transits through a gastrointestinal (GI) tract, in accordance with some embodiments of the disclosure. Similar to FIG. 7, FIG. 8 may be described in connection with the ingestible device 100 for illustrative purposes. However, this is not intended to be limiting, and plot 800 and data set 802 may be typical of data gathered by any device discussed in this application.

At 804, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels (e.g., via sensing sub-unit 126 (FIG. 2)), and at 806 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 802 around 806 jump up precipitously, which is indicative of the higher ratios of measured green reflectance levels to measured blue reflectance levels typical of the duodenum, before falling shortly thereafter. As a result of the reduced values in data set 802, ingestible device 100 determines that a reverse pyloric transition has occurred from the duodenum back to the stomach at 808 (e.g., as a result of making a determination similar to the determinations discussed in relation to 610-612 of process 600 (FIG. 6)). At 810, as a result of the values in data set 802 increasing again, ingestible device 100 determines that another pyloric transition has occurred from the stomach to the duodenum, and shortly thereafter ingestible device 100 proceeds onwards to the jejunum, ileum, and cecum.

The remainder of the data set 802 depicts the ratios of the measured green reflectance levels to the measured blue reflectance levels throughout the remainder of the GI tract. Notably, at 812, ingestible device reaches the transition point between the ileum and the cecum. As discussed above in relation to FIG. 7, the transition to the cecum is marked by a reduced standard deviation in the ratios of measured green reflectances and measured blue reflectances over time, and ingestible device 100 may be configured to detect a transition to the cecum based on determining that the standard deviation of a recent set of measurements is substantially smaller than the standard deviation of past measurements taken from the jejunum or ileum.

Figure 9:
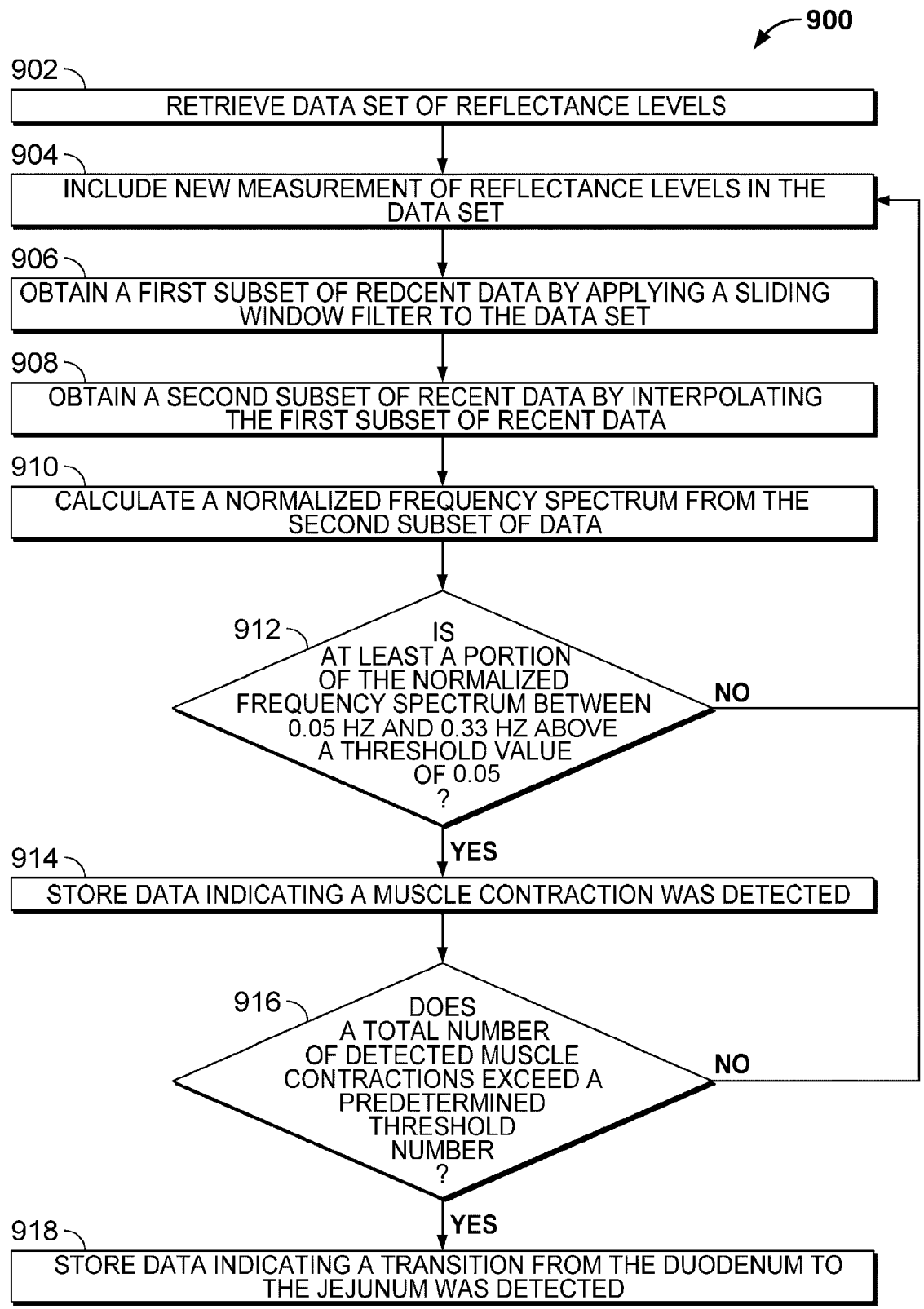
FIG. 9 is a flowchart of illustrative steps for detecting a transition from a duodenum to a jejunum, which may be used when determining a location of an ingestible device as it transits through a GI tract, in accordance with some embodiments of the disclosure.

FIG. 9 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 9 may be described in connection with the ingestible device 100 for illustrative purposes, this is not intended to be limiting, and either portions or the entirety of process 900 described in FIG. 9 may be applied to any device discussed in this application (e.g., the ingestible devices 100, 300, and 400), and any of these ingestible devices may be used to perform one or more parts of the process described in FIG. 9. Furthermore, the features of FIG. 9 may be combined with any other systems, methods or processes described in this application. For example, portions of the process described by the process in FIG. 9 may be integrated into the localization process described by FIG. 5 (e.g., as part of 520-524 of process 500 (FIG. 5)). In some embodiments, an ingestible device 100 may perform process 900 while in the duodenum, or in response to detecting entry to the duodenum. In other embodiments, an ingestible device 100 may perform process 900 while in the stomach, or in response to detecting entry into the GI tract. It is also understood that process 900 may be performed in parallel with any other process described in this disclosure (e.g., process 600 (FIG. 6)), which may enable ingestible device 100 to detect entry into various portions of the GI tract, without necessarily detecting entry into a preceding portion of the GI tract.

For illustrative purposes, FIG. 9 may be discussed in terms of ingestible device 100 generating and making determinations based on a single set of reflectance levels generated at a single wavelength by a single sensing sub-unit (e.g., sensing sub-unit 126 (FIG. 2)). However, it is understood that ingestible device 100 may generate multiple wavelengths of illumination from multiple different sensing sub-units positioned around the circumference of ingestible device (e.g., multiple sensing sub-units positioned at different locations behind window 114 of ingestible device 100 (FIG. 1), and each of the resulting reflectances may be stored as a separate data set. Moreover, each of these sets of reflectance levels may be used to detect muscle contractions by running multiple versions of process 900, each one of which processes data for a different set of reflectances corresponding to data sets obtained from measurements of different wavelengths or measurements made by different sensing sub-units.

At 902, the ingestible device (e.g., ingestible device 100, 300, or 400) retrieves a set of reflectance levels. For example, ingestible device 100 may retrieve a data set of previously recorded reflectance levels from memory (e.g., from memory circuitry of PCB 120 (FIG. 2)). Each of the reflectance levels may correspond to reflectances previously detected by ingestible device 100 (e.g., via detector 122 (FIG. 2)) from illumination generated by ingestible device 100 (e.g., via illuminator 124 (FIG. 2)), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by ingestible device 100 at periodic intervals.

At 904, the ingestible device (e.g., ingestible device 100, 300, or 400) includes new measurements of reflectance levels in the data set. For example, ingestible device 100 may be configured to detect a new reflectance (e.g., transmit illumination and detect the resulting reflectance using sensing sub-unit 126 (FIG. 2)) at regular intervals, or with sufficient speed as to detect peristaltic waves. For example, ingestible device 100 may be configured to generate illumination and measure the resulting reflectance once every three seconds (i.e., the minimum rate necessary to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time ingestible device 100 makes a new reflectance level measurement at 904, the new data is included to the data set (e.g., a data set stored within memory circuitry of PCB 120 (FIG. 2)).

At 906, the ingestible device (e.g., ingestible device 100, 300, or 400) obtains a first subset of recent data by applying a sliding window filter to the data set. For example, ingestible device 100 may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.1 Hz to 0.2 Hz for healthy human subjects). In some embodiments, ingestible device 100 may also clean the data, for example, by removing outliers from the first subset of data obtained through the use of the sliding window filter.

At 908, the ingestible device (e.g., ingestible device 100, 300, or 400) obtains a second subset of recent data by interpolating the first subset of recent data. For example, ingestible device 100 may interpolate the first subset of data in order to generate a second subset of data with a sufficient number of data points (e.g., data points spaced every 0.5 seconds or greater). In some embodiments, this may enable ingestible device 100 to also replace any outlier data points that may have been removed as part of applying the window filter at 906.

At 910, the ingestible device (e.g., ingestible device 100, 300, or 400) calculates a normalized frequency spectrum from the second subset of data. For example, ingestible device 100 may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and ingestible device 100 may be configured to have pre-stored values of a normalized discreet Fourier transform (DFT) matrix, or the rows of the DFT matrix corresponding to the 0.1 Hz to 0.2 Hz frequency components of interest, within memory (e.g., memory circuitry of PCB 120 (FIG. 2)). In this case, the ingestible device may use matrix multiplication between the DFT matrix and the data set to generate an appropriate frequency spectrum. An example data set and corresponding frequency spectrum that may be obtained by the ingestible device is discussed in greater detail in relation to FIG. 10.

At 912, the ingestible device (e.g., ingestible device 100, 300, or 400) determines whether at least a portion of the normalized frequency spectrum is between 0.1 Hz and 0.2 Hz above a threshold value of 0.5 Hz. Peristaltic waves in a healthy human subject occur at a rate between 0.1 Hz and 0.2 Hz, and an ingestible device experiencing peristaltic waves (e.g., ingestible device 400 detecting contractions in walls 406 of the jejunum (FIG. 4)) may detect sinusoidal variations in the amplitude of detected reflectances levels that follow a similar 0.1 Hz to 0.2 Hz frequency. If the ingestible device determines that a portion of the normalized frequency spectrum between 0.1 Hz and 0.2 Hz is above a threshold value of 0.5, this measurement may be consistent with peristaltic waves in a healthy human subject, and process 900 proceeds to 914 where ingestible device 100 stores data indicating a muscle contraction was detected. Alternatively, if the ingestible device determines that no portion of the normalized frequency spectrum between 0.1 Hz and 0.2 Hz above a threshold value of 0.5, process 900 proceeds directly to 904 to make new measurements and to continue to monitor for new muscle contractions. It is understood that a threshold value other than 0.5 may be used, and that the exact threshold may depend on the sampling frequency and type of frequency spectrum used by ingestible device 100.

At 914, the ingestible device (e.g., ingestible device 100, 300, or 400) stores data indicating a muscle contraction was detected. For example, ingestible device 100 may store data in memory (e.g., memory circuitry of PCB 120 (FIG. 2)) indicating that a muscle contraction was detected, and indicating the time that the muscle contraction was detected. In some embodiments, ingestible device 100 may also monitor the total number of muscle contractions detected, or the number of muscle contractions detected in a given time frame. In some embodiments, detecting a particular number of muscle contractions may be consistent with ingestible device 100 being within the jejunum (e.g., jejunum 314 (FIG. 3)) of a healthy human subject. After detecting a muscle contraction, process 900 proceeds to 916.

At 916, the ingestible device (e.g., ingestible device 100, 300, or 400) determines whether a total number of muscle contractions exceeds a predetermined threshold number. For example, ingestible device 100 may retrieve the total number of muscle contractions detected from memory (e.g., from memory circuitry of PCB 120 (FIG. 2)), and compare the total number to a threshold value. In some embodiments, the threshold value may be one, or any number larger than one. The larger the threshold value, the more muscle contractions need to be detected before ingestible device 100 stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 900 proceeds to 918 to store data indicating detection of a transition from the duodenum to the jejunum. Alternatively, if the total number of contractions does not exceed a predetermined threshold number, process 900 proceeds to 904 to include new measurements of reflectance levels in the data set. An example plot of the muscle contractions detected over time is discussed in greater detail in relation to FIG. 11.

At 918, the ingestible device (e.g., ingestible device 100, 300, or 400) stores data indicating detection of a transition from the duodenum to the jejunum. For example, ingestible device 100 may store data in memory (e.g., from memory circuitry of PCB 120 (FIG. 2)) indicating that the jejunum has been reached. In some embodiments, if ingestible device 100 is configured to perform all or part of process 900 while in the stomach, ingestible device 100 may store data at 918 indicating detection of a transition from the stomach directly to the jejunum (e.g., as a result of transitioning too quickly through the duodenum for the pyloric transition to be detected using process 600 (FIG. 6)).

In some embodiments, the ingestible device (e.g., ingestible device 100, 300, or 400) may be configured to obtain a fluid sample from the environment external to a housing of the ingestible device in response to identifying a change in the location of the ingestible device. For example, ingestible device 100 may be configured to obtain a fluid sample from the environment external to the housing of ingestible device 100 (e.g., through the use of optional opening 116 and optional rotating assembly 118 (FIG. 2)) in response to determining that the ingestible device is located within the jejunum (e.g., jejunum 314 (FIG. 3)). In some embodiments, ingestible device 100 may also be equipped with appropriate diagnostics to detect certain medical conditions based on the retrieved fluid sample, such as small intestinal bacterial overgrowth (SIBO).

In some embodiments, the ingestible device (e.g., ingestible device 100, 300, or 400) may be configured to deliver a dispensable substance that is pre-stored within the ingestible device from the ingestible device into the gastrointestinal tract in response to identifying the change in the location of the ingestible device. For example, ingestible device 100 may have a dispensable substance pre-stored within the ingestible device 100 (e.g., within a storage chamber or cavity on optional storage sub-unit 118-3 (FIG. 2)), and ingestible device 100 may be configured to dispense the substance into the gastrointestinal tract (e.g., through the use of optional opening 116 and optional rotating assembly 118 (FIG. 2)) when the ingestible device 100 detects that the ingestible device 100 is located within the jejunum (e.g., jejunum 314 (FIG. 3)). In some embodiments, this may enable ingestible device 100 to deliver substances (e.g., therapeutics and medicaments) at targeted locations within the GI tract.

In some embodiments, the ingestible device (e.g., ingestible device 100, 300, or 400) may be configured to perform an action based on the total number of detected muscle contractions. For example, ingestible device 100 may be configured to retrieve data indicative of the total number of muscle contractions (e.g., from memory circuitry of PCB 120 (FIG. 2)), and compare that to an expected number muscle contractions in a healthy individual. In response, the ingestible device may either dispense a substance into the gastrointestinal tract (e.g., through the use of optional opening 116 and optional rotating assembly 118 (FIG. 2)), or may obtain a fluid sample from the environment external to the housing of ingestible device 100 (e.g., through the use of optional opening 116 and optional rotating assembly 118 (FIG. 2)). For instance, ingestible device 100 may be configured to obtain a sample in response to determining that a number of detected muscle contractions is abnormal, and differs greatly from the expected number. As another example, ingestible device 100 may be configured to deliver a substance into the GI tract (such as a medicament), in response to determining that the detected muscle contractions are consistent with a functioning GI tract in a healthy individual.

It will be understood that the steps and descriptions of the flowcharts of this disclosure, including FIG. 9, are merely illustrative. Any of the steps and descriptions of the flowcharts, including FIG. 9, may be modified, omitted, rearranged, performed in alternate orders or in parallel, two or more of the steps may be combined, or any additional steps may be added, without departing from the scope of the present disclosure. For example, the ingestible device 100 may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of FIG. 9 may be combined with any other system, device, or method described in this application, and any of the ingestible devices or systems discussed in this application could be used to perform one or more of the steps in FIG. 9.

Figure 10:
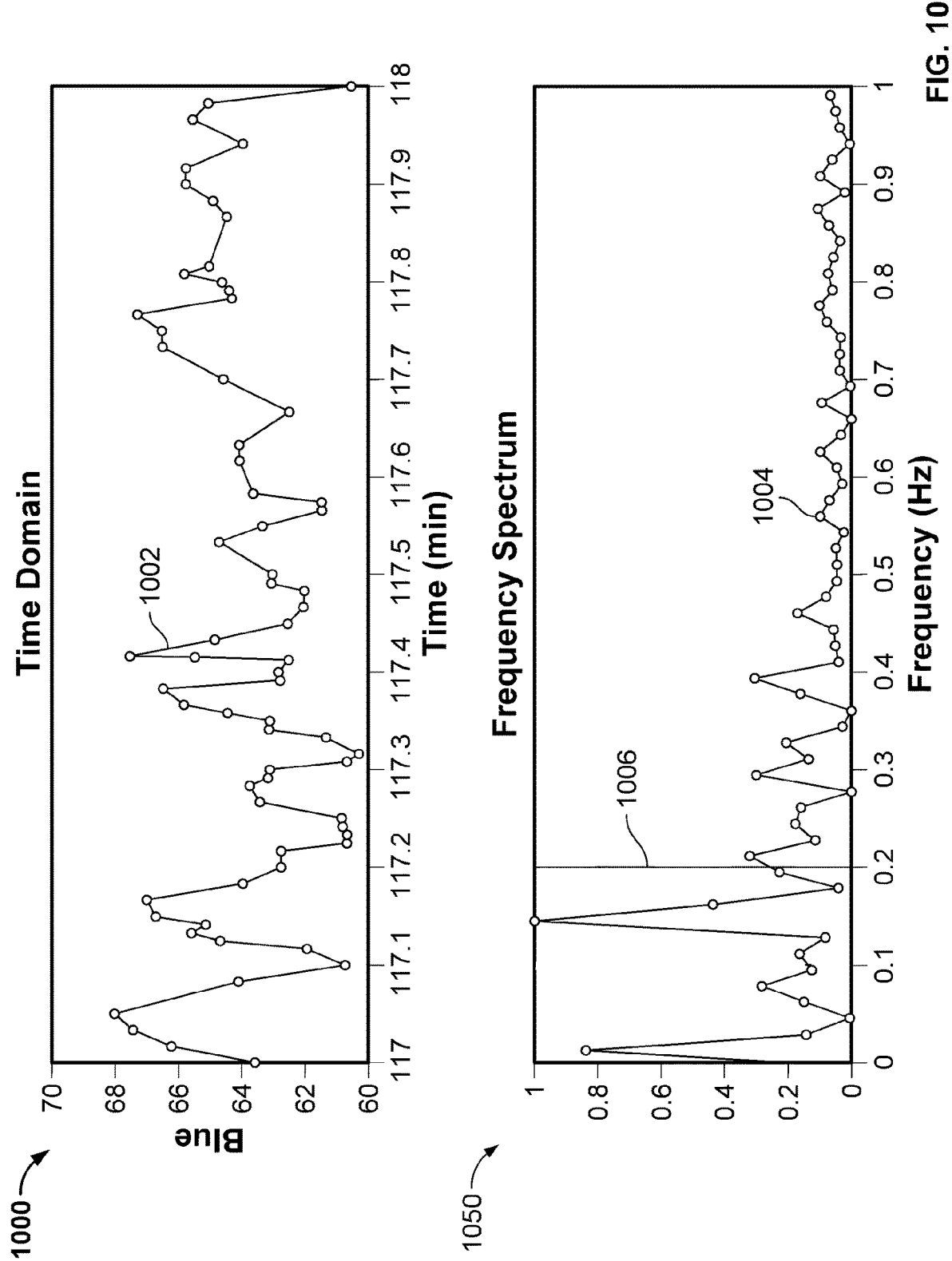
FIG. 10 is a plot illustrating data collected during an example operation of an ingestible device, which may be used when detecting a transition from a duodenum to a jejunum, in accordance with some embodiments of the disclosure.

FIG. 10 is a plot illustrating data collected during an example operation of an ingestible device, which may be used when detecting a transition from a duodenum to a jejunum, in accordance with some embodiments of the disclosure. Diagram 1000 depicts a time domain plot 1002 of a data set of reflectance levels measured by an ingestible device (e.g., the second subset of data discussed in relation to 908 of FIG. 9). In some embodiments, ingestible device 100 may be configured to gather data points at semi-regular intervals approximately 0.5 seconds apart. By comparison, diagram 1050 depicts a frequency domain plot 1004 of the same data set of reflectance levels measured by an ingestible device (e.g., as a result of ingestible device 100 calculating a frequency spectrum at 910 of FIG. 9). In some embodiments, ingestible device 100 may be configured to calculate the frequency spectrum through any convenient means.

In diagram 1050, the range of frequencies 1006 between 0.1 Hz and 0.2 Hz may be the range of frequencies that ingestible device 100 searches in order to detect muscle contractions. As shown in diagram 1050, there is a strong peak in the frequency domain plot 1004 around 0.14 Hz, which is consistent with the frequency of peristaltic motion in a healthy human individual. In this case, an ingestible device 100 analyzing frequency domain plot 1004 may be configured to determine that the data is consistent with a detected muscle contraction (e.g., using a process similar to 912 of process 900 (FIG. 9)), and may store data (e.g., in memory circuitry of PCB 120 (FIG. 2)) indicating that a muscle contraction has been detected. Because the muscle contraction was detected from the one-minute window of data ending at 118 minutes, ingestible device 100 may also store data indicating that the muscle contraction was detected at the 118-minute mark (i.e., which may indicate that the ingestible device 100 was turned on and ingested by the subject 118 minutes ago).

Figure 11:
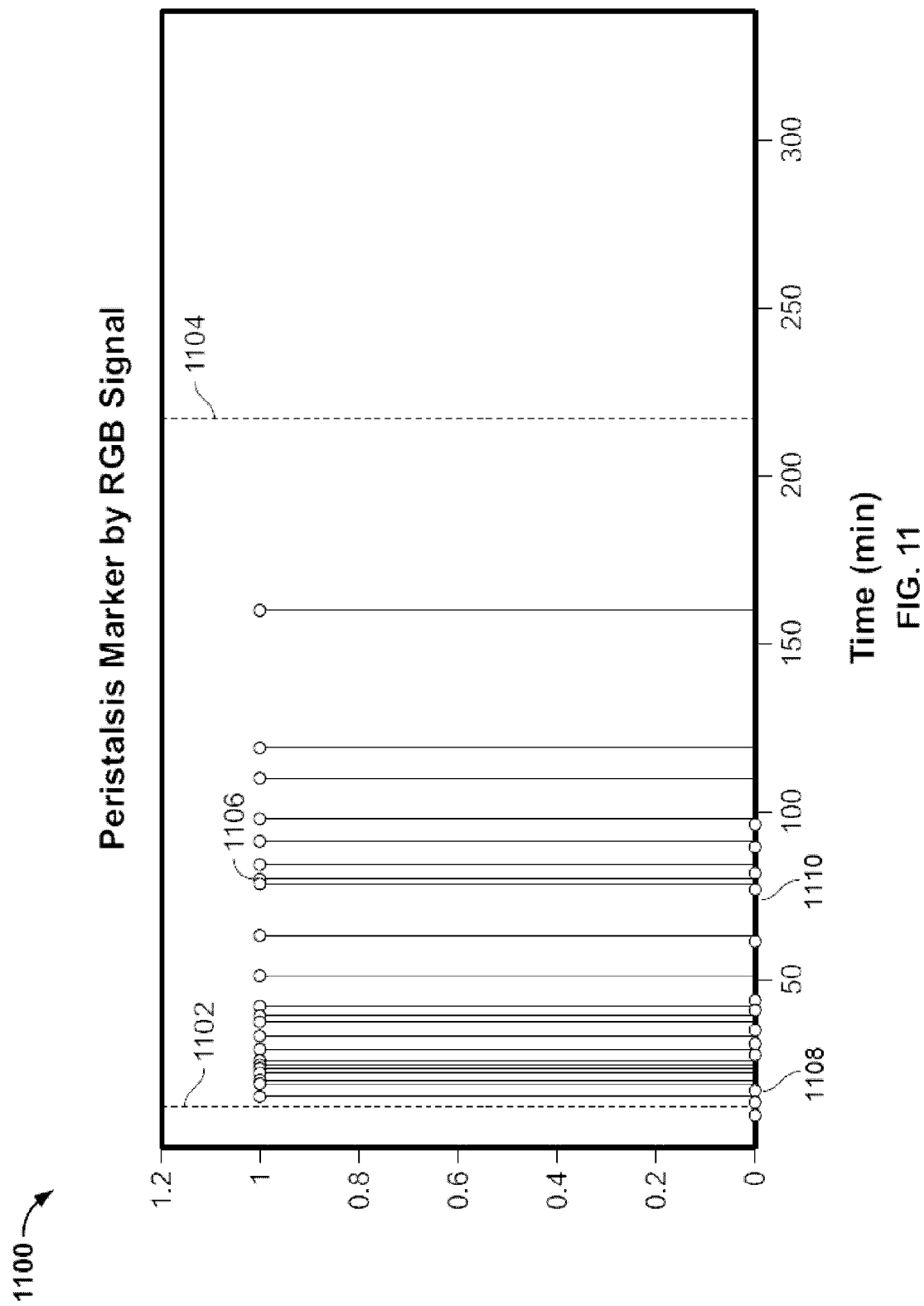
FIG. 11 is a plot illustrating muscle contractions detected by an ingestible device over time, which may be used when determining a location of an ingestible device as it transits through a GI tract, in accordance with some embodiments of the disclosure.

FIG. 11 is a plot illustrating muscle contractions detected by an ingestible device over time, which may be used when determining a location of an ingestible device as it transits through a gastrointestinal (GI) tract, in accordance with some embodiments of the disclosure. In some embodiments, ingestible device 100 may be configured to detect muscle contractions, and store data indicative of when each muscle contraction is detected (e.g., as part of 914 of process 900 (FIG. 9)). Plot 1100 depicts the detected muscle contractions 1106 over time, with each muscle contraction being represented by a vertical line reaching from "0" to "1" on the y-axis. At 1102, around the 10-minute mark, ingestible device 100 first enters the duodenum (e.g., as determined by ingestible device 100 performing process 600 (FIG. 6)). Shortly thereafter, at 1108, ingestible device 100 begins to detect several muscle contractions 1106 in quick succession, which may be indicative of the strong peristaltic waves that form in the jejunum (e.g., jejunum 314 (FIG. 3)). Later, around 1110, ingestible device 100 continues to detect intermittent muscle contractions, which may be consistent with an ingestible device 100 within the ileum. Finally at 1104, ingestible device 100 transitions out of the small intestine, and into the cecum. Notably, ingestible device 100 detects more frequent muscle contractions in the jejunum portion of the small intestine as compared to the ileum portion of the small intestine, and ingestible device 100 does not measure any muscle contractions after having exited the small intestine. In some embodiments, ingestible device 100 may incorporate this information into a localization process. For example, ingestible device 100 may be configured to detect a transition from a jejunum to an ileum in response to determining that a frequency of detected muscle contractions (e.g., the number of muscle contractions measured in a given 10-minute window) has fallen below a threshold number. As another example, ingestible device 100 may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

Figure 12:
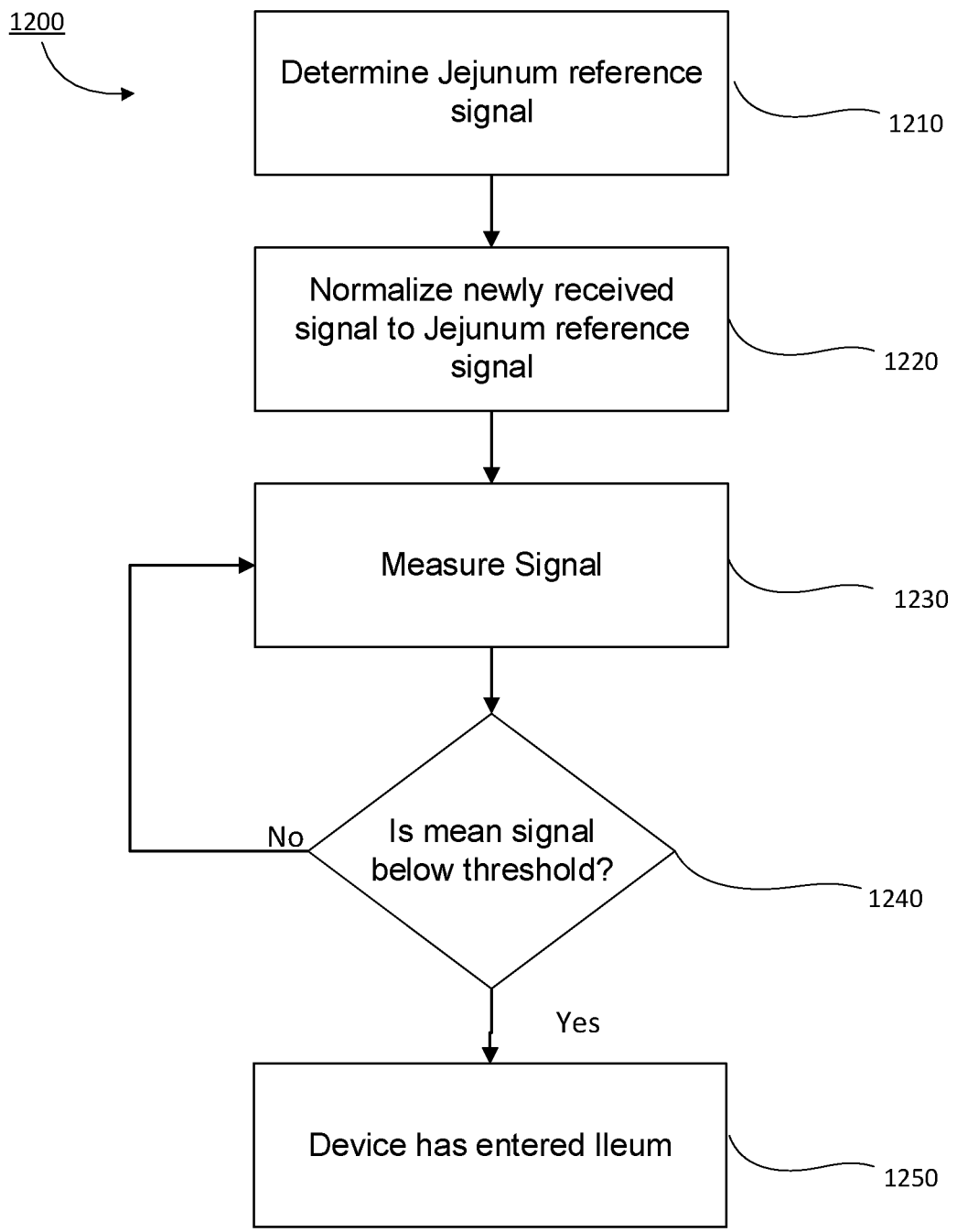
FIG. 12 is a flowchart of illustrative steps for detecting a transition from a jejunum to an ileum, which may be used when determining a location of an ingestible device as it transits through a GI tract, in accordance with some embodiments of the disclosure.

FIG. 12 is a flowchart 1200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more messentary fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 1200 represents a single sliding window process. In step 1210, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 1220, the detected signal (e.g., reflected red light) just after the period of time used in step 1210 is normalized to the reference signal determined in step 1210. In step 1230, the signal (e.g., reflected red light) is detected. In step 1240, the mean signal detected based on the single sliding window is compared to a signal threshold. The signal threshold in step 1240 is generally a fraction of the reference signal of the jejunum reference signal determined in step 1210. For example, the signal threshold can be from 60% to 90% (e.g., from 70% to 80%) of the jejunum reference signal. If the mean signal exceeds the signal threshold, then the process determines that the device has entered the ileum at step 1250. If the mean signal does not exceed the signal threshold, then the process returns to step 1230.

Figure 13:
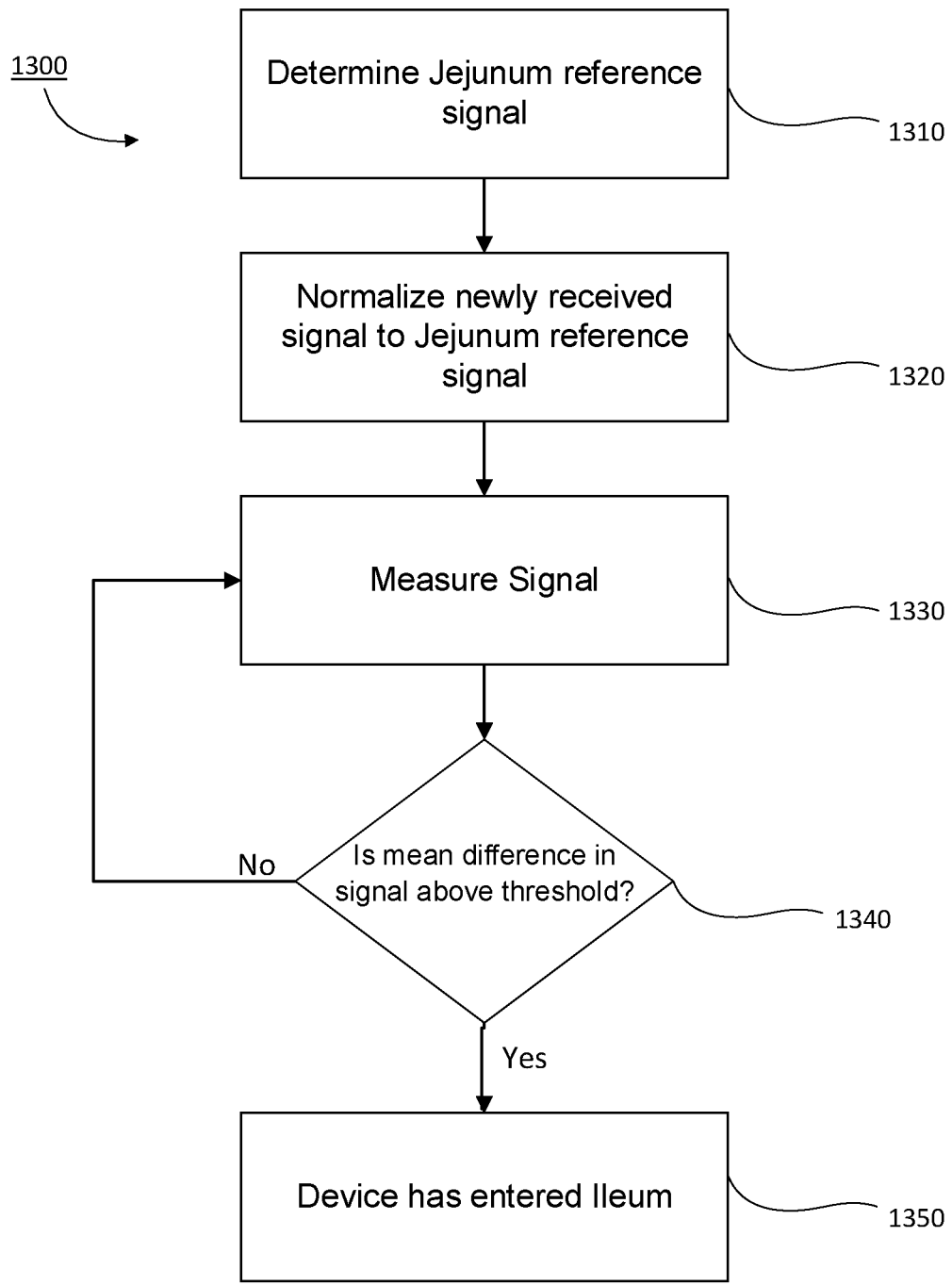
FIG. 13 is a flowchart of illustrative steps for detecting a transition from a jejunum to an ileum, which may be used when determining a location of an ingestible device as it transits through a GI tract, in accordance with some embodiments of the disclosure.

FIG. 13 is a flowchart 1200 for certain embodiments for determining a transition of the device from the jejunum to the ileum using a two sliding window process. In step 1310, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 1320, the detected signal (e.g., reflected red light) just after the period of time used in step 1310 is normalized to the reference signal determined in step 1310. In step 1330, the signal (e.g., reflected red light) is detected. In step 1340, the mean difference in the signal detected based on the two sliding windows is compared to a signal threshold. The signal threshold in step 1340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 1350. If the signal threshold is not exceeded, then the process returns to step 1330.

Figure 14:
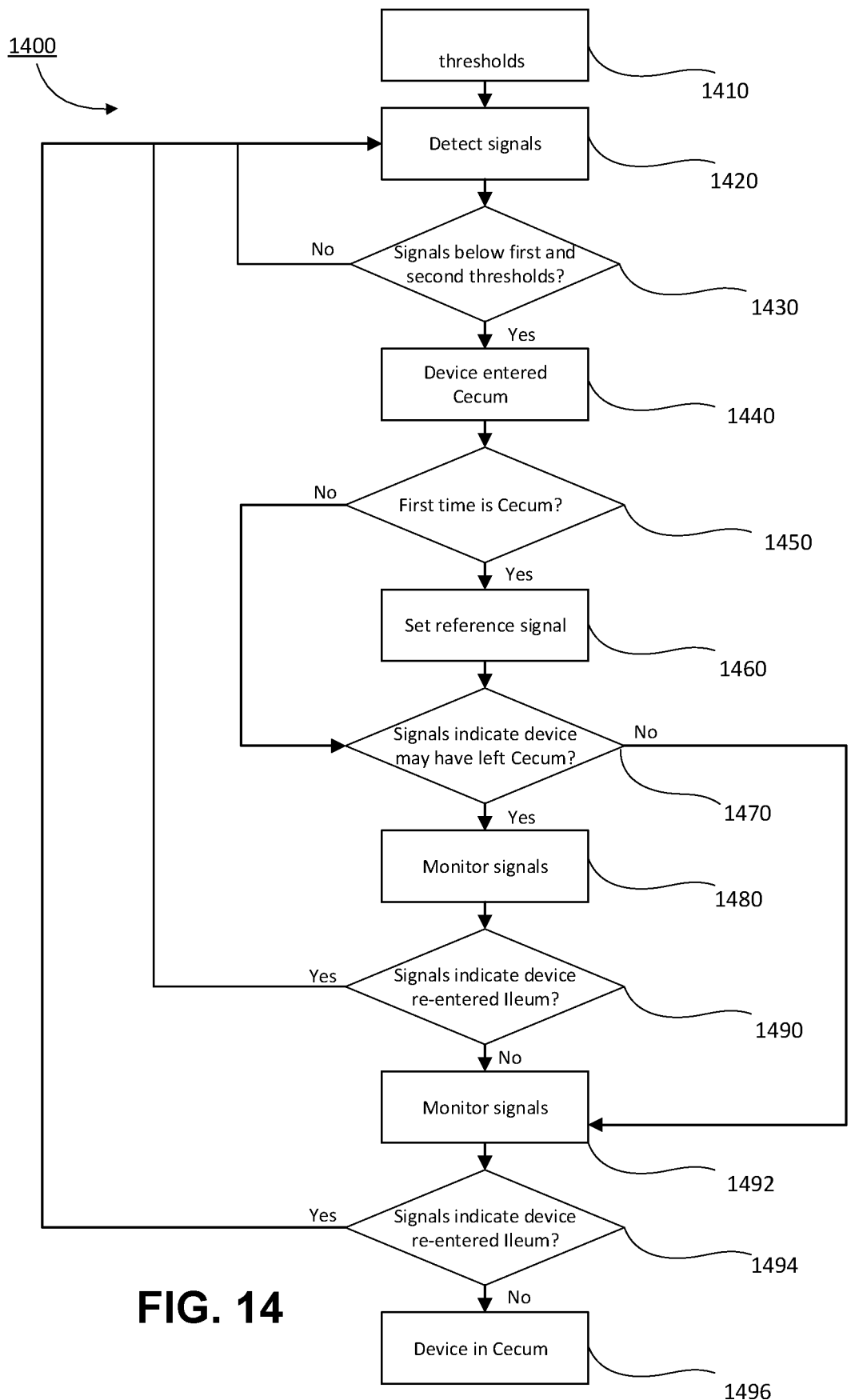
FIG. 14 is a flowchart of illustrative steps for detecting a transition from an ileum to a cecum, which may be used when determining a location of an ingestible device as it transits through a GI tract, in accordance with some embodiments of the disclosure.

FIG. 14 is a flowchart 1400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 1400, the sliding window analysis (first and second windows) discussed with respect to process 600 is continued.

Step 1410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 1420 includes detecting the signals in the first and second windows that are to be used for comparing to the first and second thresholds.

Step 1430 includes comparing the detected signals to the first and second thresholds. If the corresponding value is not below the first threshold or the corresponding value is not below the second threshold, then it is determined that the device has not left the ileum and entered the cecum, and the process returns to step 1420. If the corresponding value is below the first threshold and the corresponding value is below the second threshold, then it is determined that the device has left the ileum and entered the cecum, and the proceeds to step 1440.

Step 1450 includes determining whether it is the first time that that the device was determined to leave the ileum and enter the cecum. If it is the first time that the device was determined to leave the ileum and enter the cecum, then the process proceeds to step 1460. If it is not the first time that the device has left the ileum and entered the cecum, then the process proceeds to step 1470.

Step 1460 includes setting a reference signal. In this step the optical signal (e.g., ratio of detected red light to detected green light) as a reference signal.

Step 1470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 1460) and the coefficient of variation for the corresponding detected signal (e.g., ratio of detected green light to detected blue light) exceeds the second threshold. If it is determined that the device may have left the cecum and returned to the ileum, the process proceeds to step 1480.

Step 1480 includes continuing to detect the relevant optical signals for a period of time (e.g., at least one minute, from five minutes to 15 minutes).

Step 1490 includes determining whether the signals determined in step 1480 indicate (using the methodology discussed in step 1470) that the device re-entered the ileum. If the signals indicate that the device re-entered the ileum, the process proceeds to step 1420. If the signals indicate that the device is in the cecum, the process proceeds to step 1492.

Step 1492 includes continuing to monitor the relevant optical signals for a period of time (e.g., at least 30 minutes, at least one hour, at least two hours).

Step 1494 includes determining whether the signals determined in step 1492 indicate (using the methodology discussed in step 1470) that the device re-entered the ileum. If the signals indicate that the device re-entered the ileum, the process proceeds to step 1420. If the signals indicate that the device is in the cecum, the process proceeds to step 1496.

At step 1496, the process determines that the device is in the cecum.

Figure 15:
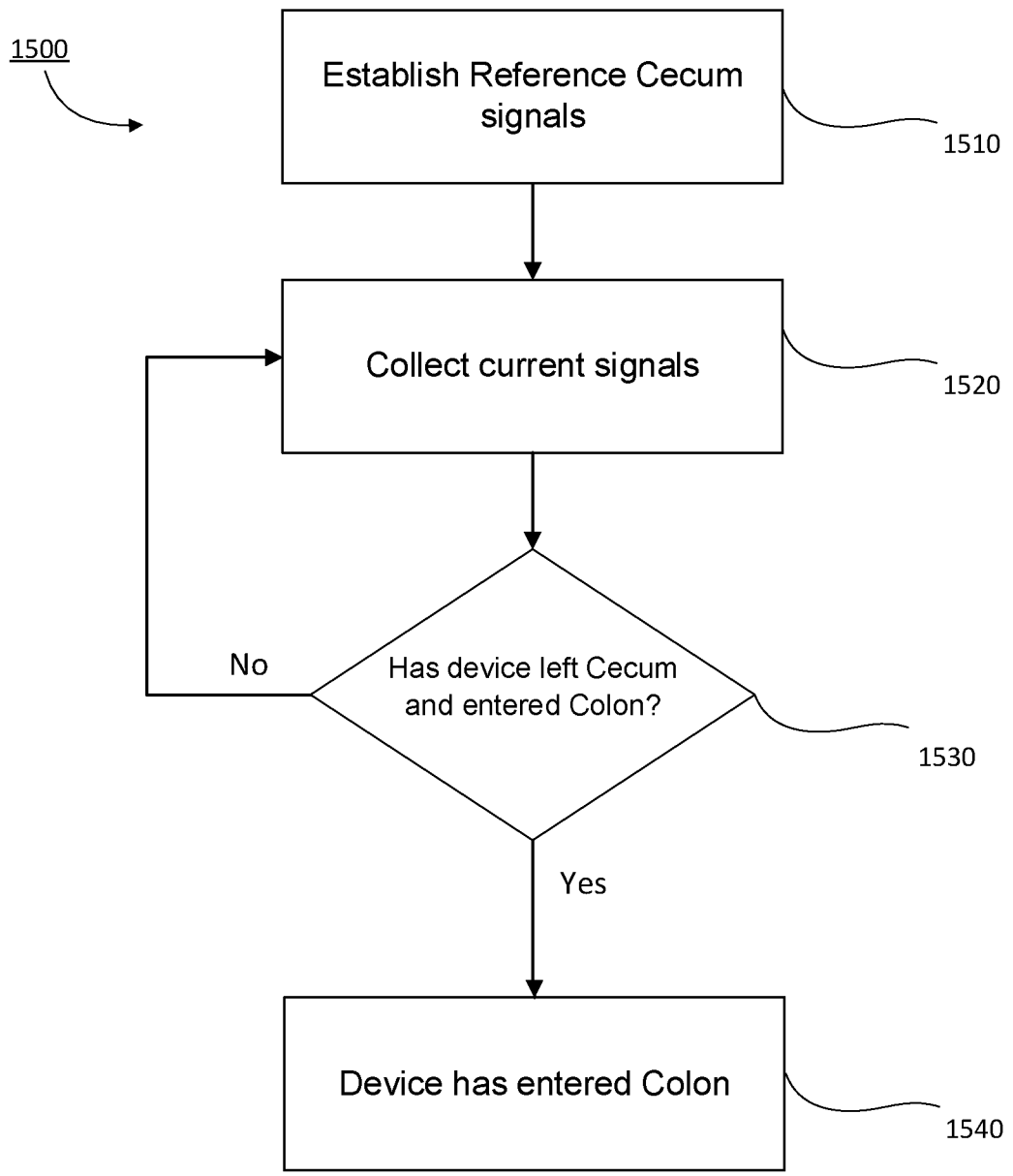
FIG. 15 is a flowchart of illustrative steps for detecting a transition from a cecum to a colon, which may be used when determining a location of an ingestible device as it transits through a GI tract, in accordance with some embodiments of the disclosure.

FIG. 15 is a flowchart 1500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 1500, the sliding window analysis (first and second windows) discussed with respect to process 1400 is continued.

In step 1510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 1480). The average values for the recorded optical signals (e.g., the ratio of reflected red signal to reflected green signal, and reflected blue signal) establish the cecum reference signals.

In step 1520, the optical signals are detected after it has been determined that the device entered the cecum (e.g., at step 1440). The optical signals are normalized to the cecum reference signals.

Step 1530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 1540. Otherwise, none of the three criteria are satisfied, the process returns to step 1520.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 500 (FIG. 5), process 600 (FIG. 6), process 900 (FIG. 9), process 1200 (FIG. 12), process 1300 (FIG. 13), process 1400 (FIG. 14) and process 1500 (FIG. 15)). Also, the applications of the ingestible devices described herein are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within PCB 120 (FIG. 2)) may be written in a high-level procedural language such as object oriented programming, a scripting language or both. Accordingly, the program code may be written in C, C++ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

Methods and Mechanisms of Delivery

Figure 16:
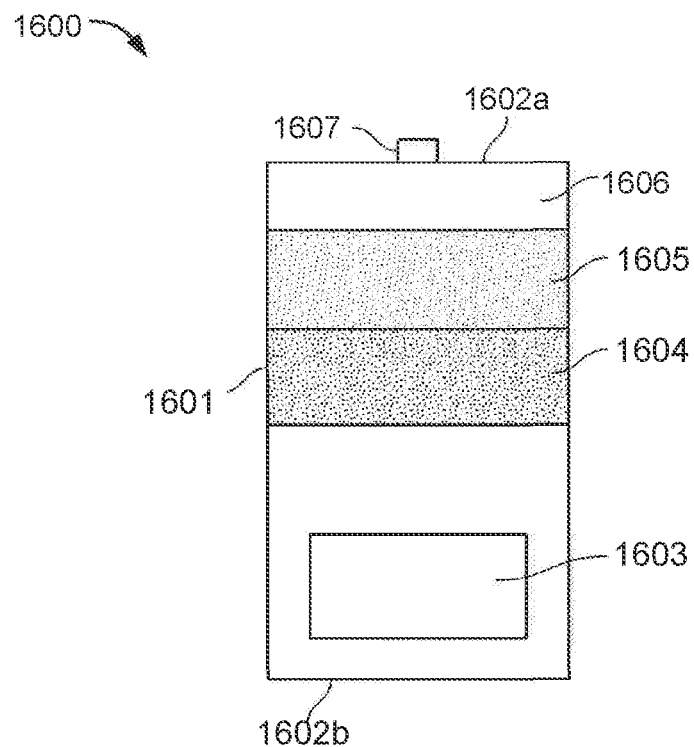
FIG. 16 illustrates an ingestible device for delivering a substance in the GI tract.

FIG. 16 provides an example mock-up diagram illustrating aspects of a structure of an ingestible device 1600 for delivering a dispensable substance, such as a formulation of a therapeutic agent described herein, according to some embodiments described herein. In some embodiments, the ingestible device 1600 may generally be in the shape of a capsule, a pill or any swallowable form that may be orally consumed by an individual. In this way, the ingestible device 1600 may be ingested by a patient and may be prescribed by healthcare practitioners and patients.

The ingestible device 1600 includes a housing 1601 that may take a shape similar to a capsule, a pill, and/or the like, which may include two ends 1602a-b. The housing 1601 may be designed to withstand the chemical and mechanical environment of the GI tract (e.g., effects of muscle contractile forces and concentrated hydrochloric acid in the stomach). A broad range of materials that may be used for the housing 1601. Examples of these materials include, but are not limited to, thermoplastics, fluoropolymers, elastomers, stainless steel and glass complying with ISO 10993 and USP Class VI specifications for biocompatibility; and any other suitable materials and combinations thereof.

In some embodiment, the wall of the housing 1601 may have a thickness of 0.5 mm-1 mm, which is sufficient to sustain an internal explosion (e.g., caused by hydrogen ignition or over pressure inside the housing).

The housing 1601 may or may not have a pH-sensitive enteric coating to detect or otherwise be sensitive to a pH level of the environment external to the ingestible device. As discussed elsewhere in the application in more detail, the ingestible device 1600 may additionally or alternatively include one more sensors, e.g., temperature sensor, optical sense.

The housing 1601 may be formed by coupling two enclosure portions together. The ingestible device 1600 may include an electronic component within the housing 1600. The electronic component may be placed proximally to an end 1602b of the housing, and includes a printed circuit board (PCB), a battery, an optical sensing unit, and/or the like.

The ingestible device 1600 further includes a gas generating cell 1603 that is configured to generate gas and thus cause an internal pressure within the housing 1601. In some embodiments, the gas generating cell may include or be connected to a separate channel or valve of the ingestible device such that gas may be release through the channel or valve to create a motion to alter the position of the ingestible device within the GI tract. Such gas release can also be used to position the ingestible device relative to the intestinal lining. In another embodiment, gas may be released through the separate channel or valve to alter the surface orientation of the intestinal tissue prior to delivery of the dispensable substance.

A traveling plunger 1604 may be placed on top of the gas generating cell 1603 within the housing 1601. The traveling plunger 1604 is a membrane that separates the gas generating cell 1603 and a storage reservoir that stores the dispensable substance 1605. In some embodiments, the traveling plunger 1604 may be a movable piston. In some embodiments, the traveling plunger 1604 may instead be a flexible membrane such as but not limited to a diaphragm. In some embodiments, the traveling plunger 1604, which may have the form of a flexible diaphragm, may be placed along an axial direction of the housing 1601, instead of being placed on top of the gas generating cell 1603. The traveling plunger or the membrane 1604 may move (when the membrane 1604 is a piston) or deform (when the membrane 1604 is a diaphragm) towards a direction of the end 1602a of the housing, when the gas generating cell 1603 generates gas to create an internal pressure that pushes the membrane 1604. In this way, the membrane or traveling plunger 1604 may push the dispensable substance 1605 out of the housing via a dispensing outlet 1607.

The housing 1601 may include a storage reservoir storing one or more dispensable substances 1605 adjacent to the traveling plunger 1604. The dispensable substance 1605 may be a therapeutic or medical agent that may take a form of a powder, a compressed powder, a fluid, a semi-liquid gel, or any other dispensable or deliverable form. The delivery of the dispensable substance 1605 may take a form such as but not limited to bolus, semi-bolus, continuous, burst drug delivery, and/or the like. In some embodiments, a single bolus is delivered proximate to the disease location. In some embodiments, more than one bolus is released at one location or more than one location. In some embodiments the release of more than one bolus is triggered according to a pre-programmed algorithm. In some embodiments the release profile is continuous. In some embodiments the release profile is time-based. In some embodiments the release profile is location-based. In some embodiments, the amount delivered is based on the severity and/or extent of the disease in the following manner. In some embodiments, the bolus is delivered in one or more of the following locations: stomach; duodenum; proximal jejunum; ileum; cecum; ascending colon; transverse colon; descending colon.

In some embodiments the dispensable substance is a small molecule therapeutic that is released in the cecum and/or other parts of the large intestine. Small molecules that are administered by typical oral routes are primarily absorbed in the small intestine, with much lower absorption taking place in the large intestine (outside of the rectum). Accordingly, an ingestible device that is capable of releasing a small molecule selectively in the large intestine (e.g., the cecum) with resulting low systemic levels (even when high doses are used) is attractive for subjects with inflammatory bowel disease in the large intestine.

In some embodiments, the storage reservoir may include multiple chambers, and each chamber stores a different dispensable substance. For example, the different dispensable substances can be released at the same time via the dispensing outlet 1607. Alternatively, the multiple chambers may take a form of different layers within the storage reservoir such that the different dispensable substance from each chamber is delivered sequentially in an order. In one example, each of the multiple chambers is controlled by a separate traveling plunger, which may be propelled by gas generation. The electronic component may control the gas generating cell 1603 to generate gas to propel a specific traveling plunger, e.g., via a separate gas generation chamber, etc., to delivery the respective substance. In some embodiments, the content of the multiple chambers may be mixed or combined prior to release, for example, to activate the drug.

The ingestible device 1600 may include a dispensing outlet 1607 at one end 1602a of the housing 1601 to direct the dispensable substance 105 out of the housing. The dispensing outlet 1607 may include an exit valve, a slit or a hole, a jet injection nozzle with a syringe, and/or the like. When the traveling plunger 1604 moves towards the end 1602a of the housing 1601, an internal pressure within the storage reservoir may increase and push the dispensing outlet to be open to let the dispensable substance 1605 be released out of the housing 1601.

In an embodiment, a pressure relief device 1606 may be placed within the housing 1601, e.g., at the end 1602a of the housing 1601.

In some embodiments, the housing 1601 may include small holes (e.g., with a diameter smaller than 2 mm), e.g., on the side of the housing 1601, or at the end 1602a to facilitate loading the dispensable substance into the storage reservoir.

In some embodiments, a feedback control circuit (e.g., a feedback resistor, etc.) may be added to send feedback from the gas generating cell 1603 to the electronic component such that when the internal pressure reaches a threshold level, the electronic component may control the gas generating cell 1603 to turn off gas generation, or to activate other safety mechanism (e.g., feedback-controlled release valve, etc.). For example, an internal pressure sensor may be used to measure the internal pressure within the ingestible device and generate feedback to the feedback control circuit.

Figure 17:
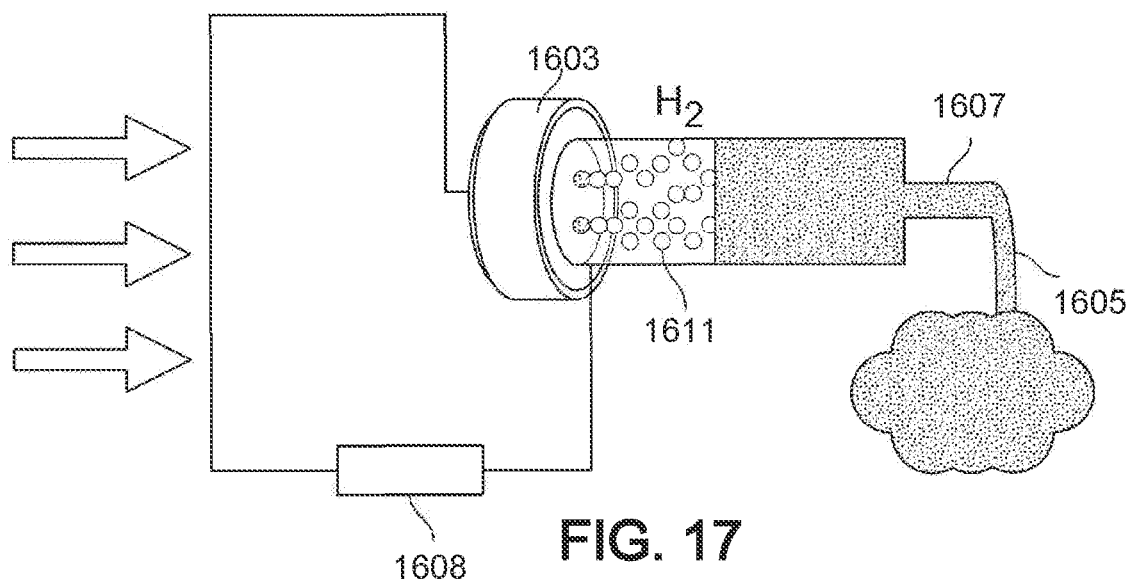
FIG. 17 illustrates aspects of a mechanism for an ingestible device with a gas generating cell configured to generate a gas to dispense a substance.

FIG. 17 provides an example diagram illustrating aspects of a mechanism for a gas generating cell 1603 configured to generate a gas to dispense a substance, according to some embodiments described herein. As shown in FIG. 17, the gas generating cell 1603 generates a gas 1611 which can propel the dispensable substance 1605 out of the dispensing outlet 1607. A variable resistor 1608 may be connected to a circuit with the gas generating cell 1603 such that the variable resistor 1608 may be used to control an intensity and/or an amount of gas 1611 (e.g., hydrogen) generated by the cell 1603. Specifically, the gas generating cell 1603 may be a battery form factor cell that is capable of generating hydrogen when a resistor is applied. In this way, as the gas generating cell 1603 only needs the use of a resistor only without any active power requirements, the gas generating cell 1603 may be integrated into an ingestible device such as a capsule with limited energy/power available. For example, the gas generating cell 1603 may be compatible with a capsule at a size of 26 mm×13 mm or smaller.

In some embodiments, based on the elution rate of gas from the cell, and an internal volume of the ingestible device, it may take time to generate sufficient gas 1611 to deliver the substance 1605, and the time required may be 30 seconds or longer. For example, the time to generate a volume of hydrogen equivalent to 500 µL of fluid would be approximately 5 minutes. A longer period of time may be needed based upon non-ideal conditions within the ingestible device, such as friction, etc. Thus, given that the production of gas (e.g., hydrogen) may take time, gas generation may need to start prior to the ingestible device arriving at the site of delivery to build pressure up within the device. The ingestible device may then need to know when it is approaching the site of delivery. For example, the device may start producing gas on an "entry transition," which is determined by temperature, so as to produce enough gas to be close to the pressure high enough to deliver the dispensable substance. The ingestible device may then only start producing gas again when it arrives at the site of delivery, which will cause the internal pressure within the ingestible device to reach a level required by the dispensing outlet to release the dispensable substance. Also, for regio-specific delivery, the ingestible device may estimate the time it takes to build up enough pressure to deliver the dispensable substance before the ingestible device arrives at a specific location, to activate gas generation.

For example, for systemic delivery, when an internal volume of the ingestible device is around 500 µL, a gas generation time of 2 hours, an initial pressure of approximately 300 pound per square inch absolute (psia) may be generated, with higher and lower pressures possible. The generated pressure may drop when air enters the storage reservoir which was previously occupied by the dispensable substance during the dispensing process. For systemic drug delivery, a force with a generated pressure of approximately 100 to 360 pound per square inch (psi) may be required for dermal penetration, e.g., to penetrate the mucosa or epithelial layer. The pressure may also vary depending on the nozzle design at the dispensing outlet, fluid viscosity, and surrounding tissue proximity and properties.

The gas 1611 that may be generated for a continuous delivery of drug (e.g., 1 cc $H_2$ in 4 hours, 16 breaths per minute at 0.5 L tidal volume) may equate to 1 cc hydrogen in approximately 2000 L of exhaled air, or approximately 0.5 ppm $H_2$, which is below physiologic values of exhaled hydrogen. Reducing this time to 10 minutes equates to approximately 13 ppm hydrogen. Thus, due to the length of intestine that may be covered during this time period, the ingestible device may possess a higher localized value than physiologic.

Figure 18:
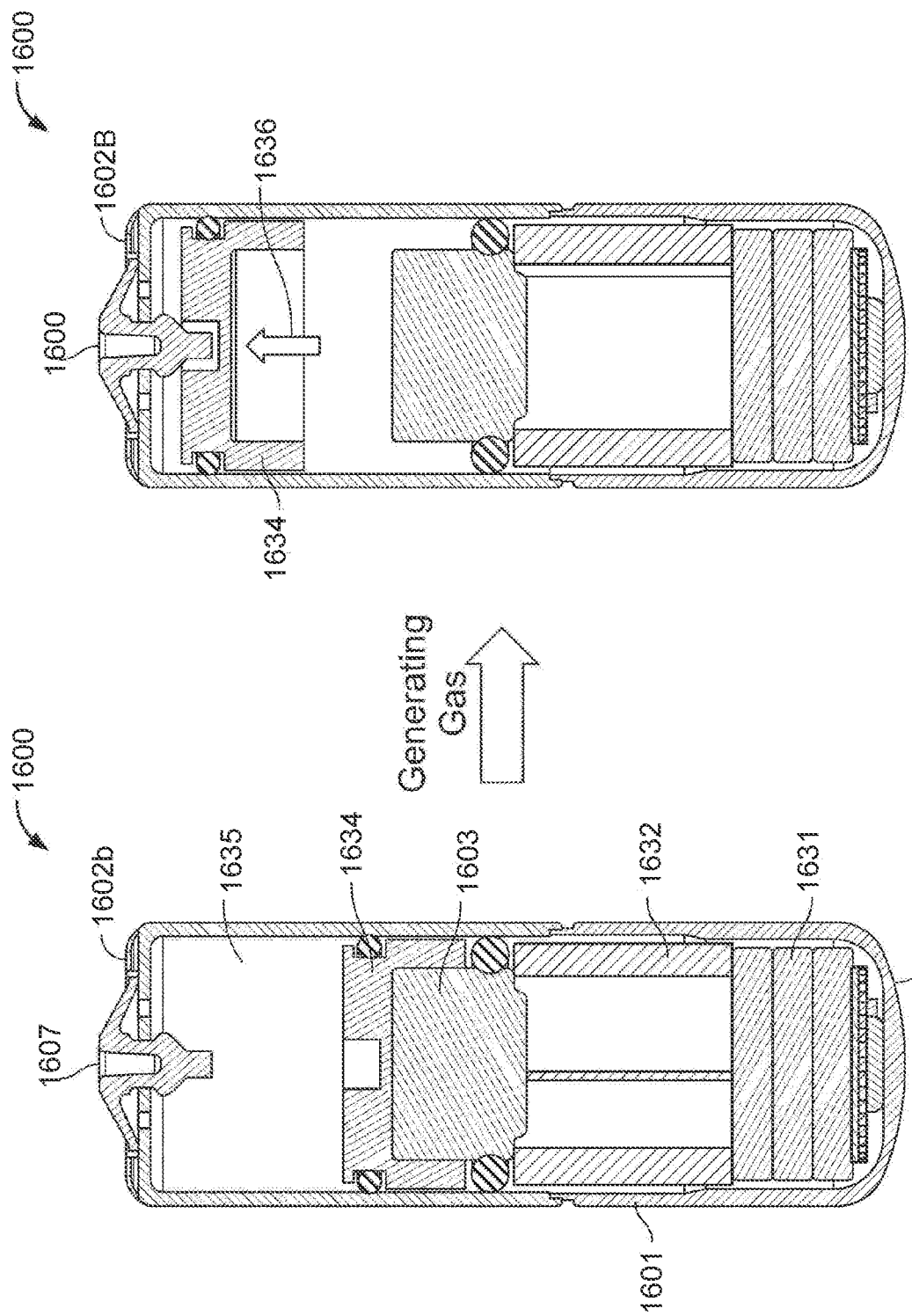
FIG. 18 illustrates an ingestible device having a piston to push for drug delivery.
Figure 19:
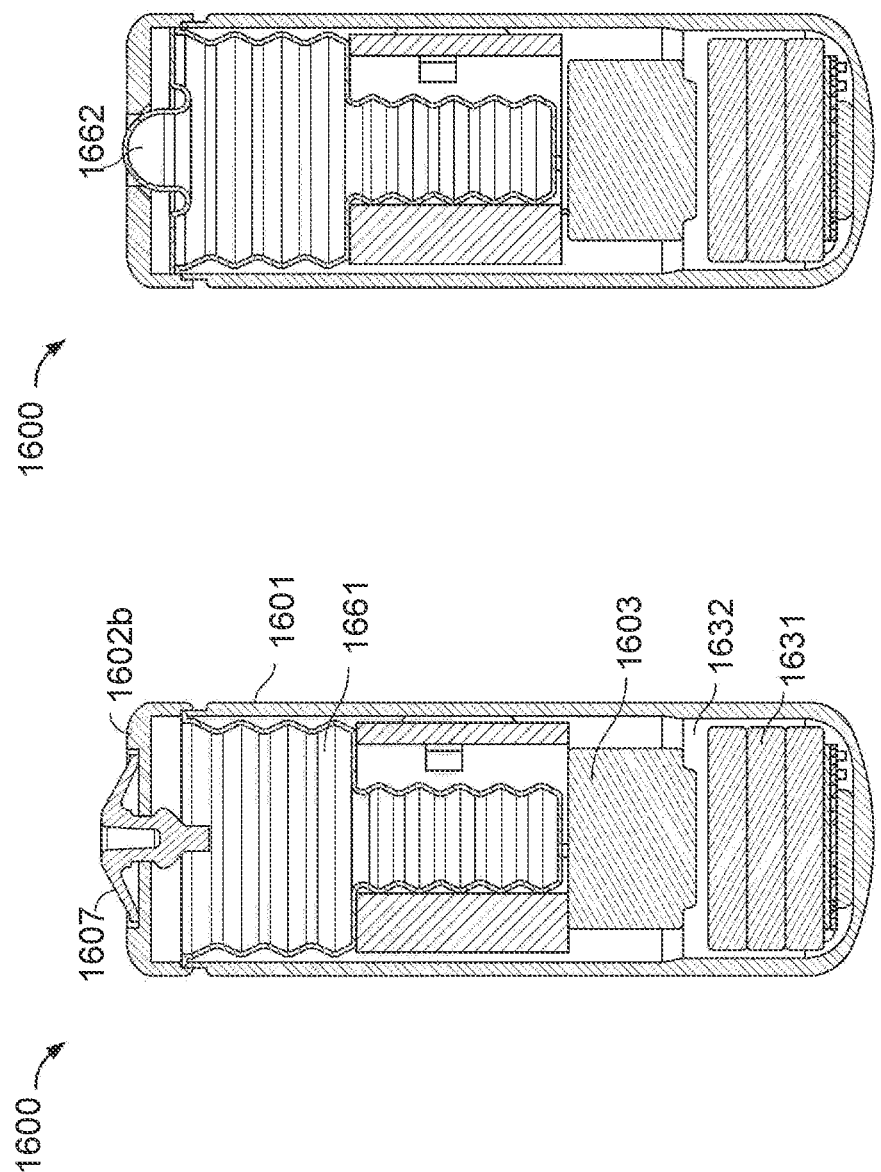
FIG. 19 illustrates an ingestible device having a bellow structure for a storage reservoir of dispensable substances.

FIGS. 18 and 19, disclosed in U.S. Provisional Application No. 62/385,553, incorporated by reference herein in its entirety, illustrates an example of an ingestible device for localized delivery of pharmaceutical compositions disclosed herein, in accordance with particular implementations. The ingestible device 1600 includes a piston or drive element 1634 to push for drug delivery, in accordance with particular implementations described herein. The ingestible device 1600 may have one or more batteries 1631 placed at one end 1602a of a housing 1601 to provide power for the ingestible device 1600. A printed circuit board (PCB) 1632 may be placed adjacent to a battery or other power source 1631, and a gas generating cell 1603 may be mounted on or above the PCB 1632. The gas generating cell 1603 may be sealed from the bottom chamber (e.g., space including 1631 and 1632) of the ingestible device 1600. A movable piston 1634 may be placed adjacent to the gas generating cell 1603. In this way, gas generation from the gas generating cell 1603 may propel a piston 1634 to move towards another end 1602b of the housing 1601 such that the dispensable substance in a reservoir compartment 1635 can be pushed out of the housing through a dispensing outlet 1607, e.g., the movement is shown at 1636, with the piston 1634 at a position after dispensing the substance. The dispensing outlet 1607 may comprise a plug. The reservoir compartment 1635 can store the dispensable substance (e.g., drug substance), or alternatively the reservoir compartment can house a storage reservoir 1661 which comprises the dispensable substance. The reservoir compartment 1635 or storage reservoir 1661 may have a volume of approximately 600 µL, or even more dispensable substance, which may be dispensed in a single bolus, or gradually over a period of time.

The battery cells 1631 may have a height of 1.65 mm each, and one to three batteries may be used. The height of the piston may be reduced with custom molded part for around 1.5 mm to save space. If the gas generating cell 1603 is integrated with the piston 1634, the overall height of the PCB, batteries and gas generating cell in total can be reduced to around 5 mm, thus providing more space for drug storage. For example, for an ingestible device of 7.8 mm in length (e.g., from end 1602a to the other end 1602b), a reservoir compartment 1635 or a storage reservoir 1661 of approximately 600 µL, may be used for drug delivery. For another example, for an ingestible device of 17.5 mm in length, a reservoir compartment 1635 or a storage reservoir 1661 of approximately 1300 µL may be used for drug release.

In some implementations, at the reservoir 1635 or 1661 for storing a therapeutically effective amount of the IL-10 or IL-10 agonist forms at least a portion of the device housing 1601. The therapeutically effective amount of the IL-10 or IL-10 agonist can be stored in the reservoir 1635 or 1661 at a particular pressure, for example, determined to be higher than a pressure inside the GI tract so that once the reservoir 1635 or 1661 is in fluid communication with the GI tract, the IL-10 or IL-10 agonist is automatically released. In certain implementations, the reservoir compartment 1635 includes a plurality of chambers, and each of the plurality of the chambers stores a different dispensable substance or a different storage reservoir 1661.

In certain embodiments, the storage reservoir 1661 is a compressible component or has compressible side walls. In particular embodiments, the compressible component can be composed, at least in part, or coated (e.g., internally) with polyvinyl chloride (PVC), silicone, DEHP (di-2-ethylhexyl phthalate), Tyvek, polyester film, polyolefin, polyethylene, polyurethane, or other materials that inhibit the IL-10 or IL-10 agonist from sticking to the reservoir and provide a sterile reservoir environment for the IL-10 or IL-10 agonist. The storage reservoir 1661 can be hermetically sealed. The reservoir compartment 1635 or storage reservoir 1661 can be configured to store IL-10 or IL-10 agonist in quantities in the range of 0.01 mL-2 mL, such as 0.05 mL-2 mL, such as 0.05 mL-2 mL, such as 0.6 mL-2 mL. In some embodiments, the storage reservoir 1661 is attachable to the device housing 1601, for example, in the reservoir compartment. Accordingly, the storage reservoir 1635 can be loaded with the IL-10 or IL-10 agonist prior to being positioned in and/or coupled to the ingestible device housing 1601. The ingestible device housing 1601 includes one or more openings configured as a loading port to load the dispensable substance into the reservoir compartment. In another embodiment, the ingestible device housing 1601 includes one or more openings configured as a vent.

As noted above, in some embodiments, a storage reservoir (optionally, containing IL-10 or an IL-10 agonist, such as a therapeutically effective amount of IL-10 or IL-10 agonist) is attachable to an ingestible device. In general, in such embodiments the storage reservoir and ingestible device can be designed in any appropriate fashion so that the storage reservoir can attach to the ingestible device when desired. Examples of designs include a storage reservoir that fits entirely within the ingestible device (e.g., in the ingestible device so that the storage reservoir is sealed within the device at the time the device is ingested by a subject), a storage reservoir that fits partially within the ingestible device, and a storage reservoir that is carried by the housing of the device. In some embodiments, the storage reservoir snap fits with the ingestible device. In certain embodiments, the storage reservoir is friction fit with the ingestible device. In some embodiments, the storage reservoir is held together with the ingestible device via a biasing mechanism, such as one or more springs, one or more latches, one or more hooks, one or more magnets, and/or electromagnetic radiation. In certain embodiments, the storage reservoir can be a piercable member. In some embodiments, the ingestible device has a sleeve into which the storage reservoir securely fits. In some embodiments, the storage reservoir is disposed in/on a slidable track/groove so that it can move onto a piercing needle when delivery of the therapeutic agent is desired. In certain embodiments, the storage reservoir is made of a soft plastic coating, which is contacted with a needle at any orientation to deliver the therapeutic agent when desired. Generally, the storage reservoir can be made of one or more appropriate materials, such as, for example, one or more plastics and/or one or more metals or alloys. Exemplary materials include silicone, polyvinyl chloride, polycarbonate and stainless steel. Optionally, the design may be such that the storage reservoir carries some or all of the electrical componentry to be used by the ingestible device. Although the foregoing discussion relates to one storage reservoir, it is to be understood that an ingestible device can be designed to carry any desired number (e.g., two, three, four, five) storage reservoirs. Different storage reservoirs can have the same or different designs. In some embodiments, the ingestible device (when fully assembled and packaged) satisfies the regulatory requirements for marketing a medical device in one or more jurisdictions selected from the United States of America, the European Union or any member state thereof, Japan, China, Brazil, Canada, Mexico, Colombia, Argentina, Chile, Peru, Russia, the UK, Switzerland, Norway, Turkey, Israel, any member state of the Gulf Cooperative Council, South Africa, India, Australia, New Zealand, South Korea, Singapore, Thailand, the Philippines, Malaysia, Viet Nam, and Indonesia.

In certain embodiments, the ingestible device housing 1601 includes one or more actuation systems (e.g., gas generating cell 1603) for pumping the IL-10 or IL-10 agonist from the reservoir 1635. In some embodiments, the actuation system can include a mechanical, electrical, electromechanical, hydraulic, and/or fluid actuation system. For example, a chemical actuation means may use chemical reaction of mixing one or more reagents to generate a sufficient volume of gas to propel the piston or drive element 1634 for drug release. The actuation system can be integrated into the reservoir compartment 1635 or can be an auxiliary system acting on or outside of the reservoir compartment 1635. For example, the actuation system can include pumping system for pushing/pulling the IL-10 or IL-10 agonist out of the reservoir compartment 1635 or the actuation system can be configured to cause the reservoir compartment 1635 to change structurally so that the volume inside of the reservoir compartment 1635 changes, thereby dispensing the IL-10 or IL-10 agonist from the reservoir compartment 1635. The actuation system can include an energy storage component such as a battery or a capacitor for powering the actuation system. The actuation system can be actuated via gas pressure or a system storing potential energy, such as energy from an elastic reservoir component being expanded during loading of the reservoir and after being positioned in the ingestible device housing 1601 being subsequently released from the expanded state when the ingestible device housing is at the location for release within the GI tract. In certain embodiments, the reservoir compartment 1635 can include a membrane portion, whereby the IL-10 or IL-10 agonist is dispensed from the reservoir compartment 1635 or storage reservoir 1661 via osmotic pressure.

In particular embodiments the storage reservoir 1661 is in a form of a bellow that is configured to be compressed via a pressure from the gas generating cell. The IL-10 or IL-10 agonist may be loaded into the bellow, which may be compressed by gas generation from the gas generating cell or other actuation means to dispense the dispensable substance through the dispensing outlet 1607 and out of the housing 1601. In some embodiments, the ingestible device includes a capillary plate placed between the gas generating cell and the first end of the housing, and a wax seal between the gas generating cell and the reservoir, wherein the wax seal is configured to melt and the dispensable substance is pushed through the capillary plate by a pressure from the gas generating cell. The shape of the bellow may aid in controlled delivery. The reservoir compartment 1635 includes a dispensing outlet, such as a valve or dome slit 1662 extending out of an end of the housing 1601, in accordance with particular implementations. Thus when the bellow is being compressed, the dispensable substance may be propelled out of the bellow through the valve or the dome slit.

In certain embodiments, the reservoir compartment 1635 includes one or more valves (e.g. a valve in the dispensing outlet 1607) that are configured to move or open to fluidly couple the reservoir compartment 1635 to the GI tract. In certain embodiments, a housing wall of the housing 1601 can form a portion of the reservoir compartment 1635. In certain embodiments, the housing walls of the reservoir serve as a gasket. One or more of the one or more valves are positioned in the housing wall of the device housing 1601, in accordance with particular implementations. One or more conduits may extend from the reservoir 1635 to the one or more valves, in certain implementations.

In certain embodiments, a housing wall of the housing 1601 can be formed of a material that is configured to dissolve, for example, in response to contact at the disease site. In certain embodiments, a housing wall of the housing 1601 can be configured to dissolve in response to a chemical reaction or an electrical signal. The one or more valves and/or the signals for causing the housing wall of the housing 1601 to dissolve or dissipate can be controlled by one or more processors or controllers positioned on PCB 1632 in the device housing 1601. The controller is communicably coupled to one or more sensors or detectors configured to determine when the device housing 1601 is proximate to a disease site. The sensors or detectors comprise a plurality of electrodes comprising a coating, in certain implementations. Releasing of the IL-10 or IL-10 agonist from the reservoir compartment 1635 is triggered by an electric signal from the electrodes resulting from the interaction of the coating with the one or more sites of disease site. The one or more sensors can include a chemical sensor, an electrical sensor, an optical sensor, an electromagnetic sensor, a light sensor, a gas sensor, and/or a radiofrequency sensor. Methods for detecting volatile organic compounds (VOCs) and other gases from a biological sample include resistive metal oxide gas sensors/mixed metal oxide gas sensors, electrochemical gas sensors, optical/IR gas sensors, conducting polymer/composite polymer resistive/capacitive gas sensors, quartz crystal microbalance gas sensors, carbon nanotubes, and pellister/calorimetric gas sensors. Examples of ingestible gas sensors are described in US Patent Publication No. US20130289368, which published on Oct. 31, 2013, US Patent Publication No. US20170284956, which published on Oct. 5, 2017, and PCT Patent Publication No. WO2016197181, which published on Dec. 15, 2016. Examples of gases that can be detected in the gastrointestinal tract using a sensor include, but are not limited to, oxygen, hydrogen, and carbon dioxide.

In particular embodiments, the device housing 1601 can include one or more pumps configured to pump the therapeutically effective amount of the IL-10 or IL-10 agonist from the reservoir compartment 1635. The pump is communicably coupled to the one or more controllers. The controller is configured to activate the pump in response to detection by the one or more detectors of the disease site and activation of the valves to allow the reservoir 1635 to be in fluid communication with the GI tract. The pump can include a fluid actuated pump, an electrical pump, or a mechanical pump.

In certain embodiments, the device housing 1601 comprises one or more anchor systems for anchoring the device housing 1601 or a portion thereof at a particular location in the GI tract adjacent the disease site. In some embodiments, a storage reservoir comprises an anchor system, and the storage reservoir comprising a releasable substance is anchored to the GI tract. The anchor system can be activated by the controller in response to detection by the one or more detectors of the disease site. In certain implementations, the anchor system includes legs or spikes configured to extend from the housing wall(s) of the device housing 1601. The spikes can be configured to retract and/or can be configured to dissolve over time. An example of an attachable device that becomes fixed to the interior surface of the GI tract is described in PCT Patent Application PCT/US2015/012209, "Gastrointestinal Sensor Implantation System", filed Jan. 21, 2015, which is hereby incorporated by reference herein in its entirety.

Figure 20:
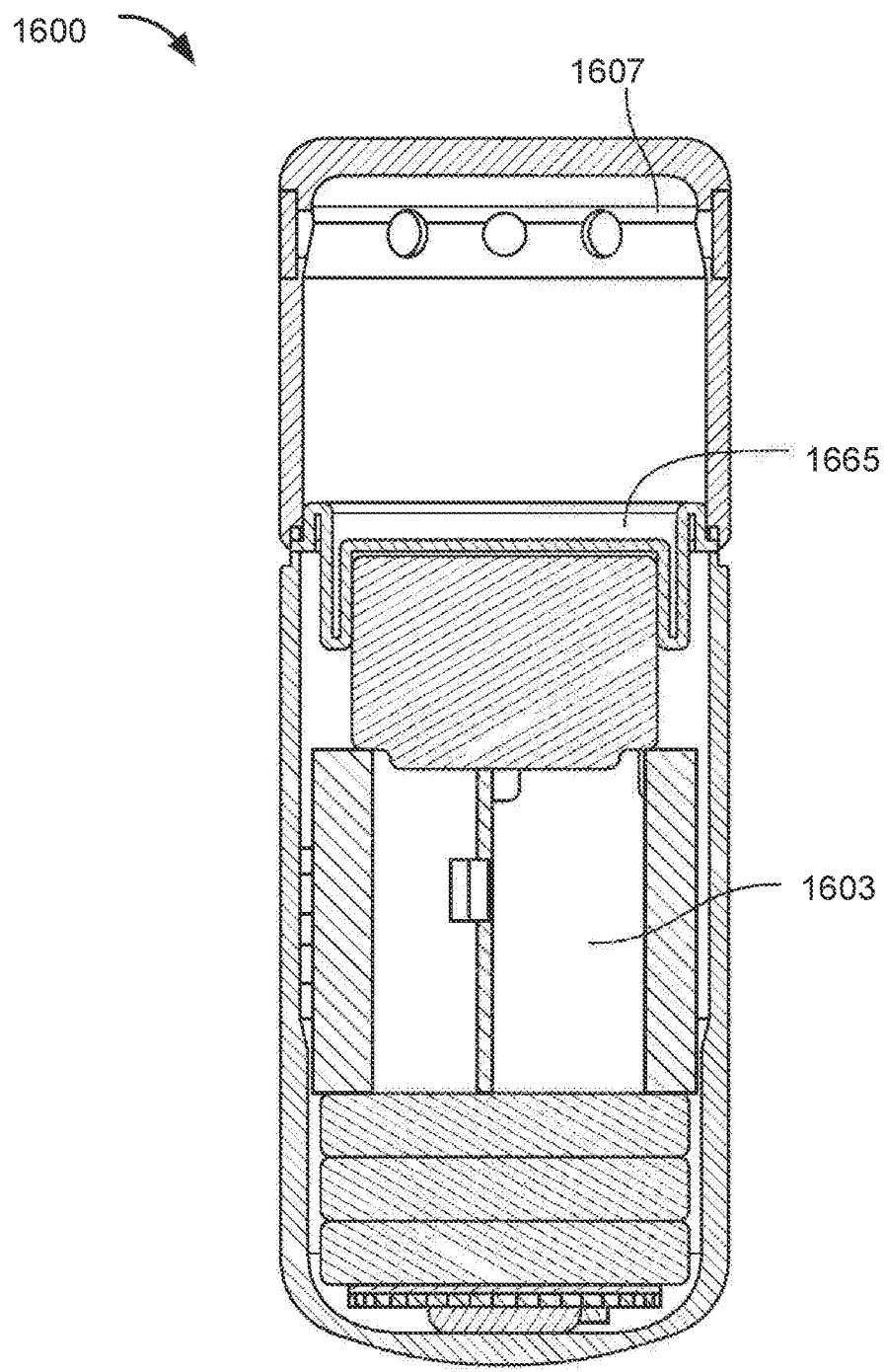
FIG. 20 illustrates an ingestible device having a flexible diaphragm to deform for drug delivery.

FIG. 20 provides an example structural diagram having a flexible diaphragm 1665 that may deform towards the dispensing outlet 1607 when the gas generating cell 1603 generates gas. The dispensable substance may then be propelled by the deformed diaphragm out of the housing through the dispensing outlet 1607. The dispensing outlet 1607 shown at FIG. 20 is in the form of a ring valve, however, any outlet design can be applied.

In some embodiments, an ingestible device can have an umbrella-shaped exit valve structure as a dispensing outlet of the ingestible device. Optionally, an ingestible device can have a flexible diaphragm to deform for drug delivery, and/or an integrated piston and gas generating cell such that the gas generating cell is movable with the piston to push for drug delivery.

In certain embodiments, an ingestible device can be anchored within the intestine by extending hooks from the ingestible device after it has entered the region of interest. For example, when the ingestible device determines it has arrived at a location within the GI tract, the hooks can be actuated to extend outside of the ingestible device to catch in the intestinal wall and hold the ingestible device in the respective location. In some embodiments, the hook can pierce into the intestinal wall to hold the ingestible device 100 in place. The hooks can be hollow. A hollow hook can be used to anchor the ingestible device and/or to dispense a substance from the dispensable substance, e.g., into the intestinal wall.

In some embodiments an ingestible device includes an intestinal gripper to grip a portion of the intestinal wall for delivering the dispensable substance. Such a gripper can include two or more arms configured to out of the device and close to grip a portion of the intestinal wall.

An injecting needle can be used with the anchoring arms to inject dispensable substance into the intestinal wall after a portion of the intestinal wall is gripped.

In some embodiments, when the gas generating cell generates gas to propel the piston to move towards the nozzle such that the dispensable substance can be pushed under the pressure to break a burst disc to be injected via the nozzle.

In some embodiments, an ingestible device has a jet delivery mechanism with enhanced usable volume of dispensable substance. For example, the nozzle may be placed at the center of the ingestible device, and gas channels may be placed longitudinally along the wall of the ingestible device to transport gas from the gas generating cell to propel the piston, which is placed at an end of the ingestible device.

In some embodiments, the ingestible device can use osmotic pressure to adhere a suction device of the ingestible device to the intestinal wall. For example, the ingestible device may have an osmotic mechanism that has a chamber storing salt crystals. The chamber can include a mesh placed in proximate to a burst valve at one end of the chamber, and a reverse osmosis (RO) membrane placed in proximate to a valve on the other end of the chamber. A suction device, e.g., two or more suction fingers, is placed outside of the chamber with an open outlet exposed to luminal fluid in the GI tract. When the osmotic mechanism is inactivated, e.g., the valve is closed so that no luminal fluid is drawn into the osmotic chamber. When the osmotic mechanism is activated by opening the valve, luminal fluid enters the ingestible device through an outlet of the suction device and enters the osmotic chamber through the valve. The salt in the chamber is then dissolved into the fluid. The RO membrane prevents any fluid to flow in the reverse direction, e.g., from inside the chamber to the valve. The fluid continues to flow until all the salt contained in the chamber is dissolved or until intestinal tissue is drawn into the suction device. As luminal fluid keeps flowing into the chamber, the solution of the luminal fluid with dissolved salt in the chamber may reduce osmotic pressure such that the suction force at may also be reduced. In this way, suction of the intestinal tissue may stall before the tissue is in contact with the valve to avoid damage to the intestinal tissue.

An ingestible device employing an osmotic mechanism can also include a suction device as illustrated. The suction device can be two or more suction fingers 347*a-b* disposed proximate to the outlet. The outlet can be connected to a storage reservoir storing the dispensable substance (e.g., therapeutic agent). The storage reservoir can contact a piston (similar to 104 in FIG. 16), which can be propelled by pressure generated from the osmotic pump to move towards the outlet. The osmotic pump can be similar to the osmotic mechanism described in the preceding paragraph. A breakaway section can be placed in proximate to the other end (opposite to the end where the outlet 107 is disposed) of the ingestible device.

In some embodiments, tumbling suction by an ingestible device is used. Such an ingestible device does not require any electronics or other actuation elements. Such an ingestible device may constantly, intermittently, or periodically tumble when travelling through the intestine. When the ingestible device tumbles to a position that the outlet is in direct contact with the intestinal wall, a suction process similar to that described in the preceding paragraph may occur. Additional structural elements such as fins, flutes or the like may be added to the outer wall of the ingestible device 100 to promote the tumbling motion.

In certain embodiments, the reservoir is an anchorable reservoir, which is a reservoir comprising one or more anchor systems for anchoring the reservoir at a particular location in the GI tract adjacent the disease site. In certain embodiments, the anchor system includes legs or spikes or other securing means such as a piercing element, a gripping element, a magnetic-flux-guiding element, or an adhesive material, configured to extend from the anchorable reservoir of the device housing. The spikes can be configured to retract and/or can be configured to dissolve over time. In some embodiments, the anchorable reservoir is suitable for localizing, positioning and/or anchoring. In some embodiments, the anchorable reservoir is suitable for localizing, and positioning and/or anchoring by an endoscope. In some embodiments, the anchorable reservoir is connected to the endoscope. In some embodiments, the anchorable reservoir is connected to the endoscope in a manner suitable for oral administration. In some embodiments, the anchorable reservoir is connected to the endoscope in a manner suitable for rectal administration. Accordingly, provided herein in some embodiments is an anchorable reservoir is connected to an endoscope wherein the anchorable reservoir comprises a therapeutically effective amount of the IL-10 or IL-10 agonist. In some embodiments the endoscope is fitted with a spray catheter.

Exemplary embodiments of anchorable reservoirs are as follows. In more particular examples of the following exemplary embodiments the reservoir is connected to an endoscope.

In one embodiment, the anchorable reservoir comprises an implant capsule for insertion into a body canal to apply radiation treatment to a selected portion of the body canal. The reservoir includes a body member defining at least one therapeutic treatment material receiving chamber and at least one resilient arm member associated with the body member for removably engaging the body canal when the device is positioned therein.

In one embodiment the anchorable reservoir has multiple suction ports and permits multiple folds of tissue to be captured in the suction ports with a single positioning of the device and attached together by a tissue securement mechanism such as a suture, staple or other form of tissue bonding. The suction ports may be arranged in a variety of configurations on the reservoir to best suit the desired resulting tissue orientation.

In some embodiments an anchorable reservoir comprises a tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

In some embodiments a reservoir for sensing one or more parameters of a patient is anchored to a tissue at a specific site and is released from a device, using a single actuator operated during a single motion. As an example, a delivery device may anchor the capsule to the tissue site and release the reservoir from the delivery device during a single motion of the actuator.

In some embodiments a device is provided comprising: a reservoir configured to contain a fluid, the reservoir having at least one outlet through which the fluid may exit the reservoir; a fluid contained within the reservoir; a primary material contained within the reservoir and having a controllable effective concentration in the fluid; and at least one electromagnetically responsive control element located in the reservoir or in a wall of the reservoir and adapted for modifying the distribution of the primary material between a first active form carried in the fluid and a second form within the reservoir in response to an incident electromagnetic control signal, the effective concentration being the concentration of the first active form in the fluid, whereby fluid exiting the reservoir carries the primary material in the first active form at the effective concentration.

In some embodiments systems and methods are provided for implementing or deploying medical or veterinary devices or reservoirs (a) operable for anchoring at least partly within a digestive tract, (b) small enough to pass through the tract per vias naturales and including a wireless-control component, (c) having one or more protrusions positionable adjacent to a mucous membrane, (d) configured to facilitate redundant modes of anchoring, (e) facilitating a "primary" material supply deployable within a stomach for an extended and/or controllable period, (f) anchored by one or more adaptable extender modules supported by a subject's head or neck, and/or (g) configured to facilitate supporting at least a sensor within a subject's body lumen for up to a day or more.

In certain embodiments, the reservoir is attachable to an ingestible device. In certain embodiments, the ingestible device comprises a housing and the reservoir is attachable to the housing. In certain embodiments, the attachable reservoir is also an anchorable reservoir, such as an anchorable reservoir comprising one or more anchor systems for anchoring the reservoir at a particular location in the GI tract as disclosed hereinabove.

Accordingly, in certain embodiments, provided herein is IL-10 or an IL-10 agonist for use in a method of treating a disease of the gastrointestinal tract as disclosed herein, wherein the IL-10 or IL-10 agonist is contained in a reservoir suitable for attachment to a device housing, and wherein the method comprises attaching the reservoir to the device housing to form the ingestible device, prior to orally administering the ingestible device to the subject.

In certain embodiments, provided herein is an attachable reservoir containing IL-10 or an IL-10 agonist for use in a method of treating a disease of the gastrointestinal tract, wherein the method comprises attaching the reservoir to a device housing to form an ingestible device and orally administering the ingestible device to a subject, wherein the IL-10 or IL-10 agonist is released by device at a location in the gastrointestinal tract of the subject that is proximate to one or more sites of disease.

In certain embodiments, provided herein is an attachable reservoir containing IL-10 or an IL-10 agonist, wherein the reservoir is attachable to a device housing to form an ingestible device that is suitable for oral administration to a subject and that is capable of releasing the IL-10 or IL-10 agonist at a location in the gastrointestinal tract of the subject that is proximate to one or more sites of disease.

In particular implementation the ingestible device includes cameras (e.g., video cameras) that affords inspection of the entire GI tract without discomfort or the need for sedation, thus avoiding many of the potential risks of conventional endoscopy. Video imaging can be used to help determine one or more characteristics of the GI tract, including the location of disease (e.g., presence or location of inflamed tissue and/or lesions associated with inflammatory bowel disease). In some embodiments, the ingestible device 101 may comprise a camera for generating video imaging data of the GI tract which can be used to determine, among other things, the location of the device. Examples of video imaging capsules include Medtronic's PillCam™ Olympus' Endocapsule®, and IntroMedic's MicroCam™. For a review of imaging capsules, see Basar et al. "Ingestible Wireless Capsule Technology: A Review of Development and Future Indication" International Journal of Antennas and Propagation (2012); 1-14). Other imaging technologies implemented with the device 101 can include thermal imaging cameras, and those that employ ultrasound or Doppler principles to generate different images (see Chinese patent application CN104473611: "Capsule endoscope system having ultrasonic positioning function".

Ingestible devices can be equipped with sources for generating reflected light, including light in the Ultraviolet, Visible, Near-infrared and/or Mid-infrared spectrum, and the corresponding detectors for spectroscopy and hyperspectral imaging. Likewise, autofluorescense may be used to characterize GI tissue (e.g., subsurface vessel information), or low-dose radiation (see Check-Cap™) can be used to obtain 3D reconstructed images.

Device Components

An ingestible device in accordance with particular embodiments of the present invention may comprise a component made of a non-digestible material and contain the IL-10 or IL-10 agonist. In some embodiments, the material is plastic.

It is envisaged that the device is single-use. The device is loaded with a drug prior to the time of administration. In some embodiments, it may be preferred that there is provided a medicinal product comprising the device pre-filled with the drug.

Anchoring Components

Several systems may actively actuate and control the capsule position and orientation in different sections of the GI tract. Examples include leg-like or anchor-like mechanisms that can be deployed by an ingestible device to resist peristaltic forces in narrowed sections of the GI tract, such as the intestine, and anchor the device to a location. Other systems employ magnetic shields of different shapes that can interact with external magnetic fields to move the device. These mechanisms may be particularly useful in areas outside of the small intestine, like the cecum and large intestine.

An anchoring mechanism may be a mechanical mechanism. For example, a device may be a capsule comprising a plurality of legs configured to steer the capsule. The number of legs in the capsule may be, for example, two, four, six, eight, ten or twelve. The aperture between the legs of the device may be up to about 35 mm; about 30 to about 35 mm; about 35 to about 75 mm; or about 70 to about 75 mm. The contact area of each leg may be varied to reduce impact on the tissue. One or more motors in the capsule may each actuate a set of legs independently from the other. The motors may be battery-powered motors.

An anchoring mechanism may be a non-mechanical mechanism. For example, a device may be a capsule comprising a permanent magnet located inside the capsule. The capsule may be anchored at the desired location of the GI tract by an external magnetic field.

An anchoring mechanism may comprise a non-mechanical mechanism and a mechanical mechanism. For example, a device may be a capsule comprising one or more legs, one or more of which are coated with an adhesive material.

Locomotion Components

Ingestible devices can be active or passive, depending on whether they have controlled or non-controlled locomotion. Passive (non-controlled) locomotion is more commonly used among ingestible devices given the challenges of implementing a locomotion module. Active (controlled) locomotion is more common in endoscopic ingestible capsules. For example, a capsule may comprise a miniaturized locomotion system (internal locomotion). Internal locomotion mechanisms may employ independent miniaturized propellers actuated by DC brushed motors, or the use of water jets. As an example, a mechanism may comprise flagellar or flap-based swimming mechanisms. As an example, a mechanism may comprise cyclic compression/extension shape-memory alloy (SMA) spring actuators and anchoring systems based on directional micro-needles. As an example, a mechanism may comprise six SMA actuated units, each provided with two SMA actuators for enabling bidirectional motion. As an example, a mechanism may comprise a motor adapted to electrically stimulating the GI muscles to generate a temporary restriction in the bowel.

As an example, a capsule may comprise a magnet and motion of the capsule is caused by an external magnetic field. For example, a locomotion system may comprise an ingestible capsule and an external magnetic field source. For example, the system may comprise an ingestible capsule and magnetic guidance equipment such as, for example, magnetic resonance imaging and computer tomography, coupled to a dedicated control interface.

In some embodiments drug release mechanisms may also be triggered by an external condition, such as temperature, pH, movement, acoustics, or combinations thereof.

Sampling Components

Ingestible devices may comprise a mechanism adapted to permit the collection of tissue samples. In some examples, this is achieved using electro-mechanical solutions to collect and store the sample inside an ingestible device. As an example, a biopsy mechanism may include a rotational tissue cutting razor fixed to a torsional spring or the use of microgrippers to fold and collect small biopsies. As an example, Over-the-scope clips (OTSC®) may be used to perform endoscopic surgery and/or biopsy. As an example of the methods disclosed herein, the method may comprise releasing IL-10 or an IL-10 agonist and collecting a sample inside the device. As an example, the method may comprise releasing IL-10 or an IL-10 agonist and collecting a sample inside the device in a single procedure.

Figure 21:
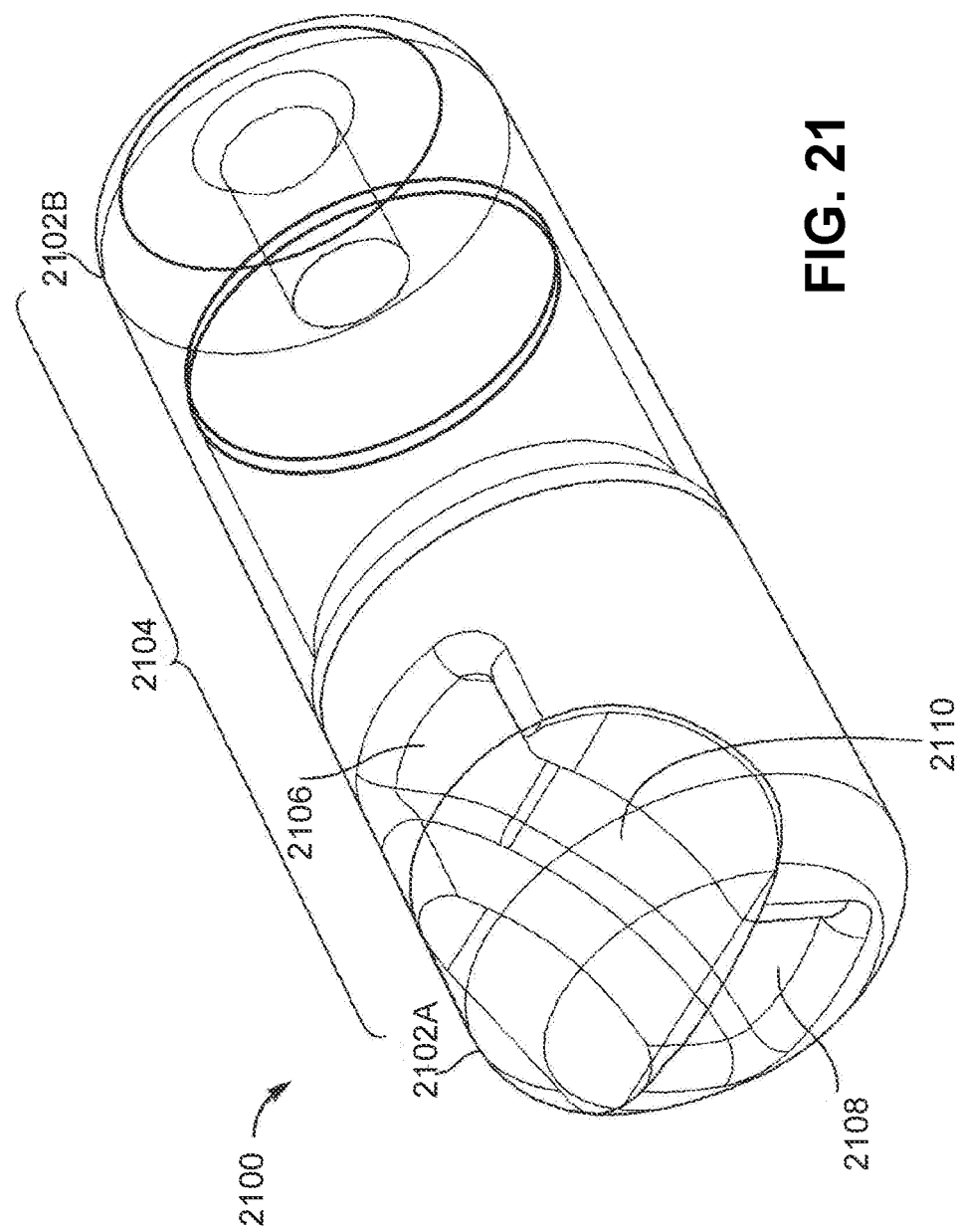
FIG. 21 shows an illustrative embodiment of an ingestible device with multiple openings in the housing.

FIG. 21 illustrates an example ingestible device 2100 with multiple openings in the housing. The ingestible device 2100 has an outer housing with a first end 2102A, a second end 2102B, and a wall 2104 extending longitudinally from the first end 2102A to the second end 2102B. Ingestible device 2100 has a first opening 2106 in the housing, which is connected to a second opening 2108 in the housing. The first opening 2106 of the ingestible device 2100 is oriented substantially perpendicular to the second opening 2108, and the connection between the first opening 2106 and the second opening 2108 forms a curved chamber 2110 within the ingestible device 2100.

The overall shape of the ingestible device 2100, or any of the other ingestible devices discussed in this disclosure, may be similar to an elongated pill or capsule.

In some embodiments, a portion of the curved chamber 2110 may be used as a sampling chamber, which may hold samples obtained from the GI tract. In some embodiments the curved chamber 2110 is subdivided into sub-chambers, each of which may be separated by a series of one or more valves or interlocks.

In some embodiments, the first opening 2106, the second opening 2108, or the curved chamber 2110 include one or more of a hydrophilic or hydrophobic material, a sponge, a valve, or an air permeable membrane.

The use of a hydrophilic material or sponge may allow samples to be retained within the curved chamber 2110, and may reduce the amount of pressure needed for fluid to enter through the first opening 2106 and dislodge air or gas in the curved chamber 2110. Examples of hydrophilic materials that may be incorporated into the ingestible device 2100 include hydrophilic polymers such as polyvinyl alcohol, polyvinyl pyrrolidone, and the like. Similarly, materials that have undergone various types of treatments, such as plasma treatments, may have suitable hydrophilic properties, and may be incorporated into the investible device 2100. Sponges may be made of any suitable material or combination of materials, such as fibers of cotton, rayon, glass, polyester, polyethylene, polyurethane, and the like. Sponges generally may be made from commercially available materials, such as those produced by Porex®.

As discussed in more detail below, in some embodiments, the sponges may be treated in order to change their absorbency or to help preserve samples.

In some embodiments, the sponges may be cut or abraded to change their absorbency or other physical properties.

Hydrophobic materials located near the second opening 2108 may repel liquids, discouraging liquid samples from entering or exiting the curved chamber 2110 through the second opening 2108. This may serve a similar function as an air permeable membrane. Examples of hydrophobic materials which may be incorporated into the ingestible device 2100 include polycarbonate, acrylics, fluorocarbons, styrenes, certain forms of vinyl, stainless steel, silicone, and the like.

The various materials listed above are provided as examples, and are not limiting. In practice, any type of suitable hydrophilic, hydrophobic, or sample preserving material may be used in the ingestible device 2100.

In some embodiments, an ingestible device includes a moveable valve as a diaphragm valve, which uses a mechanical actuator to move a flexible diaphragm in order to seal or unseal an aperture in a second portion of an inlet region, which may effectively block or unblock the inlet region. However, it will be understood that, in some embodiments, the moveable valve may be a different type of valve. For example, in some embodiments the moveable valve may be replaced by a pumping mechanism. As another example, in some embodiments the moveable valve is replaced with an osmotic valve A sampling chamber of an ingestible device can have an exit port to allow air or gas to exit the sampling chamber, while preventing at least a portion of the sample obtained by the ingestible device from exiting the sampling chamber. For example, the exit port may include a gas-permeable membrane. An ingestible device can include one-way valve as part of its exit port.

An ingestible device can include an outlet port connected to the volume within housing of the ingestible device. The outlet port may provide a path for the gas to exit the ingestible device and be released into the environment surrounding the ingestible device. This may prevent pressure from building up within the housing of the ingestible device. In some embodiments, an ingestible device does not include an outlet port, and the gas stays inside the volume of the ingestible device. In some embodiments, the outlet port may contain a gas permeable membrane, a one-way valve, a hydrophobic channel, or some other mechanism to avoid unwanted material, (e.g., fluids and solid particulates from within the GI tract), from entering the ingestible device through the outlet port.

In some embodiments, the ingestible device may include a sensor within or proximate to the sampling chamber. For example, this sensor may be used to detect various properties of a sample contained within the sampling chamber, or this sensor may be used to detect the results of an assay technique applied to the sample contained within the sampling chamber.

In some embodiments, a hydrophilic sponge is located within the sampling chamber, and the hydrophilic sponge may be configured to absorb the sample as the sample enters the sampling chamber. In some embodiments, the hydrophilic sponge fills a substantial portion of the sampling chamber, and holds the sample for an extended period of time. This may be particularly advantageous if the sample is collected from the ingestible device after the ingestible device exits the body. In some embodiments, the hydrophilic sponge is placed on only certain surfaces or fills only certain portions of the sampling chamber. For example, it may be possible to line certain walls (or all walls) of the sampling chamber with a hydrophilic sponge to assist in drawing in the sample, while leaving some (or none) of the walls of the sampling chamber uncovered. Leaving walls uncovered may allow the use of diagnostics or assay techniques that require a relatively un-obscured optical path.

In some embodiments, the ingestible device may include a sealed vacuum chamber connected to the exit port, or connected directly or indirectly to the sampling chamber. In some embodiments a pin valve may be used as a moveable valve (e.g., as moveable valve of ingestible device). In certain embodiments, a rotary valve may be used as a moveable valve (e.g., as moveable valve of ingestible device). In some embodiments, a flexible diaphragm, or diaphragm valve, may be used as a moveable valve (e.g., as moveable valve of ingestible device). In certain embodiments, a mechanism is near the diaphragm or in direct contact with the diaphragm. The spring mechanism may apply pressure to the diaphragm to oppose the pressure applied by the mechanical actuator, which may cause the flexible diaphragm to be moved into an open position when the mechanical actuator is not applying pressure to the flexible diaphragm. Additionally, this may ensure that the diaphragm valve remains open when the mechanical actuator is not applying pressure across the flexible diaphragm. In some embodiments, moving the mechanical actuator from a closed position to an open position causes a volume of the inlet region within the ingestible device to increase. This may cause the pressure within the inlet region to be reduced, generating suction to draw a sample into the inlet region. Similarly, moving the mechanical actuator from an open position to a closed position may cause the volume of the inlet region to be reduced. This may cause the pressure within the inlet region to be increased, pushing the sample out of the inlet region. Depending on the design of the inlet region, the mechanical actuator, and the moveable valve, this may push the sample into the sampling chamber rather than pushing the sample back through the opening in the ingestible device.

Figure 22:
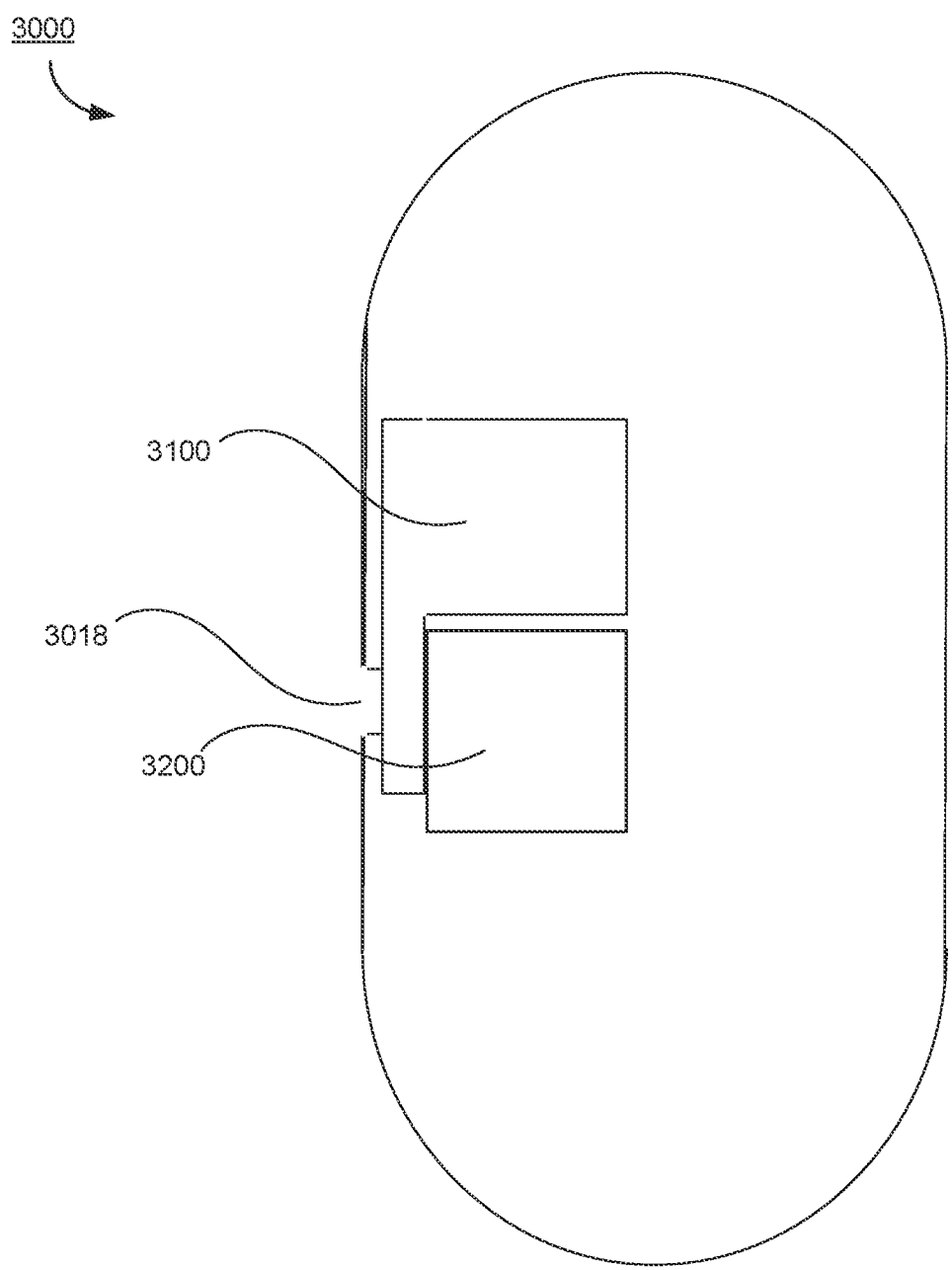
FIG. 22 shows a highly cross-section of an ingestible device including a valve system and a sampling system.

FIG. 22 depicts a cross-sectional view of a portion of the interior of ingestible device 3000. As shown in FIG. 22, the interior of ingestible device 3000 includes a valve system 3100 and a sampling system 3200. Valve system 3100 is depicted as having a portion that is flush with the opening 3018 so that valve system 3100 prevents fluid exterior to ingestible device 2000 from entering sampling system 3200. However, as described in more detail below with reference to FIGS. 22-27, valve system 3100 can change position so that valve system 3100 allows fluid exterior to ingestible device 3000 to enter sampling system 3200.

Figure 27:
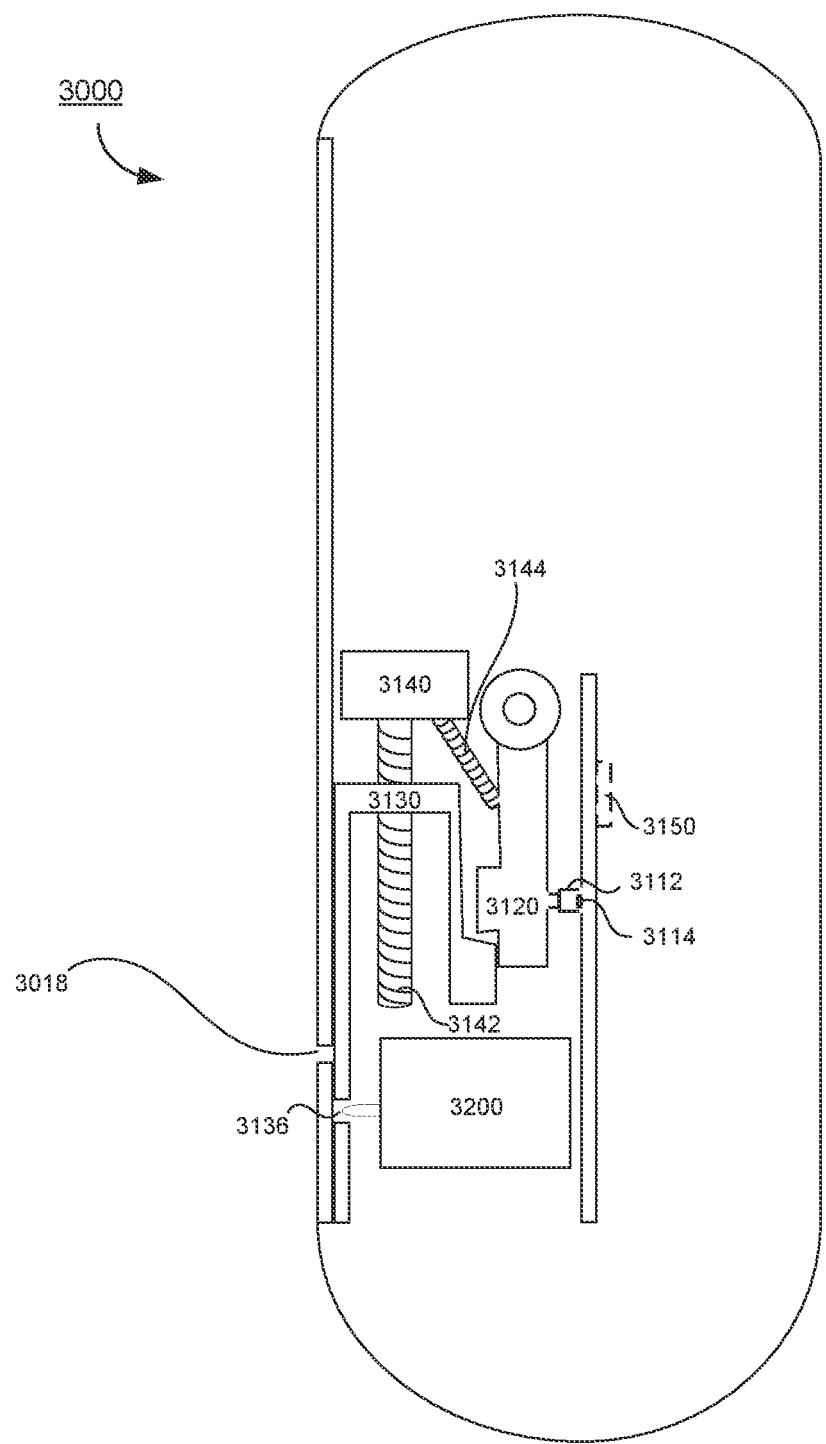
FIG. 27 illustrates a more detailed view of an ingestible device including a valve system and a sampling system.

FIGS. 23 and 27 illustrate valve system 3100 in more detail. As shown in FIG. 23, valve system 3100 includes an actuation mechanism 3110, a trigger 3120, and a gate 3130. In FIGS. 23 and 7, a leg 3132 of gate 3130 is flush against, and parallel with, housing wall 3016 so that gate leg 3132 covers opening 3018 to prevent fluid exterior to ingestible device 3000 (e.g., fluid in the GI tract) from entering the interior of ingestible device 3000. A protrusion 3134 of gate 3130 engages a lip 3122 of trigger 3120. A peg 3124 of trigger 3120 engages a wax pot 3112 of actuation mechanism 3110. Referring to FIG. 27, a biasing mechanism 3140 includes a compression spring 3142 that applies an upward force on gate 3130. Biasing mechanism 3140 also includes a torsion spring 3144 that applies a force on trigger 3120 in the counter-clockwise direction. In FIGS. 23 and 27, the force applied by torsion spring 3144 is counter-acted by the solid wax in pot 3112, and the force applied by compression spring 3142 is counter-acted by lip 3122.

FIG. 24A and FIG. 24B show an embodiment of the manner in which actuation mechanism 3110 actuates movement of trigger 3120. Similar to FIGS. 23 and 27, FIG. 24A shows a configuration in which peg 3124 applies a force against solid wax pot 3112 due to torsion spring 3144, and in which the solid nature of wax pot 3112 resists the force applied by peg 3124. A control unit 3150 is in signal communication with valve system 3100. During use of ingestible device 3000, a control unit 3150 receives a signal, indicating that the position of valve system 3100 should change, e.g., so that ingestible device 3000 can take a sample of a fluid in the GI tract. Control unit 3150 sends a signal that causes a heating system 3114 of actuation system 3100 to heat the wax in pot 3112 so that the wax melts. As shown in FIG. 24B, the melted wax is not able to resist the force applied by peg 3124 so that, under the force of torsion spring 3144, trigger 3120 moves in a counter-clockwise fashion.

Figure 25A:
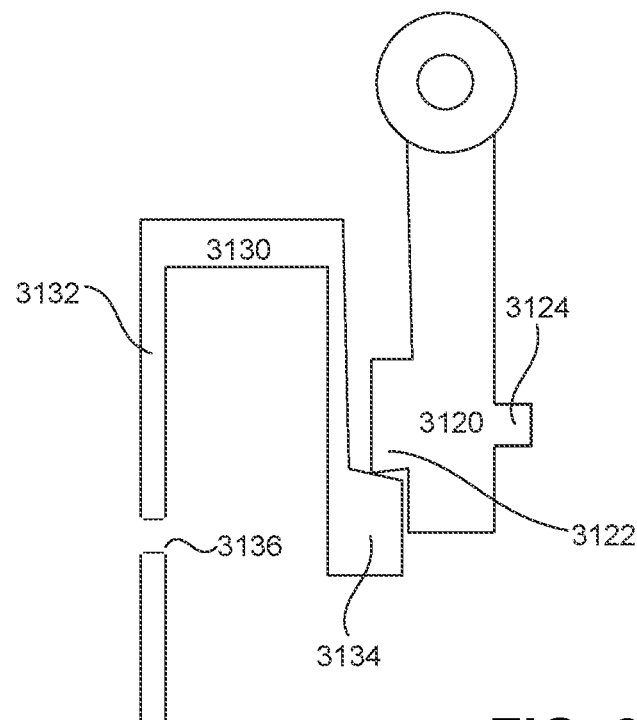
Figure 25A:
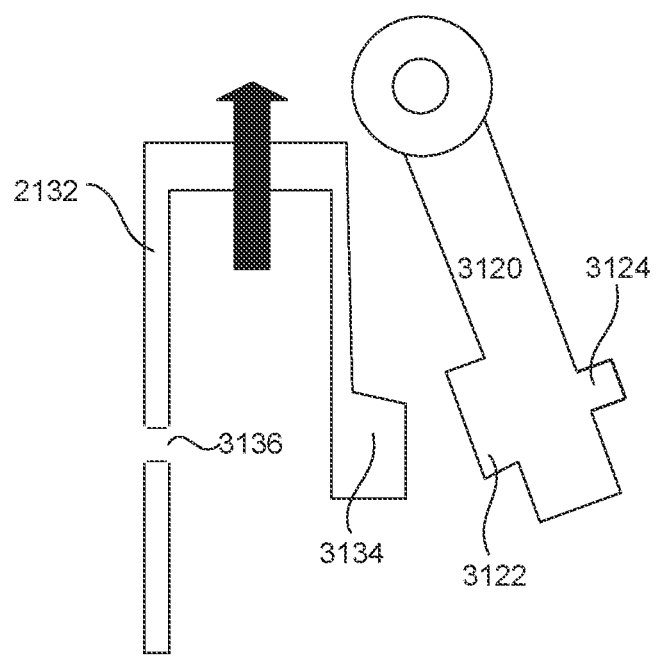

FIGS. 25A and 25B illustrate the interaction of trigger 3120 and gate 3130 before and after actuation. As shown in FIG. 25A, when wax pot 3112 is solid (corresponding to the configuration shown in FIG. 24A), protrusion 3134 engages lip 3122, which prevents the force of compression spring 3142 from moving gate 3130 upward. As shown in FIG. 25B, when the wax in pot 3112 melts (FIG. 24B), trigger 3120 moves counter-clockwise, and lip 3122 disengages from protrusion 3134. This allows the force of compression spring 3142 to move gate 3130 upward. As seen by comparing FIG. 25A to FIG. 25B, the upward movement of gate 3130 results in an upward movement of an opening 3136 in gate leg 3132.

Figures 26A, 26B:
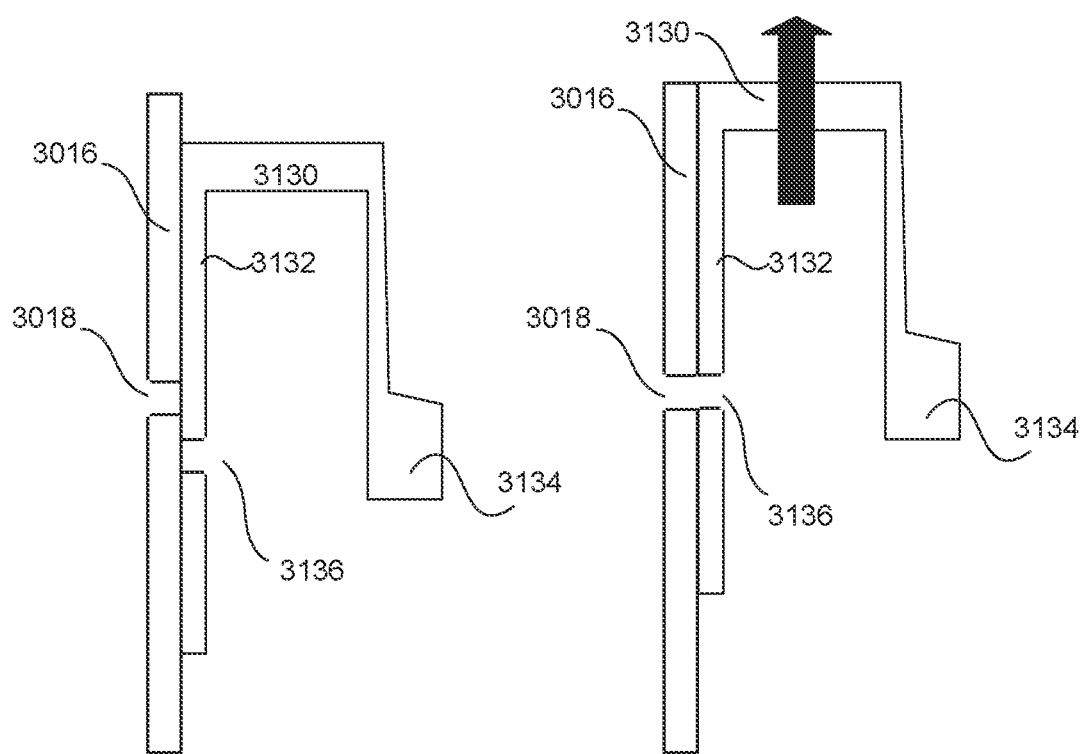
FIGS. 26A and 26B illustrate a portion of a two-stage valve system in its first and second stages, respectively.

FIGS. 26A and 26B illustrate the impact of the upward movement of opening 3136 on the ability of ingestible device 3000 to obtain a sample. As shown in FIG. 26A, when the wax in pot 3112 is solid (FIGS. 24A and 25A), opening 3136 in is not aligned with opening 3018 in wall 3016 of ingestible device 3000. Instead, gate leg 3132 covers opening 3018 and blocks fluid from entering the interior of ingestible device 3000. As shown in FIG. 26B, when the wax in pot 3112 is melted and trigger 3120 and gate 3130 have moved (FIGS. 24B and 42B), opening 3136 in gate 3130 is aligned with opening 3018 in wall 3016. In this configuration, fluid that is exterior to ingestible device 3000 (e.g., in the GI tract) can enter the interior of ingestible device 3000 via openings 3018 and 3036.

FIG. 27 illustrates a more detailed view of ingestible device 3000 including valve system 3100 and sampling system 3200.

While the foregoing description is made with regard to a valve system having one open position and one closed position (e.g., a two-stage valve system), the disclosure is not limited in this sense. Rather, the concepts described above with regard to a two stage valve system can be implemented with a valve system have more than two stages (e.g., three stages, four stages, five stages, etc.).

Figure 28:
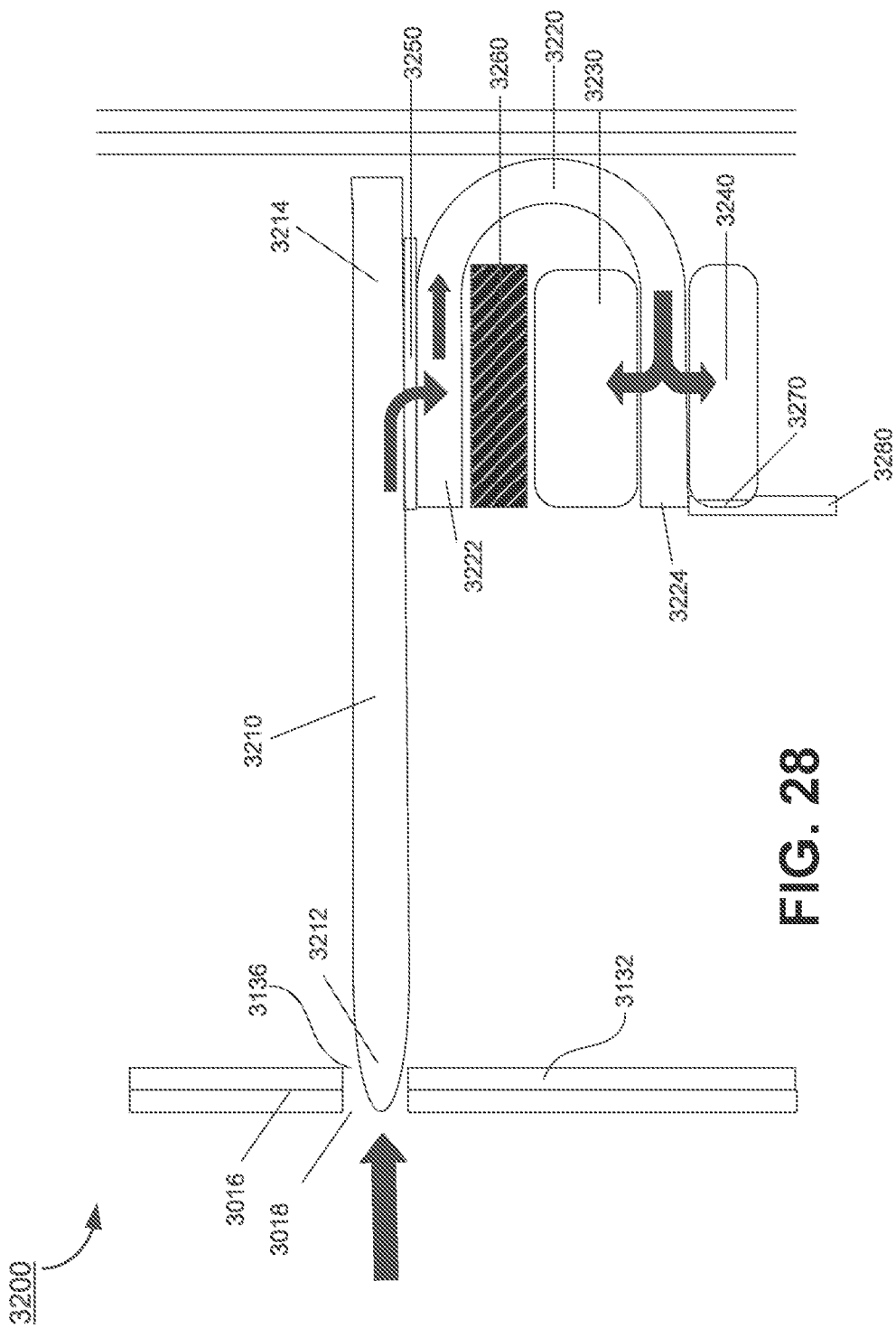
FIG. 28 illustrates a portion of an ingestible device including a sampling system and a two-stage valve system in its second stage.

As noted above in addition to a valve system, an ingestible device includes a sampling system. FIG. 28 illustrates a partial cross sectional view of ingestible device 3000 with sampling system 3200 and certain components of valve system 3100. Sampling system 3200 includes a series of sponges configured to absorb fluid from an opening, move the fluid to a location within the housing, and prepare the fluid for testing. Preparation for testing may include filtering the fluid and combining the fluid with a chemical assay. The assay may be configured to dye cells in the filtered sample. The series of sponges includes a wicking sponge 3210, a transfer sponge 3220, a volume sponge 3230, and an assay sponge 3240. Sampling system 3200 also includes a membrane 3270 located between assay sponge 3240 and a vent 3280 for gases to leave sampling system 3200. A cell filter 3250 is located between distal end 3214 of wicking sponge 3210 and a first end 3222 of transfer sponge 3220. Membrane 3270 is configured to allow one or more gases to leave sampling system 3200 via an opening 3280, while maintaining liquid in sampling system 3200.

Figure 29:
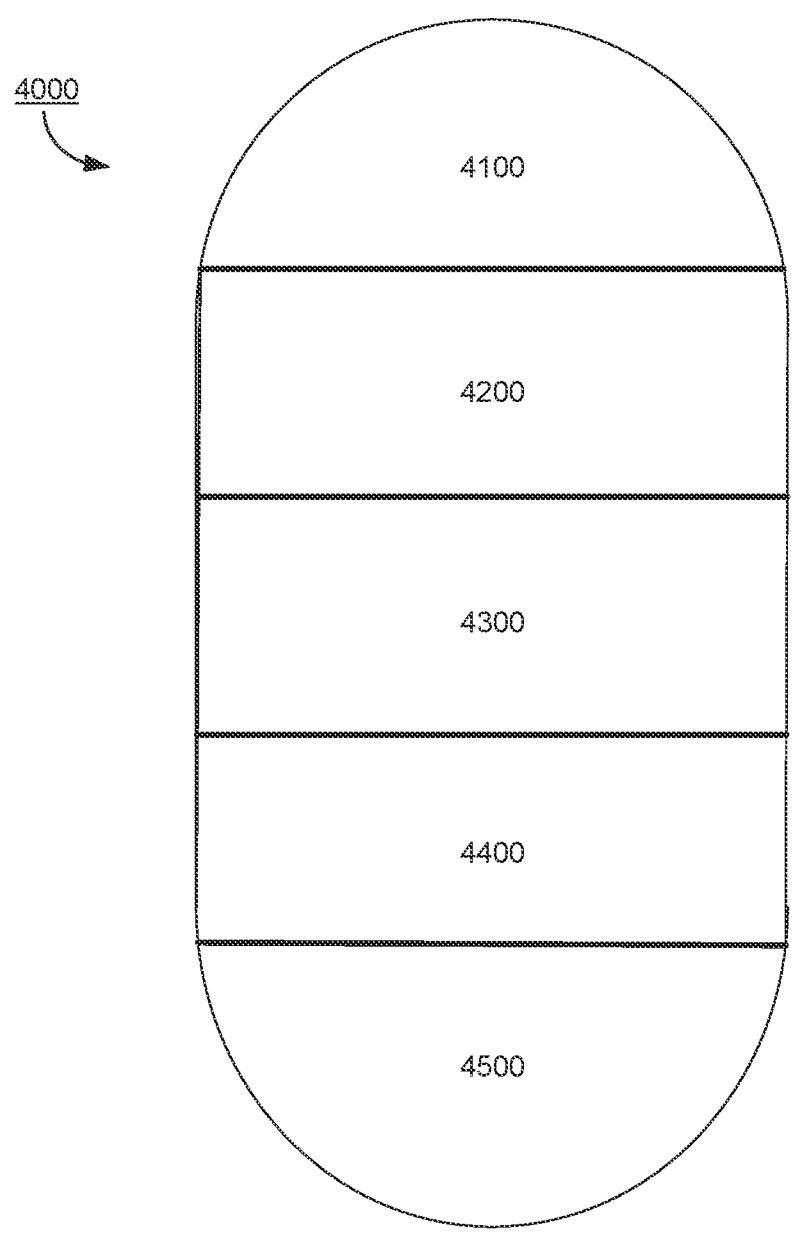
FIG. 29 is a highly schematic illustrate of an ingestible device.

FIG. 29 is a highly schematic illustration of an ingestible device 4000 that contains multiple different systems that cooperate for obtaining a sample and analyzing a sample, e.g., within the GI tract of a subject. Ingestible device 4000 includes a power system 4100 (e.g., one or more batteries), configured to power an electronics system 4200 (e.g., including a control system, optionally in signal communication with an external base station), a valve system 4300, a sampling system 4400, and an analytic system 4500. Exemplary analytical systems include assay systems, such as, for example, optical systems containing one or more sources of radiation and/or one more detectors.

Some or all of the sponges of the above-described sampling systems may contain one or more preservatives (see discussion above). Typically, the assay sponge and/or the volume sponge 3230 and/or the transfer sponge contain one or more preservatives. Typically, the preservative(s) are selected based on the analyte of interest, e.g., an analyte (such as a protein biomarker) for a GI disorder.

Communication Systems

An ingestible device may be equipped with a communication system adapted to transmit and/or receive data, including imaging and/or localization data. As an example, a communication system may employ radiofrequency transmission. Ingestible devices using radiofrequency communication are attractive because of their efficient transmission through the layers of the skin. This is especially true for low frequency transmission (UHF-433 ISM and lower, including the Medical Device Radio Communication Service band (MDRS) band 402-406 MHz). In another embodiment, acoustics are used for communications, including the transmission of data. For example, an ingestible capsule may be able to transmit information by applying one or more base voltages to an electromechanical transducer or piezoelectric (e.g., PZT, PVDF, etc.) device to cause the piezoelectric device to ring at particular frequencies, resulting in an acoustic transmission. A multi-sensor array for receiving the acoustic transmission may include a plurality of acoustic transducers that receive the acoustic transmission from a movable device such as an ingestible capsule as described in U.S. patent application Ser. No. 11/851,214 filed Sep. 6, 2007, incorporated by reference herein in its entirety.

As an example, a communication system may employ human body communication technology. Human body communication technology uses the human body as a conductive medium, which generally requires a large number of sensor electrodes on the skin. As an example, a communication system may integrate a data storage system.

Environmental Sensors

In some embodiments the device may comprise environmental sensors to measure pH, temperature, transit times, or combinations thereof. Other examples of environmental sensors include, but are not limited to a capacitance sensor, an impedance sensor, a heart rate sensor, acoustic sensor such as a microphone or hydrophone, image sensor, and/or a movement sensor. In one embodiment, the ingestible device comprises a plurality of different environmental sensors for generating different kinds of environmental data.

In order to avoid the problem of capsule retention, a thorough past medical and surgical history should be undertaken. In addition, several other steps have been proposed, including performing investigations such as barium follow-through. In cases where it is suspected that there is a high risk of retention, the patient is given a patency capsule a few days before swallowing an ingestible device. Any dissolvable non-endoscopic capsule may be used to determine the patency of the GI tract. The patency capsule is usually the same size as the ingestible device and can be made of cellophane. In some embodiments, the patency capsule contains a mixture of barium and lactose, which allows visualization by x-ray. The patency capsule may also include a radiotag or other label, which allows for it to be detected by radio-scanner externally. The patency capsule may comprise wax plugs, which allow for intestinal fluid to enter and dissolve the content, thereby dividing the capsule into small particles.

Accordingly, in some embodiments, the methods herein comprise (a) identifying a subject having a disease of the gastrointestinal tract and (b) evaluating the subject for suitability to treatment. In some embodiments, the methods herein comprise evaluating for suitability to treatment a subject identified as having a disease of the gastrointestinal tract. In some embodiments, evaluating the subject for suitability to treatment comprises determining the patency of the subject's GI tract.

In some embodiments, an ingestible device comprises a tissue anchoring mechanism for anchoring the ingestible device to a subject's tissue. For example, an ingestible device could be administered to a subject and once it reaches the desired location, the tissue attachment mechanism can be activated or deployed such that the ingestible device, or a portion thereof, is anchored to the desired location. In some embodiments, the tissue anchoring mechanism is reversible such that after initial anchoring, the tissue attachment device is retracted, dissolved, detached, inactivated or otherwise rendered incapable of anchoring the ingestible device to the subject's tissue. In some embodiments the attachment mechanism is placed endoscopically.

In some embodiments, a tissue anchoring mechanism comprises an osmotically-driven sucker. In some embodiments, the osmotically-driven sucker comprises a first valve on the near side of the osmotically-driven sucker (e.g., near the subject's tissue) and a second one-way valve that is opened by osmotic pressure on the far side of the osmotically-driven sucker, and an internal osmotic pump system comprising salt crystals and semi-permeable membranes positioned between the two valves. In such embodiments, osmotic pressure is used to adhere the ingestible device to the subject's tissue without generating a vacuum within the ingestible capsule. After the osmotic system is activated by opening the first valve, fluid is drawn in through the sucker and expelled through the second burst valve. Fluid continues to flow until all the salt contained in the sucker is dissolved or until tissue is drawn into the sucker. As liminal fluid is drawn through the osmotic pump system, solutes build up between the tissue and the first valve, reducing osmotic pressure. In some embodiments, the solute buildup stalls the pump before the tissue contacts the valve, preventing tissue damage. In some embodiments, a burst valve is used on the far side of the osmotically-driven sucker rather than a one-way valve, such that luminal fluid eventually clears the saline chamber and the osmotic flow reverses, actively pushing the subject's tissue out of the sucker. In some embodiments, the ingestible device may be anchored to the interior surface of tissues forming the GI tract of a subject. In one embodiment, the ingestible device comprises a connector for anchoring the device to the interior surface of the GI tract. The connector may be operable to ingestible device to the interior surface of the GI tract using an adhesive, negative pressure and/or fastener.

In some embodiments a device comprises a tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

In some embodiments a device includes a fixation mechanism to anchor the device to tissue within a body lumen, and a mechanism to permit selective de-anchoring of the device from the tissue anchoring site without the need for endoscopic or surgical intervention. An electromagnetic device may be provided to mechanically actuate the de-anchoring mechanism. Alternatively, a fuse link may be electrically blown to de-anchor the device. As a further alternative, a rapidly degradable bonding agent may be exposed to a degradation agent to de-anchor the device from a bonding surface within the body lumen.

In some embodiments a device is as disclosed in patent publication WO2015112575A1, incorporated by reference herein in its entirety. The patent publication is directed to a gastrointestinal sensor implantation system. In some embodiments an orally-administrable capsule comprises a tissue capture device or reservoir removably coupled to the orally-administrable capsule, where the tissue capture device including a plurality of fasteners for anchoring the tissue capture device to gastrointestinal tissue within a body In some embodiments, the ingestible device contains an electric energy emitting means, a radio signal transmitting means, a medicament storage means and a remote actuatable medicament releasing means. The capsule signals a remote receiver as it progresses through the alimentary tract in a previously mapped route and upon reaching a specified site is remotely triggered to release a dosage of medicament. Accordingly, in some embodiments, releasing the IL-10 or IL-10 agonist is triggered by a remote electromagnetic signal.

In some embodiments, the ingestible device includes a housing introducible into a body cavity and of a material insoluble in the body cavity fluids, but formed with an opening covered by a material which is soluble in body cavity fluids. A diaphragm divides the interior of the housing into a medication chamber including the opening, and a control chamber. An electrolytic cell in the control chamber generates a gas when electrical current is passed therethrough to deliver medication from the medication chamber through the opening into the body cavity at a rate controlled by the electrical current. Accordingly, in some embodiments, releasing the IL-10 or IL-10 agonist is triggered by generation in the composition of a gas in an amount sufficient to expel the IL-10 or IL-10 agonist.

In some embodiments, the ingestible device includes an oral drug delivery device having a housing with walls of water permeable material and having at least two chambers separated by a displaceable membrane. The first chamber receives drug and has an orifice through which the drug is expelled under pressure. The second chamber contains at least one of two spaced apart electrodes forming part of an electric circuit which is closed by the ingress of an aqueous ionic solution into the second chamber. When current flows through the circuit, gas is generated and acts on the displaceable membrane to compress the first chamber and expel the active ingredient through the orifice for progressive delivery to the gastrointestinal tract.

In some embodiments, the ingestible device includes an ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core. In a further embodiment the invention includes an apparatus for generating the electromagnetic radiation, the apparatus including one or more pairs of field coils supported in a housing. The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

In some embodiments, the ingestible device includes an ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core. In a further embodiment the invention includes an apparatus for generating the electromagnetic radiation, the apparatus including one or more pairs of field coils supported in a housing. The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

In some embodiments, the ingestible device is a device a swallowable capsule. A sensing module is disposed in the capsule. A bioactive substance dispenser is disposed in the capsule. A memory and logic component is disposed in the capsule and in communication with the sensing module and the dispenser.

In some embodiments, localized administration is implemented via an electronic probe which is introduced into the intestinal tract of a living organism and which operates autonomously therein, adapted to deliver one or more therapy agents. In one embodiment, the method includes loading the probe with one or more therapy agents, and selectively releasing the agents from the probe at a desired location of the intestinal tract in order to provide increased efficacy over traditional oral ingestion or intravenous introduction of the agent(s).

In some embodiments, the ingestible device includes electronic control means for dispensing the drug substantially to the diseased tissue sites of the GI tract, according to a pre-determined drug release profile obtained prior to administration from the specific mammal. Accordingly, in some embodiments, releasing the IL-10 or IL-10 agonist is triggered by an electromagnetic signal generated within the device. The releasing may occur according to a pre-determined drug release profile.

In some embodiments, the ingestible device can include at least one guide tube, one or more tissue penetrating members positioned in the guide tube, a delivery member, an actuating mechanism and a release element. The release element degrades upon exposure to various conditions in the intestine so as to release and actuate the actuating mechanism. Embodiments of the invention are particularly useful for the delivery of drugs which are poorly absorbed, tolerated and/or degraded within the GI tract.

In some embodiments, the ingestible device includes an electronic pill comprising at least one reservoir with a solid powder or granulate medicament or formulation, a discharge opening and an actuator responsive to control circuitry for displacing medicine from the reservoir to the discharge opening. The medicament or formulation comprises a dispersion of one or more active ingredients—e.g., solids in powder or granulate form—in an inert carrier matrix. Optionally, the active ingredients are dispersed using intestinal moisture absorbed into the pill via a semi-permeable wall section.

In some embodiments, the ingestible device includes a sensor comprising a plurality of electrodes having a miniature size and a lower power consumption and a coating exterior to the electrodes, wherein the coating interacts with a target condition thereby producing a change in an electrical property of the electrodes, wherein the change is transduced into an electrical signal by the electrodes. Accordingly, in some embodiments, releasing the IL-10 or IL-10 agonist is triggered by an electric signal by the electrodes resulting from the interaction of the coating with the one or more sites of disease. Further provided herein is a system for medication delivery comprising such sensor and a pill.

In some embodiments, the ingestible device includes an electronic pill comprising a plurality of reservoirs, each of the reservoirs comprising a discharge opening covered by a removable cover. The pill comprises at least one actuator responsive to control circuitry for removing the cover from the discharge opening. The actuator can for example be a spring loaded piston breaking a foil cover when dispensing the medicament. Alternatively, the cover can be a rotatable disk or cylinder with an opening which can be brought in line with the discharge opening of a reservoir under the action of the actuator.

In some embodiments, the ingestible device includes an electronically and remotely controlled pill or medicament delivery system. The pill includes a housing; a reservoir for storing a medicament; an electronically controlled release valve or hatch for dispensing one or more medicaments stored in the reservoir while traversing the gastrointestinal tract; control and timing circuitry for opening and closing the valve; and a battery. The control and timing circuitry opens and closes the valve throughout a dispensing time period in accordance with a preset dispensing timing pattern which is programmed within the control and timing circuitry. RF communication circuitry receives control signals for remotely overriding the preset dispensing timing pattern, reprogramming the control and timing circuitry or terminating the dispensing of the medicament within the body. The pill includes an RFID tag for tracking, identification, inventory and other purposes.

In some embodiments, the ingestible device includes an electronic capsule which has a discrete drive element comprising: a housing, electronics for making the electronic capsule operable, a pumping mechanism for dosing and displacing a substance, a power source for powering the electronic capsule and enabling the electronics and the pumping mechanism to operate, and a locking mechanism; and a discrete payload element comprising: a housing, a reservoir for storing the substance, one or more openings in the housing for releasing the substance from the reservoir and a locking mechanism for engaging the drive element locking mechanism. Engagement of the drive element locking mechanism with the payload element locking mechanism secures the drive element to the payload element, thereby making the electronic capsule operable and specific.

In some embodiments, the ingestible device may be a mucoadhesive device configured for release of an active agent.

In some embodiments, the ingestible device includes an apparatus that includes an ingestible medical treatment device, which is configured to initially assume a contracted state having a volume of less than 4 $cm^3$. The device includes a gastric anchor, which initially assumes a contracted size, and which is configured to, upon coming in contact with a liquid, expand sufficiently to prevent passage of the anchor through a round opening having a diameter of between 1 cm and 3 cm. The device also includes a duodenal unit, which is configured to pass through the opening, and which is coupled to the gastric anchor such that the duodenal unit is held between 1 cm and 20 cm from the gastric anchor.

In some embodiments, the ingestible device includes a medical robotic system and method of operating such comprises taking intraoperative external image data of a patient anatomy, and using that image data to generate a modeling adjustment for a control system of the medical robotic system (e.g., updating anatomic model and/or refining instrument registration), and/or adjust a procedure control aspect (e.g., regulating substance or therapy delivery, improving targeting, and/or tracking performance).

In one embodiment the ingestible device may also include one or more environmental sensors. Environmental sensor may be used to generate environmental data for the environment external to device in the gastrointestinal (GI) tract of the subject. In some embodiments, environmental data is generated at or near the location within the GI tract of the subject where a drug is delivered. Examples of environmental sensor include, but are not limited to a capacitance sensor, a temperature sensor, an impedance sensor, a pH sensor, a heart rate sensor, acoustic sensor, image sensor (e.g., a hydrophone), and/or a movement sensor (e.g., an accelerometer). In one embodiment, the ingestible device comprises a plurality of different environmental sensors for generating different kinds of environmental data.

In one embodiment, the image sensor is a video camera suitable for obtaining images in vivo of the tissues forming the GI tract of the subject. In one embodiment, the environmental data is used to help determine one or more characteristics of the GI tract, including the location of disease (e.g., presence or location of inflamed tissue and/or lesions associated with inflammatory bowel disease). In some embodiments, the ingestible device may comprise a camera for generating video imaging data of the GI tract which can be used to determine, among other things, the location of the device.

In another embodiment, the ingestible device described herein may be localized using a gamma scintigraphy technique or other radio-tracker technology as employed by Phaeton Research's Enterion™ capsule (See Teng, Renli, and Juan Maya. "Absolute bioavailability and regional absorption of ticagrelor in healthy volunteers." Journal of Drug Assessment 3.1 (2014): 43-50), or monitoring the magnetic field strength of permanent magnet in the ingestible device (see T. D. Than, et al., "A review of localization systems for robotic endoscopic capsules," IEEE Trans. Biomed. Eng., vol. 59, no. 9, pp. 2387-2399, September 2012).

In one embodiment, drug delivery is triggered when it encounters the site of disease in the GI tract.

In one embodiment, the one or more environmental sensors measure pH, temperature, transit times, or combinations thereof.

In some embodiments, releasing the IL-10 or IL-10 agonist is dependent on the pH at or in the vicinity of the location. In some embodiments the pH in the jejunum is from 6.1 to 7.2, such as 6.6. In some embodiments the pH in the mid small bowel is from 7.0 to 7.8, such as 7.4. In some embodiments the pH in the ileum is from 7.0 to 8.0, such as 7.5. In some embodiments the pH in the right colon is from 5.7 to 7.0, such as 6.4. In some embodiments the pH in the mid colon is from 5.7 to 7.4, such as 6.6. In some embodiments the pH in the left colon is from 6.3 to 7.7, such as 7.0. In some embodiments, the gastric pH in fasting subjects is from about 1.1 to 2.1, such as from 1.4 to 2.1, such as from 1.1 to 1.6, such as from 1.4 to 1.6. In some embodiments, the gastric pH in fed subjects is from 3.9 to 7.0, such as from 3.9 to 6.7, such as from 3.9 to 6.4, such as from 3.9 to 5.8, such as from 3.9 to 5.5, such as from 3.9 to 5.4, such as from 4.3 to 7.0, such as from 4.3 to 6.7, such as from 4.3 to 6.4, such as from 4.3 to 5.8, such as from 4.3 to 5.5, such as from 4.3 to 5.4. In some embodiments, the pH in the duodenum is from 5.8 to 6.8, such as from 6.0 to 6.8, such as from 6.1 to 6.8, such as from 6.2 to 6.8, such as from 5.8 to 6.7, such as from 6.0 to 6.7, such as from 6.1 to 6.7, such as from 6.2 to 6.7, such as from 5.8 to 6.6, such as from 6.0 to 6.6, such as from 6.1 to 6.6, such as from 6.2 to 6.6, such as from 5.8 to 6.5, such as from 6.0 to 6.5, such as from 6.1 to 6.5, such as from 6.2 to 6.5.

In some embodiments, releasing the IL-10 or IL-10 agonist is not dependent on the pH at or in the vicinity of the location. In some embodiments, releasing the IL-10 or IL-10 agonist is triggered by degradation of a release component located in the capsule. In some embodiments, the IL-10 or IL-10 agonist is not triggered by degradation of a release component located in the capsule. In some embodiments, wherein releasing the IL-10 or IL-10 agonist is not dependent on enzymatic activity at or in the vicinity of the location. In some embodiments, releasing the IL-10 or IL-10 agonist is not dependent on bacterial activity at or in the vicinity of the location.

In some embodiments, the pharmaceutical composition is an ingestible device, comprising:

a housing defined by a first end, a second end substantially opposite from the first end, and a wall extending longitudinally from the first end to the second end;

a reservoir located within the housing and containing the IL-10 or IL-10 agonist, wherein a first end of the reservoir is attached to the first end of the housing;

a mechanism for releasing the IL-10 or IL-10 agonist from the reservoir;

and;

an exit valve configured to allow the IL-10 or IL-10 agonist to be released out of the housing from the reservoir.

n some embodiments, the ingestible device further comprises:

an electronic component located within the housing; and a gas generating cell located within the housing and adjacent to the electronic component, wherein the electronic component is configured to activate the gas generating cell to generate gas.

In some embodiments, the ingestible device further comprises:

a safety device placed within or attached to the housing, wherein the safety device is configured to relieve an internal pressure within the housing when the internal pressure exceeds a threshold level.

In some embodiments, the pharmaceutical composition is an ingestible device, comprising:

a housing defined by a first end, a second end substantially opposite from the first end, and a wall extending longitudinally from the first end to the second end;

an electronic component located within the housing;

a gas generating cell located within the housing and adjacent to the electronic component, wherein the electronic component is configured to activate the gas generating cell to generate gas;

a reservoir located within the housing, wherein the reservoir stores a dispensable substance and a first end of the reservoir is attached to the first end of the housing;

an exit valve located at the first end of the housing, wherein the exit valve is configured to allow the dispensable substance to be released out of the first end of the housing from the reservoir; and a safety device placed within or attached to the housing, wherein the safety device is configured to relieve an internal pressure within the housing when the internal pressure exceeds a threshold level.

In some embodiments, the pharmaceutical composition is an ingestible device, comprising:

a housing defined by a first end, a second end substantially opposite from the first end, and a wall extending longitudinally from the first end to the second end;

an electronic component located within the housing, a gas generating cell located within the housing and adjacent to the electronic component, wherein the electronic component is configured to activate the gas generating cell to generate gas;

a reservoir located within the housing, wherein the reservoir stores a dispensable substance and a first end of the reservoir is attached to the first end of the housing;

an injection device located at the first end of the housing, wherein the jet injection device is configured to inject the dispensable substance out of the housing from the reservoir; and a safety device placed within or attached to the housing, wherein the safety device is configured to relieve an internal pressure within the housing.

In some embodiments, the pharmaceutical composition is an ingestible device, comprising:

a housing defined by a first end, a second end substantially opposite from the first end, and a wall extending longitudinally from the first end to the second end;

an optical sensing unit located on a side of the housing, wherein the optical sensing unit is configured to detect a reflectance from an environment external to the housing;

an electronic component located within the housing;

a gas generating cell located within the housing and adjacent to the electronic component, wherein the electronic component is configured to activate the gas generating cell to generate gas in response to identifying a location of the ingestible device based on the reflectance;

a reservoir located within the housing, wherein the reservoir stores a dispensable substance and a first end of the reservoir is attached to the first end of the housing;

a membrane in contact with the gas generating cell and configured to move or deform into the reservoir by a pressure generated by the gas generating cell; and a dispensing outlet placed at the first end of the housing, wherein the dispensing outlet is configured to deliver the dispensable substance out of the housing from the reservoir.

In one embodiment, drug delivery is triggered when it encounters the site of disease in the GI tract.

In one embodiment, the one or more environmental sensors measure pH, temperature, transit times, or combinations thereof.

In some embodiments, releasing the IL-10 or IL-10 agonist is dependent on the pH at or in the vicinity of the location. In some embodiments the pH in the jejunum is from 6.1 to 7.2, such as 6.6. In some embodiments the pH in the mid small bowel is from 7.0 to 7.8, such as 7.4. In some embodiments the pH in the ileum is from 7.0 to 8.0, such as 7.5. In some embodiments the pH in the right colon is from 5.7 to 7.0, such as 6.4. In some embodiments the pH in the mid colon is from 5.7 to 7.4, such as 6.6. In some embodiments the pH in the left colon is from 6.3 to 7.7, such as 7.0. In some embodiments, the gastric pH in fasting subjects is from about 1.1 to 2.1, such as from 1.4 to 2.1, such as from 1.1 to 1.6, such as from 1.4 to 1.6. In some embodiments, the gastric pH in fed subjects is from 3.9 to 7.0, such as from 3.9 to 6.7, such as from 3.9 to 6.4, such as from 3.9 to 5.8, such as from 3.9 to 5.5, such as from 3.9 to 5.4, such as from 4.3 to 7.0, such as from 4.3 to 6.7, such as from 4.3 to 6.4, such as from 4.3 to 5.8, such as from 4.3 to 5.5, such as from 4.3 to 5.4. In some embodiments, the pH in the duodenum is from 5.8 to 6.8, such as from 6.0 to 6.8, such as from 6.1 to 6.8, such as from 6.2 to 6.8, such as from 5.8 to 6.7, such as from 6.0 to 6.7, such as from 6.1 to 6.7, such as from 6.2 to 6.7, such as from 5.8 to 6.6, such as from 6.0 to 6.6, such as from 6.1 to 6.6, such as from 6.2 to 6.6, such as from 5.8 to 6.5, such as from 6.0 to 6.5, such as from 6.1 to 6.5, such as from 6.2 to 6.5.

In some embodiments, releasing the IL-10 or IL-10 agonist is not dependent on the pH at or in the vicinity of the location. In some embodiments, releasing the IL-10 or IL-10 agonist is triggered by degradation of a release component located in the capsule. In some embodiments, the IL-10 or IL-10 agonist is not triggered by degradation of a release component located in the capsule. In some embodiments, wherein releasing the IL-10 or IL-10 agonist is not dependent on enzymatic activity at or in the vicinity of the location. In some embodiments, releasing the IL-10 or IL-10 agonist is not dependent on bacterial activity at or in the vicinity of the location.

In some embodiments, the pharmaceutical composition is an ingestible device, comprising:

a housing defined by a first end, a second end substantially opposite from the first end, and a wall extending longitudinally from the first end to the second end;

a reservoir located within the housing and containing the IL-10 or IL-10 agonist, wherein a first end of the reservoir is attached to the first end of the housing;

a mechanism for releasing the IL-10 or IL-10 agonist from the reservoir; and;

an exit valve configured to allow the IL-10 or IL-10 agonist to be released out of the housing from the reservoir.

In some embodiments, the ingestible device further comprises:

an electronic component located within the housing; and a gas generating cell located within the housing and adjacent to the electronic component, wherein the electronic component is configured to activate the gas generating cell to generate gas.

In some embodiments, the ingestible device further comprises:

a safety device placed within or attached to the housing, wherein the safety device is configured to relieve an internal pressure within the housing when the internal pressure exceeds a threshold level.

In some embodiments, the pharmaceutical composition is an ingestible device, comprising:

a housing defined by a first end, a second end substantially opposite from the first end, and a wall extending longitudinally from the first end to the second end;

an electronic component located within the housing;

a gas generating cell located within the housing and adjacent to the electronic component, wherein the electronic component is configured to activate the gas generating cell to generate gas;

a reservoir located within the housing, wherein the reservoir stores a dispensable substance and a first end of the reservoir is attached to the first end of the housing;

an exit valve located at the first end of the housing, wherein the exit valve is configured to allow the dispensable substance to be released out of the first end of the housing from the reservoir; and a safety device placed within or attached to the housing, wherein the safety device is configured to relieve an internal pressure within the housing when the internal pressure exceeds a threshold level.

In some embodiments, the pharmaceutical composition is an ingestible device, comprising:

a housing defined by a first end, a second end substantially opposite from the first end, and a wall extending longitudinally from the first end to the second end;

an electronic component located within the housing, a gas generating cell located within the housing and adjacent to the electronic component, wherein the electronic component is configured to activate the gas generating cell to generate gas;

a reservoir located within the housing, wherein the reservoir stores a dispensable substance and a first end of the reservoir is attached to the first end of the housing;

an injection device located at the first end of the housing, wherein the jet injection device is configured to inject the dispensable substance out of the housing from the reservoir; and a safety device placed within or attached to the housing, wherein the safety device is configured to relieve an internal pressure within the housing.

In some embodiments, the pharmaceutical composition is an ingestible device, comprising:

a housing defined by a first end, a second end substantially opposite from the first end, and a wall extending longitudinally from the first end to the second end;

an optical sensing unit located on a side of the housing, wherein the optical sensing unit is configured to detect a reflectance from an environment external to the housing;

an electronic component located within the housing;

a gas generating cell located within the housing and adjacent to the electronic component, wherein the electronic component is configured to activate the gas generating cell to generate gas in response to identifying a location of the ingestible device based on the reflectance;

a reservoir located within the housing, wherein the reservoir stores a dispensable substance and a first end of the reservoir is attached to the first end of the housing;

a membrane in contact with the gas generating cell and configured to move or deform into the reservoir by a pressure generated by the gas generating cell; and a dispensing outlet placed at the first end of the housing, wherein the dispensing outlet is configured to deliver the dispensable substance out of the housing from the reservoir.

In some embodiments, the pharmaceutical composition is an ingestible device as disclosed in U.S. Patent Application Ser. No. 62/385,553, incorporated by reference herein in its entirety.

In some embodiments, the pharmaceutical composition is an ingestible device as disclosed in the following applications, each of which is incorporated by reference herein in its entirety:

U.S. Ser. Nos. 14/460,893; 15/514,413; 62/376,688; 62/385,344; 62/478,955; 62/434,188; 62/434,320; 62/431,297; 62/434,797; 62/480,187; 62/502,383; and 62/540,873.

In some embodiments, the pharmaceutical composition is an ingestible device comprising a localization mechanism as disclosed in international patent application PCT/US2015/052500, incorporated by reference herein in its entirety.

In some embodiments, the pharmaceutical composition is not a dart-like dosage form.

In some embodiments of any ingestible device disclosed herein comprising IL-10 or an IL-10 agonist, the IL-10 or IL-10 agonist is present in a therapeutically effective amount.

In case of conflict between the present specification and any subject matter incorporated by reference herein, the present specification, including definitions, will control.

Devices and Methods for Detection of Analytes in GI tract

Detection of certain analytes in the GI tract may be useful in the identification of the nature and severity of the disease, in accurately locating the site(s) of disease, and in assessing patient response to a therapeutic agent. The appropriate therapeutic agent may accordingly be released at the correct locations(s), dosage, or timing for the disease. As discussed further herein, analytes may include biomarkers associated with a disease or associated with patient response and/or therapeutic agents previously administered to treat the disease. In some embodiments, the disclosure provides an ingestible device for detecting an analyte in a sample, the ingestible device comprising a sampling chamber that is configured to hold a composition comprising: (1) a plurality of donor particles, each of the plurality of donor particles comprising a photosensitizer and having coupled thereto a first antigen-binding agent that binds to the analyte, wherein the photosensitizer, in its excited state, is capable of generating singlet oxygen; and (2) a plurality of acceptor particles, each of the plurality of acceptor particles comprising a chemiluminescent compound and having coupled thereto a second antigen-binding agent that binds to the analyte, wherein the chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In some embodiments, this disclosure provides an ingestible device for detecting an analyte in a sample, the ingestible device comprising a sampling chamber that is configured to hold an absorbable material (e.g., an absorbable pad or sponge) having absorbed therein a composition comprising: (1) a plurality of donor particles, each of the plurality of donor particles comprising a photosensitizer and having coupled thereto a first antigen-binding agent that binds to the analyte, wherein the photosensitizer, in its excited state, is capable of generating singlet oxygen; and (2) a plurality of acceptor particles, each of the plurality of acceptor particles comprising a chemiluminescent compound and having coupled thereto a second antigen-binding agent that binds to the analyte, wherein the chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In certain embodiments, the disclosure provides a kit comprising an ingestible device as described herein. In some embodiments, the kit further comprises instructions, e.g., for detecting or quantifying an analyte in a sample.

In some embodiments, the disclosure provides methods for determining an analyte in a sample. In certain embodiments, this disclosure provides a method of detecting an analyte in a fluid sample of a subject, comprising: (1) providing an ingestible device; (2) transferring the fluid sample of the subject into the sampling chamber of the ingestible device in vivo; (3) irradiating the composition held in the sampling chamber of the ingestible device with light to excite the photosensitizer; and (4) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the disclosure provides a method of detecting an analyte in a fluid sample of a subject, comprising: (1) providing an ingestible device, the device comprising a sampling chamber that is configured to hold an absorbable material (e.g., an absorbable pad or sponge) having absorbed therein a composition, as described herein; (2) transferring the fluid sample of the subject into the sampling chamber of the ingestible device in vivo; (3) fully or partially saturating the absorbable material held in the sampling chamber of the ingestible device with the fluid sample; (4) irradiating the absorbable material held in the sampling chamber of the ingestible device with light to excite the photosensitizer; and (5) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the disclosure provides a method of assessing or monitoring the need to treat a subject suffering from or at risk of overgrowth of bacterial cells in the gastrointestinal (GI) tract, comprising: (1) providing an ingestible device for detecting an analyte; (2) transferring a fluid sample from the GI tract of the subject into the sampling chamber of the ingestible device in vivo; (3) irradiating the composition held in the sampling chamber of the ingestible device with light to excite the photosensitizer; (4) measuring total luminescence or rate of change of luminescence emitted from the composition held in the sampling chamber of the ingestible device as a function of time; (5) correlating the total luminescence or the rate of change of luminescence as a function of time measured in step (4) to the amount of the analyte in the fluid sample; and (6) correlating the amount of the analyte in the fluid sample to the number of viable bacterial cells in the fluid sample. In some embodiments, a number of viable bacterial cells determined in step (6) greater than a control number of viable bacterial cells, indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (6) greater that about $10^3$ CFU/mL indicates a need for treatment. In some embodiments, a number of viable bacterial cells determined in step (6) greater that about $10^4$ CFU/mL indicates a need for treatment. In some embodiments, a number of the viable bacterial cells determined in step (6) greater than about $10^5$ CFU/mL indicates a need for treatment, e.g., with an antibiotic agent as described herein. In some embodiments, a number of viable bacterial cells determined in step (6) greater that about $10^6$ or more CFU/mL indicates a need for treatment.

In some embodiments, the total luminescence or the rate of change of luminescence as a function of time of the sponge is measured over multiple time points for an extended period of time in step (4). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver. In some embodiments, the total luminescence or the rate of change of luminescence as a function of time of the sponge is measured over multiple time points for an extended period of time in step (5). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver.

In some embodiments, the disclosure provids a method of assessing or monitoring the need to treat a subject suffering from or at risk of overgrowth of bacterial cells in the gastrointestinal tract, comprising: (1) providing an ingestible device for detecting an analyte, the device comprising a sampling chamber that is configured to hold an absorbable material (e.g., an absorbable pad or sponge) having absorbed therein a composition, as described herein; (2) transferring a fluid sample from the GI tract of the subject into the sampling chamber of the ingestible device in vivo; (3) fully or partially saturating the absorbable material held in the sampling chamber of the ingestible device with the fluid sample; (4) irradiating the absorbable material held in the sampling chamber of the ingestible device with light to excite the photosensitizer; (5) measuring total luminescence or rate of change of luminescence emitted from the composition held in the sampling chamber of the ingestible device as a function of time; (6) correlating the total luminescence or the rate of change of luminescence as a function of time measured in step (5) to the amount of the analyte in the fluid sample; and (7) correlating the amount of the analyte in the fluid sample to the number of viable bacterial cells in the fluid sample. In some embodiments, a number of viable bacterial cells determined in step (7) greater than a control number of viable bacterial cells indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (7) greater that about $10^3$ CFU/mL indicates a need for treatment. In some embodiments, a number of viable bacterial cells determined in step (7) greater that about $10^4$ CFU/mL indicates a need for treatment. In some embodiments, a number of the viable bacterial cells determined in step (7) greater than about $10^5$ CFU/mL indicates a need for treatment, e.g., with an antibiotic agent as described herein. In some embodiments, a number of viable bacterial cells determined in step (7) greater that about $10^6$ or more CFU/mL indicates a need for treatment.

In some embodiments, the disclosure, provides a method of measuring the presence, absence or amount of one or more analytes from one or more samples in the gastrointestinal tract. In some embodiments the one or more analytes are measured multiple times, for example, at different time points or at different locations. In one embodiment, a single device measures one or more analytes or more time points or locations; thereby creating a "molecular map" of a physiological region. Measurements can be taken at any location in the gastrointestinal tract. For example, in one aspect, analytes from samples from one or more of the duodenum, jejunum, ileum, ascending colon, transverse colon or descending colon can be measured to create a molecular map of the small and large intestine. In one aspect, the sample is from the duodenum. In one aspect, the sample is from the jejunum. In one aspect, the sample is from the ileum. In one aspect, the sample is from the ascending colon. In one aspect, the sample is from the transverse colon. In one aspect, the sample is from the descending colon.

In another aspect, a series of measurements can be taken over a shorter distance of the gastrointestinal tract (e.g., the ileum) to create a higher resolution molecular map. In some embodiments, previous endoscopic imaging may identify a diseased area for molecular mapping. For example, a gastroenterologist may use imaging (e.g., an endoscope equipped with a camera) to identify the presence of Crohn's Disease in the ileum and cecum of a patient, and the methods and techniques herein may be used to measure inflammation-associated analytes in this diseased area of the patient.

In a related embodiment, the inflammation-associated analytes, or any analyte, may be measured every one or more days to monitor disease flare-ups, or response to therapeutics.

Analytes

The compositions and methods described herein can be used to detect, analyze, and/or quantitate a variety of analytes in a human subject. "Analyte" as used herein refers to a compound or composition to be detected in a sample. Exemplary analytes suitable for use herein include those described in U.S. Pat. No. 6,251,581, which is incorporated by reference herein in its entirety. Broadly speaking, an analyte can be any substance (e.g., a substance with one or more antigens) capable of being detected. An exemplary and non-limiting list of analytes includes ligands, proteins, blood clotting factors, hormones, cytokines, polysaccharides, mucopolysaccharides, microorganisms (e.g., bacteria), microbial antigens, and therapeutic agents (including fragments and metabolites thereof).

For instance, the analyte may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., a human leukocyte antigen (HLA), or other cell surface antigen, or a microorganism, e.g., bacterium (e.g. a pathogenic bacterium), a fungus, protozoan, or a virus (e.g., a protein, a nucleic acid, a lipid, or a hormone). In some embodiments, the analyte can be a part of an exosome (e.g., a bacterial exosome). In some embodiments, the analyte is derived from a subject (e.g., a human subject). In some embodiments, the analyte is derived from a microorganism present in the subject. In some embodiments, the analyte is a nucleic acid (e.g., a DNA molecule or a RNA molecule), a protein (e.g., a soluble protein, a cell surface protein), or a fragment thereof, that can be detected using any of the devices and methods provided herein.

The polyvalent ligand analytes will normally be poly (amino acids), i.e., a polypeptide (i.e., protein) or a peptide, polysaccharides, nucleic acids (e.g., DNA or RNA), and combinations thereof. Such combinations include components of bacteria, viruses, chromosomes, genes, mitochondria, nuclei, cell membranes, and the like.

In some embodiments, the polyepitopic ligand analytes have a molecular weight of at least about 5,000 Da, more usually at least about 10,000 Da. In the poly(amino acid) category, the poly(amino acids) of interest may generally have a molecular weight from about 5,000 Da to about 5,000,000 Da, more usually from about 20,000 Da to 1,000,000 Da; among the hormones of interest, the molecular weights will usually range from about 5,000 Da to 60,000 Da.

In some embodiments, the monoepitopic ligand analytes generally have a molecular weight of from about 100 to 2,000 Da, more usually from 125 to 1,000 Da.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

In some embodiments, the analyte is a protein. In some embodiments, the analyte is a protein, e.g., an enzyme (e.g., a hemolysin, a protease, a phospholipase), a soluble protein, an exotoxin. In some embodiments, the analyte is a fragment of a protein, a peptide, or an antigen. In some embodiments, the analyte is a peptide of at least 5 amino acids (e.g., at least 6, at least 7, at least 8, at least 9, at least 10, at least 25, at least, 50, or at least 100 amino acids). Exemplary lengths include 6, 7, 8, 9, 10, 11, 12, 13, 14, 15, 16, 17, 18, 19, 20, 21, 22, 23, 24, 25, 26, 27, 28, 29, 30, 50, 75, or 100 amino acids. Exemplary classes of protein analytes include, but are not limited to: protamines, histones, albumins, globulins, scleroproteins, phosphoproteins, mucoproteins, chromoproteins, lipoproteins, nucleoproteins, glycoproteins, T-cell receptors, proteoglycans, cell surface receptors, membrane-anchored proteins, transmembrane proteins, secreted proteins, HLA, and unclassified proteins.

In some embodiments, the analyte is an affimer (see, e.g., Tiede et al. (2017) *eLife* 6: e24903, which is expressly incorporated herein by reference).

Exemplary analytes include: Prealbumin, Albumin, $\alpha_1$-Lipoprotein, $\alpha_1$-Antitrypsin, $\alpha_1$-Glycoprotein, Transcortin, 4.6S-Postalbumin, $\alpha_1$-glycoprotein, $\alpha_{1X}$-Glycoprotein, Thyroxin-binding globulin, Inter-$\alpha$-trypsin-inhibitor, Gc-globulin (Gc 1-1, Gc 2-1, Gc 2-2), Haptoglobin (Hp 1-1, Hp 2-1, Hp 2-2), Ceruloplasmin, Cholinesterase, $\alpha_2$-Lipoprotein(s), Myoglobin, C-Reactive Protein, $\alpha_2$-Macroglobulin, $\alpha_2$-HS-glycoprotein, Zn-$\alpha_2$-glycoprotein, $\alpha_2$-Neuramino-glycoprotein, Erythropoietin, $\beta$-lipoprotein, Transferrin, Hemopexin, Fibrinogen, Plasminogen, $\beta_2$-glycoprotein I, $\beta_2$-glycoprotein II, Immunoglobulin G (IgG) or $\gamma$G-globulin, Immunoglobulin A (IgA) or $\gamma$A-globulin, Immunoglobulin M (IgM) or $\gamma$M-globulin, Immunoglobulin D (IgD) or $\gamma$D-Globulin ($\gamma$D), Immunoglobulin E (IgE) or $\gamma$E-Globulin ($\gamma$E), Free $\kappa$ and $\lambda$ light chains, and Complement factors: C'1, (C'1q, C'1r, C'1s, C'2, C'3 ($\beta_1$A, $\alpha_2$D), C'4, C'S, C'6, C'7, C'8, C'9.

Additional examples of analytes include tumor necrosis factor-$\alpha$ (TNF$\alpha$), interleukin-12 (IL-12), IL-23, IL-6, $\alpha 2\beta 1$ integrin, $\alpha 1\beta 1$ integrin, $\alpha 4\beta 7$ integrin, integrin $\alpha 4\beta 1$ (VLA-4), E-selectin, ICAM-1, $\alpha 5\beta 1$ integrin, $\alpha 4\beta 1$ integrin, VLA-4, $\alpha 2\beta 1$ integrin, $\alpha 5\beta 3$ integrin, $\alpha 5\beta 5$ integrin, $\alpha$IIb$\beta 3$ integrin, MAdCAM-1, SMAD7, JAK1, JAK2, JAK3, TYK-2, CHST15, IL-1, IL-1$\alpha$, IL-1$\beta$, IL-18, IL-36$\alpha$, IL-36$\beta$, IL-36$\gamma$, IL-38, IL-33, IL-13, CD40L, CD40, CD3$\gamma$, CD3$\delta$, CD3$\epsilon$, CD3$\zeta$, TCR, TCR$\alpha$, TCR$\beta$, TCR$\delta$, TCR$\gamma$, CD14, CD20, CD25, IL-2, IL-2 $\beta$ chain, IL-2 $\gamma$ chain, CD28, CD80, CD86, CD49, MMP1, CD89, IgA, CXCL10, CCL11, an ELR chemokine, CCR2, CCR9, CXCR3, CCR3, CCR5, CCL2, CCL8, CCL16, CCL25, CXCR1m CXCR2m CXCL1, CXCL2, CXCL3, CXCL4, CXCL5, CXCL6, CXCL7, and CXCL8, and a nucleic acid (e.g., mRNA) encoding any of the same.

In some embodiments, the analyte is a blood clotting factor. Exemplary blood clotting factors include, but are not limited to:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |

| International designation | Name |
|---|---|
| X | Stuart-Prower factor autoprothrombin III |
| XI | Plasma thromboplastin antecedent (PTA) |
| XII | Hagemann factor |
| XIII | Fibrin-stablizing factor |

In some embodiments, the analyte is a hormone. Exemplary hormones include, but are not limited to: Peptide and Protein Hormones, Parathyroid hormone, (parathromone), Thyrocalcitonin, Insulin, Glucagon, Relaxin, Erythropoietin, Melanotropin (melancyte-stimulating hormone; intermedin), Somatotropin (growth hormone), Corticotropin (adrenocorticotropic hormone), Thyrotropin, Follicle-stimulating hormone, Luteinizing hormone (interstitial cell-stimulating hormone), Luteomammotropic hormone (luteotropin, prolactin), Gonadotropin (chorionic gonadotropin), Secretin, Gastrin, Angiotensin I and II, Bradykinin, and Human placental lactogen, thyroxine, cortisol, triiodothyronine, testosterone, estradiol, estrone, progestrone, luteinizing hormone-releasing hormone (LHRH), and immunosuppressants such as cyclosporin, FK506, mycophenolic acid, and so forth.

In some embodiments, the analyte is a peptide hormone (e.g., a peptide hormone from the neurohypophysis). Exemplary peptide hormones from the neurohypophysis include, but are not limited to: Oxytocin, Vasopressin, and releasing factors (RF) (e.g., corticotropin releasing factor (CRF), luteinizing hormone releasing factor (LRF), thyrotropin releasing factor (TRF), Somatotropin-RF, growth hormone releasing factor (GRF), follicle stimulating hormone-releasing factor (FSH-RF), prolactin inhibiting factor (PIF), and melanocyte stimulating hormone inhibiting factor (MIF)).

In some embodiments, the analyte is a cytokine or a chemokine. Exemplary cytokines include, but are not limited to: interleukin-1 (IL-1), interleukin-2 (IL-2), interleukin-6 (IL-6), epidermal growth factor (EGF), tumor necrosis factor (TNF, e.g., TNF-α or TNF-β), and nerve growth factor (NGF).

In some embodiments, the analyte is a cancer antigen. Exemplary cancer antigens include, but are not limited to: prostate-specific antigen (PSA), carcinoembryonic antigen (CEA), α-fetoprotein, Acid phosphatase, CA19.9, and CA125.

In some embodiments, the analyte is a tissue-specific antigen. Exemplary tissue specific antigens include, but are not limited to: alkaline phosphatase, myoglobin, CPK-MB, calcitonin, and myelin basic protein.

In some embodiments, the analyte is a mucopolysaccharide or a polysaccharide.

In some embodiments, the analyte is a microorganism, or a molecule derived from or produced by a microorganism (e.g., a bacteria, a virus, prion, or a protozoan). For example, in some embodiments, the analyte is a molecule (e.g., an protein or a nucleic acid) that is specific for a particular microbial genus, species, or strain (e.g., a specific bacterial genus, species, or strain). In some embodiments, the microorganism is pathogenic (i.e., causes disease). In some embodiments, the microorganism is non-pathogenic (e.g., a commensal microorganism). Exemplary microorganisms include, but are not limited to:

| | |
|---|---|
| Corynebacteria | |
| Corynebacterium diphtheria | |
| Pneumococci | |
| Diplococcus pneumoniae | |
| Streptococci | |
| Streptococcus pyrogenes | |
| Streptococcus salivarus | |
| Staphylococci | |
| Staphylococcus aureus | |
| Staphylococcus albus | |
| Neisseria | |
| Neisseria meningitidis | |
| Neisseria gonorrhea | |
| Enterobacteriaciae | |
| Escherichia coli | The coliform bacteria |
| Aerobacter aerogenes | |
| Klebsiella pneumoniae | |
| Salmonella typhosa | The Salmonellae |
| Salmonella choleraesuis | |
| Salmonella typhimurium | |
| Shigella dysenteria | The Shigellae |
| Shigella schmitzii | |
| Shigella arabinotarda | |
| Shigella flexneri | |
| Shigella boydii | |
| Shigella sonnei | |
| Other enteric bacilli | |
| Proteus vulgaris | Proteus species |
| Proteus mirabilis | |
| Proteus morgani | |
| Pseudomonas aeruginosa | |
| Alcaligenes faecalis | |
| Vibrio cholerae | |
| Hemophilus-Bordetella group | Rhizopus oryzae |
| Hemophilus influenza, H. ducryi | Rhizopus arrhizua |
| | Phycomycetes |
| Hemophilus hemophilus | Rhizopus nigricans |
| Hemophilus aegypticus | Sporotrichum schenkii |
| Hemophilus parainfluenza | Flonsecaea pedrosoi |
| Bordetella pertussis | Fonsecacea compact |
| Pasteurellae | Fonsecacea dermatidis |
| Pasteurella pestis | Cladosporium carrionii |
| Pasteurella tulareusis | Phialophora verrucosa |
| Brucellae | Aspergillus nidulans |
| Brucella melltensis | Madurella mycetomi |
| Brucella abortus | Madurella grisea |
| Brucella suis | Allescheria boydii |
| Aerobic Spore-forming Bacilli | Phialophora jeanselmei |
| Bacillus anthracis | Microsporum gypseum |
| Bacillus subtilis | Trichophyton mentagrophytes |
| Bacillus megaterium | Keratinomyces ajelloi |
| Bacillus cereus | Microsporum canis |
| Anaerobic Spore-forming Bacilli | Trichophyton rubrum |
| Clostridium botulinum | Microsporum adouini |
| Clostridium tetani | Viruses |
| Clostridium perfringens | Adenoviruses |
| Clostridium novyi | Herpes Viruses |
| Clostridium septicum | Herpes simplex |
| Clostridium histoyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |

-continued

| | |
|---|---|
| Mycobacterium paratuberculosis | Molluscum contagiosum |
| Actinomycetes (fungus-ike bacteria) | Picornaviruses |
| | |
| Actinomyces Isaeli | Poliovirus |
| Actinomyces bovis | Coxsackievirus |
| Actinomyces naeslundii | Echoviruses |
| Nocardia asteroides | Rhinoviruses |
| Nocardia brasiliensis | Myxoviruses |
| The Spirochetes | Influenza(A, B, and C) |
| | |
| Treponema pallidum | Parainfluenza (1-4) |
| Treponema pertenue | Mumps Virus |
| Spirillum minus | |
| Streptobacillus monoiliformis | Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial Virus |
| Trypanasomes | Rubella Virus |
| Mycoplasmas | Arboviruses |
| | |
| Mycoplasma pneumoniae | |
| Other pathogens | Eastern Equine Encephalitis Virus |
| | |
| Listeria monocytogenes | Western Equine Encephalitis Virus |
| Erysipeothrix rhusiopathiae | Sindbis Virus |
| Streptobacillus moniliformis | Chikugunya Virus |
| Donvania granulomatis | Semliki Forest Virus |
| Entamoeba histolytica | Mayora Virus |
| Plasmodium falciparum | St. Louis Encephalitis |
| Plasmodium japonicum | California Encephalitis Virus |
| Bartonella bacilliformis | Colorado Tick Fever Virus |
| Rickettsia (bacteria-like parasites) | Yellow Fever Virus |
| | |
| Rickettsia prowazekii | Dengue Virus |
| Rickettsia mooseri | Reoviruses |
| Rickettsia rickettsii | Reovirus Types 1-3 |
| Rickettsia conori | Retroviruses |
| Rickettsia australis | Human Immunodeficiency |
| Rickettsia sibiricus | Viruses I and II (HTLV) |
| Rickettsia akari | Human T-cell Lymphotrophic |
| Rickettsia tsutsugamushi | Virus I & II (HIV) |
| Rickettsia burnetti | Hepatitis |
| Rickettsia quintana | Hepatitis A Virus |
| Chlamydia (unclassifiable parasites bacterial/viral) | Hepatitis B Virus |
| | Hepatitis C Virus |
| Chlamydia agents (naming uncertain) | Tumor Viruses |
| | |
| Chlamydia trachomatis | |
| Fungi | Rauscher Leukemia Virus |
| | |
| Cryptococcus neoformans | Gross Virus |
| Blastomyces dermatidis | Maloney Leukemia Virus |
| Histoplasma capsulatum | |
| Coccidioides immitis | Human Papilloma Virus |
| Paracoccidioides brasliensis | |
| Candida albicans | |
| Aspergillus fumigatus | |
| Mucor corymbifer (Absidia corymbifera) | |

In some embodiments, the analyte is a bacterium. Exemplary bacteria include, but are not limited to: *Escherichia coli* (or *E. coli*), *Bacillus anthracis, Bacillus cereus, Clostridium botulinum, Clostridium difficile, Yersinia pestis, Yersinia enterocolitica, Francisella tularensis, Brucella* species, *Clostridium perfringens, Burkholderia mallei, Burkholderia pseudomallei, Staphylococcus* species, *Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilis niger, Bacillus thuringiensis, Coxiella burnetti, Faecalibacterium prausnitzii* (also known as *Bacteroides praussnitzii*), *Roseburia hominis, Eubacterium rectale, Dialister invisus, Ruminococcus albus, Ruminococcus callidus,* and *Ruminococcus bromii*. Additional exemplary bacteria include bacteria of the phyla Firmicutes (e.g., *Clostridium* clusters XIVa and IV), bacteria of the phyla Bacteroidetes (e.g., *Bacteroides fragilis* or *Bacteroides vulgatus*), and bacteria of the phyla Actinobacteria (e.g., *Coriobacteriaceae* spp. or *Bifidobacterium adolescentis*). Bacteria of the *Clostridium* cluster XIVa includes species belonging to, for example, the *Clostridium, Ruminococcus, Lachnospira, Roseburia, Eubacterium, Coprococcus, Dorea,* and *Butyrivibrio* genera. Bacteria of the *Clostridium* cluster IV includes species belonging to, for example, the *Clostridium, Ruminococcus, Eubacterium* and *Anaerofilum* genera. In some embodiments, the analyte is *Candida*, e.g., *Candida albicans*. In some embodiments, the analyte is a byproduct from a bacterium or other microorganism, e.g., helminth ova, enterotoxin (*Clostridium difficile* toxin A; TcdA) or cytotoxin (*Clostridium difficile* toxin B; TcdB).

In some embodiments, the bacterium is a pathogenic bacterium. Non-limiting examples of pathogenic bacteria belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia*. Non-limiting examples of specific pathogenic bacterial species include a strain of *Bacillus anthracis*, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumoniae*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter sakazakii*, a strain of *Enterococcus faecalis*, a strain of *Enterobacter faecium*, a strain of *Escherichia coli* (e.g., *E. coli* O157H7), a strain of *Francisella tularensis*, a strain of *Haemophilus influenza*, a strain of *Helicobacter pylori*, a strain of *Legionella pneumophila*, a strain of *Leptospira interrogans*, a strain of *Listeria monocytogenes*, a strain of *Mycobacterium leprae*, a strain of *Mycobacterium tuberculosis*, a strain of *Mycobacterium ulcerans*, a strain of *Mycoplasma* pneumonia, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes*, a strain of *Treponema pallidum*, a strain of *Vibrio cholera*, a strain of *Yersinia enterocolitica*, and, a strain of *Yersinia pestis*.

In some embodiments, the bacterium is a commensal bacterium (e.g., a probiotic). In some embodiments, the bacterium has been previously administered to a subject, e.g., as a live biotherapeutic agent. Exemplary commensal bacteria include, but are not limited to, *Faecalibacterium prausnitzii* (also referred to as *Bacteroides praussnitzii*),

*Roseburia hominis, Eubacterium rectale, Dialister invisus, Ruminococcus albus, Ruminococcus gnavus, Ruminococcus torques, Ruminococcus callidus,* and *Ruminococcus bromii.*

In some embodiments, the analyte is a virus. In some embodiments, the virus is a pathogenic virus. Non-limiting examples of pathogenic viruses belong to the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In some embodiments, the analyte is a fungus. In some embodiments, the fungi is a pathogenic fungus. Non-limiting examples of pathogenic fungi belong to the genera *Asperfillus, Canidia, Cryptococcus, Histoplasma, Pneumocystis,* and *Stachybotrys.* Non-limiting examples of specific pathogenic fungi species include a strain of *Aspergillus clavatus, Aspergillus fumigatus, Aspergillus flavus, Canidia albicans, Cryptococcus albidus, Cryptococcus gattii, Cryptococcus laurentii, Cryptococcus neoformans, Histoplasma capsulatum, Pneumocystis jirovecii, Pneumocystis carinii,* and *Stachybotrys chartarum.*

In some embodiments, the analyte is a protozoan. In some embodiments, the analyte is a pathogenic protozoan. Non-limiting examples of pathogenic protozoa belong to the genera *Acanthamoeba, Balamuthia, Cryptosporidium, Dientamoeba, Endolimax, Entamoeba, Giardia, Iodamoeba, Leishmania, Naegleria, Plasmodium, Sappinia, Toxoplasma, Trichomonas,* and *Trypanosoma.* Non-limiting examples of specific pathogenic protozoa species include a strain of *Acanthamoeba* spp., *Balamuthia mandrillaris, Cryptosporidium canis, Cryptosporidium felis, Cryptosporidium hominis, Cryptosporidium meleagridis, Cryptosporidium muris, Cryptosporidium parvum, Dientamoeba fragilis, Endolimax nana, Entamoeba dispar, Entamoeba hartmanni, Entamoeba histolytica, Entamoeba coli, Entamoeba moshkovskii, Giardia lamblia, Iodamoeba butschlii, Leishmania aethiopica, Leishmania braziliensis, Leishmania chagasi, Leishmania donovani, Leishmania infantum, Leishmania major, Leishmania mexicana, Leishmania tropica, Naegleria fowleri, Plasmodium falciparum, Plasmodium knowlesi, Plasmodium malariae, Plasmodium ovale, Plasmodium vivax, Sappinia diploidea, Toxoplasma gondii, Trichomonas vaginalis, Trypanosoma brucei,* and *Trypanosoma cruzi.*

In some embodiments, the analyte is secreted by or expressed on the cell surface of a microorganism (e.g., a bacterium, a colonic bacterium, a viable bacterium, a dead bacterium, a parasite (e.g., *Giardia lamblia, Cryptosporidium, Cystoisosporiasis belli,* and *Balantidium coli*), a virus (e.g., a herpes virus, a cytomegalovirus, a herpes simplex virus, an Epstein-Barr virus, a human papilloma virus, a rotavirus, a human herpesvirus-8; Goodgame (1999) Curr. Gastroenterol. Rep. 1(4): 292-300). In some embodiments, the analyte is secreted by or expressed on the cell surface of a Gram-negative bacterium (e.g., *E. coli, Helicobacter pylori*). In some embodiments, the analyte is secreted by or expressed on the cell surface (e.g., a bacterial surface epitope) of a Gram-positive bacterium (e.g., *Staphylococcus aureus, Clostridium botulinum, Clostridium difficile*).

In some embodiments, the analyte is a molecule expressed on the surface of a bacterial cell (e.g., a bacterial cell surface protein). In some embodiments, the analyte is a bacterial toxin (e.g., TcdA and/or TcdB from *Clostridium difficile*). In some embodiments, the analyte is CFA/I fimbriae, flagella, lipopolysaccharide (LPS), lipoteichoic acid, or a peptidoglycan. Non-limiting examples of bacterium that may express an analyte that can be detected using any of the devices and methods described herein include: *Bacillus anthracis, Bacillus cereus, Clostridium botulinum, Clostridium difficile, Escherichia coli, Yersinia pestis, Yersinia enterocolitica, Francisella tularensis, Brucella species, Clostridium perfringens, Burkholderia mallei, Burkholderia pseudomallei, Helicobacter pylori, Staphylococcus* species, *Mycobacterium* species, Group A *Streptococcus,* Group B *Streptococcus, Streptococcus pneumoniae, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilis niger, Bacillus thuringiensis, Coxiella bumetti, Candida albicans, Bacteroides Leptospira interrogans, Listeria monocytogenes, Pasteurella multocida, Salmonella typhi, Salmonella typhimurium, Shigella dysenteriae, Shigella flexneria, Shigella sonnei, Vibrio cholera,* and *Vibrio parahaemolyticus.*

In some embodiments, the analyte is a byproduct from a bacterium or another microorganism, e.g., helminth ova, enterotoxin (*Clostridium difficile* toxin A; TcdA), cytotoxin (*Clostridium difficile* toxin B; TcdB), ammonia. In some embodiments, the analyte is an antigen from a microorganism (e.g., a bacteria, virus, prion, fungus, protozoan or a parasite).

In some embodiments, the analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

In some embodiments, the analyte is a steroid selected from the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

In some embodiments, the analyte is a bile acid. In some embodiments, the presence, absence, and/or a specific level of one or more bile acids in the GI tract of a subject is indicative of a condition or disease state (e.g., a GI disorder and/or a non-GI disorder (e.g., a systemic disorder). For example, in some embodiments, the compositions and methods described herein may be used to detect and/or quantify a bile acid in the GI tract of the subject to diagnose a condition such as bile acid malabsorption (also known as bile acid diarrhea). In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof 5-HT is a molecule that plays a role in the regulation of gastrointestinal motility, secretion, and sensation. Imbalances in the levels of 5-HT are associated with several diseases including inflammatory bowel syndrome (IBS), autism, gastric ulcer formation, non-cardiac chest pain, and functional dyspepsia (see, e.g., Faure et al. (2010)

*Gastroenterology* 139(1): 249-58 and Muller et al. (2016) *Neuroscience* 321: 24-41, and International Publication No. WO 2014/188377, each of which are incorporated herein by reference). Conversion of metabolites within the serotonin, tryptophan and/or kynurenine pathways affects the levels of 5-HT in a subject. Therefore, measuring the levels of one or more of the metabolites in this pathway may be used for the diagnosis, management and treatment of a disease or disorder associated with 5-HT imbalance including but not limited to IBS, autism, carcinoid syndrome, depression, hypertension, Alzheimer's disease, constipation, migraine, and serotonin syndrome. One or more analytes in the serotonin, tryptophan and/or kynurenine pathways can be detected and/or quantitated using, for example, methods and analyte-binding agents that bind to these metabolites including, e.g., antibodies, known in the art (see, e.g., International Publication No. WO2014/188377, the entire contents of which are expressly incorporated herein by reference).

In some embodiments, the analyte is a lactam having from 5 to 6 annular members selected from barbituates, e.g., phenobarbital and secobarbital, diphenylhydantonin, primidone, ethosuximide, and metabolites thereof.

In some embodiments, the analyte is an aminoalkylbenzene, with alkyl of from 2 to 3 carbon atoms, selected from the amphetamines; catecholamines, which includes ephedrine, L-dopa, epinephrine; narceine; papaverine; and metabolites thereof.

In some embodiments, the analyte is a benzheterocyclic selected from oxazepam, chlorpromazine, tegretol, their derivatives and metabolites, the heterocyclic rings being azepines, diazepines and phenothiazines.

In some embodiments, the analyte is a purine selected from theophylline, caffeine, their metabolites and derivatives.

In some embodiments, the analyte is marijuana, cannabinol or tetrahydrocannabinol.

In some embodiments, the analyte is a vitamin such as vitamin A, vitamin B, e.g. vitamin $B_{12}$, vitamin C, vitamin D, vitamin E and vitamin K, folic acid, thiamine.

In some embodiments, the analyte is selected from prostaglandins, which differ by the degree and sites of hydroxylation and unsaturation.

In some embodiments, the analyte is a tricyclic antidepressant selected from imipramine, dismethylimipramine, amitriptyline, nortriptyline, protriptyline, trimipramine, chlomipramine, doxepine, and desmethyldoxepin.

In some embodiments, the analyte is selected from antineoplastics, including methotrexate.

In some embodiments, the analyte is an antibiotic as described herein, including, but not limited to, penicillin, chloromycetin, actinomycetin, tetracycline, terramycin, and metabolites and derivatives.

In some embodiments, the analyte is a nucleoside and nucleotide selected from ATP, NAD, FMN, adenosine, guanosine, thymidine, and cytidine with their appropriate sugar and phosphate substituents.

In some embodiments, the analyte is selected from methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

In some embodiments, the analyte is a metabolite related to a diseased state. Such metabolites include, but are not limited to spermine, galactose, phenylpyruvic acid, and porphyrin Type 1.

In some embodiments, the analyte is an aminoglycoside, such as gentamicin, kanamicin, tobramycin, or amikacin.

In some embodiments, the analyte is a pesticide. Among pesticides of interest are polyhalogenated biphenyls, phosphate esters, thiophosphates, carbamates, polyhalogenated sulfenamides, their metabolites and derivatives.

In some embodiments, the analyte has a molecular weight of about 500 Da to about 1,000,000 Da (e.g., about 500 to about 500,000 Da, about 1,000 to about 100,000 Da).

In some embodiments, the analyte is a receptor, with a molecular weight ranging from 10,000 to $2 \times 10^8$ Da, more usually from 10,000 to $10^6$ Da. For immunoglobulins, IgA, IgG, IgE and IgM, the molecular weights will generally vary from about 160,000 Da to about $10^6$ Da. Enzymes will normally range in molecular weight from about 10,000 Da to about 1,000,000 Da. Natural receptors vary widely, generally having a molecular weight of at least about 25,000 Da and may be $10^6$ or higher Da, including such materials as avidin, DNA, RNA, thyroxine binding globulin, thyroxine binding prealbumin, transcortin, etc.

In some embodiments, the term "analyte" further includes polynucleotide analytes such as those polynucleotides defined below. These include m-RNA, r-RNA, t-RNA, DNA, DNA-RNA duplexes, etc. The term analyte also includes polynucleotide-binding agents, such as, for example, restriction enzymes, trascription factors, transcription activators, transcription repressors, nucleases, polymerases, histones, DNA repair enzymes, intercalating gagents, chemotherapeutic agents, and the like.

In some embodiments, the analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest (i.e., an analyte-binding agent), such as a specific binding pair member complementary to the analyte of interest, whose presence will be detected only when the analyte of interest is present in a sample. Thus, the agent probative of the analyte becomes the analyte that is detected in an assay.

In some embodiments, the analyte a nucleic acid (e.g., a bacterial DNA molecule or a bacterial RNA molecule (e.g., a bacterial tRNA, a transfer-messenger RNA (tmRNA)). See, e.g., Sjostrom et al. (2015) Scientific Reports 5: 15329; Ghosal (2017) Microbial Pathogenesis 104: 161-163; Shen et al. (2012) Cell Host Microbe. 12(4): 509-520.

In some embodiments, the analyte is a component of an outer membrane vesicle (OMV) (e.g., an OmpU protein, Elluri et al. (2014) PloS One 9: e106731). See, e.g., Kulp and Kuehn (2010) Annual Review of microbiology 64: 163-184; Berleman and Auer (2013) Environmental microbiology 15: 347-354; Wai et al. (1995) Microbiology and immunology 39: 451-456; Lindmark et al. (2009) BMC microbiology 9: 220; Sjostrom et al. (2015) Scientific Reports 5: 15329.

In some embodiments, the analyte is G-CSF, which can stimulate the bone marrow to produce granulocytes and stem cells and release them into the bloodstream.

In some embodiments, the analyte is an enzyme such as glutathione S-transferase. For example, the ingestible device can include P28GST, a 28 kDa helminth protein from *Schistosoma* with potent immunogenic and antioxidant properties. P28GST prevents intestinal inflammation in experimental colitis through a Th2-type response with mucosal eosinophils and can be recombinantly produced (e.g., in *S. cerevisiae*). See, for example, U.S. Pat. No.

9,593,313, Driss et al., *Mucosal Immunology,* 2016 9, 322-335; and Capron et al., *Gastroenterology,* 146(5):S-638.

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, analytes are therapeutic agents or drugs. In some embodiments, analytes are biomarkers. The therapeutic agents disclosed herein are can also be analytes. Examples of biomarkers are provided herein.

In some embodiments, analytes are therapeutic agents, fragments thereof, and metabolites thereof (e.g., antibiotics). In some embodiments, the analytes are antibodies. In some embodiments, the analytes are antibiotics. Additional exemplary analytes (e.g., antibodies and antibiotics) are provided below.

a. Antibodies

In some embodiments, the analyte or the analyte-binding agent is an antibody. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv) and domain antibodies), and fusion proteins including an antibody portion, and any other modified configuration of the immunoglobulin molecule that includes an antigen recognition site. The term antibody includes antibody fragments (e.g., antigen-binding fragments) such as an Fv fragment, a Fab fragment, a F(ab')2 fragment, and a Fab' fragment. Additional examples of antigen-binding fragments include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies including the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Lazikani et al, 1997, J. Molec. Biol. 273:927-948). As used herein, a CDR may refer to CDRs defined by either approach or by a combination of both approaches.

As known in the art, a "constant region" of an antibody refers to the constant region of the antibody light chain or the constant region of the antibody heavy chain, either alone or in combination.

A "derivative" refers to any polypeptide (e.g., an antibody) having a substantially identical amino acid sequence to the naturally occurring polypeptide, in which one or more amino acids have been modified at side groups of the amino acids (e.g., an biotinylated protein or antibody). The term "derivative" shall also include any polypeptide (e.g., an antibody) which has one or more amino acids deleted from, added to, or substituted from the natural polypeptide sequence, but which retains a substantial amino acid sequence homology to the natural sequence. A substantial sequence homology is any homology greater than 50 percent.

In some embodiments, the antibody can be a humanized antibody, a chimeric antibody, a multivalent antibody, or a fragment thereof. In some embodiments, an antibody can be a scFv-Fc (Sokolowska-Wedzina et al., *Mol. Cancer Res.* 15(8):1040-1050, 2017), a VHH domain (Li et al., *Immunol. Lett.* 188:89-95, 2017), a VNAR domain (Hasler et al., *Mol. Immunol.* 75:28-37, 2016), a $(scFv)_2$, a minibody (Kim et al., *PLoS One* 10(1):e113442, 2014), or a BiTE. In some embodiments, an antibody can be a DVD-Ig (Wu et al., *Nat. Biotechnol.* 25(11):1290-1297, 2007; WO 08/024188; WO 07/024715), and a dual-affinity re-targeting antibody (DART) (Tsai et al., *Mol. Ther. Oncolytics* 3:15024, 2016), a triomab (Chelius et al., MAbs 2(3):309-319, 2010), kih IgG with a common LC (Kontermann et al., *Drug Discovery*

*Today* 20(7):838-847, 2015), a crossmab (Regula et al., *EMBO Mol. Med.* 9(7):985, 2017), an ortho-Fab IgG (Kontermann et al., *Drug Discovery Today* 20(7):838-847, 2015), a 2-in-1-IgG (Kontermann et al., *Drug Discovery Today* 20(7):838-847, 2015), IgG-scFv (Cheal et al., *Mol. Cancer Ther.* 13(7):1803-1812, 2014), scFv2-Fc (Natsume et al., *J. Biochem.* 140(3):359-368, 2006), a bi-nanobody (Kontermann et al., *Drug Discovery Today* 20(7):838-847, 2015), tanden antibody (Kontermann et al., *Drug Discovery Today* 20(7):838-847, 2015), a DART-Fc (Kontermann et al., *Drug Discovery Today* 20(7):838-847, 2015), a scFv-HSA-scFv (Kontermann et al., *Drug Discovery Today* 20(7):838-847, 2015), DNL-Fab3 (Kontermann et al., *Drug Discovery Today* 20(7):838-847, 2015), DAF (two-in-one or four-in-one), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H) IgG, IgG(L)-scFv, scFv-(L)-IgG, IgG (L,H)-Fc, IgG(H)-V, V(H)—IgG, IgG(L)-V, V(L)-IgG, KIH IgG-scFab, 2scFv-IgG, IgG-2scFv, scFv4-Ig, Zybody, DVI-IgG, nanobody (e.g., antibodies derived from *Camelus bactriamus, Calelus dromaderius*, or *Lama paccos*) (U.S. Pat. No. 5,759,808; Stijlemans et al., *J. Biol. Chem.* 279:1256-1261, 2004; Dumoulin et al., *Nature* 424:783-788, 2003; and Pleschberger et al., *Bioconjugate Chem.* 14:440-448, 2003), nanobody-HSA, a diabody (e.g., Poljak, Structure 2(12): 1121-1123, 1994; Hudson et al., *J. Immunol. Methods* 23(1-2):177-189, 1999), a TandAb (Reusch et al., mAbs 6(3): 727-738, 2014), scDiabody (Cuesta et al., *Trends in Biotechnol.* 28(7):355-362, 2010), scDiabody-CH3 (Sanz et al., *Trends in Immunol.* 25(2):85-91, 2004), Diabody-CH3 (Guo et al.), Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody (Huston et al., *Human Antibodies* 10(3-4):127-142, 2001; Wheeler et al., *Mol. Ther.* 8(3):355-366, 2003; Stocks, *Drug Discov. Today* 9(22):960-966, 2004), dock and lock bispecific antibody, ImmTAC, HSAbody, scDiabody-HSA, tandem scFv, IgG-IgG, Cov-X-Body, and scFv1-PEG-scFv2.

In some embodiments, an antibody can be an IgNAR, a bispecific antibody (Milstein and Cuello, *Nature* 305:537-539, 1983; Suresh et al., *Methods in Enzymology* 121:210, 1986; WO 96/27011; Brennan et al., *Science* 229:81, 1985; Shalaby et al., *J. Exp. Med.* 175:217-225, 1992; Kolstelny et al., *J. Immunol.* 148(5):1547-1553, 1992; Hollinger et al., *Proc. Natl. Acad. Sci. U.S.A.* 90:6444-6448, 1993; Gruber et al., *J. Immunol.* 152:5368, 1994; Tutt et al., *J. Immunol.* 147:60, 1991), a bispecific diabody, a triabody (Schoonooghe et al., *BMC Biotechnol.* 9:70, 2009), a tetrabody, scFv-Fc knobs-into-holes, a scFv-Fc-scFv, a (Fab'scFv)₂, a V-IgG, a IvG-V, a dual V domain IgG, a heavy chain immunoglobulin or a camelid (Holt et al., *Trends Biotechnol.* 21(11):484-490, 2003), an intrabody, a monoclonal antibody (e.g., a human or humanized monoclonal antibody), a heteroconjugate antibody (e.g., U.S. Pat. No. 4,676, 980), a linear antibody (Zapata et al., *Protein Eng.* 8(10: 1057-1062, 1995), a trispecific antibody (Tutt et al., *J. Immunol.* 147:60, 1991), a Fabs-in-Tandem immunoglobulin (WO 15/103072), or a humanized camelid antibody.

In some embodiments, the antibody binds specifically to a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid. Exemplary antibodies that bind to metabolites in these pathways are disclosed, for example, in International Publication No. WO2014/188377, the entire contents of which are incorporated herein by reference.

In some embodiments, the antibody is specific for a particular genus, species, or strain of a microorganism, and may therefore be used for the detection, analysis and/or quantitation of the microorganism using the detection methods described below. In some embodiments, the antibody specifically binds to a surface-specific biomolecule (e.g., a pilus subunit or a flagella protein) present in a particular genus, species or strain of microorganism, and does not cross-react with other microorganisms. In some embodiments, these antibodies may be used in the methods described herein to diagnose a subject with a particular infection or disease, or to monitor an infection (e.g., during or after treatment). In some embodiments, the antibody specifically binds to an antigen present in a particular genera, species or strain of a microorganism. Exemplary antigens, the corresponding microorganism that can be detected, and the disease caused by the microorganism (in parentheticals) include: outer membrane protein A OmpA (*Acinetobacter baumannii, Acinetobacter* infections)); HIV p24 antigen, HIV Envelope proteins (Gp120, Gp41, Gp160) (HIV (Human immunodeficiency virus), AIDS (Acquired immunodeficiency syndrome)); galactose-inhibitable adherence protein GIAP, 29 kDa antigen Eh29, GaVGaINAc lectin, protein CRT, 125 kDa immunodominant antigen, protein M17, adhesin ADH112, protein STIRP (*Entamoeba histolytica*, Amoebiasis); protective Antigen PA, edema factor EF, lethal facotor LF, the S-layer homology proteins SLH (*Bacillus anthracis*, Anthrax); nucleocapsid protein NP, glycoprotein precursor GPC, glycoprotein GP1, glycoprotein GP2 (Junin virus, Argentine hemorrhagic fever); 41 kDa allergen Asp v13, allergen Asp f3, major conidial surface protein rodlet A, protease Peplp, GPI-anchored protein Gellp, GPI-anchored protein Crflp (*Aspergillus* genus, Aspergillosis); outer surface protein A OspA, outer surface protein OspB, outer surface protein OspC, decorin binding protein A DbpA, flagellar filament 41 kDa core protein Fla, basic membrane protein A precursor BmpA (Immunodominant antigen P39), outer surface 22 kDa lipoprotein precursor (antigen IPLA7), variable surface lipoprotein vIsE (*Borrelia* genus, *Borrelia* infection); OmpA-like transmembrane domain-containing protein Omp31, immunogenic 39-kDa protein M5 P39, 25 kDa outer-membrane immunogenic protein precursor Omp25, outer membrane protein MotY Omp16, conserved outer membrane protein D15, malate dehydrogenase Mdh, component of the Type-IV secretion system (T4SS) VirJ, lipoprotein of unknown function BAB1_0187 (*Brucella* genus, Brucellosis); major outer membrane protein PorA, flagellin FlaA, surface antigen CjaA, fibronectin binding protein CadF, aspartate/glutamate-binding ABC transporter protein PeblA, protein FspA1, protein FspA2 (*Campylobacter* genus, Campylobacteriosis); glycolytic enzyme enolase, secreted aspartyl proteinases SAP1-10, glycophosphatidylinositol (GPI)-linked cell wall protein, adhesin Als3p, cell surface hydrophobicity protein CSH (usually *Candida albicans* and other *Candida* species, Candidiasis); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB (*Chlamydia trachomatis, Chlamydia*); major outer membrane protein MOMP, outer membrane protein 2 Omp2, (*Chlamydophila pneumoniae, Chlamydophila pneumoniae* infection); outer membrane protein U Porin ompU, (*Vibrio cholerae*, Cholera); surface layer proteins SLPs, Cell Wall Protein CwpV, flagellar protein FliC, flagellar protein FliD (*Clostridium difficile, Clostridium difficile* infection); acidic ribosomal protein P2 CpP2, mucin antigens Muc1, Muc2, Muc3 Muc4, Muc5, Much, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); membrane protein pp15, capsid-proximal tegument protein pp150 (Cytomegalovirus, Cytomegalovirus infection); prion protein (vCJD prion, Variant Creutzfeldt-Jakob disease (vCJD, nvCJD)); cyst wall proteins CWP1, CWP2, CWP3, variant surface protein VSP, VSP1, VSP2, VSP3, VSP4, VSP5, VSP6, 56 kDa antigen (Giardia intestinalis, Giardiasis); minor pilin-associated subunit pilC, major pilin subunit and variants pilE, pilS (*Neisseria gonorrhoeae*, Gonorrhea); outer membrane protein A OmpA, outer membrane protein C OmpC, outer membrane protein K17 OmpK17 (*Klebsiella granulomatis, Granuloma inguinale* (Donovanosis)); fibronectin-binding protein Sfb (*Streptococcus pyogenes*, Group A streptococcal infection); outer membrane protein P6 (*Haemophilus influenzae, Haemophilus influenzae* infection); integral membrane proteins, aggregation-prone proteins, O-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and 0104:H4, Hemolytic-uremic syndrome (HUS)); hepatitis A surface antigen HBAg (Hepatitis A Virus, Hepatitis A); hepatitis B surface antigen HBsAg (Hepatitis B Virus, Hepatitis B); envelope glycoprotein E1 gp32 gp35, envelope glycoprotein E2 NS1 gp68 gp70, capsid protein C, (Hepatitis C Virus, Hepatitis C); type IV pilin PilE, outer membrane protein MIP, major outer membrane protein MompS (*Legionella pneumophila*, Legionellosis (Legionnaires' disease, Pontiac fever)); minor pilin-associated subunit pilC, major pilin subunit and variants pilE, pilS (*Neisseria meningitidis*, Meningococcal disease); adhesin P1, adhesion P30 (*Mycoplasma pneumoniae, Mycoplasma* pneumonia); F1 capsule antigen, outer membrane protease Pla, (*Yersinia pestis*, Plague); surface adhesin PsaA, cell wall surface anchored protein psrP (*Streptococcus pneumoniae*, Pneumococcal infection); flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA (*Salmonella* genus, *Salmonellosis*); collagen adhesin Cna, fibronectin-binding protein A FnbA, secretory antigen SssA (*Staphylococcus* genus, Staphylococcal food poisoning); collagen adhesin Can (*Staphylococcus* genus, Staphylococcal infection); fibronectin-binding protein A FbpA (Ag85A), fibronectin-binding protein D FbpD, fibronectin-binding protein C FbpC1, heat-shock protein HSP65, protein PST-S (*Mycobacterium tuberculosis*, Tuberculosis); and outer membrane protein FobA, outer membrane protein FobB, type IV pili glycosylation protein, outer membrane protein tolC, protein TolQ (*Francisella tularensis*, Tularemia). Additional exemplary microorganisms and corresponding antigens are disclosed, e.g., in U.S. Publication No. 2015/0118264, the entire contents of which are expressly incorporated herein by reference.

In some embodiments, a plurality of antibodies (e.g., 2, 3, 4, 5, 6, 7, 8, 9, 10, 15, 20, 25, 30, or more antibodies) are used as analyte-binding agents in any of the methods described herein (e.g., to detect the presence of one or more analytes in a sample). In some embodiments, the plurality of antibodies bind to the same analyte (e.g., an antigen). In some embodiments, the plurality of antibodies bind to the same epitope present on the analyte (e.g., an antigen). In some embodiments, the plurality of antibodies bind to different epitopes present on the same analyte. In some embodiments, the plurality of antibodies bind to overlapping epitopes present on the same analyte. In some embodiments, the plurality of antibodies bind to non-overlapping epitopes present on the same analyte.

b. Antibiotics

In some embodiments, the analyte or analyte-binding agent is an antibiotic. An "antibiotic" or "antibiotic agent" refers to a substance that has the capacity to inhibit or slow down the growth of, or to destroy bacteria and/or other microorganisms. In some embodiments, the antibiotic agent is a bacteriostatic antibiotic agent. In some embodiments, the antibiotic is a bacteriolytic antibiotic agent. Exemplary antibiotic agents are set forth in the U.S. Patent Publication US 2006/0269485, which is hereby incorporated by reference herein in its entirety.

In some embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In some embodiments, the antibiotic is rifaximin.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefinenoxime, cefinetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3',4'-dideoxykanamycin B, 1,2'-N-DL-isoserylkanamycin B, 1,2'-N-[(S)-4-amino-2-hydroxybutyryl]-3',4'-dideoxykanamycin B, 1,2'-N-[(S)-4-amino-2-hydroxybutyryl]-kanamycin B, 1-N-(2-Aminobutanesulfonyl) kanamycin A, 1-N-(2-aminoethanesulfonyl)3',4'-dideoxyribostamycin, 1-N-(2-Aminoethanesulfonyl)3'-deoxyribostamycin, 1-N-(2-aminoethanesulfonyl)3'4'-dideoxykanamycin B, 1-N-(2-aminoethanesulfonyl)kanamycin A, 1-N-(2-aminoethanesulfonyl)kanamycin B, 1-N-(2-aminoethanesulfonyl)ribostamycin, 1-N-(2-aminopropanesulfonyl)3'-deoxykanamycin B, 1-N-(2-aminopropanesulfonyl)3'4'-dideoxykanamycin B, 1-N-(2-aminopropanesulfonyl)kanamycin A, 1-N-(2-aminopropanesulfonyl)kanamycin B, 1-N-(L-4-amino-2-hydroxy-butyryl)2,'3'-dideoxy-2'-fluorokanamycin A, 1-N-(L-4-amino-2-hydroxy-propionyl)2,'3'-dideoxy-2'-fluorokanamycin A, 1-N-DL-3',4'-dideoxy-isoserylkanamycin B, 1-N-DL-isoserylkanamycin, 1-N-DL-isoserylkanamycin B, 1-N-[L-(−)-(alpha-hydroxy-gamma-aminobutyryl)]-XK-62-2,2',3'-dideoxy-2'-fluorokanamycin A,2-hydroxygentamycin A3,2-hydroxygentamycin B, 2-hydroxygentamycin B1, 2-hydroxygentamycin JI-20A, 2-hydroxygentamycin JI-20B, 3"-N-methyl-4"-C-methyl-3',4'-dodeoxy kanamycin A, 3"-N-methyl-4"-C-methyl-3',4'-dodeoxy kanamycin B, 3"-N-methyl-4"-C-methyl-3',4'-dodeoxy-6'-methyl kanamycin B, 3',4'-Dideoxy-3'-eno-ribostamycin,3',4'-dideoxyneamine,3',4'-dideoxyribostamycin, 3'-deoxy-6'-N-methyl-kanamycin B, 3'-deoxyneamine, 3'-deoxyribostamycin, 3'-oxysaccharocin, 3,3'-nepotrehalosadiamine, 3-demethoxy-2"-N-formimidoylistamycin B disulfate tetrahydrate, 3-demethoxyistamycin B,3-O-demethyl-2-N-formimidoylistamycin B, 3-O-demethylistamycin B,3-trehalosamine,4",6"-dideoxydibekacin, 4-N-glycyl-KA-6606VI, 5"-Amino-3',4',5"-trideoxy-butirosin A, 6"-deoxydibekacin,6'-epifortimicin A, 6-deoxy-neomycin (structure 6-deoxy-neomycin B),6-deoxy-neomycin B, 6-deoxy-neomycin C, 6-deoxy-paromomycin, acmimycin, AHB-3',4'-dideoxyribostamycin, AHB-3'-deoxykanamycin B, AHB-3'-deoxyneamine, AHB-3'-deoxyribostamycin, AHB-4"-6"-dideoxydibekacin, AHB-6"-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gamma1, coumamidine gamma2,D,L-1-N-(alpha-hydroxy-beta-aminopropionyl)-XK-62-2, dactimicin, de-O-methyl-4-N-glycyl-KA-6606VI, de-O-methyl-KA-6606I, de-O-methyl-KA-7038I, destomycin A, destomycin B, di-N6',O3-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KG1 (stereoisomer KG1/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethyl-7-O-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Ansa-type antibiotics include, but are not limited to, 21-hydroxy-25-demethyl-25-methylth ioprotostreptovaricin, 3-methylth iorifamycin, ansamitocin, atropisostreptovaricin, awamycin, halomicin, maytansine, naphthomycin, rifabutin, rifamide, rifampicin, rifamycin, rifapentine, rifaximin (e.g., Xifaxan®), rubradirin, streptovaricin, tolypomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, ornidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-O-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, amfomycin, amythiamycin, antifungal from Zalerion arboricola, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, j aniemycin, j anthinocin, j olipeptin, katanosin, killertoxin, lipopeptide antibiotic, lipopeptide from *Zalerion* sp., lysobactin, lysozyme, macromomycin, magainin, melittin, mersacidin, mikamycin, mureidomycin, mycoplanecin, mycosubtilin, neopeptifluorin, neoviridogrisein, netropsin, nisin, nocathiacin, nocathiacin 6-deoxyglycoside, nosiheptide, octapeptide, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a *Streptomyces* compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrostefimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Dicarboxylic acids, having between about 6 and about 14 carbon atoms in their carbon atom skeleton are particularly useful in the treatment of disorders of the skin and mucosal membranes that involve microbial. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments of the present disclosure, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred. It has antibacterial effects on both aerobic and anaerobic organisms, particularly *Propionibacterium acnes* and *Staphylococcus epidermidis*, normalizes keratinization, and has a cytotoxic effect on malignant or hyperactive melanocytes. In a preferred embodiment, the dicarboxylic acid is azelaic acid in a concentration greater than 10%. Preferably, the concentration of azelaic acid is between about 10% and about 25%. In such concentrates, azelaic acid is suitable for the treatment of a variety of skin disorders, such as acne, rosacea and hyperpigmentation.

In some embodiments, the antibiotic agent is an antibiotic metal. A number of metals ions have been shown to possess antibiotic activity, including silver, copper, zinc, mercury, tin, lead, bismutin, cadmium, chromium and ions thereof. It has been theorized that these antibiotic metal ions exert their effects by disrupting respiration and electron transport systems upon absorption into bacterial or fungal cells. Antimicrobial metal ions of silver, copper, zinc, and gold, in particular, are considered safe for in vivo use. Anti-microbial silver and silver ions are particularly useful due to the fact that they are not substantially absorbed into the body. Thus, in one or more embodiment, the antibiotic metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The antibiotic metal can further be intercalated in a chelating substrate.

In further embodiments, the antibiotic metal is ionic. The ionic antibiotic metal can be presented as an inorganic or organic salt (coupled with a counterion), an organometallic complex or an intercalate. Non-binding examples of counter inorganic and organic ions are sulfadiazine, acetate, benzoate, carbonate, iodate, iodide, lactate, laurate, nitrate, oxide, and palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

In one or more embodiments, the antibiotic metal or metal ion is embedded into a substrate, such as a polymer, or a mineral (such as zeolite, clay and silica).

In one or more embodiments, the antibiotic agent includes strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents, such as quinones, are also included. Such agents possess a potent broad-spectrum activity.

In one or more embodiments, the antibiotic agent is a cationic antimicrobial agent. The outermost surface of bacterial cells universally carries a net negative charge, making them sensitive to cationic substances. Examples of cationic antibiotic agents include: quaternary ammonium compounds (QAC's)—QAC's are surfactants, generally containing one quaternary nitrogen associated with at least one major hydrophobic moiety; alkyltrimethyl ammonium bromides are mixtures of where the alkyl group is between 8 and 18 carbons long, such as cetrimide (tetradecyltrimethylammonium bromide); benzalkonium chloride, which is a mixture of n-alkyldimethylbenzyl ammonium chloride where the alkyl groups (the hydrophobic moiety) can be of variable length; dialkylmethyl ammonium halides; dialkylbenzyl ammonium halides; and QAC dimmers, which bear bi-polar positive charges in conjunction with interstitial hydrophobic regions.

In one or more embodiments, the cationic antimicrobial agent is a polymer. Cationic antimicrobial polymers include, for example, guanide polymers, biguanide polymers, or polymers having side chains containing biguanide moieties or other cationic functional groups, such as benzalkonium groups or quarternium groups (e.g., quaternary amine groups). It is understood that the term "polymer" as used herein includes any organic material including three or more repeating units, and includes oligomers, polymers, copolymers, block copolymers, terpolymers, etc. The polymer backbone may be, for example a polyethylene, ploypropylene or polysilane polymer.

In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to poly(hexamethylenebiguanide), poly(hexamethylenebiguanide) hydrochloride, poly(hexamethylenebiguanide) gluconate, poly(hexamethylenebiguanide) stearate, or a derivative thereof. In one or more embodiments, the antimicrobial material is substantially water-insoluble.

In some embodiments, the antibiotic agent is selected from the group of biguanides, triguanides, bisbiguanides and analogs thereof.

Guanides, biguanides, biguanidines and triguanides are unsaturated nitrogen containing molecules that readily obtain one or more positive charges, which make them effective antimicrobial agents. The basic structures a guanide, a biguanide, a biguanidine and a triguanide are provided below.

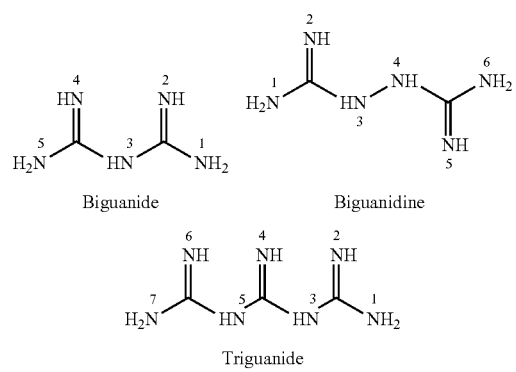

In some embodiments, the guanide, biguanide, biguanidine or triguanide, provide bi-polar configurations of cationic and hydrophobic domains within a single molecule.

Examples of guanides, biguanides, biguanidines and triguanides that are currently been used as antibacterial agents include chlorhexidine and chlorohexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can conceivably be used according to the present disclosure are chlorproguanil hydrochloride, proguanil hydrochloride (currently used as antimalarial agents), mefformin hydrochloride, phenformin and buformin hydrochloride (currently used as antidiabetic agents).

Yet, in one or more embodiments, the antibiotic is a non-classified antibiotic agent, including, without limitation, aabomycin, acetomycin, acetoxycycloheximide, acetylnanaomycin, an *Actinoplanes* sp. compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis immune substance, anti-tuberculosis immune substance, an antibiotic from *Escherichia coli*, an antibiotic from *Streptomyces* refuineus, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosylbenanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2',5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, prop-2-enylmonate, protomycin, *Pseudomonas* antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *Streptomyces arenae* antibiotic complex, streptonigrin, streptothricins, streptovitacin, streptozotocine, a strobilurin derivative, stubomycin, sulfamethoxazol-trimethoprim, sakamycin, tej eramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin and analogs, salts and derivatives thereof.

In one or more embodiments, the antibiotic agent is a naturally occurring antibiotic compound. As used herein, the term "naturally-occurring antibiotic agent" includes all antibiotics that are obtained, derived or extracted from plant or vertebrate sources. Non-limiting examples of families of naturally-occurring antibiotic agents include phenol, resorcinol, antibiotic aminoglycosides, anamycin, quinines, anthraquinones, antibiotic glycopeptides, azoles, macrolides, avilamycin, agropyrene, cnicin, aucubin antibioticsaponin fractions, berberine (isoquinoline alkaloid), arctiopicrin (sesquiterpene lactone), lupulone, humulone (bitter acids), allicin, hyperforin, echinacoside, coniosetin, tetramic acid, imanine and novoimanine.

Ciclopirox and ciclopiroxolamine possess fungicidal, fungistatic and sporicidal activity. They are active against a broad spectrum of dermatophytes, yeasts, moulds and other fungi, such as *Trichophytons* species, *Microsporum* species, *Epidermophyton* species and yeasts (*Candida albicans*, *Candida glabrata*, other *candida* species and *Cryptococcus neoformans*). Some *Aspergillus* species are sensitive to ciclopirox as are some *Penicillium*. Likewise, ciclopirox is effective against many Gram-positive and Gram-negative bacteria (e.g., *Escherichia coli*, *Proteus Pseudomonas aeruginosa*, *Staphylococcus* and *Streptococcus* species), as well as *Mycoplasma* species, *Trichomonas vaginalis* and *Actinomyces*.

Plant oils and extracts which contain antibiotic agents are also useful. Non-limiting examples of plants that contain agents include thyme, *Perilla*, lavender, tea tree, *Terfezia clayeryi*, *Micromonospora*, *Putterlickia verrucosa*, *Putterlickia pyracantha*, *Putterlickia retrospinosa*, *Maytenus ilicifolia*, *Maytenus evonymoides*, *Maytenus aquifolia*, *Faenia interjecta*, *Cordyceps sinensis*, couchgrass, holy thistle, plantain, burdock, hops, echinacea, buchu, chaparral, myrrh, red clover and yellow dock, garlic, and St. John's wort. Mixtures of the antibiotic agents as described herein may also be employed.

Combination Detection:

Any combination of the analytes disclosed herein can be detected using any of the methods described herein. In particular, any combination disclosed herein can be detected using any of the methods described herein.

A "photosensitizer" as used herein refers to a sensitizer for generation of singlet oxygen usually by excitation with light. Exemplary photosensitizers suitable for use include those described in U.S. Pat. Nos. 6,251,581, 5,516,636, 8,907,081, 6,545,012, 6,331,530, 8,247,180, 5,763,602, 5,705,622, 5,516,636, 7,217,531, and U.S. Patent Publication No. 2007/0059316, all of which are herein expressly incorporated by reference in their entireties. The photosensitizer can be photoactivatable (e.g., dyes and aromatic compounds) or chemiactivated (e.g., enzymes and metal salts). When excited by light the photosensitizer is usually a compound comprised of covalently bonded atoms, usually with multiple conjugated double or triple bonds. The compound should absorb light in the wavelength range of 200-1100 nm, usually 300-1000 nm, e.g., 450-950 nm, with an extinction coefficient at its absorbance maximum greater than 500 $M^{-1} cm^{-1}$, e.g., at least 5000 $M^{-1} cm^{-1}$, or at least 50,000 $M^{-1} cm^{-1}$ at the excitation wavelength. The lifetime of an excited state produced following absorption of light in the absence of oxygen will usually be at least 100 nsec, e.g., at least 1 µsec. In general, the lifetime must be sufficiently long to permit energy transfer to oxygen, which will normally be present at concentrations in the range of $10^{-5}$ to $10^{31\ 3}$ M depending on the medium. The sensitizer excited state will usually have a different spin quantum number (S) than its ground state and will usually be a triplet (S=1) when, as is usually the case, the ground state is a singlet (S=O). In some embodiments, the sensitizer will have a high intersystem crossing yield. That is, photoexcitation of a sensitizer will produce the long lived state (usually triplet) with an efficiency of at least 10%, at least 40%, e.g., greater than 80%. The photosensitizer will usually be at most weakly fluorescent under the assay conditions (quantum yield usually less that 0.5, or less that 0.1).

Photosensitizers that are to be excited by light will be relatively photostable and will not react efficiently with singlet oxygen. Several structural features are present in most useful sensitizers. Most sensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures. Typical sensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment. Examples of other photosensitizers that may be utilized are those that have the above properties and are enumerated in N. J. Turro, "Molecular Photochemistry," page 132, W. A. Benjamin Inc., N.Y. 1965.

In some embodiments, the photosensitizers are relatively non-polar to assure dissolution into a lipophilic member when the photosensitizer is incorporated in an oil droplet, liposome, latex particle, etc.

In some embodiments, the photosensitizers suitable for use herein include other substances and compositions that can produce singlet oxygen with or without activation by an external light source. Thus, for example, molybdate ($MoO_4^=$) salts and chloroperoxidase and myeloperoxidase plus bromide or chloride ion (Kanofsky, *J. Biol. Chem.* (1983) 259 5596) have been shown to catalyze the conversion of hydrogen peroxide to singlet oxygen and water. Either of these compositions can, for example, be included in particles and used in the assay method wherein hydrogen peroxide is included as an ancillary reagebly, chloroperoxidase is bound to a surface and molybdate is incorporated in the aqueous phase of a liposome. Also included within the scope of the invention as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A "chemiluminescent compound" as used herein refers to a substance that undergoes a chemical reaction with singlet oxygen to form a metastable intermediate that can decompose with the simultaneous or subsequent emission of light within the wavelength range of 250 to 1200 nm. Exemplary chemiluminescent compounds suitable for use include those described in U.S. Pat. Nos. 6,251,581 and 7,709,273, and Patent Cooperatio Treaty (PCT) International Application Publication No. WO1999/042838. Exemplary chemiluminescent compound includes the following:

| Chemiluminescer | Half-Life | Emission Max |
| --- | --- | --- |
| Thioxene + Diphenyl anthracence: | 0.6 seconds | 430 nm |
| Thioxene + Umbelliferone derivative | 0.6 seconds | 500 nm |
| Thioxene + Europium chelate | 0.6 seconds | 615 nm |
| Thioxene + Samarium Chelate | 0.6 seconds | 648 nm |
| Thioxene + terbium Chelate | 0.6 seconds | 540 nm |
| N-Phenyl Oxazine + Umbelliferone derivative | 30 seconds | 500 nm |
| N-Phenyl Oxazine + Europium chelate | 30 seconds | 613 nm |
| N-phenyl Oxazine + Samarium Chelate | 30 seconds | 648 nm |

-continued

| Chemiluminescer | Half-Life | Emission Max |
| --- | --- | --- |
| N-phenyl Oxazine + terbium Chelate | 30 seconds | 540 nm |
| Dioxene + Umbelliferone derivative | 300 seconds | 500 nm |
| Dioxene + Europium chelate | 300 seconds | 613 nm |
| Dioxene + Samarium Chelate | 300 seconds | 648 nm |
| N-phenyl Oxazine + terbium Chelate | 300 seconds | 540 nm |

All of the above mentioned applications are hereby expressly incorporated by reference herein in their entireties. Emission will usually occur without the presence of an energy acceptor or catalyst to cause decomposition and light emission. In some embodiments, the intermediate decomposes spontaneously without heating or addition of ancillary reagents following its formation. However, addition of a reagent after formation of the intermediate or the use of elevated temperature to accelerate decomposition will be required for some chemiluminescent compounds. The chemiluminescent compounds are usually electron rich compounds that react with singlet oxygen, frequently with formation of dioxetanes or dioxetanones. Exemplary of such compounds are enol ethers, enamines, 9-alkylidenexanthans, 9-alkylidene-N-alkylacridans, aryl vinyl ethers, dioxenes, arylimidazoles and lucigenin. Other chemiluminescent compounds give intermediates upon reaction with singlet oxygen, which subsequently react with another reagent with light emission. Exemplary compounds are hydrazides such as luminol and oxalate esters.

The chemiluminescent compounds of interest will generally emit at wavelengths above 300 nanometers and usually above 400 nm. Compounds that alone or together with a fluorescent molecule emit light at wavelengths beyond the region where serum components absorb light will be of particular use. The fluorescence of serum drops off rapidly above 500 nm and becomes relatively unimportant above 550 nm. Therefore, when the analyte is in serum, chemiluminescent compounds that emit light above 550 nm, e.g., above 600 nm may be suitable for use. In order to avoid autosensitization of the chemiluminescent compound, in some embodiments, the chemiluminescent compounds do not absorb light used to excite the photosensitizer. In some embodiments, the sensitizer is excited with light wavelengths longer than 500 nm, it will therefore be desirable that light absorption by the chemiluminescent compound be very low above 500 nm.

Where long wave length emission from the chemiluminescent compound is desired, a long wavelength emitter such as a pyrene, bound to the chemiluminescent compound can be used. Alternatively, a fluorescent molecule can be included in the medium containing the chemiluminescent compound. In some embodiments, fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, $Eu(fod)_3$, $Eu(TTA)_3$, $Ru(bpy)_3^{++}$ (wherein bpy=2,2'-dipyridyl, etc. In general these dyes act as acceptors in energy transfer processes and in some embodiments, have high fluorescent quantum yields and do not react rapidly with singlet oxygen. They can be incorporated into particles simultaneously with the incorporation of the chemiluminescent compound into the particles.

In some embodiments, the disclosure provides diffractive optics detection technology that can be used with, for example, ingestible device technology. In certain embodiments, an ingestible device includes the diffractive optics technology (e.g., diffractive optics detection system). In certain embodiments, the disclosure provides diffractive optics technology (e.g., diffractive optics detection systems) that are used outside the body of subject. As an example, an ingestible device can be used to obtain one more samples in the body (e.g., in the gastrointestinal tract) of a subject, and the diffractive optics technology can be used to analyze the sample(s). Such analysis can be performed in vivo (e.g., when the ingestible device contains the diffractive optics).

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. Diffraction gratings, like focusing optics, can be operated in both transmission and reflection modes.

In general, the light used in the diffractive optics can be of any appropriate wavelength. Exemplary wavelengths include visible light, infrared red (IR) and ultraviolet (UV). Optionally, the light can be monochromatic or polychromatic. The light can be coherent or incoherent. The light can be collimated or non-collimated. In some embodiments, the light is coherent and collimated. Generally, any appropriate light source may be used, such as, for example, a laser (e.g., a laser diode) or a light emitting diode. In some embodiments, the light source is a laser diode operating at 670 nm wavelength, e.g., at 3 mWatts power. Optionally, an operating wavelength of a laser diode can be 780 nm, e.g., when larger grating periods are used. In certain embodiments, the light source is a laser, such as, for example, a He-Ne laser, a Nd:YVO4 laser, or an argon-ion laser. In some embodiments, the light source is a low power, continuous waver laser.

The diffracted light can be detected using any appropriate light detector(s). Examples of light detectors include photodetectors, such as, for example, position sensitive photodiodes, photomultiplier tubes (PMTs), photodiodes (PDs), avalanche photodiodes (APDs), charged-coupled device (CCD) arrays, and CMOS detectors. In some embodiments, the diffracted light is detected via one or more individual photodiodes.

In general, the diffraction grating is made of a material that is transparent in the wavelength of the radiation used to illuminate the sensor. Any appropriate material may be used for the diffraction grating substrate, such as glass or a polymer. Exemplary polymers include polystyrene polymers (PSEs), cyclo-olefin polymers (COPs), polycarbonate polymers, polymethyl methacrylates, and methyl methacrylate styrene copolymers. Exemplary COPs include Zeonex (e.g., Zeonex E48R, Zeonex F52R).

The light may be incident on the diffraction grating any appropriate angle. In some embodiments, the light is incident on the diffraction grating with an angle of incidence of from 30° to 80° (e.g., from 40° to 80°, from 50° to 70°, from 55° to 65°, 60°). Optionally, the system is configured so that that diffractive grating and light source can move relative to each other In general, the light detector can be positioned with respect to the diffractive grating so that the diffraction grating can be illuminated at a desired angle of incidence and/or so that diffracted light can be detected at a desired angle and/or so that diffracted light of a desired order can be detected.

The period P of the diffraction grating can be selected as desired. In some embodiments, the period P is from 0.5 microns to 50 microns (e.g., from one micron to 15 microns, from one micron to five microns). In some embodiments, the grating is a repeating patter of 1.5 micron and 4.5 micron lines with a period of 15 microns.

The height h of the diffraction grating can be selected as desired. In certain embodiments, the height h is from one nanometer to about 1000 nanometers (e.g., from about five nanometers to about 250 nanometers, from five nanometers to 100 nanometers). In general, the diffractive optics can be prepared using any appropriate method, such as, for example, surface ablation, photolithograph (e.g., UV photolithography), laser etching, electron beam etching, nano-imprint molding, or microcontact printing.

Optionally, the diffractive optics system can include one or more additional optical elements, such as, for example, one or more mirrors, filters and/or lenses. Such optical elements can, for example, be arranged between the light source and the diffractive grating and/or between the diffractive grating and the detector.

In some of the embodiments of the devices described herein, a primary binding partner specifically binds to a secondary binding partner through non-covalent interactions (e.g., electrostatic, van der Waals, hydrophobic effect). In some embodiments, a primary binding partner specifically binds to a secondary binding partner via a covalent bond (e.g., a polar covalent bond or a non-polar covalent bond). In some embodiments of any of the devices described herein, the primary and the secondary binding partner can be interchanged. For example, the primary binding partner can be biotin, or a derivative thereof, and the secondary binding partner is avidin, or a derivative thereof. In other examples, the primary binding partner can be avidin, or a derivative thereof, and the secondary binding partner is biotin.

In some embodiments, the binding of the primary and the secondary binding partner is essentially irreversible. In some embodiments, the binding of the primary and the secondary binding partner is reversible. In some embodiments, the primary binding partner is CaptAvidin™ biotin-binding protein and the secondary binding partner is biotin, or vice versa. In some embodiments, the primary binding partner is DSB-X™ biotin and the secondary binding partner is avidin, or vice versa. In some embodiments, the primary binding partner is desthiobiotin and the secondary binding partner is avidin, or vice versa (Hirsch et al., *Anal Biochem.* 308(2): 343-357, 2002). In some embodiments, the primary binding partner is glutathione (GSH) or a derivative thereof, and the secondary binding partner is glutathione-S-transferase (GST).

In some embodiments, the primary binding partner can bind to a target analyte that is a nucleic acid (e.g., a DNA molecule, a RNA molecule). In some embodiments, the primary binding partner comprises a portion of a nucleic acid that is complementary to the nucleic acid sequence of the target analyte.

In some embodiments of any of the devices described herein, the device can include a label that binds to the target analyte and does not prevent binding of the target analyte to the primary binding partner. In some embodiments, the label can amplify the diffraction signal of the target analyte.

In some embodiments, the label is from about 1 nm to 200 nm (e.g., about 50 nm to about 200 nm).

In some embodiments, the label (e.g., any of the labels described herein) includes one or more antibodies (e.g., any of the antibodies and/or antibody fragments described herein).

In some embodiments, the label is a nanoparticle (e.g., a gold nanoparticle) that includes the primary binding partner that has a nucleic acid sequence that is complementary to the target analyte, and is covalently linked to the nanoparticle.

One or more additional steps can be performed in any of the methods described herein. In some embodiments, the one or more additional steps are performed: prior to the binding of the primary binding partner to the secondary binding partner, after the binding of the primary binding partner to the secondary binding partner, prior to the binding of the primary binding partner to the target analyte, or after the binding of the primary binding partner to the target analyte.

In some embodiments of any of the methods described herein, the determining step (during which the primary binding partner binds to the target analyte is detected) can occur in at least 15 seconds. In some embodiments, the binding of the primary binding partner to the target analyte can occur during a period of time of, for example, five at least seconds.

In some embodiments, the one or more additional steps can include: a blocking of the sensors step, at least one wash step, a capturing step, and/or a filtering step. In some embodiments, the blocking step can include blocking a sensor within the ingestible device with a solution comprising at least 1% bovine serum albumin (BSA) in a buffered solution (e.g., phosphate buffered saline (PBS), Tris buffered saline (TB S)). In some embodiments, the at least one wash step can include washing with a buffered solution (e.g., phosphate buffered saline (PBS), Tris buffered saline (TBS)). In general, blocking is performed during capsule manufacture, rather than in vivo.

In some embodiments, the capturing step includes enriching the target analyte. In some embodiments, the capturing step includes physically separating the target analyte from the remaining sample using a filter, a pore, or a magnetic bead. In some embodiments, the target analyte is captured by size exclusion.

In some embodiments, the disclosure provides methods of obtaining, culturing, and/or detecting target cells and/or target analytes in vivo within the gastrointestinal (GI) tract or reproductive tract of a subject. Associated devices are also disclosed. The methods and devices described provide a number of advantages for obtaining and/or analyzing fluid samples from a subject. In some embodiments, diluting the fluid sample increases the dynamic range of analyte detection and/or reduces background signals or interference within the sample. For example, interference may be caused by the presence of non-target analytes or non-specific binding of a dye or label within the sample. In some embodiments, culturing the sample increases the concentration of target cells and/or target analytes produced by the target cells thereby facilitating their detection and/or characterization.

In certain embodiments, the methods and devices a described herein may be used to obtain information regarding bacteria populations in the GI tract of a subject. This has a number of advantages and is less invasive than surgical procedures such as intubation or endoscopy to obtain fluid samples from the GI tract. The use of an ingestible device as described herein also allows for fluid samples to be obtained and data to be generated on bacterial populations from specific regions of the GI tract.

In some embodiments, the methods and devices described herein may be used to generate data such as by analyzing the fluid sample, dilutions thereof or cultured samples for one or more target cells and/or target analytes. The data may include, but is not limited to, the types of bacteria present in the fluid sample or the concentration of bacteria in specific regions of the GI tract. Such data may be used to determine whether a subject has an infection, such as Small Intestinal Bacterial Overgrowth (SIBO), or to characterize bacterial populations within the GI tract for diagnostic or other purposes. Thus, in some embodiments, analytes disclosed herein are indicative of disorders of the gastrointestinal tract associated with anomalous bacterial populations.

For example, in one aspect, the data may include, but is not limited to, the concentration of bacteria in a specific region of the GI tract that is one or more of the duodenum, jejunum, ileum, ascending colon, transverse colon or descending colon. In one aspect, the specific region of the GI tract is the duodenum. In one aspect, the specific region of the GI tract is the jejunum. In one aspect, the specific region of the GI tract is the ileum. In one aspect, the specific region of the GI tract is the ascending colon. In one aspect, the specific region of the GI tract is the transverse colon. In one aspect, the specific region of the GI tract is the descending colon. In a related embodiment, the data may be generated every one or more days to monitor disease flare-ups, or response to the therapeutic agents disclosed herein.

Data may be generated after the device has exited the subject, or the data may be generated in vivo and stored on the device and recovered ex vivo. Alternatively, the data can be transmitted wirelessly from the device while the device is passing through the GI tract of the subject or in place within the reproductive tract of the subject.

In some embodiments, a method comprises: providing a device comprising one or more dilution chambers and dilution fluid; transferring all or part of a fluid sample obtained from the GI tract or reproductive tract of the subject into the one or more dilution chambers in vivo; and combining the fluid sample and the dilution fluid to produce one or more diluted samples in the one or more dilution chambers.

In certain embodiments, a method comprises: providing an ingestible device comprising one or more dilution chambers; transferring all or part of a fluid sample obtained from the GI tract into the one or more dilution chambers comprising sterile media; culturing the sample in vivo within the one or more dilution chambers to produce one or more cultured samples; and detecting bacteria in the one or more cultured samples.

In some embodiments, a method comprises: providing a device comprising one or more dilution chambers; transferring all or part of a fluid sample obtained from the GI tract or reproductive tract into the one or more dilution chambers; combining all or part of the fluid sample with a dilution fluid in the one or more dilution chambers; and detecting the target analyte in the one or more diluted samples.

In certain embodiments, a device comprises: one or more dilution chambers for diluting a fluid sample obtained from the GI tract or reproductive tract; and dilution fluid for diluting the sample within the one or more dilution chambers.

In some embodiments, the device comprises: one or more dilution chambers for culturing a fluid sample obtained from the GI tract; sterile media for culturing the sample within the one or more dilution chambers; and a detection system for detecting bacteria.

In certain embodiments, a device comprises: one or more dilution chambers for culturing a fluid sample obtained from the GI tract; sterile media for culturing the sample within the one or more dilution chambers; and a detection system for detecting bacteria.

Also provided is the use of a device as described herein for diluting one or more samples obtained from the GI tract or reproductive tract of a subject. In one embodiment, there is provided the use of an ingestible device as described herein for detecting target cells and/or target analytes in vivo within the gastrointestinal (GI) tract of a subject.

Further provided is a system comprising a device as described herein and a base station. In one embodiment, the device transmits data to the base station, such as data indicative of the concentration and/or types of bacteria in the GI tract of the subject. In one embodiment, the device receives operating parameters from the base station. Some embodiments described herein provide an ingestible device for obtaining one or more samples from the GI tract or reproductive tract of a subject and diluting and/or culturing all or part of the one or more samples. The ingestible device includes a cylindrical rotatable element having a port on the wall of the cylindrical rotatable element. The ingestible device further includes a shell element wrapping around the cylindrical rotatable element to form a first dilution chamber between the cylindrical rotatable element and the shell element. The shell element has an aperture that exposes a portion of the wall of the cylindrical rotatable element to an exterior of the ingestible device.

In certain embodiments, the medical device comprises one or more dilution chambers for receiving a fluid sample from the GI tract or reproductive tract of a subject or a dilution thereof. In some embodiments, one or more dilutions of the fluid sample are cultured in one or more dilution chambers. In certain embodiments, the dilution chambers each define a known volume, optionally the same volume or different volumes. In some embodiments, the dilution chambers define a fluid volume ranging from about 10 µL to about 1 mL. The dilution chambers may define a fluid volume less than or equal to about 500 µL, less than or equal to about 250 µL, less than or equal to about 100 µL, or less than or equal to about 50 µL. In certain embodiments, the dilution chambers define a fluid volume of greater than or equal to about 10 µL, greater than or equal to about 20 µL, greater than or equal to about 30 µL, or greater than or equal to about 50 µL. In some embodiments, the dilution chambers define a fluid volume between about 10 µL and 500 µL, between about 20 µL and 250 µL, between about 30 µL and 100 µL or about 50 µL.

In some embodiments, dilution fluid in the device is combined with all or part of the fluid sample, or dilution thereof, to produce one or more dilutions. In certain embodiments, the dilution fluid is sterile media suitable for culturing one or more target cells within the dilution chambers.

In certain embodiments, the one or more dilution chambers may be filled with the dilution fluid prior to a patient ingesting the ingestible device. In some embodiments, the dilution fluid may be added into the one or more dilution chambers in vivo from a reservoir of the ingestible device. Sampling and dilution of the GI fluid sample may take place in vivo. For example, an actuator of the ingestible device may pump the dilution fluid from the reservoir into a dilution chamber when it is determined that the ingestible device is located at a predetermined location within the GI tract. In some embodiments, the dilution chambers each contain a volume of sterile media suitable for culturing a fluid sample from the GI tract or reproductive tract. In certain embodiments, the dilution chambers are at least 95%, at least 97%, at least 98%, or at least 99% full of sterile media. In some embodiments, the dilution chambers each contain oxygen to facilitate aerobic bacteria growth. In certain embodiments, a non-dilution chamber comprises oxygen and is added to one or more of the dilution chambers to facilitate aerobic bacteria growth.

In some embodiments, the culturing may take place in vivo immediately after the GI fluid sample has been diluted. Or alternatively, the culturing may take place ex vivo, e.g., when the ingestible device has been evacuated and recovered such that the dilution chamber containing the diluted GI fluid sample may be extracted and the culturing may be performed in a laboratory. The recovery of the ingestible device may be performed in a similar manner as embodiments described in U.S. Provisional Application No. 62/434,188, filed on Dec. 14, 2016, which is herein expressly incorporated by reference in its entirety.

As used herein "culturing" refers to maintaining target cells in an environment that allows a population of one or more target cells to increase in number through cell division. For example, in some embodiments, "culturing" may include combining the cells with media in an dilution chamber at a temperature that permits cell growth, optionally a temperature found in vivo within the GI tract or reproductive tract of a subject. In certain embodiments, the cells are cultured at a temperature between about 35° C. and 42° C.

As used herein "dilution fluid" refers to a fluid within the device for diluting a fluid sample from the GI tract or reproductive tract. In some embodiments, the dilution fluid is an aqueous solution. In certain embodiments, the dilution fluid comprises one or more agents that promote or inhibit the growth of an organism, such as a fungus or bacteria. In some embodiments, the dilution fluid comprises one or more agents that facilitate the detection of a target analyte, such as dyes or binding agents for target analytes.

In some embodiments, the dilution fluid is a sterile media. As used herein, "sterile media" refers to media that does not contain any viable bacteria or other cells that would grow and increase in number through cell division. Media may be rendered sterile by various techniques known in the art such as, but not limited to, autoclaving and/or preparing the media using aseptic techniques. In certain embodiments, the media is a liquid media. Examples of media suitable for culturing bacteria include nutrient broth, Lysogeny Broth (LB) (also known as Luria Broth), Wilkins chalgren, and Tryptic Soy Broth (TSB), Other growth or culture media known in the art may also be used in the methods and devices described herein. In some embodiments, the media has a carbon source, such as glucose or glycerol, a nitrogen source such as ammonium salts or nitrates or amino acids, as well as salts and/or trace elements and vitamins required for microbial growth. In certain embodiments, the media is suitable for maintaining eukaryotic cells. In some embodiments, the media comprises one or more agents that promote or inhibit the growth of bacteria, optionally agents that promote or inhibit the growth of specific types of bacteria.

In certain embodiments, the media is a selective media. As used herein, "selective media" refers to a media that allows certain types of target cells to grow and inhibits the growth of other organisms. Accordingly, the growth of cells in a selective media indicates the presence of certain types of cells within the cultured sample. For example, in some embodiments, the media is selective for gram-positive or gram-negative bacteria. In certain embodiments, the media contains crystal violet and bile salts (such as found in MacConkey agar) that inhibit the growth of gram-positive organisms and allows for the selection and isolation of gram-negative bacteria. In some embodiments, the media contains a high concentration of salt (NaCl) (such as found in Mannitol salt agar) and is selective for Gram-positive bacteria. In some embodiments, the media selectively kills eukaryotic cells or only grows prokaryotic cells, for example, using a media comprising Triton™ X-100. In certain embodiments, the media selectively kills prokaryotic cells (or alternatively only grows eukaryotic cells), for example, using a media that comprises antibiotics.

In some embodiments, the media is an indicator media. As used herein, "indicator media" refers to a media that contains specific nutrients or indicators (such as, but not limited to neutral red, phenol red, eosin y, or methylene blue) that produce a detectable signal when a certain type of cells are cultured in the indicator media.

In some embodiments, the disclosure provides a composition comprising a dye and optionally a reagent for selective lysis of eukaryotic cells. In certain embodiments, the composition comprises both a dye and a reagent for selective lysis of eukaryotic cells. In some embodiments, the composition further comprises one or more reagents independently selected from the group consisting of: a second reagent for selective lysis of eukaryotic cells (e.g., Triton X-100), an electrolyte (e.g., $MgCl_2$), an anti-fungi reagent (e.g., amphotericin-B), and an antibiotic. In some embodiments, the composition comprises water and is in the form of an aqueous solution. In some embodiments, the composition is a solid or semi-solid. In some embodiments, the compositions described here are suitable for use in a kit or device for detecting or quantifying viable bacterial cells in a sample. In some embodiments, such a device is an ingestible device for detecting or quantifying viable bacterial cells in vivo (e.g., in the GI tract). In some embodiments, viable bacterial cells in a sample are detected or quantified in the presence of one or more antibiotics to determine antibiotic resistance of the bacteria in the sample. In some embodiments, anomalous bacterial populations in a sample may be detected or quantified, for example through the use of one a composition comprising a dye as disclosed herein, to determine whether a subject has an infection, such as Small Intestinal Bacterial Overgrowth (SIBO), or to characterize bacterial populations within the GI tract for diagnostic or other purposes.

In some embodiments, a method comprises: (a) contacting the sample with a composition as described herein; and (b) measuring total fluorescence or rate of change of fluorescence as a function of time of said sample, thereby detecting viable bacterial cells in said sample. In some embodiments, a control as described herein may be employed in the method. In some embodiments, the total fluorescence or the rate of change of fluorescence as a function of time of the sample is measured over multiple time points for an extended period of time in step (b), thereby detecting viable bacterial cells in said sample. In some embodiments, the method further comprises correlating the total fluorescence or the rate of change of fluorescence as a function of time determined in step (b) to the number of viable bacterial cells in the sample. In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver.

In certain embodiments, a kit comprises a composition as described herein and instructions, e.g., for detecting or quantifying viable bacterial cells in a sample. In some embodiments, a device comprises a composition as described herein, e.g., for detecting or quantifying viable bacterial cells in a sample. The detection of live cells, as opposed to the detection of bacterial components (such as endotoxins) which can be present in the sample environment and lead to conflicting results, is the gold standard of viable plate counting and represents one of the advantages of the compositions and methods described herein.

The systems employ methods, compositions and detection systems found to accurately and reliably correlate fluorescence to total bacteria count (TBC) in an autonomous, ingestible device, or other similarly-sized device. The compositions include novel combinations of dyes, buffers and detergents that allow for the selective staining of viable bacterial cells in samples that comprise non-bacterial cells and other components that otherwise make detecting or quantifying live bacterial cells challenging. In some embodiments, the systems allow for bacteria to be quantified in near real-time and the results to be shared telemetrically outside of the device.

In certain embodiments, the disclosure provides a method of assessing or monitoring the need to treat a subject suffering from or at risk of overgrowth of bacterial cells in the gastrointestinal tract, which comprises: (a) obtaining a sample from the gastrointestinal tract of said subject; (b) contacting the sample with a composition as described herein; (c) measuring total fluorescence or rate of change of fluorescence as a function of time of said sample; and (d) correlating the total fluorescence or the rate of change of fluorescence as a function of time measured in step (c) to the number of viable bacterial cells in the sample, wherein the number of the viable bacterial cells determined in step (e) greater than about 105 CFU/mL indicates a need for treatment, e.g., with an antibiotic agent as described herein. In some embodiments, a control as described herein may be employed in the method. In some embodiments, the total fluorescence or the rate of change of fluorescence as a function of time of the sample is measured over multiple time points for an extended period of time in step (c). In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In some embodiments, the disclosure provides an absorbable material, (e.g., absorbable sponge), having absorbed therein a composition as described herein. In some embodiments, the absorbable sponge is Ahlstrom Grade 6613H (Lot 150191) or Porex PSU-567, having absorbed therein a composition as described herein. In some embodiments, the absorbable sponge may be prepared by injecting into the absorbable sponge an aqueous solution comprising a composition as described herein, and optionally further comprising a step of drying the resulting absorbable sponge.

In certain embodiments, the disclosure provides a method for detecting the presence of viable bacterial cells in a sample, which comprises: (a) fully or partially saturating an absorbable sponge as described herein, or an absorbable sponge prepared as described herein, with the sample; and (b) measuring total fluorescence or rate of change of fluorescence as a function of time of the fully or partially saturated sponge prepared in step (a), thereby detecting viable bacterial cells. In some embodiments, a control as described herein may be employed in the method. In some embodiments, the total fluorescence or the rate of change of fluorescence as a function of time of the fully or partially saturated sponge is measured over multiple time points for an extended period of time in step (b), thereby detecting viable bacterial cells in said sample. In some embodiments, the method further comprises correlating the total fluorescence or the rate of change of fluorescence as a function of time measured in step (b) to the number of viable bacterial cells in the sample. In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In one aspect, provided herein is a kit comprising an absorbable sponge as described herein and instructions, e.g., for detecting or quantifying viable bacterial cells in a sample. In another aspect, provided herein is a device comprising an absorbable sponge as described herein, e.g., for detecting or quantifying viable bacterial cells in a sample.

In certain embodiments, the disclosure provides a method of assessing or monitoring the need to treat a subject suffering from or at risk of overgrowth of bacterial cells in the gastrointestinal tract, which comprises: (a) obtaining a sample from the gastrointestinal tract of said subject; (b) fully or partially saturating an absorbable sponge described herein, or an absorbable sponge prepared as described herein, with the sample; (c) measuring total fluorescence or rate of change of fluorescence as a function of time of the fully or partially saturated sponge prepared in step (b); (d) correlating the total fluorescence or the rate of change of fluorescence as a function of time measured in step (c) to the number of viable bacterial cells in the sample, wherein the number of the viable bacterial cells as determined in step (e) greater than about $10^5$ CFU/mL indicates a need for treatment, e.g., with an antibiotic agent as described herein. In some embodiments, a control as described herein may be employed in the method. In some embodiments, the total fluorescence or the rate of change of fluorescence as a function of time of the fully or partially saturated sponge is measured over multiple time points for an extended period of time in step (c). In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment In certain embodiments, the disclosure provides and ingestible device comprising a housing; a first opening in the wall of the housing; a second opening in the first end of the housing; and a chamber connecting the first opening and the second opening, wherein at least a portion of the chamber forms a sampling chamber within the ingestible device. In some embodiments, the sampling chamber is configured to hold an absorbable sponge described herein. In some embodiments, the sampling chamber is configured to hold a sample obtained from a gastrointestinal (GI) tract of a body. In some embodiments, the ingestible device is individually calibrated (for example, by comparing to a positive or negative control as described herein), wherein the fluorescent properties of the absorbable sponge held in the sampling chamber of the device are determined prior to the introduction of the sample. The ingestible device as described herein is useful for detecting or quantifying viable bacterial cells in vivo. In some embodiments, provided herein is a method for detecting or quantifying viable bacterial cells in a GI tract sample in vivo using an ingestible device as described herein. In some embodiments, provided herein is a method of assessing or monitoring the need to treat a subject suffering from or at risk of overgrowth of bacterial cells in the GI tract in vivo using an ingestible device as described herein. In some embodiments, provided herein is a method of altering the treatment regimen of a subject suffering from or at risk of overgrowth of bacterial cells in the GI tract in vivo using an ingestible device as described herein. In one aspect, the subject is a subject suffering from or at risk of overgrowth of bacterial cells in the duodenum. In one aspect, the subject is a subject suffering from or at risk of overgrowth of bacterial cells in the jejunum. In one aspect, the subject is a subject suffering from or at risk of overgrowth of bacterial cells in the ileum. In one aspect, the subject is a subject suffering from or at risk of overgrowth of bacterial cells in the ascending colon. In one aspect, the subject is a subject suffering from or at risk of overgrowth of bacterial cells in the transverse colon. In one aspect, the subject is a subject suffering from or at risk of overgrowth of bacterial cells in the descending colon. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment. In some embodiments, the method is performed autonomously and does not require instructions, triggers or other inputs from outside the body after the device has been ingested.

"Eukaryotic" as recited herein relates to any type of eukaryotic organism excluding fungi, such as animals, in particular animals containing blood, and comprises invertebrate animals such as crustaceans and vertebrates. Vertebrates comprise both cold-blooded (fish, reptiles, amphibians) and warm blooded animal (birds and mammals). Mammals comprise in particular primates and more particularly humans "Selective lysis" as used herein is obtained in a sample when the percentage of bacterial cells in that sample that remain intact is significantly higher (e.g. 2, 5, 10, 20, 50, 100, 250, 500, or 1,000 times more) than the percentage of the eukaryotic cells in that sample that remain intact, upon treatment of or contact with a composition or device as described herein.

In some embodiments, the dye suitable for use herein is a dye that is capable of being internalized by a viable cell, binding to or reacting with a target component of the viable cell, and having fluorescence properties that are measurably altered when the dye is bound to or reacted with the target component of the viable cell. In some embodiments, the dye herein is actively internalized by penetrating viable cells through a process other than passible diffusion across cell membranes. Such internalization includes, but is not limited to, internalization through cell receptors on cell surfaces or through channels in cell membranes. In some embodiments, the target component of a viable cell to which the dye is bound to or reacted with is selected from the group consisting of: nucleic acids, actin, tubulin, enzymes, nucleotide-binding proteins, ion-transport proteins, mitochondria, cytoplasmic components, and membrane components. In some embodiments, the dye suitable for use herein is a fluorogenic dye that is capable of being internalized and metabolized by a viable cell, and wherein said dye fluoresces when metabolized by the viable cell. In some embodiments, the dye is a chemiluminescent dye that is capable of being internalized and metabolized by a viable cell, and wherein said dye becomes chemiluminescent when metabolized by the viable cell.

In some embodiments, the composition comprises a dye that fluoresces when bond to nucleic acids. Examples of such dyes include, but are not limited to, acridine orange (U.S. Pat. No. 4,190,328); calcein-AM (U.S. Pat. No. 5,314,805); DAPI; Hoechst 33342; Hoechst 33258; PicoGreen™; SYTO® 16; SYBR® Green I; Texas Red®; Redmond Red™; Bodipy® Dyes; Oregon Green™; ethidium bromide; and propidium iodide.

In some embodiments, the composition comprises a lipophilic dye that fluoresces when metabolized by a cell. In some embodiments, the dye fluoresces when reduced by a cell or a cell component. Examples of dyes that fluoresce when reduced include, but are not limited to, resazurin; $C^{12}$-resazurin; 7-hydroxy-9H-(1,3 dichloro-9,9-dimethyl-acridin-2-ol) N-oxide; 6-chloro-9-nitro-5-oxo-5H-benzo[a]phenoxazine; and tetrazolium salts. In some embodiment, the dye fluoresces when oxidized by a cell or a cell component. Examples of such dyes include, but are not limited to, dihydrocalcein AM; dihydrorhodamine 123; dihydroethidium; 2,3,4,5,6-pentafluorotetramethyl dihydrorosamine; and 3'-(p-aminophenyl) fluorescein.

In some embodiments, the composition comprises a dye that becomes chemiluminescent when oxidized by a cell or a cell component, such as luminol.

In some embodiments, the composition comprises a dye that fluoresces when de-acetylated and/or oxidized by a cell or a cell component. Examples of such dyes include, but are not limited to, dihydrorhodamines; dihydrofluoresceins; 2',7'-dichlorodihydrofluorescein diacetate; 5-(and 6-)carboxy-2',7'-dichlorodihydrofluorescein diacetate; and chloromethyl-2',7'-dichlorodihydrofluorescein diacetate acetyl ester.

In some embodiments, the composition comprises a dye that fluoresces when reacted with a peptidase. Examples of such dyes include, but are not limited to, (CBZ-Ala-Ala-Ala-Ala)$_2$-R110 elastase 2; (CBZ-Ala-Ala-Asp)2-R110 granzyme B; and 7-amino-4-methylcoumarin, N-CBZ-L-aspartyl-L-glutamyl-L-valyl-L-aspartic acid amide.

In some embodiments, the composition comprises a dye selected from the group consisting of resazurin, FDA, Calcein AM, and SYTO® 9. In some embodiments, the dye is FDA or SYTO® 9.

SYTO® 9, when used alone, labels the nucleic acid of bacteria cells. The excitation/emission wavelengths for SYTO® 9 is 480/500 nm, with the background remaining non-fluorescent. See, e.g., J. Appl. Bacteriol. 72, 410 (1992); Lett. Appl. Microbiol. 13, 58 (1991); Curr. Microbiol. 4, 321 (1980); J. Microbiol. Methods 13, 87 (1991); and Microbiol. Rev. 51, 365 (1987); and J. Med. Microbiol. 39, 147 (1993).

FDA is a non-polar, non-fluorescent compound that can cross the membranes of mammalian and bacterial cells. The acetyl esterases (present only within viable cells) hydrolyze the FDA into the fluorescent compound fluorescein. Fluorescein is a fluorescent polar compound that is retained within these cells. Living cells can be visualized in a photospectrometer when assayed with an excitation wavelength of 494 nm and an emission wavelength of 518 nm. See, e.g., Brunius, G. (1980). *Technical aspects of the use of 3',6'-Diacetyl fluorescein for vital fluorescent staining of*

*bacteria. Current Microbiol.* 4: 321-323; Jones, K. H. and Senft, J. A. (1985). *An improved method to determine cellviability by simultaneous staining with fluorescein diacetate-propidium iodide.* J. Histochem. Cytochem. 33: 77-79; Ross, R. D., Joneckis, C. C., Ordonez, J. V., Sisk, A. M., Wu, R. K., Hamburger, A. W., and Nora, R. E. (1989). *Estimation of cell survival by flow cytometric quantification of fluorescein diacetate/propidium iodide viable cell number.* Cancer Research. 49: 3776-3782.

Calcein-AM, which is an acetoxylmethyl ester of calcein, is highly lipophilic and cell permeable. Calcein-AM in itself is not fluorescent, but the calcein generated by esterase in a viable cell emits a green fluorescence with an excitation wavelength of 490 nm and an emission of 515 nm. Therefore, Calcein-AM can only stain viable cells. See, e.g., Kimura, K., et al., *Neurosci. Lett.*, 208, 53 (1998); Shimokawa, I., et al., *J. Geronto.*, 51a, b49 (1998); Yoshida, S., et al., *Clin. Nephrol.*, 49, 273 (1998); and Tominaga, H., et al., *Anal. Commun.*, 36, 47 (1999).

Resazuirn (also known as Alamar Blue) is a blue compound that can be reduced to pink resorufin which is fluorescent. This dye is mainly used in viability assays for mammalian cells. $C^{12}$-resazurin has better cell permeability than resazurin. When lipohilic $C^{12}$-resazurin crosses the cell membranes, it is subsequently reduced by living cells to make a red fluorescent resorufin. The adsorption/emission of $C^{12}$-resazurin is 563/587 nm. See, e.g., Appl Environ Microbiol 56, 3785 (1990); J Dairy Res 57, 239 (1990); J Neurosci Methods 70, 195 (1996); J Immunol Methods 210, 25 (1997); J Immunol Methods 213, 157 (1998); Antimicrob Agents Chemother 41, 1004 (1997).

In some embodiments, the composition optionally further comprises a reagent for selective lysis of eukaryotic cells. In some embodiments, the composition comprises a dye as described herein and a reagent for selective lysis of eukaryotic cells. In some embodiments, the reagent for selective lysis of eukaryotic cells is a detergent, such as a non-ionic or an ionic detergent. Examples of the reagent for selective lysis of eukaryotic cells include, but are not limited to, alkylglycosides, Brij 35 (C12E23 Polyoxyethyleneglycol dodecyl ether), Brij 58 (C16E20 Polyoxyethyleneglycol dodecyl ether), Genapol, glucanids such as MEGA-8, -9, -10, octylglucoside, Pluronic F127, Triton X-100 ($C_{14}H_{22}O$ $(C_2H_4O)_n$), Triton X-114 ($C_{24}H_{42}O_6$), Tween 20 (Polysorbate 20) and Tween 80 (Polysorbate 80), Nonidet P40, deoxycholate, reduced Triton X-100 and/or Igepal CA 630. In some embodiments, the composition comprises a dye as described herein and deoxycholate (e.g., sodium deoxycholate) as a reagent for selective lysis of eukaryotic cells. In some embodiments, the composition comprises deoxycholate at a concentration selected from 0.0001% to 1 wt %. In some embodiments, the composition comprises deoxycholate at a concentration of 0.005 wt %. In some embodiments, the composition may comprise more than one reagent for selective lysis of eukaryotic cells.

In some embodiments, the composition may comprise two different reagents for selective lysis of eukaryotic cells. In some instances, when more than one selective lysis reagents are used, more effective and/or complete selective lysis of eukaryotic cells in a sample may be achieved. For example, the composition may comprise deoxycholate (e.g., sodium deoxycholate) and Triton X-100 as two different reagents for selective lysis of eukaryotic cells. In some embodiments, the composition comprises deoxycholate (e.g., sodium deoxycholate) at a concentration selected from 0.0001% to 1 wt % (e.g., 0.005 wt %) and Triton X-100 at a concentration selected from 0.1 to 0.05 wt %.

In some embodiments, after a sample (e.g., a biological sample) is treated or contacted with a composition comprising a dye and one or more reagents for selective lysis of eukaryotic cells as described herein, the eukaryotic cells (e.g., animal cells) in the sample are selectively lysed whereby a substantial percentage (e.g., more than 20%, 40%, 60%, 80%, 90% or even more that 95%) of the bacterial cells in the same sample remains intact or alive.

In some embodiments, the composition does not comprise a reagent for selective lysis of eukaryotic cells, and such a composition is useful for detecting or quantifying viable bacterial cells in a sample (e.g., an environmental sample such as a water sample) that does not contain any eukaryotic cells.

In some embodiments, the composition further comprises an electrolyte, such as a divalent electrolyte (e.g., $MgCl_2$). In some embodiments, the composition comprises $MgCl_2$ at a concentration selected from 0.1 mM to 100 mM (e.g., a concentration selected from 0.5 mM to 50 mM).

In some embodiments, the composition further comprises water and is in a form of an aqueous solution. In some embodiments, the composition has a pH selected from 5-8 (e.g., a pH selected from 6-7.8, such as pH being 6.0). In some embodiments, the composition is a solid or a semi-solid.

In some embodiments, the composition further comprises an anti-fungal agent. Suitable anti-fungal agents for use herein include, but are not limited to, fungicidal and fungistatic agents including terbinafine, itraconazole, micronazole nitrate, thiapendazole, tolnaftate, clotrimazole and griseofulvin. In some embodiments, the anti-fungal agent is a polyene anti-fungal agent, such as amphotericin-B, nystatin, and pimaricin.

In some embodiments, the composition does not contain any anti-fungal agent. In some embodiments, the composition contains broad spectrum antibiotics but not any anti-fungal agent. Such compositions that do not contain anti-fungal agents but contain broad spectrum antibiotics may be useful in detecting or quantifying fungi (e.g., yeast) in a sample.

In some embodiments, the composition does not contain any anti-fungal agent, any antibiotics or any anti-mammalian agent. Such compositions that do not selectively lyse mammalian cells may be useful in detecting or quantifying mammalian cells (e.g., cells from the GI tract) in a sample since many dyes have a higher affinity for mammalian as compared to bacteria or fungi cells. In some embodiments, the composition contains broad spectrum antibiotics and one or more anti-fungal agents. Such compositions that contain anti-fungal agents and broad spectrum antibiotics may be useful in detecting or quantifying mammalian cells (e.g., cells from the GI tract) in a sample. The detection or quantification of mammalian cells may be useful for determining cell turnover in a subject. High cell turnover is sometimes associated with a GI injury (e.g., lesion), the presence of a tumor(s), or radiation-induced colitis or radiation enteropathy.

In some embodiments, the composition further comprises an antibiotic agent as described herein. Such a composition may be useful in detecting or quantifying antibiotic-resistant strains of bacteria in a sample.

In certain embodiments, the composition comprises Triton X-100, deoxycholate, resazurin, and $MgCl_2$. In some embodiments, the composition comprises Triton X-100, deoxycholate, resazurin, amphotericin-B and $MgCl_2$. In some embodiments, the composition comprises 0.1 wt % or 0.05 wt % Triton X-100; 0.005 wt % deoxycholate; 10 mM resazurin; 2.5 mg/L amphotericin-B and 50 mM $MgCl_2$. In some embodiments, the composition has a pH of 6.0.

In certain embodiments, the compositions are suitable for use in a kit or device, e.g., for detecting or quantifying viable bacterial cells in a sample. In some embodiments, such a device is an ingestible device for detecting or quantifying viable bacterial cells in vivo (e.g., in the GI tract).

Figure 62:
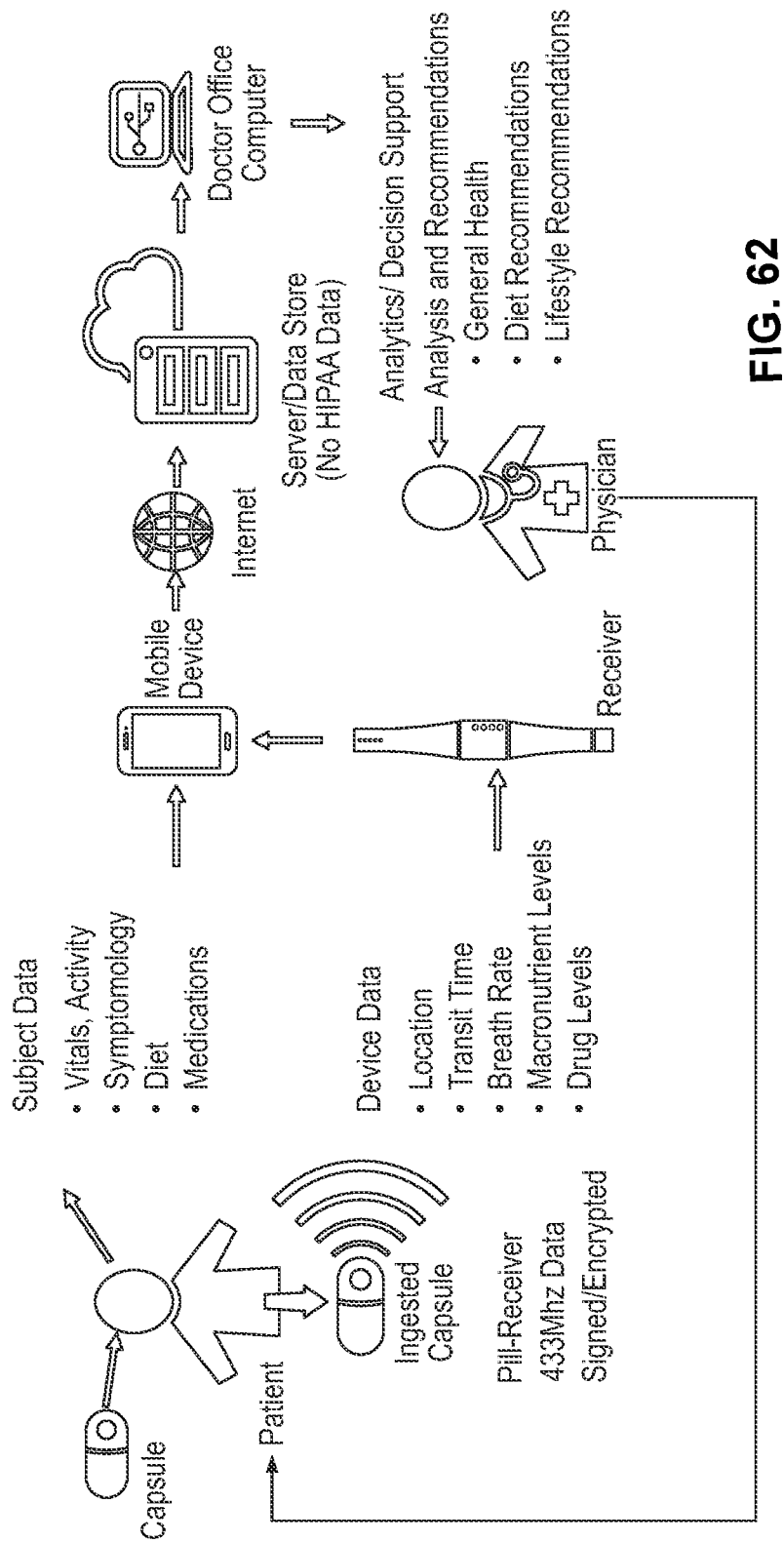
FIG. 62 illustrates a nonlimiting example of a system for collecting, communicating and/or analyzing data about a subject, using an ingestible device.

FIG. 62 illustrates a nonlimiting example of a system for collecting, communicating and/or analyzing data about a subject, using an ingestible device as disclosed herein. For example, an ingestible device may be configured to communicate with an external base station. As an example, an ingestible device can have a communications unit that communicates with an external base station which itself has a communications unit. FIG. 62 illustrates exemplary implementation of such an ingestible device. As shown in FIG. 62, a subject ingests an ingestible device as disclosed herein. Certain data about the subject (e.g., based on a collected sample) and/or the location of the ingestible device in the GI tract of the subject is collected or otherwise available and provided to a mobile device, which then forwards the data via the internet and a server/data store to a physician's office computer. The information collected by the ingestible device is communicated to a receiver, such as, for example, a watch or other object worn by the subject. The information is then communicated from the receiver to the mobile device which then forwards the data via the internet and a server/data store to a physician's office computer. The physician is then able to analyze some or all of the data about the subject to provide recommendations, such as, for example, delivery a therapeutic agent. While FIG. 62 shows a particular approach to collecting and transferring data about a subject, the disclosure is not limited. As an example, one or more of the receiver, mobile device, internet, and/or server/data store can be excluded from the data communication channel. For example, a mobile device can be used as the receiver of the device data, e.g., by using a dongle. In such embodiments, the item worn by the subject need not be part of the communication chain. As another example, one or more of the items in the data communication channel can be replaced with an alternative item. For example, rather than be provided to a physician's office computer, data may be provided to a service provider network, such as a hospital network, an HMO network, or the like. In some embodiments, subject data may be collected and/or stored in one location (e.g., a server/data store) while device data may be collected and/or stored in a different location (e.g., a different server/data store).

Locations of Treatment

In some embodiments, the IL-10 or IL-10 agonist is delivered at a location in the large intestine of the subject. In some embodiments, the location is in the proximal portion of the large intestine. In some embodiments, the location is in the distal portion of the large intestine.

In some embodiments, the IL-10 or IL-10 agonist is delivered at a location in the ascending colon of the subject. In some embodiments, the location is in the proximal portion of the ascending colon. In some embodiments, the location is in the distal portion of the ascending colon.

In some embodiments, the IL-10 or IL-10 agonist is delivered at a location in the cecum of the subject. In some embodiments, the location is in the proximal portion of the cecum. In some embodiments, the location is in the distal portion of the cecum.

In some embodiments, the IL-10 or IL-10 agonist is delivered at a location in the sigmoid colon of the subject. In some embodiments, the location is in the proximal portion of the sigmoid colon. In some embodiments, the location is in the distal portion of the sigmoid colon.

In some embodiments, the IL-10 or IL-10 agonist is delivered at a location in the transverse colon of the subject. In some embodiments, the location is in the proximal portion of the transverse colon. In some embodiments, the location is in the distal portion of the transverse colon.

In some embodiments, the IL-10 or IL-10 agonist is delivered at a location in the descending colon of the subject. In some embodiments, the location is in the proximal portion of the descending colon. In some embodiments, the location is in the distal portion of the descending colon.

In some embodiments, the IL-10 or IL-10 agonist is delivered at a location in the small intestine of the subject. In some embodiments, the location is in the proximal portion of the small intestine. In some embodiments, the location is in the distal portion of the small intestine.

In some embodiments, the IL-10 or IL-10 agonist is delivered at a location in the duodenum of the subject. In some embodiments, the location is in the proximal portion of the duodenum. In some embodiments, the location is in the distal portion of the duodenum.

In some embodiments, the IL-10 or IL-10 agonist is delivered at a location in the jejunum of the subject. In some embodiments, the location is in the proximal portion of the jejunum. In some embodiments, the location is in the distal portion of the jejunum.

In some embodiments, the IL-10 or IL-10 agonist is delivered at a location in the duodenum of the subject and is not delivered at other locations in the gastrointestinal tract. In some embodiments, the IL-10 or IL-10 agonist is delivered at a location in the duodenum of the subject and is not delivered at other locations in the gastrointestinal tract, wherein a site of disease is in the duodenum and no site of disease is present at other locations in the gastrointestinal tract. In some embodiments, the IL-10 or IL-10 agonist is delivered at a location in the duodenum of the subject and is not delivered at other locations in the gastrointestinal tract, wherein a first site of disease is in the duodenum and a second site of disease is in the stomach and no site of disease is present at other locations in the gastrointestinal tract.

In some embodiments, the IL-10 or IL-10 agonist is delivered at a location in the proximal duodenum of the subject and is not delivered at other locations in the gastrointestinal tract. In some embodiments, the IL-10 or IL-10 agonist is delivered at a location in the proximal duodenum of the subject and is not delivered at other locations in the gastrointestinal tract, wherein a site of disease is in the duodenum and no site of disease is present at other locations in the gastrointestinal tract. In some embodiments, the IL-10 or IL-10 agonist is delivered at a location in the proximal duodenum of the subject and is not delivered at other locations in the gastrointestinal tract, wherein a first site of disease is in the duodenum and a second site of disease is in the stomach and no site of disease is present at other locations in the gastrointestinal tract.

In some embodiments, the IL-10 or IL-10 agonist is delivered at a location in the jejunum of the subject and is not delivered at other locations in the gastrointestinal tract. In some embodiments, the IL-10 or IL-10 agonist is delivered at a location in the jejunum of the subject and is not delivered at other locations in the gastrointestinal tract, wherein a site of disease is in the jejunum and no site of disease is present at other locations in the gastrointestinal tract. In some embodiments, the IL-10 or IL-10 agonist is delivered at a location in the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the IL-10 or IL-10 agonist is delivered at a location in the proximal portion of the jejunum of the subject and is not delivered at other locations in the gastrointestinal tract. In some embodiments, the IL-10 or IL-10 agonist is delivered at a location in the proximal portion of the jejunum of the subject and is not delivered at other locations in the gastrointestinal tract, wherein a site of disease is in the jejunum and no site of disease is present at other locations in the gastrointestinal tract. In some embodiments, the IL-10 or IL-10 agonist is delivered at a location in the proximal portion of the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the IL-10 or IL-10 agonist is delivered at a location in the distal portion of the jejunum of the subject and is not delivered at other locations in the gastrointestinal tract. In some embodiments, the IL-10 or IL-10 agonist is delivered at a location in the distal portion of the jejunum of the subject and is not delivered at other locations in the gastrointestinal tract, wherein a site of disease is in the jejunum and no site of disease is present at other locations in the gastrointestinal tract. In some embodiments, the IL-10 or IL-10 agonist is delivered at a location in the distal portion of the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the IL-10 or IL-10 agonist is delivered at a location in the ileum of the subject. In some embodiments, the location is in the proximal portion of the ileum. In some embodiments, the location is in the distal portion of the ileum.

In some embodiments, the IL-10 or IL-10 agonist is delivered at a location in the ileum of the subject and is not delivered at other locations in the gastrointestinal tract. In some embodiments, the IL-10 or IL-10 agonist is delivered at a location in the ileum of the subject and is not delivered at other locations in the gastrointestinal tract, wherein a site of disease is in the ileum and no site of disease is present at other locations in the gastrointestinal tract. In some embodiments, the IL-10 or IL-10 agonist is delivered at a location in the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the IL-10 or IL-10 agonist is delivered at a location in the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the IL-10 or IL-10 agonist is delivered at a location in the proximal portion of the ileum of the subject and is not delivered at other locations in the gastrointestinal tract. In some embodiments, the IL-10 or IL-10 agonist is delivered at a location in the proximal portion of the ileum of the subject and is not delivered at other locations in the gastrointestinal tract, wherein a site of disease is in the ileum and no site of disease is present at other locations in the gastrointestinal tract. In some embodiments, the IL-10 or IL-10 agonist is delivered at a location in the proximal portion of the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the IL-10 or IL-10 agonist is delivered at a location in the proximal portion of the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the IL-10 or IL-10 agonist is delivered at a location in the distal portion of the ileum of the subject and is not delivered at other locations in the gastrointestinal tract. In some embodiments, the IL-10 or IL-10 agonist is delivered at a location in the distal portion of the ileum of the subject and is not delivered at other locations in the gastrointestinal tract, wherein a site of disease is in the ileum and no site of disease is present at other locations in the gastrointestinal tract. In some embodiments, the IL-10 or IL-10 agonist is delivered at a location in the distal portion of the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the IL-10 or IL-10 agonist is delivered at a location in the distal portion of the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the IL-10 or IL-10 agonist is delivered at a location in the cecum of the subject and is not delivered at other locations in the gastrointestinal tract. In some embodiments, the IL-10 or IL-10 agonist is delivered at a location in the distal portion of the cecum of the subject and is not delivered at other locations in the gastrointestinal tract, wherein a site of disease is in the cecum and/or ascending colon, and no site of disease is present at other locations in the gastrointestinal tract. In some embodiments, the IL-10 or IL-10 agonist is delivered at a location in the distal portion of the ileum or the proximal portion of the ascending colon of the subject and is not delivered at other locations in the gastrointestinal tract, wherein a first site of disease is in the cecum and a second site of disease is in the ascending colon, and no site of disease is present at other locations in the gastrointestinal tract.

In some embodiments, a site of disease is in the colon and the IL-10 or IL-10 agonist is released in the colon, such as in the cecum. In some embodiments, a site of disease is in the ascending colon and the IL-10 or IL-10 agonist is released in the ascending colon, such as in the cecum. In some embodiments, a site of disease is in the ileum and the IL-10 or IL-10 agonist is released in the ileum.

In some embodiments the subject is diagnosed with ileal Crohn's disease and the IL-10 or IL-10 agonist is released in the ileum.

In some embodiments the subject is diagnosed with ileal colonic Crohn's disease and the IL-10 or IL-10 agonist is released in both the ileum and the colon. In some more particular embodiments, the IL-10 or IL-10 agonist is released in both the ileum and the colon from the same ingestible device. In some more particular embodiments, the IL-10 or IL-10 agonist is released in the ileum from a first ingestible device and in the colon from a second ingestible device, wherein the first ingestible device and the second ingestible device are ingested at substantially the same time or at different times.

In some embodiments the subject is diagnosed with colitis throughout the colon and the IL-10 or IL-10 agonist is released (a) in the cecum, (b) in the cecum and in the transverse colon, and/or release (c) in the descending colon.

In some embodiments the subject is diagnosed with right sided colitis and the IL-10 or IL-10 agonist is released in the transverse colon or in the descending colon.

In some embodiments the subject is diagnosed with rectosigmoidal colitis and the IL-10 or IL-10 agonist is released in the descending colon.

In some embodiments, the location at which the IL-10 or IL-10 agonist is delivered is proximate to a site of disease. The site of disease may be, for example, an injury, inflamed tissue, or one or more lesions. In some embodiments, the location at which the IL-10 or IL-10 agonist is delivered is proximate to one or more sites of disease. In some embodiments, the IL-10 or IL-10 agonist is delivered 150 cm or less from the one or more sites of disease. In some embodiments, the IL-10 or IL-10 agonist is delivered 125 cm or less from the one or more sites of disease. In some embodiments, the IL-10 or IL-10 agonist is delivered 100 cm or less from the one or more sites of disease. In some embodiments, the IL-10 or IL-10 agonist is delivered 50 cm or less from the one or more sites of disease. In some embodiments, the IL-10 or IL-10 agonist is delivered 40 cm or less from the one or more sites of disease. In some embodiments, the IL-10 or IL-10 agonist is delivered 30 cm or less from the one or more sites of disease. In some embodiments, the IL-10 or IL-10 agonist is delivered 20 cm or less from the one or more sites of disease. In some embodiments, the IL-10 or IL-10 agonist is delivered 10 cm or less from the one or more sites of disease. In some embodiments, the IL-10 or IL-10 agonist is delivered 5 cm or less from the one or more sites of disease. In some embodiments, the IL-10 or IL-10 agonist is delivered 2 cm or less from the one or more sites of disease. In some embodiments, the method further comprises using an ingestible device to deliver the IL-10 or IL-10 agonist and using localization methods disclosed herein (e.g., such as discussed in Example 14 below) to determine the location of the ingestible device within the GI tract (e.g., relative to the site of disease). In some embodiments, the method further comprises using an ingestible device to deliver the IL-10 or IL-10 agonist and determining the period of time since the ingestible device was ingested to determine the location of the ingestible device within the GI tract (e.g., relative to the site of disease). In some embodiments, the method further comprises identifying the one or more sites of disease by a method comprising imaging of the gastrointestinal tract. In some embodiments, imaging of the gastrointestinal tract comprises video imaging. In some embodiments, imaging of the gastrointestinal tract comprises thermal imaging. In some embodiments, imaging of the gastrointestinal tract comprises ultrasound imaging. In some embodiments, imaging of the gastrointestinal tract comprises Doppler imaging.

In some embodiments the method does not comprise releasing more than 20% of the IL-10 or IL-10 agonist at a location that is not proximate to a site of disease. In some embodiments the method does not comprise releasing more than 10% of the IL-10 or IL-10 agonist at a location that is not proximate to a site of disease. In some embodiments the method does not comprise releasing more than 5% of the IL-10 or IL-10 agonist at a location that is not proximate to a site of disease. In some embodiments the method does not comprise releasing more than 4% of the IL-10 or IL-10 agonist at a location that is not proximate to a site of disease. In some embodiments the method does not comprise releasing more than 3% of the IL-10 or IL-10 agonist at a location that is not proximate to a site of disease. In some embodiments the method does not comprise releasing more than 2% of the IL-10 or IL-10 agonist at a location that is not proximate to a site of disease.

In some embodiments the method comprises releasing at least 80% of the IL-10 or IL-10 agonist at a location proximate to a site of disease. In some embodiments the method comprise releasing at least 90% of the IL-10 or IL-10 agonist at a location proximate to a site of disease. In some embodiments the method comprises releasing at least 95% of the IL-10 or IL-10 agonist at a location proximate to a site of disease. In some embodiments the method comprises releasing at least 96% of the IL-10 or IL-10 agonist at a location proximate to a site of disease. In some embodiments the method comprises releasing at least 97% of the IL-10 or IL-10 agonist at a location proximate to a site of disease. In some embodiments the method comprises releasing at least 98% of the IL-10 or IL-10 agonist at a location proximate to a site of disease. In some embodiments, the at least 80%, at least 90%, at least 95%, at least 96%, at least 97%, or at least 98% of the IL-10 or IL-10 agonist is delivered 150 cm or less from the one or more sites of disease. In some embodiments, the at least 80%, at least 90%, at least 95%, at least 96%, at least 97%, or at least 98% of the IL-10 or IL-10 agonist is delivered 125 cm or less from the one or more sites of disease. In some embodiments, the at least 80%, at least 90%, at least 95%, at least 96%, at least 97%, or at least 98% of the IL-10 or IL-10 agonist is delivered 100 cm or less from the one or more sites of disease. In some embodiments, the at least 80%, at least 90%, at least 95%, at least 96%, at least 97%, or at least 98% of the IL-10 or IL-10 agonist is delivered 50 cm or less from the one or more sites of disease. In some embodiments, the at least 80%, at least 90%, at least 95%, at least 96%, at least 97%, or at least 98% of the IL-10 or IL-10 agonist is delivered 40 cm or less from the one or more sites of disease. In some embodiments, the at least 80%, at least 90%, at least 95%, at least 96%, at least 97%, or at least 98% of the IL-10 or IL-10 agonist is delivered 30 cm or less from the one or more sites of disease. In some embodiments, the at least 80%, at least 90%, at least 95%, at least 96%, at least 97%, or at least 98% of the IL-10 or IL-10 agonist is delivered 20 cm or less from the one or more sites of disease. In some embodiments, the at least 80%, at least 90%, at least 95%, at least 96%, at least 97%, or at least 98% of the IL-10 or IL-10 agonist is delivered 10 cm or less from the one or more sites of disease. In some embodiments, the at least 80%, at least 90%, at least 95%, at least 96%, at least 97%, or at least 98% of the IL-10 or IL-10 agonist is delivered 5 cm or less from the one or more sites of disease. In some embodiments, the at least 80%, at least 90%, at least 95%, at least 96%, at least 97%, or at least 98% of the IL-10 or IL-10 agonist is delivered 2 cm or less from the one or more sites of disease. In some embodiments, the method further comprises using an ingestible device to deliver the IL-10 or IL-10 agonist and using localization methods disclosed herein (e.g., such as discussed in Example 14 below) to determine the location of the ingestible device within the GI tract (e.g., relative to the site of disease). In some embodiments, the method further comprises using an ingestible device to deliver the IL-10 or IL-10 agonist and determining the period of time since the ingestible device was ingested to determine the location of the ingestible device within the GI tract (e.g., relative to the site of disease).

In some embodiments, the amount of IL-10 or an IL-10 agonist that is delivered is a Human Equivalent Dose.

In some embodiments the method comprises releasing the IL-10 or IL-10 agonist at a location that is proximate to a site of disease, wherein the IL-10 or IL-10 agonist and, if applicable, any carriers, excipients or stabilizers admixed with the IL-10 or IL-10 agonist, are substantially unchanged, at the time of release of the IL-10 or IL-10 agonist at the location, relatively to the time of administration of the composition to the subject.

In some embodiments the method comprises releasing the IL-10 or IL-10 agonist at a location that is proximate to a site of disease, wherein the IL-10 or IL-10 agonist and, if applicable, any carriers, excipients or stabilizers admixed with the IL-10 or IL-10 agonist, are substantially unchanged by any physiological process (such as, but not limited to, degradation in the stomach), at the time of release of the IL-10 or IL-10 agonist at the location, relatively to the time of administration of the composition to the subject.

In some embodiments, the IL-10 or IL-10 agonist is delivered to the location by mucosal contact.

In some embodiments, a method of treatment disclosed herein includes determining the level of IL-10 or IL-10 agonist at a site of disease or a location in the gastrointestinal tract of the subject that is proximate to one or more sites of disease. In some examples, a method of treatment as described herein can include determining the level of IL-10 or IL-10 agonist at a site of disease or a location in the gastrointestinal tract of the subject that is proximate to one or more sites of disease within a time period of about 10 minutes to about 10 hours following administration of the device.

In some examples, a method of treatment disclosed herein includes determining the level of the IL-10 or IL-10 agonist at a site of disease or a location in the gastrointestinal tract of the subject that is proximate to one or more sites of disease at a time point following administration of the device that is elevated as compared to a level of the IL-10 or IL-10 agonist at the same site of disease or location at substantially the same time point in a subject following systemic administration of an equal amount of the IL-10 or IL-10 agonist.

In some examples where the IL-10 or IL-10 agonist is administered to a subject using any of the compositions or devices described herein, the IL-10 or IL-10 agonist can penetrate the GI tissue of the subject. As used herein, "GI tissue" refers to tissue in the gastrointestinal (GI) tract, such as tissue in one or more of duodenum, jejunum, ileum, cecum, ascending colon, transverse colon, descending colon, sigmoid colon, and rectum. In one particular embodiment, GI tissue refers to tissue in the proximal portion of one or more of duodenum, jejunum, ileum, cecum, ascending colon, transverse colon, descending colon, and sigmoid colon. In one particular embodiment, GI tissue refers to tissue in the distal portion of one or more of duodenum, jejunum, ileum, cecum, ascending colon, transverse colon, descending colon, and sigmoid colon. The GI tissue may be, for example, GI tissue proximate to one or more sites of disease. Accordingly, in some embodiments IL-10 or the IL-10 agonist can penetrate the dudodenum tissue proximate to one or more sites of disease. In some embodiments IL-10 or the IL-10 agonist can penetrate the jejunum tissue proximate to one or more sites of disease. In some embodiments IL-10 or the IL-10 agonist can penetrate the ileum tissue proximate to one or more sites of disease. In some embodiments IL-10 or the IL-10 agonist can penetrate the cecum tissue proximate to one or more sites of disease. In some embodiments IL-10 or the IL-10 agonist can penetrate the ascending colon tissue proximate to one or more sites of disease. In some embodiments IL-10 or the IL-10 agonist can penetrate the transverse colon tissue proximate to one or more sites of disease. In some embodiments IL-10 or the IL-10 agonist can penetrate the descending colon tissue proximate to one or more sites of disease. In some embodiments IL-10 or the IL-10 agonist can penetrate the sigmoid colon tissue proximate to one or more sites of disease. For example, IL-10 or the IL-10 agonist can penetrate one or more (e.g., two, three, or four) of the lumen/superficial mucosa, the lamina propria, the submucosa, and the tunica muscularis/serosa.

In some examples, administration of IL-10 or an IL-10 agonist using any of the compositions or devices described herein results in penetration (e.g., a detectable level of penetration) of GI tissue (e.g., one or more (e.g., two, three, or four) of the lumen/superficial mucosa, the lamina propria, the submucosa, and the tunica muscularis/serosa) within a time period of about 10 minutes to about 10 hours, about 10 minutes to about 9 hours, about 10 minutes to about 8 hours, about 10 minutes to about 7 hours, about 10 minutes to about 6 hours, about 10 minutes to about 5 hours, about 10 minutes to about 4.5 hours, about 10 minutes to about 4 hours, about 10 minutes to about 3.5 hours, about 10 minutes to about 3 hours, about 10 minutes to about 2.5 hours, about 10 minutes to about 2 hours, about 10 minutes to about 1.5 hours, about 10 minutes to about 1 hour, about 10 minutes to about 55 minutes, about 10 minutes to about 50 minutes, about 10 minutes to about 45 minutes, about 10 minutes to about 40 minutes, about 10 minutes to about 35 minutes, about 10 minutes to about 30 minutes, about 10 minutes to about 25 minutes, about 10 minutes to about 20 minutes, about 10 minutes to about 15 minutes, about 15 minutes to about 10 hours, about 15 minutes to about 9 hours, about 15 minutes to about 8 hours, about 15 minutes to about 7 hours, about 15 minutes to about 6 hours, about 15 minutes to about 5 hours, about 15 minutes to about 4.5 hours, about 15 minutes to about 4 hours, about 15 minutes to about 3.5 hours, about 15 minutes to about 3 hours, about 15 minutes to about 2.5 hours, about 15 minutes to about 2 hours, about 15 minutes to about 1.5 hours, about 15 minutes to about 1 hour, about 15 minutes to about 55 minutes, about 15 minutes to about 50 minutes, about 15 minutes to about 45 minutes, about 15 minutes to about 40 minutes, about 15 minutes to about 35 minutes, about 15 minutes to about 30 minutes, about 15 minutes to about 25 minutes, about 15 minutes to about 20 minutes, about 20 minutes to about 10 hours, about 20 minutes to about 9 hours, about 20 minutes to about 8 hours, about 20 minutes to about 7 hours, about 20 minutes to about 6 hours, about 20 minutes to about 5 hours, about 20 minutes to about 4.5 hours, about 20 minutes to about 4 hours, about 20 minutes to about 3.5 hours, about 20 minutes to about 3 hours, about 20 minutes to about 2.5 hours, about 20 minutes to about 2 hours, about 20 minutes to about 1.5 hours, about 20 minutes to about 1 hour, about 20 minutes to about 55 minutes, about 20 minutes to about 50 minutes, about 20 minutes to about 45 minutes, about 20 minutes to about 40 minutes, about 20 minutes to about 35 minutes, about 20 minutes to about 30 minutes, about 20 minutes to about 25 minutes, about 25 minutes to about 10 hours, about 25 minutes to about 9 hours, about 25 minutes to about 8 hours, about 25 minutes to about 7 hours, about 25 minutes to about 6 hours, about 25 minutes to about 5 hours, about 25 minutes to about 4.5 hours, about 25 minutes to about 4 hours, about 25 minutes to about 3.5 hours, about 25 minutes to about 3 hours, about 25 minutes to about 2.5 hours, about 25 minutes to about 2 hours, about 25 minutes to about 1.5 hours, about 25 minutes to about 1 hour, about 25 minutes to about 55 minutes, about 25 minutes to about 50 minutes, about 25 minutes to about 45 minutes, about 25 minutes to about 40 minutes, about 25 minutes to about 35 minutes, about 25 minutes to about 30 minutes, about 30 minutes to about 10 hours, about 30 minutes to about 9 hours, about 30 minutes to about 8 hours, about 30 minutes to about 7 hours, about 30 minutes to about 6 hours, about 30 minutes to about 5 hours, about 30 minutes to about 4.5 hours, about 30 minutes to about 4 hours, about 30 minutes to about 3.5 hours, about 30 minutes to about 3 hours, about 30 minutes to about 2.5 hours, about 30 minutes to about 2 hours, about 30 minutes to about 1.5 hours, about 30 minutes to about 1 hour, about 30 minutes to about 55 minutes, about 30 minutes to about 50 minutes, about 30 minutes to about 45 minutes, about 30 minutes to about 40 minutes, about 30 minutes to about 35 minutes, about 35 minutes to about 10 hours, about 35 minutes to about 9 hours, about 35 minutes to about 8 hours, about 35 minutes to about 7 hours, about 35 minutes to about 6 hours, about 35 minutes to about 5 hours, about 35 minutes to about 4.5 hours, about 35 minutes to about 4 hours, about 35 minutes to about 3.5 hours, about 35 minutes to about 3 hours, about 35 minutes to about 2.5 hours, about 35 minutes to about 2 hours, about 35 minutes to about 1.5 hours, about 35 minutes to about 1 hour, about 35 minutes to about 55 minutes, about 35 minutes to about 50 minutes, about 35 minutes to about 45 minutes, about 35 minutes to about 40 minutes, about 40 minutes to about 10 hours, about 40 minutes to about 9 hours, about 40 minutes to about 8 hours, about 40 minutes to about 7 hours, about 40 minutes to about 6 hours, about 40 minutes to about 5 hours, about 40 minutes to about 4.5 hours, about 40 minutes to about 4 hours, about 40 minutes to about 3.5 hours, about 40 minutes to about 3 hours, about 40 minutes to about 2.5 hours, about 40 minutes to about 2 hours, about 40 minutes to about 1.5 hours, about 40 minutes to about 1 hour, about 40 minutes to about 55 minutes, about 40 minutes to about 50 minutes, about 40 minutes to about 45 minutes, about 45 minutes to about 10 hours, about 45 minutes to about 9 hours, about 45 minutes to about 8 hours, about 45 minutes to about 7 hours, about 45 minutes to about 6 hours, about 45 minutes to about 5 hours, about 45 minutes to about 4.5 hours, about 45 minutes to about 4 hours, about 45 minutes to about 3.5 hours, about 45 minutes to about 3 hours, about 45 minutes to about 2.5 hours, about 45 minutes to about 2 hours, about 45 minutes to about 1.5 hours, about 45 minutes to about 1 hour, about 45 minutes to about 55 minutes, about 45 minutes to about 50 minutes, about 50 minutes to about 10 hours, about 50 minutes to about 9 hours, about 50 minutes to about 8 hours, about 50 minutes to about 7 hours, about 50 minutes to about 6 hours, about 50 minutes to about 5 hours, about 50 minutes to about 4.5 hours, about 50 minutes to about 4 hours, about 50 minutes to about 3.5 hours, about 50 minutes to about 3 hours, about 50 minutes to about 2.5 hours, about 50 minutes to about 2 hours, about 50 minutes to about 1.5 hours, about 50 minutes to about 1 hour, about 50 minutes to about 55 minutes, about 55 minutes to about 10 hours, about 55 minutes to about 9 hours, about 55 minutes to about 8 hours, about 55 minutes to about 7 hours, about 55 minutes to about 6 hours, about 55 minutes to about 5 hours, about 55 minutes to about 4.5 hours, about 55 minutes to about 4 hours, about 55 minutes to about 3.5 hours, about 55 minutes to about 3 hours, about 55 minutes to about 2.5 hours, about 55 minutes to about 2 hours, about 55 minutes to about 1.5 hours, about 55 minutes to about 1 hour, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4.5 hours, about 1 hour to about 4 hours, about 1 hour to about 3.5 hours, about 1 hour to about 3 hours, about 1 hour to about 2.5 hours, about 1 hour to about 2 hours, about 1 hour to about 1.5 hours, about 1.5 hours to about 10 hours, about 1.5 hours to about 9 hours, about 1.5 hours to about 8 hours, about 1.5 hours to about 7 hours, about 1.5 hours to about 6 hours, about 1.5 hours to about 5 hours, about 1.5 hours to about 4.5 hours, about 1.5 hours to about 4 hours, about 1.5 hours to about 3.5 hours, about 1.5 hours to about 3 hours, about 1.5 hours to about 2.5 hours, about 1.5 hours to about 2 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4.5 hours, about 2 hours to about 4 hours, about 2 hours to about 3.5 hours, about 2 hours to about 3 hours, about 2 hours to about 2.5 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5 hours, about 2.5 hours to about 4.5 hours, about 2.5 hours to about 4 hours, about 2.5 hours to about 3.5 hours, about 2.5 hours to about 3 hours, about 3 hours to about 10 hours, about 3 hours to about 9 hours, about 3 hours to about 8 hours, about 3 hours to about 7 hours, about 3 hours to about 6 hours, about 3 hours to about 5 hours, about 3 hours to about 4.5 hours, about 3 hours to about 4 hours, about 3 hours to about 3.5 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5 hours, about 3.5 hours to about 4.5 hours, about 3.5 hours to about 4 hours, about 4 hours to about 10 hours, about 4 hours to about 9 hours, about 4 hours to about 8 hours, about 4 hours to about 7 hours, about 4 hours to about 6 hours, about 4 hours to about 5 hours, about 4 hours to about 4.5 hours, about 4.5 hours to about 10 hours, about 4.5 hours to about 9 hours, about 4.5 hours to about 8 hours, about 4.5 hours to about 7 hours, about 4.5 hours to about 6 hours, about 4.5 hours to about 5 hours, about 5 hours to about 10 hours, about 5 hours to about 9 hours, about 5 hours to about 8 hours, about 5 hours to about 7 hours, about 5 hours to about 6 hours, about 6 hours to about 10 hours, about 6 hours to about 9 hours, about 6 hours to about 8 hours, about 6 hours to about 7 hours, about 7 hours to about 10 hours, about 7 hours to about 9 hours, about 7 hours to about 8 hours, about 8 hours to about 10 hours, about 8 hours to about 9 hours, or about 9 hours to about 10 hours. Penetration of GI tissue by IL-10 or an IL-10 agonist can be detected by administering a labeled IL-10 or the IL-10 agonist, and performing imaging on the subject (e.g., ultrasound, computed tomography, or magnetic resonance imaging). For example, the label can be a radioisotope, a heavy metal, a fluorophore, or a luminescent agent (e.g., any suitable radioisotopes, heavy metals, fluorophores, or luminescent agents used for imaging known in the art).

While not wishing to be bound to a particular theory, the inventors contemplate that at or near the site of release a concentration gradient of the IL-10 or IL-10 agonist is generated in the mucosa, and that administration of an IL-10 or an IL-10 agonist using a device as described herein advantageously results in a "reverse" concentration gradient when compared to the concentration gradient resulting from systemic administration. In such "reverse" concentration gradient, the drug concentration is highest from superficial to deep with respect to the mucosal surface. Systemic administration instead typically results in concentrations of the drug being highest from deep to superficial. A "reverse" concentration gradient as described above aligns more favorably with the pathophysiology of IBD.

In some embodiments, administration of IL-10 or an IL-10 agonist can provide for treatment (e.g., a reduction in the number, severity, and/or duration of one or more symptoms of any of the disorders described herein in a subject) for a time period of between about 1 hour to about 30 days, about 1 hour to about 28 days, about 1 hour to about 26 days, about 1 hour to about 24 days, about 1 hour to about 22 days, about 1 hour to about 20 days, about 1 hour to about 18 days, about 1 hour to about 16 days, about 1 hour to about 14 days, about 1 hour to about 12 days, about 1 hour to about 10 days, about 1 hour to about 8 days, about 1 hour to about 6 days, about 1 hour to about 5 days, about 1 hour to about 4 days, about 1 hour to about 3 days, about 1 hour to about 2 days, about 1 hour to about 1 day, about 1 hour to about 12 hours, about 1 hour to about 6 hours, about 1 hour to about 3 hours, about 3 hours to about 30 days, about 3 hours to about 28 days, about 3 hours to about 26 days, about 3 hours to about 24 days, about 3 hours to about 22 days, about 3 hours to about 20 days, about 3 hours to about 18 days, about 3 hours to about 16 days, about 3 hours to about 14 days, about 3 hours to about 12 days, about 3 hours to about 10 days, about 3 hours to about 8 days, about 3 hours to about 6 days, about 3 hours to about 5 days, about 3 hours to about 4 days, about 3 hours to about 3 days, about 3 hours to about 2 days, about 3 hours to about 1 day, about 3 hours to about 12 hours, about 3 hours to about 6 hours, about 6 hours to about 30 days, about 6 hours to about 28 days, about 6 hours to about 26 days, about 6 hours to about 24 days, about 6 hours to about 22 days, about 6 hours to about 20 days, about 6 hours to about 18 days, about 6 hours to about 16 days, about 6 hours to about 14 days, about 6 hours to about 12 days, about 6 hours to about 10 days, about 6 hours to about 8 days, about 6 hours to about 6 days, about 6 hours to about 5 days, about 6 hours to about 4 days, about 6 hours to about 3 days, about 6 hours to about 2 days, about 6 hours to about 1 day, about 6 hours to about 12 hours, about 12 hours to about 30 days, about 12 hours to about 28 days, about 12 hours to about 26 days, about 12 hours to about 24 days, about 12 hours to about 22 days, about 12 hours to about 20 days, about 12 hours to about 18 days, about 12 hours to about 16 days, about 12 hours to about 14 days, about 12 hours to about 12 days, about 12 hours to about 10 days, about 12 hours to about 8 days, about 12 hours to about 6 days, about 12 hours to about 5 days, about 12 hours to about 4 days, about 12 hours to about 3 days, about 12 hours to about 2 days, about 12 hours to about 1 day, about 1 day to about 30 days, about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 20 days, about 3 days to about 18 days, about 3 days to about 16 days, about 3 days to about 14 days, about 3 days to about 12 days, about 3 days to about 10 days, about 3 days to about 8 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 6 days, about 6 days to about 30 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 8 days to about 30 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 8 days to about 10 days, about 10 days to about 30 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 30 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 30 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 30 days, about 16 days to about 28 days, about 16 days to about 26 days, about 16 days to about 24 days, about 16 days to about 22 days, about 16 days to about 20 days, about 16 days to about 18 days, about 18 days to about 30 days, about 18 days to about 28 days, about 18 days to about 26 days, about 18 days to about 24 days, about 18 days to about 22 days, about 18 days to about 20 days, about 20 days to about 30 days, about 20 days to about 28 days, about 20 days to about 26 days, about 20 days to about 24 days, about 20 days to about 22 days, about 22 days to about 30 days, about 22 days to about 28 days, about 22 days to about 26 days, about 22 days to about 24 days, about 24 days to about 30 days, about 24 days to about 28 days, about 24 days to about 26 days, about 26 days to about 28 days, or about 28 days to about 30 days in a subject following first administration of IL-10 or an IL-10 agonist using any of the compositions or devices described herein. Non-limiting examples of symptoms of a disease described herein are described below.

For example, treatment can result in a decrease (e.g., about 1% to about 99% decrease, about 1% to about 95% decrease, about 1% to about 90% decrease, about 1% to about 85% decrease, about 1% to about 80% decrease, about 1% to about 75% decrease, about 1% to about 70% decrease, about 1% to about 65% decrease, about 1% to about 60% decrease, about 1% to about 55% decrease, about 1% to about 50% decrease, about 1% to about 45% decrease, about 1% to about 40% decrease, about 1% to about 35% decrease, about 1% to about 30% decrease, about 1% to about 25% decrease, about 1% to about 20% decrease, about 1% to about 15% decrease, about 1% to about 10% decrease, about 1% to about 5% decrease, about 5% to about 99% decrease, about 5% to about 95% decrease, about 5% to about 90% decrease, about 5% to about 85% decrease, about 5% to about 80% decrease, about 5% to about 75% decrease, about 5% to about 70% decrease, about 5% to about 65% decrease, about 5% to about 60% decrease, about 5% to about 55% decrease, about 5% to about 50% decrease, about 5% to about 45% decrease, about 5% to about 40% decrease, about 5% to about 35% decrease, about 5% to about 30% decrease, about 5% to about 25% decrease, about 5% to about 20% decrease, about 5% to about 15% decrease, about 5% to about 10% decrease, about 10% to about 99% decrease, about 10% to about 95% decrease, about 10% to about 90% decrease, about 10% to about 85% decrease, about 10% to about 80% decrease, about 10% to about 75% decrease, about 10% to about 70% decrease, about 10% to about 65% decrease, about 10% to about 60% decrease, about 10% to about 55% decrease, about 10% to about 50% decrease, about 10% to about 45% decrease, about 10% to about 40% decrease, about 10% to about 35% decrease, about 10% to about 30% decrease, about 10% to about 25% decrease, about 10% to about 20% decrease, about 10% to about 15% decrease, about 15% to about 99% decrease, about 15% to about 95% decrease, about 15% to about 90% decrease, about 15% to about 85% decrease, about 15% to about 80% decrease, about 15% to about 75% decrease, about 15% to about 70% decrease, about 15% to about 65% decrease, about 15% to about 60% decrease, about 15% to about 55% decrease, about 15% to about 50% decrease, about 15% to about 45% decrease, about 15% to about 40% decrease, about 15% to about 35% decrease, about 15% to about 30% decrease, about 15% to about 25% decrease, about 15% to about 20% decrease, about 20% to about 99% decrease, about 20% to about 95% decrease, about 20% to about 90% decrease, about 20% to about 85% decrease, about 20% to about 80% decrease, about 20% to about 75% decrease, about 20% to about 70% decrease, about 20% to about 65% decrease, about 20% to about 60% decrease, about 20% to about 55% decrease, about 20% to about 50% decrease, about 20% to about 45% decrease, about 20% to about 40% decrease, about 20% to about 35% decrease, about 20% to about 30% decrease, about 20% to about 25% decrease, about 25% to about 99% decrease, about 25% to about 95% decrease, about 25% to about 90% decrease, about 25% to about 85% decrease, about 25% to about 80% decrease, about 25% to about 75% decrease, about 25% to about 70% decrease, about 25% to about 65% decrease, about 25% to about 60% decrease, about 25% to about 55% decrease, about 25% to about 50% decrease, about 25% to about 45% decrease, about 25% to about 40% decrease, about 25% to about 35% decrease, about 25% to about 30% decrease, about 30% to about 99% decrease, about 30% to about 95% decrease, about 30% to about 90% decrease, about 30% to about 85% decrease, about 30% to about 80% decrease, about 30% to about 75% decrease, about 30% to about 70% decrease, about 30% to about 65% decrease, about 30% to about 60% decrease, about 30% to about 55% decrease, about 30% to about 50% decrease, about 30% to about 45% decrease, about 30% to about 40% decrease, about 30% to about 35% decrease, about 35% to about 99% decrease, about 35% to about 95% decrease, about 35% to about 90% decrease, about 35% to about 85% decrease, about 35% to about 80% decrease, about 35% to about 75% decrease, about 35% to about 70% decrease, about 35% to about 65% decrease, about 35% to about 60% decrease, about 35% to about 55% decrease, about 35% to about 50% decrease, about 35% to about 45% decrease, about 35% to about 40% decrease, about 40% to about 99% decrease, about 40% to about 95% decrease, about 40% to about 90% decrease, about 40% to about 85% decrease, about 40% to about 80% decrease, about 40% to about 75% decrease, about 40% to about 70% decrease, about 40% to about 65% decrease, about 40% to about 60% decrease, about 40% to about 55% decrease, about 40% to about 50% decrease, about 40% to about 45% decrease, about 45% to about 99% decrease, about 45% to about 95% decrease, about 45% to about 90% decrease, about 45% to about 85% decrease, about 45% to about 80% decrease, about 45% to about 75% decrease, about 45% to about 70% decrease, about 45% to about 65% decrease, about 45% to about 60% decrease, about 45% to about 55% decrease, about 45% to about 50% decrease, about 50% to about 99% decrease, about 50% to about 95% decrease, about 50% to about 90% decrease, about 50% to about 85% decrease, about 50% to about 80% decrease, about 50% to about 75% decrease, about 50% to about 70% decrease, about 50% to about 65% decrease, about 50% to about 60% decrease, about 50% to about 55% decrease, about 55% to about 99% decrease, about 55% to about 95% decrease, about 55% to about 90% decrease, about 55% to about 85% decrease, about 55% to about 80% decrease, about 55% to about 75% decrease, about 55% to about 70% decrease, about 55% to about 65% decrease, about 55% to about 60% decrease, about 60% to about 99% decrease, about 60% to about 95% decrease, about 60% to about 90% decrease, about 60% to about 85% decrease, about 60% to about 80% decrease, about 60% to about 75% decrease, about 60% to about 70% decrease, about 60% to about 65% decrease, about 65% to about 99% decrease, about 65% to about 95% decrease, about 65% to about 90% decrease, about 65% to about 85% decrease, about 65% to about 80% decrease, about 65% to about 75% decrease, about 65% to about 70% decrease, about 70% to about 99% decrease, about 70% to about 95% decrease, about 70% to about 90% decrease, about 70% to about 85% decrease, about 70% to about 80% decrease, about 70% to about 75% decrease, about 75% to about 99% decrease, about 75% to about 95% decrease, about 75% to about 90% decrease, about 75% to about 85% decrease, about 75% to about 80% decrease, about 80% to about 99% decrease, about 80% to about 95% decrease, about 80% to about 90% decrease, about 80% to about 85% decrease, about 85% to about 99% decrease, about 85% to about 95% decrease, about 85% to about 90% decrease, about 90% to about 99% decrease, about 90% to about 95% decrease, or about 95% to about 99% decrease) in one or more (e.g., two, three, four, five, six, seven, eight, or nine) of: the level of interferon-γ in GI tissue, the level of IL-1β in GI tissue, the level of IL-6 in GI tissue, the level of IL-22 in GI tissue, the level of IL-17A in the GI tissue, the level of TNFα in GI tissue, the level of IL-2 in GI tissue, and endoscopy score in a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of IL-10 or an IL-10 agonist using any of the compositions or devices described herein. Exemplary methods for determining the endoscopy score are described herein and other methods for determining the endoscopy score are known in the art. Exemplary methods for determining the levels of interferon-γ, IL-1β, IL-6, IL-22, IL-17A, TNFα, and IL-2 are described herein. Additional methods for determining the levels of these cytokines are known in the art.

In some examples, treatment can result in an increase (e.g., about 1% to about 500% increase, about 1% to about 400% increase, about 1% to about 300% increase, about 1% to about 200% increase, about 1% to about 150% increase, about 1% to about 100% increase, about 1% to about 90% increase, about 1% to about 80% increase, about 1% to about 70% increase, about 1% to about 60% increase, about 1% to about 50% increase, about 1% to about 40% increase, about 1% to about 30% increase, about 1% to about 20% increase, about 1% to about 10% increase, a 10% to about 500% increase, about 10% to about 400% increase, about 10% to about 300% increase, about 10% to about 200% increase, about 10% to about 150% increase, about 10% to about 100% increase, about 10% to about 90% increase, about 10% to about 80% increase, about 10% to about 70% increase, about 10% to about 60% increase, about 10% to about 50% increase, about 10% to about 40% increase, about 10% to about 30% increase, about 10% to about 20% increase, about 20% to about 500% increase, about 20% to about 400% increase, about 20% to about 300% increase, about 20% to about 200% increase, about 20% to about 150% increase, about 20% to about 100% increase, about 20% to about 90% increase, about 20% to about 80% increase, about 20% to about 70% increase, about 20% to about 60% increase, about 20% to about 50% increase, about 20% to about 40% increase, about 20% to about 30% increase, about 30% to about 500% increase, about 30% to about 400% increase, about 30% to about 300% increase, about 30% to about 200% increase, about 30% to about 150% increase, about 30% to about 100% increase, about 30% to about 90% increase, about 30% to about 80% increase, about 30% to about 70% increase, about 30% to about 60% increase, about 30% to about 50% increase, about 30% to about 40% increase, about 40% to about 500% increase, about 40% to about 400% increase, about 40% to about 300% increase, about 40% to about 200% increase, about 40% to about 150% increase, about 40% to about 100% increase, about 40% to about 90% increase, about 40% to about 80% increase, about 40% to about 70% increase, about 40% to about 60% increase, about 40% to about 50% increase, about 50% to about 500% increase, about 50% to about 400% increase, about 50% to about 300% increase, about 50% to about 200% increase, about 50% to about 150% increase, about 50% to about 100% increase, about 50% to about 90% increase, about 50% to about 80% increase, about 50% to about 70% increase, about 50% to about 60% increase, about 60% to about 500% increase, about 60% to about 400% increase, about 60% to about 300% increase, about 60% to about 200% increase, about 60% to about 150% increase, about 60% to about 100% increase, about 60% to about 90% increase, about 60% to about 80% increase, about 60% to about 70% increase, about 70% to about 500% increase, about 70% to about 400% increase, about 70% to about 300% increase, about 70% to about 200% increase, about 70% to about 150% increase, about 70% to about 100% increase, about 70% to about 90% increase, about 70% to about 80% increase, about 80% to about 500% increase, about 80% to about 400% increase, about 80% to about 300% increase, about 80% to about 200% increase, about 80% to about 150% increase, about 80% to about 100% increase, about 80% to about 90% increase, about 90% to about 500% increase, about 90% to about 400% increase, about 90% to about 300% increase, about 90% to about 200% increase, about 90% to about 150% increase, about 90% to about 100% increase, about 100% to about 500% increase, about 100% to about 400% increase, about 100% to about 300% increase, about 100% to about 200% increase, about 100% to about 150% increase, about 150% to about 500% increase, about 150% to about 400% increase, about 150% to about 300% increase, about 150% to about 200% increase, about 200% to about 500% increase, about 200% to about 400% increase, about 200% to about 300% increase, about 300% to about 500% increase, about 300% to about 400% increase, or about 400% to about 500% increase) in one or both of stool consistency score and weight of a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of IL-10 or an IL-10 agonist using any of the compositions or devices described herein. Exemplary methods for determining stool consistency score are described herein. Additional methods for determining a stool consistency score are known in the art.

In some embodiments, administration of IL-10 or an IL-10 agonist using any of the devices or compositions described herein can result in a ratio of GI tissue concentration of the IL-10 or the IL-10 agonist to the blood, serum, or plasma concentration of the IL-10 or the IL-10 agonist that is higher than the same ratio when the IL-10 or the IL-10 agonist is administered by traditional means (e.g., systemically or orally). Examples of a ratio of GI tissue concentration of the IL-10 or the IL-10 agonist to the blood, serum, or plasma concentration of the IL-10 or the IL-10 agonist include about 2 to about 600, about 2 to about 580, about 2 to about 560, about 2 to about 540, about 2 to about 520, about 2 to about 500, about 2 to about 480, about 2 to about 460, about 4 to about 440, about 2 to about 420, about 2 to about 400, about 2 to about 380, about 2 to about 360, about 2 to about 340, about 2 to about 320, about 2 to about 300, about 2 to about 280, about 2 to about 260, about 2 to about 240, about 2 to about 220, about 2 to about 200, about 2 to about 190, about 2 to about 180, about 2 to about 170, about 2 to about 160, about 2 to about 150, about 2 to about 140, about 2 to about 130, about 2 to about 120, about 2 to about 110, about 2 to about 100, about 2 to about 90, about 2 to about 80, about 2 to about 70, about 2 to about 60, about 2 to about 50, about 2 to about 40, about 2 to about 30, about 2 to about 20, about 2 to about 15, about 2 to about 10, about 2 to about 5, about 5 to about 600, about 5 to about 580, about 5 to about 560, about 5 to about 540, about 5 to about 520, about 5 to about 500, about 5 to about 480, about 5 to about 460, about 5 to about 440, about 5 to about 420, about 5 to about 400, about 5 to about 380, about 5 to about 360, about 5 to about 340, about 5 to about 320, about 5 to about 300, about 5 to about 280, about 5 to about 260, about 5 to about 240, about 5 to about 220, about 5 to about 200, about 5 to about 190, about 5 to about 180, about 5 to about 170, about 5 to about 160, about 5 to about 150, about 5 to about 140, about 5 to about 130, about 5 to about 120, about 5 to about 110, about 5 to about 100, about 5 to about 90, about 5 to about 80, about 5 to about 70, about 5 to about 60, about 5 to about 50, about 5 to about 40, about 5 to about 30, about 5 to about 20, about 5 to about 15, about 5 to about 10, about 10 to about 600, about 10 to about 580, about 10 to about 560, about 10 to about 540, about 10 to about 520, about 10 to about 500, about 10 to about 480, about 10 to about 460, about 10 to about 440, about 10 to about 420, about 10 to about 400, about 10 to about 380, about 10 to about 360, about 10 to about 340, about 10 to about 320, about 10 to about 300, about 10 to about 280, about 10 to about 260, about 10 to about 240, about 10 to about 220, about 10 to about 200, about 10 to about 190, about 10 to about 180, about 10 to about 170, about 10 to about 160, about 10 to about 150, about 10 to about 140, about 10 to about 130, about 10 to about 120, about 10 to about 110, about 10 to about 100, about 10 to about 90, about 10 to about 80, about 10 to about 70, about 10 to about 60, about 10 to about 50, about 10 to about 40, about 10 to about 30, about 10 to about 20, about 10 to about 15, about 15 to about 600, about 15 to about 580, about 15 to about 560, about 15 to about 540, about 15 to about 520, about 15 to about 500, about 15 to about 480, about 15 to about 460, about 15 to about 440, about 15 to about 420, about 15 to about 400, about 15 to about 380, about 15 to about 360, about 15 to about 340, about 15 to about 320, about 15 to about 300, about 15 to about 280, about 15 to about 260, about 15 to about 240, about 15 to about 220, about 15 to about 200, about 15 to about 190, about 15 to about 180, about 15 to about 170, about 15 to about 160, about 15 to about 150, about 15 to about 140, about 15 to about 130, about 15 to about 120, about 15 to about 110, about 15 to about 100, about 15 to about 90, about 15 to about 80, about 15 to about 70, about 15 to about 60, about 15 to about 50, about 15 to about 40, about 15 to about 30, about 15 to about 20, about 20 to about 600, about 20 to about 580, about 20 to about 560, about 20 to about 540, about 20 to about 520, about 20 to about 500, about 20 to about 480, about 20 to about 460, about 20 to about 440, about 20 to about 420, about 20 to about 400, about 20 to about 380, about 20 to about 360, about 20 to about 340, about 20 to about 320, about 20 to about 300, about 20 to about 280, about 20 to about 260, about 20 to about 240, about 20 to about 220, about 20 to about 200, about 20 to about 190, about 20 to about 180, about 20 to about 170, about 20 to about 160, about 20 to about 150, about 20 to about 140, about 20 to about 130, about 20 to about 120, about 20 to about 110, about 20 to about 100, about 20 to about 90, about 20 to about 80, about 20 to about 70, about 20 to about 60, about 20 to about 50, about 20 to about 40, about 20 to about 30, about 30 to about 600, about 30 to about 580, about 30 to about 560, about 30 to about 540, about 30 to about 520, about 30 to about 500, about 30 to about 480, about 30 to about 460, about 30 to about 440, about 30 to about 420, about 30 to about 400, about 30 to about 380, about 30 to about 360, about 30 to about 340, about 30 to about 320, about 30 to about 300, about 30 to about 280, about 30 to about 260, about 30 to about 240, about 30 to about 220, about 30 to about 200, about 30 to about 190, about 30 to about 180, about 30 to about 170, about 30 to about 160, about 30 to about 150, about 30 to about 140, about 30 to about 130, about 30 to about 120, about 30 to about 110, about 30 to about 100, about 30 to about 90, about 30 to about 80, about 30 to about 70, about 30 to about 60, about 30 to about 50, about 30 to about 40, about 40 to about 600, about 40 to about 580, about 40 to about 560, about 40 to about 540, about 40 to about 520, about 40 to about 500, about 40 to about 480, about 40 to about 460, about 40 to about 440, about 40 to about 420, about 40 to about 400, about 40 to about 380, about 40 to about 360, about 40 to about 340, about 40 to about 320, about 40 to about 300, about 40 to about 280, about 40 to about 260, about 40 to about 240, about 40 to about 220, about 40 to about 200, about 40 to about 190, about 40 to about 180, about 40 to about 170, about 40 to about 160, about 40 to about 150, about 40 to about 140, about 40 to about 130, about 40 to about 120, about 40 to about 110, about 40 to about 100, about 40 to about 90, about 40 to about 80, about 40 to about 70, about 40 to about 60, about 40 to about 50, about 50 to about 600, about 50 to about 580, about 50 to about 560, about 50 to about 540, about 50 to about 520, about 50 to about 500, about 50 to about 480, about 50 to about 460, about 50 to about 440, about 50 to about 420, about 50 to about 400, about 50 to about 380, about 50 to about 360, about 50 to about 340, about 50 to about 320, about 50 to about 300, about 50 to about 280, about 50 to about 260, about 50 to about 240, about 50 to about 220, about 50 to about 200, about 50 to about 190, about 50 to about 180, about 50 to about 170, about 50 to about 160, about 50 to about 150, about 50 to about 140, about 50 to about 130, about 50 to about 120, about 50 to about 110, about 50 to about 100, about 50 to about 90, about 50 to about 80, about 50 to about 70, about 50 to about 60, about 60 to about 600, about 60 to about 580, about 60 to about 560, about 60 to about 540, about 60 to about 520, about 60 to about 500, about 60 to about 480, about 60 to about 460, about 60 to about 440, about 60 to about 420, about 60 to about 400, about 60 to about 380, about 60 to about 360, about 60 to about 340, about 60 to about 320, about 60 to about 300, about 60 to about 280, about 60 to about 260, about 60 to about 240, about 60 to about 220, about 60 to about 200, about 60 to about 190, about 60 to about 180, about 60 to about 170, about 60 to about 160, about 60 to about 150, about 60 to about 140, about 60 to about 130, about 60 to about 120, about 60 to about 110, about 60 to about 100, about 60 to about 90, about 60 to about 80, about 60 to about 70, about 70 to about 600, about 70 to about 580, about 70 to about 560, about 70 to about 540, about 70 to about 520, about 70 to about 500, about 70 to about 480, about 70 to about 460, about 70 to about 440, about 70 to about 420, about 70 to about 400, about 70 to about 380, about 70 to about 360, about 70 to about 340, about 70 to about 320, about 70 to about 300, about 70 to about 280, about 70 to about 260, about 70 to about 240, about 70 to about 220, about 70 to about 200, about 70 to about 190, about 70 to about 180, about 70 to about 170, about 70 to about 160, about 70 to about 150, about 70 to about 140, about 70 to about 130, about 70 to about 120, about 70 to about 110, about 70 to about 100, about 70 to about 90, about 70 to about 80, about 80 to about 600, about 80 to about 580, about 80 to about 560, about 80 to about 540, about 80 to about 520, about 80 to about 500, about 80 to about 480, about 80 to about 460, about 80 to about 440, about 80 to about 420, about 80 to about 400, about 80 to about 380, about 80 to about 360, about 80 to about 340, about 80 to about 320, about 80 to about 300, about 80 to about 280, about 80 to about 260, about 80 to about 240, about 80 to about 220, about 80 to about 200, about 80 to about 190, about 80 to about 180, about 80 to about 170, about 80 to about 160, about 80 to about 150, about 80 to about 140, about 80 to about 130, about 80 to about 120, about 80 to about 110, about 80 to about 100, about 80 to about 90, about 90 to about 600, about 90 to about 580, about 90 to about 560, about 90 to about 540, about 90 to about 520, about 90 to about 500, about 90 to about 480, about 90 to about 460, about 90 to about 440, about 90 to about 420, about 90 to about 400, about 90 to about 380, about 90 to about 360, about 90 to about 340, about 90 to about 320, about 90 to about 300, about 90 to about 280, about 90 to about 260, about 90 to about 240, about 90 to about 220, about 90 to about 200, about 90 to about 190, about 90 to about 180, about 90 to about 170, about 90 to about 160, about 90 to about 150, about 90 to about 140, about 90 to about 130, about 90 to about 120, about 90 to about 110, about 90 to about 100, about 100 to about 600, about 100 to about 580, about 100 to about 560, about 100 to about 540, about 100 to about 520, about 100 to about 500, about 100 to about 480, about 100 to about 460, about 100 to about 440, about 100 to about 420, about 100 to about 400, about 100 to about 380, about 100 to about 360, about 100 to about 340, about 100 to about 320, about 100 to about 300, about 100 to about 280, about 100 to about 260, about 100 to about 240, about 100 to about 220, about 100 to about 200, about 100 to about 190, about 100 to about 180, about 100 to about 170, about 100 to about 160, about 100 to about 150, about 100 to about 140, about 100 to about 130, about 100 to about 120, about 100 to about 110, about 110 to about 600, about 110 to about 580, about 110 to about 560, about 110 to about 540, about 110 to about 520, about 110 to about 500, about 110 to about 480, about 110 to about 460, about 110 to about 440, about 110 to about 420, about 110 to about 400, about 110 to about 380, about 110 to about 360, about 110 to about 340, about 110 to about 320, about 110 to about 300, about 110 to about 280, about 110 to about 260, about 110 to about 240, about 110 to about 220, about 110 to about 200, about 110 to about 190, about 110 to about 180, about 110 to about 170, about 110 to about 160, about 110 to about 150, about 110 to about 140, about 110 to about 130, about 110 to about 120, about 120 to about 600, about 120 to about 580, about 120 to about 560, about 120 to about 540, about 120 to about 520, about 120 to about 500, about 120 to about 480, about 120 to about 460, about 120 to about 440, about 120 to about 420, about 120 to about 400, about 120 to about 380, about 120 to about 360, about 120 to about 340, about 120 to about 320, about 120 to about 300, about 120 to about 280, about 120 to about 260, about 120 to about 240, about 120 to about 220, about 120 to about 200, about 120 to about 190, about 120 to about 180, about 120 to about 170, about 120 to about 160, about 120 to about 150, about 120 to about 140, about 120 to about 130, about 130 to about 600, about 130 to about 580, about 130 to about 560, about 130 to about 540, about 130 to about 520, about 130 to about 500, about 130 to about 480, about 130 to about 460, about 130 to about 440, about 130 to about 420, about 130 to about 400, about 130 to about 380, about 130 to about 360, about 130 to about 340, about 130 to about 320, about 130 to about 300, about 130 to about 280, about 130 to about 260, about 130 to about 240, about 130 to about 220, about 130 to about 200, about 130 to about 190, about 130 to about 180, about 130 to about 170, about 130 to about 160, about 130 to about 150, about 130 to about 140, about 140 to about 600, about 140 to about 580, about 140 to about 560, about 140 to about 540, about 140 to about 520, about 140 to about 500, about 140 to about 480, about 140 to about 460, about 140 to about 440, about 140 to about 420, about 140 to about 400, about 140 to about 380, about 140 to about 360, about 140 to about 340, about 140 to about 320, about 140 to about 300, about 140 to about 280, about 140 to about 260, about 140 to about 240, about 140 to about 220, about 140 to about 200, about 140 to about 190, about 140 to about 180, about 140 to about 170, about 140 to about 160, about 140 to about 150, about 150 to about 600, about 150 to about 580, about 150 to about 560, about 150 to about 540, about 150 to about 520, about 150 to about 500, about 150 to about 480, about 150 to about 460, about 150 to about 440, about 150 to about 420, about 150 to about 400, about 150 to about 380, about 150 to about 360, about 150 to about 340, about 150 to about 320, about 150 to about 300, about 150 to about 280, about 150 to about 260, about 150 to about 240, about 150 to about 220, about 150 to about 200, about 150 to about 190, about 150 to about 180, about 150 to about 170, about 150 to about 160, about 160 to about 600, about 160 to about 580, about 160 to about 560, about 160 to about 540, about 160 to about 520, about 160 to about 500, about 160 to about 480, about 160 to about 460, about 160 to about 440, about 160 to about 420, about 160 to about 400, about 160 to about 380, about 160 to about 360, about 160 to about 340, about 160 to about 320, about 160 to about 300, about 160 to about 280, about 160 to about 260, about 160 to about 240, about 160 to about 220, about 160 to about 200, about 160 to about 190, about 160 to about 180, about 160 to about 170, about 170 to about 600, about 170 to about 580, about 170 to about 560, about 170 to about 540, about 170 to about 520, about 170 to about 500, about 170 to about 480, about 170 to about 460, about 170 to about 440, about 170 to about 420, about 170 to about 400, about 170 to about 380, about 170 to about 360, about 170 to about 340, about 170 to about 320, about 170 to about 300, about 170 to about 280, about 170 to about 260, about 170 to about 240, about 170 to about 220, about 170 to about 200, about 170 to about 190, about 170 to about 180, about 180 to about 600, about 180 to about 580, about 180 to about 560, about 180 to about 540, about 180 to about 520, about 180 to about 500, about 180 to about 480, about 180 to about 460, about 180 to about 440, about 180 to about 420, about 180 to about 400, about 180 to about 380, about 180 to about 360, about 180 to about 340, about 180 to about 320, about 180 to about 300, about 180 to about 280, about 180 to about 260, about 180 to about 240, about 180 to about 220, about 180 to about 200, about 180 to about 190, about 190 to about 600, about 190 to about 580, about 190 to about 560, about 190 to about 540, about 190 to about 520, about 190 to about 500, about 190 to about 480, about 190 to about 460, about 190 to about 440, about 190 to about 420, about 190 to about 400, about 190 to about 380, about 190 to about 360, about 190 to about 340, about 190 to about 320, about 190 to about 300, about 190 to about 280, about 190 to about 260, about 190 to about 240, about 190 to about 220, about 190 to about 200, about 200 to about 600, about 200 to about 580, about 200 to about 560, about 200 to about 540, about 200 to about 520, about 200 to about 500, about 200 to about 480, about 200 to about 460, about 200 to about 440, about 200 to about 420, about 200 to about 400, about 200 to about 380, about 200 to about 360, about 200 to about 340, about 200 to about 320, about 200 to about 300, about 200 to about 280, about 200 to about 260, about 200 to about 240, about 200 to about 220, about 220 to about 600, about 220 to about 580, about 220 to about 560, about 220 to about 540, about 220 to about 520, about 220 to about 500, about 220 to about 480, about 220 to about 460, about 220 to about 440, about 220 to about 420, about 220 to about 400, about 220 to about 380, about 220 to about 360, about 220 to about 340, about 220 to about 320, about 220 to about 300, about 220 to about 280, about 220 to about 260, about 220 to about 240, about 240 to about 600, about 240 to about 580, about 240 to about 560, about 240 to about 540, about 240 to about 520, about 240 to about 500, about 240 to about 480, about 240 to about 460, about 240 to about 440, about 240 to about 420, about 240 to about 400, about 240 to about 380, about 240 to about 360, about 240 to about 340, about 240 to about 320, about 240 to about 300, about 240 to about 280, about 240 to about 260, about 260 to about 600, about 260 to about 580, about 260 to about 560, about 260 to about 540, about 260 to about 520, about 260 to about 500, about 260 to about 480, about 260 to about 460, about 260 to about 440, about 260 to about 420, about 260 to about 400, about 260 to about 380, about 260 to about 360, about 260 to about 340, about 260 to about 320, about 260 to about 300, about 260 to about 280, about 280 to about 600, about 280 to about 580, about 280 to about 560, about 280 to about 540, about 280 to about 520, about 280 to about 500, about 280 to about 480, about 280 to about 460, about 280 to about 440, about 280 to about 420, about 280 to about 400, about 280 to about 380, about 280 to about 360, about 280 to about 340, about 280 to about 320, about 280 to about 300, about 300 to about 600, about 300 to about 580, about 300 to about 560, about 300 to about 540, about 300 to about 520, about 300 to about 500, about 300 to about 480, about 300 to about 460, about 300 to about 440, about 300 to about 420, about 300 to about 400, about 300 to about 380, about 300 to about 360, about 300 to about 340, about 300 to about 320, about 320 to about 600, about 320 to about 580, about 320 to about 560, about 320 to about 540, about 320 to about 520, about 320 to about 500, about 320 to about 480, about 320 to about 460, about 320 to about 440, about 320 to about 420, about 320 to about 400, about 320 to about 380, about 320 to about 360, about 320 to about 340, about 340 to about 600, about 340 to about 580, about 340 to about 560, about 340 to about 540, about 340 to about 520, about 340 to about 500, about 340 to about 480, about 340 to about 460, about 340 to about 440, about 340 to about 420, about 340 to about 400, about 340 to about 380, about 340 to about 360, about 360 to about 600, about 360 to about 580, about 360 to about 560, about 360 to about 540, about 360 to about 520, about 360 to about 500, about 360 to about 480, about 360 to about 460, about 360 to about 440, about 360 to about 420, about 360 to about 400, about 360 to about 380, about 380 to about 600, about 380 to about 580, about 380 to about 560, about 380 to about 540, about 380 to about 520, about 380 to about 500, about 380 to about 480, about 380 to about 460, about 380 to about 440, about 380 to about 420, about 380 to about 400, about 400 to about 600, about 400 to about 580, about 400 to about 560, about 400 to about 540, about 400 to about 520, about 400 to about 500, about 400 to about 480, about 400 to about 460, about 400 to about 440, about 400 to about 420, about 420 to about 600, about 420 to about 580, about 420 to about 560, about 420 to about 540, about 420 to about 520, about 420 to about 500, about 420 to about 480, about 420 to about 460, about 420 to about 440, about 440 to about 600, about 440 to about 580, about 440 to about 560, about 440 to about 540, about 440 to about 520, about 440 to about 500, about 440 to about 480, about 440 to about 460, about 460 to about 600, about 460 to about 580, about 460 to about 560, about 460 to about 540, about 460 to about 520, about 460 to about 500, about 460 to about 480, about 480 to about 600, about 480 to about 580, about 480 to about 560, about 480 to about 540, about 480 to about 520, about 480 to about 500, about 500 to about 600, about 500 to about 580, about 500 to about 560, about 500 to about 540, about 500 to about 520, about 520 to about 600, about 520 to about 580, about 520 to about 560, about 520 to about 540, about 540 to about 600, about 540 to about 580, about 540 to about 560, about 560 to about 600, about 560 to about 580, or about 580 to about 600.

Additional examples of a ratio of GI tissue concentration of the IL-10 or the IL-10 agonist to the blood, serum, or plasma concentration of the IL-10 or the IL-10 agonist include to 1.1 to 600, 1.2 to 600, 1.3 to 600, 1.4 to 600, 1.5 to 600, 1.6 to 600, 1.7 to 600, 1.8 to 600, or 1.9 to 600, such as 1.1, 1.2, 1.3, 1.4, 1.5, 1.6, 1.7, 1.8, or 1.9.

In some examples, administration of the IL-10 or the IL-10 agonist using any of the devices or compositions described herein can result in a ratio of GI tissue concentration of the IL-10 or the IL-10 agonist to the blood, serum, or plasma concentration of the IL-10 or the IL-10 agonist of, e.g., about 2.8 to about 6.0, about 2.8 to about 5.8, about 2.8 to about 5.6, about 2.8 to about 5.4, about 2.8 to about 5.2, about 2.8 to about 5.0, about 2.8 to about 4.8, about 2.8 to about 4.6, about 2.8 to about 4.4, about 2.8 to about 4.2, about 2.8 to about 4.0, about 2.8 to about 3.8, about 2.8 to about 3.6, about 2.8 to about 3.4, about 2.8 to about 3.2, about 2.8 to about 3.0, about 3.0 to about 6.0, about 3.0 to about 5.8, about 3.0 to about 5.6, about 3.0 to about 5.4, about 3.0 to about 5.2, about 3.0 to about 5.0, about 3.0 to about 4.8, about 3.0 to about 4.6, about 3.0 to about 4.4, about 3.0 to about 4.2, about 3.0 to about 4.0, about 3.0 to about 3.8, about 3.0 to about 3.6, about 3.0 to about 3.4, about 3.0 to about 3.2, about 3.2 to about 6.0, about 3.2 to about 5.8, about 3.2 to about 5.6, about 3.2 to about 5.4, about 3.2 to about 5.2, about 3.2 to about 5.0, about 3.2 to about 4.8, about 3.2 to about 4.6, about 3.2 to about 4.4, about 3.2 to about 4.2, about 3.2 to about 4.0, about 3.2 to about 3.8, about 3.2 to about 3.6, about 3.2 to about 3.4, about 3.4 to about 6.0, about 3.4 to about 5.8, about 3.4 to about 5.6, about 3.4 to about 5.4, about 3.4 to about 5.2, about 3.4 to about 5.0, about 3.4 to about 4.8, about 3.4 to about 4.6, about 3.4 to about 4.4, about 3.4 to about 4.2, about 3.4 to about 4.0, about 3.4 to about 3.8, about 3.4 to about 3.6, about 3.6 to about 6.0, about 3.6 to about 5.8, about 3.6 to about 5.6, about 3.6 to about 5.4, about 3.6 to about 5.2, about 3.6 to about 5.0, about 3.6 to about 4.8, about 3.6 to about 4.6, about 3.6 to about 4.4, about 3.6 to about 4.2, about 3.6 to about 4.0, about 3.6 to about 3.8, about 3.8 to about 6.0, about 3.8 to about 5.8, about 3.8 to about 5.6, about 3.8 to about 5.4, about 3.8 to about 5.2, about 3.8 to about 5.0, about 3.8 to about 4.8, about 3.8 to about 4.6, about 3.8 to about 4.4, about 3.8 to about 4.2, about 3.8 to about 4.0, about 4.0 to about 6.0, about 4.0 to about 5.8, about 4.0 to about 5.6, about 4.0 to about 5.4, about 4.0 to about 5.2, about 4.0 to about 5.0, about 4.0 to about 4.8, about 4.0 to about 4.6, about 4.0 to about 4.4, about 4.0 to about 4.2, about 4.2 to about 6.0, about 4.2 to about 5.8, about 4.2 to about 5.6, about 4.2 to about 5.4, about 4.2 to about 5.2, about 4.2 to about 5.0, about 4.2 to about 4.8, about 4.2 to about 4.6, about 4.2 to about 4.4, about 4.4 to about 6.0, about 4.4 to about 5.8, about 4.4 to about 5.6, about 4.4 to about 5.4, about 4.4 to about 5.2, about 4.4 to about 5.0, about 4.4 to about 4.8, about 4.4 to about 4.6, about 4.6 to about 6.0, about 4.6 to about 5.8, about 4.6 to about 5.6, about 4.6 to about 5.4, about 4.6 to about 5.2, about 4.6 to about 5.0, about 4.6 to about 4.8, about 4.8 to about 6.0, about 4.8 to about 5.8, about 4.8 to about 5.6, about 4.8 to about 5.4, about 4.8 to about 5.2, about 4.8 to about 5.0, about 5.0 to about 6.0, about 5.0 to about 5.8, about 5.0 to about 5.6, about 5.0 to about 5.4, about 5.0 to about 5.2, about 5.2 to about 6.0, about 5.2 to about 5.8, about 5.2 to about 5.6, about 5.2 to about 5.4, about 5.4 to about 6.0, about 5.4 to about 5.8, about 5.4 to about 5.6, about 5.6 to about 6.0, about 5.6 to about 5.8, or about 5.8 to about 6.0. Accordingly, in some embodiments, a method of treatment disclosed herein can include determining the ratio of the level of the IL-10 or IL-10 agonist in the GI tissue to the level of the IL-10 or IL-10 agonist in the blood, serum, or plasma of a subject at substantially the same time point following administration of the device is about 2.8 to about 6.0. Exemplary methods for measuring the concentration of IL-10 or the IL-10 agonist in the plasma or the GI tissue of a subject are described herein. Additional methods for measuring the concentration of IL-10 or the IL-10 agonist in the plasma or the GI tissue of a subject are known in the art.

Accordingly, in some embodiments, a method of treatment disclosed herein includes determining the level of the IL-10 or IL-10 agonist in the GI tissue (e.g., one or more of any of the exemplary GI tissues described herein). In some embodiments, a method of treatment disclosed herein can include determining the level of IL-10 or IL-10 agonist in one or more (e.g., two, three, or four) of the lumen/superficial mucosa, the lamina propria, the submucosa, and the tunica muscularis/serosa.

In some embodiments, a method of treatment disclosed herein includes determining that the level of the IL-10 or IL-10 agonist in the GI tissue (e.g., one or more of any of the exemplary types of GI tissues described herein) at a time point following administration of the device is higher than the level of IL-10 or IL-10 agonist in the GI tissue at substantially the same time point following systemic administration of an equal amount of the IL-10 or IL-10 agonist. In some embodiments, a method of treatment disclosed herein can include determining that the level of the IL-10 or IL-10 agonist in one or more (e.g., two, three, or four) of the lumen/superficial mucosa, the lamina propria, the submucosa, and the tunica muscularis/serosa at a time point following administration of the device is higher than the level of the IL-10 or IL-10 agonist in one or more (e.g., two, three, or four) of the lumen/superficial mucosa, the lamina propria, the submucosa, and the tunica muscularis/serosa at substantially the same time point following systemic administration of an equal amount of the IL-10 or IL-10 agonist.

In some embodiments, a method of treatment disclosed herein includes determining the level of IL-10 or IL-10 agonist in the feces of the subject. In some embodiments, a method of treatment disclosed herein includes determining the level of IL-10 or IL-10 agonist in the GI tissue, e.g., in one or more (e.g., two, three, or four) of the lumen/superficial mucosa, the lamina propria, the submucosa, and the tunica muscularis/serosa within a time period of about 10 minutes to about 10 hours following administration of the device.

In some embodiments, a method of treatment as disclosed herein comprises determining the level of the IL-10 or IL-10 agonist at the location of disease following administration of the device.

In some embodiments, a method of treatment as disclosed herein comprises determining that the level of IL-10 or IL-10 agonist at the location of disease at a time point following administration of the device is higher than the level of the IL-10 or IL-10 agonist at the same location of disease at substantially the same time point following systemic administration of an equal amount of the IL-10 or IL-10 agonist.

In some embodiments, a method of treatment as disclosed herein comprises determining that the level of IL-10 or IL-10 agonist in plasma in a subject at a time point following administration of the device is lower than the level of the IL-10 or IL-10 agonist in plasma in a subject at substantially the same time point following systemic administration of an equal amount of the IL-10 or IL-10 agonist.

In some embodiments, a method of treatment as disclosed herein comprises determining the level of the IL-10 or IL-10 agonist in the tissue of the subject within a time period of about 10 minutes to 10 hours following administration of the device.

Some examples of any of the methods described herein can, e.g., result in a selective suppression of a local inflammatory response (e.g., an inflammatory response in local GI tissue), while maintaining the systemic immune response (e.g., blood). The GI tissue may be, for example, GI tissue proximate to one or more sites of disease. FAs used herein, "GI content" refers to the content of the gastrointestinal (GI) tract, such as the content of one or more of duodenum, jejunum, ileum, cecum, ascending colon, transverse colon, descending colon, sigmoid colon, and rectum, more particularly of the proximal portion of one or more of duodenum, jejunum, ileum, cecum, ascending colon, transverse colon, descending colon, and sigmoid colon, or of the distal portion of one or more of duodenum, jejunum, ileum, cecum, ascending colon, transverse colon, descending colon, and sigmoid colon. Accordingly, in some embodiments, the methods described herein can result in a selective suppression of the inflammatory response in the dudodenum tissue proximate to one or more sites of disease, while maintaining the systemic immune response. In some embodiments, the methods described herein can result in a selective suppression of the inflammatory response in the jejunum tissue proximate to one or more sites of disease, while maintaining the systemic immune response. In some embodiments, the methods described herein can result in a selective suppression of the inflammatory response in the ileum tissue proximate to one or more sites of disease, while maintaining the systemic immune response. In some embodiments, the methods described herein can result in a selective suppression of the inflammatory response in the cecum tissue proximate to one or more sites of disease, while maintaining the systemic immune response. In some embodiments, the methods described herein can result in a selective suppression of the inflammatory response in the ascending colon tissue proximate to one or more sites of disease, while maintaining the systemic immune response. In some embodiments, the methods described herein can result in a selective suppression of the inflammatory response in the transverse colon tissue proximate to one or more sites of disease, while maintaining the systemic immune response. In some embodiments, the methods described herein can result in a selective suppression of the inflammatory response in the descending colon tissue proximate to one or more sites of disease, while maintaining the systemic immune response. In some embodiments, the methods described herein can result in a selective suppression of the inflammatory response in the sigmoid colon tissue proximate to one or more sites of disease, while maintaining the systemic immune response. In some examples, the methods described herein can result in a 1% increase to 500% increase (e.g., a 1% increase to 450% increase, a 1% increase to 400% increase, a 1% increase to 350% increase, a 1% increase to 300% increase, a 1% increase to 250% increase, a 1% increase to 200% increase, a 1% increase to 190% increase, a 1% increase to 180% increase, a 1% increase to 170% increase, a 1% increase to 160% increase, a 1% increase to 150% increase, a 1% increase to 140% increase, a 1% increase to 130% increase, a 1% increase to 120% increase, a 1% increase to 110% increase, a 1% increase to 100% increase, a 1% increase to 90% increase, a 1% increase to 80% increase, a 1% increase to 70% increase, a 1% increase to 60% increase, a 1% increase to 50% increase, a 1% increase to 40% increase, a 1% increase to 30% increase, a 1% increase to 25% increase, a 1% increase to 20% increase, a 1% increase to 15% increase, a 1% increase to 10% increase, a 1% increase to 5% increase, a 5% increase to 500% increase, a 5% increase to 450% increase, a 5% increase to 400% increase, a 5% increase to 350% increase, a 5% increase to 300% increase, a 5% increase to 250% increase, a 5% increase to 200% increase, a 5% increase to 190% increase, a 5% increase to 180% increase, a 5% increase to 170% increase, a 5% increase to 160% increase, a 5% increase to 150% increase, a 5% increase to 140% increase, a 5% increase to 130% increase, a 5% increase to 120% increase, a 5% increase to 110% increase, a 5% increase to 100% increase, a 5% increase to 90% increase, a 5% increase to 80% increase, a 5% increase to 70% increase, a 5% increase to 60% increase, a 5% increase to 50% increase, a 5% increase to 40% increase, a 5% increase to 30% increase, a 5% increase to 25% increase, a 5% increase to 20% increase, a 5% increase to 15% increase, a 5% increase to 10% increase, a 10% increase to 500% increase, a 10% increase to 450% increase, a 10% increase to 400% increase, a 10% increase to 350% increase, a 10% increase to 300% increase, a 10% increase to 250% increase, a 10% increase to 200% increase, a 10% increase to 190% increase, a 10% increase to 180% increase, a 10% increase to 170% increase, a 10% increase to 160% increase, a 10% increase to 150% increase, a 10% increase to 140% increase, a 10% increase to 130% increase, a 10% increase to 120% increase, a 10% increase to 110% increase, a 10% increase to 100% increase, a 10% increase to 90% increase, a 10% increase to 80% increase, a 10% increase to 70% increase, a 10% increase to 60% increase, a 10% increase to 50% increase, a 10% increase to 40% increase, a 10% increase to 30% increase, a 10% increase to 25% increase, a 10% increase to 20% increase, a 10% increase to 15% increase, a 15% increase to 500% increase, a 15% increase to 450% increase, a 15% increase to 400% increase, a 15% increase to 350% increase, a 15% increase to 300% increase, a 15% increase to 250% increase, a 15% increase to 200% increase, a 15% increase to 190% increase, a 15% increase to 180% increase, a 15% increase to 170% increase, a 15% increase to 160% increase, a 15% increase to 150% increase, a 15% increase to 140% increase, a 15% increase to 130% increase, a 15% increase to 120% increase, a 15% increase to 110% increase, a 15% increase to 100% increase, a 15% increase to 90% increase, a 15% increase to 80% increase, a 15% increase to 70% increase, a 15% increase to 60% increase, a 15% increase to 50% increase, a 15% increase to 40% increase, a 15% increase to 30% increase, a 15% increase to 25% increase, a 15% increase to 20% increase, a 20% increase to 500% increase, a 20% increase to 450% increase, a 20% increase to 400% increase, a 20% increase to 350% increase, a 20% increase to 300% increase, a 20% increase to 250% increase, a 20% increase to 200% increase, a 20% increase to 190% increase, a 20% increase to 180% increase, a 20% increase to 170% increase, a 20% increase to 160% increase, a 20% increase to 150% increase, a 20% increase to 140% increase, a 20% increase to 130% increase, a 20% increase to 120% increase, a 20% increase to 110% increase, a 20% increase to 100% increase, a 20% increase to 90% increase, a 20% increase to 80% increase, a 20% increase to 70% increase, a 20% increase to 60% increase, a 20% increase to 50% increase, a 20% increase to 40% increase, a 20% increase to 30% increase, a 20% increase to 25% increase, a 25% increase to 500% increase, a 25% increase to 450% increase, a 25% increase to 400% increase, a 25% increase to 350% increase, a 25% increase to 300% increase, a 25% increase to 250% increase, a 25% increase to 200% increase, a 25% increase to 190% increase, a 25% increase to 180% increase, a 25% increase to 170% increase, a 25% increase to 160% increase, a 25% increase to 150% increase, a 25% increase to 140% increase, a 25% increase to 130% increase, a 25% increase to 120% increase, a 25% increase to 110% increase, a 25% increase to 100% increase, a 25% increase to 90% increase, a 25% increase to 80% increase, a 25% increase to 70% increase, a 25% increase to 60% increase, a 25% increase to 50% increase, a 25% increase to 40% increase, a 25% increase to 30% increase, a 30% increase to 500% increase, a 30% increase to 450% increase, a 30% increase to 400% increase, a 30% increase to 350% increase, a 30% increase to 300% increase, a 30% increase to 250% increase, a 30% increase to 200% increase, a 30% increase to 190% increase, a 30% increase to 180% increase, a 30% increase to 170% increase, a 30% increase to 160% increase, a 30% increase to 150% increase, a 30% increase to 140% increase, a 30% increase to 130% increase, a 30% increase to 120% increase, a 30% increase to 110% increase, a 30% increase to 100% increase, a 30% increase to 90% increase, a 30% increase to 80% increase, a 30% increase to 70% increase, a 30% increase to 60% increase, a 30% increase to 50% increase, a 30% increase to 40% increase, a 40% increase to 500% increase, a 40% increase to 450% increase, a 40% increase to 400% increase, a 40% increase to 350% increase, a 40% increase to 300% increase, a 40% increase to 250% increase, a 40% increase to 200% increase, a 40% increase to 190% increase, a 40% increase to 180% increase, a 40% increase to 170% increase, a 40% increase to 160% increase, a 40% increase to 150% increase, a 40% increase to 140% increase, a 40% increase to 130% increase, a 40% increase to 120% increase, a 40% increase to 110% increase, a 40% increase to 100% increase, a 40% increase to 90% increase, a 40% increase to 80% increase, a 40% increase to 70% increase, a 40% increase to 60% increase, a 40% increase to 50% increase, a 50% increase to 500% increase, a 50% increase to 450% increase, a 50% increase to 400% increase, a 50% increase to 350% increase, a 50% increase to 300% increase, a 50% increase to 250% increase, a 50% increase to 200% increase, a 50% increase to 190% increase, a 50% increase to 180% increase, a 50% increase to 170% increase, a 50% increase to 160% increase, a 50% increase to 150% increase, a 50% increase to 140% increase, a 50% increase to 130% increase, a 50% increase to 120% increase, a 50% increase to 110% increase, a 50% increase to 100% increase, a 50% increase to 90% increase, a 50% increase to 80% increase, a 50% increase to 70% increase, a 50% increase to 60% increase, a 60% increase to 500% increase, a 60% increase to 450% increase, a 60% increase to 400% increase, a 60% increase to 350% increase, a 60% increase to 300% increase, a 60% increase to 250% increase, a 60% increase to 200% increase, a 60% increase to 190% increase, a 60% increase to 180% increase, a 60% increase to 170% increase, a 60% increase to 160% increase, a 60% increase to 150% increase, a 60% increase to 140% increase, a 60% increase to 130% increase, a 60% increase to 120% increase, a 60% increase to 110% increase, a 60% increase to 100% increase, a 60% increase to 90% increase, a 60% increase to 80% increase, a 60% increase to 70% increase, a 70% increase to 500% increase, a 70% increase to 450% increase, a 70% increase to 400% increase, a 70% increase to 350% increase, a 70% increase to 300% increase, a 70% increase to 250% increase, a 70% increase to 200% increase, a 70% increase to 190% increase, a 70% increase to 180% increase, a 70% increase to 170% increase, a 70% increase to 160% increase, a 70% increase to 150% increase, a 70% increase to 140% increase, a 70% increase to 130% increase, a 70% increase to 120% increase, a 70% increase to 110% increase, a 70% increase to 100% increase, a 70% increase to 90% increase, a 70% increase to 80% increase, a 80% increase to 500% increase, a 80% increase to 450% increase, a 80% increase to 400% increase, a 80% increase to 350% increase, a 80% increase to 300% increase, a 80% increase to 250% increase, a 80% increase to 200% increase, a 80% increase to 190% increase, a 80% increase to 180% increase, a 80% increase to 170% increase, a 80% increase to 160% increase, a 80% increase to 150% increase, a 80% increase to 140% increase, a 80% increase to 130% increase, a 80% increase to 120% increase, a 80% increase to 110% increase, a 80% increase to 100% increase, a 80% increase to 90% increase, a 90% increase to 500% increase, a 90% increase to 450% increase, a 90% increase to 400% increase, a 90% increase to 350% increase, a 90% increase to 300% increase, a 90% increase to 250% increase, a 90% increase to 200% increase, a 90% increase to 190% increase, a 90% increase to 180% increase, a 90% increase to 170% increase, a 90% increase to 160% increase, a 90% increase to 150% increase, a 90% increase to 140% increase, a 90% increase to 130% increase, a 90% increase to 120% increase, a 90% increase to 110% increase, a 90% increase to 100% increase, a 100% increase to 500% increase, a 100% increase to 450% increase, a 100% increase to 400% increase, a 100% increase to 350% increase, a 100% increase to 300% increase, a 100% increase to 250% increase, a 100% increase to 200% increase, a 100% increase to 190% increase, a 100% increase to 180% increase, a 100% increase to 170% increase, a 100% increase to 160% increase, a 100% increase to 150% increase, a 100% increase to 140% increase, a 100% increase to 130% increase, a 100% increase to 120% increase, a 100% increase to 110% increase, a 110% increase to 500% increase, a 110% increase to 450% increase, a 110% increase to 400% increase, a 110% increase to 350% increase, a 110% increase to 300% increase, a 110% increase to 250% increase, a 110% increase to 200% increase, a 110% increase to 190% increase, a 110% increase to 180% increase, a 110% increase to 170% increase, a 110% increase to 160% increase, a 110% increase to 150% increase, a 110% increase to 140% increase, a 110% increase to 130% increase, a 110% increase to 120% increase, a 120% increase to 500% increase, a 120% increase to 450% increase, a 120% increase to 400% increase, a 120% increase to 350% increase, a 120% increase to 300% increase, a 120% increase to 250% increase, a 120% increase to 200% increase, a 120% increase to 190% increase, a 120% increase to 180% increase, a 120% increase to 170% increase, a 120% increase to 160% increase, a 120% increase to 150% increase, a 120% increase to 140% increase, a 120% increase to 130% increase, a 130% increase to 500% increase, a 130% increase to 450% increase, a 130% increase to 400% increase, a 130% increase to 350% increase, a 130% increase to 300% increase, a 130% increase to 250% increase, a 130% increase to 200% increase, a 130% increase to 190% increase, a 130% increase to 180% increase, a 130% increase to 170% increase, a 130% increase to 160% increase, a 130% increase to 150% increase, a 130% increase to 140% increase, a 140% increase to 500% increase, a 140% increase to 450% increase, a 140% increase to 400% increase, a 140% increase to 350% increase, a 140% increase to 300% increase, a 140% increase to 250% increase, a 140% increase to 200% increase, a 140% increase to 190% increase, a 140% increase to 180% increase, a 140% increase to 170% increase, a 140% increase to 160% increase, a 140% increase to 150% increase, a 150% increase to 500% increase, a 150% increase to 450% increase, a 150% increase to 400% increase, a 150% increase to 350% increase, a 150% increase to 300% increase, a 150% increase to 250% increase, a 150% increase to 200% increase, a 150% increase to 190% increase, a 150% increase to 180% increase, a 150% increase to 170% increase, a 150% increase to 160% increase, a 160% increase to 500% increase, a 160% increase to 450% increase, a 160% increase to 400% increase, a 160% increase to 350% increase, a 160% increase to 300% increase, a 160% increase to 250% increase, a 160% increase to 200% increase, a 160% increase to 190% increase, a 160% increase to 180% increase, a 160% increase to 170% increase, a 170% increase to 500% increase, a 170% increase to 450% increase, a 170% increase to 400% increase, a 170% increase to 350% increase, a 170% increase to 300% increase, a 170% increase to 250% increase, a 170% increase to 200% increase, a 170% increase to 190% increase, a 170% increase to 180% increase, a 180% increase to 500% increase, a 180% increase to 450% increase, a 180% increase to 400% increase, a 180% increase to 350% increase, a 180% increase to 300% increase, a 180% increase to 250% increase, a 180% increase to 200% increase, a 180% increase to 190% increase, a 190% increase to 500% increase, a 190% increase to 450% increase, a 190% increase to 400% increase, a 190% increase to 350% increase, a 190% increase to 300% increase, a 190% increase to 250% increase, a 190% increase to 200% increase, a 200% increase to 500% increase, a 200% increase to 450% increase, a 200% increase to 400% increase, a 200% increase to 350% increase, a 200% increase to 300% increase, a 200% increase to 250% increase, a 250% increase to 500% increase, a 250% increase to 450% increase, a 250% increase to 400% increase, a 250% increase to 350% increase, a 250% increase to 300% increase, a 300% increase to 500% increase, a 300% increase to 450% increase, a 300% increase to 400% increase, a 300% increase to 350% increase, a 350% increase to 500% increase, a 350% increase to 450% increase, a 350% increase to 400% increase, a 400% increase to 500% increase, a 400% increase to 450% increase, or a 450% increase to 500% increase) in one or more (e.g., two, three, four, five, six, seven, eight, nine, or ten) of: the plasma, serum, or blood level of IL-6; the plasma, serum, or blood level of IL-2; the plasma, serum, or blood level of IL-1β; the plasma, serum, or blood level of TNFα; the plasma, serum, or blood level of IL-17A; the plasma, serum, or blood level of IL-22; the plasma, serum, or blood level of interferon-γ; the level of blood Th memory cells (CD44$^+$CD45RB$^-$CD4$^+$ cells); and the level of α4β7 expression in blood cells; e.g., each as compared to the corresponding level in a subject systemically administered the same dose of the same IL-10 or IL-10 agonist. Methods for determining the plasma, serum, or blood level of IL-6; the plasma, serum, or blood level of IL-2; the plasma, serum, or blood level of IL-1β; the plasma, serum, or blood level of TNFα; the plasma, serum, or blood level of IL-17A; the plasma, serum, or blood level of IL-22; the plasma, serum, or blood level of interferon-γ; the level of blood Th memory cells (CD44$^+$CD45RB$^-$CD4$^+$ cells); and the level of α4β7 expression in blood cells are known in the art.

In some examples of any of the methods described herein can result, e.g., in a 1% to 99% decrease (or any of the subranges of this range described herein) in one or more (e.g., two, three, four, five, six, or seven) of: the level of interferon-γ in GI tissue or GI content; the level of IL-1β in GI tissue or GI content; the level of IL-6 in GI tissue or GI content; the level of IL-22 in GI tissue or GI content; the level of IL-17A in GI tissue or GI content; the level of TNFα in GI tissue or GI content; and the level of IL-2 in GI tissue or GI content, e.g., as compared to the corresponding level in a subject not administered a treatment, or not administered IL-10 or an IL-10 agonist locally as disclosed herein. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the duodenum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the ileum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the jejunum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the cecum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the ascending colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the transverse colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the descending colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-γ; the level of IL-1β; the level of IL-6; the level of IL-22; the level of IL-17A; the level of TNFα; and the level of IL-2, in the sigmoid colon tissue proximate to one or more sites of disease.

In some embodiments, the IL-10 or IL-10 agonist is delivered to the location by a process that does not comprise systemic transport of the IL-10 or IL-10 agonist.

In some embodiments, the amount of the IL-10 or IL-10 agonist that is administered is from about 0.02 mg to about 500 mg. In some embodiments, the amount of the IL-10 or IL-10 agonist that is administered is from about 1 mg to about 500 mg. In some embodiments, the amount of the IL-10 or IL-10 agonist that is administered is from about 0.02 mg to about 200 mg. In some embodiments, the amount of the IL-10 or IL-10 agonist that is administered is from about 0.1 mg to about 150 mg. In some embodiments, the amount of the IL-10 or IL-10 agonist that is administered is from about 0.5 mg to about 100 mg. In some embodiments, the amount of the IL-10 or IL-10 agonist that is administered is from about 1 mg to about 100 mg. In some embodiments, the amount of the IL-10 or IL-10 agonist that is administered is from about 5 mg to about 40 mg. In some embodiments, the amount of the IL-10 or the IL-10 agonist is administered as an escalating dose of 10 mg, followed by 20 mg, followed by 30 mg; or an escalating dose of 20 mg, followed by 30 mg, followed by 50 mg.

In some embodiments, the amount of the IL-10 or the IL-10 agonist is administered in a dose of, e.g., about 1 mg to about 300 mg, about 1 mg to about 250 mg, about 1 mg to about 200 mg, about 1 mg to about 195 mg, about 1 mg to about 190 mg, about 1 mg to about 185 mg, about 1 mg to about 180 mg, about 1 mg to about 175 mg, about 1 mg to about 170 mg, about 1 mg to about 165 mg, about 1 mg to about 160 mg, about 1 mg to about 155 mg, about 1 mg to about 150 mg, about 1 mg to about 145 mg, about 1 mg to about 140 mg, about 1 mg to about 135 mg, about 1 mg to about 130 mg, about 1 mg to about 125 mg, about 1 mg to about 120 mg, about 1 mg to about 115 mg, about 1 mg to about 110 mg, about 1 mg to about 105 mg, about 1 mg to about 100 mg, about 1 mg to about 95 mg, about 1 mg to about 90 mg, about 1 mg to about 85 mg, about 1 mg to about 80 mg, about 1 mg to about 75 mg, about 1 mg to about 70 mg, about 1 mg to about 65 mg, about 1 mg to about 60 mg, about 1 mg to about 55 mg, about 1 mg to about 50 mg, about 1 mg to about 45 mg, about 1 mg to about 40 mg, about 1 mg to about 35 mg, about 1 mg to about 30 mg, about 1 mg to about 25 mg, about 1 mg to about 20 mg, about 1 mg to about 15 mg, about 1 mg to about 10 mg, about 1 mg to about 5 mg, about 5 mg to about 200 mg, about 5 mg to about 195 mg, about 5 mg to about 190 mg, about 5 mg to about 185 mg, about 5 mg to about 180 mg, about 5 mg to about 175 mg, about 5 mg to about 170 mg, about 5 mg to about 165 mg, about 5 mg to about 160 mg, about 5 mg to about 155 mg, about 5 mg to about 150 mg, about 5 mg to about 145 mg, about 5 mg to about 140 mg, about 5 mg to about 135 mg, about 5 mg to about 130 mg, about 5 mg to about 125 mg, about 5 mg to about 120 mg, about 5 mg to about 115 mg, about 5 mg to about 110 mg, about 5 mg to about 105 mg, about 5 mg to about 100 mg, about 5 mg to about 95 mg, about 5 mg to about 90 mg, about 5 mg to about 85 mg, about 5 mg to about 80 mg, about 5 mg to about 75 mg, about 5 mg to about 70 mg, about 5 mg to about 65 mg, about 5 mg to about 60 mg, about 5 mg to about 55 mg, about 5 mg to about 50 mg, about 5 mg to about 45 mg, about 5 mg to about 40 mg, about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 200 mg, about 10 mg to about 195 mg, about 10 mg to about 190 mg, about 10 mg to about 185 mg, about 10 mg to about 180 mg, about 10 mg to about 175 mg, about 10 mg to about 170 mg, about 10 mg to about 165 mg, about 10 mg to about 160 mg, about 10 mg to about 155 mg, about 10 mg to about 150 mg, about 10 mg to about 145 mg, about 10 mg to about 140 mg, about 10 mg to about 135 mg, about 10 mg to about 130 mg, about 10 mg to about 125 mg, about 10 mg to about 120 mg, about 10 mg to about 115 mg, about 10 mg to about 110 mg, about 10 mg to about 105 mg, about 10 mg to about 100 mg, about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 200 mg, about 15 mg to about 195 mg, about 15 mg to about 190 mg, about 15 mg to about 185 mg, about 15 mg to about 180 mg, about 15 mg to about 175 mg, about 15 mg to about 170 mg, about 15 mg to about 165 mg, about 15 mg to about 160 mg, about 15 mg to about 155 mg, about 15 mg to about 150 mg, about 15 mg to about 145 mg, about 15 mg to about 140 mg, about 15 mg to about 135 mg, about 15 mg to about 130 mg, about 15 mg to about 125 mg, about 15 mg to about 120 mg, about 15 mg to about 115 mg, about 15 mg to about 110 mg, about 15 mg to about 105 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 200 mg, about 20 mg to about 195 mg, about 20 mg to about 190 mg, about 20 mg to about 185 mg, about 20 mg to about 180 mg, about 20 mg to about 175 mg, about 20 mg to about 170 mg, about 20 mg to about 165 mg, about 20 mg to about 160 mg, about 20 mg to about 155 mg, about 20 mg to about 150 mg, about 20 mg to about 145 mg, about 20 mg to about 140 mg, about 20 mg to about 135 mg, about 20 mg to about 130 mg, about 20 mg to about 125 mg, about 20 mg to about 120 mg, about 20 mg to about 115 mg, about 20 mg to about 110 mg, about 20 mg to about 105 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 200 mg, about 25 mg to about 195 mg, about 25 mg to about 190 mg, about 25 mg to about 185 mg, about 25 mg to about 180 mg, about 25 mg to about 175 mg, about 25 mg to about 170 mg, about 25 mg to about 165 mg, about 25 mg to about 160 mg, about 25 mg to about 155 mg, about 25 mg to about 150 mg, about 25 mg to about 145 mg, about 25 mg to about 140 mg, about 25 mg to about 135 mg, about 25 mg to about 130 mg, about 25 mg to about 125 mg, about 25 mg to about 120 mg, about 25 mg to about 115 mg, about 25 mg to about 110 mg, about 25 mg to about 105 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 200 mg, about 30 mg to about 195 mg, about 30 mg to about 190 mg, about 30 mg to about 185 mg, about 30 mg to about 180 mg, about 30 mg to about 175 mg, about 30 mg to about 170 mg, about 30 mg to about 165 mg, about 30 mg to about 160 mg, about 30 mg to about 155 mg, about 30 mg to about 150 mg, about 30 mg to about 145 mg, about 30 mg to about 140 mg, about 30 mg to about 135 mg, about 30 mg to about 130 mg, about 30 mg to about 125 mg, about 30 mg to about 120 mg, about 30 mg to about 115 mg, about 30 mg to about 110 mg, about 30 mg to about 105 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 200 mg, about 35 mg to about 195 mg, about 35 mg to about 190 mg, about 35 mg to about 185 mg, about 35 mg to about 180 mg, about 35 mg to about 175 mg, about 35 mg to about 170 mg, about 35 mg to about 165 mg, about 35 mg to about 160 mg, about 35 mg to about 155 mg, about 35 mg to about 150 mg, about 35 mg to about 145 mg, about 35 mg to about 140 mg, about 35 mg to about 135 mg, about 35 mg to about 130 mg, about 35 mg to about 125 mg, about 35 mg to about 120 mg, about 35 mg to about 115 mg, about 35 mg to about 110 mg, about 35 mg to about 105 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 200 mg, about 40 mg to about 195 mg, about 40 mg to about 190 mg, about 40 mg to about 185 mg, about 40 mg to about 180 mg, about 40 mg to about 175 mg, about 40 mg to about 170 mg, about 40 mg to about 165 mg, about 40 mg to about 160 mg, about 40 mg to about 155 mg, about 40 mg to about 150 mg, about 40 mg to about 145 mg, about 40 mg to about 140 mg, about 40 mg to about 135 mg, about 40 mg to about 130 mg, about 40 mg to about 125 mg, about 40 mg to about 120 mg, about 40 mg to about 115 mg, about 40 mg to about 110 mg, about 40 mg to about 105 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 200 mg, about 45 mg to about 195 mg, about 45 mg to about 190 mg, about 45 mg to about 185 mg, about 45 mg to about 180 mg, about 45 mg to about 175 mg, about 45 mg to about 170 mg, about 45 mg to about 165 mg, about 45 mg to about 160 mg, about 45 mg to about 155 mg, about 45 mg to about 150 mg, about 45 mg to about 145 mg, about 45 mg to about 140 mg, about 45 mg to about 135 mg, about 45 mg to about 130 mg, about 45 mg to about 125 mg, about 45 mg to about 120 mg, about 45 mg to about 115 mg, about 45 mg to about 110 mg, about 45 mg to about 105 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 200 mg, about 50 mg to about 195 mg, about 50 mg to about 190 mg, about 50 mg to about 185 mg, about 50 mg to about 180 mg, about 50 mg to about 175 mg, about 50 mg to about 170 mg, about 50 mg to about 165 mg, about 50 mg to about 160 mg, about 50 mg to about 155 mg, about 50 mg to about 150 mg, about 50 mg to about 145 mg, about 50 mg to about 140 mg, about 50 mg to about 135 mg, about 50 mg to about 130 mg, about 50 mg to about 125 mg, about 50 mg to about 120 mg, about 50 mg to about 115 mg, about 50 mg to about 110 mg, about 50 mg to about 105 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 200 mg, about 55 mg to about 195 mg, about 55 mg to about 190 mg, about 55 mg to about 185 mg, about 55 mg to about 180 mg, about 55 mg to about 175 mg, about 55 mg to about 170 mg, about 55 mg to about 165 mg, about 55 mg to about 160 mg, about 55 mg to about 155 mg, about 55 mg to about 150 mg, about 55 mg to about 145 mg, about 55 mg to about 140 mg, about 55 mg to about 135 mg, about 55 mg to about 130 mg, about 55 mg to about 125 mg, about 55 mg to about 120 mg, about 55 mg to about 115 mg, about 55 mg to about 110 mg, about 55 mg to about 105 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 200 mg, about 60 mg to about 195 mg, about 60 mg to about 190 mg, about 60 mg to about 185 mg, about 60 mg to about 180 mg, about 60 mg to about 175 mg, about 60 mg to about 170 mg, about 60 mg to about 165 mg, about 60 mg to about 160 mg, about 60 mg to about 155 mg, about 60 mg to about 150 mg, about 60 mg to about 145 mg, about 60 mg to about 140 mg, about 60 mg to about 135 mg, about 60 mg to about 130 mg, about 60 mg to about 125 mg, about 60 mg to about 120 mg, about 60 mg to about 115 mg, about 60 mg to about 110 mg, about 60 mg to about 105 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 200 mg, about 65 mg to about 195 mg, about 65 mg to about 190 mg, about 65 mg to about 185 mg, about 65 mg to about 180 mg, about 65 mg to about 175 mg, about 65 mg to about 170 mg, about 65 mg to about 165 mg, about 65 mg to about 160 mg, about 65 mg to about 155 mg, about 65 mg to about 150 mg, about 65 mg to about 145 mg, about 65 mg to about 140 mg, about 65 mg to about 135 mg, about 65 mg to about 130 mg, about 65 mg to about 125 mg, about 65 mg to about 120 mg, about 65 mg to about 115 mg, about 65 mg to about 110 mg, about 65 mg to about 105 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 200 mg, about 70 mg to about 195 mg, about 70 mg to about 190 mg, about 70 mg to about 185 mg, about 70 mg to about 180 mg, about 70 mg to about 175 mg, about 70 mg to about 170 mg, about 70 mg to about 165 mg, about 70 mg to about 160 mg, about 70 mg to about 155 mg, about 70 mg to about 150 mg, about 70 mg to about 145 mg, about 70 mg to about 140 mg, about 70 mg to about 135 mg, about 70 mg to about 130 mg, about 70 mg to about 125 mg, about 70 mg to about 120 mg, about 70 mg to about 115 mg, about 70 mg to about 110 mg, about 70 mg to about 105 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 200 mg, about 75 mg to about 195 mg, about 75 mg to about 190 mg, about 75 mg to about 185 mg, about 75 mg to about 180 mg, about 75 mg to about 175 mg, about 75 mg to about 170 mg, about 75 mg to about 165 mg, about 75 mg to about 160 mg, about 75 mg to about 155 mg, about 75 mg to about 150 mg, about 75 mg to about 145 mg, about 75 mg to about 140 mg, about 75 mg to about 135 mg, about 75 mg to about 130 mg, about 75 mg to about 125 mg, about 75 mg to about 120 mg, about 75 mg to about 115 mg, about 75 mg to about 110 mg, about 75 mg to about 105 mg, about 75 mg to about 100 mg, about 75 mg to about 95 mg, about 75 mg to about 90 mg, about 75 mg to about 85 mg, about 75 mg to about 80 mg, about 80 mg to about 200 mg, about 80 mg to about 195 mg, about 80 mg to about 190 mg, about 80 mg to about 185 mg, about 80 mg to about 180 mg, about 80 mg to about 175 mg, about 80 mg to about 170 mg, about 80 mg to about 165 mg, about 80 mg to about 160 mg, about 80 mg to about 155 mg, about 80 mg to about 150 mg, about 80 mg to about 145 mg, about 80 mg to about 140 mg, about 80 mg to about 135 mg, about 80 mg to about 130 mg, about 80 mg to about 125 mg, about 80 mg to about 120 mg, about 80 mg to about 115 mg, about 80 mg to about 110 mg, about 80 mg to about 105 mg, about 80 mg to about 100 mg, about 80 mg to about 95 mg, about 80 mg to about 90 mg, about 80 mg to about 85 mg, about 85 mg to about 200 mg, about 85 mg to about 195 mg, about 85 mg to about 190 mg, about 85 mg to about 185 mg, about 85 mg to about 180 mg, about 85 mg to about 175 mg, about 85 mg to about 170 mg, about 85 mg to about 165 mg, about 85 mg to about 160 mg, about 85 mg to about 155 mg, about 85 mg to about 150 mg, about 85 mg to about 145 mg, about 85 mg to about 140 mg, about 85 mg to about 135 mg, about 85 mg to about 130 mg, about 85 mg to about 125 mg, about 85 mg to about 120 mg, about 85 mg to about 115 mg, about 85 mg to about 110 mg, about 85 mg to about 105 mg, about 85 mg to about 100 mg, about 85 mg to about 95 mg, about 85 mg to about 90 mg, about 90 mg to about 200 mg, about 90 mg to about 195 mg, about 90 mg to about 190 mg, about 90 mg to about 185 mg, about 90 mg to about 180 mg, about 90 mg to about 175 mg, about 90 mg to about 170 mg, about 90 mg to about 165 mg, about 90 mg to about 160 mg, about 90 mg to about 155 mg, about 90 mg to about 150 mg, about 90 mg to about 145 mg, about 90 mg to about 140 mg, about 90 mg to about 135 mg, about 90 mg to about 130 mg, about 90 mg to about 125 mg, about 90 mg to about 120 mg, about 90 mg to about 115 mg, about 90 mg to about 110 mg, about 90 mg to about 105 mg, about 90 mg to about 100 mg, about 90 mg to about 95 mg, about 95 mg to about 200 mg, about 95 mg to about 195 mg, about 95 mg to about 190 mg, about 95 mg to about 185 mg, about 95 mg to about 180 mg, about 95 mg to about 175 mg, about 95 mg to about 170 mg, about 95 mg to about 165 mg, about 95 mg to about 160 mg, about 95 mg to about 155 mg, about 95 mg to about 150 mg, about 95 mg to about 145 mg, about 95 mg to about 140 mg, about 95 mg to about 135 mg, about 95 mg to about 130 mg, about 95 mg to about 125 mg, about 95 mg to about 120 mg, about 95 mg to about 115 mg, about 95 mg to about 110 mg, about 95 mg to about 105 mg, about 95 mg to about 100 mg, about 100 mg to about 200 mg, about 100 mg to about 195 mg, about 100 mg to about 190 mg, about 100 mg to about 185 mg, about 100 mg to about 180 mg, about 100 mg to about 175 mg, about 100 mg to about 170 mg, about 100 mg to about 165 mg, about 100 mg to about 160 mg, about 100 mg to about 155 mg, about 100 mg to about 150 mg, about 100 mg to about 145 mg, about 100 mg to about 140 mg, about 100 mg to about 135 mg, about 100 mg to about 130 mg, about 100 mg to about 125 mg, about 100 mg to about 120 mg, about 100 mg to about 115 mg, about 100 mg to about 110 mg, about 100 mg to about 105 mg, about 105 mg to about 200 mg, about 105 mg to about 195 mg, about 105 mg to about 190 mg, about 105 mg to about 185 mg, about 105 mg to about 180 mg, about 105 mg to about 175 mg, about 105 mg to about 170 mg, about 105 mg to about 165 mg, about 105 mg to about 160 mg, about 105 mg to about 155 mg, about 105 mg to about 150 mg, about 105 mg to about 145 mg, about 105 mg to about 140 mg, about 105 mg to about 135 mg, about 105 mg to about 130 mg, about 105 mg to about 125 mg, about 105 mg to about 120 mg, about 105 mg to about 115 mg, about 105 mg to about 110 mg, about 110 mg to about 200 mg, about 110 mg to about 195 mg, about 110 mg to about 190 mg, about 110 mg to about 185 mg, about 110 mg to about 180 mg, about 110 mg to about 175 mg, about 110 mg to about 170 mg, about 110 mg to about 165 mg, about 110 mg to about 160 mg, about 110 mg to about 155 mg, about 110 mg to about 150 mg, about 110 mg to about 145 mg, about 110 mg to about 140 mg, about 110 mg to about 135 mg, about 110 mg to about 130 mg, about 110 mg to about 125 mg, about 110 mg to about 120 mg, about 110 mg to about 115 mg, about 115 mg to about 200 mg, about 115 mg to about 195 mg, about 115 mg to about 190 mg, about 115 mg to about 185 mg, about 115 mg to about 180 mg, about 115 mg to about 175 mg, about 115 mg to about 170 mg, about 115 mg to about 165 mg, about 115 mg to about 160 mg, about 115 mg to about 155 mg, about 115 mg to about 150 mg, about 115 mg to about 145 mg, about 115 mg to about 140 mg, about 115 mg to about 135 mg, about 115 mg to about 130 mg, about 115 mg to about 125 mg, about 115 mg to about 120 mg, about 120 mg to about 200 mg, about 120 mg to about 195 mg, about 120 mg to about 190 mg, about 120 mg to about 185 mg, about 120 mg to about 180 mg, about 120 mg to about 175 mg, about 120 mg to about 170 mg, about 120 mg to about 165 mg, about 120 mg to about 160 mg, about 120 mg to about 155 mg, about 120 mg to about 150 mg, about 120 mg to about 145 mg, about 120 mg to about 140 mg, about 120 mg to about 135 mg, about 120 mg to about 130 mg, about 120 mg to about 125 mg, about 125 mg to about 200 mg, about 125 mg to about 195 mg, about 125 mg to about 190 mg, about 125 mg to about 185 mg, about 125 mg to about 180 mg, about 125 mg to about 175 mg, about 125 mg to about 170 mg, about 125 mg to about 165 mg, about 125 mg to about 160 mg, about 125 mg to about 155 mg, about 125 mg to about 150 mg, about 125 mg to about 145 mg, about 125 mg to about 140 mg, about 125 mg to about 135 mg, about 125 mg to about 130 mg, about 130 mg to about 200 mg, about 130 mg to about 195 mg, about 130 mg to about 190 mg, about 130 mg to about 185 mg, about 130 mg to about 180 mg, about 130 mg to about 175 mg, about 130 mg to about 170 mg, about 130 mg to about 165 mg, about 130 mg to about 160 mg, about 130 mg to about 155 mg, about 130 mg to about 150 mg, about 130 mg to about 145 mg, about 130 mg to about 140 mg, about 130 mg to about 135 mg, about 135 mg to about 200 mg, about 135 mg to about 195 mg, about 135 mg to about 190 mg, about 135 mg to about 185 mg, about 135 mg to about 180 mg, about 135 mg to about 175 mg, about 135 mg to about 170 mg, about 135 mg to about 165 mg, about 135 mg to about 160 mg, about 135 mg to about 155 mg, about 135 mg to about 150 mg, about 135 mg to about 145 mg, about 135 mg to about 140 mg, about 140 mg to about 200 mg, about 140 mg to about 195 mg, about 140 mg to about 190 mg, about 140 mg to about 185 mg, about 140 mg to about 180 mg, about 140 mg to about 175 mg, about 140 mg to about 170 mg, about 140 mg to about 165 mg, about 140 mg to about 160 mg, about 140 mg to about 155 mg, about 140 mg to about 150 mg, about 140 mg to about 145 mg, about 145 mg to about 200 mg, about 145 mg to about 195 mg, about 145 mg to about 190 mg, about 145 mg to about 185 mg, about 145 mg to about 180 mg, about 145 mg to about 175 mg, about 145 mg to about 170 mg, about 145 mg to about 165 mg, about 145 mg to about 160 mg, about 145 mg to about 155 mg, about 145 mg to about 150 mg, about 150 mg to about 200 mg, about 150 mg to about 195 mg, about 150 mg to about 190 mg, about 150 mg to about 185 mg, about 150 mg to about 180 mg, about 150 mg to about 175 mg, about 150 mg to about 170 mg, about 150 mg to about 165 mg, about 150 mg to about 160 mg, about 150 mg to about 155 mg, about 155 mg to about 200 mg, about 155 mg to about 195 mg, about 155 mg to about 190 mg, about 155 mg to about 185 mg, about 155 mg to about 180 mg, about 155 mg to about 175 mg, about 155 mg to about 170 mg, about 155 mg to about 165 mg, about 155 mg to about 160 mg, about 160 mg to about 200 mg, about 160 mg to about 195 mg, about 160 mg to about 190 mg, about 160 mg to about 185 mg, about 160 mg to about 180 mg, about 160 mg to about 175 mg, about 160 mg to about 170 mg, about 160 mg to about 165 mg, about 165 mg to about 200 mg, about 165 mg to about 195 mg, about 165 mg to about 190 mg, about 165 mg to about 185 mg, about 165 mg to about 180 mg, about 165 mg to about 175 mg, about 165 mg to about 170 mg, about 170 mg to about 200 mg, about 170 mg to about 195 mg, about 170 mg to about 190 mg, about 170 mg to about 185 mg, about 170 mg to about 180 mg, about 170 mg to about 175 mg, about 175 mg to about 200 mg, about 175 mg to about 195 mg, about 175 mg to about 190 mg, about 175 mg to about 185 mg, about 175 mg to about 180 mg, about 180 mg to about 200 mg, about 180 mg to about 195 mg, about 180 mg to about 190 mg, about 180 mg to about 185 mg, about 185 mg to about 200 mg, about 185 mg to about 195 mg, about 185 mg to about 190 mg, about 190 mg to about 200 mg, about 190 mg to about 195 mg, or about 195 mg to about 200 mg.

In some embodiments, the subject is administered the dose of the IL-10 or IL-10 agonist once a day. In some embodiments, the subject is administered the dose of the IL-10 or IL-10 agonist once every two days.

In some embodiments, the amount of the IL-10 or IL-10 agonist that is administered is less than an amount that is effective when the IL-10 or IL-10 agonist is delivered systemically.

In some embodiments, the amount of the IL-10 or IL-10 agonist that is administered is an induction dose. In some embodiments, such induction dose is effective to induce remission of the TNF and cytokine storm and healing of acute inflammation and lesions. In some embodiments, the induction dose is administered once a day. In some embodiments, the induction dose is administered once every two days. In some embodiments, the induction dose is administered once every three days. In some embodiments, the induction dose is administered once a week. In some embodiments, the induction dose is administered once a day, once every three days, or once a week, over a period of about 6-8 weeks.

In some embodiments, the method comprises administering (i) an amount of the IL-10 or IL-10 agonist that is an induction dose, and (ii) an amount of the IL-10 or IL-10 agonist that is a maintenance dose, in this order. In some embodiments, step (ii) is repeated one or more times. In some embodiments, the induction dose is equal to the maintenance dose. In some embodiments, the induction dose is greater than the maintenance dose. In some embodiments, the induction dose is five times greater than the maintenance dose. In some embodiments, the induction dose is two times greater than the maintenance dose.

In some embodiments, the induction dose is the same as or higher than an induction dose administered systemically for treatment of the same disorder to a subject. In more particular embodiments, the induction dose is the same as or higher than an induction dose administered systemically for treatment of the same disorder to a subject, and the maintenance dose is lower than the maintenance dose administered systemically for treatment of the same disorder to a subject. In some embodiments, the induction dose is the same as or higher than an induction dose administered systemically for treatment of the same disorder to a subject, and the maintenance dose is higher than the maintenance dose administered systemically for treatment of the same disorder to a subject.

In some embodiments an induction dose of the IL-10 or IL-10 agonist and a maintenance dose of the IL-10 or IL-10 agonist are each administered to the subject by administering a pharmaceutical composition comprising a therapeutically effective amount of the IL-10 or IL-10 agonist, wherein the pharmaceutical composition is a device. In some embodiments an induction dose of the IL-10 or IL-10 agonist is administered to the subject in a different manner from the maintenance dose. As an example, the induction dose may be administered systemically. In some embodiments, the induction dose may be administered other than orally. As an example, the induction dose may be administered rectally. As an example, the induction dose may be administered intravenously. As an example, the induction dose may be administered subcutaneously. In some embodiments, the induction dose may be administered by spray catheter.

In some embodiments, the concentration of the IL-10 or IL-10 agonist delivered at the location in the gastrointestinal tract is 10%, 25%, 50%, 75%, 100%, 200%, 300%, 400%, 500%, 1000%, 2000% greater than the concentration of the IL-10 or IL-10 agonist in plasma.

In some embodiments, the method provides a concentration of the IL-10 or IL-10 agonist at a location that is a site of disease or proximate to a site of disease that is 2-100 times greater than at a location that is not a site of disease or proximate to a site of disease.

In some embodiments, the method comprises delivering the IL-10 or IL-10 agonist at the location in the gastrointestinal tract as a single bolus.

In some embodiments, the method comprises delivering the IL-10 or IL-10 agonist at the location in the gastrointestinal tract as more than one bolus.

In some embodiments, the method comprises delivering the IL-10 or IL-10 agonist at the location in the gastrointestinal tract in a continuous manner.

In some embodiments, the method comprises delivering the IL-10 or IL-10 agonist at the location in the gastrointestinal tract over a time period of 20 or more minutes.

In some embodiments, the method provides a concentration of the IL-10 or IL-10 agonist in the plasma of the subject that is less than 10 µg/ml. In some embodiments, the method provides a concentration of the IL-10 or IL-10 agonist in the plasma of the subject that is less than 3 µg/ml. In some embodiments, the method provides a concentration of the IL-10 or IL-10 agonist in the plasma of the subject that is less than 1 µg/ml. In some embodiments, the method provides a concentration of the IL-10 or IL-10 agonist in the plasma of the subject that is less than 0.3 µg/ml. In some embodiments, the method provides a concentration of the IL-10 or IL-10 agonist in the plasma of the subject that is less than 0.1 µg/ml. In some embodiments, the method provides a concentration of the IL-10 or IL-10 agonist in the plasma of the subject that is less than 0.01 µg/ml. In some embodiments, the method provides a concentration of the IL-10 or IL-10 agonist in the plasma of the subject that is less than 0.001 µg/ml. In some embodiments, the values of the concentration of the IL-10 or IL-10 agonist in the plasma of the subject provided herein refer to $C_{trough}$, that is, the lowest value of the concentration prior to administration of the next dose.

In some embodiments, the method provides a concentration of the IL-10 or the IL-10 agonist in the plasma of the subject that is, e.g., about 1 ng/L to about 100 ng/mL, about 1 ng/mL to about 95 ng/mL, about 1 ng/mL to about 90 ng/mL, about 1 ng/mL to about 85 ng/mL, about 1 ng/mL to about 80 ng/mL, about 1 ng/mL to about 75 ng/mL, about 1 ng/mL to about 70 ng/mL, about 1 ng/mL to about 65 ng/mL, about 1 ng/mL to about 60 ng/mL, about 1 ng/mL to about 55 ng/mL, about 1 ng/mL to about 50 ng/mL, about 1 ng/mL to about 45 ng/mL, about 1 ng/mL to about 40 ng/mL, about 1 ng/mL to about 35 ng/mL, about 1 ng/mL to about 30 ng/mL, about 1 ng/mL to about 25 ng/mL, about 1 ng/mL to about 20 ng/mL, about 1 ng/mL to about 15 ng/mL, about 1 ng/mL to about 10 ng/mL, about 1 ng/mL to about 5 ng/mL, about 2 ng/L to about 100 ng/mL, about 2 ng/mL to about 95 ng/mL, about 2 ng/mL to about 90 ng/mL, about 2 ng/mL to about 85 ng/mL, about 2 ng/mL to about 80 ng/mL, about 2 ng/mL to about 75 ng/mL, about 2 ng/mL to about 70 ng/mL, about 2 ng/mL to about 65 ng/mL, about 2 ng/mL to about 60 ng/mL, about 2 ng/mL to about 55 ng/mL, about 2 ng/mL to about 50 ng/mL, about 2 ng/mL to about 45 ng/mL, about 2 ng/mL to about 40 ng/mL, about 2 ng/mL to about 35 ng/mL, about 2 ng/mL to about 30 ng/mL, about 2 ng/mL to about 25 ng/mL, about 2 ng/mL to about 20 ng/mL, about 2 ng/mL to about 15 ng/mL, about 2 ng/mL to about 10 ng/mL, about 2 ng/mL to about 5 ng/mL, about 5 ng/L to about 100 ng/mL, about 5 ng/mL to about 95 ng/mL, about 5 ng/mL to about 90 ng/mL, about 5 ng/mL to about 85 ng/mL, about 5 ng/mL to about 80 ng/mL, about 5 ng/mL to about 75 ng/mL, about 5 ng/mL to about 70 ng/mL, about 5 ng/mL to about 65 ng/mL, about 5 ng/mL to about 60 ng/mL, about 5 ng/mL to about 55 ng/mL, about 5 ng/mL to about 50 ng/mL, about 5 ng/mL to about 45 ng/mL, about 5 ng/mL to about 40 ng/mL, about 5 ng/mL to about 35 ng/mL, about 5 ng/mL to about 30 ng/mL, about 5 ng/mL to about 25 ng/mL, about 5 ng/mL to about 20 ng/mL, about 5 ng/mL to about 15 ng/mL, about 5 ng/mL to about 10 ng/mL, about 10 ng/L to about 100 ng/mL, about 10 ng/mL to about 95 ng/mL, about 10 ng/mL to about 90 ng/mL, about 10 ng/mL to about 85 ng/mL, about 10 ng/mL to about 80 ng/mL, about 10 ng/mL to about 75 ng/mL, about 10 ng/mL to about 70 ng/mL, about 10 ng/mL to about 65 ng/mL, about 10 ng/mL to about 60 ng/mL, about 10 ng/mL to about 55 ng/mL, about 10 ng/mL to about 50 ng/mL, about 10 ng/mL to about 45 ng/mL, about 10 ng/mL to about 40 ng/mL, about 10 ng/mL to about 35 ng/mL, about 10 ng/mL to about 30 ng/mL, about 10 ng/mL to about 25 ng/mL, about 10 ng/mL to about 20 ng/mL, about 10 ng/mL to about 15 ng/mL, about 15 ng/L to about 100 ng/mL, about 15 ng/mL to about 95 ng/mL, about 15 ng/mL to about 90 ng/mL, about 15 ng/mL to about 85 ng/mL, about 15 ng/mL to about 80 ng/mL, about 15 ng/mL to about 75 ng/mL, about 15 ng/mL to about 70 ng/mL, about 15 ng/mL to about 65 ng/mL, about 15 ng/mL to about 60 ng/mL, about 15 ng/mL to about 55 ng/mL, about 15 ng/mL to about 50 ng/mL, about 15 ng/mL to about 45 ng/mL, about 15 ng/mL to about 40 ng/mL, about 15 ng/mL to about 35 ng/mL, about 15 ng/mL to about 30 ng/mL, about 15 ng/mL to about 25 ng/mL, about 15 ng/mL to about 20 ng/mL, about 20 ng/L to about 100 ng/mL, about 20 ng/mL to about 95 ng/mL, about 20 ng/mL to about 90 ng/mL, about 20 ng/mL to about 85 ng/mL, about 20 ng/mL to about 80 ng/mL, about 20 ng/mL to about 75 ng/mL, about 20 ng/mL to about 70 ng/mL, about 20 ng/mL to about 65 ng/mL, about 20 ng/mL to about 60 ng/mL, about 20 ng/mL to about 55 ng/mL, about 20 ng/mL to about 50 ng/mL, about 20 ng/mL to about 45 ng/mL, about 20 ng/mL to about 40 ng/mL, about 20 ng/mL to about 35 ng/mL, about 20 ng/mL to about 30 ng/mL, about 20 ng/mL to about 25 ng/mL, about 25 ng/L to about 100 ng/mL, about 25 ng/mL to about 95 ng/mL, about 25 ng/mL to about 90 ng/mL, about 25 ng/mL to about 85 ng/mL, about 25 ng/mL to about 80 ng/mL, about 25 ng/mL to about 75 ng/mL, about 25 ng/mL to about 70 ng/mL, about 25 ng/mL to about 65 ng/mL, about 25 ng/mL to about 60 ng/mL, about 25 ng/mL to about 55 ng/mL, about 25 ng/mL to about 50 ng/mL, about 25 ng/mL to about 45 ng/mL, about 25 ng/mL to about 40 ng/mL, about 25 ng/mL to about 35 ng/mL, about 25 ng/mL to about 30 ng/mL, about 30 ng/L to about 100 ng/mL, about 30 ng/mL to about 95 ng/mL, about 30 ng/mL to about 90 ng/mL, about 30 ng/mL to about 85 ng/mL, about 30 ng/mL to about 80 ng/mL, about 30 ng/mL to about 75 ng/mL, about 30 ng/mL to about 70 ng/mL, about 30 ng/mL to about 65 ng/mL, about 30 ng/mL to about 60 ng/mL, about 30 ng/mL to about 55 ng/mL, about 30 ng/mL to about 50 ng/mL, about 30 ng/mL to about 45 ng/mL, about 30 ng/mL to about 40 ng/mL, about 30 ng/mL to about 35 ng/mL, about 35 ng/L to about 100 ng/mL, about 35 ng/mL to about 95 ng/mL, about 35 ng/mL to about 90 ng/mL, about 35 ng/mL to about 85 ng/mL, about 35 ng/mL to about 80 ng/mL, about 35 ng/mL to about 75 ng/mL, about 35 ng/mL to about 70 ng/mL, about 35 ng/mL to about 65 ng/mL, about 35 ng/mL to about 60 ng/mL, about 35 ng/mL to about 55 ng/mL, about 35 ng/mL to about 50 ng/mL, about 35 ng/mL to about 45 ng/mL, about 35 ng/mL to about 40 ng/mL, about 40 ng/L to about 100 ng/mL, about 40 ng/mL to about 95 ng/mL, about 40 ng/mL to about 90 ng/mL, about 40 ng/mL to about 85 ng/mL, about 40 ng/mL to about 80 ng/mL, about 40 ng/mL to about 75 ng/mL, about 40 ng/mL to about 70 ng/mL, about 40 ng/mL to about 65 ng/mL, about 40 ng/mL to about 60 ng/mL, about 40 ng/mL to about 55 ng/mL, about 40 ng/mL to about 50 ng/mL, about 40 ng/mL to about 45 ng/mL, about 45 ng/L to about 100 ng/mL, about 45 ng/mL to about 95 ng/mL, about 45 ng/mL to about 90 ng/mL, about 45 ng/mL to about 85 ng/mL, about 45 ng/mL to about 80 ng/mL, about 45 ng/mL to about 75 ng/mL, about 45 ng/mL to about 70 ng/mL, about 45 ng/mL to about 65 ng/mL, about 45 ng/mL to about 60 ng/mL, about 45 ng/mL to about 55 ng/mL, about 45 ng/mL to about 50 ng/mL, about 50 ng/L to about 100 ng/mL, about 50 ng/mL to about 95 ng/mL, about 50 ng/mL to about 90 ng/mL, about 50 ng/mL to about 85 ng/mL, about 50 ng/mL to about 80 ng/mL, about 50 ng/mL to about 75 ng/mL, about 50 ng/mL to about 70 ng/mL, about 50 ng/mL to about 65 ng/mL, about 50 ng/mL to about 60 ng/mL, about 50 ng/mL to about 55 ng/mL, about 55 ng/L to about 100 ng/mL, about 55 ng/mL to about 95 ng/mL, about 55 ng/mL to about 90 ng/mL, about 55 ng/mL to about 85 ng/mL, about 55 ng/mL to about 80 ng/mL, about 55 ng/mL to about 75 ng/mL, about 55 ng/mL to about 70 ng/mL, about 55 ng/mL to about 65 ng/mL, about 55 ng/mL to about 60 ng/mL, about 60 ng/L to about 100 ng/mL, about 60 ng/mL to about 95 ng/mL, about 60 ng/mL to about 90 ng/mL, about 60 ng/mL to about 85 ng/mL, about 60 ng/mL to about 80 ng/mL, about 60 ng/mL to about 75 ng/mL, about 60 ng/mL to about 70 ng/mL, about 60 ng/mL to about 65 ng/mL, about 65 ng/L to about 100 ng/mL, about 65 ng/mL to about 95 ng/mL, about 65 ng/mL to about 90 ng/mL, about 65 ng/mL to about 85 ng/mL, about 65 ng/mL to about 80 ng/mL, about 65 ng/mL to about 75 ng/mL, about 65 ng/mL to about 70 ng/mL, about 70 ng/L to about 100 ng/mL, about 70 ng/mL to about 95 ng/mL, about 70 ng/mL to about 90 ng/mL, about 70 ng/mL to about 85 ng/mL, about 70 ng/mL to about 80 ng/mL, about 70 ng/mL to about 75 ng/mL, about 75 ng/L to about 100 ng/mL, about 75 ng/mL to about 95 ng/mL, about 75 ng/mL to about 90 ng/mL, about 75 ng/mL to about 85 ng/mL, about 75 ng/mL to about 80 ng/mL, about 80 ng/L to about 100 ng/mL, about 80 ng/mL to about 95 ng/mL, about 80 ng/mL to about 90 ng/mL, about 80 ng/mL to about 85 ng/mL, about 85 ng/L to about 100 ng/mL, about 85 ng/mL to about 95 ng/mL, about 85 ng/mL to about 90 ng/mL, about 90 ng/L to about 100 ng/mL, about 90 ng/mL to about 95 ng/mL, or about 95 ng/mL to about 100 ng/mL.

In some embodiments, the method provides a concentration $C_{max}$ of the IL-10 or IL-10 agonist in the plasma of the subject that is less than 10 µg/ml. In some embodiments, the method provides a concentration $C_{max}$ of the IL-10 or IL-10 agonist in the plasma of the subject that is less than 3 µg/ml. In some embodiments, the method provides a concentration $C_{max}$ of the IL-10 or IL-10 agonist in the plasma of the subject that is less than 1 µg/ml. In some embodiments, the method provides a concentration $C_{max}$ of the IL-10 or IL-10 agonist in the plasma of the subject that is less than 0.3 µg/ml. In some embodiments, the method provides a concentration $C_{max}$ of the IL-10 or IL-10 agonist in the plasma of the subject that is less than 0.1 µg/ml. In some embodiments, the method provides a concentration $C_{max}$ of the IL-10 or IL-10 agonist in the plasma of the subject that is less than 0.01 µg/ml.

In some embodiments, the method does not comprise delivering IL-10 or an IL-10 agonist rectally to the subject.

In some embodiments, the method does not comprise delivering IL-10 or an IL-10 agonist via an enema to the subject.

In some embodiments, the method does not comprise delivering IL-10 or an IL-10 agonist via suppository to the subject.

In some embodiments, the method does not comprise delivering IL-10 or an IL-10 agonist via instillation to the rectum of a subject.

In some embodiments, the methods disclosed herein comprise producing a therapeutically effective degradation product of the IL-10 or IL-10 agonist in the gastrointestinal tract. In some embodiments, a therapeutically effective amount of the degradation product is produced.

In some embodiments, the methods comprising administering the IL-10 or IL-10 agonist in the manner disclosed herein disclosed herein result in a reduced immunosuppressive properties relative to methods of administration of the IL-10 or IL-10 agonist systemically.

In some embodiments, the methods comprising administering the IL-10 or IL-10 agonist in the manner disclosed herein disclosed herein result in reduced immunogenicity relative to methods of administration of the IL-10 or IL-10 agonist systemically.

Methods for Treating Colitis in Subjects in Immune-Oncology Therapy

In some embodiments, provided herein is a method for treating colitis as disclosed herein in a subject, comprising releasing IL-10 or an IL-10 agonist at a location in the gastrointestinal tract of the subject that is proximate to one or more sites of disease, wherein the method comprises administering to the subject a pharmaceutical composition comprising a therapeutically effective amount of the IL-10 or IL-10 agonist, wherein the colitis is associated with treatment of the subject with one or more immuno-oncology agents. In some embodiments, the pharmaceutical composition is an ingestible device. In some embodiments, the pharmaceutical composition is an ingestible device and the method comprises administering orally to the subject the pharmaceutical composition.

In some embodiments, at least one of the one or more immuno-oncology agents is a chemotherapeutic agent. In some embodiments, the chemotherapeutic agent is a chemotherapeutic immunomodulator. In some embodiments, the chemotherapeutic immunomodulator is an immune checkpoint inhibitor.

In some embodiments, the immune checkpoint inhibitor targets an immune checkpoint protein or decreases an activity of an immune checkpoint protein selected from the group of CTLA-4, PD-1, PD-L1, PD-1-PD-L1, PD-1-PD-L2, interleukin 2 (IL 2), indoleamine 2,3-dioxygenase (IDO), IL 10, transforming growth factor-β (TGFβ), T cell immunoglobulin and mucin 3 (TIM3 or HAVCR2), Galectin 9-TIM3, Phosphatidylserine—TIM3, lymphocyte activation gene 3 protein (LAG3), MEW class II—LAG3, 4 1BB-4 1BB ligand, OX40-OX40 ligand, GITR, GITR ligand—GITR, CD27, CD70-CD27, TNFRSF25, TNFRSF25-TL1A, CD40L, CD40-CD40 ligand, HVEM-LIGHT-LTA, HVEM, HVEM—BTLA, HVEM—CD160, HVEM—LIGHT, HVEM-BTLA-CD160, CD80, CD80-PDL-1, PDL2-CD80, CD244, CD48-CD244, CD244, ICOS, ICOS-ICOS ligand, B7 H3, B7 H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine—TIM3, SIRPA-CD47, VEGF, Neuropilin, CD160, CD30, and CD155.

In some examples, the immune checkpoint inhibitor is selected from the group consisting of: Urelumab, PF 05082566, MEDI6469, TRX518, Varlilumab, CP 870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS 986016, MGA271, Lirilumab, IPH2201, Emactuzumab, INCB024360, Galunisertib, Ulocuplumab, BKT140, Bavituximab, CC 90002, Bevacizumab, and MNRP1685A, and MGA271.

In some examples, the immune checkpoint inhibitor targets or decreases an activity of CTLA-4. In some embodiments, the immune checkpoint inhibitor is an antibody. In some embodiments, the antibody is ipilimumab or tremelimumab.

In some examples, the immune checkpoint inhibitor targets PD1 or PD-L1. In some examples, the immune checkpoint inhibitor is selected from nivolumab, lambroizumab, and BMS-936559.

In some embodiments, at least one of the one or more immuno-oncology agents is a T-cell capable of expressing a chimeric antigen receptor (CAR). In some embodiments, at least one of the one or more immuno-oncology agents is a PI-3-kinase inhibitor.

In some embodiments, the treatment of the subject with one or more immuno-oncology agents further comprises treatment of the subject with an immunosuppressant.

In some embodiments, provided herein is a method for reducing the development of colitis in a subject administered an immuno-oncology agent, comprising releasing IL-10 or an IL-10 agonist at a location in the gastrointestinal tract of the subject that is proximate to one or more sites of disease, wherein the method comprises administering to the subject a pharmaceutical composition comprising a therapeutically effective amount of the IL-10 or IL-10 agonist. In some embodiments, the pharmaceutical composition is an ingestible device. In some embodiments, the pharmaceutical composition is an ingestible device and the method comprises administering orally to the subject the pharmaceutical composition.

In some embodiments of these methods, a subject is administered at least one dose of an immuno-oncology agent prior to administering a pharmaceutical composition comprising any of the devices described herein as described herein to the subject. In some embodiments of these methods, a subject is first administered any of the devices as described herein, prior to administration of the first dose of the immuno-oncology agent. In some embodiments of these methods, the immuno-oncology agent is administered at substantially the same time as the device described herein.

Also provided herein are methods of treating a subject having a cancer that include: administering a first dose of an immuno-oncology agent to the subject; monitoring one or more biomarkers, markers, or symptoms of colitis (e.g., any of the biomarkers, markers, or symptoms of colitis described herein or known in the art); identifying a subject having a level of a biomarker or marker, or having a symptom of colitis; and releasing IL-10 or an IL-10 agonist at a location in the gastrointestinal tract of the subject that is proximate to one or more sites of disease, wherein the method comprises administering to the subject a pharmaceutical composition comprising a therapeutically effective amount of the IL-10 or IL-10 agonist. In some embodiments, the pharmaceutical composition is an ingestible device. In some embodiments, the pharmaceutical composition is an ingestible device and the method comprises administering orally to the subject the pharmaceutical composition.

Also provided herein are methods of reducing the severity of colitis in a subject having a cancer and administered an immuno-oncology agent that include administering to the subject any of the devices described herein.

In some embodiments, provided herein is a method for treating colitis in a subject comprising:

determining that the subject has colitis associated with treatment of the subject with one or more immuno-oncology agents; and releasing IL-10 or an IL-10 agonist at a location in the gastrointestinal tract of the subject that is proximate to one or more sites of colitis, wherein the method comprises administering to the subject a pharmaceutical composition comprising a therapeutically effective amount of the IL-10 or IL-10 agonist. In some embodiments, the pharmaceutical composition is an ingestible device. In some embodiments, the pharmaceutical composition is an ingestible device and the method comprises administering orally to the subject the pharmaceutical composition.

In some embodiments, provided herein is a method for treating colitis in a subject comprising:

determining that the subject has colitis associated with treatment of the subject with one or more immuno-oncology agents; and administering to the subject an ingestible device comprising any of the IL-10 or IL-10 agonists described herein, to treat the colitis.

In some embodiments, provided herein is a method for treating colitis, comprising releasing IL-10 or an IL-10 agonist at a location in the gastrointestinal tract of a subject who has been determined to have colitis associated with treatment of the subject with one or more immuno-oncology agents, wherein the location is proximate to one or more sites of colitis, wherein the method comprises administering to the subject a pharmaceutical composition comprising a therapeutically effective amount of the IL-10 or IL-10 agonist. In some embodiments, the pharmaceutical composition is an ingestible device. In some embodiments, the pharmaceutical composition is an ingestible device and the method comprises administering orally to the subject the pharmaceutical composition.

In some embodiments, provided herein is a method for treating colitis, comprising administering an ingestible device comprising any of the IL-10 or IL-10 agonists described herein to a subject who has been determined to have colitis associated with treatment of the subject with one or more immuno-oncology agents.

In some embodiments, provided herein is an ingestible device comprising any of the IL-10 or IL-10 agonists described herein for treating colitis associated with treatment of a subject with one or more immuno-oncology agents.

Monitoring Progress of Disease

In some embodiments, the methods provided herein comprise monitoring the progress of the disease. In some embodiments, monitoring the progress of the disease comprises measuring the levels of IBD serological markers. In some embodiments, monitoring the progress of the disease comprises determining mucosal healing at the location of release. In some embodiments, monitoring the progress of the disease comprises determining the Crohn's Disease Activity Index (CDAI) over a period of about 6-8 weeks, or over a period of about 52 weeks, following administration of the IL-10 or IL-10 agonist. In some embodiments, monitoring the progress of the disease comprises determining the Harvey-Bradshaw Index (HBI) following administration of the IL-10 or IL-10 agonist. Possible markers may include the following: anti-glycan antibodies: anti-*Saccharomices cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbirl flagellin; anti-12 antibody; autoantibodies targeting the exocrine pancreas (PAB); perinuclear anti-neutrophil antibody (pANCA). In some embodiments, monitoring the progress of the disease comprises measuring the IL-10 or IL-10 agonist levels in serum over a period of about 1-14 weeks, such as about 6-8 weeks following administration of the IL-10 or IL-10 agonist, including at the 6-8 week time point. In some embodiments, monitoring the progress of the disease comprises measuring the IL-10 or IL-10 agonist levels in serum over a period of about 52 weeks following administration of the IL-10 or IL-10 agonist, including at the 52 week time point.

Patients Condition, Diagnosis and Treatment

In some embodiments herein, the method of treating a disease of the gastrointestinal tract that comprises releasing IL-10 or an IL-10 agonist at a location in the gastrointestinal tract that is proximate to one or more sites of disease comprises one or more of the following:

a) identifying a subject having a disease of the gastrointestinal tract, for example by endoscopy or colonoscopy;

b) determination of the severity of the disease, for example with reference to the Mayo Clinic Score, the Crohn's Disease Activity Index (CDAI), the Harvey-Bradshaw Index (HBI), or a combination of the above;

c) determination of the location of the disease, for example as determined by the presence of lesions indicative of the disease;

d) evaluating the subject for suitability to treatment, for example by determining the patency of the subject's GI tract, for example if the indication is small intestinal diseases, pancolitis, Crohn's disease, or if the patients has strictures or fistulae;

e) administration of an induction dose or of a maintenance dose of a drug, such as the IL-10 or IL-10 agonist or such as another drug that is effective in the treatment of IBD conditions;

f) monitoring the progress of the disease, for example with reference to the Mayo Clinic Score, the Crohn's Disease Activity Index (CDAI), the Harvey-Bradshaw Index (HBI), the PRO, PRO2 or PRO3 tools, or a combination of the above; and/or g) optionally repeating steps e) and f) one or more times, for example over a period of about 1-14 weeks, such as about 6-8 weeks following administration of the IL-10 or IL-10 agonist, including at the 6-8 week time point, or over a period of about 52 weeks following administration of the IL-10 or IL-10 agonist, including at the 52 week time point.

As used herein, an induction dose is a dose of drug that may be administered, for example, at the beginning of a course of treatment, and that is higher than the maintenance dose administered during treatment. An induction dose may also be administered during treatment, for example if the condition of the patients becomes worse.

As used herein, a maintenance dose is a dose of drug that is provided on a repetitive basis, for example at regular dosing intervals.

In some embodiments the IL-10 or IL-10 agonist is released from an ingestible device.

In some embodiments herein, the method of treating a disease of the gastrointestinal tract that comprises releasing IL-10 or an IL-10 agonist at a location in the gastrointestinal tract that is proximate to one or more sites of disease comprises a) hereinabove.

In some embodiments herein, the method of treating a disease of the gastrointestinal tract that comprises releasing IL-10 or an IL-10 agonist at a location in the gastrointestinal tract that is proximate to one or more sites of disease comprises b) hereinabove.

In some embodiments herein, the method of treating a disease of the gastrointestinal tract that comprises releasing IL-10 or an IL-10 agonist at a location in the gastrointestinal tract that is proximate to one or more sites of disease comprises c) hereinabove.

In some embodiments herein, the method of treating a disease of the gastrointestinal tract that comprises releasing IL-10 or an IL-10 agonist at a location in the gastrointestinal tract that is proximate to one or more sites of disease comprises d) hereinabove.

In some embodiments herein, the method of treating a disease of the gastrointestinal tract that comprises releasing IL-10 or an IL-10 agonist at a location in the gastrointestinal tract that is proximate to one or more sites of disease comprises e) hereinabove.

In some embodiments herein, the method of treating a disease of the gastrointestinal tract that comprises releasing IL-10 or an IL-10 agonist at a location in the gastrointestinal tract that is proximate to one or more sites of disease comprises f) hereinabove.

In some embodiments herein, the method of treating a disease of the gastrointestinal tract that comprises releasing IL-10 or an IL-10 agonist at a location in the gastrointestinal tract that is proximate to one or more sites of disease comprises g) hereinabove.

In some embodiments herein, the method of treating a disease of the gastrointestinal tract that comprises releasing IL-10 or an IL-10 agonist at a location in the gastrointestinal tract that is proximate to one or more sites of disease comprises a) and b) hereinabove. In some embodiments herein, the method of treating a disease of the gastrointestinal tract that comprises releasing IL-10 or an IL-10 agonist at a location in the gastrointestinal tract that is proximate to one or more sites of disease comprises a) and c) hereinabove. In some embodiments herein, the method of treating a disease of the gastrointestinal tract that comprises releasing IL-10 or an IL-10 agonist at a location in the gastrointestinal tract that is proximate to one or more sites of disease comprises a) and d) hereinabove. In some embodiments herein, the method of treating a disease of the gastrointestinal tract that comprises releasing IL-10 or an IL-10 agonist at a location in the gastrointestinal tract that is proximate to one or more sites of disease comprises a) and e) hereinabove. In some embodiments herein, the method of treating a disease of the gastrointestinal tract that comprises releasing IL-10 or an IL-10 agonist at a location in the gastrointestinal tract that is proximate to one or more sites of disease comprises a) and f) hereinabove. In some embodiments herein, the method of treating a disease of the gastrointestinal tract that comprises releasing IL-10 or an IL-10 agonist at a location in the gastrointestinal tract that is proximate to one or more sites of disease comprises a) and g) hereinabove. In some embodiments herein, the method of treating a disease of the gastrointestinal tract that comprises releasing IL-10 or an IL-10 agonist at a location in the gastrointestinal tract that is proximate to one or more sites of disease comprises b) and c) hereinabove. In some embodiments herein, the method of treating a disease of the gastrointestinal tract that comprises releasing IL-10 or an IL-10 agonist at a location in the gastrointestinal tract that is proximate to one or more sites of disease comprises b) and d) hereinabove. In some embodiments herein, the method of treating a disease of the gastrointestinal tract that comprises releasing IL-10 or an IL-10 agonist at a location in the gastrointestinal tract that is proximate to one or more sites of disease comprises b) and e) hereinabove. In some embodiments herein, the method of treating a disease of the gastrointestinal tract that comprises releasing IL-10 or an IL-10 agonist at a location in the gastrointestinal tract that is proximate to one or more sites of disease comprises b) and f) hereinabove. In some embodiments herein, the method of treating a disease of the gastrointestinal tract that comprises releasing IL-10 or an IL-10 agonist at a location in the gastrointestinal tract that is proximate to one or more sites of disease comprises b) and g) hereinabove. In some embodiments herein, the method of treating a disease of the gastrointestinal tract that comprises releasing IL-10 or an IL-10 agonist at a location in the gastrointestinal tract that is proximate to one or more sites of disease comprises c) and d) hereinabove. In some embodiments herein, the method of treating a disease of the gastrointestinal tract that comprises releasing IL-10 or an IL-10 agonist at a location in the gastrointestinal tract that is proximate to one or more sites of disease comprises c) and e) hereinabove. In some embodiments herein, the method of treating a disease of the gastrointestinal tract that comprises releasing IL-10 or an IL-10 agonist at a location in the gastrointestinal tract that is proximate to one or more sites of disease comprises c) and f) hereinabove. In some embodiments herein, the method of treating a disease of the gastrointestinal tract that comprises releasing IL-10 or an IL-10 agonist at a location in the gastrointestinal tract that is proximate to one or more sites of disease comprises c) and g) hereinabove. In some embodiments herein, the method of treating a disease of the gastrointestinal tract that comprises releasing IL-10 or an IL-10 agonist at a location in the gastrointestinal tract that is proximate to one or more sites of disease comprises d) and e) hereinabove. In some embodiments herein, the method of treating a disease of the gastrointestinal tract that comprises releasing IL-10 or an IL-10 agonist at a location in the gastrointestinal tract that is proximate to one or more sites of disease comprises d) and f) hereinabove. In some embodiments herein, the method of treating a disease of the gastrointestinal tract that comprises releasing IL-10 or an IL-10 agonist at a location in the gastrointestinal tract that is proximate to one or more sites of disease comprises d) and g) hereinabove. In some embodiments herein, the method of treating a disease of the gastrointestinal tract that comprises releasing IL-10 or an IL-10 agonist at a location in the gastrointestinal tract that is proximate to one or more sites of disease comprises e) and f) hereinabove. In some embodiments herein, the method of treating a disease of the gastrointestinal tract that comprises releasing IL-10 or an IL-10 agonist at a location in the gastrointestinal tract that is proximate to one or more sites of disease comprises g) hereinabove.

In some embodiments, one or more steps a) to e) herein comprise endoscopy of the gastrointestinal tract. In some embodiments, one or more steps a) to e) herein comprise colonoscopy of the gastrointestinal tract. In some embodiments, one or more steps a) to e) herein is performed one or more times. In some embodiments, such one or more of such one or more steps a) to e) is performed after releasing the IL-10 or IL-10 agonist at the location in the gastrointestinal tract that is proximate to one or more sites of disease.

In some embodiments, the method comprises administering one or more maintenance doses following administration of the induction dose in step e). In some embodiments an induction dose of the IL-10 or IL-10 agonist and a maintenance dose of the IL-10 or IL-10 agonist are each administered to the subject by administering a pharmaceutical composition comprising a therapeutically effective amount of the IL-10 or IL-10 agonist. In some embodiments an induction dose of the IL-10 or IL-10 agonist is administered to the subject in a different manner from the maintenance dose. As an example, the maintenance dose may be administered systemically, while the maintenance dose is administered locally using a device. In one embodiment, a maintenance dose is administered systemically, and an induction dose is administered using a device every 1, 2, 3, 4, 5, 6, 7, 10, 15, 20, 25, 30, 35, 40, or 45 days. In another embodiment, a maintenance dose is administered systemically, and an induction dose is administered when a disease flare up is detected or suspected.

In some embodiments, the induction dose is a dose of the IL-10 or IL-10 agonist administered in an ingestible device as disclosed herein. In some embodiments, the maintenance dose is a dose of the IL-10 or IL-10 agonist administered in an ingestible device as disclosed herein.

In some embodiments, the induction dose is a dose of the IL-10 or IL-10 agonist administered in an ingestible device as disclosed herein. In some embodiments, the maintenance dose is a dose of the IL-10 or IL-10 agonist delivered systemically, such as orally with a tablet or capsule, or subcutaneously, or intravenously.

In some embodiments, the induction dose is a dose of the IL-10 or IL-10 agonist delivered systemically, such as orally with a tablet or capsule, or subcutaneously, or intravenously. In some embodiments, the maintenance dose is a dose of the IL-10 or IL-10 agonist administered in an ingestible device as disclosed herein.

In some embodiments, the induction dose is a dose of the IL-10 or IL-10 agonist administered in an ingestible device as disclosed herein. In some embodiments, the maintenance dose is a dose of a second agent as disclosed herein delivered systemically, such as orally with a tablet or capsule, or subcutaneously, or intravenously.

In some embodiments, the induction dose is a dose of a second agent as disclosed herein delivered systemically, such as orally with a tablet or capsule, or subcutaneously, or intravenously. In some embodiments, the maintenance dose is a dose of the IL-10 or IL-10 agonist administered in an ingestible device as disclosed herein.

In one embodiment of the methods provided herein, the patient is not previously treated with IL-10 or an IL-10 agonist. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the Mayo Clinic Score <2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and >1-point decrease in rectal bleeding subscore or absolute rectal bleeding score of 0 or 1.

In some embodiments, the method comprises identifying the disease site substantially at the same time as releasing the IL-10 or IL-10 agonist.

In some embodiments, the method comprises monitoring the progress of the disease. In some embodiments, monitoring the progress of the disease comprises measuring the weight of the subject over a period of about 1-14 weeks, such as about 6-8 weeks following administration of the IL-10 or IL-10 agonist, including at the 6-8 week time point, or over a period of about 52 weeks following administration of the IL-10 or IL-10 agonist, including at the 52 week time point. In some embodiments, monitoring the progress of the disease comprises measuring the food intake of the subject; measuring the level of blood in the feces of the subject; measuring the level of abdominal pain of the subject; and/or a combination of the above, for example over a period of about 1-14 weeks, such as about 6-8 weeks following administration of the IL-10 or IL-10 agonist, including at the 6-8 week time point, or over a period of about 52 weeks following administration of the IL-10 or IL-10 agonist, including at the 52 week time point.

In some embodiments, the method comprises administering IL-10 or an IL-10 agonist with a spray catheter. For example, administering IL-10 or an IL-10 agonist with a spray catheter may be performed in step (e) hereinabove.

In some embodiments, the method does not comprise administering IL-10 or an IL-10 agonist with a spray catheter.

Pharmaceutical Formulations

As used herein, a "formulation" of IL-10 or an IL-10 agonist may refer to either the IL-10 or IL-10 agonist in pure form—such as, for example, the lyophilized IL-10 or IL-10 agonist—or a mixture of the IL-10 or IL-10 agonist with one or more physiologically acceptable carriers, excipients or stabilizers. Thus, therapeutic formulations or medicaments can be prepared by mixing the IL-10 or IL-10 agonist having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) antibody; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX<®>, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

A formulation of IL-10 or an IL-10 agonist as disclosed herein, e.g., sustained-release formulations, can further include a mucoadhesive agent, e.g., one or more of polyvinyl pyrolidine, methyl cellulose, sodium carboxyl methyl cellulose, hydroxyl propyl cellulose, carbopol, a polyacrylate, chitosan, a eudragit analogue, a polymer, and a thiomer. Additional examples of mucoadhesive agents that can be included in a formulation with IL-10 or an IL-10 agonist are described in, e.g., Peppas et al., *Biomaterials* 17(16):1553-1561, 1996; Kharenko et al., *Pharmaceutical Chemistry J.* 43(4):200-208, 2009; Salamat-Miller et al., *Adv. Drug Deliv. Reviews* 57(11):1666-1691, 2005; Bernkop-Schnurch, *Adv. Drug Deliv. Rev.* 57(11):1569-1582, 2005; and Harding et al., *Biotechnol. Genet. Eng. News* 16(1):41-86, 1999.

In some embodiments, components of a formulation may include any one of the following components, or any combination thereof:

Acacia, Alginate, Alginic Acid, Aluminum Acetate, an antiseptic, Benzyl Alcohol, Butyl Paraben, Butylated Hydroxy Toluene, an antioxidant. Citric acid, Calcium carbonate, Candelilla wax, a binder, Croscarmellose sodium, Confectioner sugar, Colloidal silicone dioxide, Cellulose, Carnuba wax, Corn starch, Carboxymethylcellulose calcium, Calcium stearate, Calcium disodium EDTA, Chelation agents, Copolyvidone, Castor oil hydrogenated, Calcium hydrogen phosphate dehydrate, Cetylpyridine chloride, Cysteine HCl, Crosspovidone, Dibasic Calcium Phosphate, Disodium hydrogen phosphate, Dimethicone, Erythrosine Sodium, Ethyl Cellulose, Gelatin, Glyceryl monooleate, Glycerin, Glycine, Glyceryl monostearate, Glyceryl behenate, Hydroxy propyl cellulose, Hydroxyl propyl methyl cellulose, Hypromellose, HPMC Pthalate, Iron oxides or ferric oxide, Iron oxide yellow, Iron oxide red or ferric oxide, Lactose (hydrous or anhydrous or monohydrate or spray dried), Magnesium stearate, Microcrystalline cellulose, Mannitol, Methyl cellulose, Magnesium carbonate, Mineral oil, Methacrylic acid copolymer, Magnesium oxide, Methyl paraben, PEG, Polysorbate 80, Propylene glycol, Polyethylene oxide, Propylene paraben, Polaxamer 407 or 188 or plain, Potassium bicarbonate, Potassium sorbate, Potato starch, Phosphoric acid, Polyoxy140 stearate, Sodium starch glycolate, Starch pregelatinized, Sodium crossmellose, Sodium lauryl sulfate, Starch, Silicon dioxide, Sodium benzoate, Stearic acid, Sucrose base for medicated confectionery, a granulating agent, Sorbic acid, Sodium carbonate, Saccharin sodium, Sodium alginate, Silica gel, Sorbiton monooleate, Sodium stearyl fumarate, Sodium chloride, Sodium metabisulfite, Sodium citrate dehydrate, Sodium starch, Sodium carboxy methyl cellulose, Succinic acid, Sodium propionate, Titanium dioxide, Talc, Triacetin, Triethyl citrate.

Accordingly, in some embodiments of the method of treating a disease as disclosed herein, the method comprises administering to the subject a pharmaceutical composition that is a formulation as disclosed herein. In some embodiments the formulation is a dosage form, which may be, as an example, a solid form such as, for example, a capsule, a tablet, a sachet, or a lozenge; or which may be, as an example, a liquid form such as, for example, a solution, a suspension, an emulsion, or a syrup.

In some embodiments the formulation is not comprised in an ingestible device. In some embodiments wherein the formulation is not comprised in an ingestible device, the formulation may be suitable for oral administration. The formulation may be, for example, a solid dosage form or a liquid dosage form as disclosed herein. In some embodiments wherein the formulation is not comprised in an ingestible device, the formulation may be suitable for rectal administration. The formulation may be, for example, a dosage form such as a suppository or an enema. In embodiments where the formulation is not comprised in an ingestible device, the formulation releases the IL-10 or IL-10 agonist at a location in the gastrointestinal tract of the subject that is proximate to one or more sites of disease. Such localized release may be achieved, for example, with a formulation comprising an enteric coating. Such localized release may be achieved, an another example, with a formulation comprising a core comprising one or more polymers suitable for controlled release of an active substance. A non-limiting list of such polymers includes: poly(2-(diethylamino)ethyl methacrylate, 2-(dimethylamino)ethyl methacrylate, poly(ethylene glycol), poly(2-aminoethyl methacrylate), (2-hydroxypropyl)methacrylamide, poly(β-benzyl-1-aspartate), poly(N-isopropylacrylamide), and cellulose derivatives.

In some embodiments the formulation is comprised in an ingestible device as disclosed herein. In some embodiments wherein the formulation is comprised in an ingestible device, the formulation may be suitable for oral administration. The formulation may be, for example, a solid dosage form or a liquid dosage form as disclosed herein. In some embodiments the formulation is suitable for introduction and optionally for storage in the device. In some embodiments the formulation is suitable for introduction and optionally for storage in the reservoir comprised in the device. In some embodiments the formulation is suitable for introduction and optionally for storage in the reservoir comprised in the device. Thus, in some embodiments, provided herein is a reservoir comprising a therapeutically effective amount of IL-10 or an IL-10 agonist, wherein the reservoir is configured to fit into an ingestible device. In some embodiments, the reservoir comprising a therapeutically effective amount of IL-10 or an IL-10 agonist is attachable to an ingestible device. In some embodiments, the reservoir comprising a therapeutically effective amount of IL-10 or an IL-10 agonist is capable of anchoring itself to the subject's tissue. As an example, the reservoir capable of anchoring itself to the subject's tissue comprises silicone. As an example, the reservoir capable of anchoring itself to the subject's tissue comprises polyvinyl chloride.

In some embodiments the formulation is suitable for introduction in the spray catheters disclosed herein.

The formulation/medicament herein may also contain more than one active compound as necessary for the particular indication being treated, for example, those with complementary activities that do not adversely affect each other. For instance, the formulation may further comprise another the IL-10 or IL-10 agonist or a chemotherapeutic agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the IL-10 or IL-10 agonist, which matrices are in the form of shaped articles, e.g., films, or microcapsule. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated IL-10 or IL-10 agonists remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical formulations may contain one or more IL-10 or IL-10 agonists. The pharmaceutical formulations may be formulated in any manner known in the art. In some embodiments the formulations include one or more of the following components: a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811, incorporated by reference herein in its entirety). The formulations can be formulated and enclosed in ampules, disposable syringes, or multiple dose vials. Where required, proper fluidity can be maintained by, for example, the use of a coating, such as lecithin, or a surfactant. Controlled release of the IL-10 or IL-10 agonist can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

In some embodiments, the IL-10 or IL-10 agonist is present in a pharmaceutical formulation within the device.

In some embodiments, the IL-10 or IL-10 agonist is present in solution within the device.

In some embodiments, the IL-10 or IL-10 agonist is present in a suspension in a liquid medium within the device.

In some embodiments, data obtained from cell culture assays and animal studies can be used in formulating an appropriate dosage of any given IL-10 or IL-10 agonist. The effectiveness and dosing of any IL-10 or IL-10 agonist can be determined by a health care professional or veterinary professional using methods known in the art, as well as by the observation of one or more disease symptoms in a subject (e.g., a human). Certain factors may influence the dosage and timing required to effectively treat a subject (e.g., the severity of the disease or disorder, previous treatments, the general health and/or age of the subject, and the presence of other diseases).

In some embodiments, the subject is further administered an additional therapeutic agent (e.g., any of the additional therapeutic agents described herein). The additional therapeutic agent can be administered to the subject at substantially the same time as the IL-10 or IL-10 agonist or pharmaceutical composition comprising it is administered and/or at one or more other time points. In some embodiments, the additional therapeutic agent is formulated together with the IL-10 or IL-10 agonist (e.g., using any of the examples of formulations described herein).

In some embodiments, the subject is administered a dose of the IL-10 or IL-10 agonist at least once a month (e.g., at least twice a month, at least three times a month, at least four times a month, at least once a week, at least twice a week, three times a week, once a day, or twice a day). The IL-10 or IL-10 agonist may be administered to a subject chronically. Chronic treatments include any form of repeated administration for an extended period of time, such as repeated administrations for one or more months, between a month and a year, one or more years, more than five years, more than 10 years, more than 15 years, more than 20 years, more than 25 years, more than 30 years, more than 35 years, more than 40 years, more than 45 years, or longer. Alternatively, or in addition, chronic treatments may be administered. Chronic treatments can involve regular administrations, for example one or more times a day, one or more times a week, or one or more times a month. For example, chronic treatment can include administration (e.g., intravenous administration) about every two weeks (e.g., between about every 10 to 18 days).

A suitable dose may be the amount that is the lowest dose effective to produce a desired therapeutic effect. Such an effective dose will generally depend upon the factors described herein. If desired, an effective daily dose of IL-10 or IL-10 agonist can be administered as two, three, four, five, or six or more sub-doses administered separately at appropriate intervals throughout the day, optionally, in unit dosage forms.

In some examples, administration of IL-10 or an IL-10 agonist using any of the compositions or devices described herein can result in the onset of treatment (e.g., a reduction in the number, severity, or duration of one or more symptoms and/or markers of any of the diseases described herein) or drug-target engagement in a subject within a time period of about 10 minutes to about 10 hours, about 10 minutes to about 9 hours, about 10 minutes to about 8 hours, about 10 minutes to about 7 hours, about 10 minutes to about 6 hours, about 10 minutes to about 5 hours, about 10 minutes to about 4.5 hours, about 10 minutes to about 4 hours, about 10 minutes to about 3.5 hours, about 10 minutes to about 3 hours, about 10 minutes to about 2.5 hours, about 10 minutes to about 2 hours, about 10 minutes to about 1.5 hours, about 10 minutes to about 1 hour, about 10 minutes to about 55 minutes, about 10 minutes to about 50 minutes, about 10 minutes to about 45 minutes, about 10 minutes to about 40 minutes, about 10 minutes to about 35 minutes, about 10 minutes to about 30 minutes, about 10 minutes to about 25 minutes, about 10 minutes to about 20 minutes, about 10 minutes to about 15 minutes, about 15 minutes to about 10 hours, about 15 minutes to about 9 hours, about 15 minutes to about 8 hours, about 15 minutes to about 7 hours, about 15 minutes to about 6 hours, about 15 minutes to about 5 hours, about 15 minutes to about 4.5 hours, about 15 minutes to about 4 hours, about 15 minutes to about 3.5 hours, about 15 minutes to about 3 hours, about 15 minutes to about 2.5 hours, about 15 minutes to about 2 hours, about 15 minutes to about 1.5 hours, about 15 minutes to about 1 hour, about 15 minutes to about 55 minutes, about 15 minutes to about 50 minutes, about 15 minutes to about 45 minutes, about 15 minutes to about 40 minutes, about 15 minutes to about 35 minutes, about 15 minutes to about 30 minutes, about 15 minutes to about 25 minutes, about 15 minutes to about 20 minutes, about 20 minutes to about 10 hours, about 20 minutes to about 9 hours, about 20 minutes to about 8 hours, about 20 minutes to about 7 hours, about 20 minutes to about 6 hours, about 20 minutes to about 5 hours, about 20 minutes to about 4.5 hours, about 20 minutes to about 4 hours, about 20 minutes to about 3.5 hours, about 20 minutes to about 3 hours, about 20 minutes to about 2.5 hours, about 20 minutes to about 2 hours, about 20 minutes to about 1.5 hours, about 20 minutes to about 1 hour, about 20 minutes to about 55 minutes, about 20 minutes to about 50 minutes, about 20 minutes to about 45 minutes, about 20 minutes to about 40 minutes, about 20 minutes to about 35 minutes, about 20 minutes to about 30 minutes, about 20 minutes to about 25 minutes, about 25 minutes to about 10 hours, about 25 minutes to about 9 hours, about 25 minutes to about 8 hours, about 25 minutes to about 7 hours, about 25 minutes to about 6 hours, about 25 minutes to about 5 hours, about 25 minutes to about 4.5 hours, about 25 minutes to about 4 hours, about 25 minutes to about 3.5 hours, about 25 minutes to about 3 hours, about 25 minutes to about 2.5 hours, about 25 minutes to about 2 hours, about 25 minutes to about 1.5 hours, about 25 minutes to about 1 hour, about 25 minutes to about 55 minutes, about 25 minutes to about 50 minutes, about 25 minutes to about 45 minutes, about 25 minutes to about 40 minutes, about 25 minutes to about 35 minutes, about 25 minutes to about 30 minutes, about 30 minutes to about 10 hours, about 30 minutes to about 9 hours, about 30 minutes to about 8 hours, about 30 minutes to about 7 hours, about 30 minutes to about 6 hours, about 30 minutes to about 5 hours, about 30 minutes to about 4.5 hours, about 30 minutes to about 4 hours, about 30 minutes to about 3.5 hours, about 30 minutes to about 3 hours, about 30 minutes to about 2.5 hours, about 30 minutes to about 2 hours, about 30 minutes to about 1.5 hours, about 30 minutes to about 1 hour, about 30 minutes to about 55 minutes, about 30 minutes to about 50 minutes, about 30 minutes to about 45 minutes, about 30 minutes to about 40 minutes, about 30 minutes to about 35 minutes, about 35 minutes to about 10 hours, about 35 minutes to about 9 hours, about 35 minutes to about 8 hours, about 35 minutes to about 7 hours, about 35 minutes to about 6 hours, about 35 minutes to about 5 hours, about 35 minutes to about 4.5 hours, about 35 minutes to about 4 hours, about 35 minutes to about 3.5 hours, about 35 minutes to about 3 hours, about 35 minutes to about 2.5 hours, about 35 minutes to about 2 hours, about 35 minutes to about 1.5 hours, about 35 minutes to about 1 hour, about 35 minutes to about 55 minutes, about 35 minutes to about 50 minutes, about 35 minutes to about 45 minutes, about 35 minutes to about 40 minutes, about 40 minutes to about 10 hours, about 40 minutes to about 9 hours, about 40 minutes to about 8 hours, about 40 minutes to about 7 hours, about 40 minutes to about 6 hours, about 40 minutes to about 5 hours, about 40 minutes to about 4.5 hours, about 40 minutes to about 4 hours, about 40 minutes to about 3.5 hours, about 40 minutes to about 3 hours, about 40 minutes to about 2.5 hours, about 40 minutes to about 2 hours, about 40 minutes to about 1.5 hours, about 40 minutes to about 1 hour, about 40 minutes to about 55 minutes, about 40 minutes to about 50 minutes, about 40 minutes to about 45 minutes, about 45 minutes to about 10 hours, about 45 minutes to about 9 hours, about 45 minutes to about 8 hours, about 45 minutes to about 7 hours, about 45 minutes to about 6 hours, about 45 minutes to about 5 hours, about 45 minutes to about 4.5 hours, about 45 minutes to about 4 hours, about 45 minutes to about 3.5 hours, about 45 minutes to about 3 hours, about 45 minutes to about 2.5 hours, about 45 minutes to about 2 hours, about 45 minutes to about 1.5 hours, about 45 minutes to about 1 hour, about 45 minutes to about 55 minutes, about 45 minutes to about 50 minutes, about 50 minutes to about 10 hours, about 50 minutes to about 9 hours, about 50 minutes to about 8 hours, about 50 minutes to about 7 hours, about 50 minutes to about 6 hours, about 50 minutes to about 5 hours, about 50 minutes to about 4.5 hours, about 50 minutes to about 4 hours, about 50 minutes to about 3.5 hours, about 50 minutes to about 3 hours, about 50 minutes to about 2.5 hours, about 50 minutes to about 2 hours, about 50 minutes to about 1.5 hours, about 50 minutes to about 1 hour, about 50 minutes to about 55 minutes, about 55 minutes to about 10 hours, about 55 minutes to about 9 hours, about 55 minutes to about 8 hours, about 55 minutes to about 7 hours, about 55 minutes to about 6 hours, about 55 minutes to about 5 hours, about 55 minutes to about 4.5 hours, about 55 minutes to about 4 hours, about 55 minutes to about 3.5 hours, about 55 minutes to about 3 hours, about 55 minutes to about 2.5 hours, about 55 minutes to about 2 hours, about 55 minutes to about 1.5 hours, about 55 minutes to about 1 hour, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4.5 hours, about 1 hour to about 4 hours, about 1 hour to about 3.5 hours, about 1 hour to about 3 hours, about 1 hour to about 2.5 hours, about 1 hour to about 2 hours, about 1 hour to about 1.5 hours, about 1.5 hours to about 10 hours, about 1.5 hours to about 9 hours, about 1.5 hours to about 8 hours, about 1.5 hours to about 7 hours, about 1.5 hours to about 6 hours, about 1.5 hours to about 5 hours, about 1.5 hours to about 4.5 hours, about 1.5 hours to about 4 hours, about 1.5 hours to about 3.5 hours, about 1.5 hours to about 3 hours, about 1.5 hours to about 2.5 hours, about 1.5 hours to about 2 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4.5 hours, about 2 hours to about 4 hours, about 2 hours to about 3.5 hours, about 2 hours to about 3 hours, about 2 hours to about 2.5 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5 hours, about 2.5 hours to about 4.5 hours, about 2.5 hours to about 4 hours, about 2.5 hours to about 3.5 hours, about 2.5 hours to about 3 hours, about 3 hours to about 10 hours, about 3 hours to about 9 hours, about 3 hours to about 8 hours, about 3 hours to about 7 hours, about 3 hours to about 6 hours, about 3 hours to about 5 hours, about 3 hours to about 4.5 hours, about 3 hours to about 4 hours, about 3 hours to about 3.5 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5 hours, about 3.5 hours to about 4.5 hours, about 3.5 hours to about 4 hours, about 4 hours to about 10 hours, about 4 hours to about 9 hours, about 4 hours to about 8 hours, about 4 hours to about 7 hours, about 4 hours to about 6 hours, about 4 hours to about 5 hours, about 4 hours to about 4.5 hours, about 4.5 hours to about 10 hours, about 4.5 hours to about 9 hours, about 4.5 hours to about 8 hours, about 4.5 hours to about 7 hours, about 4.5 hours to about 6 hours, about 4.5 hours to about 5 hours, about 5 hours to about 10 hours, about 5 hours to about 9 hours, about 5 hours to about 8 hours, about 5 hours to about 7 hours, about 5 hours to about 6 hours, about 6 hours to about 10 hours, about 6 hours to about 9 hours, about 6 hours to about 8 hours, about 6 hours to about 7 hours, about 7 hours to about 10 hours, about 7 hours to about 9 hours, about 7 hours to about 8 hours, about 8 hours to about 10 hours, about 8 hours to about 9 hours, or about 9 hours to about 10 hours of administration of a dose of IL-10 or an IL-10 agonist using any of the devices or compositions described herein. Drug-target engagement may be determined, for example, as disclosed in Simon G M, Niphakis M J, Cravatt B F, *Nature chemical biology.* 2013; 9(4):200-205, incorporated by reference herein in its entirety.

In some embodiments, administration of IL-10 or an IL-10 agonist using any of the devices or compositions described herein can provide for treatment (e.g., a reduction in the number, severity, and/or duration of one or more symptoms and/or markers of any of the disorders described herein in a subject) for a time period of between about 1 hour to about 30 days, about 1 hour to about 28 days, about 1 hour to about 26 days, about 1 hour to about 24 days, about 1 hour to about 22 days, about 1 hour to about 20 days, about 1 hour to about 18 days, about 1 hour to about 16 days, about 1 hour to about 14 days, about 1 hour to about 12 days, about 1 hour to about 10 days, about 1 hour to about 8 days, about 1 hour to about 6 days, about 1 hour to about 5 days, about 1 hour to about 4 days, about 1 hour to about 3 days, about 1 hour to about 2 days, about 1 hour to about 1 day, about 1 hour to about 12 hours, about 1 hour to about 6 hours, about 1 hour to about 3 hours, about 3 hours to about 30 days, about 3 hours to about 28 days, about 3 hours to about 26 days, about 3 hours to about 24 days, about 3 hours to about 22 days, about 3 hours to about 20 days, about 3 hours to about 18 days, about 3 hours to about 16 days, about 3 hours to about 14 days, about 3 hours to about 12 days, about 3 hours to about 10 days, about 3 hours to about 8 days, about 3 hours to about 6 days, about 3 hours to about 5 days, about 3 hours to about 4 days, about 3 hours to about 3 days, about 3 hours to about 2 days, about 3 hours to about 1 day, about 3 hours to about 12 hours, about 3 hours to about 6 hours, about 6 hours to about 30 days, about 6 hours to about 28 days, about 6 hours to about 26 days, about 6 hours to about 24 days, about 6 hours to about 22 days, about 6 hours to about 20 days, about 6 hours to about 18 days, about 6 hours to about 16 days, about 6 hours to about 14 days, about 6 hours to about 12 days, about 6 hours to about 10 days, about 6 hours to about 8 days, about 6 hours to about 6 days, about 6 hours to about 5 days, about 6 hours to about 4 days, about 6 hours to about 3 days, about 6 hours to about 2 days, about 6 hours to about 1 day, about 6 hours to about 12 hours, about 12 hours to about 30 days, about 12 hours to about 28 days, about 12 hours to about 26 days, about 12 hours to about 24 days, about 12 hours to about 22 days, about 12 hours to about 20 days, about 12 hours to about 18 days, about 12 hours to about 16 days, about 12 hours to about 14 days, about 12 hours to about 12 days, about 12 hours to about 10 days, about 12 hours to about 8 days, about 12 hours to about 6 days, about 12 hours to about 5 days, about 12 hours to about 4 days, about 12 hours to about 3 days, about 12 hours to about 2 days, about 12 hours to about 1 day, about 1 day to about 30 days, about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 20 days, about 3 days to about 18 days, about 3 days to about 16 days, about 3 days to about 14 days, about 3 days to about 12 days, about 3 days to about 10 days, about 3 days to about 8 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 6 days, about 6 days to about 30 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 8 days to about 30 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 8 days to about 10 days, about 10 days to about 30 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 30 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 30 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 30 days, about 16 days to about 28 days, about 16 days to about 26 days, about 16 days to about 24 days, about 16 days to about 22 days, about 16 days to about 20 days, about 16 days to about 18 days, about 18 days to about 30 days, about 18 days to about 28 days, about 18 days to about 26 days, about 18 days to about 24 days, about 18 days to about 22 days, about 18 days to about 20 days, about 20 days to about 30 days, about 20 days to about 28 days, about 20 days to about 26 days, about 20 days to about 24 days, about 20 days to about 22 days, about 22 days to about 30 days, about 22 days to about 28 days, about 22 days to about 26 days, about 22 days to about 24 days, about 24 days to about 30 days, about 24 days to about 28 days, about 24 days to about 26 days, about 26 days to about 30 days, about 26 days to about 28 days, or about 28 days to about 30 days in a subject following first administration of IL-10 or an IL-10 agonist using any of the compositions or devices described herein. Non-limiting examples of symptoms and/or markers of a disease described herein are described below.

For example, treatment can result in a decrease (e.g., about 1% to about 99% decrease, about 1% to about 95% decrease, about 1% to about 90% decrease, about 1% to about 85% decrease, about 1% to about 80% decrease, about 1% to about 75% decrease, about 1% to about 70% decrease, about 1% to about 65% decrease, about 1% to about 60% decrease, about 1% to about 55% decrease, about 1% to about 50% decrease, about 1% to about 45% decrease, about 1% to about 40% decrease, about 1% to about 35% decrease, about 1% to about 30% decrease, about 1% to about 25% decrease, about 1% to about 20% decrease, about 1% to about 15% decrease, about 1% to about 10% decrease, about 1% to about 5% decrease, about 5% to about 99% decrease, about 5% to about 95% decrease, about 5% to about 90% decrease, about 5% to about 85% decrease, about 5% to about 80% decrease, about 5% to about 75% decrease, about 5% to about 70% decrease, about 5% to about 65% decrease, about 5% to about 60% decrease, about 5% to about 55% decrease, about 5% to about 50% decrease, about 5% to about 45% decrease, about 5% to about 40% decrease, about 5% to about 35% decrease, about 5% to about 30% decrease, about 5% to about 25% decrease, about 5% to about 20% decrease, about 5% to about 15% decrease, about 5% to about 10% decrease, about 10% to about 99% decrease, about 10% to about 95% decrease, about 10% to about 90% decrease, about 10% to about 85% decrease, about 10% to about 80% decrease, about 10% to about 75% decrease, about 10% to about 70% decrease, about 10% to about 65% decrease, about 10% to about 60% decrease, about 10% to about 55% decrease, about 10% to about 50% decrease, about 10% to about 45% decrease, about 10% to about 40% decrease, about 10% to about 35% decrease, about 10% to about 30% decrease, about 10% to about 25% decrease, about 10% to about 20% decrease, about 10% to about 15% decrease, about 15% to about 99% decrease, about 15% to about 95% decrease, about 15% to about 90% decrease, about 15% to about 85% decrease, about 15% to about 80% decrease, about 15% to about 75% decrease, about 15% to about 70% decrease, about 15% to about 65% decrease, about 15% to about 60% decrease, about 15% to about 55% decrease, about 15% to about 50% decrease, about 15% to about 45% decrease, about 15% to about 40% decrease, about 15% to about 35% decrease, about 15% to about 30% decrease, about 15% to about 25% decrease, about 15% to about 20% decrease, about 20% to about 99% decrease, about 20% to about 95% decrease, about 20% to about 90% decrease, about 20% to about 85% decrease, about 20% to about 80% decrease, about 20% to about 75% decrease, about 20% to about 70% decrease, about 20% to about 65% decrease, about 20% to about 60% decrease, about 20% to about 55% decrease, about 20% to about 50% decrease, about 20% to about 45% decrease, about 20% to about 40% decrease, about 20% to about 35% decrease, about 20% to about 30% decrease, about 20% to about 25% decrease, about 25% to about 99% decrease, about 25% to about 95% decrease, about 25% to about 90% decrease, about 25% to about 85% decrease, about 25% to about 80% decrease, about 25% to about 75% decrease, about 25% to about 70% decrease, about 25% to about 65% decrease, about 25% to about 60% decrease, about 25% to about 55% decrease, about 25% to about 50% decrease, about 25% to about 45% decrease, about 25% to about 40% decrease, about 25% to about 35% decrease, about 25% to about 30% decrease, about 30% to about 99% decrease, about 30% to about 95% decrease, about 30% to about 90% decrease, about 30% to about 85% decrease, about 30% to about 80% decrease, about 30% to about 75% decrease, about 30% to about 70% decrease, about 30% to about 65% decrease, about 30% to about 60% decrease, about 30% to about 55% decrease, about 30% to about 50% decrease, about 30% to about 45% decrease, about 30% to about 40% decrease, about 30% to about 35% decrease, about 35% to about 99% decrease, about 35% to about 95% decrease, about 35% to about 90% decrease, about 35% to about 85% decrease, about 35% to about 80% decrease, about 35% to about 75% decrease, about 35% to about 70% decrease, about 35% to about 65% decrease, about 35% to about 60% decrease, about 35% to about 55% decrease, about 35% to about 50% decrease, about 35% to about 45% decrease, about 35% to about 40% decrease, about 40% to about 99% decrease, about 40% to about 95% decrease, about 40% to about 90% decrease, about 40% to about 85% decrease, about 40% to about 80% decrease, about 40% to about 75% decrease, about 40% to about 70% decrease, about 40% to about 65% decrease, about 40% to about 60% decrease, about 40% to about 55% decrease, about 40% to about 50% decrease, about 40% to about 45% decrease, about 45% to about 99% decrease, about 45% to about 95% decrease, about 45% to about 90% decrease, about 45% to about 85% decrease, about 45% to about 80% decrease, about 45% to about 75% decrease, about 45% to about 70% decrease, about 45% to about 65% decrease, about 45% to about 60% decrease, about 45% to about 55% decrease, about 45% to about 50% decrease, about 50% to about 99% decrease, about 50% to about 95% decrease, about 50% to about 90% decrease, about 50% to about 85% decrease, about 50% to about 80% decrease, about 50% to about 75% decrease, about 50% to about 70% decrease, about 50% to about 65% decrease, about 50% to about 60% decrease, about 50% to about 55% decrease, about 55% to about 99% decrease, about 55% to about 95% decrease, about 55% to about 90% decrease, about 55% to about 85% decrease, about 55% to about 80% decrease, about 55% to about 75% decrease, about 55% to about 70% decrease, about 55% to about 65% decrease, about 55% to about 60% decrease, about 60% to about 99% decrease, about 60% to about 95% decrease, about 60% to about 90% decrease, about 60% to about 85% decrease, about 60% to about 80% decrease, about 60% to about 75% decrease, about 60% to about 70% decrease, about 60% to about 65% decrease, about 65% to about 99% decrease, about 65% to about 95% decrease, about 65% to about 90% decrease, about 65% to about 85% decrease, about 65% to about 80% decrease, about 65% to about 75% decrease, about 65% to about 70% decrease, about 70% to about 99% decrease, about 70% to about 95% decrease, about 70% to about 90% decrease, about 70% to about 85% decrease, about 70% to about 80% decrease, about 70% to about 75% decrease, about 75% to about 99% decrease, about 75% to about 95% decrease, about 75% to about 90% decrease, about 75% to about 85% decrease, about 75% to about 80% decrease, about 80% to about 99% decrease, about 80% to about 95% decrease, about 80% to about 90% decrease, about 80% to about 85% decrease, about 85% to about 99% decrease, about 85% to about 95% decrease, about 85% to about 90% decrease, about 90% to about 99% decrease, about 90% to about 95% decrease, or about 95% to about 99% decrease) in one or more (e.g., two, three, four, five, six, seven, eight, or nine) of: the level of interferon-γ in GI tissue, the level of IL-1β in GI tissue, the level of IL-6 in GI tissue, the level of IL-22 in GI tissue, the level of IL-17A in GI tissue, the level of TNFα in GI tissue, the level of IL-2 in GI tissue, and endoscopy score in a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of IL-10 or an IL-10 agonist using any of the compositions or devices described herein. As used herein, "GI tissue" refers to tissue in the gastrointestinal (GI) tract, such as tissue in one or more of duodenum, jejunum, ileum, cecum, ascending colon, transverse colon, descending colon, sigmoid colon, and rectum, more particularly in the proximal portion of one or more of duodenum, jejunum, ileum, cecum, ascending colon, transverse colon, descending colon, and sigmoid colon, or in the distal portion of one or more of duodenum, jejunum, ileum, cecum, ascending colon, transverse colon, descending colon, and sigmoid colon. The GI tissue may be, for example, GI tissue proximate to one or more sites of disease. Exemplary methods for determining the endoscopy score are described herein and other methods for determining the endoscopy score are known in the art. Exemplary methods for determining the levels of interferon-γ, IL-1β, IL-6, IL-22, IL-17A, TNFα, and IL-2 are described herein. Additional methods for determining the levels of these cytokines are known in the art.

In some examples, treatment can result in an increase (e.g., about 1% to about 500% increase, about 1% to about 400% increase, about 1% to about 300% increase, about 1% to about 200% increase, about 1% to about 150% increase, about 1% to about 100% increase, about 1% to about 90% increase, about 1% to about 80% increase, about 1% to about 70% increase, about 1% to about 60% increase, about 1% to about 50% increase, about 1% to about 40% increase, about 1% to about 30% increase, about 1% to about 20% increase, about 1% to about 10% increase, a 10% to about 500% increase, about 10% to about 400% increase, about 10% to about 300% increase, about 10% to about 200% increase, about 10% to about 150% increase, about 10% to about 100% increase, about 10% to about 90% increase, about 10% to about 80% increase, about 10% to about 70% increase, about 10% to about 60% increase, about 10% to about 50% increase, about 10% to about 40% increase, about 10% to about 30% increase, about 10% to about 20% increase, about 20% to about 500% increase, about 20% to about 400% increase, about 20% to about 300% increase, about 20% to about 200% increase, about 20% to about 150% increase, about 20% to about 100% increase, about 20% to about 90% increase, about 20% to about 80% increase, about 20% to about 70% increase, about 20% to about 60% increase, about 20% to about 50% increase, about 20% to about 40% increase, about 20% to about 30% increase, about 30% to about 500% increase, about 30% to about 400% increase, about 30% to about 300% increase, about 30% to about 200% increase, about 30% to about 150% increase, about 30% to about 100% increase, about 30% to about 90% increase, about 30% to about 80% increase, about 30% to about 70% increase, about 30% to about 60% increase, about 30% to about 50% increase, about 30% to about 40% increase, about 40% to about 500% increase, about 40% to about 400% increase, about 40% to about 300% increase, about 40% to about 200% increase, about 40% to about 150% increase, about 40% to about 100% increase, about 40% to about 90% increase, about 40% to about 80% increase, about 40% to about 70% increase, about 40% to about 60% increase, about 40% to about 50% increase, about 50% to about 500% increase, about 50% to about 400% increase, about 50% to about 300% increase, about 50% to about 200% increase, about 50% to about 150% increase, about 50% to about 100% increase, about 50% to about 90% increase, about 50% to about 80% increase, about 50% to about 70% increase, about 50% to about 60% increase, about 60% to about 500% increase, about 60% to about 400% increase, about 60% to about 300% increase, about 60% to about 200% increase, about 60% to about 150% increase, about 60% to about 100% increase, about 60% to about 90% increase, about 60% to about 80% increase, about 60% to about 70% increase, about 70% to about 500% increase, about 70% to about 400% increase, about 70% to about 300% increase, about 70% to about 200% increase, about 70% to about 150% increase, about 70% to about 100% increase, about 70% to about 90% increase, about 70% to about 80% increase, about 80% to about 500% increase, about 80% to about 400% increase, about 80% to about 300% increase, about 80% to about 200% increase, about 80% to about 150% increase, about 80% to about 100% increase, about 80% to about 90% increase, about 90% to about 500% increase, about 90% to about 400% increase, about 90% to about 300% increase, about 90% to about 200% increase, about 90% to about 150% increase, about 90% to about 100% increase, about 100% to about 500% increase, about 100% to about 400% increase, about 100% to about 300% increase, about 100% to about 200% increase, about 100% to about 150% increase, about 150% to about 500% increase, about 150% to about 400% increase, about 150% to about 300% increase, about 150% to about 200% increase, about 200% to about 500% increase, about 200% to about 400% increase, about 200% to about 300% increase, about 300% to about 500% increase, about 300% to about 400% increase, or about 400% to about 500% increase) in one or both of stool consistency score and weight of a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of IL-10 or an IL-10 agonist using any of the compositions or devices described herein. Exemplary methods for determining stool consistency score are described herein. Additional methods for determining a stool consistency score are known in the art.

Accordingly, in some embodiments, a method of treatment disclosed herein includes determining the level of a marker at the location of disease in a subject (e.g., either before and/or after administration of the device). In some embodiments, the marker is a biomarker and the method of treatment disclosed herein comprises determining that the level of a biomarker at the location of disease is a subject following administration of the device is decreased as compared to the level of the biomarker at the same location of disease in a subject either before administration or at the same time point following systemic administration of an equal amount of the IL-10 or IL-10 agonist. In some examples, the level of the biomarker at the same location of disease following administration of the device is 1% decreased to 99% decreased as compared to the level of the biomarker at the same location of disease in a subject either before administration or at the same time point following systemic administration of an equal amount of the IL-10 or IL-10 agonist. In some embodiments, the level of the marker is one or more of: the level of interferon-γ in GI tissue, the level of IL-17A in the GI tissue, the level of TNFα in the GI tissue, the level of IL-2 in the GI tissue, and the endoscopy score in a subject.

In some embodiments, the method of treatment disclosed herein includes determining that the level of a marker at a time point following administration of a device is lower than the level of the marker at a time point following administration of the device is lower than the level of the marker in a subject prior to administration of the device or in a subject at substantially the same time point following systemic administration of an equal amount of the IL-10 or IL-10 agonist. In some examples, the level of the marker following administration of the device is 1% decreased to 99% decreased as compared to the level of the marker in a subject prior to administration of the device or in a subject at the same time point following systemic administration of an equal amount of the IL-10 or IL-10 agonist. In some examples, a method of treatment disclosed herein includes determining the level of the biomarker at the location of disease in a subject within a time period of about 10 minutes to 10 hours following administration of the device.

In some embodiments, a method of treatment described herein includes: (i) determining the ratio $R_B$ of the level $L_{1B}$ of a biomarker at the location of disease at a first time point following administration of the device and the level $L_{2B}$ of the biomarker at the same location of disease in a subject at substantially the same time point following systemic administration of an equal amount of the IL-10 or IL-10 agonist; (ii) determining the ratio of $R_D$ of the level of $L_{1D}$ of the IL-10 or IL-10 agonist at the same location and the substantially the same time point as in (i) and the level $L_{2D}$ of the IL-10 or IL-10 agonist at the same location of disease in a subject at substantially the same time point following systemic administration of an equal amount of the IL-10 or IL-10 agonist; and (iii) determining the ratio of $R_B/R_D$.

In some embodiments, a method of treatment disclosed herein can include: (i) determining the ratio $R_B$ of the level $L_{1B}$ of a biomarker at the location of disease at a time point following administration of the device and the level $L_{2B}$ of the biomarker at the same location of disease in a subject at substantially the same time point following systemic administration of an equal amount of the IL-10 or IL-10 agonist; (ii) determining the ratio $R_D$ of the level $L_{1D}$ of the IL-10 or IL-10 agonist at the same location and at substantially the time point as in (i) and the level $L_2D$ of the IL-10 or IL-10 agonist in a subject at the same location of disease at substantially the same time point following systemic administration of an equal amount of the IL-10 or IL-10 agonist; and (iii) determining the product $R_B \times R_D$.

In some embodiments, a method of treatment disclosed herein can include determining that the level of a marker in a subject at a time point following administration of the device is elevated as compared to a level of the marker in a subject prior to administration of the device or a level at substantially the same time point in a subject following systemic administration of an equal amount of the IL-10 or IL-10 agonist. In some examples, the level of the marker at a time point following administration of the device is 1% increased or 400% increased as compared to the level of the marker in a subject prior to administration of the device or a level at substantially the same time point in a subject following systemic administration of an equal amount of the IL-10 or IL-10 agonist. In some examples, the level of the marker is one or more of subject weight and stool consistency (e.g., stool consistency score). In some examples, a method of treatment disclosed herein includes determining the level of the marker in a subject within a period of about 10 minutes to about 10 hours following administration of the device.

In some embodiments, a method of treatment disclosed herein can include determining the level of a marker in a subject's blood, serum or plasma.

An illustrative list of examples of biomarkers for GI disorders includes interferon-γ, IL-1β, IL-6, IL-22, IL-17A, TNFα, IL-2, memory cells (CD44$^+$CD45RB$^-$CD4$^+$ cells); α4β7; VEGF; ICAM; VCAM; SAA; Calprotectin; lactoferrin; FGF2; TGFb; ANG-1; ANG-2; PLGF; Biologics (Infliximab; Humira; Stelara; Vedolizumab; Simponi; Jak inhibitors; Others); EGF; IL12/23p40; GMCSF; A4 B7; AeB7; CRP; SAA; ICAM; VCAM; AREG; EREG; HB-EGF; HRG; BTC; TGFα; SCF; TWEAK; MMP-9; MMP-6; Ceacam CD66; IL10; ADA; Madcam-1; CD166 (AL CAM); FGF2; FGF7; FGF9; FGF19; ANCA Antineutrophil cytoplasmic antibody; ASCAA Anti-*Saccharomyces Cerevisiae* Antibody IgA; ASCAG Anti-*Saccharomyces Cerevisiae* Antibody IgG; CBir1 Anti-*Clostridium* cluster XIVa flagellin CBir1 antibody; A4-Fla2 Anti-*Clostridium* cluster XIVa flagellin 2 antibody; FlaX Anti-*Clostridium* cluster XIVa flagellin X antibody; OmpC Anti-*Escherichia coli* Outer Membrane Protein C; ANCA Perinuclear AntiNeutrophil Cytoplasmic Antibody; AREG Amphiregulin Protein; BTC Betacellulin Protein; EGF Epidermal Growth Factor EREG Epiregulin Protein; HBEGF Heparin Binding Epidermal Growth Factors; HGF Hepatocyte Growth Factor; HRG Neuregulin-1; TGFA Transforming Growth Factor alpha; CRP C-Reactive Protein; SAA Serum Amyloid A; ICAM-1 Intercellular Adhesion Molecule 1; VCAM-1 Vascular Cell Adhesion Molecule 1; fibroblasts underlying the intestinal epithelium; and HGF.

In some embodiments, a marker is an IBD biomarker, such as, for example: anti-glycan; anti-*Saccharomices cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbir1 flagellin; anti-12 antibody; autoantibodies targeting the exocrine pancreas (PAB); and perinuclear anti-neutrophil antibody (pANCA); and calprotectin.

In some embodiments, a biomarker is associated with membrane repair, fibrosis, angiogenesis. In certain embodiments, a biomarker is an inflammatory biomarker, an anti-inflammatory biomarker, an MMP biomarker, an immune marker, or a TNF pathway biomarker. In some embodiments, a biomarker is gut specific.

For tissue samples, HER2 can be used as a biomarker relating to cytotoxic T cells. Additionally, other cytokine levels can be used as biomarkers in tissue (e.g., phospho STAT 1, STAT 3 and STAT 5), in plasma (e.g., VEGF, VCAM, ICAM, IL-6), or both.

In some embodiments, the biomarkers include one or more immunoglobulins, such as, for example, immunoglobulin M (IgM), immunoglobulin D (IgD), immunoglobulin G (IgG), immunoglobulin E (IgE) and/or immunoglobulin A (IgA). In some embodiments, IgM is a biomarker of infection and/or inflammation. In some embodiments, IgD is a biomarker of autoimmune disease. In some embodiments, IgG is a biomarker of Alzheimer's disease and/or for cancer. In some embodiments, IgE is a biomarker of asthma and/or allergen immunotherapy. In some embodiments, IgA is a biomarker of kidney disease.

In some embodiments, the biomarker is High Sensitivity C-reactive Protein (hsCRP); 7 α-hydroxy-4-cholesten-3-one (7C4); Anti-Endomysial IgA (EMA IgA); Anti-Human Tissue Transglutaminase IgA (tTG IgA); Total Serum IgA by Nephelometry; Fecal Calprotectin; or Fecal Gastrointestinal Pathogens.

In some embodiments, the biomarker is
a) an anti-gliadin IgA antibody, an anti-gliadin IgG antibody, an anti-tissue transglutaminase (tTG) antibody, an anti-endomysial antibody;
b) i) a serological marker that is ASCA-A, ASCA-G, ANCA, pANCA, anti-OmpC antibody, anti-CBir1 antibody, anti-FlaX antibody, or anti-A4-Fla2 antibody;
b) ii) an inflammation marker that is VEGF, ICAM, VCAM, SAA, or CRP;
b) iii) the genotype of the genetic markers ATG16L1, ECM1, NKX2-3, or STAT3;
c) a bacterial antigen antibody marker;
d) a mast cell marker;
e) an inflammatory cell marker;
f) a bile acid malabsorption (BAM) marker;
g) a kynurenine marker;
or
h) a serotonin marker.

In some embodiments, the bacterial antigen antibody marker is selected from the group consisting of an anti-Fla1 antibody, anti-Fla2 antibody, anti-FlaA antibody, anti-FliC antibody, anti-FliC2 antibody, anti-FliC3 antibody, anti-YBaN1 antibody, anti-ECFliC antibody, anti-Ec0FliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-Ec0Stx2A antibody, anti-CjcdtB/C antibody, anti-CdtcdA/B antibody, and combinations thereof.

In some embodiments, the mast cell marker is selected from the group consisting of beta-tryptase, histamine, prostaglandin E2 (PGE2), and combinations thereof.

In some embodiments, the inflammatory marker is selected from the group consisting of CRP, ICAM, VCAM, SAA, GRO.alpha., and combinations thereof.

In some embodiments, the bile acid malabsorption marker is selected from the group consisting of 7α-hydroxy-4-cholesten-3-one, FGF19, and a combination thereof.

In some embodiments, the kynurenine marker is selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the serotonin marker is selected from the group consisting of serotonin (5-HT), 5-hydroxyindoleacetic acid (5-HIAA), serotonin-O-sulfate, serotonin-O-phosphate, and combinations thereof.

In some embodiments, the biomarker is a biomarker as disclosed in U.S. Pat. No. 9,739,786, incorporated by reference herein in its entirety.

The following markers can be expressed by mesenchymal stem cells (MSC): CD105, CD73, CD90, CD13, CD29, CD44, CD10, Stro-1, CD271, SSEA-4, CD146, CD49f, CD349, GD2, 3G5, SSEA-3, SISD2, Stro-4, MSCA-1, CD56, CD200, PODX1, Sox11, or TM4SF1 (e.g., 2 or more, 3 or more, 4 or more, 5 or more, 6 or more, 7 or more, 8 or more, 9 or more, or 10 or more of such markers), and lack expression of one or more of CD45, CD34, CD14, CD19, and HLA-DR (e.g., lack expression of two or more, three or more, four or more, or five or more such markers). In some embodiments, MSC can express CD105, CD73, and CD90. In some embodiments, MSC can express CD105, CD73, CD90, CD13, CD29, CD44, and CD10. In some embodiments, MSC can express CD105, CD73, and CD90 and one or more stemness markers such as Stro-1, CD271, SSEA-4, CD146, CD49f, CD349, GD2, 3G5, SSEA-3. SISD2, Stro-4, MSCA-1, CD56, CD200, PODX1, Sox11, or TM4SF1. In some embodiments, MSC can express CD105, CD73, CD90, CD13, CD29, CD44, and CD10 and one or more stemness markers such as Stro-1, CD271, SSEA-4, CD146, CD49f, CD349, GD2, 3G5, SSEA-3. SISD2, Stro-4, MSCA-1, CD56, CD200, PODX1, Sox11, or TM4SF1. See, e.g., Lv, et al., *Stem Cells*, 2014, 32:1408-1419.

Intestinal stem cells (ISC) can be positive for one or more markers such as Musashi-1 (Msi-1), Asc12, Bmi-1, Doublecortin and Ca2+/calmodulin-dependent kinase-like 1 (DCAMKL1), and Leucin-rich repeat-containing G-protein-coupled receptor 5 (Lgr5). See, e.g., Mohamed, et al., Cytotechnology, 2015 67(2): 177-189.

Any of the foregoing biomarkers can be used as a biomarker for one or more of other conditions as appropriate.

In some embodiments of the methods herein, the methods comprise determining the time period of onset of treatment following administration of the device.

Combination Therapy:

The IL-10 or IL-10 agonists disclosed herein may be optionally used with additional agents in the treatment of the diseases disclosed herein. Nonlimiting examples of such agents for treating or preventing inflammatory bowel disease in such adjunct therapy (e.g., Crohn's disease, ulcerative colitis) include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal antiinflammatory drugs (NSAIDs); ganciclovir; tacrolimus; lucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocriptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD 11a and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002) and see also definition below); biologic agents that interfere with T cell helper signals, such as anti-CD40 receptor or anti-CD40 ligand (CD 154), including blocking antibodies to CD40-CD40 ligand. (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Non-limiting examples of adjunct agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinyl-imidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TP1O; T Cell Sciences, Inc.); slow-release mesalazine; antagonists of platelet activating factor (PAF); ciprofloxacin; and lignocaine. Examples of agents for UC are sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

In other embodiments, IL-10 or an IL-10 agonist as described herein can be administered with one or more of: a CHST15 inhibitor, a IL-6 receptor inhibitor, a TNF inhibitor, an integrin inhibitor, a JAK inhibitor, a SMAD7 inhibitor, a IL-13 inhibitor, an IL-1 receptor inhibitor, a TLR agonist, an immunosuppressant, a live biotherapeutic such as a stem cell, an IL-12/IL-23 inhibitor, copaxone, a CD40 inhibitor, or an S1P-inhibitor (e.g., etrasimod or ozanimod). In other embodiments, IL-10 or an IL-10 agonist as described herein can be administered with a vitamin C infusion, one or more corticosteroids, and optionally thiamine.

In some embodiments, the methods disclosed herein comprise administering (i) the IL-10 or IL-10 agonist as disclosed herein, and (ii) a second agent orally, intravenously or subcutaneously, wherein the second agent in (ii) is the same IL-10 or IL-10 agonist in (i); a different IL-10 or IL-10 agonist; or an agent having a different biological target from the IL-10 or IL-10 agonist.

In some embodiments, the methods disclosed herein comprise administering (i) the IL-10 or IL-10 agonist in the manner disclosed herein, and (ii) a second agent orally, intravenously or subcutaneously, wherein the second agent in (ii) is an agent suitable for treating an inflammatory bowel disease.

In some embodiments, the IL-10 or IL-10 agonist is administered prior to the second agent. In some embodiments, the IL-10 or IL-10 agonist is administered after the second agent. In some embodiments, the IL-10 or IL-10 agonist and the second agent are administered substantially at the same time. In some embodiments, the IL-10 or IL-10 agonist is delivered prior to the second agent. In some embodiments, the IL-10 or IL-10 agonist is delivered after the second agent. In some embodiments, the IL-10 or IL-10 agonist and the second agent are delivered substantially at the same time.

In some embodiments, the second agent is an agent suitable for the treatment of a disease of the gastrointestinal tract. In some embodiments, the second agent is an agent suitable for the treatment of an inflammatory bowel disease. In some embodiments, the second agent is administered intravenously. In some embodiments, the second agent is administered subcutaneously. In some embodiments, the second agent is methotrexate.

In some embodiments, delivery of the IL-10 or IL-10 agonist to the location, such as delivery to the location by mucosal contact, results in systemic immunogenicity levels at or below systemic immunogenicity levels resulting from administration of the IL-10 or IL-10 agonist systemically. In some embodiments comprising administering the IL-10 or IL-10 agonist in the manner disclosed herein and a second agent systemically, delivery of the IL-10 or IL-10 agonist to the location, such as delivery to the location by mucosal contact, results in systemic immunogenicity levels at or below systemic immunogenicity levels resulting from administration of the IL-10 or IL-10 agonist systemically and the second agent systemically. In some embodiments, the method comprises administering the IL-10 or IL-10 agonist in the manner disclosed herein and a second agent, wherein the amount of the second agent is less than the amount of the second agent when the IL-10 or IL-10 agonist and the second agent are both administered systemically. In some aspects of these embodiments, the second agent is IL-10 or an IL-10 agonist.

In some embodiments, the method comprises administering the IL-10 or IL-10 agonist in the manner disclosed herein and does not comprise administering a second agent.

Example 1—Preclinical Murine Colitis Model

Experimental Induction of Colitis

Colitis is experimentally induced to mice via the dextran sulfate sodium (DSS)-induced colitis model. This model is widely used because of its simplicity and many similarities with human ulcerative colitis. Briefly, mice are subjected to DSS via cecal catheterization, which is thought to be directly toxic to colonic epithelial cells of the basal crypts, for several days until colitis is induced.

Groups

Mice are allocated to one of seven cohorts, depending on the agent that is administered:
 1. Control (no agent)
 2. Adalimumab (2.5 mg/kg)
 3. Adalimumab (5 mg/kg)
 4. Adalimumab (10 mg/kg)

The control or agent is applied to a damaged mucosal surface of the bowel via administration through a cecal catheter at the dose levels described above.

Additionally, for each cohort, the animals are separated into two groups. One group receives a single dose of the control or agent on day 10 or 12. The other group receives daily (or similar) dosing of the control or agent.

Analysis

For each animal, efficacy is determined (e.g., by endoscopy, histology, etc.), and cytotoxic T-cell levels are determined in blood, feces, and tissue (tissue levels are determined after animal sacrifice). For tissue samples, levels HER2 are additionally determined, and the level of cytotoxic T cells is normalized to the level of HER2. Additionally, other cytokine levels are determined in tissue (e.g., phospho STAT 1, STAT 3 and STAT 5), in plasma (e.g., VEGF, VCAM, ICAM, IL-6), or both.

Pharmacokinetics are determined both systemically (e.g., in the plasma) and locally (e.g., in colon tissue). For systemic pharmacokinetic analysis, blood and/or feces is collected from the animals at one or more timepoints after administration (e.g., plasma samples are collected at 15 minutes, 30 minutes, 1 hour, 2 hours, 4 hours, and/or 8 hours after administration). Local/colon tissue samples are collected once after animal sacrifice.

Example 2a—Development of Preclinical Porcine Colitis Model

Experimental Induction of Colitis

Female swine weighing approximately 35 to 45 kg at study start are fasted at least 24 hours prior to intra-rectal administration of trinitrobenzene sulfonic acid (TNBS). Animals are lightly anesthetized during the dosing and endoscopy procedure. An enema to clean the colon is used, if necessary. One animal is administered 40 ml of 100% EtOH mixed with 5 grams of TNBS diluted in 10 ml of water via an enema using a ball-tipped catheter. The enema is deposited in the proximal portion of the descending colon just past the bend of the transverse colon. The TNBS is retained at the dose site for 12 minutes by use of two Foley catheters with 60-ml balloons placed in the mid-section of the descending colon below the dose site. A second animal is similarly treated, but with a solution containing 10 grams of TNBS. An Endoscope is employed to positively identify the dose site in both animals prior to TNBS administration. Dosing and endoscopy are performed by a veterinary surgeon Seven (7) days after TNBS administration, after light anesthesia, the dose site and mucosal tissues above and below the dose site are evaluated by the veterinary surgeon using an endoscope. Pinch Biopsies are obtained necessary, as determined by the surgeon. Based on the endoscopy findings, the animals may be euthanized for tissue collection on that day, or may proceed on study pending the results of subsequent endoscopy exams for 1 to 4 more days. Macroscopic and microscopic alterations of colonic architecture, possible necrosis, thickening of the colon, and substantial histologic changes are observed at the proper TNBS dose.

Clinical signs (e.g., ill health, behavioral changes, etc.) are recorded at least daily during acclimation and throughout the study. Additional pen-side observations are conducted twice daily (once-daily on weekends). Body weight is measured for both animals Days 1 and 7 (and on the day of euthanasia if after Day 7).

On the day of necropsy, the animals are euthanized via injection of a veterinarian-approved euthanasia solution. Immediately after euthanasia in order to avoid autolytic changes, colon tissues are collected, opened, rinsed with saline, and a detailed macroscopic examination of the colon is performed to identify macroscopic finings related to TNBS-damage. Photos are taken. Tissue samples are taken from the proximal, mid, and distal transverse colon; the dose site; the distal colon; the rectum; and the anal canal. Samples are placed into NBF and evaluated by a board certified veterinary pathologist.

Example 2b—Pharmacokinetic/Pharmacodynamic and Bioavailability of Adalimumab after Topical Application Groups Sixteen (16) swine (approximately 35 to 45 kg at study start) are allocated to one of five groups:
1. Vehicle Control: (3.2 mL saline); intra-rectal; (n=2)
2. Treated Control: Adalimumab (40 mg in 3.2 mL saline); subcutaneous; (n=2)
3. Adalimumab (low): Adalimumab (40 mg in 3.2 mL saline); intra-rectal; (n=4)
4. Adalimumab (med): Adalimumab (80 mg in 3.2 mL saline); intra-rectal; (n=4)
5. Adalimumab (high): Adalimumab (160 mg in 3.2 mL saline); intra-rectal; (n=4)

On Day 0, the test article is applied to a damaged mucosal surface of the bowel via intra-rectal administration or subcutaneous injection by a veterinary surgeon at the dose levels and volume described above.

Clinical Observations and Body Weight

Clinical observations are conducted at least once daily. Clinical signs (e.g., ill health, behavioral changes, etc.) are recorded on all appropriate animals at least daily prior to the initiation of experiment and throughout the study until termination. Additional clinical observations may be performed if deemed necessary. Animals whose health condition warrants further evaluation are examined by a Clinical Veterinarian. Body weight is measured for all animals Days −6, 0, and after the last blood collections.

Samples

Blood:

Blood is collected (cephalic, jugular, and/or catheter) into EDTA tubes during acclimation on Day-7, just prior to dose on Day 0, and 0.5, 1, 2, 4, 6, 8, 12, 24, and 48 hours post-dose. The EDTA samples are split into two aliquots and one is centrifuged for pharmacokinetic plasma and either analyzed immediately, or stored frozen (−80° C.) for later pharmacokinetic analyses. The remaining sample of whole blood is used for pharmacodynamic analyses.

Feces:

Feces is collected Day −7, 0 and 0.5, 1, 2, 4, 6, 8, 12, 24 and 48 hours post-dose, and either analyzed immediately, or flash-frozen on liquid nitrogen and stored frozen at −70° C. pending later analysis of drug levels and inflammatory cytokines.

Tissue:

Immediately after euthanasia in order to avoid autolytic changes, colon tissues are collected, opened, rinsed with saline, and a detailed macroscopic examination of the colon is performed to identify macroscopic finings related to TNBS-damage. Triplicate samples of normal and damaged tissues are either analyzed immediately, or are flash-frozen on liquid nitrogen and stored frozen at −70° C. pending later analysis of drug concentration, inflammatory cytokines and histology.

Samples are analyzed for adalimumab levels (local mucosal tissue levels and systemic circulation levels), and for levels of inflammatory cytokines including TNF-alpha.

Terminal Procedures

Animals are euthanized as per the schedule in Table AA, where one animal each of Vehicle and Treated Control groups is euthanized at 6 and 48 hours post-dose, and one animal of each the adalimumab groups are euthanized at 6, 12, 24 and 48 hours post-dose. Animals are discarded after the last blood collection unless retained for a subsequent study.

cutaneous injection by a veterinary surgeon at the dose levels and volume described above.

Clinical Observations

Clinical signs (e.g., ill health, behavioral changes, etc.) are recorded on all appropriate animals at least daily prior to the initiation of experiment and throughout the study until termination. Additional clinical observations may be per-

TABLE AA

|  | Sample size | Dose | Route | Days | | | | | | | | Hours | | | | | | | | | |
|---|---|---|---|---|---|---|---|---|---|---|---|---|---|---|---|---|---|---|---|---|---|
|  |  |  |  | −7 | −6 | −5 | −4 | −3 | −2 | −1 | 0 | 0.5 | 1 | 2 | 4 | 6 | 8 | 12 | 24 | 48 |
| General |  |  |  |  |  |  |  |  |  |  |  |  |  |  |  |  |  |  |  |  |
| Fast |  |  |  | • |  |  |  |  |  |  |  |  |  |  |  |  |  |  |  |  |
| Food/Water |  | ad libidum | oral |  | • | • | • | • | • | • | • | • | • | • | • | • | • | • | • | • |
| Observations |  |  |  |  |  |  |  |  |  |  |  |  |  |  |  |  |  |  |  |  |
| clinical observations |  |  |  |  | • | • | • | • | • | • | • | • |  |  |  |  |  |  | • | • |
| body weight |  |  |  |  | • |  |  |  |  |  | • |  |  |  |  |  |  |  | • | • |
| Treatments (groups) |  |  |  |  |  |  |  |  |  |  |  |  |  |  |  |  |  |  |  |  |
| TNBS (all animals) |  |  | intra rectal |  |  |  | • |  |  |  |  |  |  |  |  |  |  |  |  |  |
| 1. Vehicle control | n = 2 | 1.6 mL saline (vehicle) | intra rectal |  |  |  |  |  |  |  | • |  |  |  |  |  |  |  |  |  |
| euthanized |  |  |  |  |  |  |  |  |  |  |  |  |  |  |  | n = 1 |  |  |  | n = 1 |
| 2. Treated control | n = 2 | 40 mg in 1.6 mL saline | subcutaneous |  |  |  |  |  |  |  | • |  |  |  |  |  |  |  |  |  |
| euthanized |  |  |  |  |  |  |  |  |  |  |  |  |  |  |  | n = 1 |  |  |  | n = 1 |
| 3. Adalimumab (low) | n = 4 | 40 mg in 1.6 mL saline | intra rectal |  |  |  |  |  |  |  | • |  |  |  |  |  |  |  |  |  |
| euthanized |  |  |  |  |  |  |  |  |  |  |  |  |  |  |  | n = 1 |  |  | n = 1 | n = 1 | n = 1 |
| 4. Adalimumab (med) | n = 4 | 80 mg in 1.6 mL saline | intra rectal |  |  |  |  |  |  |  | • |  |  |  |  |  |  |  |  |  |
| euthanized |  |  |  |  |  |  |  |  |  |  |  |  |  |  |  | n = 1 |  |  | n = 1 | n = 1 | n = 1 |
| 5. Adalimumab (high) | n = 4 | 160 mg in 1.6 mL saline | intra rectal |  |  |  |  |  |  |  | • |  |  |  |  |  |  |  |  |  |
| euthanized |  |  |  |  |  |  |  |  |  |  |  |  |  |  |  | n = 1 |  |  | n = 1 | n = 1 | n = 1 |
| Adalimumab (required) |  | 1200 |  |  |  |  |  |  |  |  |  |  |  |  |  |  |  |  |  |  |
| Samples |  |  |  |  |  |  |  |  |  |  |  |  |  |  |  |  |  |  |  |  |
| Blood |  |  | cephalic, jugular or catheter | • |  |  |  |  |  |  | • | • | • | • | • |  | • | • | • | • |
| Fecal |  |  | rectal | • |  |  |  |  |  |  | • | • | • | • | • |  | • | • | • | • |
| Tissue |  |  | necropsy | • |  |  |  |  |  |  |  |  |  |  |  | • |  | • | • | • |

Example 2c—Pharmacokinetic/Pharmacodynamic and Bioavailability of Adalimumab After Topical Application Groups DSS-induced colitis Yorkshire-Cross Farm Swine (approximately 5-10 kg at study start) are allocated to one of five groups:
1. Vehicle Control: (saline); intra-rectal;
2. Treated Control: Adalimumab (13 mg in saline); subcutaneous;
3. Adalimumab: Adalimumab (13 mg in saline); intra-rectal;

At t=0, the test article is applied to a damaged mucosal surface of the bowel via intra-rectal administration or subformed if deemed necessary. Animals whose health condition warrants further evaluation are examined by a Clinical Veterinarian.

Samples

Blood:

Blood is collected (cephalic, jugular, and/or catheter) into EDTA tubes during acclimation on Day-7, just prior to dose on Day 0, and 12 hours post-dose. The EDTA samples are split into two aliquots and one is centrifuged for pharmacokinetic plasma and either analyzed immediately, or stored frozen (−80° C.) for later pharmacokinetic analyses. The remaining sample of whole blood is used for pharmacodynamic analyses.

Feces:

Feces is collected Day −7, 0 and 12 hours post-dose, and either analyzed immediately, or flash-frozen on liquid nitrogen and stored frozen at −70° C. pending later analysis of drug levels and inflammatory cytokines.

Tissue:

Immediately after euthanasia (12 hours after dosing) in order to avoid autolytic changes, colon tissues are collected, opened, rinsed with saline, and a detailed macroscopic examination of the colon is performed to identify macroscopic finings related to DSS-damage. Triplicate samples of normal and damaged tissues are either analyzed immediately, or are flash-frozen on liquid nitrogen and stored frozen at −70° C. pending later analysis of drug concentration, inflammatory cytokines and histology.

Samples are analyzed for adalimumab levels (local mucosal tissue levels and systemic circulation levels), and for levels of inflammatory cytokines including TNF-alpha.

Terminal Procedures

Animals are euthanized at 12 hours post-dose.

Example 3. Comparison of Systemic Versus Intracecal Delivery of an Anti-IL-12 Antibody The objective of this study was to compare the efficacy of an IL-12 inhibitor (anti-IL-12 p40; anti-p40 mAb; BioXCell (Cat #: BE0051)), when dosed systemically versus intracecally, to the treat dextran sulfate sodium salt (DSS)-induced colitis in male C57Bl/6 mice.

Materials and Methods

Mice

Normal male C57Bl/6 mice between the ages of 6-8 weeks old, weighing 20-24 g, were obtained from Charles River Laboratories. The mice were randomized into thirteen groups of twelve animals and two groups of eight animals, and housed in groups of 6-8 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

Animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/Kg every day for the first 5 days post surgery.

Induction of Colitis

Colitis was induced in male C57Bl/6 mice by exposure to 3% DSS drinking water (MP Biomedicals #0260110) from Day 0 to Day 5. Fresh DSS/water solutions were made again on Day 3 and any of the remaining original DSS solution will be discarded.

Assessment of Colitis

All animals were weighed daily and visually assessed for the presence of diarrhea and/or bloody stool at the time of dosing. The mice underwent two video endoscopies, one on day 10 and one on day 14, to assess colitis severity. Images were captured from each animal at the most severe region of disease identified during the endoscopy, and assessed using the rubric demonstrated in Table 1.1. Additionally, stool consistency was scored during the endoscopy using this rubric (Table 1.2) (0=Normal, well-formed pellet, 1=Loose stool, soft, staying in shape, 2=Loose stool, abnormal form with excess moisture, 3=Watery or diarrhea, 4=Bloody diarrhea). At necropsy, intestinal contents, peripheral blood, and tissue, and cecum/colon contents were collected for analysis.

TABLE 1.1

Endoscopy Scoring

| Score | Description of Endoscopy Score |
|---|---|
| 0 | Normal |
| 1 | Loss of vascularity |
| 2 | Loss of vascularity and friability |
| 3 | Friability and erosions |
| 4 | Ulcerations and bleeding |

TABLE 1.2

Stool Consistency Score

| Score | Description of Stool Consistency |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Treatment of Colitis

Mice were treated with anti-IL-12 p40 during the acute phase of colitis due to its efficacy in the treatment of DSS-induced colitis. The test article was dosed at a volume of 0.1 mL/20 g from days 0 to 14. Anti-IL-12 p40 was administered intraperitoneally at a dose of 10 mg/kg every 3 days, and intracecally at a dose of 10 mg/kg, either every 3 days or every day. There was also a lower dose of 1 mg/kg given every day intracecally. The control groups were not administered drugs, and the vehicles (sterile PBS) were administered the placebo drug intraperitoneally and intracecally every day. These drugs were given from days 5-14, which is 9 days of administration. A more detailed explanation of dosing and groups can be seen in Table 1.3.

TABLE 1.3

Groups of Animals

| Group # | # of Animals | DSS | Cecal Cannula | Treatment | Dose (mg/kg) | Route | Dosing Schedule |
|---|---|---|---|---|---|---|---|
| 1 | 8 males | — | NO | — | — | — | — |
| 2 | 8 males | — | YES | — | — | — | — |
| 3 | 12 males | 3% DSS (day 0-5) | NO | Vehicle | — | PO | QD day 0-14 |
| 4 | 12 males | 3% DSS (day 0-5) | YES | Vehicle | — | IC | QD day 0-14 |
| 5 | 12 males | 3% DSS (day 0-5) | NO | Anti-p40 | 10 | IP | Q3 0,3,6,9,12 |

TABLE 1.3-continued

Groups of Animals

| Group # | # of Animals | DSS | Cecal Cannula | Treatment | Dose (mg/kg) | Route | Dosing Schedule |
|---|---|---|---|---|---|---|---|
| 6 | 12 males | 3% DSS (day 0-5) | YES | Anti-p40 | 10 | IC | Q3 0,3,6,9,12 |
| 7 | 12 males | 3% DSS (day 0-5) | YES | Anti-p40 | 10 | IC | QD day 0-14 |
| 8 | 12 males | 3% DSS (day 0-5) | YES | Anti-p40 | 1 | IC | QD day 0-14 |

Sample Collection

Intestinal contents, peripheral blood, and tissue were collected at sacrifice on day 14, as follows: at the end of each study period, mice were euthanized by $CO_2$ inhalation immediately following endoscopy on day 14. The blood was collected via cardiac puncture into $K_2$EDTA-coated tubes and centrifuged at 4000×g for 10 minutes. The blood cell pellet was retained and snapped frozen. The resulting plasma was then split into two separate cryotubes, with 100 μL in one tube and the remainder in the second. Plasma and cell pellet were also collected, flash frozen, and stored at −80 degrees Celsius.

The cecum and colon were removed from each animal and contents were collected, weighed, and snap frozen in separate cryovials. The colon was excised, rinsed, measured, weighed, and then trimmed to 6 cm in length and divided into 5 pieces. The most proximal 1 cm of colon was snapped frozen for subsequent bioanalysis of test article levels. Of the remaining 5 cm of colon, the most distal and proximal 1.5-cm sections was placed in formalin for 24 hours then transferred to 70% ethanol for subsequent histological evaluation. The middle 2-cm portion was bisected longitudinally and placed into two separate cryotubes, weighed, and snap frozen in liquid nitrogen.

Results

Figure 30:
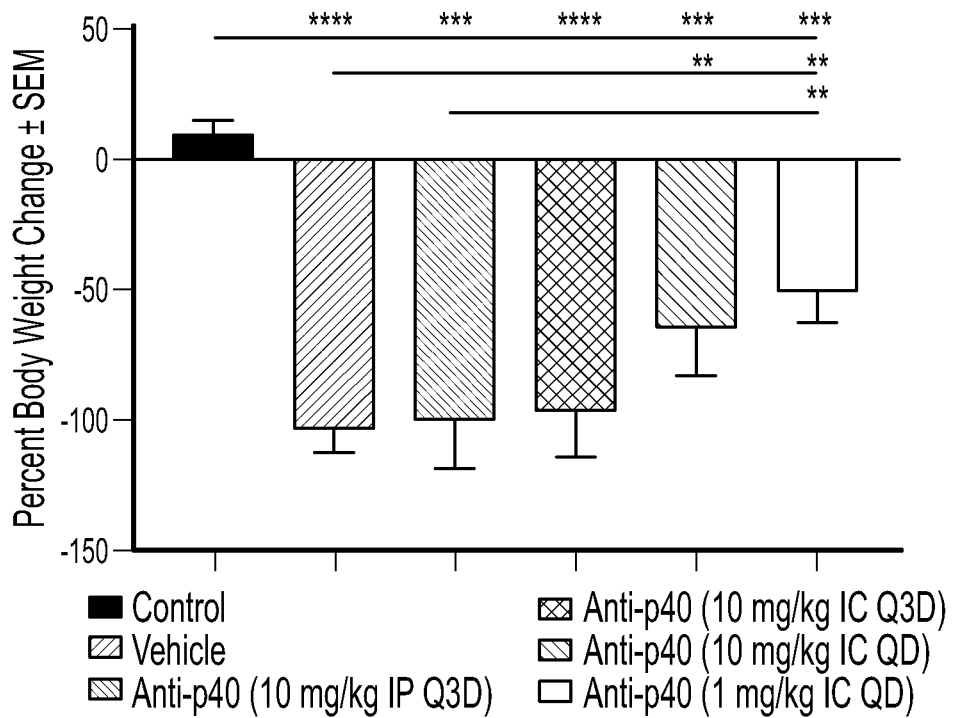
FIG. 30 is a graph showing the percentage (%) change in body weight at day 14 (±SEM) for DSS mice treated with anti-IL-12 p40 antibody intraperitoneally (10 mg/kg) every third day (Q3D) or intracecally (10 mg/kg or 1 mg/kg) daily (QD), when compared to mice treated with anti-IL-12 p40 antibody intraperitoneally (10 mg/kg) every third day (Q3D) and vehicle control (Vehicle). Mann-Whitney's U¬-test and Student's t-test were used for statistical analysis on non-Gaussian and Gaussian data respectively. A value of $p<0.05$ was considered significant (Graph Pad Software, Inc.).

The data in FIG. 30 show that the DSS mice that were intracecally administered an anti-IL-12 p40 (IgG2A) antibody had decreased weight loss as compared to DSS mice that were intraperitoneally administered the anti-IL-12 p40 antibody.

Figure 31:
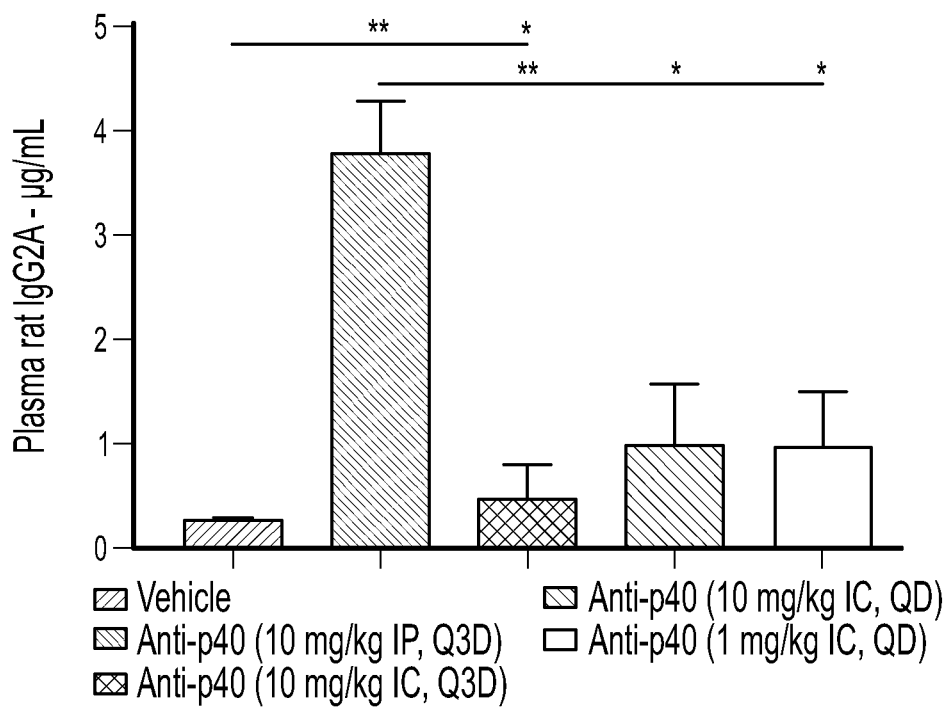
FIG. 31 is a graph showing the concentration of anti-IL-12 p40 rat IgG2A (µg/mL) in plasma of anti-IL-12 p40 intraperitoneally (10 mg/kg) and intracecally (10 mg/kg and 1 mg/kg) administered treatment groups given daily (QD) or every third day (Q3D) when compared to vehicle control (Vehicle) and when IP is compared to IC. ELISA analysis was used to determine the concentration of anti-IL-12 p40 (IgG2A). Data presented as mean±SEM. Mann-Whitney's U¬-test and Student's t-test were used for statistical analysis on non-Gaussian and Gaussian data respectively. A value of $p<0.05$ was considered significant (Graph Pad Software, Inc.).
Figure 32:
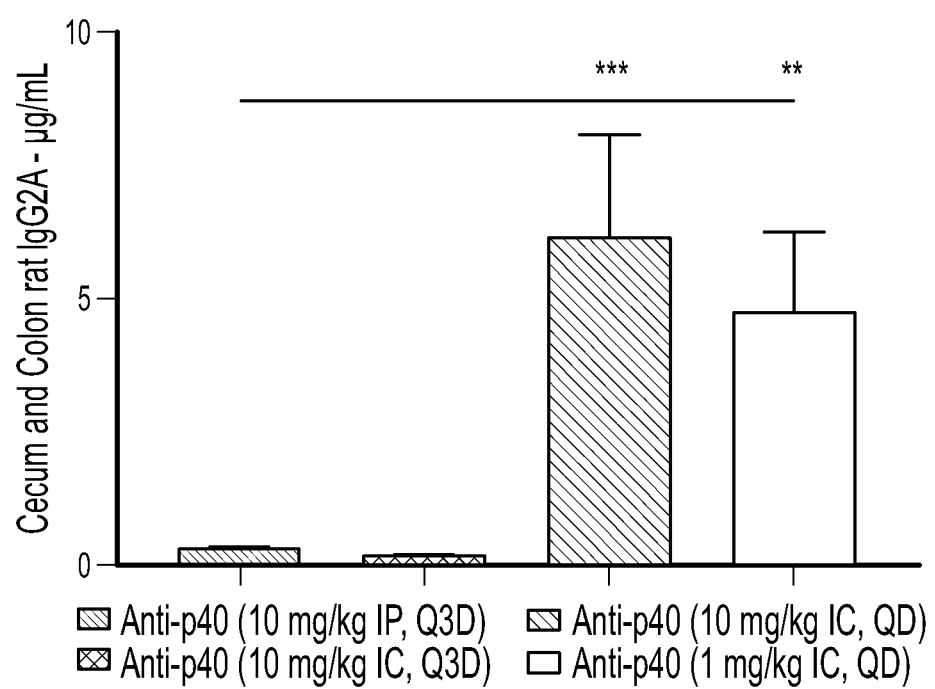
FIG. 32 is a graph showing the concentration of anti-IL-12 p40 antibody (IgG2A) (µg/mL) in the cecum and colon content of anti-IL-12 p40 antibody intraperitoneally (10 mg/kg) and intracecally (10 mg/kg and 1 mg/kg) administered treatment groups given daily (QD) or every third day (Q3D), when compared to vehicle control (Vehicle) and when IP is compared to IC. ELISA analysis was used to determine the concentration of rat IgG2A. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

The data in FIG. 31 show that the plasma concentration of the anti-IL-12 p40 antibody was decreased in DSS mice that were intracecally administered the anti-IL-12 p40 antibody as compared to DSS mice that were intraperitoneally administered the anti-IL-12 p40 antibody. The data in FIG. 32 show that the cecum and colon concentration of the anti-IL-12 p40 antibody is increased in DSS mice that were intracecally administered the anti-IL-12 p40 antibody as compared to the DSS mice that were intraperitoneally administered the anti-IL-12 p40 antibody.

Figure 33:
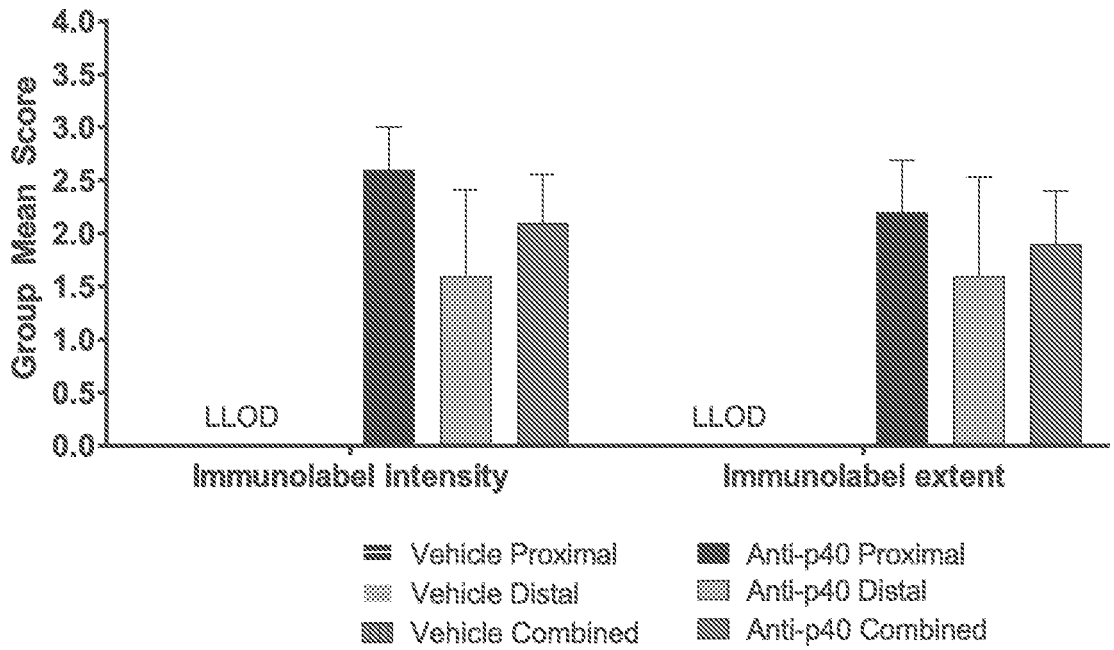
FIG. 33 is a graph showing the mean overall tissue immunolabel scores (intensity and extent) in acute DSS colitis mouse colon of anti-IL-12 p40 antibody intracecally-treated versus vehicle control-treated DSS mice. Data presented as mean±SEM.
Figure 34:
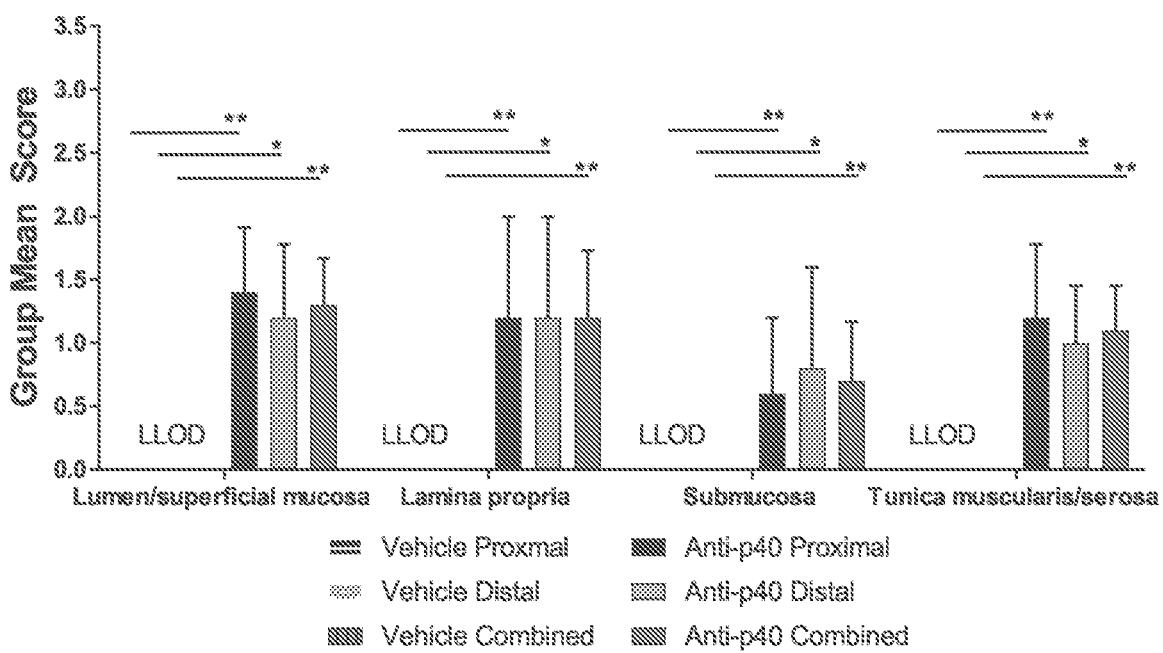
FIG. 34 is a graph showing the mean location-specific immunolabel scores in acute DSS colitis mouse colon of anti-IL-12 p40 intracecally-treated versus vehicle control-treated DSS mice. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 35:
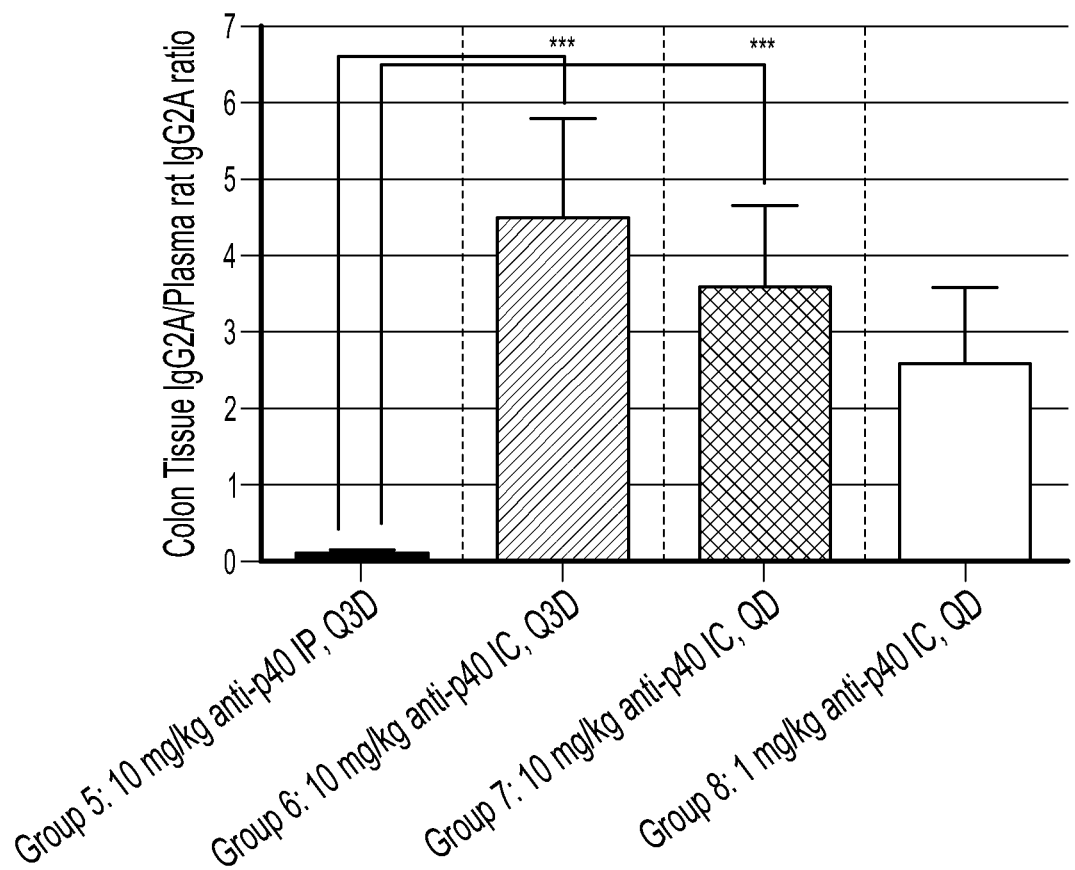
FIG. 35 is a graph showing the ratio of anti-IL-12 p40 antibody in the colon tissue to the plasma concentration of the anti-IL-12 p40 antibody in mice treated with the anti-IL-12 p40 antibody on day 0 (Q0) or day 3 (Q3D) of the study, when measured at the same time point after the initial dosing. An outlier animal was removed from Group 5.

The data in FIGS. 33 and 34 show that the anti-IL-12 p40 antibody is able to penetrate colon tissues (the lumen superficial, lamina propria, submucosa, and tunica muscularis/serosa) in DSS mice intracecally administered the anti-IL-12 p40 antibody, while the anti-IL-12 p40 antibody did not detectably penetrate the colon tissues of DSS mice intraperitoneally administered the anti-IL-12 p40 antibody. The data in FIG. 35 also show that the ratio of the concentration of anti-IL-12 p40 antibody in colon tissue to the concentration of the anti-IL-12 p40 antibody in plasma is increased in DSS mice intracecally administered the anti-IL-12 p40 antibody as compared to the ratio in DSS mice intraperitoneally administered the anti-IL-12 p40 antibody.

Figure 36:
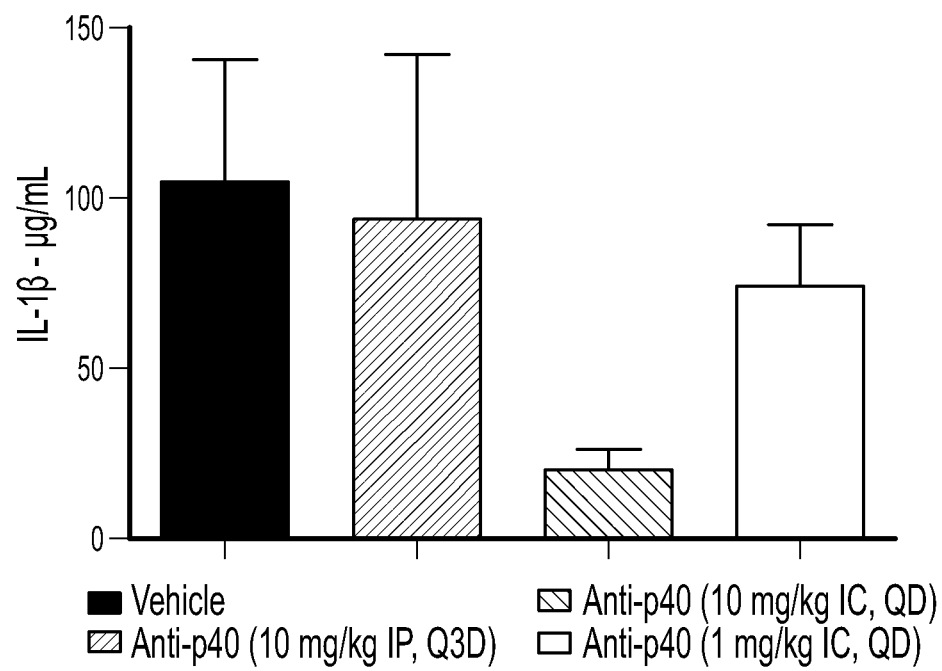
FIG. 36 is a graph showing the concentration of Il-1β (µg/mL) in colon tissue lysate of acute DSS colitis mice treated with anti-IL-12 p40 intraperitoneally (10 mg/kg) every third day (Q3D) or intracecally (10 mg/kg or 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 37:
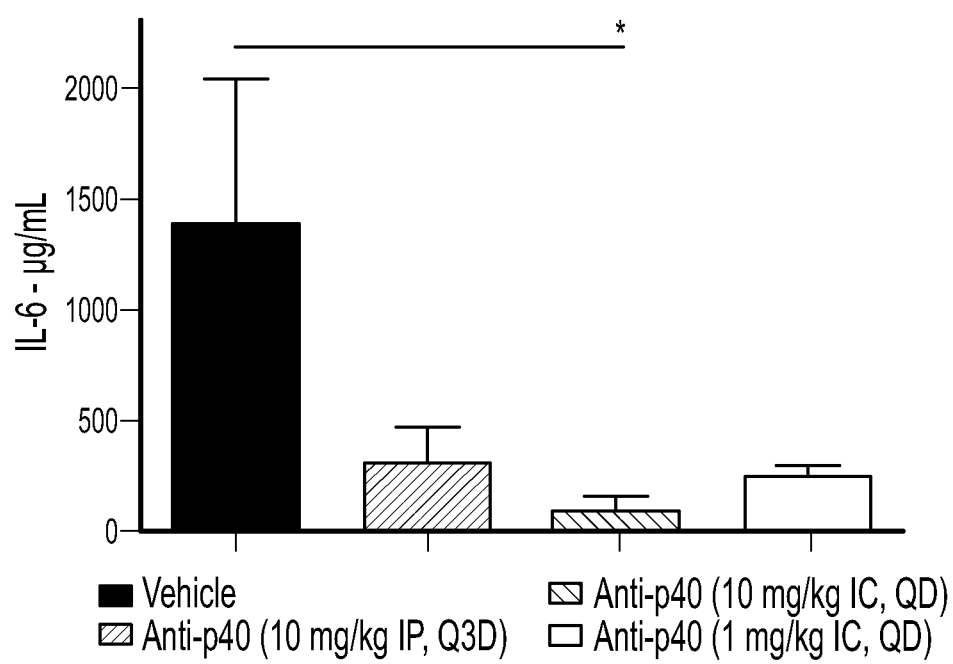
FIG. 37 is a graph showing the concentration of Il-6 (μg/mL) in colon tissue lysate of acute DSS colitis mice treated with anti-IL-12 p40 intraperitoneally (10 mg/kg) every third day (Q3D) or intracecally (10 mg/kg or 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of p<0.05 was considered significant (Graph Pad Software, Inc.
Figure 38:
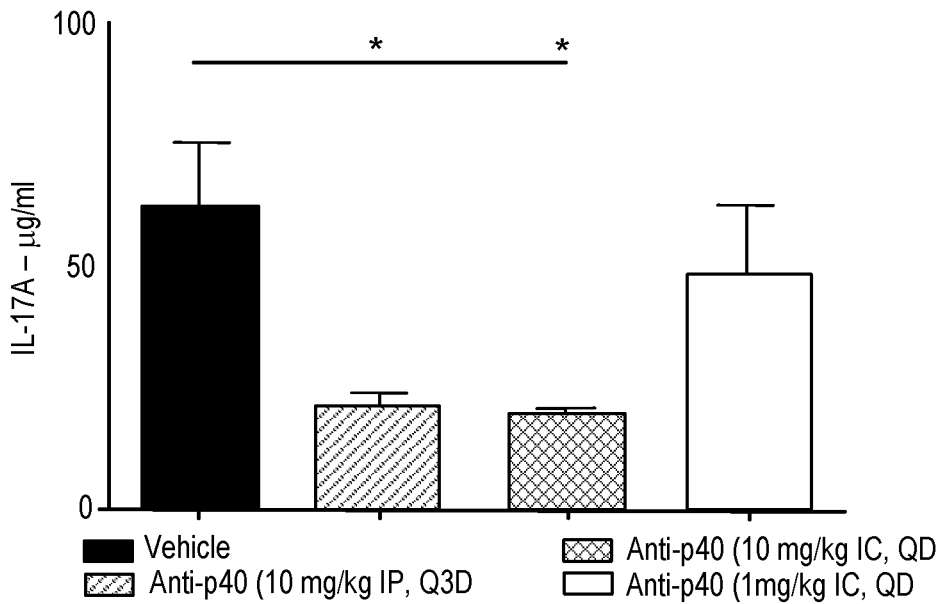
FIG. 38 is a graph showing the concentration of Il-17A (μg/mL) in colon tissue lysate of acute DSS colitis mice treated with anti-IL-12 p40 intraperitoneally (10 mg/kg) every third day (Q3D) or intracecally (10 mg/kg and 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of p<0.05 was considered significant (Graph Pad Software, Inc.).

The data in FIG. 36 show that the concentration of IL-1β in colon tissue is decreased in DSS mice intracecally administered the anti-IL-12 p40 antibody as compared to the concentration of IL-1β in colon tissue in DSS mice intraperitoneally administered the anti-IL-12 p40 antibody. The data in FIG. 37 show that the concentration of IL-6 in colon tissue is decreased in DSS mice intracecally administered the anti-IL-12 p40 antibody as compared to the concentration of IL-6 in colon tissue in DSS mice intraperitoneally administered the anti-IL-12 p40 antibody. The data in FIG. 38 show that the concentration of IL-17A in colon tissue is decreased in DSS mice intracecally administered the anti-IL-12 p40 antibody as compared to the concentration of IL-17A in colon tissue in DSS mice intraperitoneally administered the anti-IL-12 p40 antibody.

No significant differences in clinical observations or gastrointestinal-specific adverse effects, including stool consistency and/or bloody stool, were observed due to cannulation or intra-cecal treatments when compared with vehicle. No toxicity resulting from the treatments was reported. A significant reduction in body weight-loss (AUC) was found in groups treated with anti-IL-12 p40 antibody (10 mg/kg and 1 mg/kg, QD) via intra-cecal delivery when compared with vehicle control and intraperitoneal delivery (10 mg/kg, Q3D). The immunohistochemistry staining in anti-IL-12 p40 antibody (10 mg/kg, QD) treatment groups showed penetration of the antibody in all layers of colon tissue, including lumen mucosa, lamina propria, submucosa, tunica muscularis, via intra-cecal delivery. The distribution of anti-IL-12 p40 antibody was found in all segments of the colon, however, higher levels were detected in the proximal region. A significantly higher mean concentration of anti-IL-12 p40 antibody was found in the gastrointestinal contents and colon tissues when delivered via intra-cecal administration (Anti-p40: 10 mg/kg and 1 mg/kg, QD) compared with intraperitoneal administration (anti-p40: 10 mg/kg, Q3D). The blood level of anti-IL-12 p40 antibody was significantly higher when delivered via intraperitoneal administration (Q3D) as compared to intra-cecal administration (Q3D & QD). The concentrations of inflammatory cytokines, including IL-1β, IL-6, and IL-17, were significantly reduced by anti-IL-12 p40 antibody (10 mg/kg, QD) treatment when delivered via intra-cecal administration as compared to vehicle controls.

In sum, these data show that the compositions and devices provided herein can suppress the local immune response in the intestine, while having less of a suppressive effect on the systemic immune response of an animal. These data also suggest that the presently claimed compositions and devices will provide for treatment of colitis and other pro-inflammatory disorders of the intestine.

Example 4. Comparison of Systemic Versus Intracecal Delivery of an Anti-Integrin α4β7 Antibody The objective of this study was to compare the efficacy of an integrin inhibitor (anti-integrin α4β7; anti-LPAM1; DATK-32 mAb; BioXCell (Cat #: BE0034)) when dosed systemically versus intracecally for treating dextran sulfate sodium salt (DSS)-induced colitis in male C57Bl/6 mice.

Materials and Methods

Mice

Normal male C57Bl/6 mice between the ages of 6-8 weeks old, weighing 20-24 g, were obtained from Charles River Laboratories. The mice were randomized into thirteen groups of twelve animals and two groups of eight animals, and housed in groups of 6-8 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/Kg every day for the first 5 days post-surgery.

Induction of Colitis

Colitis was induced in male C57Bl/6 mice by exposure to 3% DSS drinking water (MP Biomedicals #0260110) from day 0 to day 5. Fresh DSS/water solutions were made again on day 3 and any of the remaining original DSS solution will be discarded.

Assessment of Colitis

All animals were weighed daily and visually assessed for the presence of diarrhea and/or bloody stool at the time of dosing. Mice underwent two video endoscopies, one on day 10 and one on day 14, to assess colitis severity. Images were captured from each animal at the most severe region of disease identified during the endoscopy, and assessed using the rubric demonstrated in Table 2.1. Additionally, stool consistency was scored during the endoscopy using this rubric (Table 2.2) (0=Normal, well-formed pellet, 1=Loose stool, soft, staying in shape, 2=Loose stool, abnormal form with excess moisture, 3=Watery or diarrhea, 4=Bloody diarrhea). At necropsy, intestinal contents, peripheral blood and tissue, and cecum/colon contents were collected for analysis.

TABLE 2.1

Endoscopy Score

| Score | Description of Endoscopy Score |
|---|---|
| 0 | Normal |
| 1 | Loss of vascularity |
| 2 | Loss of vascularity and friability |
| 3 | Friability and erosions |
| 4 | Ulcerations and bleeding |

TABLE 2.2

Stool Consistency Score

| Score | Description of Stool Consistency |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Treatment of Colitis

Mice were treated with DATK32 during the acute phase of colitis due to its efficacy in the treatment of DSS-induced colitis. The test article was dosed at a volume of 0.1 mL/20 g from days 0 to 14. DATK32 was administered intraperitoneally at a dose of 25 mg/kg every 3 days, and intracecally at a dose of 25 mg/kg, either every 3 days or every day. There was also a lower dose of 5 mg/kg given every day intracecally. The control groups were not administered drugs, and the vehicle (sterile PBS) was administered as the placebo drug intraperitoneally and intracecally every day. These drugs were given from days 5-14, which is 9 days of administration. A more detailed explanation of dosing and groups can be seen in Table 2.3.

TABLE 2.3

Groups of Mice

| Group # | # of Animals | DSS | Cecal Cannula | Treatment | Dose (mg/kg) | Route | Dosing Schedule |
|---|---|---|---|---|---|---|---|
| 1 | 8 males | — | NO | — | — | — | — |
| 2 | 8 males | — | YES | — | — | — | — |
| 3 | 12 males | 3% DSS (day 0-5) | NO | Vehicle | — | PO | QD day 0-14 |
| 4 | 12 males | 3% DSS (day 0-5) | YES | Vehicle | — | IC | QD day 0-14 |
| 9 | 12 males | 3% DSS (day 0-5) | NO | DATK32 | 25 | IP | Q3 0,3,6,9,12 |
| 10 | 12 males | 3% DSS (day 0-5) | YES | DATK32 | 25 | IC | Q3 0,3,6,9,12 |
| 11 | 12 males | 3% DSS (day 0-5) | YES | DATK32 | 25 | IC | QD day 0-14 |
| 12 | 12 males | 3% DSS (day 0-5) | YES | DATK32 | 5 | IC | QD day 0-14 |

Sample Collection

Intestinal contents, peripheral blood, and tissue were collected at sacrifice on day 14, as follows: at the end of each study period, mice were euthanized by $CO_2$ inhalation immediately following endoscopy on day 14. The blood was collected via cardiac puncture into $K_2$EDTA-coated tubes and centrifuged at 4000×g for 10 minutes. The blood cell pellet was retained and snapped frozen. The resulting plasma was then split into two separate cryotubes, with 100 µL in one tube and the remainder in the second. Plasma and the cell pellet were also collected, flash frozen, and stored at −80 degrees Celsius. An ELISA was used to determine the level of rat IgG2A.

The cecum and colon were removed from each animal and contents were collected, weighed, and snap frozen in separate cryovials. The colon was excised, rinsed, measured, weighed, and then trimmed to 6 cm in length and divided into 5 pieces. The most proximal 1 cm of colon was snapped frozen for subsequent bioanalysis of anti-DATK32 levels. Of the remaining 5 cm of colon, the most distal and proximal 1.5-cm sections was placed in formalin for 24 hours then transferred to 70% ethanol for subsequent histological evaluation. The middle 2-cm portion was bisected longitudinally and placed into two separate cryotubes, weighed, and snap frozen in liquid nitrogen.

There was an additional collection of 100 μL of whole blood from all animals and processed for FACS analysis of α4 and/β7 expression on T-helper memory cells. Tissue and blood were immediately placed in FACS buffer (1×PBS containing 2.5% fetal calf serum) and analyzed using the following antibody panel (Table 2.4).

TABLE 2.4

Fluorophore Labelled Antibodies Used in FACS Analysis

| Antibody Target | Flurochrome | Purpose |
|---|---|---|
| CD4 | APC-Vio770 | Defines T-Helper Cells |
| CD44 | VioBlue | Memory/Naive Discrimination |
| CD45RB | FITC | Memory/Naive Discrimination |
| α4 | APC | Defines T-helper memory subset of interest |
| β7 | PE | Defines T-helper memory subset of interest |
| CD16/32 | — | Fc Block |

Results

Figure 39:
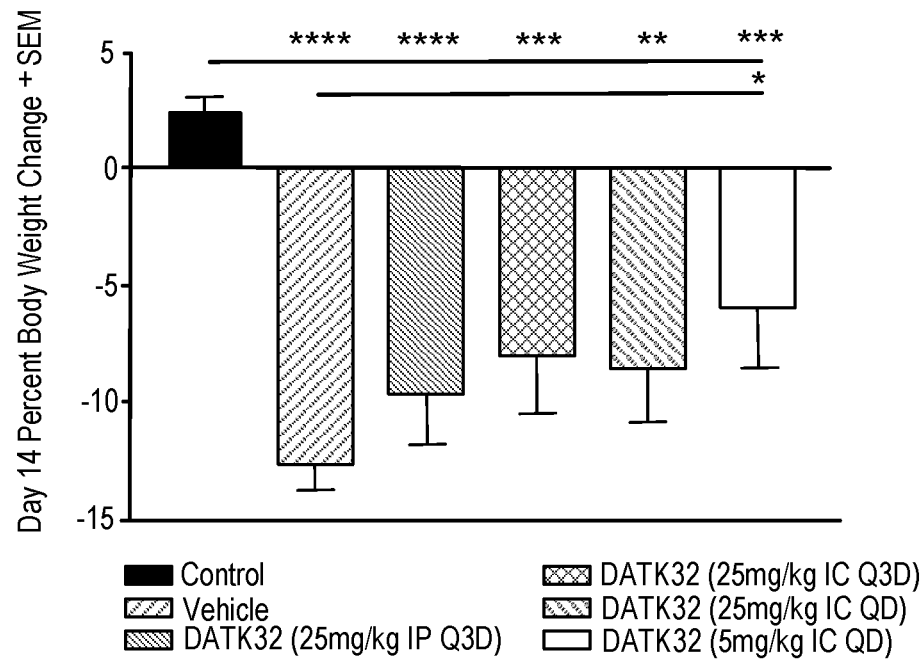
FIG. 39 is a graph showing the percentage (%) change in body weight at day 14 (±SEM) for DSS mice treated with DATK32 (anti-α4β7) antibody intraperitoneally (25 mg/kg) every third day (Q3D) or intracecally (25 mg/kg or 5 mg/kg) administered daily (QD), when compared to vehicle control (Vehicle) and when IC is compared to IP. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 40:
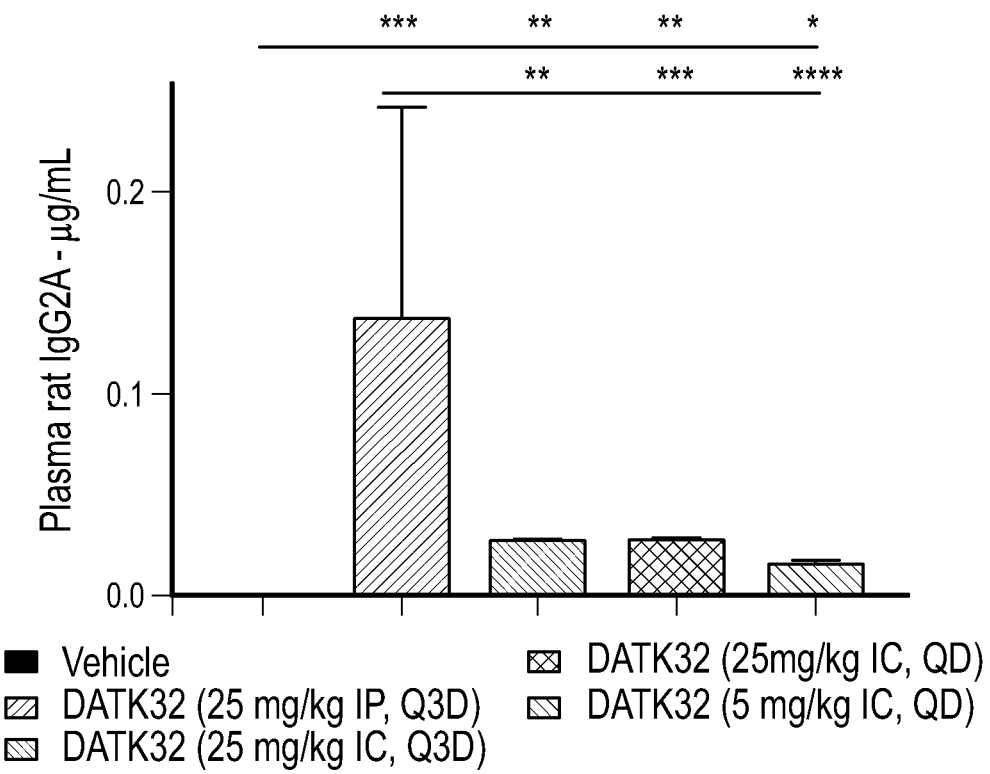
FIG. 40 is a graph showing the plasma concentration of DATK32 rat IgG2A (μg/mL) of intraperitoneally (25 mg/kg) and intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 41:
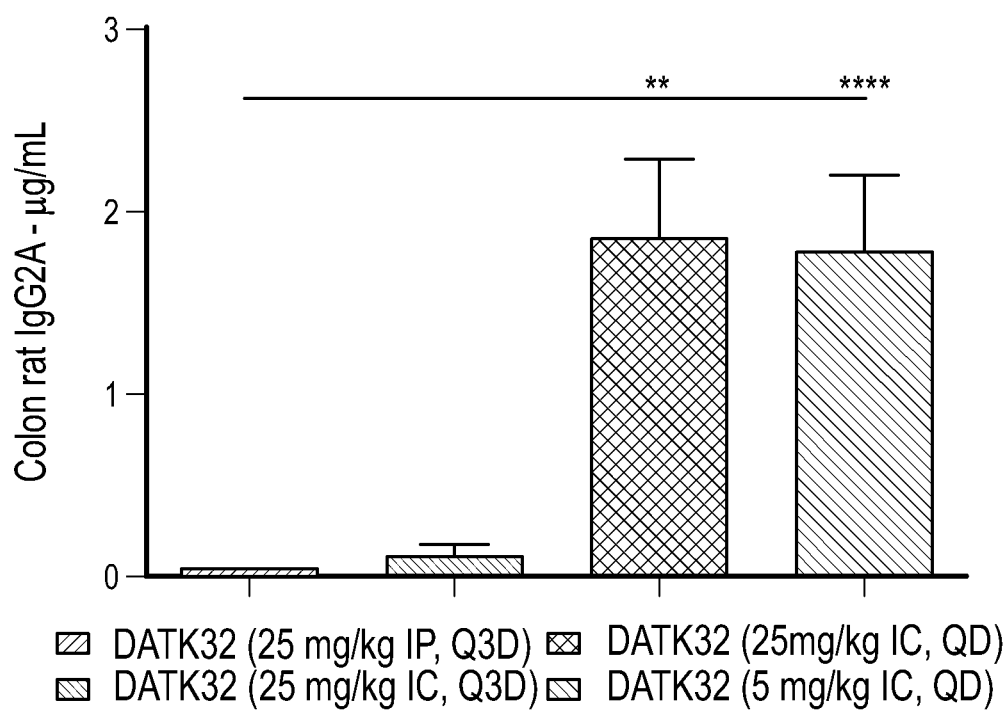
FIG. 41 is a graph showing the concentration of DATK32 rat IgG2A antibody (μg/mL) in cecum and colon content of intraperitoneally (25 mg/kg) or intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 42:
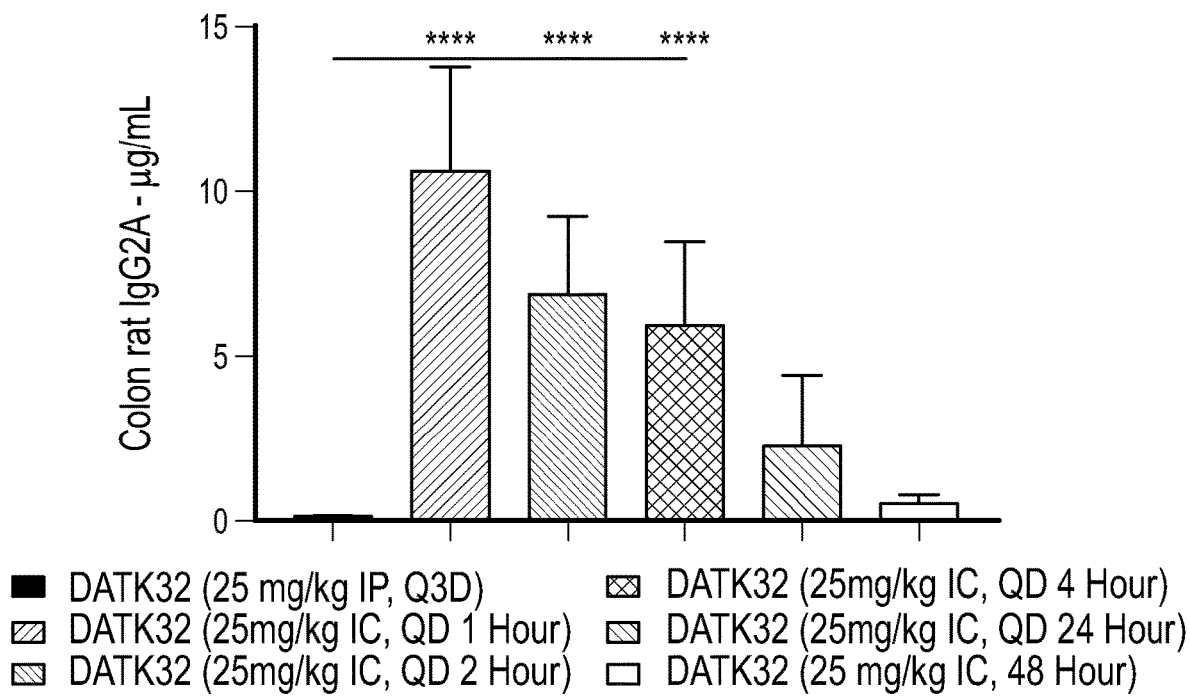
FIG. 42 is a graph showing the concentration of DATK32 rat IgG2A (μg/mL) in the colon content of intraperitoneally (25 mg/kg) or intracecally (25 mg/kg and 5 mg/kg) administered treatment groups given daily (QD), and concentration over time (1, 2, 4, 24, and 48 hours), where IP is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 43:
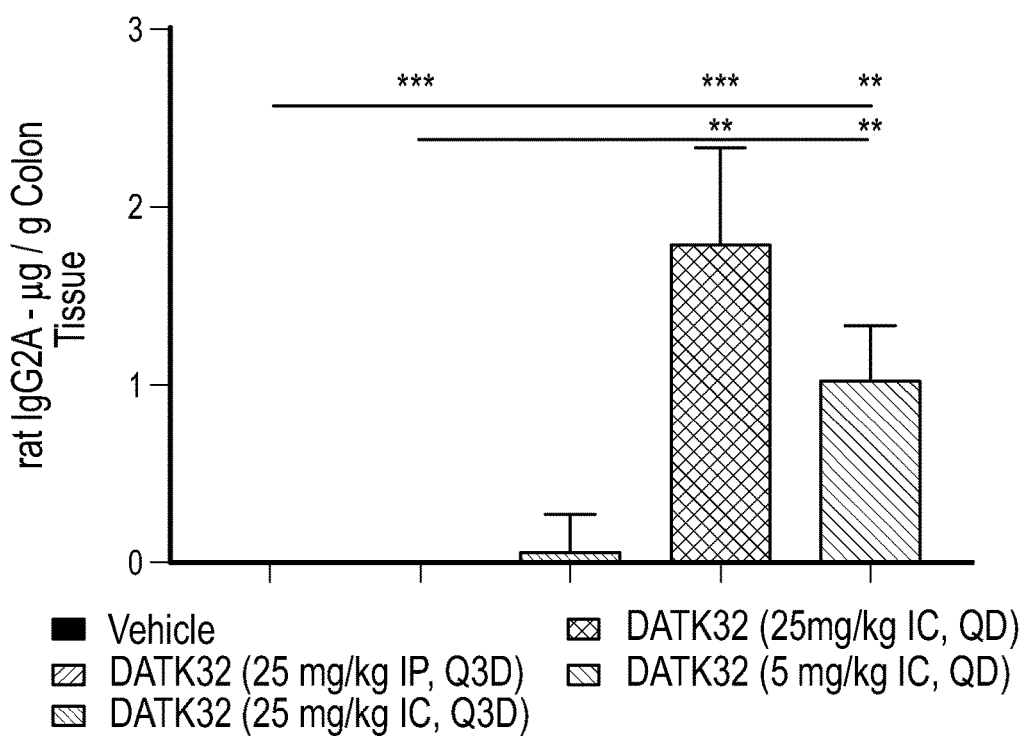
FIG. 43 is a graph showing the concentration of DATK32 rat IgG2A (μg/g) in colon tissue of intraperitoneally (25 mg/kg) or intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 44:
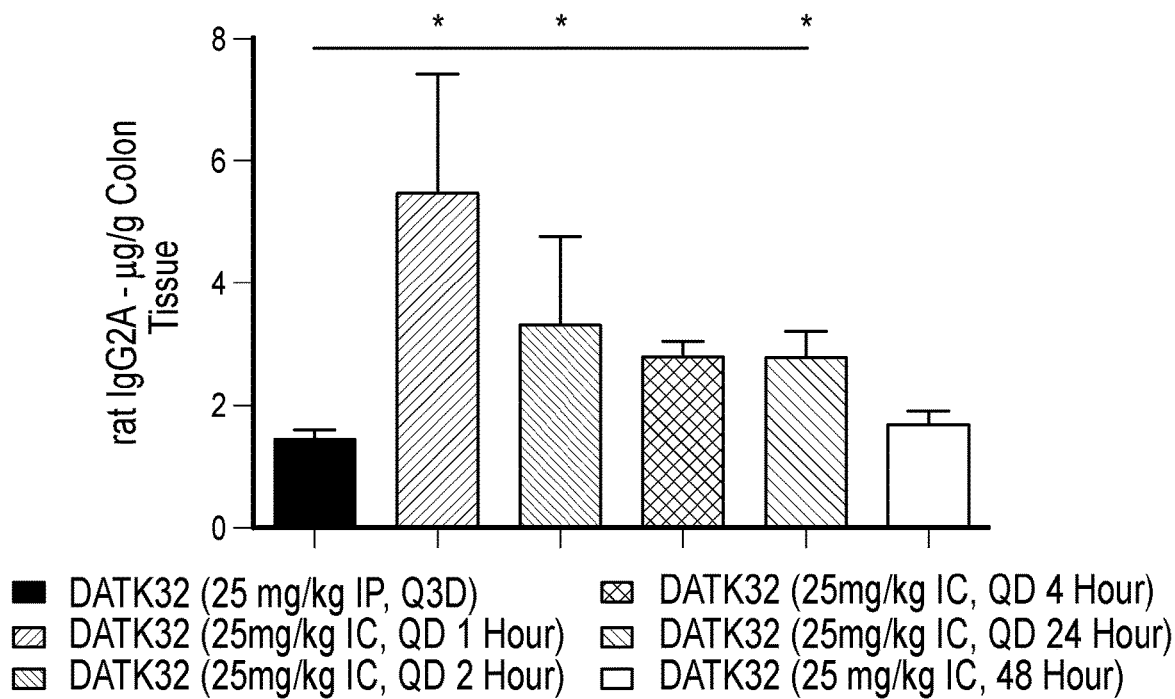
FIG. 44 is a graph showing the concentration of DATK32 rat IgG2A (μg/g) in the colon tissue of intraperitoneally (25 mg/kg) or intracecally (25 mg/kg and 5 mg/kg) administered treatment groups given daily (QD), and the concentration over time (1, 2, 4, 24, and 48 hours) was determined, where IP is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 45:
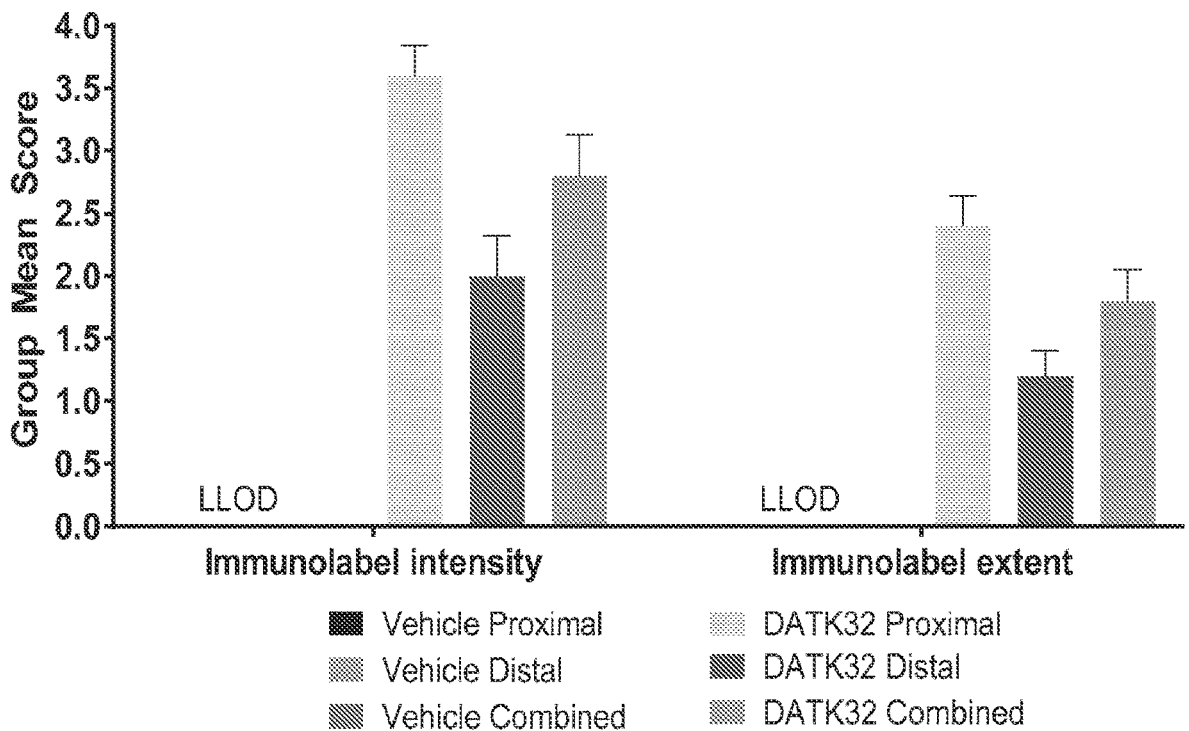
FIG. 45 is a graph showing the mean overall tissue immunolabel scores (intensity and extent) in acute DSS colitis mouse colon of DATK32 (anti-α4β7) antibody treated versus vehicle control (Vehicle) treated DSS mice. The data are presented as mean±SEM.
Figure 46:
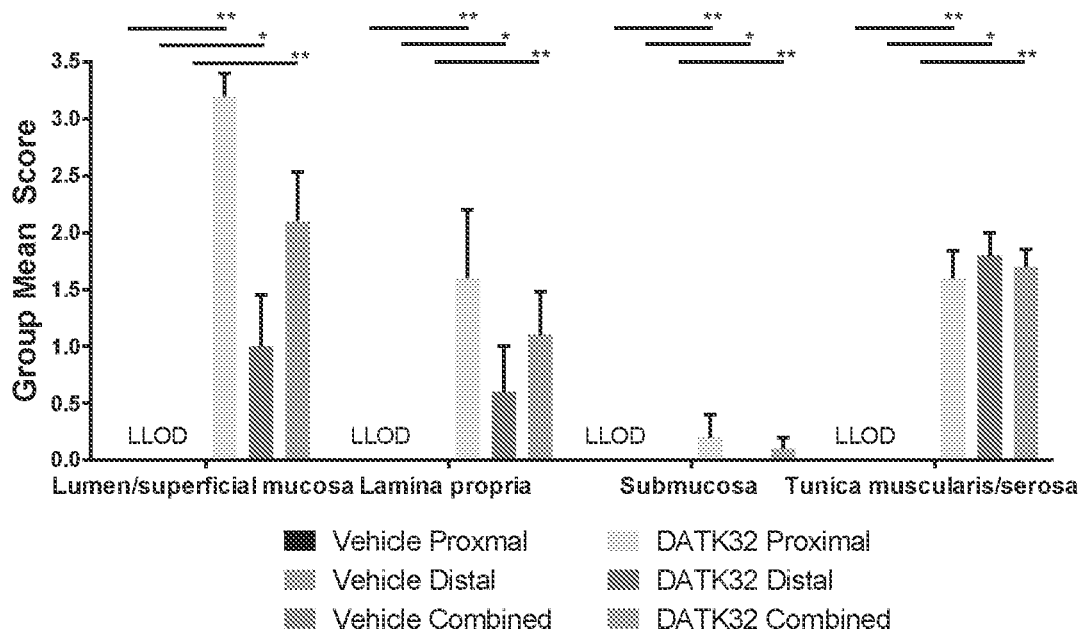
FIG. 46 is a graph showing the mean location-specific immunolabel scores in acute DSS colitis mouse colon of DATK32 (anti-α4β7) antibody-treated versus vehicle control (Vehicle)-treated DSS mice. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 47:
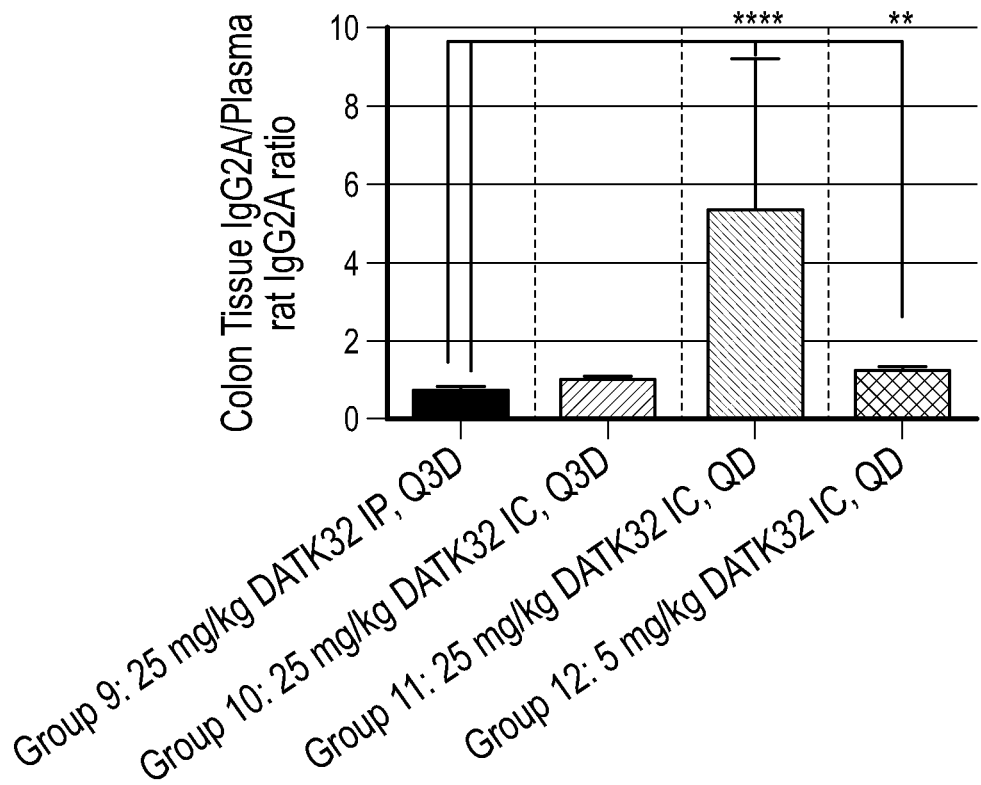
FIG. 47 is a graph showing the ratio of the DATK-32 antibody in the colon tissue to the plasma concentration of the DATK-32 antibody in mice treated with the DATK-32 antibody on day 0 (Q0) or day 3 (Q3D) of the study (Groups 9-12), when measured after initial dosing.

The data in FIG. 39 show decreased weight loss in DSS mice intracecally administered DATK antibody as compared to DSS mice that were intraperitoneally administered the DATK antibody. The data in FIG. 40 show that DSS mice intracecally administered DATK antibody have a decreased plasma concentration of DATK antibody as compared to DSS mice that were intraperitoneally administered DATK antibody. The data in FIGS. 41 and 42 show that DSS mice intracecally administered DATK antibody have an increased concentration of DATK antibody in the cecum and colon content as compared to DSS mice intraperitoneally administered DATK antibody. The data in FIGS. 43 and 44 show that DSS mice intracecally administered DATK antibody have an increased concentration of DATK antibody in colon tissue as compared to DSS mice intraperitoneally administered DATK antibody. The data in FIGS. 45 and 46 show an increased level of penetration of DATK antibody into colon tissue in DSS mice intracecally administered the DATK antibody as compared to an intracecal vehicle control (PBS). The data in FIG. 47 show that DSS mice intracecally administered DATK antibody have an increased ratio of the concentration of DATK antibody in colon tissue to the plasma concentration of the DATK antibody, as compared to the same ratio in DSS mice intraperitoneally administered the DATK antibody.

Figure 48:
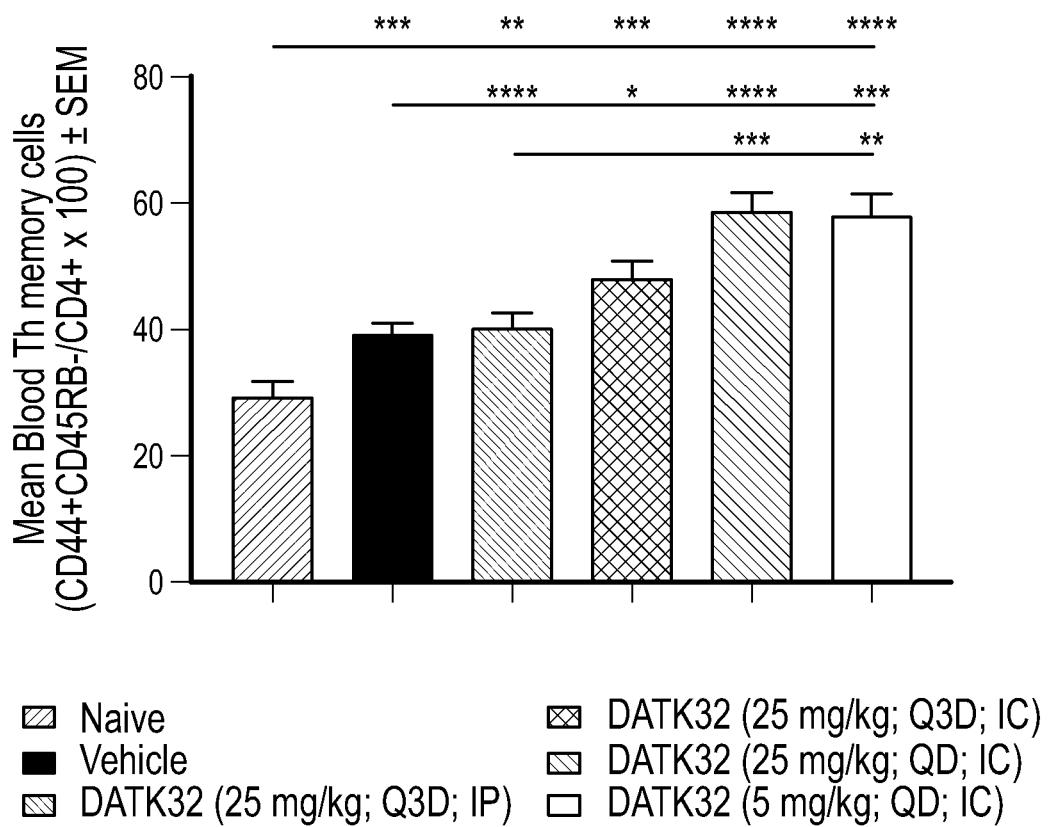
FIG. 48 is a graph showing the mean percentage of Th memory cells (mean±SEM) in blood for DATK32 (anti-α4β7) antibody intraperitoneally (25 mg/kg) or intracecally (25 mg/kg or 5 mg/kg) administered treatment groups given daily (QD) or every third day (Q3D), when compared to vehicle control (Vehicle) and when IP is compared to IC. Mean percentage Th memory cells were measured using FACS analysis. Data presented as mean±SEM. Mann-Whitney's U-test and Student's t-test were used for statistical analysis on non-Gaussian and Gaussian data respectively. A value of p<0.05 was considered significant (Graph Pad Software, Inc.).

The data in FIG. 48 show that DSS mice intracecally administered the DATK antibody have an increased percentage of blood Th memory cells as compared to DSS mice intraperitoneally administered the DATK antibody.

No significant differences in clinical observations or gastrointestinal-specific adverse effects, including stool consistency and/or bloody stool, were observed due to cannulation or intra-cecal treatments when compared with vehicle. No toxicity resulting from the treatments was reported. A significant reduction in body weight-loss was also found with DATK32 (5 mg/kg, QD) treatment (IC) when compared to vehicle control at the endpoint (day 14). The immunohistochemistry staining in DATK32 (25 mg/kg, QD) treatment groups showed penetration of DATK32 in all layers of colon tissue, including lumen mucosa, lamina propria, submucosa, tunica muscularis, via intra-cecal delivery. The distribution of DATK32 was found in all segments of the colon, however, higher levels were detected in the proximal region. A significantly higher mean concentration of DATK32 was found in gastrointestinal contents and colon tissues when delivered via intra-cecal administration (DATK32: 25 mg/kg and 5 mg/kg, QD) as compared to intraperitoneal administration (DATK32: 25 mg/kg, Q3D). The blood level of DATK32 was significantly higher when delivered via intraperitoneal administration (Q3D) as compared to intra-cecal administration (Q3D & QD). The pharmacokinetics of DATK32 (25 mg/kg, QD) showed significantly higher mean concentrations of DATK32 when delivered via intra-cecal administration at 1, 2, and 4 h post-dose in the gastrointestinal contents, and 1, 2, 4 and 24 h in colon tissue as compared with the mean concentrations of DATK32 following intraperitoneal administration. The mean number of gut-homing T cells (Th memory cells) was significantly higher in the blood of groups treated with DATK32 via intra-cecal administration (QD 25 mg/kg and QD 5 mg/kg) as compared to the groups treated with DATK32 via intraperitoneal administration (Q3D 25 mg/kg). The mean number of Th memory cells was significantly lower in the Peyer's Patches of groups treated with DATK32 via intra-cecal administration (QD 25 mg/kg and 5 mg/kg) as compared to the groups treated with DATK32 via intraperitoneal administration (Q3D 25 mg/kg). The mean number of Th memory cells in mesenteric lymph nodes (MLN) was significantly lower in groups treated with DATK32 via intra-cecal administration (QD and Q3D 25 mg/kg and QD 5 mg/kg) as compared to the groups treated with DATK32 via intraperitoneal administration (Q3D 25 mg/kg).

In sum, these data show that the compositions and devices provided herein can suppress the local immune response in the intestine, while having less of a suppressive effect on the systemic immune response of an animal. These data also show that the release of DATK-32 antibody in the colon can result in a suppression of leukocyte recruitment and may provide for the treatment of colitis and other pro-inflammatory diseases of the intestine.

Example 5. An Assessment of DATK32 Bio-Distribution Following Intracecal Administration in Male C57Bl/6 Mice The objective of this study is to assess DATK32 bio-distribution when dosed intracecally in male C57Bl/6 mice. A minimum of 10 days prior to the start of the experiment a cohort of animals will undergo surgical implantation of a cecal cannula. A sufficient number of animals will undergo implantation to allow for 24 cannulated animals to be enrolled in the main study (e.g., 31 animals). Animals were dosed with vehicle or test article via intracecal injection (IC) on Day 0 as indicated in Table 3. Animals from all groups were sacrificed for terminal sample collection three hours following test article administration.

Materials and Methods

Mice

Normal male C57Bl/6 mice between the ages of 6-8 weeks old, weighing 20-24 g, were obtained from Charles River Laboratories. The mice were randomized into two groups of twelve animals, and housed in groups of 12 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/Kg every day for the first 5 days post-surgery.

Dosing

Animals were dosed IC at a volume of 0.075 mL/animal on Days 0 as indicated in Table 3.

Sacrifice

All animals were euthanized by $CO_2$ inhalation three hours after dosing on Day 0.

Sample Collection

Terminal blood was collected and prepared for plasma using $K_2$EDTA as the anti-coagulant. The plasma will be split into two cryotubes, with 50 μL in one tube (PK analysis) and the remainder in another (other). Both samples were flash-frozen in liquid nitrogen. Plasma was stored at −80° C. for downstream analysis. Mesenteric lymph nodes (mLN) were collected, weighed, and flash-frozen in liquid nitrogen. Mesenteric lymph nodes were stored at −80° C. for downstream analysis. The small intestine was excised and rinsed, and the most distal 1 cm of ilium was dissected, weighed, and flash-frozen in liquid nitrogen. The samples were stored at −80° C. for downstream analysis. The cecum and colon were removed from each animal and contents collected, weighed, and snap frozen in separate cryovials. The samples were stored at −80° C. for downstream analysis. The colon was rinsed, and the most proximal 1 cm of colon was weighed and flash-frozen in liquid nitrogen. The snap frozen tissues were stored at −80° C.

TABLE 3

Study Design

| Group | N° Animals | Treatment | Route | Schedule | Terminal Collections Day 0 |
|---|---|---|---|---|---|
| 1 | 12 | Vehicle (PBS) | IC | Day 0** | Blood (plasma) |
| 2 | 12 | DATK32 (625 μg)* | | | Small intestine mLN Colon Colon Contents Cecum Contents |

*Per mouse. TA was administered in 0.075 mL/animal. DATK32 was delivered in sterile PBS.
**Animals were dosed on Day 0 and collections were performed 3 hours later.

Results

The data in FIGS. 63A-F show no significant differences in clinical observations. No gastrointestinal-specific or adverse effects were found in the group administered DATK32 via intra-cecal administration as compared to the group administered a vehicle control. No toxicity resulting from the treatments was reported. The level of DATK32 in the group intra-cecally administered DATK32 was significantly higher in cecum and colon content, and colon tissue compared to the group administered a vehicle control at 3 h post-dose. A small amount of DATK32 was also detected in plasma, small intestine, and mesenteric lymph node in the group intra-cecally administered DATK32.

Example 6. Pharmacokinectics/Pharmacodynamics and Bioavailability of Adalimumab when Applied to a TNBS-Damaged Mucosal Surface (Induced Colitis) in Swine The purpose of this non-Good Laboratory Practice (GLP) study was to explore the PK/PD, and bioavailability of adalimumab when applied to a TNBS-damaged mucosal surface (induced colitis) in Yorkshire-Cross farm swine, and to determine an appropriate dose and frequency for studies where a drug will be delivered by the ingestible device system. The ingestible device system will be capable of delivering a TNF inhibitor (adalimumab) topically and locally to damaged mucosa in human patients with inflammatory bowel disease (IBD). The TNBS-induced colitis model was validated when a single administration on Day 1 of 40 mL of 100% ethanol (EtOH) mixed with 5 grams of TNBS diluted in 10 mL of water via an enema using a rubber catheter resulted in the intended reproducible induction of damaged mucosal surface (induced colitis) in Yorkshire-Cross farm swine.

This study investigated whether topical delivery of adalimumab would result in increased local mucosal tissue levels with limited drug reaching systemic circulation, as compared to subcutaneous administration; whether local mucosal tissue levels of drug would be greater in damaged tissues when compared to normal tissues; whether increasing the dose of drug would result in increased mucosal tissue levels in local and distal TNBS-damaged tissues; and whether topical delivery of adalimumab would result in reductions in inflammatory cytokines such as TNF-α in damaged tissues, feces, and possibly blood.

Figure 49:
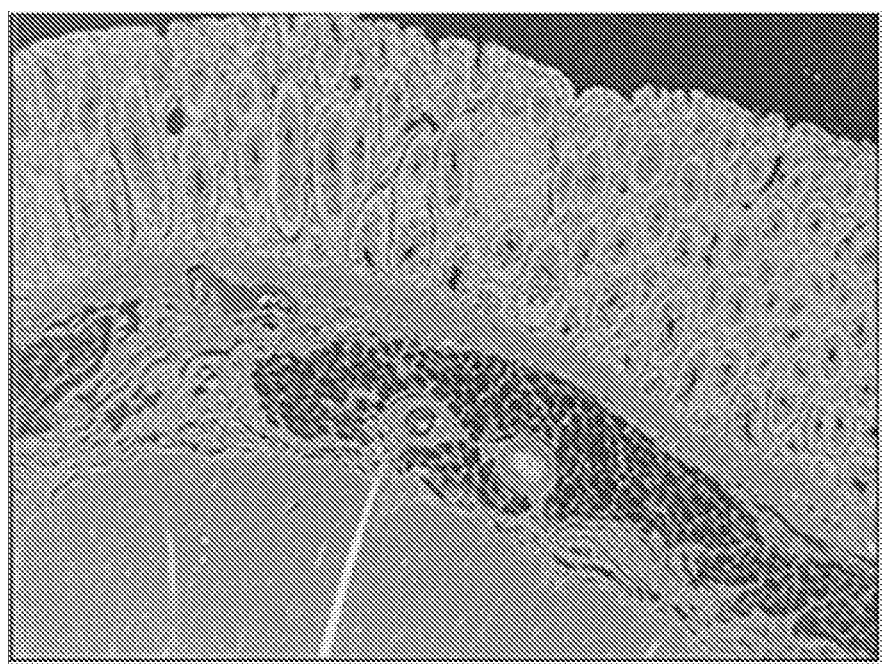
FIG. 49 is an exemplary image of a histological section of a distal transverse colon of Animal 1501 showing no significant lesions (i.e., normal colon).
Figure 50:
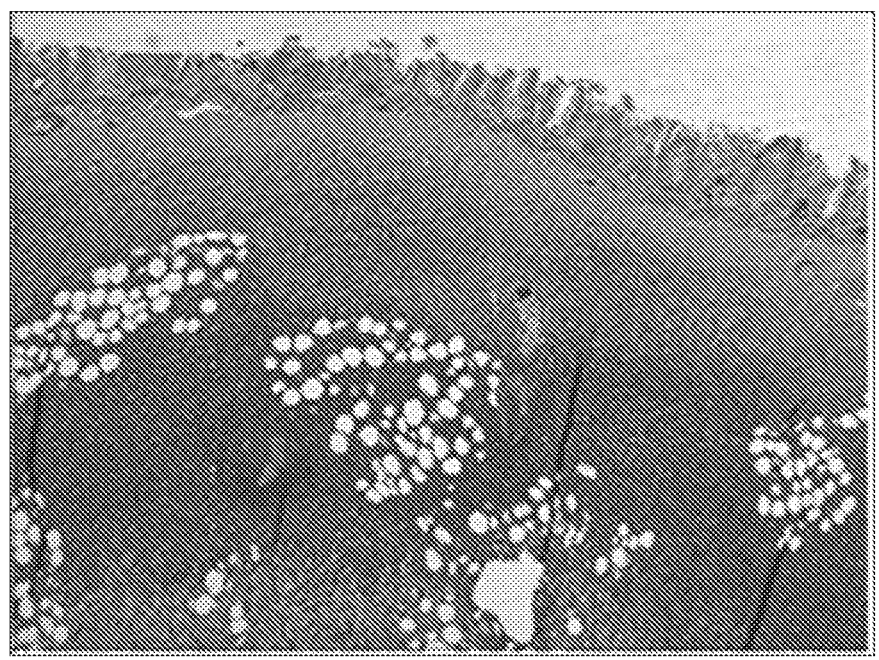
FIG. 50 is an exemplary image of a histological section of a distal transverse colon of Animal 2501 (treated with TNBS) showing areas of necrosis and inflammation.

All animals were subjected to intra-rectal administration of trinitrobenzene sulfonic acid (TNBS) to induce chronic colitis on day −2. All animals were fasted prior to colitis induction. Bedding was removed and replaced with rubber mats on day −3 to prevent ingestion of straw bedding material. The dose was 40 mL of 100% EtOH mixed with 5 grams of TNBS diluted in 10 mL of water, then instilled into the colon intra-rectally using a flexible gavage tube by a veterinary surgeon (deposited in a 10-cm portion of the distal colon and proximal rectum, and retained for 12 minutes by use of two Foley catheters with 60-mL balloons). Approximately 3 days after induction, macroscopic and microscopic alterations of colonic architecture were apparent: some necrosis, thickening of the colon, and substantial histologic changes were observed (FIGS. 49 and 50). The study employed 15 female swine (approximately 35 to 45 kg at study start) allocated to one of five groups. Group 1 employed three animals that were the treated controls. Each animal in Group 1 was administered adalimumab by subcutaneous injection at 40 mg in 0.8 mL saline. Groups 2, 3, 4, and 5 employed 3 animals in each group. Animals in these groups were administered intra-rectal adalimumab at 40 mg in 0.8 mL saline. The test drug (adalimumab) was administered to all groups on study day 1. The intra-rectal administrations (Groups 2-5) were applied to damaged mucosal surface of the bowel vial intra-rectal administration by a veterinary surgeon. Blood (EDTA) was collected from all animals (cephalic, jugular, or catheter) on day −3 (n=15), −1

(n=15), and 6 (n=15), 12 (n=12), 24 (n=9), and 48 (n=6) hours post-dose (87 bleeds total). The EDTA samples were split into two aliquots, and one was centrifuged for PK plasma, and stored frozen (−80° C.) for PK analyses and reporting. Fecal samples were collected for the same time-points (87 fecal collections). Fecal samples were flash-frozen in liquid nitrogen and then stored at −80° C. for analysis of drug levels and inflammatory cytokines. Groups 2, 3, 4, and 5 were euthanized and subjected to gross necropsy and tissue collection 6, 12, 24, and 48 hours post-dose, respectively. Group 1 was similarly euthanized and necropsied 48 hours post-dose. The animals were euthanized via injection of a veterinarian-approved euthanasia solution as per the schedule. Immediately after euthanasia in order to avoid autolytic changes, colon tissues were collected, opened, rinsed with saline, and a detailed macroscopic examination of the colon were performed to identify macroscopic findings related to TNBS-damage. Tissue samples were taken from the proximal, mid, and distal transverse colon; the dose site; and the distal colon. Each tissue sample was divided into two approximate halves; one tissue section was placed into 10% neutral buffered formalin (NBF) and evaluated by a Board certified veterinary pathologist, and the remaining tissue section was flash frozen in liquid nitrogen and stored frozen at −80° C. Clinical signs (ill health, behavioral changes, etc.) were recorded daily beginning on day −3. Additional pen-side observations were conducted once or twice daily. Animals observed to be in ill health were examined by a veterinarian. Body weight was measured for all animals on day −3, and prior to scheduled euthanasia. Table 4.1, depicted below, shows the study design.

Materials and Methods

Test Article

Adalimumab (EXEMPTIA™) is a Tumour Necrosis Factor (TNF) inhibitor. A single dose was pre-filled in a syringe (40 mg in a volume of 0.8 mL).

TABLE 4.1

Study Design Table

| | Sample size | Dose | Route | Days | | | | Hours | | | | | | | | |
|---|---|---|---|---|---|---|---|---|---|---|---|---|---|---|---|---|
| | | | | −3 | −2 | −1 | 1 | 0.5 | 1 | 2 | 4 | 6 | 8 | 12 | 24 | 48 |
| General Fast | | | | • | | | | | | | | | | | | |
| Food/Water | | ad libidum | oral | | • | • | • | • | • | • | • | | | | | |
| Observations clinical observations | | | | | • | • | • | • | | | | | | | • | • |
| body weight | | | | | • | | | • | | | | | | | • | • |
| Treatments (groups) | | | | | | | | | | | | | | | | |
| TNBS (all animals) | | | intra rectal | | | | • | | | | | | | | | |
| 1. Treated control | n = 3 | 40mg in 0.8 mL saline | sub-cutaneous | | | | | • | | | | | | | | |
| euthanized | | | | | | | | | | | | | | | | n = 3 |
| 2. Adalimumab | n = 3 | 40mg in 0.8 mL saline | intra rectal | | | | | • | | | | | | | | |
| euthanized | | | | | | | | | | | | | n = 3 | | | |
| 3. Adalimumab | n = 3 | 40mg in 0.8 mL saline | intra rectal | | | | | • | | | | | | | | |
| euthanized | | | | | | | | | | | | | | n = 3 | | |
| 4. Adalimumab | n = 3 | 40mg in 0.8 mL saline | intra rectal | | | | | • | | | | | | | | |
| euthanized | | | | | | | | | | | | | | | n = 3 | |
| 5. Adalimumab | n = 3 | 40mg in 0.8 mL saline | intra rectal | | | | | • | | | | | | | | |
| euthanized | | | | | | | | | | | | | | | | n = 3 |
| Adalimumab (required) | | 600 | | | | | | | | | | | | | | |
| Samples | | | | | | | | | | | | | | | | |
| PBMCs | | | cephalic, jugular or catheter | | | | | • | | | • | | • | • | • | • |
| Serum | | | cephalic, jugular or catheter | • | • | • | | | | | | • | | • | • | • |

TABLE 4.1-continued

Study Design Table

| | | | | Days | | | | Hours | | | | | | | |
|---|---|---|---|---|---|---|---|---|---|---|---|---|---|---|---|
| | | | | −3 | −2 | −1 | 1 | 0.5 | 1 | 2 | 4 | 6 | 8 | 12 | 24 | 48 |
| Fecal | | | rectal | • | • | • | | | | | | • | | • | • | • |
| Tissue Analysis | | | necropsy | | | | | | | | | • | | • | • | • |
| Histopathology | 1 location | 4 locations | | | | | | | | | | | | | | |
| inflammed | 45 | 180 | H&E | | | | | | | | | | | | | |
| normal | 45 | 180 | H&E | | | | | | | | | | | | | |
| Blood | | | | | | | | | | | | | | | | |
| adalimumab | 57 | | pbl | | | | 15 | | | | | 15 | | 12 | 9 | 6 |
| TNFα | 87 | | pbl | 15 | | 15 | 15 | | | | | 15 | | 12 | 9 | 6 |
| Feces | | | | | | | | | | | | | | | | |
| adalimumab | 57 | | pbl | | | | 15 | | | | | 15 | | 12 | 9 | 6 |
| TNFα | 87 | | pbl | 15 | | 15 | 15 | | | | | 15 | | 12 | 9 | 6 |
| Tissue Inflammed | | | | | | | | | | | | | | | | |
| adalimumab | 45 | 180 | pbl | | | | | | | | | 3 | | 3 | 3 | 6 |
| TNFα | 45 | 180 | pbl | | | | | | | | | 3 | | 3 | 3 | 6 |
| HER2 | 45 | 180 | pbl | | | | | | | | | 3 | | 3 | 3 | 6 |
| Normal | | | | | | | | | | | | | | | | |
| adalimumab | 45 | 180 | pbl | | | | | | | | | 3 | | 3 | 3 | 6 |
| TNFα | 45 | 180 | pbl | | | | | | | | | 3 | | 3 | 3 | 6 |
| HER2 | 45 | 180 | pbl | | | | | | | | | 3 | | 3 | 3 | 6 |

Results

Figure 51:
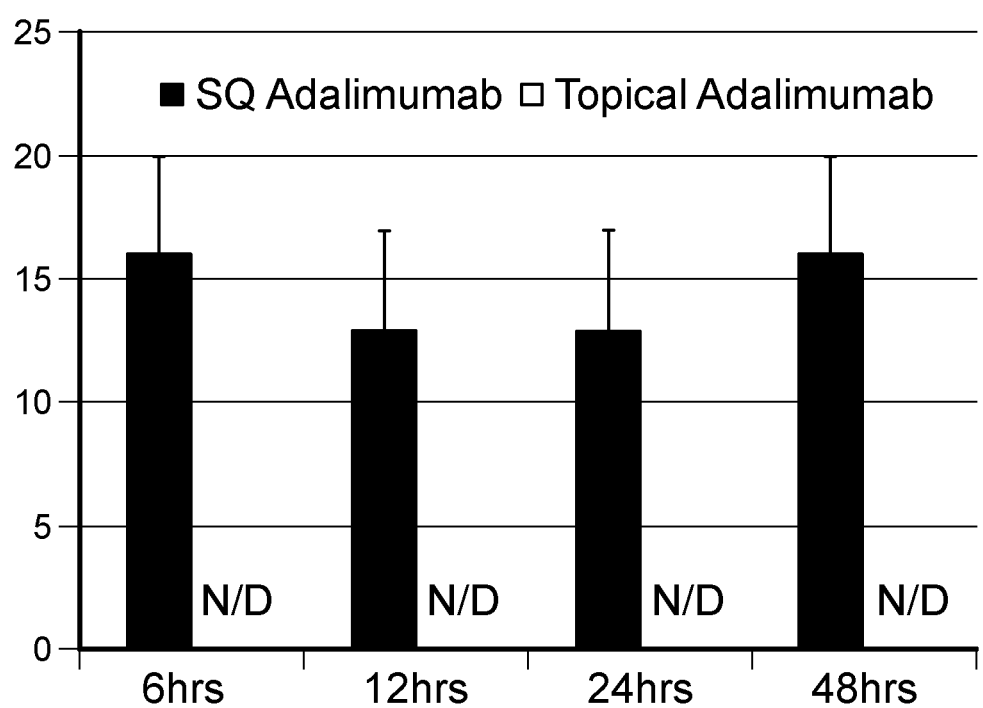
FIG. 51 is a representative graph of plasma adalimumab concentrations over time following a single subcutaneous (SQ) or topical administration of adalimumab. The plasma concentrations of adalimumab were determined 6, 12, 24, and 48 hours after administration of adalimumab. N/D=not detectable.
Figure 53:
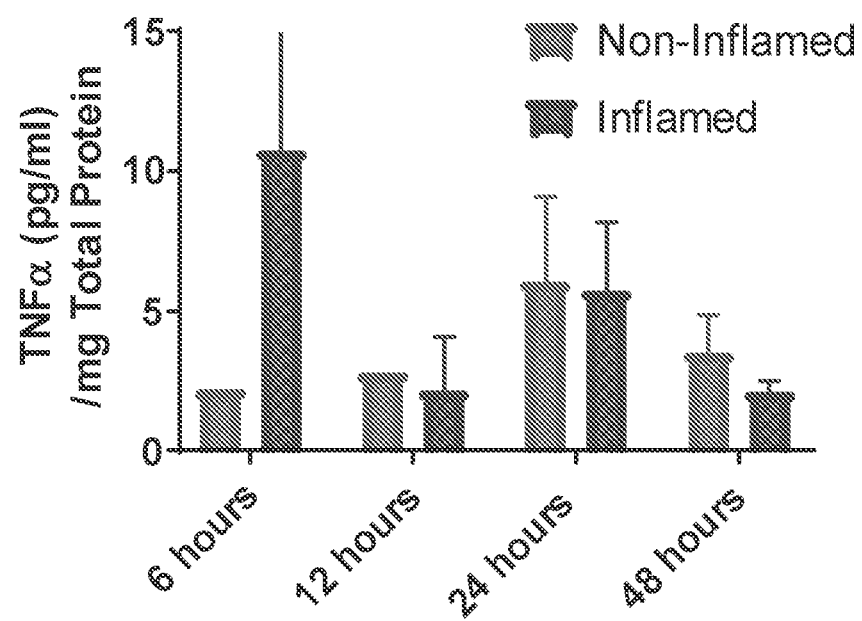
FIG. 53 is a graph showing the concentration of TNFα (μg/mL per mg of total protein) in non-inflamed and inflamed colon tissue after intracecal administration of adalimumab, as measured 6, 12, 24, and 24 hours after the initial dosing.
Figure 54:
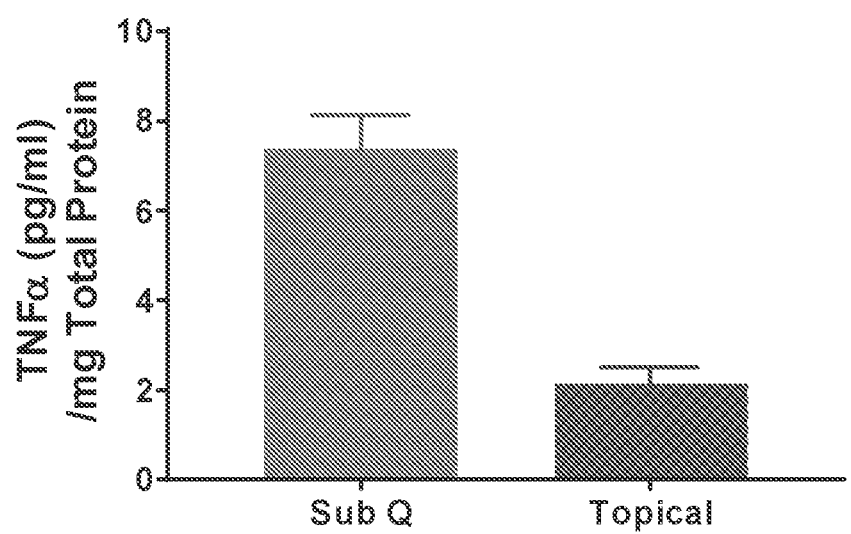
FIG. 54 is a graph showing the concentration of TNFα (μg/mL per mg of total protein) in colon tissue after subcutaneous or intracecal (topical) administration of adalimumab, as measured 48 hours after the initial dosing.

While subcutaneously administered adalimumab was detected at all times points tested in plasma, topically administered adalimumab was barely detectable in plasma (FIGS. 51 and 52). Both topical delivery and subcutaneous delivery of adalimumab resulted in reduced levels of TNF-α in colon tissue of TNBS-induced colitis animals, yet topical delivery of adalimumab was able to achieve a greater reduction in TNF-α levels (FIGS. 53 and 54).

Either subcutaneous or intra-rectal administration of adalimumab was well tolerated and did not result in death, morbidity, adverse clinical observations, or body weight changes. A decreased level of total TNBS-related inflammatory response was observed by adalimumab treatment via intra-rectal administration when applied to the damaged mucosal surface of the bowel when compared to subcutaneous delivery. A significantly higher concentration of adalimumab was measured in blood following subcutaneous delivery as compared to the blood concentration following intra-rectal administration. Intra-rectal administration of adalimumab decreased the total and normalized TNFα concentration over time (6-48 h) and was more effective at reducing TNFα at the endpoint (48 h) as compared to groups administered adalimumab subcutaneously.

In sum, these data show that the compositions and devices provided herein can suppress the local immune response in the intestine, while having less of a suppressive effect on the systemic immune response of an animal. For example, these data show that intracecal administration of adalimumab using a device as described herein can provide for local delivery of adalimumab to the site of disease, without suppressing the systemic immune response. These data also show that local administration of adalimumab using a device as described herein can result in a significant reduction of the levels of TNFα in diseases animals.

Example 7. Comparison of Systemic Versus Intracecal Delivery of Cyclosporine A

The objective of this study was to compare the efficacy of an immunosuppressant agent (cyclosporine A; CsA) when dosed systemically versus intracecally to treat dextran sulfate sodium salt (DSS)-induced colitis in male C57Bl/6 mice.

Experimental Design

A minimum of 10 days prior to the start of the experiment a cohort of animals underwent surgical implantation of a cecal cannula. A sufficient number of animals underwent implantation to allow for 44 cannulated animals to be enrolled in the main study (e.g., 76 animals). Colitis was induced in 60 male C5Bl/6 mice by exposure to 3% DSS-treated drinking water from day 0 to day 5. Two groups of eight additional animals (cannulated and non-cannulated) served as no-disease controls (Groups 1 and 2). Animals were dosed with cyclosporine A via intraperitoneal injection (IP), oral gavage (PO), or intracecal injection (IC) from day 0 to 14 as indicated in Table 5.1. All animals were weighed daily and assessed visually for the presence of diarrhea and/or bloody stool at the time of dosing. Mice underwent video endoscopy on days 10 and 14 to assess colitis severity. Images were captured from each animal at the most severe region of disease identified during endoscopy. Additionally, stool consistency was scored during endoscopy using the parameters defined in Table 5.2. Following endoscopy on day 14, animals from all groups were sacrificed and underwent terminal sample collection.

Specifically, animals in all treatment groups dosed on day 14 were sacrificed at a pre-dosing time point, or 1, 2, and 4 hours after dosing (n=3/group/time point). Terminal blood was collected via cardiac puncture and prepared for plasma using $K_2$EDTA as the anti-coagulant. The blood cell pellet was retained and snap frozen while the resulting plasma was split into two separate cryotubes, with 100 μL in one tube and the remainder in the second. Additionally, the cecum and colon were removed from all animals; the contents were collected, weighed, and snap frozen in separate cyrovials. The colon was then rinsed, measured, weighed, and then trimmed to 6 cm in length and divided into five pieces. The most proximal 1 cm of colon was snap frozen for subsequent bioanalysis of cyclosporine A levels. Of the remaining 5 cm of colon, the most distal and proximal 1.5-cm sections were each placed in formalin for 24 hours, then transferred to 70% ethanol for subsequent histological evaluation. The middle 2-cm portion was bisected longitudinally and placed into two separate cryotubes, weighed, and snap frozen in liquid nitrogen. All plasma and frozen colon tissue were stored at −80° C. for selected end point analysis. For all control animals in Groups 1-4, there was an additional collection of 100 µL of whole blood from all animals which was then processed for FACS analysis of α4 and β7 expression on $T_H$ memory cells. The details of the study are shown in Table 5.1.

TABLE 5.1

Study Design

| Group Number | 1 | 2 | 3 | 4 | 13 | 14 | 15 |
|---|---|---|---|---|---|---|---|
| Number of Animals | 8 | 8 | 12 | 12 | 12 | 12 | 12 |
| Cecal Cannula | NO | YES | NO | YES | NO | YES | YES |
| DSS | N/A | N/A | 3% DSS on Day 0 to Day 5 | | | | |
| Treatment | none | none | vehicle | vehicle | CsA | CsA | CsA |
| Dose (mg/kg) | N/A | N/A | N/A | N/A | 10 | 10 | 3 |
| Route | N/A | N/A | N/A | N/A | PO | IC | IC |
| Dosing Schedule | N/A | N/A | QD: Day 0 to 14 | QD: Day 0 to 14 | QD: Day 0 to 14 | QD: Day 0 to 14 | QD: Day 0 to 14 |
| Endoscopy Schedule* | Days 10 and 14 | | | | | | |
| Endpoints Day 14 | Endoscopy, Colon weight/length, stool score Terminal Collection (all groups): Cecal contents, colon contents, plasma, and colon tissue FACS analysis collection of Groups 1-4: Whole blood for the following FACS panel: CD4, CD44, CD45RB, α4, β7, CD16/32 | | | | | | |
| PK Sacrifice (Day 14) | N = 3/ time points At pre-dose and 1, 2, and 4 hours post-dosing | | | | | | |

*Animals were dosed once (QD) on Day 14 and plasma collected (K2EDTA) at pre-dosing, 1, 2, and 4 hours post-dosing from n =3/group/time point. Each collection was terminal.

Experimental Procedures

Cecal Cannulation

Animals were placed under isoflurance anesthesia, and the cecum exposed via a mid-line incision in the abdomen. A small point incision was made in the distal cecum through which 1-2 cm of the cannula was inserted. The incision was closed with a purse-string suture using 5-0 silk. An incision was made in the left abdominal wall through which the distal end of the cannula was inserted and pushed subcutaneously to the dorsal aspect of the back. The site was washed copiously with warmed saline prior to closing the abdominal wall. A small incision was made in the skin of the back between the shoulder blades, exposing the tip of the cannula. The cannula was secured in place using suture, wound clips, and tissue glue. All animals received 1 mL of warm sterile saline (subcutaneous injection) and were monitored closely until fully recovered before returning to the cage. All animals received buprenorphine at 0.6 mg/kg BID for the first 3 days, and Baytril® at 10 mg/kg QD for the first 5 days following surgery.

Disease Induction

Colitis was induced on day 0 via addition of 3% DSS (MP Biomedicals, Cat #0260110) to the drinking water. Fresh DSS/water solutions were made on day 3 and any of the remaining original DSS solution was discarded.

Dosing

Animals were dosed by oral gavage (PO), intraperitoneal injection (IP), or intracecal injection (IC) at a volume of 0.1 mL/20 g on days 0 to 14 as indicated in Table 5.1.

Body Weight and Survival

Animals were observed daily (weight, morbidity, survival, presence of diarrhea, and/or bloody stool) in order to assess possible differences among treatment groups and/or possible toxicity resulting from the treatments.

Animals Found Dead or Moribund

Animals were monitored on a daily basis and those exhibiting weight loss greater than 30% were euthanized, and samples were not collected from these animals.

Endoscopy

Each mouse underwent video endoscopy on days 10 and 14 using a small animal endoscope (Karl Storz Endoskope, Germany) under isoflurane anesthesia. During each endoscopic procedure still images as well as video were recorded to evaluate the extent of colitis and the response to treatment. Additionally, we attempted to capture an image from each animal at the most severe region of disease identified during endoscopy. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the parameters defined in Table 5.2.

TABLE 5.2

Stool Consistency

| Score | Description |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Tissue/Blood for FACS

Tissue and blood were immediately placed in FACS buffer (1x phosphate-buffered saline (PBS) containing 2.5% fetal calf serum (FCS)) and analyzed using the antibody panel in Table 5.3.

TABLE 5.3

FACS Antibody Panel

| Antibody Target | Fluorochrome | Purpose |
|---|---|---|
| CD4 | APC-Vio770 | Defines $T_H$ cells |
| CD44 | VioBlue | Memory/Naïve discrimination |
| CD45RB | FITC | Memory/Naïve discrimination |
| α4 | APC | Defines $T_H$-memory subset of interest |
| β7 | PE | Defines $T_H$-memory subset of interest |
| CD16/32 | — | Fc block |

Results

Figure 55:
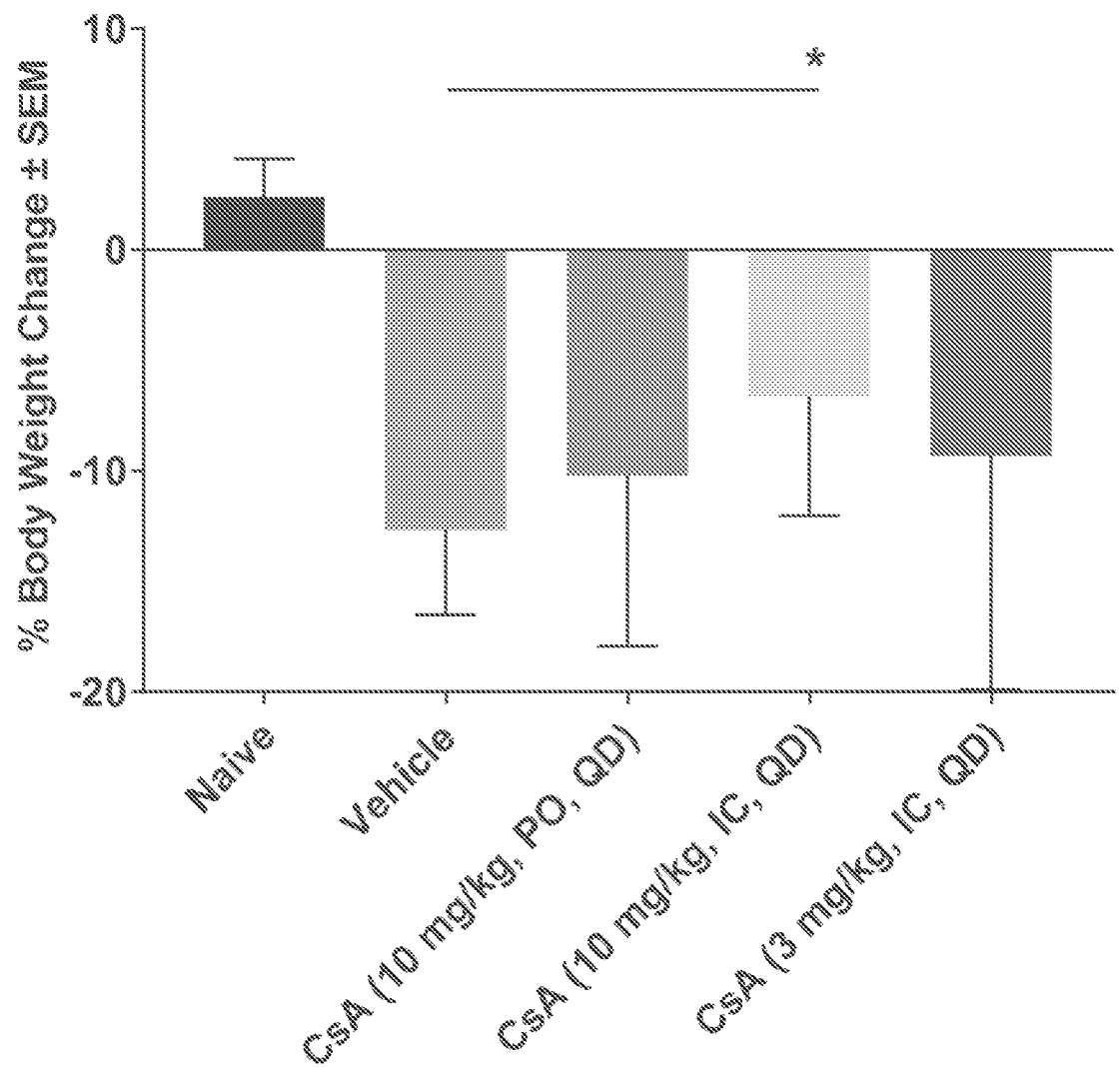
FIG. 55 is a graph showing the percentage (%) change in body weight at day 14 (±SEM) in acute DSS colitis mice treated with cyclosporine A orally (10 mg/kg) every third day (Q3D) or intracecally (10 mg/kg or 3 mg/kg) daily (QD), when compared to vehicle control (Vehicle). Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 56:
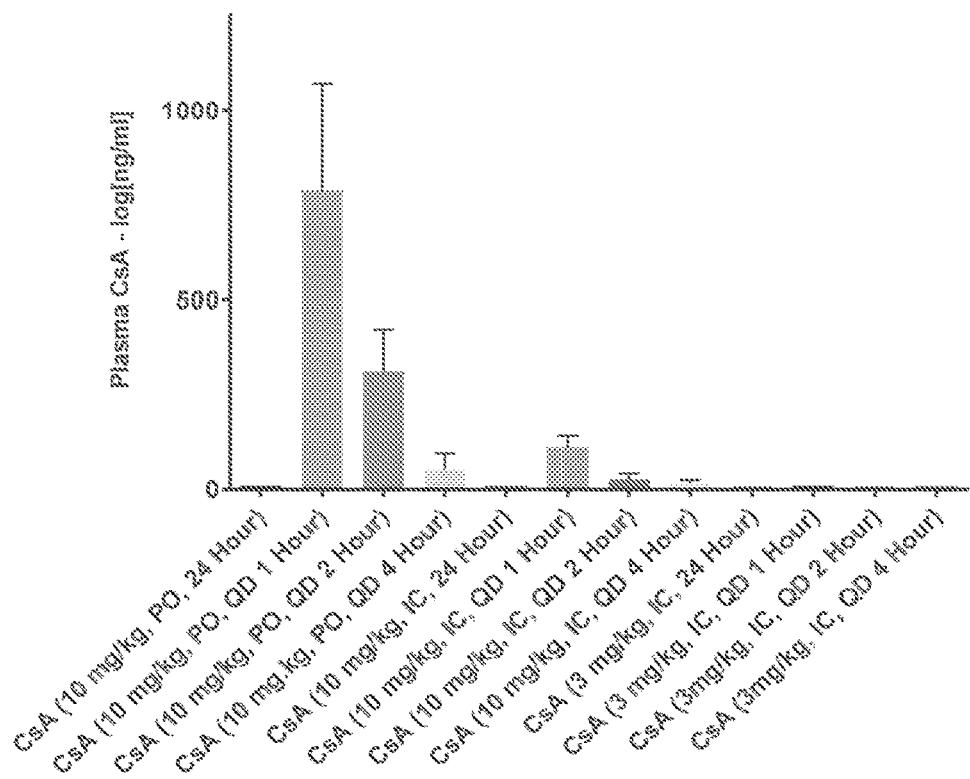
FIG. 56 is a graph showing the plasma cyclosporine A (CsA) (ng/mL) concentration over time (1 h, 2 h, 4 h, and 24 h) in acute DSS colitis mice treated daily (QD) with orally (PO) (10 mg/kg) or intracecally (IC) (10 mg/kg or 3 mg/kg) administered CsA. Data presented as mean±SEM.
Figure 57:
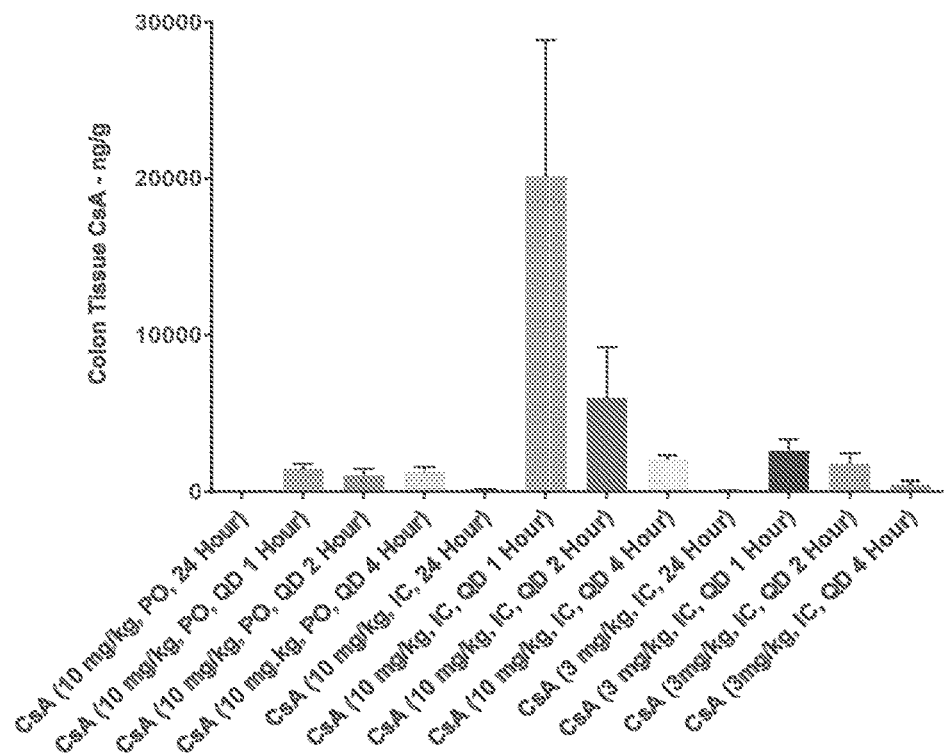
FIG. 57 is a graph showing the colon tissue cyclosporine A (CsA) (ng/g) concentration over time (1 h, 2 h, 4 h and 24 h) in acute DSS colitis mice treated daily (QD) with orally (PO) (10 mg/kg) or intracecally (IC) (10 mg/kg or 3 mg/kg) administered CsA. Data presented as mean±SEM.
Figure 58:
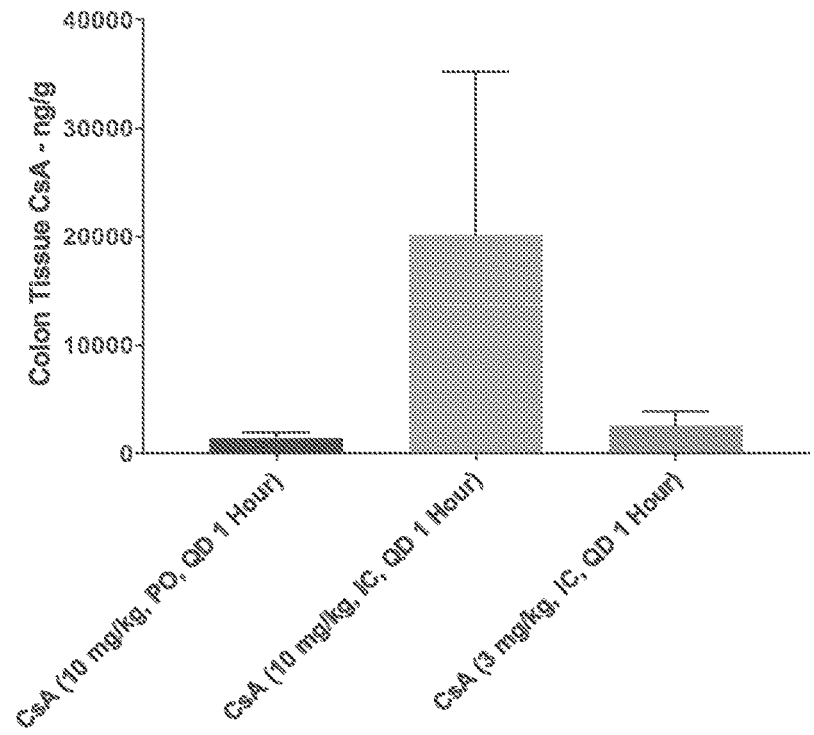
FIG. 58 is a graph showing the peak colon tissue cyclosporine A (CsA) (ng/g) concentration in acute DSS colitis mice treated daily (QD) with orally (PO) (10 mg/kg) or intracecally (IC) (10 mg/kg or 3 mg/kg) administered CsA. Data presented as mean±SEM.
Figure 59:
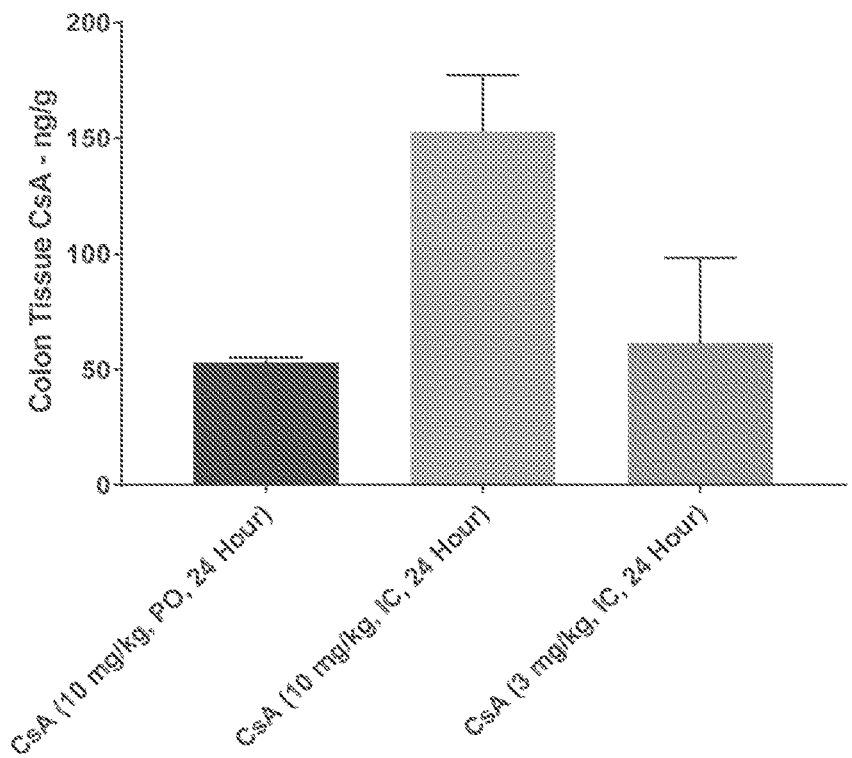
FIG. 59 is a graph showing the trough tissue concentration of cyclosporine (CsA) (ng/g) in colon of acute DSS colitis mice treated daily (QD) with orally (PO) (10 mg/kg) or intracecally (IC) (10 mg/kg or 3 mg/kg) administered CsA. Data presented as mean±SEM.

The data in FIG. 55 show a decrease in weight loss is observed in DSS mice intracecally administered cyclosporine A as compared to DSS mice orally administered cyclosporine A. The data in FIG. 56 show a decrease in plasma concentration of cyclosporine A in DSS mice intracecally administered cyclosporine A as compared to DSS mice orally administered cyclosporine A. The data in FIGS. 57-59 show an increased concentration of cyclosporine A in the colon tissue of DSS mice intracecally administered cyclosporine A as compared to the concentration of cyclosporine A in the colon tissue of DSS mice orally administered cyclosporine A.

Figure 60:
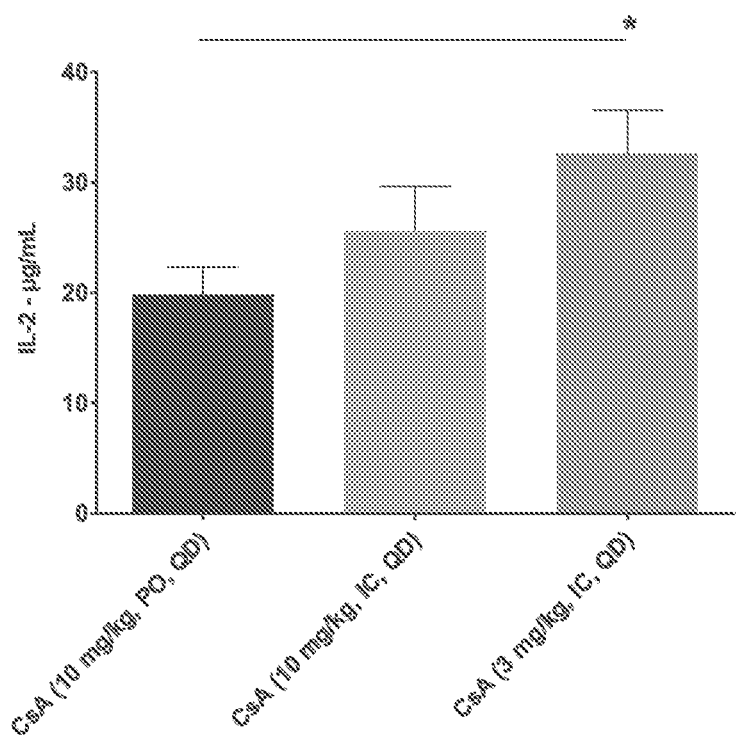
FIG. 60 is a graph showing the interleukin-2 (Il-2) concentration (µg/mL) in colon tissue of acute DSS colitis mice treated daily (QD) with orally (PO) (10 mg/kg) or intracecally (IC) (10 mg/kg or 3 mg/kg) administered CsA, where PO is compared to IC. Data presented as mean±SEM. Mann-Whitney's U-test and Student's t-test were used for statistical analysis on non-Gaussian and Gaussian data respectively. A value of p<0.05 was considered significant (Graph Pad Software, Inc.).
Figure 61:
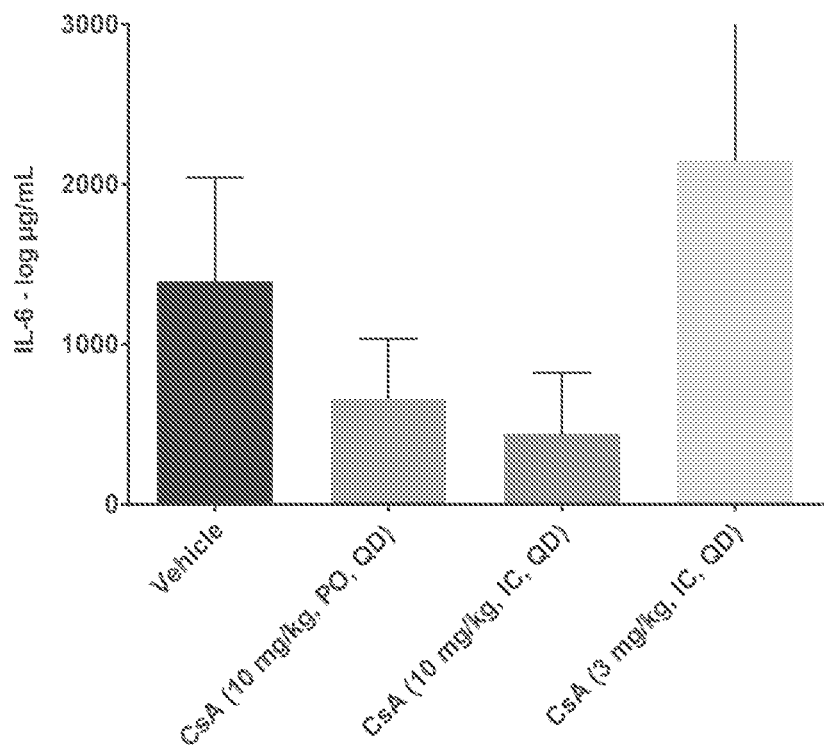
FIG. 61 is a graph showing the interleukin-6 (Il-6) concentration (µg/mL) in colon tissue of acute DSS colitis mice treated daily (QD) with orally (PO) (10 mg/kg) or intracecally (IC) (10 mg/kg or 3 mg/kg) administered CsA. Data presented as mean±SEM.

The data in FIG. 60 show that DSS mice intracecally administered cyclosporine A have an increased concentration of IL-2 in colon tissue as compared to DSS mice orally administered cyclosporine A. The data in FIG. 61 show that DSS mice intracecally administered cyclosporine A have a decreased concentration of IL-6 in colon tissue as compared to DSS mice orally administered cyclosporine A.

In sum, these data show that the compositions and devices provided herein can suppress the local immune response in the intestine, while having less of a suppressive effect on the systemic immune response of an animal. For example, these data demonstrate that the present compositions and devices can be used to release cyclosporine A to the intestine and that this results in a selective immune suppression in the colon, while having less of an effect on the immune system outside of the intesting. These data also suggest that the present compositions and devices will provide for the treatment of colitis and other pro-inflammatory disorders of the intestine.

Example 8. Bellows Testing: Drug Stability Bench Test

Experiments were run to evaluate the effects that bellows material would have on the function of a drug used as the dispensable substance. The experiments also evaluated the effects on drug function due to shelf life in the bellows.

Figure 64:
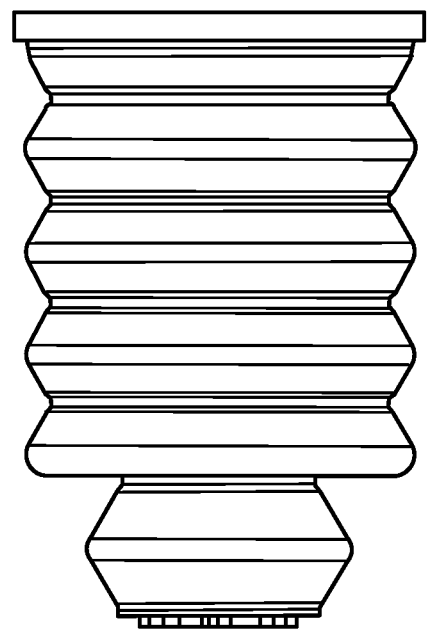
FIG. 64 illustrates a tapered silicon bellows.
Figure 65:
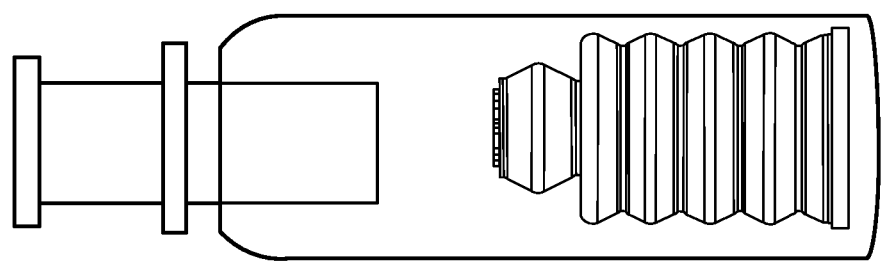
FIG. 65 illustrates a tapered silicone bellows in the simulated device jig.
Figure 66:
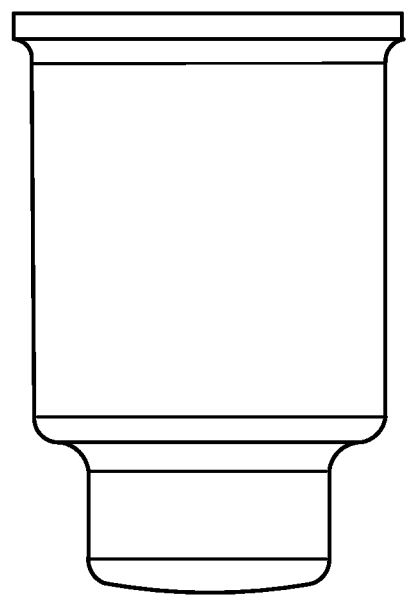
FIG. 66 illustrates a smooth PVC bellows.
Figure 67:
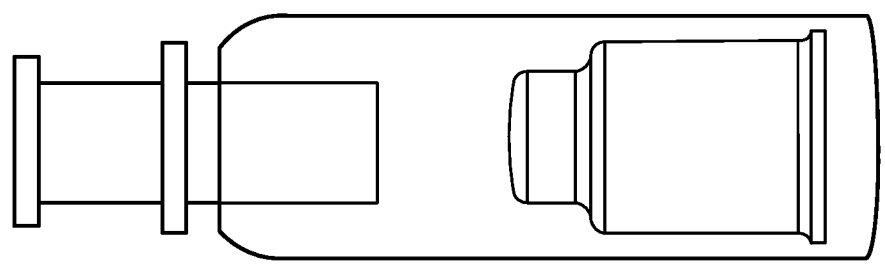
FIG. 67 illustrates a smooth PVC bellows in the simulated device jig.

The adalimumab was loaded into simulated device jigs containing either tapered silicone bellows or smooth PVC bellows and allowed to incubate for 4, 24, or 336 hours at room temperature while protected from light. FIG. 64 illustrates the tapered silicone bellows, and FIG. 65 illustrates the tapered silicone bellows in the simulated device jig. FIG. 66 illustrates the smooth PVC bellows, and FIG. 67 illustrates the smooth PVC in the simulated device jig.

Figure 68:
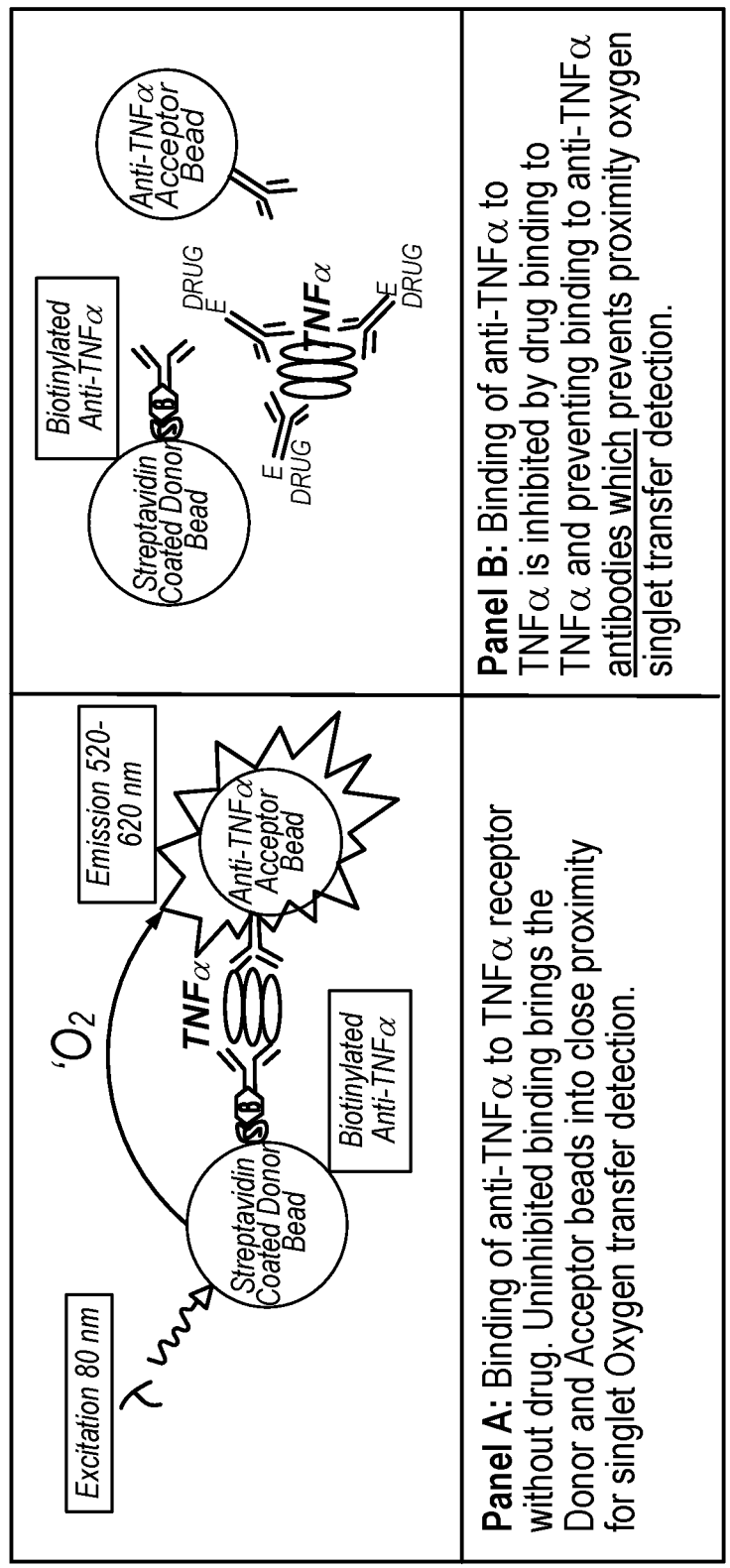
FIG. 68 demonstrates a principle of a competition assay performed in an experiment.

The drug was subsequently extracted using the respective dispensing systems and tested by a competitive inhibition assay. The test method has been developed from the literature (Velayudhan et al., "Demonstration of functional similarity of proposed biosimilar ABP501 to adalimumab" BioDrugs 30:339-351 (2016) and Barbeauet et al., "Application Note: Screening for inhibitors of TNFα/s TNFR1 Binding using AlphaScreen™ Technology". PerkinElmer Technical Note ASC-016. (2002)), as well as pre-testing development work using control drug and experiments using the provided AlphaLISA test kits. FIG. 68 demonstrates the principle of the competition assay performed in the experiment.

The bellows were loaded as follows: aseptically wiped the dispensing port of the simulated ingestible device jig with 70% ethanol; allowed to air dry for one minute; used an adalimumab delivery syringe to load each set of bellows with 200 µL of drug; took a photo of the loaded device; gently rotated the device such that the drug is allowed to come in contact with all bellows surfaces; protected the bellows from light; and incubate at room temperature for the predetermined time period to allow full contact of the drug with all bellows' surfaces.

The drug was extracted as follows: after completion of the incubation period; the device jig was inverted such that the dispensing port was positioned over a sterile collection microfuge tube and petri dish below; five cubic centimeters of air was drawn into an appropriate syringe; the lure lock was attached to the device jig; the syringe was used to gently apply positive pressure to the bellow with air such that the drug was recovered in the collection microfuge tube; where possible, a video of drug dispensing was taken; samples were collected from each bellows type; a control drug sample was collected by directly dispensing 200 µL of drug from the commercial dispensing syringe into a sterile microfuge tube; the control drug-free sample was collected by directly dispensing 200 µL of PBS using a sterile pipette into a sterile microfuge tube; the collected drug was protected from light; and the drug was diluted over the following dilution range (250, 125, 25, 2.5, 0.25, 0.025, 0.0125, 0.0025 µg) in sterile PBS to determine the $IC_{50}$ range of the drug.

To determine any effects storage conditions may have on drug efficacy in the device, the drug (stored either in the syringe, silicon bellows, PVC bellows) was stored at room temperature while protected from light for 24 hours and 72 hours. Samples were then extracted and the steps in the preceding paragraph were repeated.

The AlphaLISA (LOCI™) test method was used. Human TNFα standard dilution ranges were prepared as described in Table 6.

TABLE 6

| Tube | Vol. of human TNFα (µL) | Vol. of dilent (µL) * | [human TNFα] in standard curve | |
|---|---|---|---|---|
| | | | (g/mL in 5 µL) | (pg/mL in 5 µL) |
| A | 10 µL of reconstituted human TNFα | 90 | 1E-07 | 100 000 |
| B | 60 µL of tube A | 140 | 3E-08 | 30 000 |
| C | 60 µL of tube B | 120 | 1E-06 | 10 000 |
| D | 60 µL of tube C | 140 | 3E-00 | 3 000 |
| E | 60 µL of tube D | 120 | 1E-09 | 1 000 |
| F | 60 µL of tube E | 140 | 3E-10 | 300 |
| G | 60 µL of tube F | 120 | 1E-10 | 100 |
| H | 60 µL of tube G | 140 | 3E-11 | 30 |
| I | 60 µL of tube H | 120 | 1E-11 | 10 |
| J | 60 µL of tube I | 140 | 3E-12 | 3 |
| K | 60 µL of tube J | 120 | 1E-12 | 1 |
| L | 60 µL of tube K | 140 | 3E-13 | 0.3 |
| M ** (background) | 0 | 100 | 0 | 0 |
| N ** (background) | 0 | 100 | 0 | 0 |
| O ** (background) | 0 | 100 | 0 | 0 |
| P ** (background) | 0 | 100 | 0 | 0 |

The test was performed as follows: the above standard dilution ranges were in a separate 96-well plate; to ensure consistent mixing, samples were mixed up and down gently with a pipette five times; a 384-well test plate was prepared according to the test layout diagram depicted Table 7; five microliters of 10,000 pg/mL TNFα standard from the previously made dilution plate was added to each corresponding concentration as shown in Table 6; five microliters of recovered drug (directly from the commercial syringe (A), from the silicone bellows (B Si), from the PVC bellows (B PVC), or from the PBS control (C) was added into the corresponding wells described in Table 5; the test plate was incubated for one hour at room temperature while protected from light; 10 microliters of acceptor beads were added to each previously accessed well; the wells were incubated for 30 minutes at room temperature while protected from light; 10 µL of biotinylated antibody was added to each previously accessed well; the wells were incubated for 15 minutes at room temperature, while protected from light; the room lights were darkened and 25 microliters of streptavidin (SA) donor beads were added to each previously accessed well; the wells were incubated for 30 minutes at room temperature while protected from light; the plate was read in Alpha Mode; and the results were recorded. Upon addition of reagent(s) in the various steps, each well was pipetted up and down three times to achieve good mixing.

Figure 69:
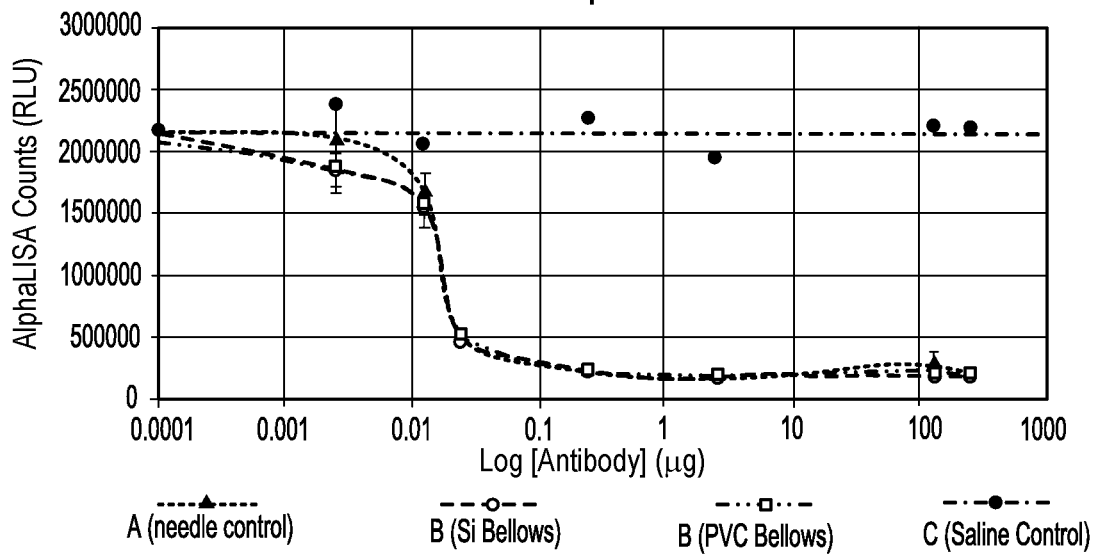
FIG. 69 shows AlphaLISA data.
Figure 70:
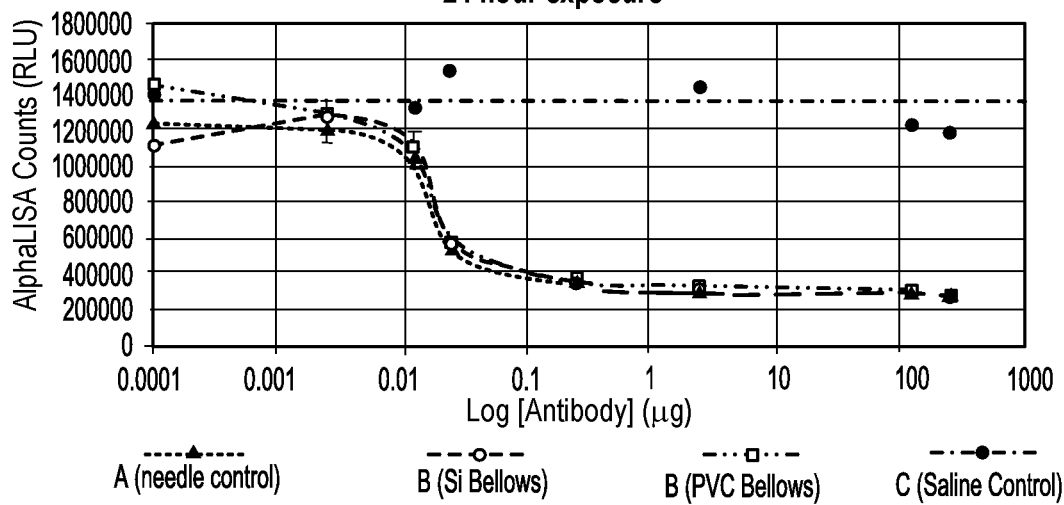
FIG. 70 shows AlphaLISA data.
Figure 71:
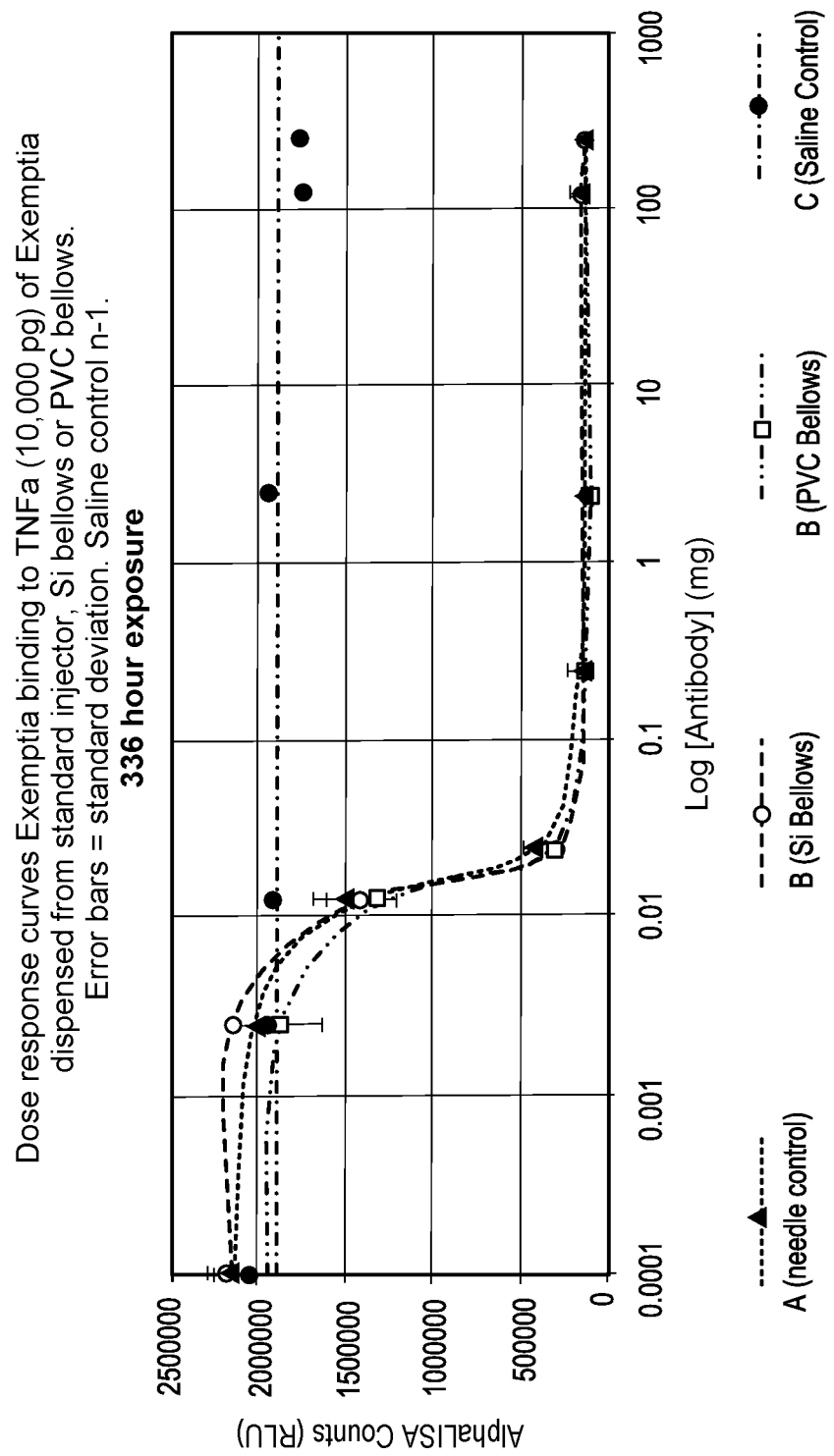
FIG. 71 shows AlphaLISA data.

The data are shown in FIGS. 69-71. The data demonstrate that the bellows do not negatively impact the drug function after shelf lives of 4 hours, 24 hours, or 336 hours. The $IC_{50}$ values of the drug dispensed from the bellows were comparable to the $IC_{50}$ values of the standard dispensation method (Table 6). A slight right shift was noted in the bellows curves after 24 hours (FIG. 70), but this shift was well within the error bars of the curves. Tables 8-11 represent data of FIGS. 69-71, respectively. Of note, when comparing mean (n=5) RFU data between test articles over the concentration ranges significant differences (p<0.05) were discerned. However, these significant differences did not favor either test article over time, suggesting that they were not related to the performance of the material in response to the drug (FIGS. 69-71).

TABLE 7

|   | 1 | 2 | 3 | 4 | 5 | 6 | 7 | 8 | 9 | 10 | 11 | 12 | 13 |
|---|---|---|---|---|---|---|---|---|---|---|---|---|---|
| A | STD2 1.00E+05 | | STD10 10 | 250 A | 250 A | 250 A | 250 A | 250 A | 250 B Si | 250 B Si | 250 B Si | 250 B Si | 250 B Si |
| B | | | | | | | | | | | | | |
| C | STD3 30000 | | STD11 3 | 125 A | 125 A | 125 A | 125 A | 125 A | 125 B Si | 125 B Si | 125 B Si | 125 B Si | 125 B Si |
| D | | | | | | | | | | | | | |
| E | STD4 10000 | | STD12 1 | 25 A | 25 A | 25 A | 25 A | 25 A | 25 B Si | 25 B Si | 25 B Si | 25 B Si | 25 B Si |
| G | STD5 3000 | | STD13 0.333 | 2.5 A | 2.5 A | 2.5 A | 2.5 A | 2.5 A | 2.5 B Si | 2.5 B Si | 2.5 B Si | 2.5 B Si | 2.5 B Si |
| H | | | | | | | | | | | | | |
| I | STD6 1000 | | Blank 0 | 0.25 A | 0.25 A | 0.25 A | 0.25 A | 0.25 A | 0.25 B Si | 0.25 B Si | 0.25 B Si | 0.25 B Si | 0.25 B Si |
| J | | | | | | | | | | | | | |
| K | STD7 300 | | Blank 0 | 0.025 A | 0.025 A | 0.025 A | 0.025 A | 0.025 A | 0.025 B Si | 0.025 B Si | 0.025 B Si | 0.025 B Si | 0.025 B Si |
| L | | | | | | | | | | | | | |
| M | STD8 100 | | Blank 0 | 0.013 A | 0.013 A | 0.013 A | 0.013 A | 0.013 A | 0.013 B Si | 0.013 B Si | 0.013 B Si | 0.013 B Si | 0.013 B Si |
| N | | | | | | | | | | | | | |
| O | STD9 30 | | Blank 0 | 0.003 A | 0.003 A | 0.003 A | 0.003 A | 0.003 A | 0.003 B Si | 0.003 B Si | 0.003 B Si | 0.003 B Si | 0.003 B Si |
| P | | | | | | | | | | | | | |

|   | 14 | 15 | 16 | 17 | 18 | 19 | 20 | 21 | 22 | 23 |
|---|---|---|---|---|---|---|---|---|---|---|
| A | 250 B PVC | 250 B PVC | 250 B PVC | 250 B PVC | 250 B PVC | 250 C | 250 C | 250 C | 250 C | 250 C |
| B | | | | | | | | | | |
| C | 125 B PVC | 125 B PVC | 125 B PVC | 125 B PVC | 125 B PVC | 125 C | 125 C | 125 C | 125 C | 125 C |
| D | | | | | | | | | | |
| E | 25 B PVC | 25 B PVC | 25 B PVC | 25 B PVC | 25 B PVC | 25 C | 25 C | 25 C | 25 C | 25 C |
| G | 2.5 B PVC | 2.5 B PVC | 2.5 B PVC | 2.5 B PVC | 2.5 B PVC | 2.5 C | 2.5 C | 2.5 C | 2.5 C | 2.5 C |
| H | | | | | | | | | | |
| I | 0.25 B PVC | 0.25 B PVC | 0.25 B PVC | 0.25 B PVC | 0.25 B PVC | 0.25 C | 0.25 C | 0.25 C | 0.25 C | 0.25 C |
| J | | | | | | | | | | |
| K | 0.025 B PVC | 0.025 B PVC | 0.025 B PVC | 0.025 B PVC | 0.025 B PVC | 0.025 C | 0.025 C | 0.025 C | 0.025 C | 0.025 C |
| L | | | | | | | | | | |
| M | 0.013 B PVC | 0.013 B PVC | 0.013 B PVC | 0.013 B PVC | 0.013 B PVC | 0.013 C | 0.013 C | 0.013 C | 0.013 C | 0.013 C |
| N | | | | | | | | | | |
| O | 0.003 B PVC | 0.003 B PVC | 0.003 B PVC | 0.003 B PVC | 0.003 B PVC | 0.003 C | 0.003 C | 0.003 C | 0.003 C | 0.003 C |
| P | | | | | | | | | | |

TABLE 8

|  | Needle control (A) | Silicone Bellows (B) | PVC Bellows (C) |
| --- | --- | --- | --- |
| 4 Hours | 0.0174 | 0.0169 | 0.0172 |
| 24 Hours | 0.0180 | 0.0180 | 0.0180 |
| 336 Hours | 0.0144 | 0.0159 | 0.0163 |

TABLE 9

Statistics (Student's T-test, 2 tailed, non-pair-wise, for significance $p < 0.05$)

| Drug (micrograms) | Needle control (A) vs. Silicone (B) | Needle control (A) vs. PVC | Silicone vs. PVC |
| --- | --- | --- | --- |
| 0.0001 | 0.911 | 0.008* | 0.268 |
| 0.0025 | 0.138 | 0.390 | 0.822 |
| 0.0125 | 0.122 | 0.118 | 0.771 |
| 0.025 | 0.143 | 0.465 | 0.020* |
| 0.25 | 0.591 | 0.984 | 0.350 |
| 2.5 | 0.243 | 0.124 | 0.169 |
| 125 | 0.867 | 0.688 | 0.182 |
| 250 | 0.681 | 0.184 | 0.108 |

*$p < 0.5$ data set

TABLE 10

Statistics (Student's T-test, 2 tailed, non-pair-wise, for significance $p < 0.05$)

| Drug (micrograms) | Needle control (A) vs. Silicone (B) | Needle control (A) vs. PVC | Silicone vs. PVC |
| --- | --- | --- | --- |
| 0.0001 | 0.132 | 0.038* | 0.292 |
| 0.0025 | 0.003* | 0.076 | 0.575 |
| 0.0125 | 0.161 | 0.022* | 0.783 |
| 0.025 | 0.058 | 0.078 | 0.538 |
| 0.25 | 0.974 | 0.384 | 0.198 |
| 2.5 | 0.714 | 0.080 | 0.017* |
| 125 | 0.873 | 0.731 | 0.269 |
| 250 | 0.798 | 0.956 | 0.903 |

*$p < 0.5$ data set

TABLE 11

Statistics (Student's T-test, 2 tailed, non-pair-wise, for significance $p < 0.05$)

| Drug (micrograms) | Needle control (A) vs. Silicone (B) | Needle control (A) vs. PVC | Silicone vs. PVC |
| --- | --- | --- | --- |
| 0.0001 | 0.858449 | 0.036847* | 0.026444* |
| 0.0025 | 0.087379 | 0.280302 | 0.046767* |
| 0.0125 | 0.469282 | 0.057232 | 0.117194 |
| 0.025 | 0.02758* | 0.078234 | 0.373419 |
| 0.25 | 0.411548 | 0.258928 | 0.400498 |
| 2.5 | 0.368959 | 0.156574 | 0.006719* |
| 125 | 0.948649 | 0.246702 | 0.463735 |
| 250 | 0.485046 | 0.128993 | 0.705543 |

*$p < 0.5$ data set

Example 9. A Comparison Study of Systemic Vs Intracecal Delivery of SMAD7 Bio-Distribution in DSS-Induced Colitis in Male C57Bl/6 Mice The objective of this study was to compare the efficacy of novel test articles, e.g., fluorescent SMAD7 antisense oligonucleotides (SMAD7 AS), when dosed systemically versus intracecally in the treatment of DSS-induced colitis, in male C57Bl/6 mice.

Experimental Design

A minimum of 10 days prior to the start of the experiment a cohort of animals underwent surgical implantation of a cecal cannula. A sufficient number of animals underwent implantation to allow for 12 cannulated animals to be enrolled in the main study (i.e., 16 animals).

Colitis was induced in 12 male C57Bl/6 mice (Groups 4-5) by exposure to 3% DSS-treated drinking water from Day 0 to Day 5. Three groups of six additional animals per group (n=6 cannulated; n=12 non-cannulated; Groups 1-3) served as no-disease controls (Groups 1-3). All animals were weighed daily and assessed visually for the presence of diarrhea and/or bloody stool during this time.

Animals were dosed with test-article via oral gavage (PO) or intracecal injection (IC) once on Day 9 as indicated in Table 12. The animals in Group 0 were not dosed. The animals in Groups 2 and 4 were dosed PO with SMAD7 antisense. The animals in Groups 3 and 5 were dosed IC with SMAD7 antisense.

All animals were euthanized by $CO_2$ inhalation 12 hours after dosing, on Day 10. Terminal blood was collected into two $K_2$EDTA tubes and processed for plasma. Both plasma and pellet samples were snap-frozen in liquid nitrogen and stored at −80° C. Cecum contents were removed and the contents were split into two aliquots. Both aliquots were weighed and snap frozen in separate cryovials in liquid nitrogen. The cecum was excised and bisected longitudinally; each piece is separately weighed and flash-frozen in liquid nitrogen. The colon contents were removed and the contents were split into two aliquots. Both aliquots were weighed and snap frozen in separate cryovials in liquid nitrogen. The colon was then rinsed, and the most proximal 2 cm of colon was collected. This 2-cm portion was bisected longitudinally; each piece was separately weighed and flash-frozen in liquid nitrogen. Snap-frozen blood pellet, cecum/colon contents, and tissue samples were used for downstream fluorometry or RP-HPLC. The details of the study design are shown in Table 12.

TABLE 12

Study design

| Group | No Animals | Cecal Cannula | Colitis Induction | Treatment | Route | Schedule | Terminal Collections Day 10 |
| --- | --- | --- | --- | --- | --- | --- | --- |
| 1 | 6 | NO | — | — | — | — | Whole blood, |
| 2 | 6 | NO |  | Fluorescently | PO | QD | plasma, cecal |

TABLE 12-continued

Study design

| Group | No Animals | Cecal Cannula | Colitis Induction | Treatment | Route | Schedule | Terminal Collections Day 10 |
|---|---|---|---|---|---|---|---|
| 3 | 6 | YES | | labeled | IC | Day 9** | contents, colon |
| 4 | 6 | NO | 3% DSS | SMAD7 | PO | | contents, cecal |
| 5 | 6 | YES | Days 0-5 | antisense 50 μg* | IC | | tissue, colon tissue |

*Per mouse. TA is administered in 0.075 mL/animal.
**Animals are dosed on Day 9 and collections are performed 12 hours later.

Materials and Methods

Mice

Normal male C57Bl/6 mice between the ages of 6-8 weeks old, weighing 20-24 g, were obtained from Charles River Laboratories. The mice were randomized into five groups of six mice each, and housed in groups of 8-15 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum, where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals were administered 1 mL of warm sterile saline (subcutaneous injection) and were monitored closely until recovery before returning to their cage. All animals were administered 0.6 mg/kg BID buprenorphine for the first 3 days, and Baytril® at 10 mg/Kg every day for the first 5 days post-surgery.

Disease Induction

Colitis was induced on Day 0 via addition of 3% DSS (MP Biomedicals, Cat #0260110) to the drinking water. Fresh DSS/water solutions was provided on Day 3 and any of the remaining original DSS solution is discarded.

Body Weight and Survival

Animals were observed daily (weight, morbidity, survival, presence of diarrhea and/or bloody stool) in order to assess possible differences among treatment groups and/or possible toxicity resulting from the treatments.

Animals Found Dead or Moribund

Animals were monitored on a daily basis. Animals exhibiting weight loss greater than 30% were euthanized, and samples were not collected from these animals.

Dosing

Animals were dosed with test-article via oral gavage (PO) or intracecal injection (IC) once on Day 9 as indicated in Table 12. Animals in Group 0 were not dosed. Animals in Groups 2 and 4 were dosed PO with SMAD7 antisense. Animals in Groups 3 and 5 were dosed IC with SMAD7 antisense.

Sacrifice

All animals were euthanized by $CO_2$ inhalation 12 hours after dosing, on Day 10.

Sample Collection

Intestinal contents, peripheral blood and tissue were collected at sacrifice on Day 10, as follows:

Blood/Plasma

Terminal blood was collected into two $K_2$EDTA tubes and processed for plasma. The approximate volume of each blood sample was recorded prior to centrifugation. Both plasma and pellet samples were snap-frozen in liquid nitrogen and stored at −80° C. The first pellet sample (sample 1) was used for fluorometry. The second pellet sample (sample 2) was used for RP-HPLC.

Cecum Contents

Cecum contents was removed and contents were split into two aliquots. Both aliquots were weighed and snap frozen in separate cryovials in liquid nitrogen. The first sample (sample 1) was used for fluorometry. The second sample (sample 2) was used for RP-HPLC.

Cecum

The cecum was excised and bisected longitudinally; each piece was separately weighed and snap-frozen. The first sample (sample 1) was used for fluoremetry. The second sample (sample 2) was used for RP-HPLC.

Colon Contents

Colon contents were removed and contents were split into two aliquots. Both aliquots were weighed and snap frozen in separate cryovials in liquid nitrogen. The first sample (sample 1) was used for fluorometry. The second sample (sample 2) was used for RP-HPLC.

Colon

The colon was rinsed, and the most proximal 2 cm of colon was collected and bisected longitudinally. Each piece was separately weighed and flash-frozen in liquid nitrogen. The first sample (sample 1) was used for fluorometry. The second sample (sample 2) was used for RP-HPLC.

SMAD7 Antisense Bioanalysis

Samples flash-frozen for fluorometry were homogenized in 0.5 mL buffer RLT+(Qiagen). Homogenate was centrifuged (4000×g; 10 minutes), and supernatant was collected. Forty microliters of the sample was diluted 1:6 in 200 μL of bicarbonate solution and 100 μL of diluted supernatant was analyzed on a fluorescent plate reader (485 excitation; 535 emission) in duplicate.

Prior to the above, assay development was performed as follows. Samples (as indicated in Sample Collection) were harvested from a naïve animal and flash-frozen. Samples were then homogenized in 0.5 mL buffer RLT+, homogenate was centrifuged (4000×g; 10 minutes) and supernatant was collected and diluted 1:6 with bicarbonate solution (i.e., 0.5 mL supernatant was added to 2.5 mL of PBS). An aliquot (0.200 mL (90 μL for each duplicate) of each diluted sample was pipetted into 15 (14 dilution of FAM-AS-SAMD7+ blank control) Eppendorf tubes. One tube was set-aside to be used as a blank sample. Ten microliters of fluorescently-labeled SMAD7 antisense was then spiked into all other sample to achieve final concentrations of 50 µg/mL, 16.67 µg/mL, 5.56 µg/mL, 1.85 µg/mL, 0.62 µg/mL, 0.21 µg/mL, 0.069 µg/mL, 0.023 µg/mL, 7.6 ng/mL, 2.5 ng/mL, 0.847 ng/mL, 0.282 ng/mL, 0.094 ng/mL, and 0.024 ng/mL respectively. The fluorescently-labeled SMAD7 antisense was prepared and serially diluted such that the volume added to each organ homogenate sample was the same for each of the above concentrations. These samples were analyzed on a fluorescent plate reader (485 excitation; 535 emission) in duplicate.

Processing for RP-HPLC

Samples flash-frozen for RP-HPLC were homogenized in buffer RLT+(Qiagen). Homogenate was centrifuged (4000× g; 10 minutes), and supernatant was used to perform RP-HPLC analysis.

Results

Figure 73:
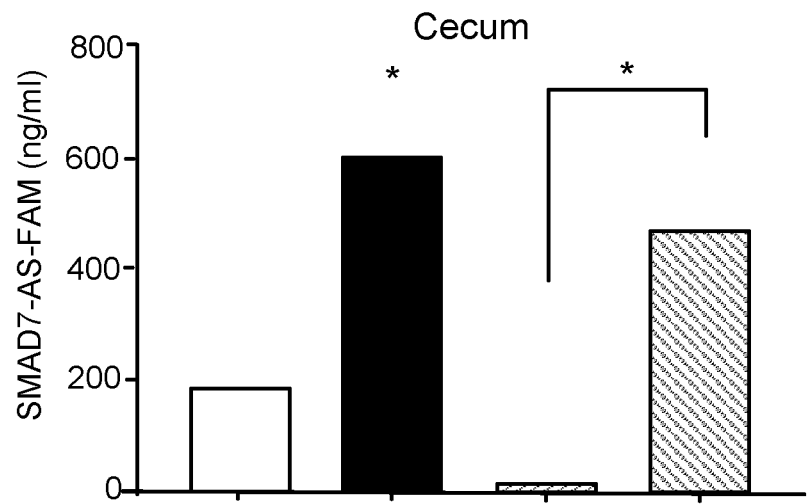
FIG. 73 is a graph showing the level of FAM-SMAD7-AS oligonucleotide in the cecum tissue of DSS-induced colitis mice at 12-hours. The bars represent from left to right, Groups 2 through 5 in the experiment described in Example 9.
Figure 74:
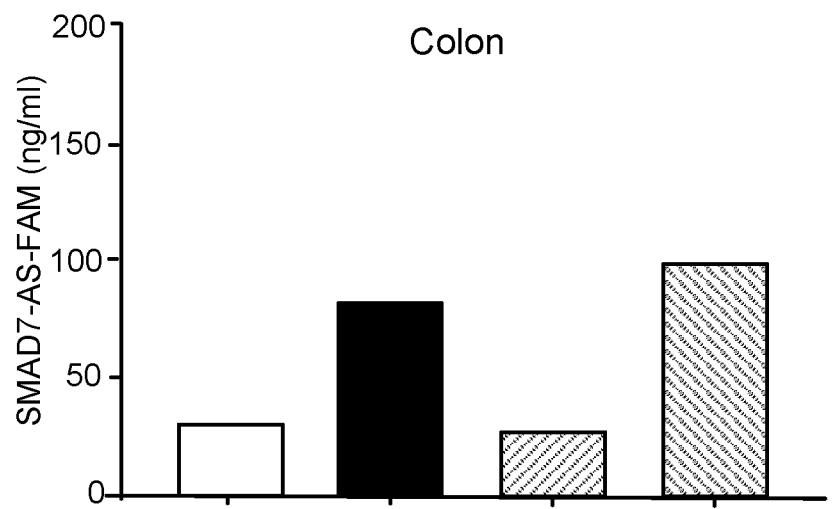
FIG. 74 is a graph showing the level of FAM-SMAD7-AS oligonucleotide in the colon tissue of DSS-induced colitis mice at 12-hours. The bars represent from left to right, Groups 2 through 5 in the experiment described in Example 9.
Figure 75:
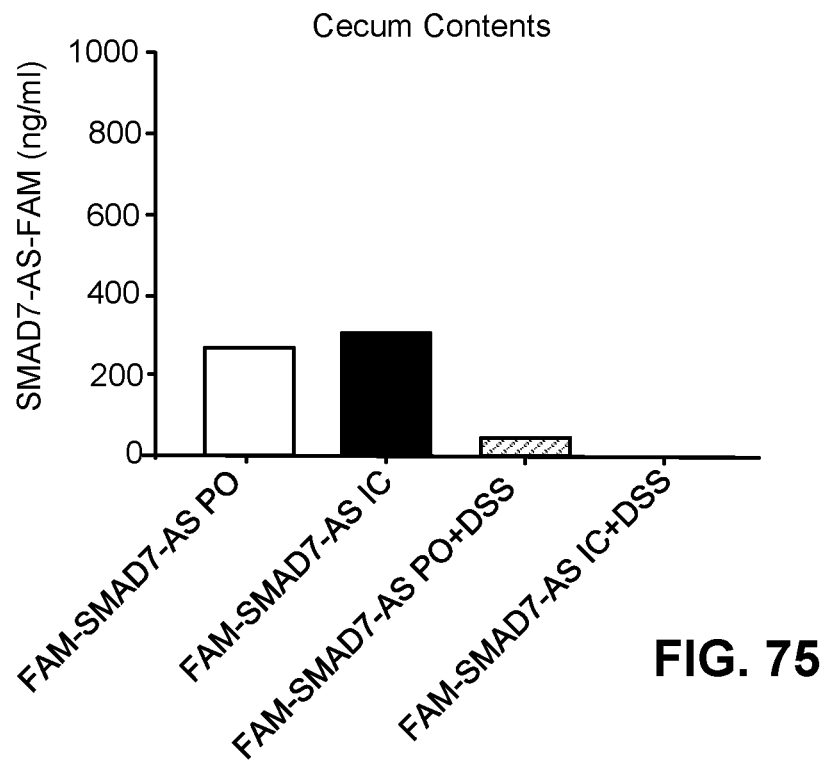
FIG. 75 is a graph showing the level of FAM-SMAD7-AS oligonucleotide in the cecum contents of DSS-induced colitis mice at 12-hours. The bars represent from left to right, Groups 2 through 5 in the experiment described in Example 9.

The data in FIGS. 73 and 74 show that significantly more SMAD7 anstisense oligonucleotide was present in cecum tissue and colon tissue for mice with or without DSS treatment that were intra-cecally administered the SMAD7 antisense oligonucleotide as compared to mice with or without DSS treatment that were orally administered the SMAD7 antisense oligonucleotide. The data in FIG. 75 show that there is about the same level of SMAD7 antisense oligonucleotide in the cecum contents of mice with or without DSS treatment that were orally or intra-cecally administered the SMAD7 antisense oligonucleotide. No SMAD7 antisense oligonucleotide was found in the plasma or white blood cell pellet of SMAD7 antisense oligonucleotide treated mice.

No significant differences were observed in clinical observations, GI-specific adverse effects or toxicity due to FAM-AS-SMAD7 treatment via PO vs IC. No fluorescent detection of FAM-AS-SMAD7 was found in plasma and whole blood cell pellets across all treatment groups. A significant higher fluorescent signal (RFU) of FAM-AS-SMAD7 was found in cecum tissue when delivered intra-cecally compared with PO in both normal and DSS-induced models (FIG. 83). A slight higher RFU was also found in colon tissue when delivered intra-cecally, however, the overall signal is 10 times lower (FIG. 84). A significant higher RFU was found in colon content when delivered intra-cecally compared with PO in a normal mouse model (FIG. 85). This result was not seen in cecum content across all treatment groups (FIG. 86), indicating a better tissue absorption of oligos in cecum tissue from cecal content when delivered intra-cecally, but not in colon content at 12 hours post-treatment.

Example 10. Comparison of the Tissue, Plasma, and GI Content Pharmacokinetics of Tacrolimus Through Oral Vs. Intra-Cecal Ingestible Device Delivery in Yorkshire-Cross Farm Swine The primary objective of this study was to compare the tissue, plasma, rectal sample, and GI content pharmacokinetics of tacrolimus through oral versus intra-cecal ingestible device delivery in normal Yorkshire-Cross farm swine.

This study compares the effects of administration of: a single intra-cecal administration of an ingestible device containing 0.8 mL sterile vehicle solution (80% alcohol, 20% castor oil (HCO-60)); a single oral dose of tacrolimus at 4 mg/0.8 mL (in sterile vehicle solution); and a single intra-cecal administration of an ingestible device containing either 1 mg/0.8 mL (in sterile vehicle solution), 2 mg/0.8 mL (in sterile vehicle solution), or 4 mg/0.8 mL (in sterile vehicle solution).

This study employed five groups of three female swine weighing approximately 45 to 50 kg at study start. Swine were randomly placed into animal rooms/pens as they are transferred from the delivery vehicle without regard to group. Group numbers were assigned to the rooms in order of room number. No further randomization procedure was employed. The study design is provided in Table 13.

TABLE 13

Study Design Table

| General | Group size | Dose | Route | Days Pre-Dose | | | | | Hours Post-dose | | | | | | |
|---|---|---|---|---|---|---|---|---|---|---|---|---|---|---|---|
| | | | | −11 | −10 | −5 | −1 | 1 | 0.5 | 1 | 2 | 3 | 4 | 6 | 12 |
| Fast | | | | • | | | • | | | | | | | | |
| Food/Water Observations | | ad libidum | | | • | • | | • | • | • | • | • | • | • | • |
| clinical observations | | Day-10~-5 & Day 1 | | | • | • | | • | • | • | • | • | • | • | • |
| body weight* | | | | | • | • | | • | | | | | | | • |
| Treatments (Groups) | | | | | | | | | | | | | | | |
| 1. Vehicle control | n = 3 | 0.8 mL (20% HCO-60, 80% EtOH) | IC | | | | | | | | | | | | |
| Surgical placement of IC port** | | | | | | | | • | | | | | | | |
| Euthanized | | (1 Ingestible Device) | | | | | | | | | | | | | n = 3 |
| 2. Tacrolimus (PO) | n = 3 | 4 mg in 0.8 mL 0.08 mg/kg | Oral | | | | | | | • | | | | | |
| Surgical placement of IC port** | | | | | | | | • | | | | | | | |
| Euthanized | | (solution) | | | | | | | | | | | | | n = 3 |
| 3. Tacrolimus (IC) | n = 3 | 1 mg in 0.8 mL 0.02 mg/kg | IC | | | | | | | • | | | | | |
| Surgical placement of IC port** | | | | | | | | • | | | | | | | |

TABLE 13-continued

| | | | | | | | | | | | |
|---|---|---|---|---|---|---|---|---|---|---|---|
| Euthanized | | (1 Ingestible Device) | | | | | | | | | n = 3 |
| 4. Tacrolimus (IC) Surgical placement of IC port** | n = 3 | 2 mg in 0.8 mL 0.04 mg/kg | IC | | • | • | | | | | |
| Euthanized | | (1 Ingestible Device) | | | | | | | | | n = 3 |
| 5. Tacrolimus (IC) Surgical placement of IC port** | n = 3 | 4 mg in 0.8 mL 0.08 mg/kg | IC | | • | • | | | | | |
| Euthanized | | (1 Ingestible Device) | | | | | | | | | n = 3 |
| Tacrolimus (required) Samples***** | | 20 mg | | | | | | | | | |
| Plasma | | | cephalic, jugular or catheter | | | • | • | • | • | • | • |
| Rectal contents | | | rectal | | | • | | • | | • | • |
| Tissue*** | ×5 | | necropsy | | | | | | | | • |
| Luminal contents**** | ×5 | | necropsy | | | | | | | | • |
| Analysis (Agrilux Charles River) | Total Samples | | | | | | | | | | |
| Plasma | | | | | | | | | | | |
| [Tacrolimus] Rectal contents | 105 | | | | | 15 | 15 | 15 | 15 | 15 | 15 | 15 |
| [Tacrolimus] Tissue (intact)*** | 60 | | | | | | 15 | 15 | | 15 | 15 |
| [Tacrolimus] Luminal contents | 105 | | | | | | | | | | 105 |
| [Tacrolimus] Tissue after removing luminal content | 75 | | | | | | | | | | 75 |
| [Tacrolimus] | 75 | | | | | | | | | | 75 |

Note:
*Animal weight was ~45-50 kg for drug doses proposed.
**Surgical placement of IC port in all animals to control.
***Tissue samples [drug] (five GI section cecum (CAC); proximal colon (PCN); transverse colon (TCN); distal colon (DCN); rectum (RTM), plus mesenteric lymph nodes and Peyer's Patch).
****Luminal contents (cecum (CAC); proximal colon (PCN); transverse colon (TCN); distal colon (DCN); rectum (RTM)).

Animals in Group 1 received an ingestible device containing 0.8 mL of vehicle solution (80% alcohol, 20% HCO-60). Animals in Group 2 received orally 4 mL liquid formulation of tacrolimus at 4 mg/0.8 mL per animal (Prograf: 5 mg/mL). Animals in Group 3 received intra-cecally an ingestible device containing tacrolimus at 1 mg in 0.8 mL per ingestible device. Animals in Group 4 received intra-cecally an ingestible device containing tacrolimus at 2 mg in 0.8 mL per ingestible device. Animals in Group 5 received intra-cecally an ingestible device containing tacrolimus at 4 mg in 0.8 mL per ingestible device. To control for potential confounding effects of the surgery, all groups fast on Day −11 at least 24 hr before being subjected to anesthesia followed by surgical placements of a cecal port by a veterinary surgeon at Day −10. All animals were fasted for at least 12 hr prior to dosing on Day 1. Animals were dosed via either intra-cecal dosing (IC) or oral dosing (PO) at Day 1 (between 6-8 p.m.). All animals resumed feeding at approximately 4 hours after dose (11-12 p.m. after dosing).

Animals in Group 1 (Vehicle Control) were administered a single intra-cecal ingestible device containing 0.8 mL Vehicle solution (80% alcohol, 20% castor oil (HCO-60)) on Day 1. On Day −10 the animals were anesthetized, and a veterinary surgeon surgically placed an intra-cecal port in each animal. On Day 1, each animal was placed into a sling then a single intra-cecal ingestible device containing 0.8 mL vehicle solution (80% alcohol, 20% castor oil (HCO-60)) is introduced by the veterinary surgeon into the cecum via the cecal port in each animal. Following ingestible device placement, the animals were removed from the slings and placed back into their pens with water. All animals resumed feeding at approximately 4 hours after dose. Samples of rectal contents were collected for pharmacokinetic analyses from each animal at each of 1, 3, 6, and 12 hours post-ingestible device placement using a fecal swab (rectal swab). A total of 60 samples were collected.

Approximately 200–400 mg of rectal content were collected, if available, with a fecal swab (Copan Diagnostics Nylon Flocked Dry Swabs, 502CS01). The fecal swab was pre-weighed and weighed after collection in the collection tube (Sterile Tube and Cap No Media, PFPM913S), and the sample weight was recorded. The fecal swab was broken via the breakpoint, and was stored in the collection tube, and immediately frozen at −70° C. Whole blood (2 mL) was collected into $K_2$EDTA coated tubes for pharmacokinetics at each time-point of pre-dose and 1, 2, 3, 4, 6 and 12 hours post-dose. Immediately following euthanasia, tissue was collected. A total of 105 samples were collected.

For tissue necropsy, small intestine fluid and cecal fluid were collected separately from all the animals into two separate square plastic bottles, and stored at −20° C. The length and diameter of the cecum and the colon was measured from one animal in each group and recorded for reference. Tissues were collected for pharmacokinetic analyses and include mesenteric lymph nodes, a Peyer's Patch, and five gastrointestinal sections, including cecum, proximal colon, transverse colon, distal colon, and rectum. All samples were weighed, and the tissue sample weights were recorded. In each of the five gastrointestinal sections, tissue samples were collected in three different areas where the mucosal surface was visible and not covered by luminal content by using an 8.0-mm punch biopsy tool. Around 3 grams of the total punched sample were collected into a pre-weighed 15-mL conical tube, and the tissue weight was recorded. Three mesenteric lymph nodes were collected from different areas and weighed. At least one Peyer's Patch was collected and weighed. Tissues were snap-frozen in liquid nitrogen and stored frozen at approximately −70° C. or below (total of 105 samples).

Luminal contents were collected for pharmacokinetic analyses from the surface of the tissue from each of five gastrointestinal sections: cecum, proximal colon, transverse colon, distal colon, and rectum (total of 75). The contents were collected in pre-weighed 15-mL conical tubes and the sample weights were recorded. Samples were snap-frozen in liquid nitrogen stored frozen at approximately −70° C. or below.

After removing the luminal content, another set of tissue samples from 3 different areas were collected via an 8.0-mm punch biopsy in each section of the five tissue gastrointestinal sections described above. Around 3 grams of the total punched sample were collected into a pre-weighed 15-mL conical tube, and the tissue weight was recorded (total of 75). Tissues were snap-frozen in liquid nitrogen and stored frozen at approximately −70° C. or below.

A 30-cm length of jejunum (separated into two 15 cm lengths), and the remaining distal and transverse colon tissue sample (after tissue and luminal content were collected for PK) were collected in one animal in each group of treatment, snap-frozen in liquid nitrogen and stored frozen at approximately −70° C. or below. All samples for pharmacokinetic analyses were stored on dry ice before analyses.

Group 2 animals were administered a single oral dose of tacrolimus at 4 mg/0.8 mL (0.08-mg/kg) (in the vehicle solution) on Day 1. Plasma, rectal content sample, tissue collection, GI content collection and related procedures/ storage/shipments was the same as those employed in Group 1.

Group 3 animals were administered a single intra-cecal ingestible device containing tacrolimus at 1-mg/0.8 mL (0.02 mg/kg) (in the vehicle solution) on Day 1 by a veterinary surgeon. Plasma, rectal content sample, tissue collection, GI content collection and related procedures/ storage/shipments was the same as those employed in Group 1. All samples were analyzed for tacrolimus.

Group 4 animals were administered a single intra-cecal ingestible device of tacrolimus at 2 mg/0.8 mL (0.04 mg/kg) (in sterile vehicle solution) on Day 1 by a veterinary surgeon. Plasma, rectal content sample, tissue collection, GI content collection and related procedures/storage/shipments were the same as those employed in Group 1. All samples were analyzed for tacrolimus.

Group 5 animals are administered a single intra-cecal ingestible device containing tacrolimus at 4 mg/0.8 mL (0.08 mg/kg) (in the vehicle solution) on Day 1 by a veterinary surgeon. Plasma, rectal content sample, tissue collection, GI content collection and related procedures/storage/shipments were the same as those employed in Group 1. All samples were analyzed for tacrolimus.

Detailed clinical observations were conducted daily from Day −10 to −5, and on Day 1. Additional pen-side observations were conducted at least once each day. The animals remained under constant clinical observation for the entire 12 hours from dose until euthanasia. Body weights were collected on Day −10, Day −5, and pre-dose on Day 1. Animals were euthanized via injection of a veterinarian-approved euthanasia.

Test Article and Formulation
1. Vehicle solution, 20 mL
Description: 80% alcohol, 20% PEG-60 castor oil
Physical characteristics: clear liquid solution.
2. Prograf (tacrolimus injection), 10 ampules
Description: A sterile solution containing the equivalent of 5 mg anhydrous tacrolimus in 1 mL. Tacrolimus is macrolide immunosuppressant and the active ingredient of Prograf. 0.8 mL of Prograf (5 mg/mL) was administered through oral gavage per animal in group 2. Prograf (5 mg/mL) was diluted 2× folds (2.5 mg/mL) and 4× folds (1.25 mg/mL) by using vehicle solution. 0.8 mL of each concentration, 1.25 mg/mL, 2.5 mg/mL, and 5 mg/mL of Prograf, was injected into a DSS ingestible device for group 3, 4, and 5.
Formulation: Each mL contained polyoxyl 60 hydrogenated castor oil (HCO-60), 200 mg, and dehydrated alcohol, USP, 80.0% v/v.
Physical characteristics: clear liquid solution.
3. DDS ingestible device containing Tacrolimus
Description: Three (3) DDS ingestible devices containing vehicle solution for Group 1, three (3) DSS ingestible devices containing 1 mg tacrolimus for Group 3, three (3) DDS ingestible devices containing 2 mg tacrolimus for Group 4, and three (3) DDS ingestible devices containing 4 mg tacrolimus for Group 5.

Acclimation
Animals were acclimated prior to study initiation for at least 7 days. Animals in obvious poor health were not placed on study.

Concurrent Medication
Other than veterinary-approved anesthetics and medications used during surgery to install the ileocecal ports, or for vehicle or test article administration, and analgesia and antibiotics post-surgery, no further medications were employed.

Feed
All swine were fasted at least 24 hours before being anesthetized and properly medicated for surgery or overnight before dosing. Otherwise, animals were fed ad-libitum. Tap water was pressure-reduced and passed through a particulate filter, then a carbon filter prior to supply to an automatic watering system. Water was supplied ad libitum. There were no known contaminants in the feed or water that would be expected to interfere with this study.

Figure 76:
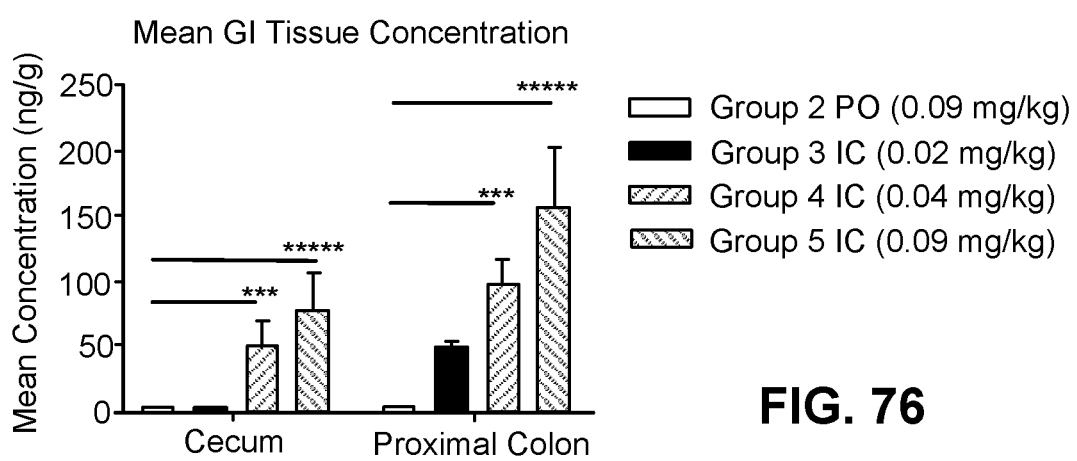
FIG. 76 is a graph showing the mean concentration of tacrolimus in the cecum tissue and the proximal colon tissue 12 hours after intra-cecal or oral administration of tacrolimus to swine as described in Example 10.

Results
The data in FIG. 76 show that the mean concentration of tacrolimus in the cecum tissue and the proximate colon tissue were higher in swine that were inta-cecally administered tacrolimus as compared to swine that were orally administered tacrolimus. These data suggest that intra-cecal administration of tacrolimus is able to locally deliver tacrolimus to the tissues in the GI tract of a mammal, while not decreasing the systemic immune system of a mammal.

All blood trough concentrations were <10 ng/mL and exposure AUC <2000-12 ng·h/mL (FIGS. 87-89). Significantly higher Cmax values (9.20±3.30 and 21.80±4.73 ng/mL) were observed in groups treated with high (0.09 mg/kg) and moderate (0.04 mg/kg) dose of tacrolimus when delivered through IC capsule as compared to the Cmax values following PO delivery of tacrolimus (0.09 mg/kg). Significantly higher tissue (spiral and transverse colon) and luminal content (spiral, transverse, and distal colon) concentrations were observed in groups treated with high and moderate dose tacrolimus delivered through IC capsule as compared to the levels observed in animals administered tacrolimus via PO. No measurable level of tracrolimus was detected in tissue when animals were delivered tacrolimus via PO, despite systemic concentrations equivalent to low dose IC group (0.02 mg/kg) (FIGS. 90 and 91). A higher rectal content concentration was observed at 12 hours post-treatment in the IC capsule groups (FIG. 92), while no detectable level was observed in the PO group.

Example 11. Comparison of the Tissue, Plasma, and GI Content Pharmacokinetics of Adalimumab Through SC Vs. Intra-Cecal Ingestible Device Delivery in Yorkshire-Cross Farm Swine in DSS-Induced Colitis The purpose of this non-Good Laboratory Practice (GLP) study is to explore the PK/PD and bioavailability of adalimumab when applied to (Dextran Sulfate Sodium Salt) DSS-induced colitis in Yorkshire-cross farm swine, and to evaluate topical Humira (adalimumab or ADA) in DSS-colitis in swine. Colitis was induced in weanling YorkShire-Cross farm swine by administering DSS once daily for 7 consecutive days via oral gastric intubation. The dose levels were chosen based on the doses and regimens used to induce colitis in weanling pigs. The doses of DSS were 1.275 or 2.225 g/k/day for Groups 2 and 3 respectively.

This study used one group of 19- to 21-day old weanling swine, and 2 groups of three, 19- to 20-day old weanling swine that weighed from 6.5 to 7.5 kg on arrival. To induce colitis, on study day 1 through and including day 7, animals in Groups 2 and 3 were administered once daily oral (gastric intubation) doses of DSS at 8.5% or 15% w/v for dose levels of 1.275 or 2.25 g/kg/day, respectively (Groups 2 and 3 respectively, 2 hours before morning feeding). The Group 1 control animals were administered sterile saline only. Each animal was placed in a sling for dosing. Animals were fasted at least 6 hours prior to each dose. See Study Table below.

| Group | Route | Animal #[1] | DSS % w/v | mg/ml | Volume (ml) | Total g[2] | g/kg | Frequency[3] | Total DSS needed | ADA treatment[4] | Endpoints[5,6,7] |
|---|---|---|---|---|---|---|---|---|---|---|---|
| 1 (Animal 1501) | oral/ gastric intubation | 1 | 0 | 0 | 105 | 0 | 0 | QD, 7 day | 0 | Day 8 (Vehicle) | Body weights, clinical signs, & necropsy and IHC at 3 hr post ADA |
| 2 (Animals 2501, 2502, and 2504) | oral/ gastric intubation | 3 | 8.5% | 85 | 105 | 8.925 | 1.275 | UD, 7 day | 187.425 | Day 8 (rectal 13 mg) | Body weights, clinical signs, & necropsy and IHC at 3 hr post ADA |
| 3 | oral/ gastric intubation | 3 | 15% | 150 | 105 | 15.75 | 2.25 | QD, 7 day | 330.75 | Day 8 (rectal 13 mg) | Body weights, clinical signs, & necropsy and IHC at 3 hr post ADA |

1. Animal weighed around 6.5-7.5 kg
2. Daily clinical signs and body weight were closely monitored throughout the study. If severe clinical signs or body weight loss is observed at day 1~3 after dosing, the DSS dosing was shortened to 5 days.
3. 0.8 mL of ADA solution was dosed rectally to the colon via an endoscope
4. Necropsy was done to observe GI inflammation and overall histopathology
5. 5-cm length opened tissue samples harvested for immunohistochemistry from terminal ileum, cecum, proximal colon; spiral colon, transverse colon; distal colon, rectum, and included other gastrointestinal sites of inflammation depending on the necropsy results.
6. ~3 g of punch biopsy sample and ~200 mg luminal content snap frozen for adalimumab measurement and three extra 5-cm length open tissue samples taking down for immunohistochemistry staining of ADA at the site where ADA was administrated. Additional tissue biopsy samples were collected from 3 different areas at proximal colon and proximal region of transverse colon in each animal.

The day following the last DSS dose, using endoscopy and a catheter, at 13 mg adalimumkab/0.8 mL/pig (one 40 mg adalimumab/0.8 mL dosage syringe was divided into 3 parts and diluted with PBS) was placed in the proximal portion of the descending colon just past the bend of the transverse colon. Alternatively, 13 mg of adalimumab was diluted with PBS to a volume suitable for dosing post-weanling swine. Prior to dosing, endoscopy photographs were taken of the mucosal surface of the colon. Animals were anesthetized during adalimumab dosing. Prior to adalimumab dosing, animals were housed on rubber mats to prevent ingestion of bedding material, and were fasted at least 24 hours. The colon was cleansed using an enema prior to the procedure.

All animals were properly euthanized approximately 3 hours post-adalimumab-dose for tissue collections and subjected to a gross necropsy with emphasis on the severity of colitis (immediately after euthanasia, in order to avoid autolytic changes). All samples for histology were fixed in a fixation medium and the punch-biopsy sample snap-frozen in liquid nitrogen and stored frozen (−70° C.).

To measure drug content, tissue samples and luminal content were collected by gently removing and collecting luminal content first, then using an 8.0 mm-punch biopsy tool. Biopsies from three different areas at the site of adalimumab administration were collected in each animal. Additional tissue biopsy samples were collected from three different areas at the proximal colon, and the proximal region of transverse colon in each animal.

Approximately 3 g of total punched sample and 200 mg of luminal content were collected in a pre-weighed conical tubes and the tissue weighed was recorded.

Approximately, a 5-cm length of open gastrointestinal tissue sample including terminal ileum, cecum (CAC); proximal colon (PCN); transverse colon (TCN); spiral colon, distal colon (DCN), and rectum was collected, gently rinsed in saline to remove luminal material, and individually fixed in fixation buffer (10% neutral buffered formalin). Also, a 5-cm length of open gastrointestinal tissue from 3 different areas near the site of adalimumab administration was collected and fixed in formalin in the same manner for immunohistochemical staining for adalimumab. Tissue samples for histopathology were fixed in 10% neutral buffered formalin for 18~24 hr, and transferred to 70% ethanol. HUMIRA® was supplied in single-use, 1-mL pre-filled glass syringes, as a sterile, preservative-free solution for subcutaneous administration. The solution of HUMIRA® was clear and colorless, with a pH of about 5.2. Each syringe delivered 0.8 mL (40 mg adalimumab) of drug product. Each vial contained approximately 0.9 mL of solution to deliver 0.8 mL (40 mg adalimumab) of drug product. Each 0.8 mL HUMIRA® contained 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for injection. Sodium hydroxide was added as necessary to adjust pH.

All animals were randomized into groups of three. Animals were dosed once with adalimumab via subcutaneous (SC), perirectal (PR), or intracecal (IC) administration.

The concentration of adalimumab and TNFα was measured in plasma at 1, 2, 3, 4, 6, and 12 hours post-dose. The concentration of adalimumab was measured in rectal contents at 1, 3, 6, and 12 hours post-dose and in luminal content at 12 hours post-dose. Concentration of adalimumab and TNFα, HER2, and total protein was measured in gastrointestinal tissue, e.g., cecum sample (CAC), proximal colon sample (PCN), transverse colon sample (TCN), distal colon sample (DCNi) inflamed, distal colon non-inflamed sample (DCNn), and rectum sample (RTM), at 12 hours post-dose.

Treatment with 8.5% DSS (oral; Day 1 to Day 7) induced mild body weight loss, hemorrhage diarrhea, soft bloody stool, and moderate colitis in swine. Necropsy revealed marked edema and full thickness of mucosal erosion from the proximal colon through the distal rectum. The 8.5% DSS-induced animals were treated with adalimumab at day 8. No significant differences in clinical observations, GI-specific adverse effects or toxicity due to adalimumab treatment were observed. The 15% DSS (oral; day 1 to day 7)-induced animals had marked mucosal sloughing and hemorrhage from cecum to rectum and severe colitis. All of the animals were euthanized early on day 5.

Significant lesions of colitis were found in animals treated with 8.5% DSS and were characterized by inflammation that involved mucosa and submucosa, loss of surface epithelium (erosion), and intestinal crypts (FIGS. 93 and 94). There was little, if any, evidence of regeneration. The ileum and cecum were unremarkable in all animals except cecum from one animal (animal 2504) that was treated with 8.5% DSS, which had lesions of inflammation and loss of surface and crypt epithelium (FIGS. 95-99). Lesions of colitis were significant and consistent in all other segments of the large intestine from animals treated with 8.5% DSS. The severity and character of the changes were not remarkably different among the different segments or among these animals. Staining for human IgG was most consistent and intense at the adalimumab administration site and localized to the luminal surface of the mucosal epithelium or inflammatory exudate at the luminal surface, and penetration of adalimumab is found in the lamina propria near the luminal surface (FIG. 100).

Example 12. Human Clinical Trial of Treatment of Ulcerative Colitis Using Adalimumab As a proof of concept, the patient population of this study is patients that (1) have moderate to severe ulcerative colitis, regardless of extent, and (2) have had an insufficient response to a previous treatment, e.g., a conventional therapy (e.g., 5-ASA, corticosteroid, and/or immunosuppressant) or a FDA-approved treatment. In this placebo-controlled eight-week study, patients are randomized. All patient undergo a colonoscopy at the start of the study (baseline) and at week 8. Patients enrolled in the study are assessed for clinical status of disease by stool frequency, rectal bleeding, abdominal pain, physician's global assessment, and biomarker levels such as fecal calprotectin and hsCRP. The primary endpoint is a shift in endoscopy scores from Baseline to Week 8. Secondary and exploratory endpoints include safety and tolerability, change in rectal bleeding score, change in abdominal pain score, change in stool frequency, change in partial Mayo score, change in Mayo score, proportion of subjects achieving endoscopy remission, proportion of subjects achieving clinical remission, change in histology score, change in biomarkers of disease such as fecal calprotectin and hsCRP, level of adalimumab in the blood/tissue/stool, change in cytokine levels (e.g., TNFα, IL-6) in the blood and tissue.

Figure 72:
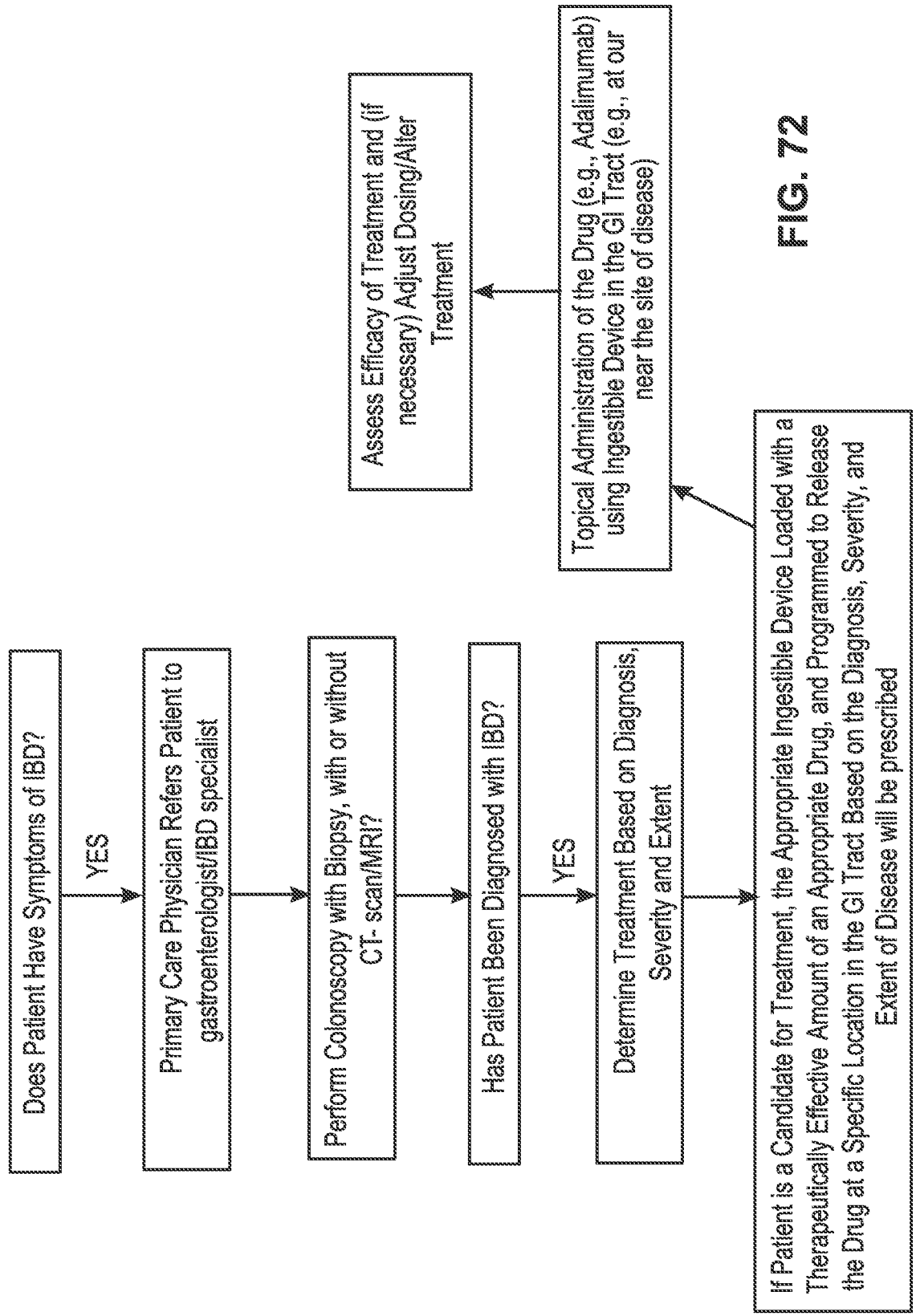
FIG. 72 is a flowchart of illustrative steps of a clinical protocol, in accordance with some embodiments of the disclosure.

FIG. 72 describes an exemplary process of what would occur in clinical practice, and when, where, and how the ingestible device will be used. Briefly, a patient displays symptoms of ulcerative colitis, including but not limited to: diarrhea, bloody stool, abdominal pain, high c-reactive protein (CRP), and/or high fecal calprotectin. A patient may or may not have undergone a colonoscopy with diagnosis of ulcerative colitis at this time. The patient's primary care physician refers the patient. The patient undergoes a colonoscopy with a biopsy, CT scan, and/or MRI. Based on this testing, the patient is diagnosed with ulcerative colitis. Most patients are diagnosed with ulcerative colitis by colonoscopy with biopsy. The severity based on clinical symptoms and endoscopic appearance, and the extent, based on the area of involvement on colonoscopy with or without CT/MRI is documented. Treatment is determined based on diagnosis, severity and extent.

For example, treatment for a patient that is diagnosed with ulcerative colitis is an ingestible device programmed to release a single bolus of a therapeutic agent, e.g., 40 mg adalimumab, in the cecum or proximal to the cecum. Prior to administration of the treatment, the patient is fasted overnight and is allowed to drink clear fluids. Four hours after swallowing the ingestible device, the patient can resume a normal diet. An ingestible device is swallowed at the same time each day. The ingestible device is not recovered.

In some embodiments, there may be two different ingestible devices: one including an induction dose (first 8 to 12 weeks) and a different ingestible device including a different dose or a different dosing interval.

In some examples, the ingestible device can include a mapping tool, which can be used after 8 to 12 weeks of induction therapy, to assess the response status (e.g., based on one or more of the following: drug level, drug antibody level, biomarker level, and mucosal healing status). Depending on the response status determined by the mapping tool, a subject may continue to receive an induction regimen or maintenance regimen of adalimumab.

In different clinical studies, the patients may be diagnosed with Crohn's disease and the ingestible devices (including adalimumab) can be programmed to release adalimumab in the cecum, or in both the cecum and transverse colon.

In different clinical studies, the patients may be diagnosed with illeocolonic Crohn's disease and the ingestible devices (including adalimumab) can be programmed to release adalimumab in the late jejunum or in the jejunum and transverse colon.

Example 13. Pharmacokinetic Study of Oral Vs. Intra-Cecal Administration of Tacrolimus in Yorkshire-Cross Farm Swine The primary objective of this study was to study the pharmacokinetics of oral versus intra-cecal administration of tacrolimus in normal Yorkshire-Cross farm swine.

This study compares the effects of administration of: a single intra-cecal administration of a device containing 0.8 mL sterile vehicle solution (80% alcohol, 20% castor oil (HCO-60)); a single oral dose of tacrolimus at 0.09 mg/kg (in sterile vehicle solution); and a single intra-cecal administration of a device containing either 0.02 mg/kg (in sterile vehicle solution), 0.04 mg/kg (in sterile vehicle solution), or 0.09 mg/kg (in sterile vehicle solution).

This study employed five groups of three female swine weighing approximately 45 to 50 kg at study start. Swine were randomly placed into animal rooms/pens as they are transferred from the delivery vehicle without regard to group. Group numbers were assigned to the rooms in order of room number. No further randomization procedure was employed. The study design is provided in Table 14.

TABLE 14

Study Design

| Treatments | | | Dosage mg/kg | HED mg | Route | Endpoints |
|---|---|---|---|---|---|---|
| Group 1 | Vehicle control | n = 3 | 0 | 0 | Intra-cecal capsule | [Tacrolimus] in blood and rectal content at 1~12 hr post dose, and GI tissue & GI content at 12 hr post dose |
| Group 2 | Tacro-limus | n = 3 | 0.09 | 6.60 | Oral solution | |
| Group 3 | Tacro-limus | n = 3 | 0.02 | 1.65 | Intra-cecal capsule | |
| Group 4 | Tacro-limus | n = 3 | 0.04 | 3.30 | Intra-cecal capsule | |
| Group 5 | Tacro-limus | n = 3 | 0.09 | 6.60 | Intra-cecal capsule | |

Animals in Group 1 received intra-cecally a device containing a vehicle solution (80% alcohol, 20% HCO-60). Animals in Group 2 received orally a liquid formulation of tacrolimus at 0.09 mg/kg per animal. Animals in Group 3 received intra-cecally a device containing tacrolimus at 0.02 mg/kg per device. Animals in Group 4 received intra-cecally a device containing tacrolimus 0.04 mg/kg per device. Animals in Group 5 received intra-cecally a device containing tacrolimus 0.09 mg/kg per device.

Samples of rectal contents were collected for pharmacokinetic analyses from each animal at each of 1, 3, 6, and 12 hours post-device placement using a fecal swab (rectal swab).

The concentration of tacrolimus measured was measured in the blood at 1-, 2-, 3-, 4-, 6-, and 12-hours post-dose. The concentration of tacrolimus was measured in rectal contents at 1-, 3-, 6-, and 12-hours post-dose, and in the gastrointestinal tissue and luminal content, e.g., the cecum tissue and lumen, the proximal colon tissue and lumen, the spiral colon tissue and lumen, the transverse colon tissue and lumen, and the distal colon tissue and lumen, at 12 hours post-dose.

Results

Figure 77:
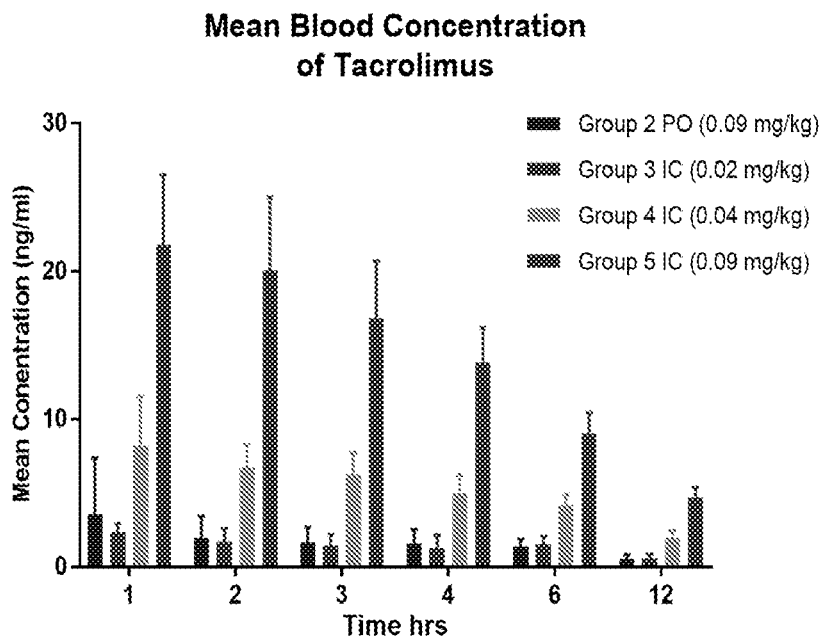
FIG. 77 is a graph showing the mean concentration of tacrolimus in the blood 1 hour, 2 hours, 3 hours, 4 hours, 6 hours and 12 hours after intra-cecal (IC) or oral administration (PO) of tacrolimus to swine as described in Example 13.
Figure 78:
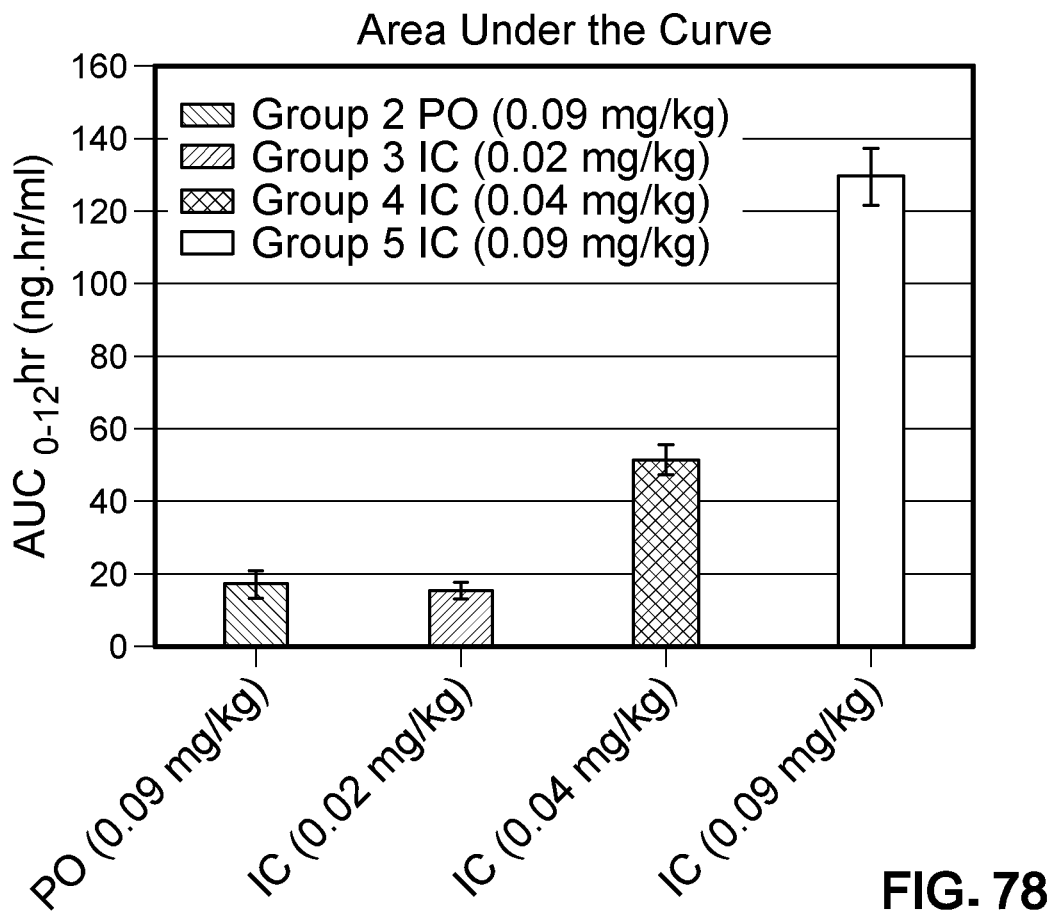
FIG. 78 is a graph showing the $AUC_{0-12}$ hours of tacrolimus in the blood after intra-cecal (IC) or oral administration (PO) of tacrolimus in swine as described in Example 13.
Figure 79:
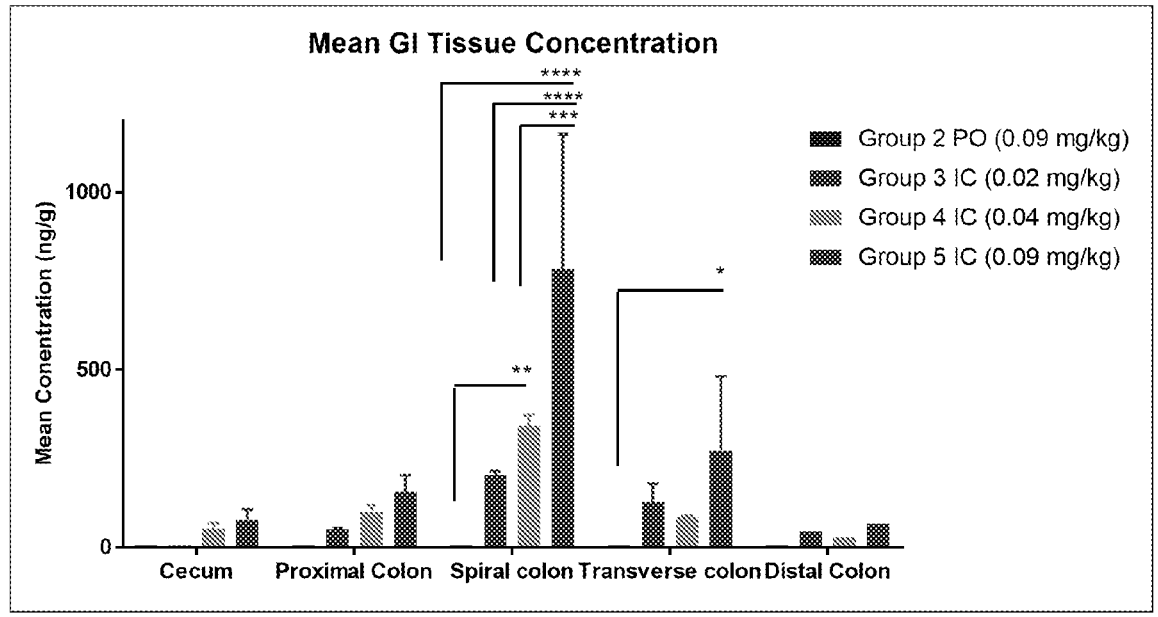
FIG. 79 is a graph showing the mean concentration of tacrolimus in the cecum tissue, the proximal colon tissue, the spiral colon tissue, the transverse colon tissue, and the distal colon tissue after intra-cecal (IC) or oral administration (PO) of tacrolimus in swine as described in Example 13. **P<0.0001, *P<0.001.
Figure 80:
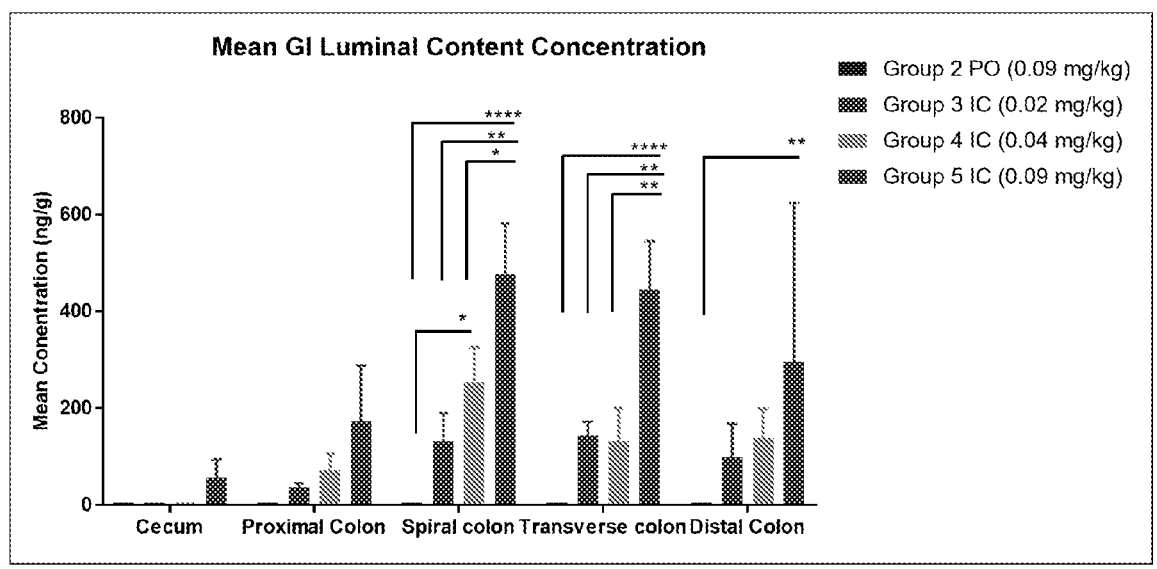
FIG. 80 is a graph showing the mean concentration of tacrolimus in the cecum lumen, the proximal lumen, the spiral colon lumen, the transverse colon lumen, and the distal colon lumen in swine after intra-cecal (IC) or oral administration (PO) of tacrolimus in swine as described in Example 13. **P<0.0001, *P<0.001
Figure 81:
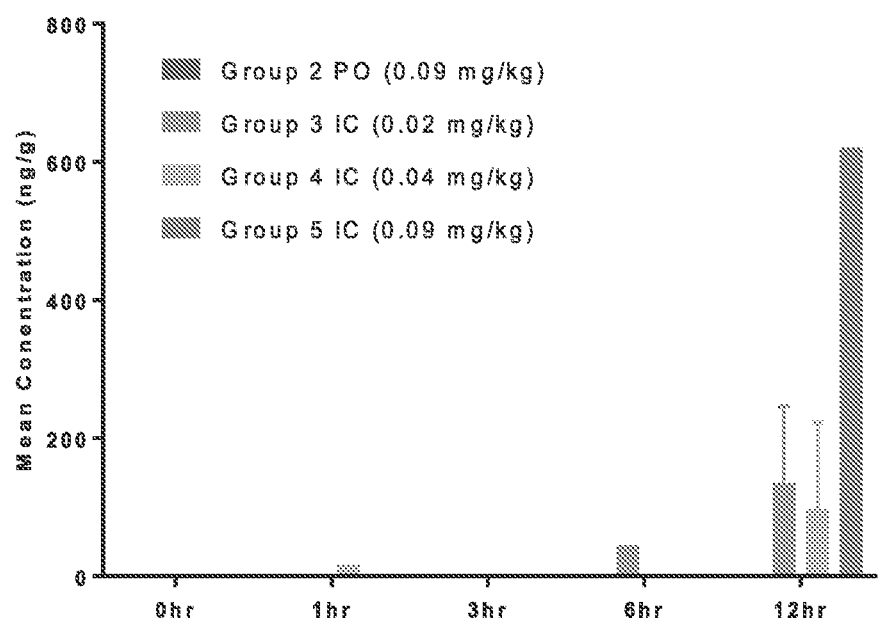
FIG. 81 is a bar graph showing the mean concentration of tacrolimus in the rectal content 1 hour, 3 hours, 6 hours and 12 hours after intra-cecal (IC) or oral administration (PO) of tacrolimus to swine as described in Example 13.
Figure 82:
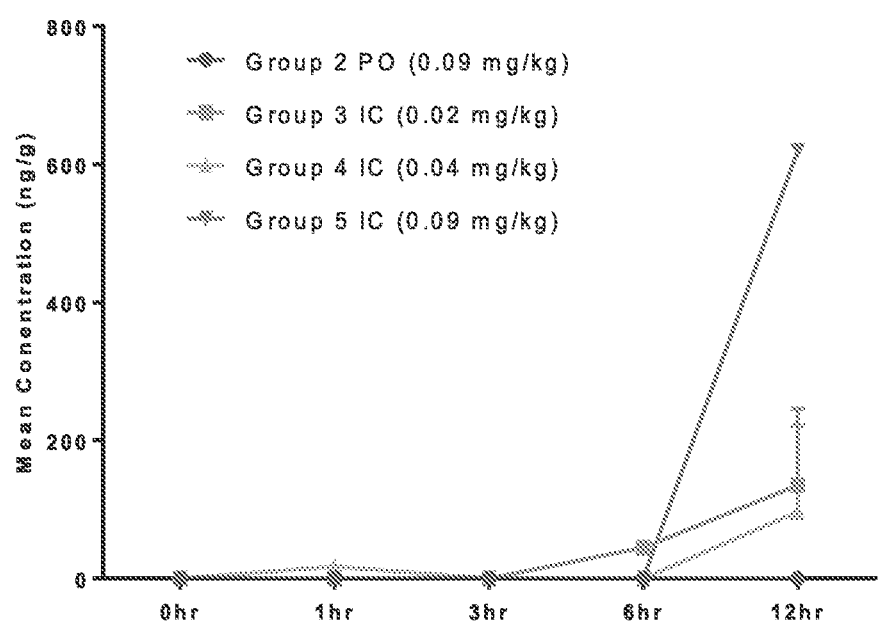
FIG. 82 is a line graph showing the mean concentration of tacrolimus in the rectal content 1 hour, 3 hours, 6 hours and 12 hours after intra-cecal (IC) or oral administration (PO) of tacrolimus to swine as described in Example 13.

The data in FIGS. 77 and 78 show that the mean concentration and $AUC_{0-12}$ hours of tacrolimus in the blood was higher in swine that were intra-cecally administered tacrolimus as compared to swine that were orally administered tacrolimus even at the same concentration (0.09 mg/kg). The data in FIG. 79 show that the mean concentration of tacrolimus in the spiral colon tissue and the transverse colon tissue were statistically higher in swine that were intacecally administered tacrolimus as compared to swine that were orally administered tacrolimus. The data in FIG. 80 show that the mean concentration of tacrolimus in the spiral colon lumen, the transverse colon lumen, and the distal colon lumen were statistically higher in swine that were inta-cecally administered tacrolimus as compared to swine that were orally administered tacrolimus. The data in FIGS. 81 and 82 show that the mean concentration of tacrolimus in the rectal concent was higher in swine that were intra-cecally administered tacrolimus as compared to swine that were orally administered tacrolimus even at the same concentration, particularly at 12 hours post-dose.

These data suggest that intra-cecal administration of tacrolimus is able to locally deliver tacrolimus to the tissues in the GI tract of a mammal.

A summary of the results are shown in Table 15.

TABLE 15

Summary of Results

| Route | PO | IC | IC | IC |
|---|---|---|---|---|
| Dosage (mg/kg) | 0.09 | 0.02 | 0.04 | 0.09 |
| Cmax (ng/ml) | 3.53 ± 3.84 | 2.39 ± 0.57 | 9.197 ± 3.30 | 21.8 ± 4.73 |
| Trough (12 hr) (ng/ml) | 0.568 ± 0.291 | 0.746 ± 0.038 | 1.96 ± 0.491 | 4.35 ± 0.561 |
| AUC $_{0\_12\ hr}$ (ng~hr/ml) | 16.83 ± 3.641 | 15.29 ± 2.36 | 51.35 ± 4.04 | 129.6 ± 7.83 |

Tables 16 and 17 provide the tissue and plasma ratios of the animals in Groups 2-5.

TABLE 16-1

Tissue $_{(mean)}$ (ng/g)/ AUG$_{(0-12\ hr)}$(ng·hr/ml) ratios

| | Group 2 PO (0.09 mg/kg) | | | Group 3 IC (0.02 mg/kg) | | |
|---|---|---|---|---|---|---|
| | Tissue (ng/g) | AUC 0-12 hr (ng·hr/ml) | Ratio | Tissue (ng/g) | AUC 0-12 hr (ng·hr/ml) | Ratio |
| Cecum | | 16.83 | 0 | | 15.29 | 0.00 |
| Proximal Colon | | 16.83 | 0 | 50.20 | 15.29 | 3.28 |
| Spiral colon | | 16.83 | 0 | 204.00 | 15.29 | 13.34 |
| Transverse colon | | 16.83 | 0 | 128.20 | 15.29 | 8.38 |
| Distal Colon | | 16.83 | 0 | 44.70 | 15.29 | 2.92 |

TABLE 16-2

Tissue $_{(mean)}$ (ng/g)/ AUG$_{(0-12\ hr)}$ (ng·hr/ml) ratios

| | Group 4 IC (0.04 mg/kg) | | | Group 5 IC (0.09 mg/kg) | | |
|---|---|---|---|---|---|---|
| | Tissue (ng/g) | AUC 0-12hr (ng·hr/ml) | Ratio | Tissue (ng/g) | AUC 0-12hr (ng·hr/ml) | Ratio |
| Cecum | 52.3 | 51.35 | 1.019 | 77.3 | 129.6 | 0.60 |
| Proximal Colon | 98.3 | 51.35 | 1.914 | 157.0 | 129.6 | 1.21 |
| Spiral colon | 342.3 | 51.35 | 6.667 | 783.3 | 129.6 | 6.04 |
| Transverse colon | 85.8 | 51.35 | 1.670 | 272.0 | 129.6 | 2.10 |
| Distal Colon | 28.7 | 51.35 | 0.559 | 67.7 | 129.6 | 0.52 |

TABLE 17-1

Tissue $_{(mean)}$ (ng/g)/ Trough$_{(12\ hr)}$(ng/ml)

| | Group 2 PO (0.09 mg/kg) | | | Group 3 IC (0.02 mg/kg) | | |
|---|---|---|---|---|---|---|
| | Tissue (ng/g) | Trough level (12 hr) | Ratio | Tissue (ng/g) | Trough level (12 hr) | Ratio |
| Cecum | | 0.568 | 0 | | 0.746 | 0.00 |
| Proximal Colon | | 0.568 | 0 | 50.20 | 0.746 | 67.29 |
| Spiral colon | | 0.568 | 0 | 204.00 | 0.746 | 273.46 |
| Transverse colon | | 0.568 | 0 | 128.20 | 0.746 | 171.85 |
| Distal Colon | | 0.568 | 0 | 44.70 | 0.746 | 59.92 |

TABLE 17-2

Tissue $_{(mean)}$ (ng/g)/ Trough$_{(12\ hr)}$(ng/ml)

| | Group 4 IC (0.04 mg/kg) | | | Group 5 IC (0.09 mg/kg) | | |
|---|---|---|---|---|---|---|
| | Tissue (ng/g) | Trough level (12 hr) | Ratio | Tissue (ng/g) | Trough level (12 hr) | Ratio |
| Cecum | 52.3 | 1.96 | 26.684 | 77.3 | 4.35 | 17.78 |
| Proximal Colon | 98.3 | 1.96 | 50.136 | 157.0 | 4.35 | 36.09 |
| Spiral colon | 342.3 | 1.96 | 174.660 | 783.3 | 4.35 | 180.08 |
| Transverse colon | 85.8 | 1.96 | 43.759 | 272.0 | 4.35 | 62.53 |
| Distal Colon | 28.7 | 1.96 | 14.643 | 67.7 | 4.35 | 15.56 |

Example 14

An ingestible medical device according to the disclosure ("TLC1") was tested on 20 subjects to investigate its localization ability. TLC1 was a biocompatible polycarbonate ingestible device that contained a power supply, electronics and software. An onboard software algorithm used time, temperature and reflected light spectral data to determine the location of the ingestible device as it traveled the GI tract. The ingestible device is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the ingestible device was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For Pill-Cam, the algorithm was as follows:
1. Start mouth-esophagus transition detection after ingestible device is activated/administrated
2. Check whether Green <102.3 and Blue <94.6
   a. If yes, mark as mouth-esophagus transition
   b. If no, continue to scan the data
3. After detecting mouth-esophagus transition, continue to monitor Green and Blue signals for another 30 seconds, in case of location reversal
   a. If either Green >110.1 or Blue >105.5, mark it as mouth-esophagus location reversal
   b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two-minute gap between the front (first) and back (second) windows. The two-minute gap was designed, at least in part, to skip the rapid transition from stomach to small intestine and capture the small intestine signal after ingestible device settles down in small intestine. The algorithm was as follows:
1. Start to check for stomach-duodenum transition after ingestible device enters stomach
2. Setup the two windows (front and back)
   a. Time length of each window: 3 minutes for TLC1; 30 seconds for PillCam
   b. Time gap between two windows: 2 minutes for both devices
   c. Window sliding step size: 0.5 minute for both devices
3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the timestamp when reversal happened and then repeat steps a-c to look for the next pyloric transition
      ii. If the ingestible device has not gone back to stomach 2 hours after previously confirmed pyloric transition, stops location reversal monitoring and assume the ingestible device would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the ingestible device went back to stomach after first the first stomach-duodenum transition. The total agreement between the TLC1 algorithm detection and CT scans was 17/17=100%.

For one of the PillCam subjects, the ingestible device stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:
1. Good cases (48 subjects):
   a. For 25 subjects, our detection matches exactly with the physician's notes
   b. For 19 subjects, the difference between the two detections is less than five minutes
   c. For four subjects, the difference between the two detections is less than 10 minutes (The full transition could take up to 10 minutes before the GB signal settled)
2. Failed cases (6 subjects):
   a. Four subjects had high standard deviation of Green/Blue signal in the stomach
   b. One subject had bile in the stomach, which greatly affected Green/Blue in stomach
   c. One subject had no Green/Blue change at pyloric transition The total agreement for the PillCam stomach-duodenum transition localization algorithm detection and physician's notes was 48/54=89%.

Duodenum-Jejenum Transition

For TLC1, it was assumed that the device left the duodenum and entered the jejenum three minutes after it was determined that the device entered the duodenum. Of the 17 subjects noted above with respect to the TLC1 investigation of the stomach-duodenum transition, 16 of the subjects mentioned had CT images that confirmed that the duodenum-jejunum transition was located somewhere between stomach and jejunum. One of the 17 subjects had a prolonged transit time in duodenum. The total agreement between algorithm detection and CT scans was 16/17=94%.

For PillCam, the duodenum-jejunum transition was not determined.

Jejenum-Ileum Transition

It is to be noted that the jejunum is redder and more vascular than ileum, and that the jejunum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:

1. Obtain 20 minutes of Red signal after the duodenum-jejenum transition, average the data and record it as the jejunum reference signal
2. Start to check the jejunum-ileum transition 20 minutes after the device enters the jejunum
   a. Normalize the newly received data by the jejunum reference signal
   b. Two approaches:
      i. Single-sliding-window analysis
         Set the transition flag if the mean of reflected red signal is less than 0.8
      ii. Two-sliding-window analysis:
         Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:

1. Single-sliding-window analysis:
   a. 11 cases having jejunum-ileum transition detected somewhere between jejunum and cecum
   b. 24 cases having jejunum-ileum transition detected after cecum
   c. 19 cases having no jejunum-ileum transition detected
   d. Total agreement: 11/54=20%
2. Two-sliding-window analysis:
   a. 30 cases having jejunum-ileum transition detected somewhere between jejunum and cecum
   b. 24 cases having jejunum-ileum transition detected after cecum
   c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:

1. Start to monitor ileum-cecum transition after the ingestible device enters the stomach
2. Setup the two windows (front (first) and back (second))
   a. Use a five-minute time length for each window
   b. Use a 10-minute gap between the two windows
   c. Use a one-minute window sliding step size
3. Compare signals in the two sliding windows
   a. Set ileum-cecum transition flag if
      i. Reflected red/green has a significant change or is lower than a threshold
      ii. Coefficient of variation of reflected green/blue is lower than a threshold
   b. If this is the first ileum-cecum transition detected, record average reflected red/green signal in small intestine as small intestine reference signal
   c. Mark location reversal (i.e. ingestible device returns to terminal ileum) if
      i. Reflected red/green is statistically comparable with small intestine reference signal
      ii. Coefficient of variation of reflected green/blue is higher than a threshold
   d. If a possible ileum-cecum transition is detected, continue to scan for another 10 minutes for TLC1 (15 minutes for PillCam) in case of false positive flag
      i. If within this time frame (10 minutes for TLC1, 15 minutes for PillCam), location reversal is detected, the previous ileum-cecum transition flag is a false positive flag. Clear the flag and continue to check
      ii. If no location reversal has been identified within this time frame (10 minutes for TLC1, 15 minutes for PillCam) following the possible ileum-cecum transition flag, mark it as a confirmed ileum-cecum transition
   e. Continue monitoring data for another 2 hours after the confirmed ileum-cecum transition, in case of location reversal
      i. If a location reversal is identified, flag the timestamp when reversal happened and then repeat steps a-d to look for the next ileum-cecum transition
      ii. If the ingestible device has not gone back to small intestine 2 hours after previously confirmed ileum-cecum transition, stop location reversal monitoring and assume the ingestible device would stay in large intestinal area The flag setting and location reversal criteria particularly designed for TLC1 device were as follows:

1. Set ileum-cecum transition flag if
   a. The average reflected red/Green in the front window is less than 0.7 or mean difference between the two windows is higher than 0.6
   b. And the coefficient of variation of reflected green/blue is less than 0.02
2. Define as location reversal if
   a. The average reflected red/green in the front window is higher than small intestine reference signal
   b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:
1. Good cases (39 subjects):
    a. For 31 subjects, the difference between the PillCam detection and the physician's notes was less than five minutes
    b. For 3 subjects, the difference between the PillCam detection and the physician's notes was less than 10 minutes
    c. For 5 subjects, the difference between the PillCam detection and the physician's notes was less than 20 minutes (the full transition can take up to 20 minutes before the signal settles)
2. Marginal/bad cases (13 subjects):
    a. Marginal cases (9 subjects)
        i. The PillCam ileum-cecum transition detection appeared in the terminal ileum or colon, but the difference between the two detections was within one hour
    b. Failed cases (4 subjects)
        i. Reasons of failure:
            1. The signal already stabilized in the terminal ileum
            2. The signal was highly variable from the entrance to exit
            3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition

Data demonstrated that, for TLC1, mean signal of reflected red/green provided the most statistical difference before and after the cecum-colon transition. Data also demonstrated that, for TLC1, the coefficient of variation of reflected blue provided the most statistical contrast at cecum-colon transition. The same signals were used for PillCam. The cecum-colon transition localization algorithm was as follows:
1. Obtain 10 minutes of reflected red/green and reflected blue signals after ileum-cecum transition, average the data and record it as the cecum reference signals
2. Start to check cecum-colon transition after ingestible device enters cecum (The cecum-colon transition algorithm is dependent on the ileum-cecum transition flag)
    a. Normalize the newly received data by the cecum reference signals
    b. Two-sliding-window analysis:
        i. Use two adjacent 10 minute windows
        ii. Set the transition flag if any of the following criteria were met The mean difference in reflected red/green was more than 4× the standard deviation of reflected red/green in the back (second) window The mean of reflected red/green in the front (first) window was higher than 1.03

The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:
1. 27 cases had the cecum-colon transition detected somewhere between the cecum and the colon
2. one case had the cecum-colon transition detected in the ileum
3. 24 cases had no cecum-colon transition localized The total agreement: 27/52=52%.

The following table summarizes the localization accuracy results.

| Transition | TLC1 | PillCam |
| --- | --- | --- |
| Stomach-Duodenum | 100% (17/17) | 89% (48/54) |
| Duodenum-Jejenum | 94% (16/17) | N/A |
| Ileum-Cecum | 89% (16/18) | 75% (39/52) |
| Ileum-terminal ileum/cecum/colon | 100% (18/18) | 92% (48/52) |

OTHER EMBODIMENTS

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, and the appended listing of embodiments should be given the broadest interpretation consistent with the description as a whole.

The invention claimed is:

1. A method of treating ulcerative colitis in a subject, the method comprising: orally administering to the subject an ingestible device comprising: an ingestible housing comprising a reservoir, the reservoir containing a pharmaceutical formulation comprising a therapeutically effective amount of an IL-10 receptor agonist selected from the group consisting of recombinant human IL-10, pegylated IL-10, viral IL-10, IL-10 fusion protein, IL-10 antibody or antigen-binding fragment thereof, and IL-10 peptide mimetic; a release mechanism having a closed state wherein the pharmaceutical formulation is retained in the reservoir and an open state which allows for the release of the pharmaceutical formulation from the reservoir to the exterior of the ingestible device; an actuator which controls the transition of the release mechanism from the closed state to the open state; a light source configured to produce light that interacts with a gastrointestinal (GI) tract of the subject to provide light reflectance; a detector configured to detect the light reflectance to detect the GI tract; and a processor coupled to the detector and to the actuator, wherein the processor triggers the actuator to cause the release mechanism to transition from the closed state to the open state when the ingestible device is located in the cecum based on the detected light reflectance, wherein the cecum has been predetermined to be proximal to one or more disease sites, thereby releasing the pharmaceutical formulation comprising the IL-10 receptor agonist from the ingestible device when the ingestible device is located in the cecum of the subject.

2. The method of claim 1, wherein the one or more disease sites is in the colon.

3. The method of claim 1, wherein the IL-10 receptor agonist is an antibody or an antigen-binding antibody fragment.

4. The method of claim 1, wherein the IL-10 receptor agonist is a recombinant IL-10 or a pegylated recombinant IL-10.

5. The method of claim 4, wherein the IL-10 receptor agonist is a pegylated recombinant human IL-10.

6. The method of claim 1, wherein the ingestible device further comprises one or more machine-readable hardware storage devices that stores instructions that are executable by the processor to determine that the ingestible device is in the cecum of the subject to an accuracy of at least 70%.

7. The method of claim 1, wherein the method further comprises determining the location of the ingestible device in the cecum of the subject to an accuracy of at least 85%.

8. The method of claim 1, wherein the ingestible device is configured to detect light reflectance from an environment external to the housing.

9. The method of claim 8, wherein the detected reflectance indicates that the ingestible device is located in the cecum of the subject.

10. The method of claim 9, wherein the detected reflectance autonomously triggers the release of the pharmaceutical formulation comprising the IL-10 receptor agonist from the ingestible device.

11. The method of claim 8, wherein the detected reflectance comprises light of at least two different wavelengths.

12. The method of claim 8, wherein determining the location of the ingestible device in the cecum comprises detecting a transition of the ingestible device from the ileum to the cecum.

13. The method of claim 12, wherein detecting the transition of the ingestible device from the ileum to the cecum comprises detecting a change in the ratio of reflected red light to reflected green light.

14. The method of claim 13, wherein detecting the transition of the ingestible device from the ileum to the cecum further comprises detecting a change in the ratio of reflected green light to reflected blue light.

15. The method of claim 1, wherein the ingestible device comprises a gas generating cell located within the housing, wherein the gas generating cell is capable of generating a gas; and the ingestible device is configured so that, when the gas generating cell generates the gas, the gas creates an internal pressure that forces a release mechanism from a closed state, which retains the IL-10 receptor agonist in the reservoir, to an open state, thereby allowing for the release of the IL-10 receptor agonist from the reservoir to the exterior of the device.

16. The method of claim 15, wherein the reservoir is configured to friction fit with the ingestible device.

17. The method of claim 15, wherein the reservoir is configured to attach to the housing of the ingestible device.

18. The method of claim 15, wherein the ingestible device comprises a safety device placed within or attached to the housing, wherein the safety device is configured to relieve the internal pressure within the housing when the internal pressure exceeds a threshold level.

19. The method of claim 1, further comprising releasing the pharmaceutical formulation comprising the IL-10 receptor agonist to the cecum as a bolus.

20. The method of claim 1, further comprising determining the level of the IL-10 receptor agonist in the plasma of the subject following the oral administration of the ingestible device, wherein the level of the IL-10 receptor agonist is lower than the level of the IL-10 receptor agonist in the plasma of a subject at substantially the same time point following systemic administration of an equal amount of the IL-10 receptor agonist.

21. The method of claim 1, wherein releasing the IL-10 receptor agonist from the ingestible device is not dependent on pH, enzymatic activity or bacterial activity at or in the vicinity of the predetermined location.

22. The method of claim 4, wherein the IL-10 receptor agonist is a recombinant human IL-10.

23. The method of claim 1, wherein the IL-10 receptor agonist is a fusion protein.

24. The method of claim 23, wherein the fusion protein comprises an IL-10 protein, or a functional fragment thereof, and a fusion partner that targets the IL-10 receptor agonist to inflamed tissue.

25. The method of claim 24, wherein the fusion partner is an antibody or antigen-binding antibody fragment.

26. The method of claim 24, wherein the inflamed tissue is inflamed gastrointestinal tissue.

27. The method of claim 23, wherein the fusion protein comprises recombinant human IL-10.

* * * * *